US009445581B2

(12) United States Patent
Bradley et al.

(10) Patent No.: US 9,445,581 B2
(45) Date of Patent: Sep. 20, 2016

(54) ANIMAL MODELS AND THERAPEUTIC MOLECULES

(75) Inventors: Allan Bradley, Cambridge (GB); E-Chiang Lee, Cambridge (GB); Qi Liang, Cambridge (GB); Wei Wang, Cambridge (GB); Dominik Spensberger, Cambridge (GB); Hui Liu, Cambridge (GB); Jasper Clube, Cambridge (GB)

(73) Assignee: Kymab Limited, Cambridge (GB)

( * ) Notice: Subject to any disclaimer, the term of this patent is extended or adjusted under 35 U.S.C. 154(b) by 0 days.

(21) Appl. No.: 13/433,084

(22) Filed: Mar. 28, 2012

(65) Prior Publication Data
US 2013/0263293 A1 Oct. 3, 2013

(51) Int. Cl.
| | |
|---|---|
| *C12P 21/00* | (2006.01) |
| *A01K 67/027* | (2006.01) |
| *C12N 5/06* | (2006.01) |
| *C12P 21/08* | (2006.01) |
| *C07K 16/46* | (2006.01) |
| *C12N 15/85* | (2006.01) |
| *C07K 16/12* | (2006.01) |
| *C07K 16/18* | (2006.01) |
| *C07K 16/00* | (2006.01) |

(52) U.S. Cl.
CPC .......... *A01K 67/0278* (2013.01); *C07K 16/00* (2013.01); *C07K 16/1239* (2013.01); *C07K 16/18* (2013.01); *C07K 16/46* (2013.01); *C07K 16/462* (2013.01); *C12N 15/85* (2013.01); *C12N 15/8509* (2013.01); *A01K 2217/072* (2013.01); *A01K 2217/075* (2013.01); *A01K 2217/15* (2013.01); *A01K 2227/105* (2013.01); *A01K 2267/01* (2013.01); *C07K 2317/21* (2013.01); *C07K 2317/92* (2013.01)

(58) Field of Classification Search
CPC .................... A01K 67/0278; A01K 2217/07; A01K 2217/075; A01K 2227/105; C12N 15/8509; C07K 16/46; C07K 16/462
USPC ..................... 800/6, 18; 435/328; 530/387.3
See application file for complete search history.

(56) References Cited

U.S. PATENT DOCUMENTS

| | | | |
|---|---|---|---|
| 5,169,939 A | 12/1992 | Gefter et al. .............. 530/387.3 |
| 5,545,807 A | 8/1996 | Surani et al. ..................... 800/2 |
| 5,770,429 A | 6/1998 | Lonberg et al. ........... 435/240.2 |
| 5,789,215 A | 8/1998 | Berns et al. ............... 435/172.3 |
| 5,939,598 A | 8/1999 | Kucherlapati et al. ......... 800/25 |
| 6,162,963 A | 12/2000 | Kucherlapati et al. ......... 800/18 |
| 6,596,541 B2 | 7/2003 | Murphy et al. .............. 435/463 |
| 6,673,986 B1 | 1/2004 | Kucherlapati et al. ......... 800/18 |
| 6,713,610 B1 | 3/2004 | Kucherlapati et al. .. 530/388.23 |
| 6,833,268 B1 | 12/2004 | Green et al. ............... 435/320.1 |
| 6,914,128 B1 | 7/2005 | Salfeld et al. ............. 530/387.3 |
| 6,998,514 B2 † | 2/2006 | Bruggemann |
| 7,119,248 B1 | 10/2006 | Rajewsky et al. ................ 800/6 |
| 7,205,148 B2 | 4/2007 | Economides et al. ........ 435/462 |
| 7,435,871 B2 † | 10/2008 | Green |
| 7,501,552 B2 | 3/2009 | Lonberg et al. .................. 800/6 |
| 7,910,798 B2 | 3/2011 | Tanamachi et al. ............ 800/18 |
| 7,932,431 B2 | 4/2011 | Bruggemann ................. 800/18 |
| 8,158,419 B2 | 4/2012 | Lonberg et al. .............. 435/328 |
| 8,502,018 B2 † | 8/2013 | Murphy |
| 8,642,835 B2 | 2/2014 | MacDonald et al. ........... 800/16 |
| 2002/0088016 A1 | 7/2002 | Bruggemann ................. 800/18 |
| 2003/0108925 A1 | 6/2003 | Dix et al. .......................... 435/6 |
| 2003/0217373 A1 | 11/2003 | Green et al. ...................... 800/6 |
| 2005/0048621 A1 | 3/2005 | Grasso et al. .............. 435/69.1 |
| 2006/0015949 A1 | 1/2006 | Lonberg et al. .................. 800/5 |
| 2006/0015957 A1 | 1/2006 | Lonberg et al. ................ 800/18 |
| 2006/0021074 A1 | 1/2006 | Kellerman et al. ............ 800/18 |
| 2006/0199204 A1 | 9/2006 | Dix et al. ........................ 800/16 |
| 2007/0280945 A1 | 12/2007 | Stevens et al. ............ 424/145.1 |
| 2008/0098490 A1 | 4/2008 | Jakobovits et al. ............ 800/13 |
| 2009/0083870 A1 | 3/2009 | Horn et al. ...................... 800/13 |
| 2009/0196112 A1 | 8/2009 | Cho .............................. 365/200 |
| 2009/0209036 A1 | 8/2009 | Reynaud et al. .............. 435/455 |
| 2010/0069614 A1 | 3/2010 | Houtzager et al. ........ 530/387.1 |
| 2010/0146647 A1 | 6/2010 | Logtenberg et al. ............. 800/4 |
| 2010/0196367 A1 | 8/2010 | Day .......................... 424/130.1 |
| 2011/0138489 A1 | 6/2011 | Tanamachi et al. .............. 800/6 |
| 2011/0145937 A1 | 6/2011 | MacDonald et al. ............. 800/6 |
| 2011/0236378 A1 | 9/2011 | Green et al. ............... 424/133.1 |
| 2012/0070861 A1 † | 3/2012 | Macdonald |
| 2012/0073004 A1 | 3/2012 | Macdonald et al. ............ 800/18 |

(Continued)

FOREIGN PATENT DOCUMENTS

| | | | | |
|---|---|---|---|---|
| EP | 2 307 503 A1 | 11/2001 | ............. A61K 39/42 |
| EP | 1780272 A1 | 5/2007 | ............. C12N 15/00 |

(Continued)

OTHER PUBLICATIONS

Bruggemann, Marianne, 2004, US 20040231012 A1.*
Houdebine, L-M., 2002, Journal of Biotechnology, vol. 98, p. 145-160.*
Goldman et al., 2004, Med Sci Monit, vol. 10, No. 11, RA274-285.*
Sigmund, C., Jun. 2000, Arterioscler. Thromb. Vasc. Biol., p. 1425-1429.*
Houdebine, Louis-Marie, 2007, Methods in Molecular Biology, vol. 360, p. 163-202.*
Carstea et al., 2009, World Journals of Stem Cells, vol. 1, No. 1, p. 22-29.*
Macdonald et al., Mar. 22, 2012, US 20120070861 A1.*
Andrew Murphy, "VelocImmune: Immunoglobulin Variable Region Humanized Mice", *Recombinant Antibodies for Immunotherapy.* 1st ed. Cambridge: Cambridge University Press, 2009. 100-108.

(Continued)

*Primary Examiner* — Shin Lin Chen
(74) *Attorney, Agent, or Firm* — Sunstein Kann Murphy & Timbers LLP

(57) ABSTRACT

The invention discloses methods for the generation of chimaeric human—non-human antibodies and chimaeric antibody chains, antibodies and antibody chains so produced, and derivatives thereof including fully humanized antibodies; compositions comprising the disclosed antibodies, antibody chains and derivatives, as well as cells, non-human mammals and vectors, suitable for use in the disclosed methods.

27 Claims, 84 Drawing Sheets

(56) References Cited

U.S. PATENT DOCUMENTS

| | | | | |
|---|---|---|---|---|
| 2012/0167237 | A1 | 6/2012 | Bradley et al. | 800/9 |
| 2012/0204278 | A1 | 8/2012 | Bradley et al. | 800/18 |
| 2012/0233715 | A1 | 9/2012 | Kuroiwa et al. | 800/3 |
| 2012/0322108 | A1 | 12/2012 | Macdonald et al. | 435/69.6 |
| 2013/0039850 | A1 | 2/2013 | Lonberg et al. | 424/1.49 |
| 2013/0102031 | A1 | 4/2013 | King et al. | 435/69.6 |
| 2013/0160153 | A1 | 6/2013 | Macdonald et al. | 800/18 |
| 2013/0212719 | A1 | 8/2013 | Macdonald et al. | 800/6 |
| 2013/0254911 | A1 | 9/2013 | Macdonald et al. | 800/18 |
| 2013/0323790 | A1 | 12/2013 | Macdonald et al. | 435/70.2 |
| 2013/0323791 | A1 | 12/2013 | Macdonald et al. | 435/91.1 |
| 2013/0326647 | A1 | 12/2013 | Macdonald et al. | 800/18 |
| 2013/0333057 | A1 | 12/2013 | Macdonald et al. | 800/6 |
| 2014/0017228 | A1 | 1/2014 | Macdonald et al. | 424/132.1 |
| 2014/0130193 | A1 | 5/2014 | Macdonald et al. | 800/18 |
| 2014/0130194 | A1 | 5/2014 | Macdonald et al. | 800/18 |
| 2014/0137275 | A1 | 5/2014 | Macdonald et al. | 800/18 |
| 2014/0213773 | A1 | 7/2014 | Macdonald et al. | 530/387.3 |

FOREIGN PATENT DOCUMENTS

| | | | | |
|---|---|---|---|---|
| GB | 2398784 A | | 9/2004 | A01K 67/027 |
| KR | 1020050042792 A | | 5/2005 | A01K 67/027 |
| WO | WO 90/04036 | | 4/1990 | C12P 21/08 |
| WO | WO 91/00906 | | 1/1991 | C12N 15/00 |
| WO | WO 91/10741 | | 7/1991 | C12P 21/06 |
| WO | WO 94/02602 | | 2/1994 | C12N 15/00 |
| WO | WO 94/04667 | | 3/1994 | C12N 15/00 |
| WO | WO 96/30498 | | 10/1996 | C12N 15/00 |
| WO | WO 98/24884 | | 6/1998 | C12N 5/00 |
| WO | WO 98/24893 | | 6/1998 | C12N 15/00 |
| WO | WO 99/45962 | | 9/1999 | A61K 39/295 |
| WO | WO 02/08409 | A2 | 1/2002 | C12N 15/00 |
| WO | WO 02/36789 | | 5/2002 | C12N 15/85 |
| WO | WO 02/43478 | | 6/2002 | A01K 67/027 |
| WO | WO 02/053596 | A2 | 7/2002 | C07K 16/28 |
| WO | WO 02/059263 | | 8/2002 | |
| WO | WO-02066630 | A1 | 8/2002 | |
| WO | WO 02/070648 | A2 | 9/2002 | |
| WO | WO 03/006639 | A1 | 1/2003 | C12N 5/10 |
| WO | WO 03/047336 | A2 | 6/2003 | |
| WO | WO 03/061363 | A2 | 7/2003 | |
| WO | WO 2004/050838 | A2 | 6/2004 | |
| WO | WO 2005/003364 | A2 | 1/2005 | C12N 15/90 |
| WO | WO 2005/019463 | A1 | 3/2005 | C12N 15/85 |
| WO | WO 2006/044492 | | 4/2006 | C12N 15/52 |
| WO | WO 2006/122442 | A1 | 11/2006 | C12N 9/22 |
| WO | WO 2007/096779 | A2 | 8/2007 | |
| WO | WO-2007117410 | A2 | 10/2007 | |
| WO | WO 2008/022391 | A1 | 2/2008 | C07K 16/28 |
| WO | WO 2008/054606 | A2 | 5/2008 | C07K 16/00 |
| WO | WO 2008/070367 | A2 | 6/2008 | C12N 15/09 |
| WO | WO-2008076379 | A2 | 6/2008 | |
| WO | WO 2008/094178 | A2 | 8/2008 | C12Q 1/68 |
| WO | WO 2008/103474 | A1 | 8/2008 | C12N 15/13 |
| WO | WO 2008/118970 | A2 | 10/2008 | A61K 48/00 |
| WO | WO 2008/122886 | A2 | 10/2008 | C12N 15/85 |
| WO | WO 2008/151081 | A1 | 12/2008 | C12N 15/85 |
| WO | WO-2009013620 | A2 | 1/2009 | |
| WO | WO 2009/018411 | A1 | 2/2009 | C07K 16/28 |
| WO | WO 2009/023540 | A1 | 2/2009 | A61K 39/395 |
| WO | WO-2009076464 | A2 | 6/2009 | |
| WO | WO 2009/080254 | A1 | 7/2009 | C07K 16/46 |
| WO | WO 2009/094178 | A2 | 7/2009 | C09B 67/08 |
| WO | 2010/039900 | A2 † | 9/2009 | |
| WO | WO 2009/118524 | A2 | 10/2009 | C12N 5/00 |
| WO | WO 2009/143472 | A2 | 11/2009 | C07K 16/46 |
| WO | WO-2009143472 | A2 | 11/2009 | |
| WO | WO 2009/157771 | A2 | 12/2009 | A01K 67/027 |
| WO | WO 2010/039900 | A2 | 4/2010 | C12N 15/13 |
| WO | WO-2010039900 | A2 | 4/2010 | |
| WO | WO 2010/070263 | A1 | 6/2010 | C12N 15/85 |
| WO | WO 2010/097385 | A1 | 9/2010 | C07K 16/24 |
| WO | WO 2010/113039 | A1 | 10/2010 | C12N 5/00 |
| WO | WO 2011/004192 | A1 | 1/2011 | A01K 67/027 |
| WO | WO 2011/008093 | A1 | 1/2011 | C07K 16/00 |
| WO | WO 2011/056864 | A1 | 5/2011 | C12P 21/06 |
| WO | WO 2011/097603 | A1 | 8/2011 | C12N 15/85 |
| WO | WO 2011/158009 | A1 | 12/2011 | A01K 67/027 |
| WO | WO 2011/163311 | A1 | 12/2011 | C12N 15/85 |
| WO | WO2011/163311 | A1 * | 12/2011 | |
| WO | WO 2011/163314 | A1 | 12/2011 | C12N 15/85 |
| WO | WO 2012/018764 | A1 | 2/2012 | C12N 15/85 |
| WO | WO 2012/023053 | A2 | 2/2012 | |
| WO | WO 2012/141798 | A1 | 10/2012 | C12N 15/85 |
| WO | WO 2012/148873 | A2 | 11/2012 | A01K 67/027 |
| WO | WO 2013/022782 | A1 | 2/2013 | C12N 15/85 |
| WO | WO 2013/041844 | A2 | 3/2013 | C12N 15/85 |
| WO | WO 2013/041845 | A2 | 3/2013 | C12N 15/85 |
| WO | WO 2013/059230 | A1 | 4/2013 | C12N 15/85 |
| WO | WO 2013/061098 | A2 | 5/2013 | C12N 15/85 |
| WO | WO 2013/096142 | | 6/2013 | A01K 67/027 |
| WO | WO 2013/116609 | A1 | 8/2013 | A01K 67/027 |

OTHER PUBLICATIONS

Briney, et al., "Human Peripheral Blood Antibodies with Long HCDR3s Are Established Primarily at Original Recombination Using a Limited Subset of Germline Genes," PLoS One, May 2012, vol. 7, Issue 5, e36750, 13 pages.

Brüggemann, et al., "Human Antibody Production in Transgenic Mice: Expression from 100 kb of the Human IgH Locus," European Journal of Immunology, May 1991, vol. 21, Issue 5, pp. 1323-1326.

Feeney, "Genetic and Epigenetic Control of V Gene Rearrangement Frequency," V(D)J Recombination Advances in Experimental Medicine and Biology, 2009, vol. 650, 2009, pp. 73-81.

Green, "Antibody Engineering via Genetic Engineering of the Mouse: XenoMouse Strains are a Vehicle for the Facile Generation of Therapeutic Human Monoclonal Antibodies," Journal of Immunological Methods, Dec. 10, 1999, vol. 231, Issues 1-2, pp. 11-23.

Huang, et al., "Structural Basis of Tyrosine Sulfation and VH-Gene Usage in Antibodies that Recognize the HIV Type 1 Coreceptor-Binding Site on gp120," PSNA, Mar. 2, 2004, vol. 101, No. 9, pp. 2706-2711.

Jakobovits, et al, "From XenoMouse Technology to Panitumumas, the First Fully Human Antibody Product from Transgenic Mice", Nature Biotechnology, vol. 25, No. 10, Oct. 2007, pp. 1134-1143.

Jung, et al., "Mechanism and Control of V(D)J Recombination at the Immunoglobulin Heavy Chain Locus," Annual Review of Immunology, Apr. 2006, vol. 24, pp. 541-570.

Liu, et al., "Potent and Broad Anti-HIV-1 Activity Exhibited by a Glycosyl-Phosphatidylinositol-Anchored Peptide Derived from the CDR H3 of Broadly Neutralizing Antibody PG16," Journal of Virology, Sep. 2011, vol. 85, No. 17, pp. 8467-8476.

Mendez, et al., "Functional Transplant of Megabase Human Immunoglobulin Loci Recapitulates Human Antibody Response in Mice," Nature Genetics, Feb. 1997, vol. 15, pp. 146-156.

Nadel, et al., "Sequence of the Spacer in the Recombination Signal Sequence Affects V(D)J Rearrangement Frequency and Correlates with Nonrandom Vκ Usage In Vivo," J. Exp. Med., May 4, 1998, vol. 187, No. 9, pp. 1495-1503.

Nicholson, et al., "Antibody Repertoires of Four- and Five-Feature Translocus Mice Carrying Human Immunoglobulin Heavy Chain and κ and λ Light Chain Yeast Artificial Chromosomes1," The Journal of Immunology, Dec. 15, 1999, vol. 163, No. 12, pp. 6898-6906.

Schroeder, et al., "Preferential utilization of conserved immunoglobulin heavy chain variable gene segments during human fetal life," Proceeding of the National Academy of Sciences of the United States of America, Aug. 1990, vol. 87, pp. 6146-6150.

Yu, et al., Differential Usage of VH Gene Segments Is Mediated by cis Elements, The Journal of Immunology, Oct. 1, 1998, vol. 161, No. 7, pp. 3444-3454.

European Patent Office, International Search Report and Written Opinion, International Application No. PCT/GB2012/052298, Jun. 13, 2013, 22 pages.

European Patent Office, International Search Report, International Application No. PCT/GB2010/51122, dated Sep. 29, 2010.

(56) References Cited

OTHER PUBLICATIONS

European Patent Office, International Search Report and Written Opinion, Application No. PCT/BG2013/050682, 17 pages, dated Sep. 25, 2013.
European Patent Office, Examiners Report re: allowability, International Application No. PT/GB2010/51122.
Adams, D., et al., "A Genome-Wide, End-Sequenced 129Sv BAC Library Resource for Targeting Vector Construction," Genomics, vol. 86, No. 6, pp. 753-758, Dec. 2005.
Askew, R., et al., "Site-Directed Point Mutations in Embryonic Stem Cells: a Gene-Targeting Tag-and-Exchange Strategy," Molecular and Cellular Biology, vol. 13, No. 7, pp. 4115-4124, Jul. 1993.
Auerbach, et al., "Establishment and Chimera Analysis of 129/SvEv- and C57BL/6-Derived Mouse Embryonic Stem Cell Lines," Biotechniques, vol. 29: No. 5, pp. 1024-1032, Nov. 2000.
Baker et al., "Homologous Recombination between Transferred and Chromosomal Immunoglobulin Kappa Genes," Molecular and Cellular Biology, vol. 8, No. 10, pp. 4041-4047, Oct. 1988.
Barreto et al., "AID From Bony Fish Catalyzes Class Switch Recombination,"Journal of Experimental Medicine, vol. 202, No. 6, pp. 1-6, Sep. 2005.
Bates et al., "Chromosomal Position of a VH Gene Segment Determines Its Activation and Inactivation as a Substrate for V(D)J Recombination," The Journal of Experimental Medicine, vol. 204, No. 13, pp. 3247-3256, Dec. 2007.
Beard et al., "Efficient Method to Generate Single-Copy Transgenic Mice by Site-Specific Integration in Embryonic Stem Cells," Genesis, vol. 44, No. 1, pp. 23-28, Jan. 2006.
Beck et al., "Nucleotide Sequence and Exact Localization of the Neomycin Phosphotransferase Gene from Transposon Tn5," Gene, vol. 19, No. 3, pp. 327-336, Oct. 1982.
Berg et al., "Inverted repeats of Tn5 are Transposable Elements," Proceedings of the National Academy of Science USA, Genetics, vol. 79, No. 8, pp. 2632-2635, Apr. 1982.
Bethke et al., "Segmental Genomic Replacement by Cre-Mediated Recombination: Genotoxic Stress Activation of the P53 Promoter in Single-Copy Transformants," Nucleic Acids Research, vol. 25, No. 14, pp. 2828-2834, Jul. 1997.
Billiard, et al., "Ongoing Dll4-Notch Signaling is Required for T-Cell Homeostasis in the Adult Thymus," European Journal of immunology, Aug. 4, 2011, vol. 41, No. 8, pp. 2207-2216, Aug. 2011.
Bolland et al., "Antisense Intergenic Transcription Precedes *Igh* D-to-J Recombination and is Controlled by the Intronic Enhancer Eμ," Molecular and Cellular Biology, vol. 27, No. 15, pp. 5523-5533, Aug. 2007.
Bonin et al., "Isolation, Microinjection, and Transfer of Mouse Blastocysts" Methods in Molecular Biology, vol. 158, Gene Knockout Protocols, pp. 121-134.
Bottaro et al., "Deletion of the IgH Intronic Enhancer and Associated Matrix-Attachment Regions Decreases, But Does Not Abolish, Class Switching at the μ Locus," International Immunology, vol. 10, No. 6, pp. 799-806, Jun. 1998.
Bradley et al., "Formation of Germ-Line Chimaeras From Embryo-Derived Teratocarcinoma Cell Lines," Nature, vol. 309, No. 5965, pp. 255-256, May 1984.
Breden et al., "Comparison of Antibody Repertoires Produced by HIV-1 Infection, Other Chronic and Acute Infections, and Systemic Autoimmune Disease," PLoS One., vol. 6, No, 3, pp. 1-11, Mar. 2011.
Brocker et al., "Evolutionary Divergence and Functions of the ADAM and ADAMTS Gene Families" Human Genomics, vol. 4, No. 2, pp. 43-55, Oct. 2009.
Brüggemann, "Human Antibody Expression in Transgenic Mice," Archivum Immunologiae et Therapiae Experimentalis, vol. 49, No, 3, pp. 203-208, 2001.
Brüggemann et al., "Immunoglobulin Heavy Chain Locus of the Rat: Striking Homology to Mouse Antibody Genes," Proceedings of the National Academy of Science USA, Immunology, vol. 83, No. 16, pp. 6075-6079, Aug. 1986.
Brüggemann et al., "A Repertoire of Monoclonal Antibodies with Human Heavy Chains from Transgenic Mice," Proceedings of the National Academy of Science USA, Immunology, vol. 86, No. 17, pp. 6709-6713, Sep. 1989.
Buehr et al., "Capture of Authentic Embryonic Stem Cells from Rat Blastocysts," Cell, vol. 135, No. 7, pp. 1287-1298, Dec. 2008.
Cadinanos et al., "Generation of an Inducible and Optimized Piggyback Transposon System," Nucleic Acids Research, vol. 35, No. 12, Jun. 2007.
Carstea, et al., "Germline Competence of Mouse ES and iPS Cell Lines: Chimera Technologies and Genetic Background," World Journal of Stem Cells, vol. 1, No. 1, pp. 22-29, Dec. 2009.
Chen et al., "B Cell Development in Mice that Lack One or Both Immunoglobulin Kappa Light Chain Genes," The EMBO Journal, vol. 12, No. 3, pp. 821-830, Mar. 1993.
Chen et al., "Immunoglobulin Heavy Chain Gene Replacement: A Mechanism of Receptor Editing" Immunity, vol. 3, No. 6, pp. 747-755, Dec. 1995.
Cho, "Testicular and Epididymal Adams: Expression and Function During Fertilization," Nature Reviews Urology, vol. 9, No. 10, pp. 550-560, Oct. 2012.
Choi et al., "Characterization and Comparative Genomic Analysis of Intronless Adams with Testicular Gene Expression," Genomics, vol. 83, No. 4, pp. 636-646, Aug. 2003.
Clark et al., "Trends in Antibody Sequence Changes During the Somatic Hypermutation Process," The Journal of Immunology, vol. 177, No. 1, pp. 333-340, Jul. 2006.
Clark et al., "A Future for Transgenic Livestock," Nature Reviews Genetics, vol. 4, No. 10, pp. 825-833, Oct. 2003.
Colbere Garapin et al., "A New Dominant Hybrid Selective Marker for Higher Eukaryotic Cells" Journal of Molecular Biology, vol. 150, No. 1, pp. 1-14, Jul. 1981.
Collins, et al., "A Mouse for All Reasons," Cell, vol. 128, No. 1, pp. 9-13, Jan. 2007.
Combriato, et al., "Regulation of Human Igλ Light Chain Gene Expression by NF-κB1," Journal of Immunology, vol. 168, No. 3, pp. 1259-1266, Feb. 2002.
Conrath, et al., "Camel Single-Domain Antibodies as Modular Building Units in Bispecific and Bivalent Antibody Constructs," The Journal of Biological Chemistry, vol. 276, No. 10, pp. 7346-7350, Mar. 2001.
Copeland et al., "Recombineering: A Powerful New Tool for Mouse Functional Genomic," Nature Reviews Genetics, vol. 2, No. 10, pp. 769-869, Oct. 2001.
Corti et al, "A Neutralizing Antibody Selected from Plasma Cells That Binds to Group 1 and Group 2 Influenza A Hemagglutinins" Science, vol. 333, No. 6044, pp. 850-856, Aug. 2011.
Cuesta et al., "Multivalent Antibodies: When Design Surpasses Evolution," Trends Biotechnology, vol. 28, No. 7, pp. 355-362, Jul. 2010.
De Saint Vincent et al., "Homologous Recombination in Mammalian Cells Mediates Formation of a Functional Gene From Two Overlapping Gene Fragments," Proceedings of the National Academy of Science, USA vol. 80, No. 7, pp. 2002-2006, Apr. 1983.
DeChiara et al., "VelociMouse: Fully ES Cell-Derived F0-Generation Mice Obtained from the Injection of ES Cells into Eight-Cell-Stage Embryos," Gene Knockout Protocols: Second Edition, vol. 530, pp. 311-324, 2009.
DeChiara et al., "Producing Fully ES Cell-Derived Mice from Eight-Cell Stage Embryo Injections," Methods in Enzymology, vol. 476, Chapter 16, pp. 285-294, Jan. 2010.
Denome et al., "Patterns of Polyadenylation Site Selection in Gene Constructs Containing Multiple Polyadenylation Signals," Molecular and Cellular Biology, vol. 8, No. 11, pp. 4829-4839, Nov. 1988.
Diez-Roux et al., "A High-Resolution Anatomical Atlas of the Transcriptome in the Mouse Embryo," PLoS Biology, vol. 9, No. 1, pp. 1-13, Jan. 2011.

(56) References Cited

OTHER PUBLICATIONS

Ding, et al., "Generation of High-Affinity Fully Human Anti-Interleukin-8 Antibodies from its cDNA by Two-Hybrid Screening and Affinity Maturation in Yeast," Protein Science, vol. 19, No. 10, pp. 1957-1966, Oct. 2010.

DiNoia et al., "Molecular Mechanisms of Antibody Somatic Hypermutation," Annual Review of Biochemistry, vol. 76, No. 1, pp. 1-22, 2007.

Doetschman et al., "Establishment of Hamster Blastocyst-Derived Embryonic Stein (ES) Cells," Developmental Biology, vol. 127, No. 1, pp. 224-227, May 1988.

Doetschman, et al., "Targeted Mutation of the Hprt Gene in Mouse Embryonic Stem Cells," Proceedings of the National Academy of Science USA, vol. 85, No. 22, pp. 8583-8587, Nov. 1988.

Doyle, et al., "The Construction of Transgenic and Gene Knockout/Knockin Mouse Models of Human Disease," Transgenic Research, vol. 21, No. 2, pp. 327-349, Apr. 2012.

1000 Genomes Project Consortium, "A Map of Human Genome Variation From Population-Scale Sequencing," Nature, vol. 467, No. 7319, pp. 1061-1074, Oct. 2012.

Durdik et al., "Isotype Switching by a Microinjected μ Immunoglobulin Heavy Chain Gene in Transgenic Mice," Proceedings of the National Academy of Science USA, Immunology, vol. 86, No. 7, pp. 2346-2350, Apr. 1989.

Edwards, et al, "The ADAM Metalloproteinases," Molecular Aspects of Medicine, vol. 29, No. 5, pp. 258-289, Oct. 2008.

Eisener-Dorman, et al., "Cautionary insights on knockout mouse studies: The gene or not the gene?" Brain, Behavior, and Immunity, vol. 23, No. 3, pp. 318-324, Sep. 2009.

Ekiert et al., "A Highly Conserved Neutralizing Epitope on Group 2 Influenza A Viruses," Science, vol. 333, No. 6044, pp. 843-850, Aug. 2011.

Evans, "Fertilin B and Other Adams as Integrin Ligands: Insights Into Cell Adhesion and Fertilization," BioEssays vol. 23, No. 7, pp. 628-639, Jul. 2001.

Featherstone et al., "The Mouse Immunoglobulin Heavy Chain V-D Intergenic Sequence Contains Insulators That May Regulate Ordered V(D)J Recombination," The Journal of Biological Chemistry, vol. 285, No. 13, pp. 9327-9338, Mar. 2010.

Fell et al., "Homologous Recombination in Hybridoma Cells: Heavy Chain Chimeric Antibody Produced by Gene Targeting," Proceedings of the National Academy of Science USA, vol. 86, No. 21, pp. 8507-8511, Nov. 1989.

Feschotte et al., "DNA Transposons and the Evolution of Eukaryotic Genomes.," Annual Review of Genetics, vol. 41, pp. 331-368, 2007.

Folger et al., "Patterns of Integration of DNA Microinjected into Cultured Mammalian Cells: Evidence for Homologous Recombination Between Injected Plasmid DNA Molecules," Molecular and Cellular Biology, vol. 2, No. 11, pp. 1372-1387, Nov. 1982.

Forconi et al., "The Normal IGHV1-69-Derived B-Cell Repertoire Contains Stereotypic Patterns Characteristic of Unmutated CLL," vol. 115, No. 1, pp. 71-77, Jan. 2010.

Fukita et al., "Somatic Hypermutation in the Heavy Chain Locus Correlates with Transcription," Immunity, vol. 9, No. 1, pp. 106-114, Jul. 1998.

Gefter et al., "Expression of a VHC kappa chimaeric protein in mouse myeloma cells," Nature, vol. 309, No. 5966, pp. 364-367, May 1984.

Gerdes et al., "Physical Map of the Mouse λ Light Chain and Related Loci," Immunogenetics, vol. 54, No. 1, pp. 62-65, Apr. 2002.

Gerstein et al., "Isotype Switching of an Immunoglobulin Heavy Chain Transgene Occurs by DNA Recombination Between Different Chromosomes." Cell, vol. 63, No. 3, pp. 537-548, Nov. 1990.

Geurts et al., "Knockout Rats via Embryo Microinjection of Zinc-Finger Nucleases," Science, vol. 325, No. 5939, p. 433, Jul. 2009.

Giallourakis, et al., "Elements Between the *Igh* Variable (V) and Diversity (D) Clusters Influence Antisense Transcription and Lineage-Specific V(D)J Recombination," Proceedings of the National Academy of Science USA, vol. 107, No. 51, pp. 22207-22212, Dec. 2010.

Gluzman, "SV40-Transformed Simian Cells Support the Replication of Early SV40 Mutants," Cell, vol. 23, No. 1, pp. 175-182, Jan. 1981.

Goodhart, et al., "Rearrangement and Expression of Rabbit Immunoglobulin Kappa Light Chain Gene in Transgenic Mice," Proceedings of the National Academy of Sciences USA, vol. 84, No. 12, pp. 4229-4233, Jun. 1987.

Gorman et al., "The IgK enhancer influences the ratio of IgK Versus Igλ B lymphocytes" Immunity, vol. 5, No. 3, pp. 241-252, Sep. 1996.

Gorny et al., "Human Anti-V3 HIV-1 Monoclonal Antibodies Encoded by the VH5-51/VL Lambda Genes Define a Conserved Antigenic Structure," PLoS One, vol. 6, No, 12, pp. 1-10, Dec. 2011.

Goyenechea et al., "Cells Strongly Expressing Ig(Kappa) Transgenes Show Clonal Recruitment of Hypermutation: a Role for Both MAR and the Enhancers," The EMBO Journal, vol. 16, No. 13, pp. 3987-3994, Jul. 1997.

Gu et al., "Independent Control of Immunoglobulin Switch Recombination at Individual Switch Regions Evidenced Through Cre-Loxp-Mediated Gene Targeting," Cell, vol. 73, No. 6, pp. 1155-1164, Jun. 1993.

Guerrero et al., "The Bleomycin Resistance Gene of Transposon Tn5 is an Excellent Marker for Transformation of Corynebacteria," Applied Microbiology Biotechnology, vol. 36, No. 6, pp. 759-762, Mar. 1992.

Guntaka, "Transcription Termination and Polyadenylation in Retroviruses" Microbiological Reviews, vol. 57, No. 3, pp. 511-521, Sep. 1993.

Han et al., "Comprehensive Analysis of Reproductive Adams: Relationship of ADAM4 and ADAM6 with an ADAM Complex Required for Fertilization in Mice," Biology of Reproduction, vol. 80, No. 5, pp. 1001-1008, Jan. 2009.

Hasty et al., "Target Frequency and Integration Pattern for Insertion and Replacement Vectors in Embryonic Stem Cells," Molecular and Cellular Biology, vol. 11, No. 9, pp. 4509-4517, Sep. 1991.

Hagiwara, "Transgenic Expression of Vpreb-3 Under the Control of the Immunoglobulin Heavy Chain Enhancer and SV40 Promoter," Kobe Journal of Medical Sciences, vol. 42, No. 1, pp. 43-59, Feb. 1996 (English Abstract).

Hendricks, et al., "Organization of the Variable Region of the Immunoglobulin Heavy-Chain Gene Locus of the Rat," Immunogentics, vol. 62, No. 7, pp. 479-486, Jul. 2010.

Houvila et al., "Shedding Light on ADAM Metalloproteinases," Trends in Biochemical Sciences, vol. 30, No. 7, pp. 413-422, Jul. 2005.

Hudziak et al., "Establishment of Mammalian Cell Lines Containing Multiple Nonsense Mutations and Functional Suppressor tRNA Genes," Cell, vol. 31, No. 1, pp. 137-146, Nov. 1982.

Iglesias-Ussel, et al, "Forced Expression of AID Facilitates the Isolation of Class Switch Variants From Hybridoma Cells," Journal of Immunological Methods, vol. 316, No. 1-2, pp. 59-66, Oct. 2006.

Ivics et al., "The Expanding Universe of Transposon Technologies for Gene and Cell Engineering," Mobile DNA, vol. 1, No. 1, pp. 1-25, Dec. 2010.

Ivics et al., "The Sleeping Beauty Transposable Element: Evolution, Regulation and Genetic Applications," Current Issues in Molecular Biology, vol. 6, No. 1, pp. 43-55, Jan. 2004.

Izsvak et al., "Sleeping Beauty Transposition: Biology and Applications for Molecular Therapy," Molecular Therapy, vol. 9, No. 2, pp. 147-156, Feb. 2004.

Jacob et al., "Gene Targeting in the Rat: Advances and Opportunities," Trends in Genetics, vol. 26, No. 12, pp. 510-518, Dec. 2010.

Janssens, et al., "Generation of Heavy-Chain-Only Antibodies in Mice," Proceedings of the National Academy of Sciences USA, vol. 103, No. 41, pp. 15130-15135, Oct. 2006.

Jendreyko, et al., "Intradiabodies, Bispecific, Tetravalent Antibodies for the Simultaneous Functional Knockout of Two Cell Surface Receptors." The Journal of Biological Chemistry, vol. 278, No. 48, pp. 47812-47819, Nov. 2003.

(56) References Cited

OTHER PUBLICATIONS

Kaminski, et al., "Antibody Class Switching Differs Among SJL, C57BL/6 and 129 Mice," International Immunology, vol. 19, No. 4, pp. 545-556, Apr. 2007.
Kellerman, et al, "Developing the Xenomouse Technology for Evaluating Immunogenicity ," AntibOZ 2 Conference, Australia, 2004.
Kim et al., "CHO Cells in Biotechnology for Production of Recombinant Proteins: Current State and Further Potential" Applied Microbiology Biotechnology, vol. 93, No. 3, pp. 917-930, Feb. 2012.
Kim, et al., "Expression and Relationship of Male Reproductive Adams in Mouse," Biology of Reproduction, vol. 74, No. 4, pp. 744-750, Apr. 2006.
Kingzette et al., "Trans-Chromosomal Recombination Within the Ig Heavy Chain Switch Region in B Lymphocytes," Proceedings of the National Academy of Science, vol. 95, pp. 11840-11845, Sep. 1998.
Kitamura et al., "A B Cell-Deficient Mouse by Targeted Disruption of the Membrane Exon of the Immunoglobulin Chain Gene," Nature, vol. 350, No. 6317, pp. 423-426, Apr. 1991.
Kling, "News in Brief," Nature Biotechnology, vol. 25, No. 6, p. 613, Jun. 2007.
Kohrer et al., "Import of Amber and Ochre Suppressor Trims into Mammalian Cells: A General Approach to Site-Specific Insertion of Arnino Acid Analogues Into Proteins," Proceedings of The National Academy of Science USA, vol. 98, No. 25, pp. 214310-14315, Dec. 2001.
Kostenuik, et al., "Denosumab, a Fully Human Monoclonal Antibody to RANKL, Inhibits Bone Resorption and Increases BMD in Knock-In Mice that Supplemental Express Chimeric (Murine/Human) RANKL," Journal of Bone and Mineral Research, vol. 24, No. 2, pp. 182-195, Feb. 2009.
Kotzamaris et al., "Recombining Overlapping Bacs Into a Single Larger BAC," BMC Biotechnology, vol. 4, No. 1, pp. 1-10, Jan. 2004.
Krause, "Epitope-Specific Human Influenza Antibody Repertoires Diversify by B Cell Intraclonal Sequence Divergence and Interclonal Convergence," The Journal of Immunology, vol. 187, No. 7, pp. 3704-3711, Aug. 2011.
Kruif et al., "Human Immunoglobulin Repertoires Against Tetanus Toxoid Contain a Large and Diverse Fraction of High-Affinity Promiscuous Vh Genes," Journal of Molecular Biology, vol. 387, pp. 548-558, Feb. 2009.
Krutskikh et al., "Epididymal Protein Rnase10 Is Required for Post-Testicular Sperm Maturation and Male Fertility," The FASEB Journal, vol. 26, No. 10, pp. 4198-4209, Oct. 2012.
Kucherlapati et al., "Homologous Recombination Between Plasmids in Mammalian Cells Can Be Enhanced by Treatment of Input DNA," Proceedings of The National Academy of Science USA, Genetics, vol. 81, pp. 3135-3157, May 1984.
Kuroiwa et al., "Sequential Targeting of the Genes Encoding Immunoglobulin and Prion Protein in Cattle," Nature Genetics, vol. 36, No. 7, pp. 775-780, Jul. 2004.
Laventie, et al., "Heavy Chain-Only Antibodies and Tetravalent Bispecific Antibody Neutralizing *Staphylococcus Aureus* Leukotoxins," Proceedings of the National Academy of Sciences (USA), vol. 108, No. 39, pp. 16404-16409, Sep. 2011.
Lee et al, "Human C5ar Knock-In Mice Facilitate the Production and Assessment of Anti-Inflammatory Monoclonal Antibodies," Nature Biotechnology, vol. 24, No. 10, pp. 1279-1284, Oct. 2006.
Li et al., "Transgenic Mice with a Diverse Human T Cell Antigen Receptor Repertoire," Nature Medicine, vol. 16, No. 9, pp. 1029-1035, Sep. 2010.
Li et al., "The Minimum Internal and External Sequence Requirements for Transposition of the Eukaryotic Transformation Vector PiggyBac," Molecular Genetics and Genomics, vol. 266, No. 2, pp. 190-198, Oct. 2001.
Li et al., "Crafting Rat Genomes With Zinc Fingers," Nature Biotechnology, vol. 29, No. 1, pp. 39-41, Jan. 2011.
Li et al., "Germline Competent Embryonic Stem Cells Derived from Rat Blastocysts," Cell, vol. 135, No. 7, pp. 1299-1310, Dec. 2008.
Liao et al., "Generation of induced Pluripotent Stem Cell Lines from Adult Rat Cells," Cell Stem Cell Brief Report, vol. 4, pp. 11-15, Jan. 2009.
Luciw et al., "Location and Function of Retroviral and SV40 Sequences that Enhance Biochemical Transformation after Microinjection of DNA," Cell, vol. 33, No. 3, pp. 705-176, Jul. 1983.
Luo et al., "Chromosomal Transposition of a Tc1/Mariner-Like Element in Mouse Embryonic Stem Cells," Proc. Natl. Acad. Sci. USA, Genetics, vol. 95, No. 18, pp. 10769-10773, Sep. 1998.
Lonberg, "Human Antibodies from Transgenic Animals," Nature Biotechnology, vol. 23, No. 9, pp. 1117-1125, Sep. 2005.
Loveslati, et al., "A Study of Gm Allotypes and Immunoglobulin Heasy Gamma IGHG Genes in Berbers, Arabs and Sub-Saharan Africans From Jerba Island, Tunisia" Blackwell Science Ltd., European Journal of Immunogenetics, vol. 28, No. 5, pp. 531-538, Oct. 2001.
Luby, et al., "The Mu Switch Region Tandem Repeats are Important, but not Required, for Antibody Class Switch Recombination," The Journal of Experimental Medicine, vol. 193, No. 2, pp. 159-168, Jan. 2001.
Macdonald, et al., "Precise and In Situ Genetic Humanization of 6 Mb of Mouse Immunoerlobulin Genes," Proceedings of the National Academy of Sciences (USA), vol. 111, No. 14, 5147-5152, Apr. 2014.
Mack et al., "A Small Bispecific Antibody Construct Expressed as a Functional Single-Chain Molecule with High Tumor Cell Cytotoxicity," Proceedings of the National Academy of Science USA, Immunology, vol. 92, pp. 7021-7025, Jul. 1995.
Makris et al., "Mutational Analysis of Insertion Sequence 50 (IS50) and Transposon 5 (Tn5) Ends," Proceedings of the National Academy of Science USA, Genetics, vol. 85, No. 7, pp. 2224-2228, Apr. 1988.
Mallender et al., "Construction, Expression, and Activity of a Bivalent Bispecific Single-chain Antibody," The Journal of Biological Chemistry, vol. 269, No. 1, pp. 199-206. Jan. 1994.
Manis, et al., "Mechanism and Control of Class-Switch Recombination," Trends in Immunology, vol. 23, Issue 1, pp. 31-39, Jan. 2002.
Marcello et al., "Lack of Tyrosylprotein Sulfotransferase-2 Activity Results in Altered Sperm-Egg Interactions and Loss of ADAM3 and ADAM6 in Epididymal Sperm," The Journal of Biological Chemistry, vol. 286, No. 15, pp. 13060-13070, Apr. 2011.
Martensson et al., "Role of the surrogate light chain and the pre-B-cell receptor in mouse B-cell development," Immunology, vol. 101, pp. 435-441, 2000.
Maitta, et al., "Immunogenicity and Efficacy of *Cryptococcus neoformans* Capsular Polysaccharide Glucuronoxylomannan Peptide Mimotope-Protein Conjugates in Human Immunoglobulin Transgenic Mice," Infection and Immunity, vol. 72, No. 1, pp. 196-208, Jan. 2004.
Mattila, P.S., et al., "Extensive Allelic Sequence Variation in the J Region of the Human Immunoglobulin Heavy Chain Gene Locus," European Journal of Immunology, vol. 25, No. 9, pp. 2578-2582, Sep. 1995.
Maul et al., "AID and Somatic Hypermutation," Advances in Immunology, vol. 105, pp. 159-191, 2010.
McCreath et al., "Production of Gene-Targeted Sheep by Nuclear Transfer From Cultured Somatic Cells," Nature, vol. 405, pp. 1066-1070, Jul. 2000.
Mejia et al., "The Assembly of Large BACs by in Vivo Recombination," Genomics, vol. 70, pp. 165-170, 2000.
Milner, et al, "Polymorphism and Utilization of Human $V_H$ Genes," Annals of the New York Academy of Sciences, vol. 764, pp. 50-61, Sep. 1995.
Mir, Kalim U., "Sequencing Genomes: From Individuals to Populations," Briefings in Functional Genomics and Proteomics, vol. 8, No. 5, pp. 367-378, 2009.
Moran, Nuala, "Mouse Platforms Jostle for Slice of Humanized Antibody Market," Nature Biotechnology, vol. 31, pp. 267-268, 2013.

(56) References Cited

OTHER PUBLICATIONS

Moreau et al., "The SV40 72 Base Repair Repeat Has a Striking Effect on Gene Expression Both in SV40 and Other Chimeric Recombinants," Nuclear Acids Research, vol. 9, No. 22, pp. 6047-6068, 1981.
Moreno et al., "The Emerging Role of Matrix Metalloproteases of the ADAM Family in Male Germ Cell Apoptosis," Spermatogenesis, vol. 1, No. 3, pp. 195-208, Jul./Aug./Sep. 2011.
Mouellic et al., "Pattern of Transcription of the Homeo Gene Hox-3.1 in the Mouse Embryo," Genes and Development, vol. 2, pp. 125-135, 1988.
Mortuza et al., "Immunoglobulin Heay-Chain Gene Rearrangement in Adult Acute Lymphoblastic Leukemia Reveals Preferential Usage of JH-Proximal Variable Gene Segments," Blood, vol. 97, No. 9, pp. 2716-2726, May 2001.
Murphy, et al., "Mice with Megabase Humanization of Their Immunoglobulin Genes Generate Antibodies as Efficiently as Normal Mice," Proceedings of The National Academy of Science, vol. 111, No. 14, pp. 5153-5158, Apr. 2014.
Nagle, "Regeneron Helps Make Sanofi Velocimmune to Its 'Weak' Pipeline," Outsourcing-Pharmac.com, 2 pages, Dec. 3, 2007.
Nandi et al., "Regulated Expression of Genes Inserted at the Human Chromosomal B-Globin Locus by Homologous Recombination," Proceedings of the National Academy of Science USA, Cell Biology, vol. 85, pp. 3845-3849, Jun. 1998.
Narayanan et al., "Bacterial Artificial Chromosome Mutagenesis Using Recombineering" Journal of Biomedicine and Biotechnology, vol. 2011, 10 pages, Dec. 2010.
Nelson et al., "Development Trends for Human Monoclonal Antibody Therapeutics," Nature Reviews Drug Discovery, vol. 9, pp. 767-774, Oct. 2010.
Neuberger et al., "Somatic Hypermutation," Current Opinion in Immunology, vol. 7, pp. 248-254, 1995.
Niemann et al., "Transgenic Farm Animals: Present and Future," Review of Science and Technology, vol. 24, No. 1, pp. 285-298, Apr. 2005.
Oancea et al., "Expression of the (Recombinant) Endogenous Immunoglobulin Heavy-Chain Locus requires the Intronic Matrix Attachment Regions," Molecular and Cellular Biology, vol. 17, No. 5, pp. 2658-2668, May 1997.
Oberdoerffer et al., "Unidirectional Cre-Mediated Genetic Inversion in Mice Using the Mutant Loxp Pair Lox66/Lox71," Nucleic Acids Research, vol. 31, No. 22, pp. 1-7, Nov. 2003.
Ohlin, et al., "The Human Antibody Repertoire to Infectious Agents: Implications for Disease Pathogensis," Molecular Immunology, vol. 40, Issue 1, pp. 1-11, Sep. 2003.
Ohm-Laursen, et al., "Identification of Two New Alleles, IGHV3-23*04 and IGHJ6*04, and the Complete Sequence of the IGHV3-H Pseudogene in the Human Immunoglobulin Locus and Their Prevalences in Danish Caucasians," Immunogenetics, vol. 57, No. 9, pp. 621-627.
Osborn et al., "High-Affinity IgG Antibodies Develop Naturally in Ig-Knockout Rats Carrying Germline Human IgH/Ig k/Igλ Loci Bearing the Rat $C_h$ Region," The Journal of Immunology, vol. 190, No. 4, pp. 1481-1490, Feb. 2013.
Osoegawa et al., "Bacterial Aartificial Chromosome Libraries for Mouse Sequencing and Functional Analysis," Genome Research, vol. 10, No. 1, pp. 16-28, Jan. 2000.
Pavlicek et al., "Ancient Transposable Elements, Processed Pseudogenes, and Endogenous Retroviruses," Genomic Disorders, pp. 57-72, 2006.
Pelham et al., "Expression of a *Drosophila* Heat Shock Protein in Mammalian Cells: Transient Association with Nucleoli after Heat Shock," Philosophical Transactions of the Royal Society, vol. 307, No. 1132, pp. 301-307, Dec. 1984.
Perlot et al., "Antisense Transcripts From Immunoglobulin Heavy-Chain Locus V(D)J and Switch Regions," Proceedings of the National Academy of Science, vol. 105, No. 10, pp. 3843-3848, Mar. 2008.

Perlot et al., "Cis-Regulatory Elements and Epigenetic Changes Control Genomic Rearrangements of the IgH Locus," Advances in Immunology, vol. 99, pp. 1-32, 2008.
Pettitt, et al., "Agouti C57BL/6N Embryonic Stem Cells for Mouse Genetic Resources," Nature Methods, vol. 6, No. 7, pp. 493-495, Jul. 2009.
Plasterk et al., "Resident Aliens: The Tc1/Mariner Superfamily of Transposable Elements," Trends in Genetics, vol. 15, No. 8, pp. 326-333, Aug. 1999.
Ponsel, et al., "High Affinity, Developability and Functional Size: The Holy Grail of Combinatorial Antibody Library Generation," Molecules, vol. 16, No. 5, pp. 3675-3700, May 2011.
Popov et al., "A Human Immunoglobulin λ Locus is Similarly Well Expressed in Mice and Humans," Journal of Experimental Medicine, vol. 189, No. 10, pp. 1611-1619, May 1999.
Pramanik, et al., "Segmental Duplication as One of the Driving Forces Underlying the Diversity of the Human Immunoglobulin Heavy Chain Variable Gene Region," BMC Genomics, vol. 12, No. 78, Jan. 2011.
Primakoff et al., "Penetration, Adhesion, and Fusion in Mammalian Sperm-Egg Interaction," Science, vol. 296, pp. 2183-2185, Jun. 2002.
Primakoff et al., "The ADAM Gene Family: Surface Proteins With Adhesion and Protease Activity," Trends in Genetics, vol. 16, No. 2, pp. 83-87, Feb. 2000.
Puente et al., "Comparative Genomic Analysis of Human and Chimpanzee Proteases," Genomics, vol. 86, No. 6, pp. 638-647, Dec. 2005.
Prosser, et al., "Mosaic Complementation Demonstrates a Regulatory Role for Myosin Viia in Actin Dynamics of Stereocilia," Molecular and Cellular Biology, vol. 28, No. 5, pp. 1702-1712, Mar. 2008.
Prosser, et al., "A Resource of Vectors and ES Cells for Targeted Deletion of Micrornas in Mice," Nature Biotechnology, vol. 29, No. 9, pp. 840-845, Sep. 2011.
Pruzina et al., "Human Monoclonal Antibodies to HIV-1 Gp140 From Mice Bearing YAC-Based Human Immunoglobulin Transloci," Protein Engineering, Design & Selection, vol. 24, No. 10, pp. 791-799, Aug. 2011.
Qu et al., "Gene Targeting of ErbB3 Using a Cre-Mediated Unidirectional DNA Inversion Strategy," Technology Report, Genesis, vol. 44, pp. 477-486, 2006.
Ray, et al., "Ectopic Expression of a C-Kitw42 Minigene in Transgenic Mice: Recapitulation of W Phenotypes and Evidence for C-Kit Function in Melanoblast Progenitors," Genes & Development, vol. 5, pp. 2265-2273, 1991.
Raynard et al., "Cis-Acting Regulatory Sequences Promote High-Frequency Gene Conversion Between Repeated Sequences in Mammalian Cells," Nucleic Acids Research, vol. 32, No. 19, pp. 5916-5927, Nov. 2004.
Reddy et al., "Monoclonal Antibodies Isolated Without Screening by Analyzing the Variable-Gene Repertoire of Plasma Cells," Nature Biotechnology, vol. 28, No. 9, pp. 965-971, Sep. 2010.
Regeneron, "Big Pharma Vies for Mice," Nature Biotechnology, vol. 25, No. 6, p. 613, Jun. 2007.
Retter, "Sequence and Characterization of the Ig Heavy Chain Constant and Partial Variable Region of the Mouse Strain 129S1," The Journal of Immunology, vol. 179. pages 2419-2427, 2007.
Rivera, et al., "Genetic Background and the Dilemma of Translating Mouse Studies to Humans," Immunity, vol. 28, No. 1, pp. 1-4, Jan. 2008.
Rodriguez, et al., "High-Efficiency Deleter Mice Show That FLPe is an Alternative to Cre-loxP," Nature Genetics, vol. 25, pp. 139-140, Jun. 2000.
Rogozin et al., "Cutting Edge: DGYW/WRCH Is a Better Predictor of Mutability at G:c Bases in Ig Hypermutation Than the Widely Accepted RGYW/WRCY Motif and Probably Reflects a Two-Step Activation-Induced Cytidine Deaminase-Triggered Process," Journal of Immunology, vol. 172, pp. 3382-3384, 2004.
Sakai et al., "Recombination and Transcription of the Endogenous Ig Heavy Chain Locus is Effected by the Ig Heavy Chain Intronic

(56) References Cited

OTHER PUBLICATIONS

Enhancer Core Region in the Absence of the Matrix Attachment Regions," Proceedings of the National Academy of Science, vol. 96, pp. 1526-1531, Feb. 1999.
Sarkar et al., "Molecular Evolutionary Analysis of the Widespread *PiggyBac* Transposon Family and Related "Domesticated" Sequences," Molecular Genetics and Genomics, vol. 270, pp. 173-180, 2003.
Sasso et al., "Expression of the Immunoglobulin Vh Gene 51p1 Is Proportional to its Germline Gene Copy Number," Journal of Clinical Investigation, vol. 97, No. 9, pp. 2074-2080, May 1996.
Sasso, et al., "Ethnic Differences in Polymorphism of an Immunoglobulin $V_h3$ Gene," Journal of Clinical Investigation, vol. 96, No. 3, pp. 1591-1600, Sep. 1995.
Sauer, "Functional Expression of the Cre-Lox Site-Specific Recombination System in the Yeast *Saccharomyces cerevisiae*," Molecular and Cellular Biology, vol. 7, No. 6, pp. 2087-2096, Jun. 1987.
Sauer et al., "Cre-Stimulated Recombination at loxP-Containing DNA Sequences Placed into the Mammalian Genome," Nucleic Acids Research, vol. 17, No. 1, pp. 147-161, 1989.
Sauer et al., "Site-Specific DNA Recombination in Mammalian Cells by the Cre Recombinase of Bacteriophage P1," PNAS USA, Genetics, vol. 85, pages 5166-5170, 1988.
Schnutgen et al., "A Directional Strategy for Monitoring Cre-Mediated Recombination at the Cellular Level in the Mouse," Nature Biotechnology, vol. 21, pp. 562-565, May 2003.
Schlake et al., "Use of Mutated FLP Recognition Target (FRT) Sites for the Exchange of Expression Cassettes at Defined Chromosomal Loci," Biochemistry, vol. 33, pp. 12746-12751, 1994.
Schrock et al., "Comparative Genomic Hybridization (CGH)—Detection of Unbalanced Genetic Aberrations Using Conventional Micro-Array Techniques," Molecular Cytogenetics, Unit 8.12.1, Supplement 18, 30 pages, 2001.
Schroeder, et al., "Preferential Utilization of Conserved Immunoglobulin Heavy Chain Variable Gene Segments During Human Fetal Life," PNAS USA, vol. 87, pp. 6146-6150, Aug. 1990.
Schweinfest et al., "A Heat-Shock-Inducible Eukaryotic Expression Vector," Gene. 71, pp. 207-210, 1988.
Scott, "Mice with a Human Touch," Nature Biotechnology, vol. 25, pp. 1075-1077, Dec. 2007.
Seals, et al., "The Adams Family of Metalloproteases: Multidomain Proteins With Multiple Functions," Genes & Development, vol. 17, No. 1, pp. 7-30, Jan. 2003.
Seed et al., "Purification of Genomic Sequences From Bacteriophage Libraries by Recombination and Selection In Vivo," Nucleic Acids Research, vol. 11, No. 8, pp. 2427-2445, 1983.
Sen, et al., "Multiple Nuclear Factors Interact With the Immunoglobulin Enhancer Sequences," Cell, vol. 46, pp. 705-716, Aug. 1986.
Seong, et al., "To Knockout in 129 or in C57BL/6: That is the Question," Trends in Genetics, vol. 20, No. 2, pp. 59-62, Feb. 2004.
Serwe et al., "V(D)J Recombination in B Cells is Impaired but Not Blocked by Targeted Deletion of the Immunoglobulin Heavy Chain Intron Enhancer," The EMBO Journal, vol. 12, No. 6, pp. 2321-2327, 1993.
Shaul, et al., "Homologous Recombination Between a Defective Virus and a Chromosomal Sequence in Mammalian Cells," Proceedings of the National Academy of Sciences (USA), vol. 89, pages 3781-3784, Jun. 1985.
Shi, et al., "Comparative Analysis of Human and Mouse Immunoglobulin Variable Heavy Regions from IMGT/LIGM-DB with IMGT/HighV-QUEST," Theoretical Biology and Medical Modelling, vol. 11, pp. 1-11, Nov. 2014.
Shimizu et al., "Immunoglobulin Double-Isotype Expression by Trans-mRNA in a Human Immunoglobulin Transgenic Mouse," Proceedings of the National Academy of Science USA, Immunology, vol. 86, pp. 8020-8023, Oct. 1989.
Shultz, et al., "Humanized Mice in Translational Biomedical Research," The Journal of Immunology, vol. 7, No. 2, pp. 118-130, Feb. 2007.
Sirac, et al., "Role of the Monoclonal K Chain V Domain and Reversibility of Renal Damage in a Transgenic Model of Acquired Fanconi Syndrome," Blood, vol. 108, No. 2, pp. 536-543, Jul. 2006.
Skarnes, et al., "A Conditional Knockout Resource for the Genome-Wide Study of Mouse Gene Function," Nature, vol. 474, pp. 337-342, Jun. 2011.
Simpson, et al., "Genetic Variation Among 129 Substrains and its importance for Targeted Mutagenesis in Mice," Nature Genetics, vol. 16, pp. 19-27.
Skoultchi et al., "Expression of Genes Inserted at the Human B-Globin Locus by Homologous Recombination," Developmental Control of Globin Gene Expression, vol. 251, pp. 581-594, 1987.
Smithies, "Direct Alteration of a Gene in the Human Genome," Journal of Inheritable Metabolic Disease, vol. 9, Suppl. 1, pp. 92-97, 1986.
Smithies et al., "Insertion of DNA Sequences into the Human Chromosomal B-Globin Locus by Homologous Recombination," Nature, vol. 317, No. 19, pp. 230-234, Sep. 1985.
Sohn et al., "Somatic Hypermutation of an Immunoglobulin μ Heavy Chain Transgene," Journal of Experimental Medicine, vol. 177, pp. 493-504, Feb. 1993.
Song et al., "Accurate Modification of a Chromosomal Plasmid by Homologous Recombination in Human Cells," Proceedings of the National Academy of Science USA, Genetics, vol. 84, pp. 6820-6824, Oct. 1987.
Sonoda et al., "B Cell Development under the Condition of Allelic Inclusion," Immunology, vol. 6, pp. 225-233, Mar. 1997.
Storb et al., "Physical Linkage of Mouse Genes by Pulsed-Field Gel Electrophoresis Suggests that the Rearrangement Process Favors Proximate Target Sequences," Molecular and Cellular Biology, vol. 9, No. 2, pp. 711-718, Feb. 1989.
Stevens et al., "Human Antibody Discovery, VelocImmune—A Novel Platform," Pharma Focus Asia, Clinical Trials Issue 8, pp. 1-5, 2008.
Suárez, et al., "Rearrangement of Only One Human IGHV Gene is Sufficient to Generate a Wide Repertoire of Antigen Specific Antibody Responses in Transgenic Mice," Molecular Immunology, vol. 43, No. 11, pp. 1827-2835, Dec. 2006.
Taki et al., "Targeted Insertion of a Variable Region Gene into the Immunoglobulin Heavy Chain Locus," Science, vol. 262, pp. 1268-1271, Nov. 1993.
Talbot et al.,"Cell Adhesion and Fertilization: Steps in Oocyte Transport, Sperm-Zona Pellucida interactions, and Sperm-Egg Fusion," Biology of Reproduction 68, pp. 1-9, 2003.
Te Riele, et al., "Highly Efficient Gene Targeting in Embryonic Stem Cells Through Homologous Recombination with isogenic DNA Constructs," Proceedings of the National Academy of Sciences (USA), vol. 89, pages 5128-5132, Jun. 1992.
Thomas et al., "High Frequency Targeting of Genes to Specific Sites in the Mammalian Genome," Cell, vol. 44, pp. 419-428, Feb. 1986.
Thomas et al., "Introduction of Homologous DNA Sequences Into Mammalian Cells Induces Mutations in the Cognate Gene" Nature, vol. 324, Nov. 1986.
Thomas et al., "Site-Directed Mutagenesis by Gene Targeting in Mouse Embryo-derived stem cells," Cell, vol. 51, pp. 503-512, Nov. 1987.
Tomizuka, et al., "Double Trans-Chromosomic Mice: Maintenance of Two Individual Human Chromosome Fragments Containing Ig Heavy and K Loci and Expression of Fully Human Antibodies," Proceedings of the National Academy of Sciences (USA), vol. 97, No. 2, pp. 722-727, Jan. 2000.
Torres et al., "Laboratory Protocols for Conditional Gene Targeting," Institute for Genetics, University of Cologne, pp. 37-40, 1997.
Ungrin et al., "Strict Control of Telomerase Activation Using Cre-Mediated Inversion", BMC Biotechnology, vol. 6, pp. 1-9, 2006.
Valenzuela, et al., "High-Throughput Engineering of the Mouse Genome Coupled with High-Resolution Expression Analysis," Nature Biotechnology vol. 21, No. 6, p. 652-659 and vol. 21, No. 7, p. 822, Jun. 2003.
Van Spriel, et al., "Immunotherapeutic Perspective for Bispecific Antibodies," Immunology Today, vol. 21, No. 8, pp. 391-397, Aug. 2000.

(56) References Cited

OTHER PUBLICATIONS

Vassilieva et al., "Establishment of SSEA-1 and Oct. 4 Expressing Rat Embryonic Stem-Like Cell Lines and Effects of Cytokines of the IL-6 Family on Clonal Growth," Experimental Cell Research, vol. 258, pp. 361-373, 2000.

Vasicek, et al., "Structure and Expression of the Human Immunoglobulin λ Genes," Journal of Experimental Medicine, vol. 172, pp. 609-620, Aug. 1990.

Venken et al., "P[acman]: A BAC Transgenic Platform for Targeted Insertion of Large DNA Fragments in *D. melanogaster*," Science, vol. 314, pp. 1747-1751, Dec. 2006.

Vora et al., "Altering the Antibody Repertoire via Transgene Homologous Recombination: Evidence for Global and Clone-autonomous Regulation of Antigen-driven B Cell Differentiation," Journal of Experimental Medicine, vol. 181, pp. 271-281, Jan. 1995.

Wallace et al., "Manipulating the Mouse Genome to Engineer Precise Functional Syntenic Replacements with Human Sequence," Cell, vol. 128, No. 1, pp. 197-209, Jan. 2007.

Wang et al., "AID Upmutants Isolated Using a High-Throughput Screen Highlight the Immunity/Cancer Balance Limiting DNA Deaminase Activity," Nature Structural & Molecular Biology, vol. 16, No. 7, Jul. 2009.

Wang et al., "Altering the Spectrum of Immunoglobulin V Gene Somatic Hypermutation by Modifying the Active Site of AID," Journal of Experimtal Medicine, vol. 207, No. 1, pp. 141-153, Jan. 2010.

Wang et al., "Catching a Moving Target," Science, Biochemistry, vol. 333, pp. 834-835, Aug. 2011.

Wang, et al., "Chromosomal Transposition of PiggyBac in Mouse Embryonic Stem Cells," Proceedings of the National Academy of Sciences (USA), vol. 105, No. 27, pp. 9290-9295, Jul. 2008.

Wang, et al., "Many Human Immunoglobulin Heavy-Chain IGHV Gene Polymorphisms Have Been Reported in Error," Immunology and Cell Biology, vol. 86, No. 2, pp. 111-115, Feb. 2008.

Waterson, et al., "Initial Sequencing and Comparative Analysis of the Mouse Genome," Nature, vol. 420, No. 6915, pp. 520-562, Dec. 2002.

White, et al, "Genome-Wide Generation and Systematic Phenotyping of Knockout Mice Reveals New Roles for Many Genes," Cell, vol. 154, No. 2: pp. 452-464, Jul. 2013.

Wilkie et al., "Analysis of the Integrant in MyK-103 Transgenic Mice in Which Males Fail to Transmit the Integrant," Molecular and Cellular Biology, pp. 1646-1655, May 1987.

Williams et al., "Unequal VH Gene Rearrangement Frequency Within the Large Vh7183 Gene Family is not Due to Recombination Signal Sequence Variation, and Mapping of the Genes Shows a Bias of Rearrangement Base on Chromosomal Location," The Journal of Immunology, vol. 167, No. 1, pp. 257-263, Jul. 2001.

Xu, et al., "Combinatorial Surrobody Libraries," Proceedings of the National Academy of Sciences (USA), vol. 105, No. 31, pp. 10756-10761, Aug. 2008.

Yancopoulous et al., "Preferential Utilization of the Most JH-Proximal VH Gene Segments in Pre-B-Cell Lines," Nature, vol. 311, pp. 727-733, 1984.

Zhao, Shaving, "A Comprehensive BAC Resource," Nucleic Acids Research, vol. 29, No, 1, Jan. 2001.

Zheng et al., Engineering Mouse Chromosomes with Cre-loxP: Range, Efficiency, and Somatic Applications, Molecular and Cellular Biology, vol. 20, No. 2, pp. 648-655, Jan. 2000.

Zou et al., "Cre-loxP-Mediated Gene Replacement: A Mouse Strain Producing Humanized Antibodies," Current Biology, vol. 4, No. 12, pp. 1099-1104, Dec. 1994.

GenBank Accession No. X97051 S64822, accessed Aug. 6, 2014, 29 pages.

Nucleotide Sequence RID Y55HBK1W114, accessed Aug. 6, 2014, 2 pages.

Arnaout et al, "High-resolution description of antibody heavy-chain repertoires in human," PloS ONE,. vol. 6, Issue 8, pp. 1-8.

Bhattacharya, et al., "Switch Region Identity Plays an Important Role in Ig Class Switch Recombination," Journal of Immunology, vol. 184, pp. 6242-6248, Apr. 28, 2010.

Blankenstein, et al., "Immunoglobulin $V_H$ Region Genes of the Mouse are Organized in Overlapping Clusters," European Journal of Immunology, vol. 17, No. 9, pp. 1351-1357, Jul. 13, 1987.

Bogen, et al., "A Rearranged λ2 Light Gene Chain Retards But Does Not Exclude χ and λ1 Expression," vol. 21, No. 10, pp. 2391-2395, Oct. 1991.

Brezinchek, et al., "Analysis of the Human $V_H$ Gene Repertoire," The American Society for Clinical Investigations, Inc., vol. 99, No. 10, pp. 2488-2501, May 1997.

Brüggemann, et al., "Strategies for Expressing Human Antibody Repertories in Transgenic Mice," Immunology Today, vol. 17, No. 8, pp. 391-397, Aug. 1996.

Corbett, et al., "Sequence of the Human Immunoglobulin Diversity (D) Segment Locus: A Systematic Analysis Provides No Evidence for the Use of DIR Segments, Inverted D Segments, "Minor" D Segments or D-D Recombination," Journal of Molecular Biology, vol. 270, No. 4, pp. 587-597, Jul. 25, 1997.

Deng, et al., "Reexamination of Gene Targeting Frequency as a Function of the Extent of Homology between the Targeting Vector and the Target Locus," Molecular and Cellular Biology, vol. 12, No. 8, pp. 3365-3371, Aug. 1992.

Fujieda, et al., "Multiple Types of Chimeric Germ-Line Ig Heavy Chain Transcripts in Human B Cells: Evidence for Trans-Splicing of Human Ig RNA," The Journal of Immunology, vol. 157, No. 8, pp. 3450-3459, Oct. 15, 1996.

Gallo, et al., "The Human Immunoglobulin Loci Introduced Into Mice: V (D) and J Gene Segment Usage Similar to That of Adult Humans," European Journal of Immunology, vol. 30, pp. 534-540, Aug. 28, 2000.

Gavilondo, et al, "Antibody Engineering at the Millennium," BioTechniques, vol. 29, No. 1, pp. 128-145, Jul. 2000.

Giusti, et al., "Hypermutation is Observed Only in Antibody H Chain V Region Transgenes That Have Recombined with Endogenous Immunoglobulin H DNA: Implications for the Location of *cis*-acting Elements Required for Somatic Mutation," The Journal of Experimental Medicine, vol. 177, pp. 797-809, Mar. 1, 1993.

Glanville, et al., "Naïve Antibody Gene-Segment Frequencies Are Heritable and Unaltered by Chronic Lymphocyte Ablation," Proceedings of the National Academy of Sciences, USA, vol. 108, No. 50, pp. 20066-20071, Dec. 13, 2011.

Green, et al, Antigen-Specific Human Monoclonal Antibodies From Mice Engineered With Human *lg* Heavy and Light Chain YACs, Nature Genetics, vol. 7, No. 1, pp. 13-21, May 1994.

Green, et al, Regulation of B Cell Development by Variable Gene Complexity in Mice Reconstituted with Human Immunoglobulin Yeast Artificial Chromosomes, The Journal of Experimental Medicine, vol. 188, No. 3, pp. 483-495, Aug. 3, 1998.

Harding, et al, "Class Switching in Human Immunoglobulin Transgenic Mice," Annals of New York Academy of Science, vol. 764, pp. 536-546, Sep. 29, 1995.

Houldsworth, et al, "Comparative Genomic Hybridization: an Overview," American Journal of Pathology, vol. 145, No. 6, pp. 1253-1260, Dec. 1994.

Huang, et al., "Structural Basis of Tyrosine Sulfation and VH-Gene Usage in Antibodies that Recognize the HIV Type 1 Coreceptor-Binding Site on gp120," PSNA, vol. 101, No. 9, pp. 2706-2711, Mar. 2, 2004.

Jakobovits, et al, "Production of Fully Human Antibodies by Transgenic Mice," Biotechnology, vol. 6, No. 5, pp. 561-566, Oct. 1995.

Jakobovits, "The Long-Awaited Magic Bullets: Therapeutic Human Monoclonal Antibodies from Transgenic Mice," Expert Opinion on Investigational Drugs, vol. 7, No. 4, pp. 607-614, Apr. 1998.

Jessen, et al., "Molecular Analysis of Metastasis in a Polyomavirus Middle T Mouse Model: The Role of Osteopontin," Breast Cancer Research, vol. 6, No. 3, pp. R157-R169, Feb. 25, 2004.

Johnston, et al., "Complete Sequence Assembly and Characterization of the C57BL/6 Mouse Ig Heavy Chain V Region," The Journal of Immunology, vol. 176, No. 7, pp. 4221-4234, Apr. 1, 2006.

(56) References Cited

OTHER PUBLICATIONS

Jung, et al., "Mechanism and Control of V(D)J Recombination at the Immunoglobulin Heavy Chain Locus," Annual Review of Immunology, vol. 24, pp. 541-570, Apr. 2006.
Karu, et al, "Recombinant Antibody Technology," Institute for Laboratory Animal Research, vol. 37, No. 3, pp. 132-141, 1995.
Kenter, et al., "Three Dimensional Architecture of the IgH Locus Facilitates Class Switch Recombination," Annals of the New York Academy of Sciences, vol. 1267, No. 1, pp. 86-94, Sep. 1, 2012.
Kouskoff, et al, "Cassette Vectors Directing Expression of T Cell Receptor Genes in Transgenic Mice," Journal of Immunology Methods, vol. 180, pp. 273-280, Mar. 27, 1995.
Lee, et al., "Complete Humanization of the Mouse Immunoglobulin Loci Enables Efficient Therapeutic Antibody Discovery," Nature Biotechnology, vol. 32, No. 4, pp. 356-363, Mar. 16, 2014.
Lefranc, Marie-Paule, "Nomenclature of the Human Immunoglobulin Heavy (IGH) Genes," Experimental and Clinical Immunogenetics, vol. 18, pp. 100-1116, Aug. 31, 2000.
Lefranc, Marie-Paule, "Nomenclature of the Human Immunoglobulin lambda (IGL) Genes," Experimental and Clinical Immunogenetics, Mar. 17, 2001.
Lefranc et al, "The Immunoglobulin Facts Book," Academic Press, May 2001, ISBN:978-0-08-057447-9 (Abstract).
Ma, et al, "Human Antibody Expression in Transgenic Rats: Comparison of Chimeric IgH Loci With Human VH, D and JH but Bearing Different Rat C-Gene Regions," Journal of Immunological Methods, vol. 400-401, pp. 78-86, Dec. 31, 2013.
McMurry, et al, "Enhancer Control of Local Accessibility of V(D)J Recombinase," Molecular and Cellular Biology, vol. 17, No. 8, pp. 4553-4561, Aug. 1997.
Monaco, et al., "YACs, BACs, PACs and MACs: Artificial Chromosomes as Research Tools," Tends in Biotechnology, vol. 12, No. 7, pp. 280-286, Jul. 1994.
Mortuza et al., "Immunoglobulin Heavy-Chain Gene Rearrangement in Adult Acute Lymphoblastic Leukemia Reveals Preferential Usage of JH-Proximal Variable Gene Segments," Blood, vol. 97, No. 9, pp. 2716-2726, May 2001.
Müller, Ulrike, "Ten Years of Gene Targeting: Targeted Mouse Mutants, From Vector Design to Phenotype Analysis," Mechanisms of Development, vol. 82, Issues 1-2, pp. 3-21, Apr. 1999.
Muyrers, et al, "Rapid Modification of Bacterial Artificial Chromosomes by ET-Recombination," Nucleic Acids Research, vol. 27, No. 6, pp. 1555-1557, Feb. 2, 1999.
Narayanan, et al., "Efficient and Precise Engineering of a 200 Kb β-Globin Human/Bacterial Artificial Chromosome in *E. Coli* Dh10b Using an Inducible Homologous Recombination System," Gene Therapy, vol. 6, No. 3, pp. 442-447, Mar. 1999.
Rosner, et al., "Third Complementarity-Determining Region of Mutated VH Immunoglobulin Genes Contains Shorter V, D, J, P, and N Components Than Non-Mutated Genes," Immunology, vol. 103, No. 2, pp. 179-187, Jun. 2001.
Seidl, et al, "An Expressed Neo® Cassette Provides Required Functions of the 1gamma2b Exon for Class Switching," International Immunology, vol. 10, No. 11, pp. 1683-1692, Nov. 1998.
Seidl, et al., "Position-Dependent Inhibition of Class-Switch Recombination by PGK-neo$^r$ Cassettes Inserted Into the Immunoglobulin Heavy Chain Constant Region Locus," Proceedings of the National Academy of Sciences,USA, vol. 96, No. 6, pp. 3000-3005, Mar. 16, 1999.
Shih, Heather H., "Discovery Process for Antibody-Based Therapeutics," Development of Antibody-Based Therapeutics, Chapter 2, pp. 9-32, Apr. 24, 2012.
Schultz, et al, Humanized Mice in Translational Biomedical Research,"Nature Reviews Immunology," vol. 7, No. 2, pp. 118-130, Feb. 2007.
Soukharev, et al., "Segmental Genomic Replacement in Embryonic Stem Cells by Double *lox* Targeting," Nucleic Acids Research, vol. 27, No. 18, pp. e21-i to e21-viii, Jun. 1, 1999.
Spanopoulou, et al., "Functional Immunoglobulin Transgenes Guide Ordered B-Cell Differentiation in Rag-1-Deficient Mice," Genes & Development, vol. 8, No. 9, pp. 1030-1042, May 1, 1994.
Stavnezer, et al., "Mechanism and Regulation of Class Switch Recombination," Annual Review of Immunology, vol. 26, pp. 261-292, Apr. 2008.
Stevens, Sean, Regeneron Pharmaceuticals, "Human Antibody Discovery," VelocImmune—A novel Platform, Pharma Focus Asia, Issue 8, p. 72-74, 2008.
Tan, et al., "A Human-Mouse Chimeric Immunoglobulin Gene With a Human Variable Region Is Expressed in Mouse Myeloma Cells," The Journal of Immunology vol. 135, No. 5, pp. 3564-3567, Nov. 1, 1985.
Taylor, et al., "Human Immunoglobulin Transgenes Undergo Rearrangement, Somatic Mutation and Class Switching in Mice That Lack Endogenous IgM," International Immunology, vol. 6, No. 4, pp. 579-591, Apr. 1994.
Thykhaer, et al., "Gene Targeting Approaches Using Positive-Negative Selection and Large Flanking Regions," Plant molecular Biology, vol. 35, No. 4, pp. 523-530, Nov. 1997.
Tucker, et al., "Mouse IgA Heavy Chain Gene Sequence: Implications for Evolution of Immunoglobulin Hinge Axons," Proceedings of the National Academy of Sciences, USA, vol. 78, No. 12, pp. 7684-7688, Dec. 2008.
Waterhouse, et al., "Combinatorial Infection and In Vivo Recombination: A Strategy for Making Large Phage Antibody Repertories," Nucleic Acids Research, vol. 21, No. 9, pp. 2265-2266. May 11, 1993.
Waterson, et al, "Initial sequencing and comparative analysis of the mouse genome," Nature, vol. 420, pp. 520-562, Dec. 5, 2002.
Wuerffel, et al., "S-S Synapsis during Class Switch Recombination is Promoted by Distantly Located Transcriptional Elements and Activation-Induced Deaminase," Immunity, vol. 27, Issue 5, pp. 711-722, Nov. 26, 2007.
Xu, et al., "Deletion of the Igκ Light Chain Intronic Enhancer/Matrix Attachment Region Impairs but Does Not Abolish VκJκ Rearrangement," Immunity, vol. 4, pp. 377-385, Apr. 1, 1996.
Yang, et al., "Homologous Recombination Based Modification in *Esherichia Coli* and Germline Transmission in Transgenic Mice of a Bacterial Artificial Chromosome," Nature Biotechnology, vol. 15, No. 9, pp. 859-865, Sep. 1997.
Yu, et al., Differential Usage of VH Gene Segments is Mediated by cis Elements, The Journal of Immunology, vol. 161, No. 7, pp. 3444-3454, Oct. 1, 1998.
Yu, et al., "Engineering Chromosomal Rearrangements in Mice," Nature Reviews Genetics, vol. 2, No. 10, pp. 780-790, Oct. 2001.
Zemlin et al,"Expressed Murine and Human CDR-H3 Intervals of Equal Length Exhibit Distinct Repertoires that Differ in their Amino Acid Composition and Predicted Range of Structures," Journal of Molecular Biology, vol. 334, No. 5 pp. 733-749, Dec. 2003.
Zhang, et al., "A New Logic for DNA Engineering Using Recombination in *Escherichia Coli*," Nature Genetics, vol. 20, No. 2, pp. 123-128, Oct. 1998.
Zou et al., "Cre-loxP-mediated Gene Replacement: A Mouse Strain Producing Humanized Antibodies," Current Biology, vol. 4, No. 12, pp. 1099-1104, 1994.
Opposition against EP2421357 Animal Models and Therapeutic Molecules in the name of Kymab Limited, 39 pages, dated Oct. 23, 2013.
Notice of Opposition to European Patent EP2421357, 41 pages, dated Oct. 22, 2013.
Opposition against EP2421357 B1 in the name of Kymab Limited Statement of Facts and Arguments pertaining to Application No. 10734546.4, dated Oct. 23, 2013, 29 pages.
GenBank Accession No. AC111740.4 GI:24818723, accessed Nov. 9, 2002, 42 pages.
Third Party Observation in PCT/GB2012/052960 dated Apr. 2, 2014, 3 pages.
Charles Lyon, Attorney for Applicant, Third Party Pre-Issuance Submission Under 37 C.F.R. §1.290 in U.S. Appl. No. 14/056,700, Nov. 28, 2014, 6 pages.

(56) References Cited

OTHER PUBLICATIONS

Charles Lyon, Attorney for Applicant, Third Party Pre-Issuance Submission Under 37 C.F.R. §1.290 in U.S. Appl. No. 14/056,434, Filed Dec. 15, 2014, 6 pages.
Charles Lyon, Attorney for Applicant, Third Party Pre-Issuance Submission Under 37 C.F.R. §1.290 in U.S. Appl. No. 14/040,405, Filed Jan. 16, 2015, 18 pages.
Charles Lyon, Attorney for Applicant, Third Party Pre-Issuance Submission Under 37 C.F.R. §1.290 in U.S. Appl. No. 14/056,707, Nov. 28, 2014, 13 pages.
Charles Lyon, Attorney for Applicant, Third Party Pre-Issuance Submission Under 37 C.F.R. §1.290 in U.S. Appl. No. 14/137,902, Nov. 13, 2014, 12 pages.
European Patent Office, Munich, Dr. Martin Grund, Third Party Observations according to Article 115 EPC regarding EP12171791. 2, dated Feb. 26, 2014, 9 pages.
European Patent Office, Munich, Dr. Martin Grund, Third Party Observations according to Article 115 EPC regarding EP 12194970. 5, dated Mar. 5, 2014, 9 pages.
European Patent Office, Munich, Dr. Martin Grund, Third Party Observations according to Article 115 EPC regarding EP 12194977.0 dated Mar. 26, 2014, 4 pages.
European Patent Office, Munich, Dr. Martin Grund, Third Party Observations according to Article 115 EPC regarding EP 121717923.8 dated Jun. 25, 2014, 7 pages.
European Patent Office, Munich, Dr. Martin Grund, Third Party Observations according to Article 114(2) EPC regarding EP12 195041.4 dated Jul. 30, 2014, 5 pages.
European Patent Office, Munich, Dr. Martin Grund, Third Party Observations according to Article 114(2) EPC regarding EP12171791.2 dated Aug. 4, 2014, 6 pages.
European Patent Office, Munich, Dr. Martin Grund, Third Party Observations according to Article 114(2) EPC regarding EP12194970.5 dated Aug. 12, 2014, 5 pages.
European Patent Office, Munich, Dr. Martin Grund, Third Party Observations according to Article 115 EPC regarding EP 11705964.2 dated Oct. 9, 2013, 8 pages.
European Patent Office, Munich, Dr. Martin Grund, Third Party Observations according to Article 115 EPC regarding EP 11705964.2 dated Apr. 30, 2014, 4 pages.
European Patent Office, Munich, Dr. Martin Grund, Third Party Observations according to Article 115 EPC regarding EP 11705964.2 dated Feb. 26, 2015, 5 pages.
European Patent Office, Munich, Dr. Martin Grund, Third Party Observations according to Article 115 EPC regarding EP12795606. 8, dated Feb. 26, 2014, 6 pages.
European Patent Office, Munich, Dr. Martin Grund, Third Party Observations according to Article 115 EPC regarding EP 12 795606.8 dated Mar. 26, 2015, 4 pages.
Baker et al., Adaptation of TCR Expression Vectors for the Construction of Mouse-Human Chimeric MBP-Specific TCR Transgenes, Journal of Neuroscience Research, vol. 45, No. 4, pp. 487-491, Aug. 15, 1996.
Butler, Immunoglobulin diversity, B-cell and antibody repertoire development in large farm animals, Rev. Sci. Tech. Office Int'l Epiz.17(1), 43-70, 1998.
Clark, IgG Effector Mechanisms, Chemical Immunology, vol. 65, pp. 88-110, 1997.
Davies et al., Creation of Mice Expressing Human Antibody Light Chains by Introduction of a Yeast Artificial Chromosome Containing the Core Region of the Human IgK Locus. Biotechnology (NY). Aug. 1993;11(8):911-4.
Fleischer et al., Reactivity of Mouse T-Cell Hybridomas Expressing Human Vbeta Gene Segments With Staphylococcal and Streptococcal Superantigens, Infection and Immunity, vol. 64, No. 3, pp. 987-994, Mar. 1996.
Gama Sosa et al., Animal transgenesis: an overview, Brain Struct Funct, 214:91-109, 2010.
Giraldo et al., Size Matters: Use of YACs, BACs and PACs in Transgenic Animals, Transgenic Research, 10(2): 83-103, 2001.
Jackson Laboratory, Breeding Strategies for Maintaining Colonies of Laboratory Mice, A Jackson Laboratory Recourse Manual, 1-29, 2007.
Janeway et al., Immunobiology: The Immune System in Health and Disease, 5th edition. New York: Garland Science; 1-5, 2001.
Kaushik et al., Novel insight into antibody diversification from cattle, Veterinary Immunology and Immunopathology 87, 347-350, 2002.
Neuberger et al., Isotype Exclusion and Transgene Down-Regulation in Immunoglobulin-Lambda Transgenic Mice, Nature, vol. 338, pp. 350-352, Mar. 23, 1989.
Parng et al., Gene Conversion Contributes to Ig Light Chain Diversity in Cattle, The Journal of Immunology, 157:5478-5486, 1996.
Qi et al, A New Transgenic Rat Model of Hepatic Steatosis and the Metabolic Syndrome, Hypertension, 45:1004-1011, 2005.
Ramirez-Solis et al, Chromosome engineering in mice, Nature, 378, 14: 720-724, 1995.
Ren et al., Targeted Insertion Results in a Rhombomere 2-Specific Hoxa2 Knockdown and Ectopic Activation of Hoxal Expression, Developmental Dynamics, 225: 305-315, 2002.
Ristevski, Making Better Transgenic Models, Conditional, Temporal, and Spatial Approaches, Molecular Biotechnology, 29, 153-163, 2005.
Scapini et al., Myeloid Cells, BAFF, and IFN-λ Establish an Inflammatory Loop That Exacerbates Autoimmunity in Lyn-Deficient Mice, The Journal of Experimental Medicine, vol. 207, No. 8, pp. 1757-1773, Jul. 12, 2010.
Shi et al., The mapping of transgenes by fluorescence in situ hybridization on G-banded mouse chromosomes. Mamm Genome. Jun. 1994;5(6):337-41.
Smith, Gene transfer in higher animals: theoretical considerations and key concepts, Journal of Biotechnology 99:1-22, 2002.
Takeda et al. Construction of chimaeric processed immunoglobulin genes containing mouse variable and human constant region sequences, Nature, 314:452-454, Apr. 4, 1985.
Vollmer et al., Antigen Contacts by Ni-Reactive TCR: Typical αβ Chain Cooperation Versus A Chain-Dominated Specificity, International Immunity, 12(12):1723-1731, May 31, 2000.
Wagner et al., Antibodies generated from human immunoglobulin miniloci in transgenic mice, Nucleic Acids Res., 22(8): 1389-1393, 1994.
Wilke et al., "Diagnosis of Haploidy and Triploidy Based on Measurement of Gene Copy Number By Real-Time PCR," Human Mutation vol. 16, Issue 5, pp. 431-436, Nov. 2000.
Intellectual Property Office, International Search Report, Application No. GB1116122.1, dated Feb. 2, 2012, 1 page.
Intellectual Property Office, Corrected International Search Report and Opinion, Application No. GB1122047.2, 5 pages, dated Apr. 20, 2012.
European Patent Office, Extended European Search Report, Application No. 12194977.0, 9 pages, dated Jul. 17, 2013.
European Patent Office, Extended European Search Report, Application No. 12195041.4 8 pages, dated Nov. 18, 2013.
Statement of Fact and Arguments in Support of Opposition pertaining to Application No. 10734546.4, 41 pages, dated Oct. 22, 2013.
GenBank, Accession No. X97051 S64822, accessed Nov. 14, 2006, 26 pages.
NCBI Accession No. NT_114985, 1 page, Dec. 27, 2013.
Combriato and Klobeck, 2002, Journal of Immunology 168: 1259-1266.†

* cited by examiner
† cited by third party

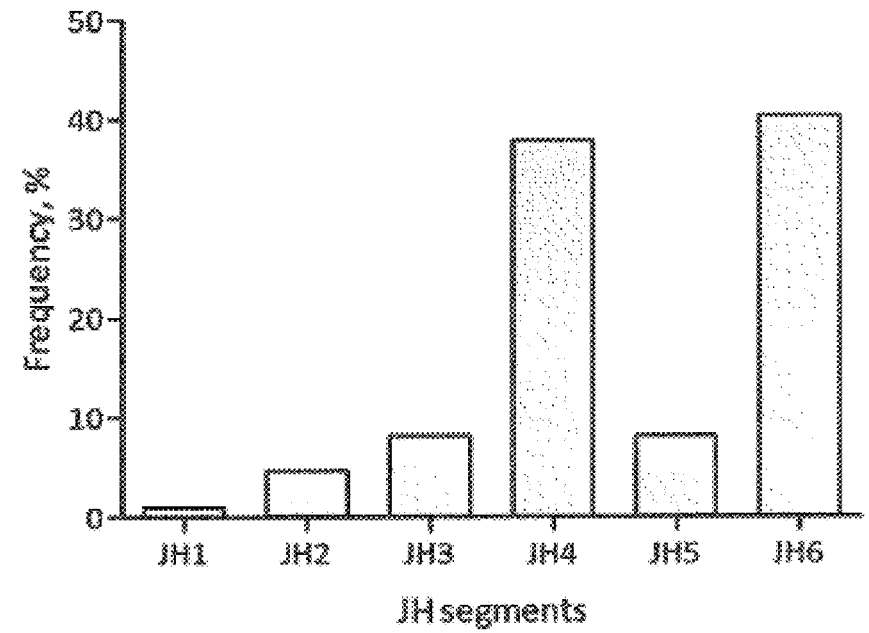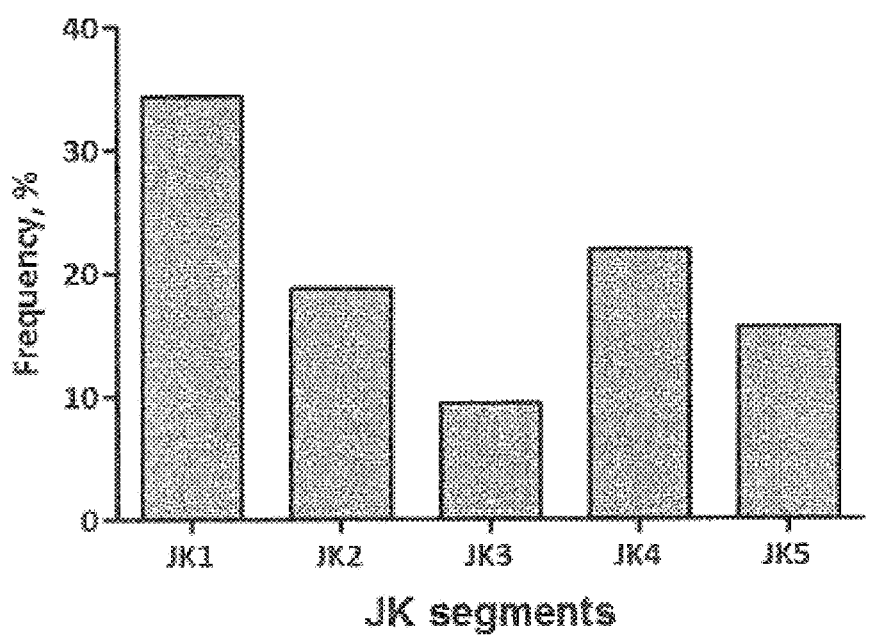
Fig. 35

Distribution of JH Usage Within Each VHs

| | JH1 | JH2 | JH3 | JH4 | JH5 | JH6 |
|---|---|---|---|---|---|---|
| V2-5 | | 1 | 5 | 5 | 2 | 1 |
| V4-4 | 1 | 1 | 1 | 1 | | 8 |
| V1-3 | 1 | 6 | 6 | 49 | 13 | 40 |
| V1-2 | | | | 1 | | 1 |
| V6-1 | | 1 | 4 | 18 | 1 | 29 |
| Total | 2 | 9 | 16 | 74 | 16 | 79 |

The data includes 196 independent sequences.

Fig. 39

Distribution of DH Usage Within Each VHs

| | V4-4 | V3-3 | V1-3 | V4-4 | V5-5 | V5-7 | V6-6 | V3-3 | V3-3 | V4-4 | V3-3 | V5-5 | V3-3 |
|---|---|---|---|---|---|---|---|---|---|---|---|---|---|
| V2-5 | 1 | 5 | | 1 | | | | | 1 | | | | |
| V4-4 | | | | | | | | | | | | | |
| V1-3 | 1 | 5 | 1 | 1 | 2 | | 1 | 1 | 13 | 25 | | 1 | 12 |
| V1-2 | | | | | | | | | | 1 | | | |
| V6-1 | 1 | 5 | 3 | 1 | 1 | | | | 3 | 10 | | 1 | 4 |
| T | 1 | 3 | 3 | 1 | 0 | 0 | 1 | 17 | 44 | 0 | 2 | 16 |

Fig. 40 (1)

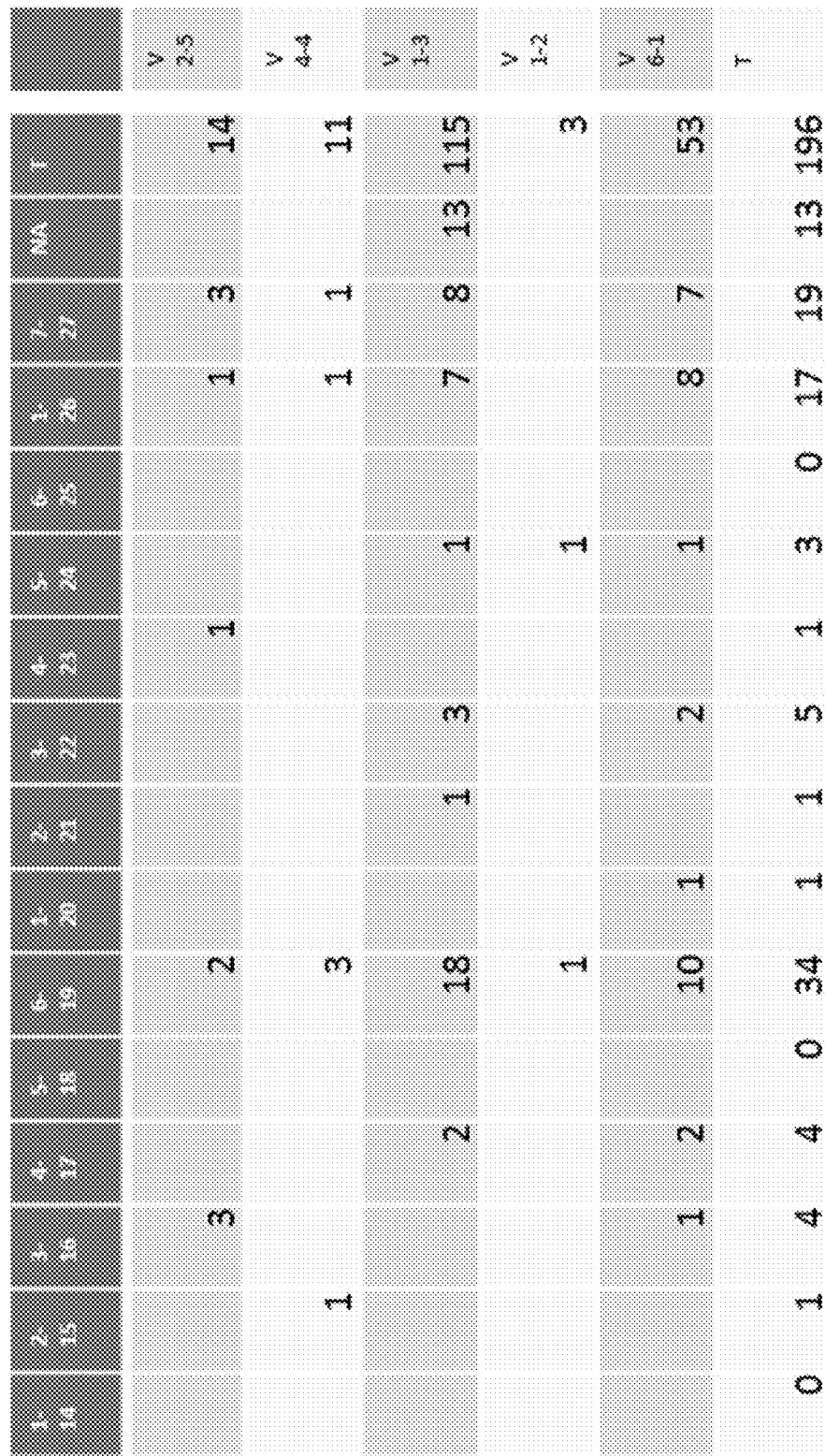
Fig. 40 (2)

Nucleotide Gain or Loss at VJ Joints Generates IGK Variants

| | $V_\kappa 1\text{-}8$ | $J_\kappa 1$ | $C_\kappa$ |
|---|---|---|---|
| $V\kappa1\text{-}8J\kappa1$ | ACCCT-  | GTGGACGTTCGGCCAAGGGACCAAGGTGGAAATC | AAACGGGCTGA |
| | ACCCACGT | GGACGTTCGGCCAAGGGACCAAGGTGGAAATC | AAACGGGCTGA |
| | ACCCACGT | GGACGTTCGGCCAAGGGACCAAGGTGGAAATC | AAACGGGCTGA |
| | ACCC-- | GTGGACGTTCGGCCAAGGGACCAAGGTGGAAATC | AAACGGGCTGA |
| | ACCC-- | GTGGACGTTCGGCCAAGGGACCAAGGTGGAAATC | AAACGGGCTGA |
| | ACCC--- | GTGGACGTTCGGCCAAGGGACCAAGGTGGAAATC | AAACGGGCTGA |
| | ACCC--- | GTGGACGTTCGGCCAAGGGACCAAGGTGGAAATC | AAACGGGCTGA |
| | ACC---- | GGACGTTCGGCCAAGGGACCAAGGTGGAAATC | AAACGGGCTGA |
| | ACC---- | GGACGTTCGGCCAAGGGACCAAGGTGGAAATC | AAACGGGCTGA |
| | ACC---- | GGACGTTCGGCCAAGGGACCAAGGTGGAAATC | AAACGGGCTGA |
| | ACC---- | GGACGTTCGGCCAAGGGACCAAGGTGGAAATC | AAACGGGCTGA |
| | ACCCTC-- | GGACGTTCGGCCAAGGGACCAAGGTGGAAATC | AAACGGGCTGA |
| | ACCCTC-- | GGACGTTCGGCCAAGGGACCAAGGTGGAAATC | AAACGGGCTGA |
| | ACCCTC-- | GGACGTTCGGCCAAGGGACCAAGGTGGAAATC | AAACGGGCTGA |
| | ACCCTC-- | GGACGTTCGGCCAAGGGACCAAGGTGGAAATC | AAACGGGCTGA |
| | ACCCTC-- | GGACGTTCGGCCAAGGGACCAAGGTGGAAATC | AAACGGGCTGA |
| | ACCCTC-- | GGACGTTCGGCCAAGGGACCAAGGTGGAAATC | AAACGGGCTGA |
| | ACCCCC-- | GGACGTTCGGCCAAGGGACCAAGGTGGAAATC | AAACGGGCTGA |
| | ACCCCC-- | GGACGTTCGGCCAAGGGACCAAGGTGGAAATC | AAACGGGCTGA |

Fig. 41 (1)

Nucleotide Gain or Loss at VJ Joints Generates IGK Variants

```
E6, F5, G6
SSFSASTLQRPRTFGQGTKVEIKRADAAPTVSIFPPSSEQLTASVVC
ASTLQRPRTFGQGTKVEIKRADAAPTVSIFPPSSEQLTSGGASVVC
SYPRTFGQGTKVEIKRADAAPTVSIFPPSSEQLTSGGASVVC
FLNNFYPKDINVKWKIDGSERQNGV

E2
HILQCIHYRRQSHHHLSGESGYStopQLFSLVSAKTRESPStopAP
DLCCIHEAKMGPIKVQRQWIMDREHSHHQLPAVStopRFCNLL
LSTVLStopLPTMTFGQGTKVEIKRADAAPTVSIFPPSSEQLT
SGGASVVCFLNNFYPKDINVKWKIDGSERQNGV E10, G8
SSFSASTLQRTFGQKVPSRFSGSGSGTDFTLTVSIFPPSEQ
ASTLQRTFGQKVPSRFSGSGSGTDFTLTVSIFPPSEQ
SYRTFGQKVEIKNADAAPTVSIFPPSSEQLTSGGASVVCF
LNNFYPKDINVKWKIDGERQNGV F3, F12
SSFSASTLQRTFGQGTKVEIKRADAAPTYYCQVVC
ASTLQRWTFGQKDIHSRFSGSGSGTDFTLTVSIFPPSSEQ
SYPWNFYPKDINVKWKIDGERQNGV H1
SSFSRSTLQRPRTFGQGTKVEIKRADAAPKYCQVVC
ASTLQRPRTFGQGTKVEIKRADAAPTYSGGASVVC
SYPRTFGQGTKVEIKRADAAPKEDFATYCQSAVVC
FLNNFYPKDINVKWKIDGSERQNGV
```

Fig. 41 (2)

Hypermutation in J Regions Generates IGK Variants

| | Vκ1-6 | Jκ1 | Cκ |
|---|---|---|---|
| Vκ1-6Jκ1 | tacccctgTGGACGTTCGGCCAAGGGACCAAGGTGGAAATCAAACggctg |
| A-01 | TACCC--GTGGACGTTCGGCCAAGGGACCAAGGTGGAAATCAAACGGGCTG |
| A-01 | TACCC--GTGGACGTTCGGCCAAGGGACCAAGGTGGAAATCAAACGGGCTG |
| A_02 | TACCC--GTGGACGTTCGGCCAAGGGACCAAGGTGGAAATCAAACGGGCTG |
| A_02 | TACCC--GTGGACGTTCGGCCAAGGGACCAAGGTGGAAATCAAACGGGCTG |
| A_08 | TACCC--GTGGACGTTCGGCCAAGGGACCAAGGTGGAAATCAAACGGGCTG |
| A_08 | TACCC--GTGGACGTTCGGCCAAGGGACCAAGGTGGAAATCAAACGGGCTG |
| A_10 | TACCC--GTGGACGTTCGGCCAAGGGACCAAGGTGGAAATCAAACGGGCTG |
| A_10 | TACCC--GTGGACGTTCGGCCAAGGGACCAAGGTGGAAATCAAACGGGCTG |
| A_11 | TACCC--GTGGACGTTCGGCCAAGGGACCAAGGTGGAAATCAAACGGGCTG |
| A_11 | TACCC--GTGGACGTTCGGCCAAGGGACCAAGGTGGAAATCAAACGGGCTG |
| A_04 | TACCCTC-GGACGTTCGGCCAAGGGACCAAGGTGGAAATCAAACGGGCTG |
| A_04 | TACCCTC-GGACGTTCGGCCAAGGGACCAAGGTGGAAATCAAACGGGCTG |
| A_07 | TACCCTC-GGACGTTCGGCCAAGGGACCAAGGTGGAAATCAAACGGGCTG |
| A_07 | TACCCTC-GGACGTTCGGCCAAGGGACCAAGGTGGAAATCAAACGGGCTG |
| B_12 | TACCCTC-GGACGTTCGGTGGAGGCACCAAGGTGGAAATCAAACGGGCTG |
| B_12 | TACCCTC-GGACGTTCGGTGGAGGCACCAAGCTGGAAATCAAACGGGCTG |
| C_06 | TACCCTC-GGACGTTCGGTGGAGGCACCAAGCTGGAAATCAAACGGGCTG |
| C_06 | TACCCTC-GGACGTTCGGTGGAGGCACCAAGCTGGAAATCAAACGGGCTG |

Fig. 42 (1)

Hypermutation in J Regions Generates IGK Variants

```
A1, A2, A8, A10, A11, A12, B3, B5, B7, C8, D5, D6
KLLIYAASSLQSGVPSRFSGSGSGTDFTLTISSLQPEDFATYYC
LQDYNYPWTFGQGTKVEIKRADAAPTVSIFPPSSEQLTSGGASV
VCFLNNFYPKDINVKWKIDGSERQNGV

A4, A5, A7, B4, B9, B11, C3, C4, C7, C12, D7
KLLIYAASSLQSGVPSRFSGSGSGTDFTLTISSLQPEDFATYYC
LQDYNYPRTFGQGTKVEIKRADAAPTVSIFPPSSEQLTSGGASV
VCFLNNFYPKDINVKWKIDGSERQNGV

B12, C6, D3
KLLIYAASSLQSGVPSRFSGSGSGTDFTLTISSLQPEDFATYYC
LQDYNYPRTFGGGTKLEIKRADAAPTVSIFPPSSEQLTSGGASV
VCFLNNFYPKDINVKWKIDGSERQNGV
```

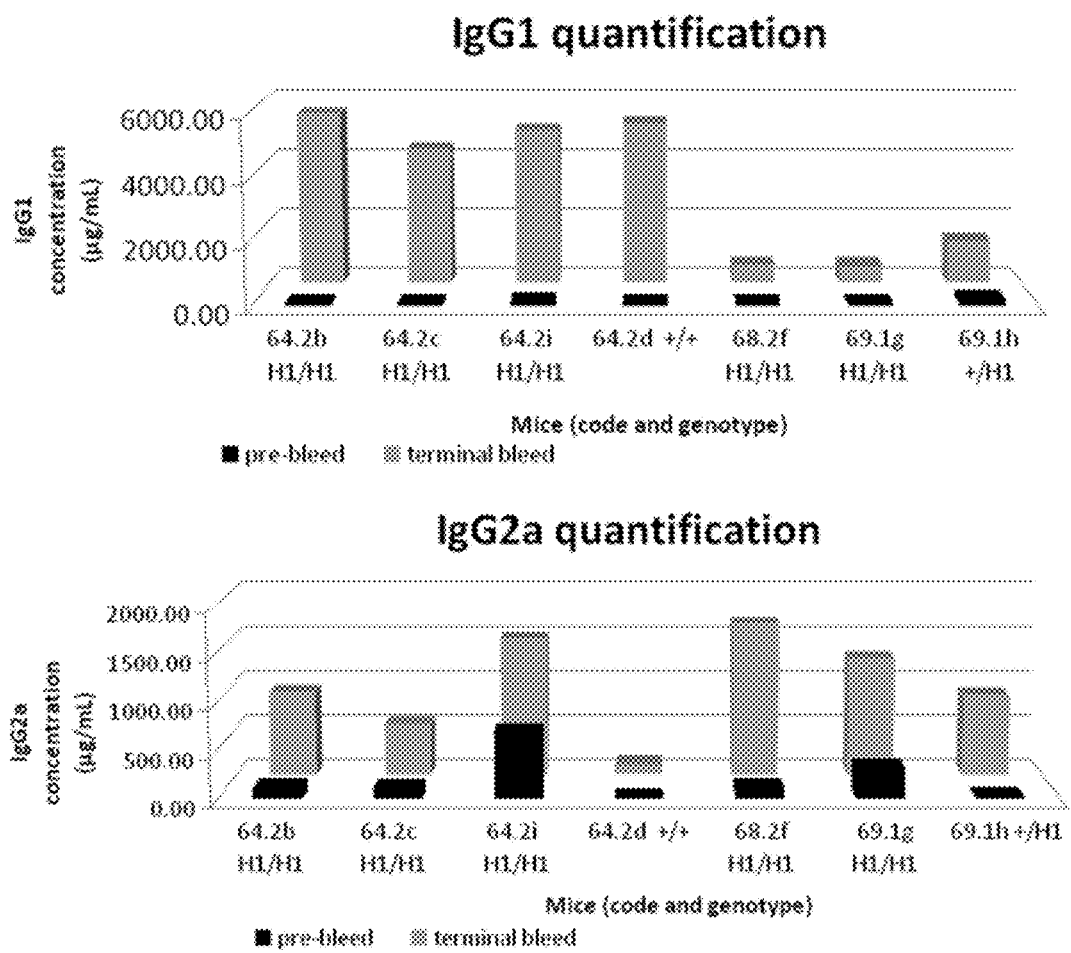
Fig. 54A(1)

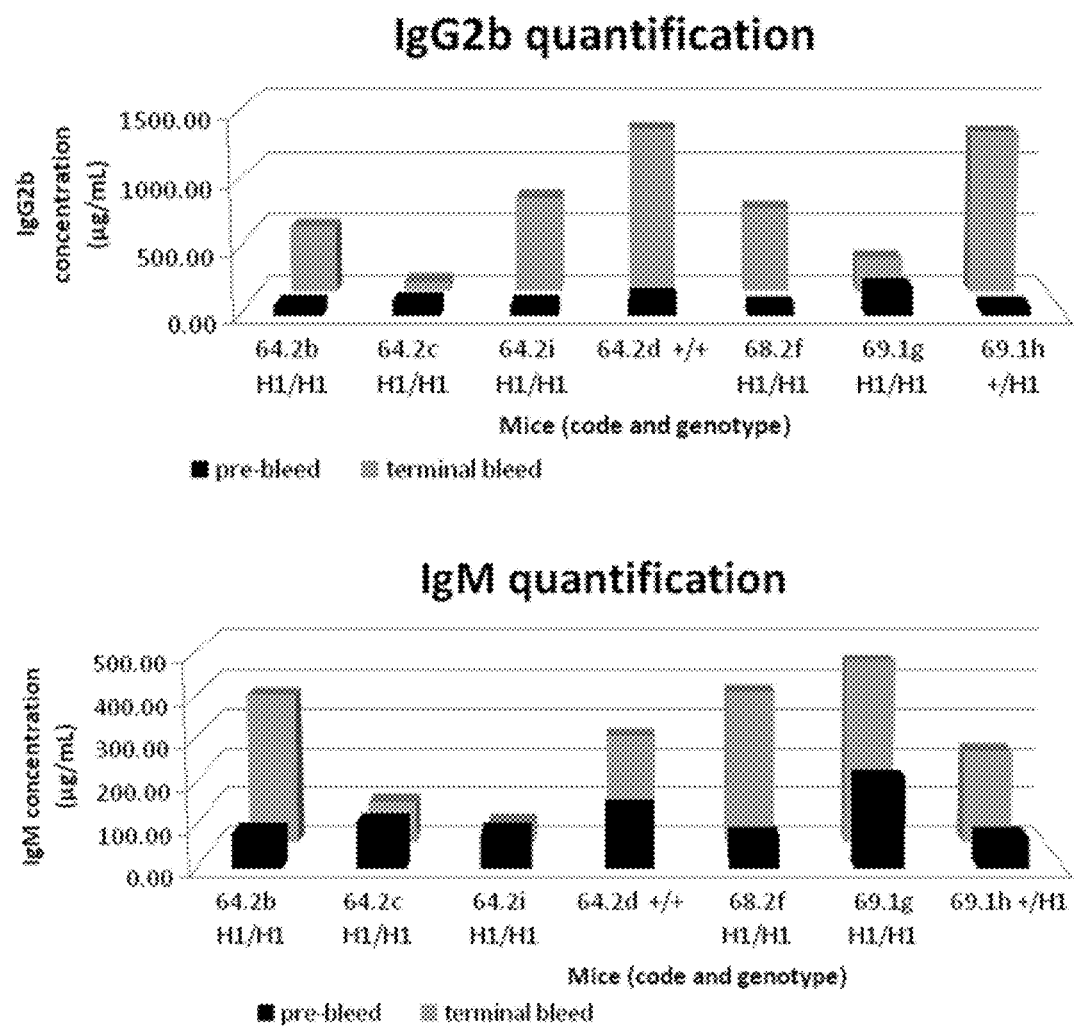
Fig. 54A(2)

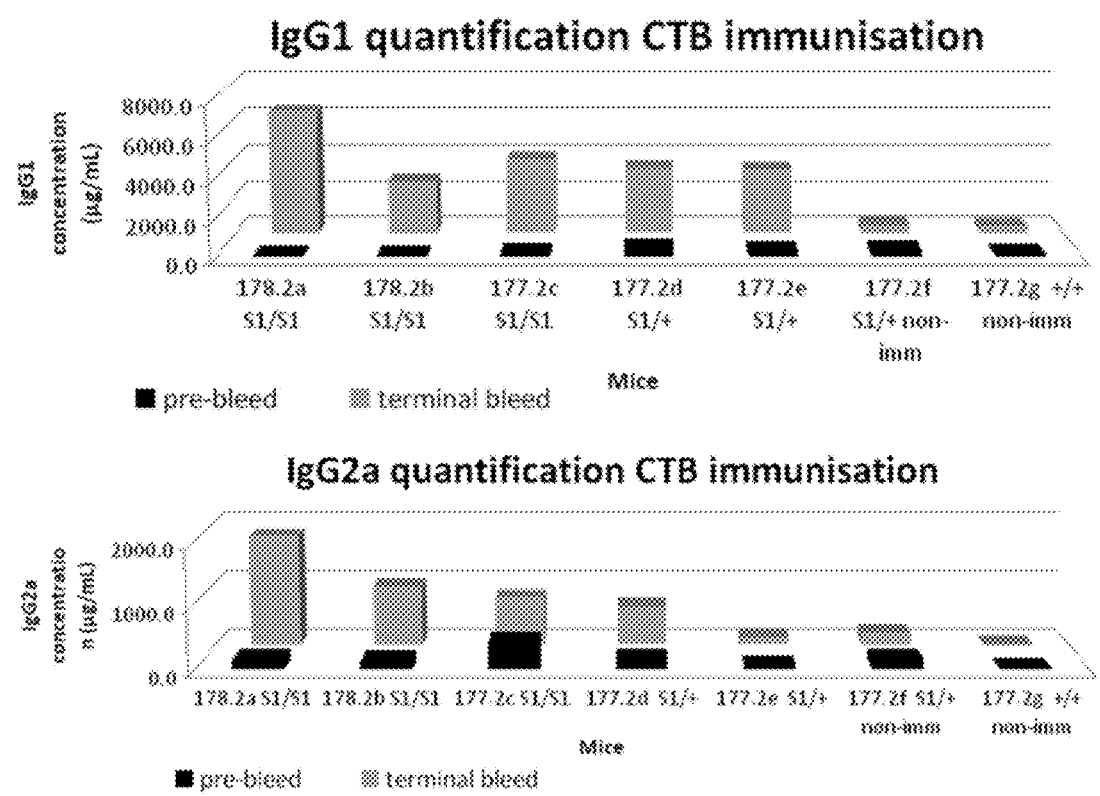
Fig. 54B(1)

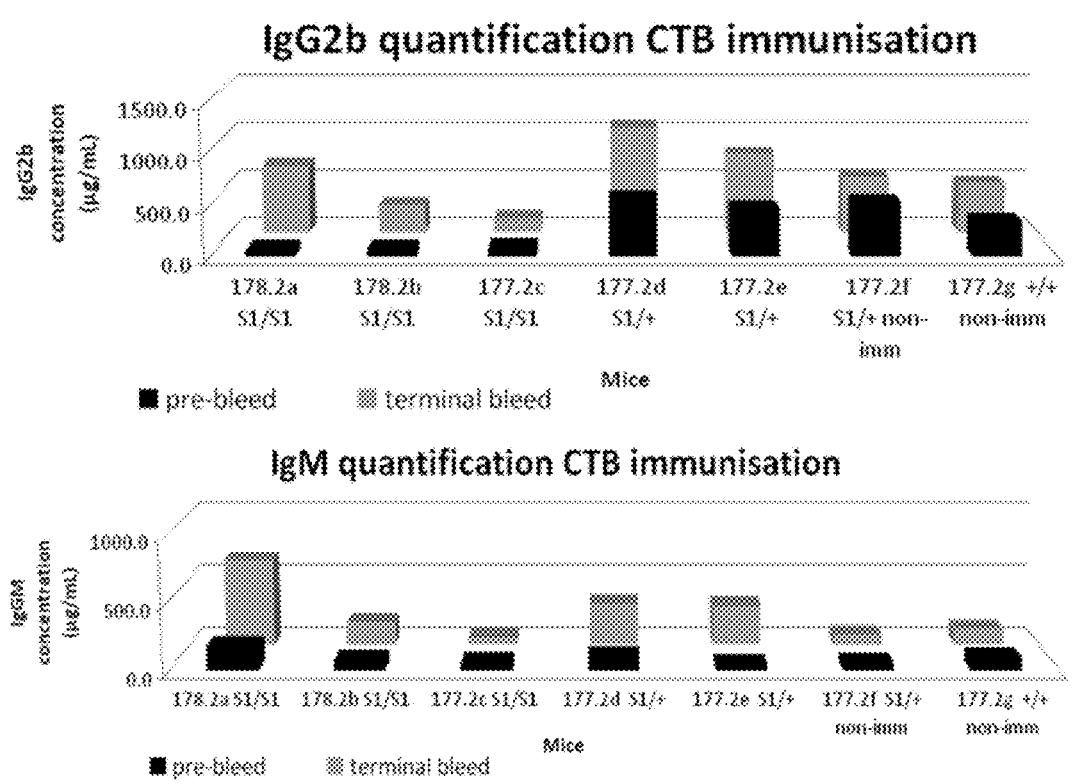
Fig. 54B(2)

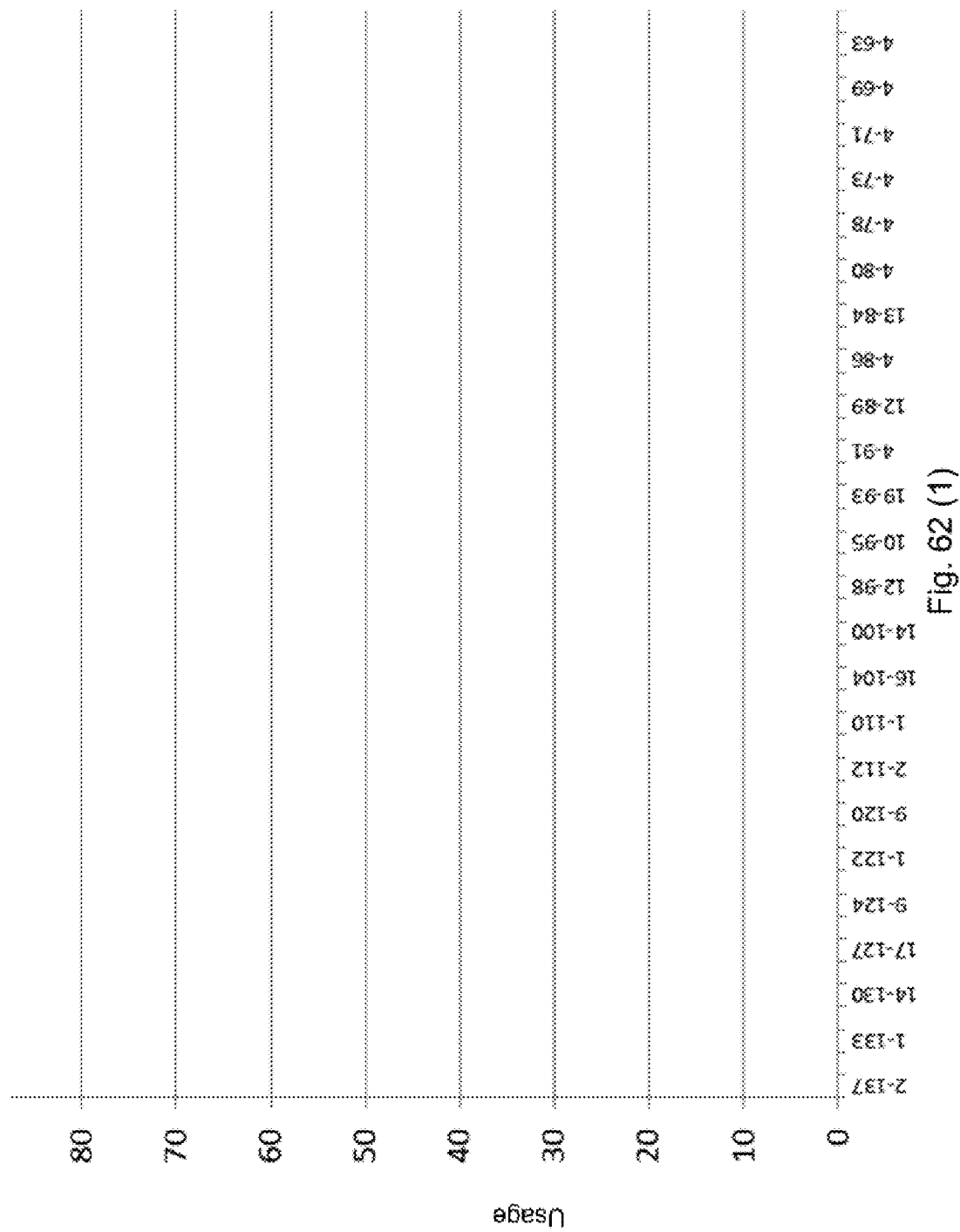

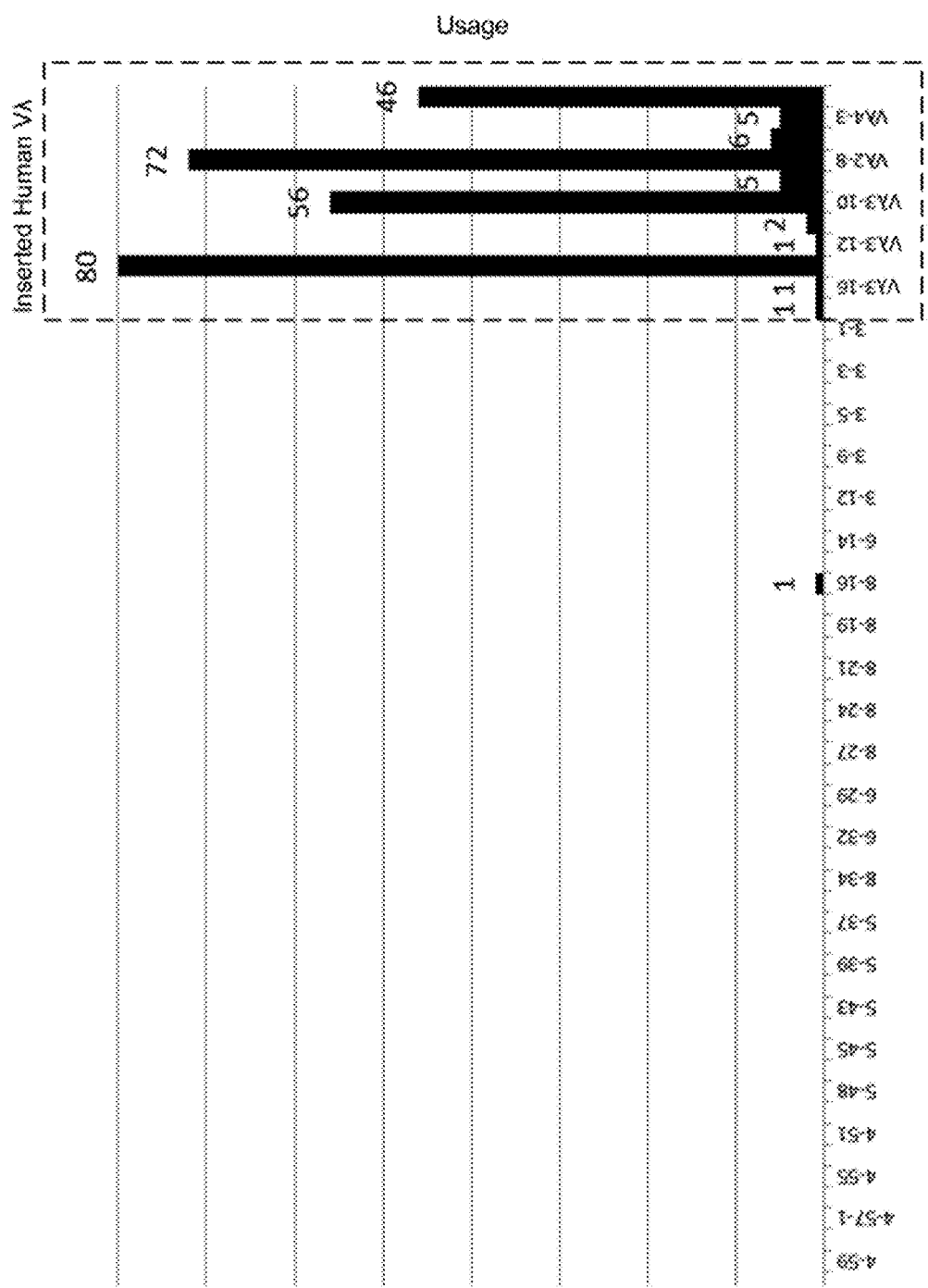
Fig. 62 (2)

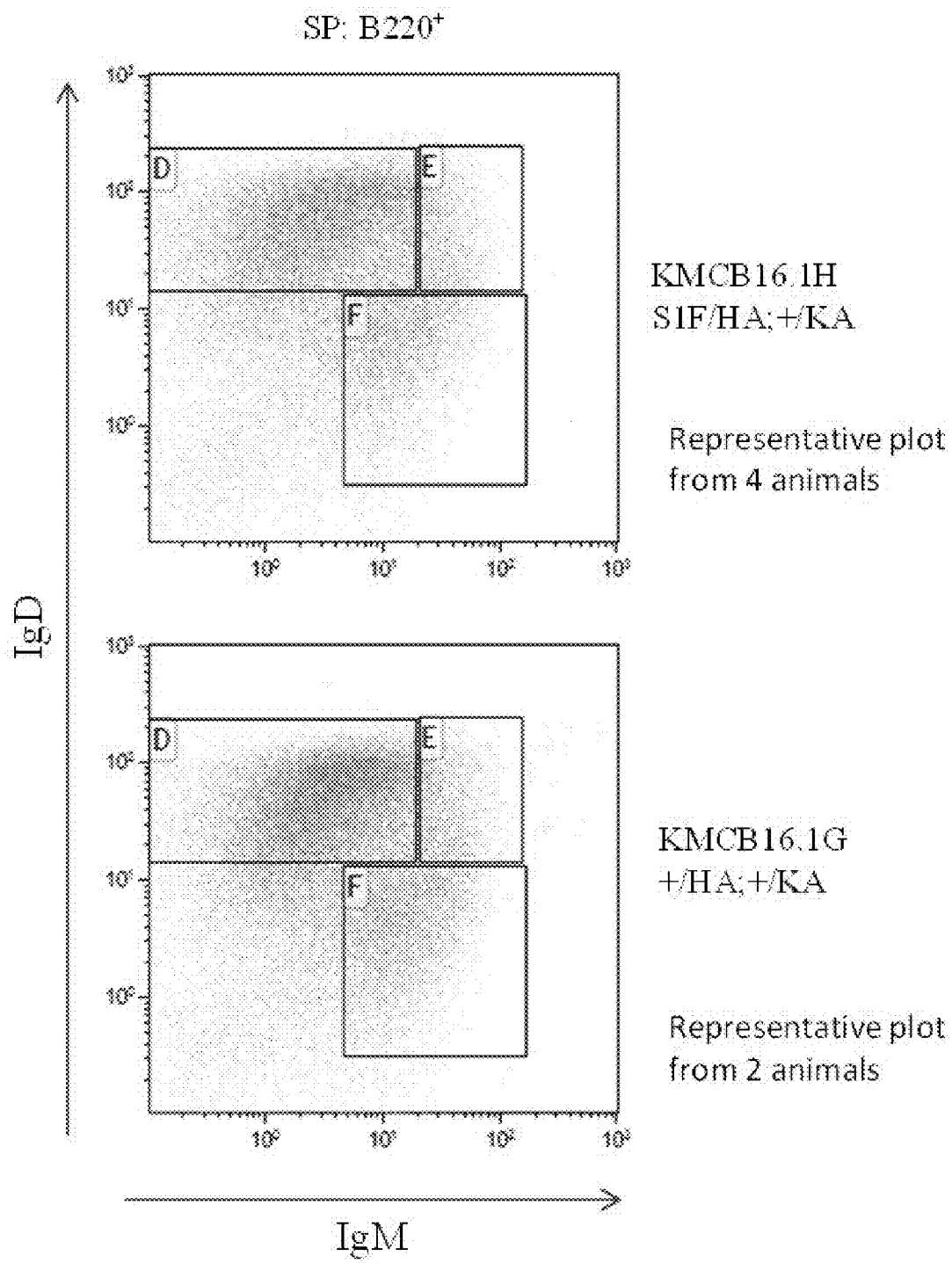
Fig. 66A (1)

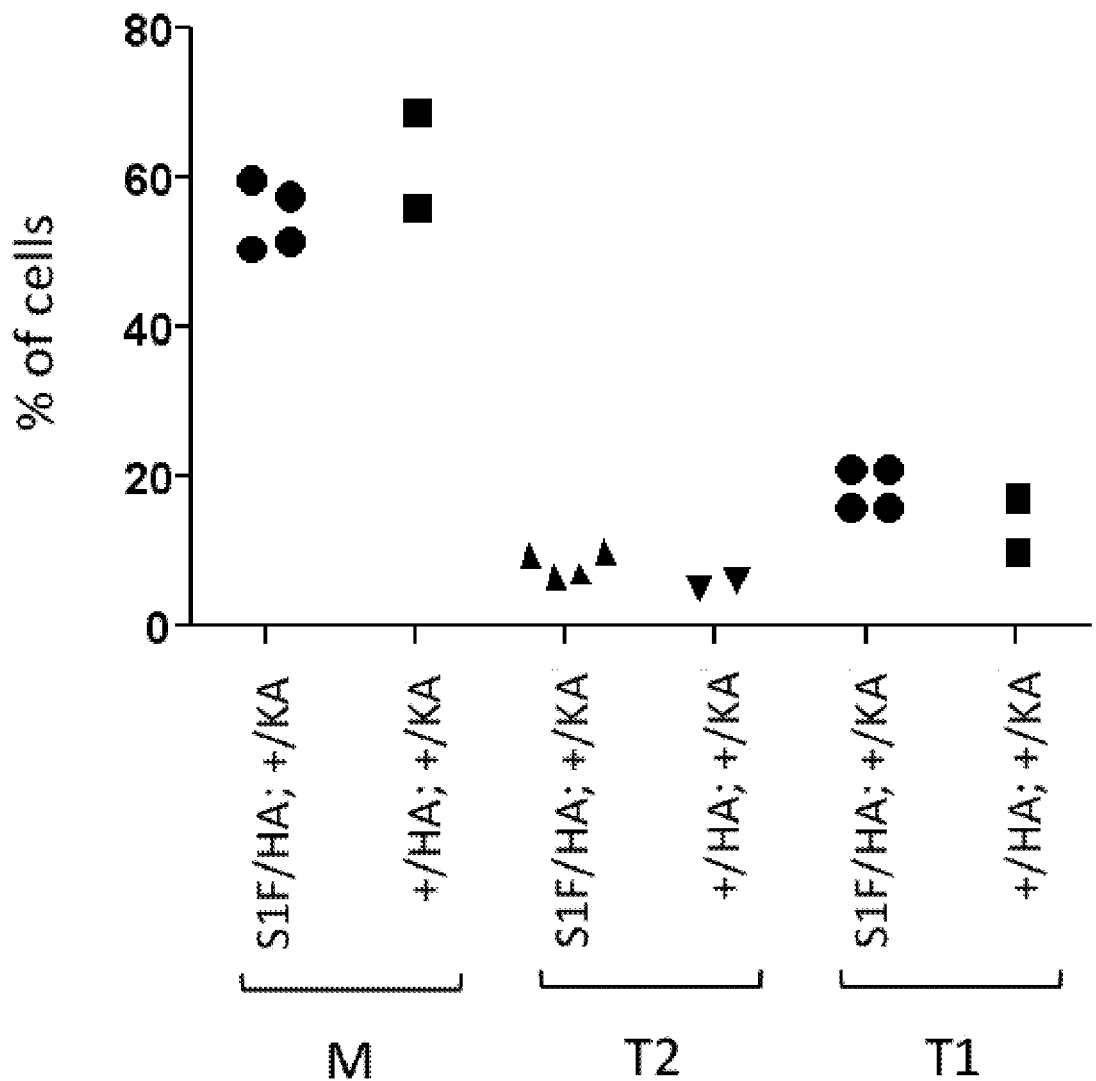
Fig. 66A (2)

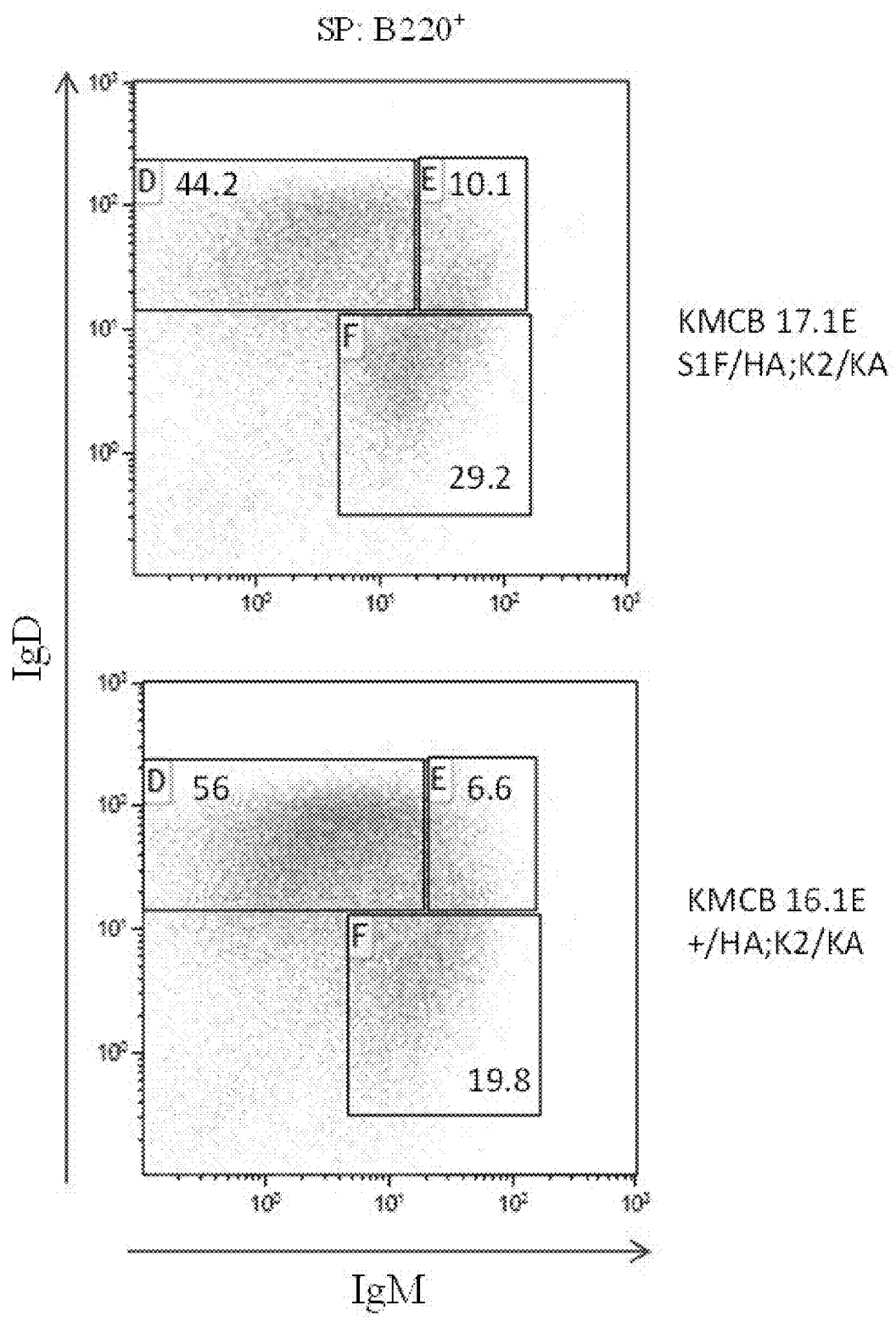
Fig. 66B (1)

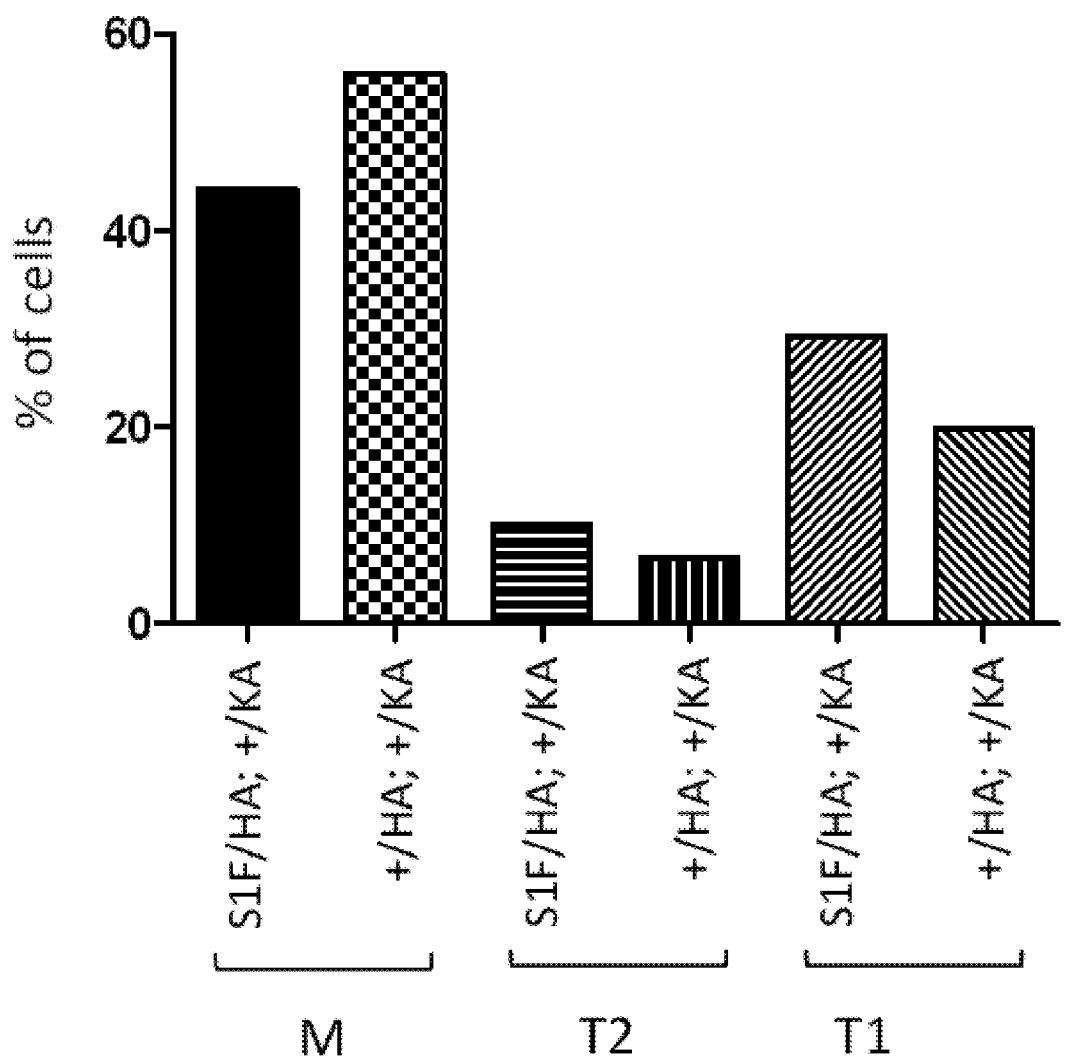
Fig. 66B (2)

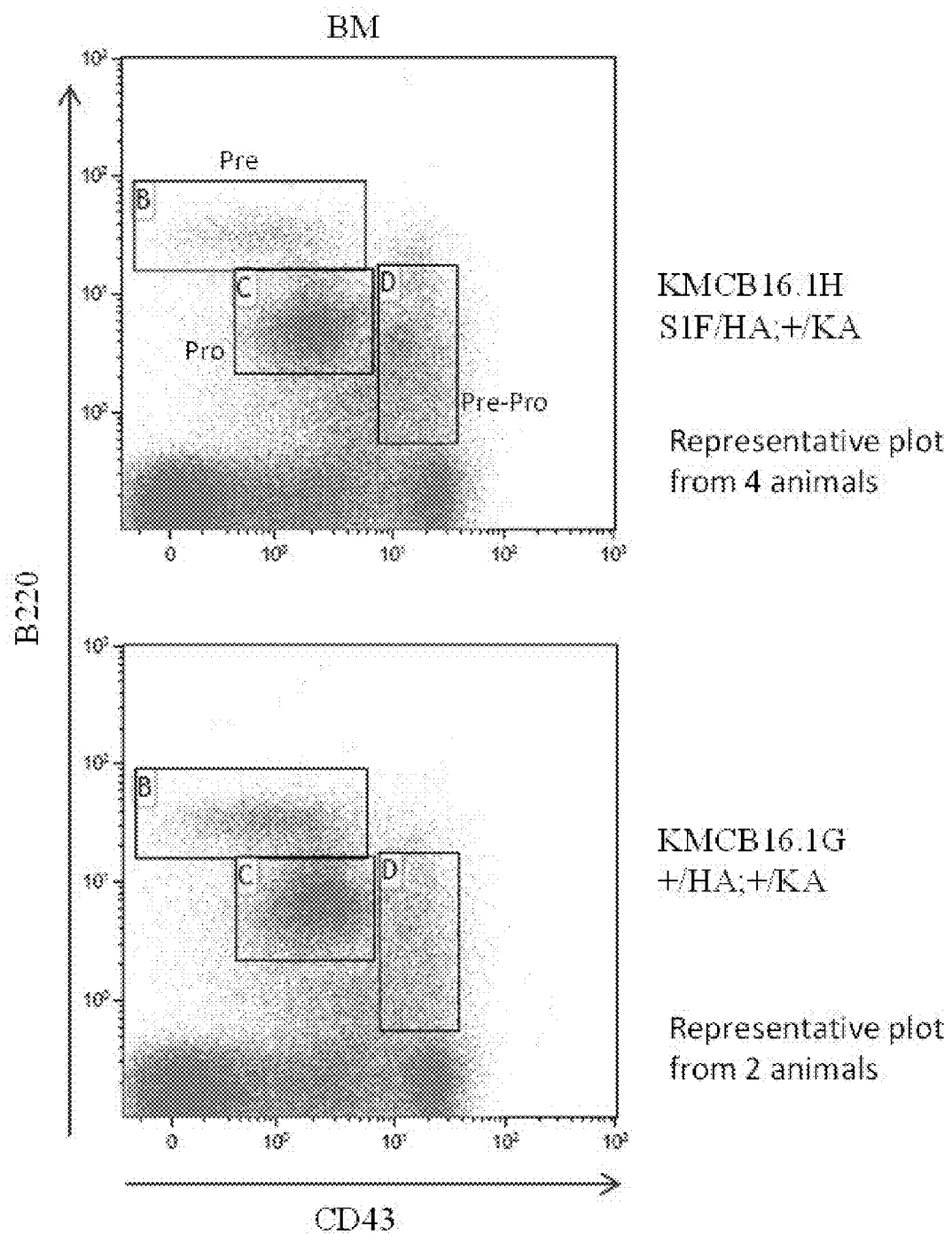
Fig. 67A (1)

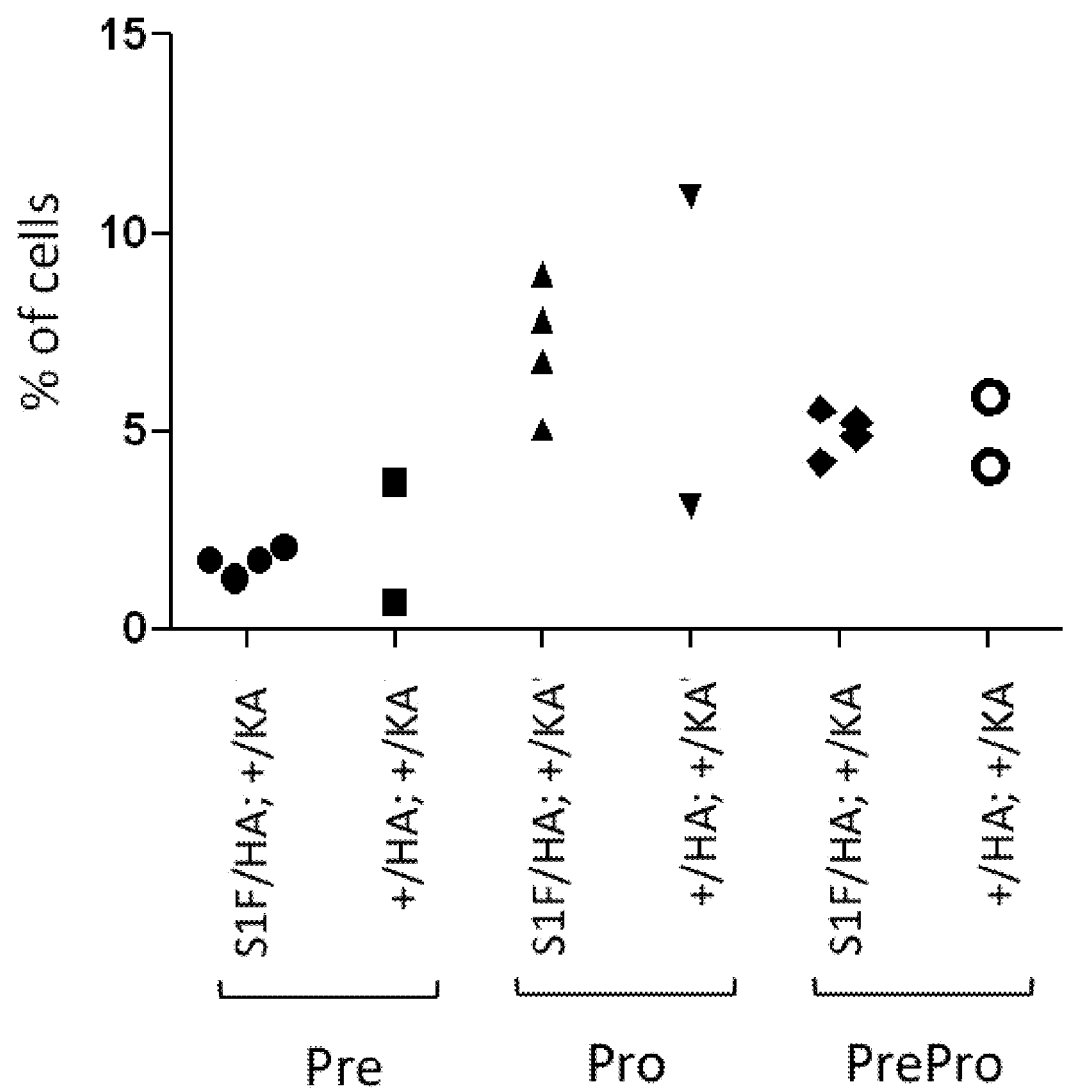
Fig. 67A (2)

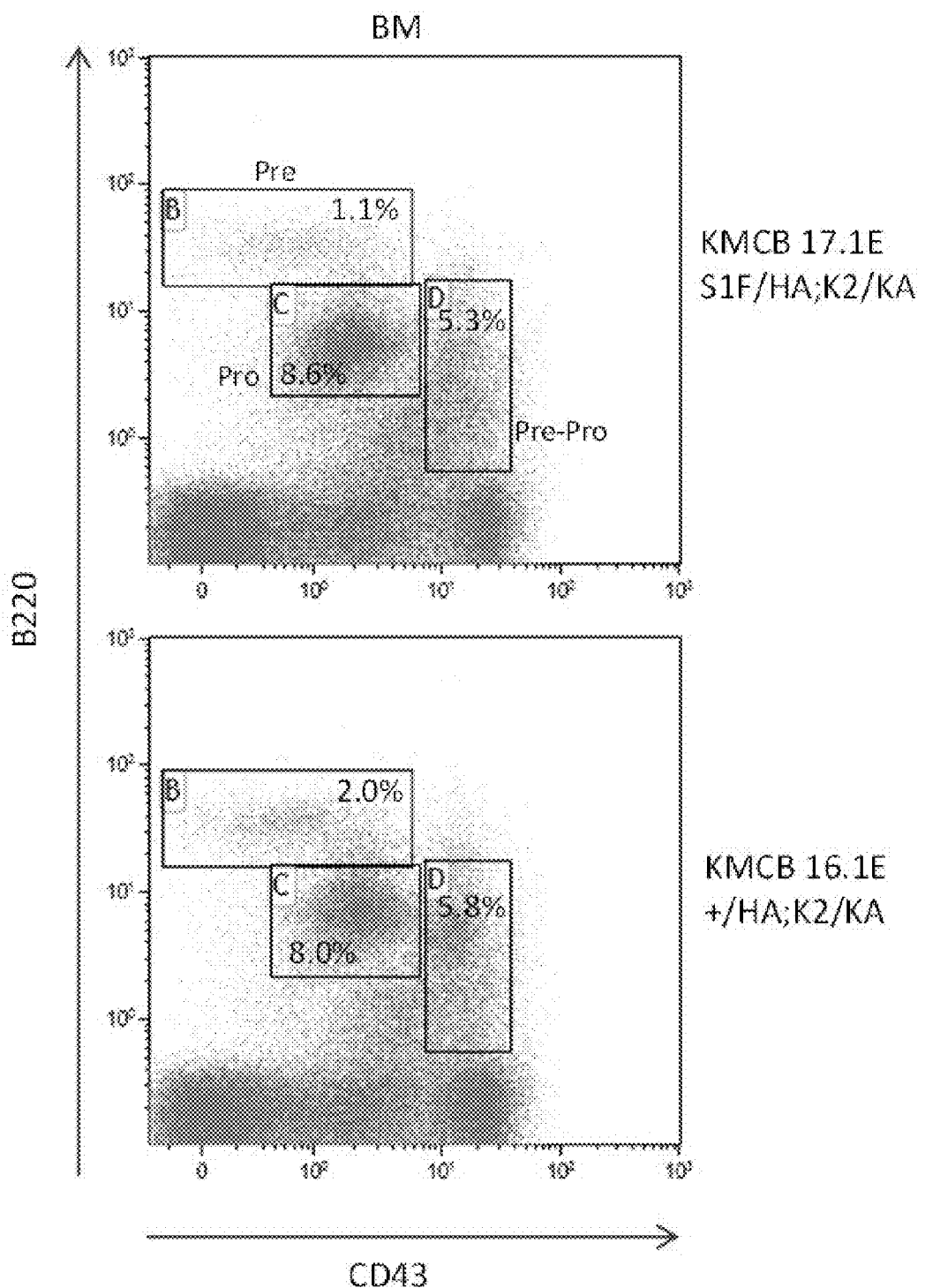
Fig. 67B (1)

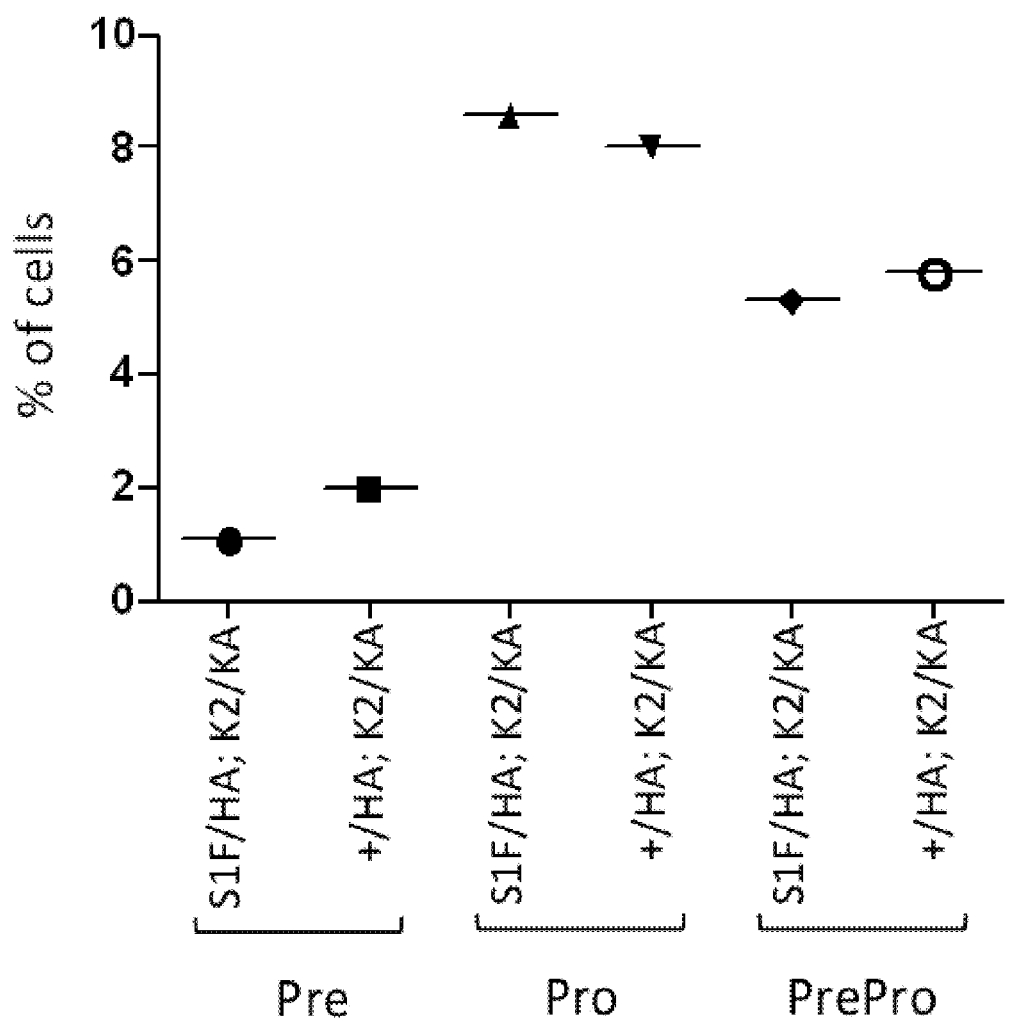
Fig. 67B (2)

ANIMAL MODELS AND THERAPEUTIC MOLECULES

BACKGROUND

The present invention relates inter alia to non-human animals and cells that are engineered to contain exogenous DNA, such as human immunoglobulin gene DNA, their use in medicine and the study of disease, methods for production of non-human animals and cells, and antibodies and antibody chains produced by such animals and derivatives thereof.

In order to get around the problems of humanizing antibodies a number of companies set out to generate mice with human immune systems. The strategy used was to knockout the heavy and light chain loci in ES cells and complement these genetic lesions with transgenes designed to express the human heavy and light chain genes. Although fully human antibodies could be generated, these models have several major limitations:
(i) The size of the heavy and light chain loci (each several Mb) made it impossible to introduce the entire loci into these models. As a result the transgenic lines recovered had a very limited repertoire of V-regions, most of the constant regions were missing and important distant enhancer regions were not included in the transgenes.
(ii) The very low efficiency of generating the large insert transgenic lines and the complexity and time required to cross each of these into the heavy and light chain knockout strains and make them homozygous again, restricted the number of transgenic lines which could be analysed for optimal expression.
(iii) Individual antibody affinities rarely reached those which could be obtained from intact (non-transgenic) animals.

WO2007117410 discloses chimaeric constructs for expressing chimaeric antibodies.

WO2010039900 discloses knock in cells and mammals having a genome encoding chimaeric antibodies.

The present invention provides, inter alia, a process for the generation in non-human mammals of antibodies that comprise a human Ig variable region, and further provides non-human animal models for the generation of such antibodies.

SUMMARY OF THE INVENTION

All nucleotide co-ordinates for the mouse are those corresponding to NCBI m37 for the mouse C57BL/6J strain, e.g. April 2007 ENSEMBL Release 55.37h, e.g. NCBI37 July 2007 (NCBI build 37) (e.g. UCSC version mm9 see World Wide Web (www) genome.ucsc.edu and World Wide Web (www) genome.ucsc.edu/FAQ/FAQreleases.html) unless otherwise specified. Human nucleotides coordinates are those corresponding to GRCh37 (e.g. UCSC version hg 19, World Wide Web (www) genome.ucsc.edu/FAQ/FAQreleases.html), February 2009 ENSEMBL Release 55.37, or are those corresponding to NCBI36, Ensemble release 54 unless otherwise specified. Rat nucleotides are those corresponding to RGSC 3.4 December 2004 ENSEMBL release 55.34w, or Baylor College of Medicine HGSC v3.4 November 2004 (e.g., UCSC m4, see World Wide Web (www) genome.ucsc.edu and World Wide Web (www) genome.ucsc.edu/FAQ/FAQreleases.html) unless otherwise specified.

In the present invention, methods are disclosed for constructing a chimaeric human heavy and light chain loci in a non-human mammal, for example a mouse. Reference to work in mice herein is by way of example only, and reference to mice is taken to include reference to all non-human mammals unless otherwise apparent from the disclosure, with mice being preferred as the non-human mammal.

In one aspect the invention relates to a non-human mammal whose genome comprises:
(a) a plurality of human IgH V regions, one or more human D regions and one or more human J regions upstream of the host non-human mammal constant region; and
(b) optionally one or more human Ig light chain kappa V regions and one or more human Ig light chain kappa J regions upstream of the host non-human mammal kappa constant region and/or one or more human Ig light chain lambda V regions and one or more human Ig light chain lambda J regions upstream of the host non-human mammal lambda constant region;
wherein the non-human mammal is able to produce a repertoire of chimaeric antibodies, or chimaeric light or heavy chains, having a non-human mammal constant region and a human variable region.

In one aspect the invention relates to non-human mammal whose genome comprises
(a) a plurality of human Ig light chain kappa V regions and one or more human Ig light chain kappa J regions upstream of the host non-human mammal kappa constant region and/or a plurality of human Ig light chain lambda V regions and one or more human Ig light chain lambda J regions upstream of the host non-human mammal lambda constant region; and
(b) optionally one or more human IgH V regions, one or more human D regions and one or more human J regions upstream of the host non-human mammal constant region;
wherein the non-human mammal is able to produce a repertoire of chimaeric antibodies, or chimaeric light or heavy chains, having a non-human mammal constant region and a human variable region.

In one aspect the invention relates to non-human mammalian cell whose genome comprises
(a) a plurality of human IgH V regions, one or more human D regions and one or more human J regions upstream of the host non-human mammal constant region and
(b) optionally one or more human Ig light chain kappa V regions and one or more human Ig light chain kappa J regions upstream of the host non-human mammal kappa constant region and/or one or more human Ig light chain lambda V regions and one or more human Ig light chain lambda J regions upstream of the host non-human mammal lambda constant region.

In one aspect the invention relates to a non-human mammalian cell whose genome comprises
(a) a plurality of human Ig light chain kappa V regions and one or more human Ig light chain kappa J regions upstream of the host non-human mammal kappa constant region and/or a plurality of human Ig light chain lambda V regions and one or more human Ig light chain lambda J regions upstream of the host non-human mammal lambda constant region; and
(b) optionally one or more human IgH V regions, one or more human D regions and one or more human J regions upstream of the host non-human mammal constant region;

In a further aspect the invention relates to a method for producing a non-human cell or mammal comprising inserting into a non-human mammal cell genome, such as an ES cell genome;
(a) a plurality of human IgH V regions, one or more human D regions and one or more human J regions upstream of the host non-human mammal constant region; and
(b) optionally one or more human Ig light chain kappa V regions and one or more human Ig light chain kappa J regions upstream of the host non-human mammal kappa constant region and/or one or more human Ig light chain lambda V regions and one or more human Ig light chain lambda J regions upstream of the host non-human mammal lambda constant region; respectively, the insertion being such that the non-human cell or mammal is able to produce a repertoire of chimaeric antibodies having a non-human mammal constant region and a human variable region, wherein steps (a) and (b) can be carried out in either order and each of steps (a) and (b) can be carried out in a stepwise manner or as a single step. Insertion may be by homologous recombination.

In a further aspect the invention relates to a method for producing an antibody or antibody chain specific to a desired antigen the method comprising immunizing a transgenic non-human mammal as disclosed herein with the desired antigen and recovering the antibody or antibody chain.

In a further aspect the invention relates to a method for producing a fully humanised antibody comprising immunizing a transgenic non-human mammal as disclosed herein with the desired antigen, recovering the antibody or cells producing the antibody and then replacing the non-human mammal constant region with a human constant region, for example by protein or DNA engineering.

In a further aspect the invention relates to humanised antibodies and antibody chains produced according to the present invention, both in chimaeric (for example, mouse-human) and fully humanised form, as well as fragments and derivatives of said antibodies and chains, and use of said antibodies, chains and fragments in medicine, including diagnosis.

In a further aspect the invention relates to use of a non-human mammal as described herein as a model for the testing of drugs and vaccines.

In one aspect the invention relates to a non-human mammal whose genome comprises:
(a) a plurality of human IgH V regions, one or more human D regions and one or more human J regions upstream of the host non-human mammal constant region; and
(b) optionally one or more human Ig light chain kappa V regions and one or more human Ig light chain kappa J regions upstream of the host non-human mammal kappa constant region and/or one or more human Ig light chain lambda V regions and one or more human Ig light chain lambda J regions upstream of the host non-human mammal lambda constant region;
wherein the non-human mammal is able to produce a repertoire of chimaeric antibodies or antibody chains having a non-human mammal constant region and a human variable region.

In a further aspect the invention relates to a non-human mammal whose genome comprises:
(a) a plurality of human Ig light chain kappa V regions and one or more human Ig light chain kappa J regions upstream of the host non-human mammal kappa constant region and/or a plurality of human Ig light chain lambda V regions and one or more human Ig light chain lambda J regions upstream of the host non-human mammal lambda constant region; and
(b) optionally one or more human IgH V regions, one or more human D regions and one or more human J regions upstream of the host non-human mammal constant;
wherein the non-human mammal is able to produce a repertoire of chimaeric antibodies having a non-human mammal constant region and a human variable region.

Optionally the non-human mammal genome is modified to prevent expression of fully host-species specific antibodies.

In one aspect the inserted human DNA comprises at least 50% of the human heavy chain variable (V) genes, such as at least 60%, at least 70%, at least 80%, at least 90%, and in one aspect all of the human V genes.

In one aspect the inserted human DNA comprises at least 50% of the human heavy chain diversity (D) genes, such as at least 60%, at least 70%, at least 80%, at least 90%, and in one aspect all of the human D genes.

In one aspect the inserted human DNA comprises at least 50% of the human heavy chain joining (J) genes, such as at least 60%, at least 70%, at least 80%, at least 90%, and in one aspect all of the human J genes.

In one aspect the inserted human DNA comprises at least 50% of the human light chain Variable (V) genes, such as at least 60%, at least 70%, at least 80%, at least 90%, and in one aspect all of the human light chain V genes.

In one aspect the inserted human DNA comprises at least 50% of the human light chain joining (J) genes, such as at least 60%, at least 70%, at least 80%, at least 90%, and in one aspect all of the human light chain J genes.

The inserted human genes may be derived from the same individual or different individuals, or be synthetic or represent human consensus sequences.

Although the number of V D and J regions is variable between human individuals, in one aspect there are considered to be 51 human V genes, 27 D and 6 J genes on the heavy chain, 40 human V genes and 5 J genes on the kappa light chain and 29 human V genes and 4 J genes on the lambda light chain (Janeway and Travers, Immunobiology, Third edition)

In one aspect the human heavy chain locus inserted into the non-human mammal contains the full repertoire of human V, D and J regions, which in the genome is in functional arrangement with the non-human mammal constant regions such that functional chimaeric antibodies can be produced between the human variable and non-human mammal constant regions. This total inserted human heavy chain genetic material is referred to herein as the human IgH VDJ region, and comprises DNA from a human genome that encodes all the exons encoding human V, D and J portions and suitably also the associated introns. Similarly, reference to the human Ig light chain kappa V and J regions herein refers to human DNA comprising all the exons encoding V and J regions and suitably also the associated introns of the human genome. Reference to the human Ig light chain lambda V and J regions herein refers to human DNA comprising all the exons encoding V and J regions and suitably also the associated introns of the human genome.

Human variable regions are suitably inserted upstream of a non-human mammal constant region, the latter comprising all of the DNA required to encode the full constant region or a sufficient portion of the constant region to allow the formation of an effective chimaeric antibody capable of specifically recognising an antigen.

In one aspect the chimaeric antibodies or antibody chains have a part of a host constant region sufficient to provide one or more effector functions seen in antibodies occurring naturally in a host mammal, for example that they are able interact with Fc receptors, and/or bind to complement.

Reference to a chimaeric antibody or antibody chain having a host non mammal constant region herein therefore is not limited to the complete constant region but also includes chimaeric antibodies or chains which have all of the host constant region, or a part thereof sufficient to provide one or more effector functions. This also applies to non-human mammals and cells and methods of the invention in which human variable region DNA may be inserted into the host genome such that it forms a chimaeric antibody chain with all or part of a host constant region. In one aspect the whole of a host constant region is operably linked to human variable region DNA.

The host non-human mammal constant region herein is preferably the endogenous host wild-type constant region located at the wild type locus, as appropriate for the heavy or light chain. For example, the human heavy chain DNA is suitably inserted on mouse chromosome 12, suitably adjacent the mouse heavy chain constant region.

In one aspect the insertion of the human DNA, such as the human VDJ region is targeted to the region between the J4 exon and the Cµ locus in the mouse genome IgH locus, and in one aspect is inserted between co-ordinates 114,667,090 and 114,665,190, or at co-ordinate 114,667,091, after 114,667,090. In one aspect the insertion of the human DNA, such as the human light chain kappa VJ is targeted into mouse chromosome 6 between co-ordinates 70,673,899 and 70,675,515, suitably at position 70,674,734, or an equivalent position in the lambda mouse locus on chromosome 16.

In one aspect the host non-human mammal constant region for forming the chimaeric antibody may be at a different (non endogenous) chromosomal locus. In this case the inserted human DNA, such as the human variable VDJ or VJ region(s) may then be inserted into the non-human genome at a site which is distinct from that of the naturally occurring heavy or light constant region. The native constant region may be inserted into the genome, or duplicated within the genome, at a different chromosomal locus to the native position, such that it is in a functional arrangement with the human variable region such that chimaeric antibodies of the invention can still be produced.

In one aspect the human DNA is inserted at the endogenous host wild-type constant region located at the wild type locus between the host constant region and the host VDJ region.

Reference to location of the variable region upstream of the non-human mammal constant region means that there is a suitable relative location of the two antibody portions, variable and constant, to allow the variable and constant regions to form a chimaeric antibody or antibody chain in vivo in the mammal. Thus, the inserted human DNA and host constant region are in functional arrangement with one another for antibody or antibody chain production.

In one aspect the inserted human DNA is capable of being expressed with different host constant regions through isotype switching. In one aspect isotype switching does not require or involve trans switching. Insertion of the human variable region DNA on the same chromosome as the relevant host constant region means that there is no need for trans-switching to produce isotype switching.

As explained above, the transgenic loci used for the prior art models were of human origin, thus even in those cases when the transgenes were able to complement the mouse locus so that the mice produced B-cells producing fully human antibodies, individual antibody affinities rarely reached those which could be obtained from intact (non-transgenic) animals. The principal reason for this (in addition to repertoire and expression levels described above) is the fact that the control elements of the locus are human. Thus, the signalling components, for instance to activate hyper-mutation and selection of high affinity antibodies are compromised.

In contrast, in the present invention, host non-human mammal constant regions are maintained and it is preferred that at least one non-human mammal enhancer or other control sequence, such as a switch region, is maintained in functional arrangement with the non-human mammal constant region, such that the effect of the enhancer or other control sequence, as seen in the host mammal, is exerted in whole or in part in the transgenic animal.

This approach above is designed to allow the full diversity of the human locus to be sampled, to allow the same high expression levels that would be achieved by non-human mammal control sequences such as enhancers, and is such that signalling in the B-cell, for example isotype switching using switch recombination sites, would still use non-human mammal sequences.

A mammal having such a genome would produce chimaeric antibodies with human variable and non-human mammal constant regions, but these could be readily humanized, for example in a cloning step. Moreover the in vivo efficacy of these chimaeric antibodies could be assessed in these same animals.

In one aspect the inserted human IgH VDJ region comprises, in germline configuration, all of the V, D and J regions and intervening sequences from a human.

In one aspect 800-1000 kb of the human IgH VDJ region is inserted into the non-human mammal IgH locus, and in one aspect a 940, 950 or 960 kb fragment is inserted. Suitably this includes bases 105,400,051 to 106,368,585 from human chromosome 14.

In one aspect the inserted IgH human fragment consists of bases 105,400,051 to 106,368,585 from chromosome 14. In one aspect the inserted human heavy chain DNA, such as DNA consisting of bases 105,400,051 to 106,368,585 from chromosome 14, is inserted into mouse chromosome 12 between the end of the mouse J4 region and the Eµ region, suitably between co-ordinates 114,667,090 and 114,665,190, or at co-ordinate 114,667,091, after 114,667,090. In one aspect the insertion is between co-ordinates 114,667,089 and 114,667,090 (co-ordinates refer to NCBI m37, for the mouse C57BL/6J strain), or at equivalent position in another non-human mammal genome.

In one aspect the inserted human kappa VJ region comprises, in germline configuration, all of the V and J regions and intervening sequences from a human. Suitably this includes bases 88,940,356 to 89,857,000 from human chromosome 2, suitably approximately 917 kb. In a further aspect the light chain VJ insert may comprise only the proximal clusters of V segments and J segments. Such an insert would be of approximately 473 kb. In one aspect the human light chain kappa DNA, such as the human IgK fragment of bases 88,940,356 to 89,857,000 from human chromosome 2, is suitably inserted into mouse chromosome 6 between co-ordinates 70,673,899 and 70,675,515, suitably at position 70,674,734. These co-ordinates refer to NCBI36 for the human genome, ENSEMBL Release 54 and NCBIM37 for the mouse genome, relating to mouse strain C57BL/6J.

In one aspect the human lambda VJ region comprises, in germline configuration, all of the V and J regions and intervening sequences from a human.

Suitably this includes analogous bases to those selected for the kappa fragment, from human chromosome 2.

A cell or non-human mammal of the invention, in one embodiment, comprises an insertion of human heavy chain variable region DNA between co-ordinates 114, 666, 183 and 114, 666, 725, such as between 114 666 283 and 114 666 625, optionally between co-ordinates 114,666,335 and 114,666,536, optionally between 114,666,385 and 114,666,486, or between 114,666,425 and 114,666,446, or between 114,666,435 and 114,666,436 of mouse chromosome 12 with reference to NCBIM37 for the mouse genome, relating to mouse strain C57BL/6J or an equivalent position of mouse chromosome 12 from a different mouse strain or an equivalent position in the genome of another non-human vertebrate, e.g., a rat. The insertion between co-ordinates 114,666,435 and 114,666,436 relating to mouse strain C57BL/6J is equivalent to an insertion between co-ordinates 1207826 and 1207827 on chromosome 12 with reference to the 129/SvJ genomic sequence of the GenBank® access number NT114985.2. An insertion may be made at equivalent position in another genome, such as another mouse genome. In an example of this embodiment, the cell or mammal of the invention comprises a human IgH VDJ region which comprises or consists of nucleotides 106,328,851-107,268,544, such as nucleotides 106,328,901-107,268,494, such as nucleotides 106,328,941-107,268,454, such as nucleotides 106,328,951-107,268,444 of human Chromosome 14, with reference to the GRCH37/hg19 sequence database, or insertion of equivalent nucleotides relating to chromosome 14 from a different human sequence or database. The human insertion may be made between the regions indicated above.

A cell or mammal of the invention, in one embodiment, comprises an insertion of the human kappa VJ region, suitably comprising or consisting of, in germline configuration, all of the V and J regions and intervening sequences from a human, the insertion of the human DNA being made between co-ordinates 70,673,918-70,675,517, such as between co-ordinates 70,674,418 and 70 675,017, such as between co-ordinates 70,674,655-70,674,856, such as between co-ordinates 70,674,705-70,674,906, such as between co-ordinates 70,674,745-70,674,766, such as between co-ordinates 70,674,755 and 70,674,756 of mouse chromosome 6, numbering with reference to NCBIM37 for the mouse genome, relating to mouse strain C57BL/6J, or an insertion at an equivalent position in another genome, such as another mouse genome. In an example of this embodiment, a cell or mammal of the invention comprises an insertion of nucleotides 89,159,079-89,630,437 and/or 89,941,714-90,266,976 of human chromosome 2 with reference to the GRCH37/hg19 sequence database (or equivalent nucleotides relating to chromosome 2 from a different human sequence or database), such as an insertion of these 2 discrete fragments without the intervening sequence, or an insertion of the complete 89,159,079-90,266,976 region.

The insertion may comprise, or consist, of:
(i) nucleotides 89,158,979-89,630,537, such as 89,159,029-89,630,487, such as 89,159,069-89,630,447, such as 89,159,079-89,630,437, optionally in addition to fragment (ii) below (ii) nucleotides 89,941,614-90,267,076, such as 89,941,664-90,267,026, such as 89, 941,704-90,266,986, such as 89,941,714-90,266,976; optionally in addition to fragment (i)
(iii) nucleotides 89,158,979-90,267,076, such as nucleotides 89,159,079-90,266,976.

The human insertion may be made between the regions indicated above.

In an embodiment, a cell or mammal of the invention comprises an insertion of a human lambda region which comprises at least one human J$\lambda$ region (eg, a germline region) and at least one human C$\lambda$ region (eg, a germline region), optionally C$_\lambda$6 and/or C$_\lambda$7. For example, the cell or mammal comprises a plurality of human J$\lambda$ regions, optionally two or more of J$_\lambda$1, J$_\lambda$2, J$_\lambda$6 and J$_\lambda$7, optionally all of J$_\lambda$1, J$_\lambda$2, J$_\lambda$6 and J$_\lambda$7. In an example, the cell or mammal comprises at least one human J$_\lambda$-C$_\lambda$ cluster, optionally at least J$_\lambda$7-C$_\lambda$7.

In one aspect the human JC cluster is inserted 3' of the last endogenous J lambda or is inserted 3' of the last endogenous J kappa region, suitably immediately 3' of these sequences, or substantially immediately 3' of these sequences.

In one aspect the insertion into the mouse lambda locus is made downstream of the endogenous C1 gene segment, for example where there is a 3' J1C1 cluster, suitably immediately 3' of the C1 segment, or substantially immediately 3' of the segment.

In one aspect (e.g. cell or non-human mammal) a human JC cluster is inserted into a kappa locus and any resulting cell or animal is heterozygous at that locus, such that the cell has one chromosome with human lambda DNA inserted into the kappa locus, and another chromosome with human kappa DNA at the endogenous kappa locus.

In an embodiment, a cell or mammal of the invention comprises a human E$\lambda$ enhancer.

A cell or mammal may of the invention comprise an inserted human lambda VJ region, suitably comprising or consisting of, in germline configuration, all of the V and J regions and intervening sequences from a human, the inserted region comprises or consisting of nucleotides 22,375,509-23,327,984, such as nucleotides 22,375,559-23,327,934, such as nucleotides 22,375,599-23,327,894, such as nucleotides 22,375,609-23,327,884 from human Chromosome 22, with reference to the GRCH37/hg19 sequence database, or equivalent DNA from another human sequence or database. The insertion into the mouse genome may be made between co-ordinates 19,027,763 and 19,061,845, such as between co-ordinates 19,037,763 and 19,051,845, such as between co-ordinates 19,047,451 and 19,047,652, such as between co-ordinates 19,047,491 and 19,047,602, such as between co-ordinates 19,047,541 and 19,047,562, such as between co-ordinates 19,047,551 and 19,047,552 of mouse Chromosome 16 (with reference to NCBIM37 for the mouse genome, relating to mouse strain C57BL/6J, equivalent to co-ordinates 1,293,646-1,293,647 of the 129 SvJ genomic sequence in the sequence file of NT_039630.4), or may be an insertion at an equivalent position in other genome, such as another mouse genome. The insertion of the human lambda nucleic acid into the mouse genome may alternatively be made between co-ordinates 70,673,918 and 70,675,517, such as between co-ordinates 70,674,418 and 70 675,017, such as between co-ordinates 70,674,655 and 70,674,856, such as between co-ordinates 70,674,705 and 70,674,806, such as between co-ordinates 70,674,745 and 70,674,766, such as between co-ordinates 70,674,755 and 70,674,756 of mouse Chromosome 6 (with reference to NCBIM37 for the mouse genome, relating to mouse strain C57BL/6J) or equivalent in another genome. The human insertion may be made between the regions indicated above.

All specific human fragments described above may vary in length, and may for example be longer or shorter than defined as above, such as 500 bases, 1 KB, 2K, 3K, 4K, 5 KB, 10 KB, 20 KB, 30 KB, 40 KB or 50 KB or more, which suitably comprise all or part of the human V(D)J region, whilst preferably retaining the requirement for the final insert to comprise human genetic material encoding the complete heavy chain region and light chain region, as appropriate, as described above.

In one aspect the 5' end of the human insert described above is increased in length. Where the insert is generated in a stepwise fashion then the increase in length is generally in respect of the upstream (5') clone.

In one aspect the 3' end of the last inserted human gene, generally the last human J gene to be inserted is less than 2 kb, preferably less than 1 KB from the human-mouse join region.

In one aspect the non-human mammal comprises some or all of the human light chain kappa VJ region as disclosed herein but not the human light chain lambda VJ region.

In one aspect the cell or non-human mammal comprises a fully human lambda locus (lambda VJC regions from a human), a chimaeric kappa locus (human kappa VJ regions operatively linked to a host kappa constant region) and a chimaeric heavy chain locus, having a human VDJ region operatively linked to a host heavy chain constant region.

In a further aspect the genome comprises an insertion of V, D (heavy chain only) and J genes as described herein at the heavy chain locus and one light chain locus, or at the heavy chain locus and both light chain loci. Preferably the genome is homozygous at one, or both, or all three loci.

In another aspect the genome may be heterozygous at one or more of the loci, such as heterozygous for DNA encoding a chimaeric antibody chain and native (host cell) antibody chain. In one aspect the genome may be heterozygous for DNA capable of encoding 2 different antibody chains of the invention, for example, comprising 2 different chimaeric heavy chains or 2 different chimaeric light chains.

In one aspect the invention relates to a non-human mammal or cell, and methods for producing said mammal or cell, as described herein, wherein the inserted human DNA, such as the human IgH VDJ region and/or light chain V, J regions are found on only one allele and not both alleles in the mammal or cell. In this aspect a mammal or cell has the potential to express both an endogenous host antibody heavy or light chain and a chimaeric heavy or light chain.

In a further aspect of the invention the human VDJ region, or light chain VJ region, is not used in its entirety, but parts of the equivalent human VDJ or VJ region, such as the exons, from other species may be used, such as one or more V, D, or J exons from other species, or regulatory sequences from other species. In one aspect the sequences used in place of the human sequences are not human or mouse. In one aspect the sequences used may be from rodent, or, primate such as chimp. For example, 1, 2, 3, 4, or more, or all of the J regions from a primate other than a human may be used to replace, one, 2, 3, 4, or more or all of the human J exons in the VDJ/VJ region of the cells and animals of the invention.

In a further aspect the inserted human DNA, such as the human IgH VDJ region, and/or light chain VJ regions, may be inserted such that they are operably linked in the genome with a mu constant region from a non-human, non-mouse species, such as a rodent or primate sequence, such as a rat sequence.

Other non-human, non-mouse species from which DNA elements may be used in the present invention include rabbits, lamas, dromedary, alpacas, camels and sharks.

In one aspect the inserted human DNA, such as the human VDJ or VJ region, is not operably linked to the endogenous host mu sequence but rather to a non-host mu sequence.

Operable linkage suitably allows production of an antibody heavy or light chain comprising the human variable region.

In one aspect the inserted human DNA, such as the human IgH VDJ region (and/or light chain VJ regions) may be inserted into the host chromosome together with mu constant region nucleic acid which is not host mu constant region nucleic acid, and preferably is a mu constant region from a non-mouse, non-human species. Suitably the inserted human DNA, such as the human VDJ region (and/or light chain VJ regions) is operably linked to a non-human, non-mouse mu, and is able to form a chimaeric antibody heavy or light chain. In another aspect a non-mouse, non-human mu may be inserted into the host chromosome on a separate genetic element to that of the human variable region, or at a different location in the genome, suitably operably linked to the variable region such that a chimaeric antibody heavy or light chain can be formed.

In an additional aspect the invention relates to a non-human mammal or a cell whose genome comprises a plurality of human IgH V regions, one or more human D regions and one or more human J regions upstream of a host non-human mammal light chain constant region, arranged such that the cell or mammal is able to express a chimaeric antibody chain. The invention also relates to a non-human mammal or a cell whose genome additionally or alternatively comprises a plurality of human Ig light chain V regions, and one or more human J regions upstream of a host non-human mammal heavy chain constant region, such that the cell or mammal is able to express a chimaeric antibody chain. The cell or mammal may be able to express an antibody having both heavy and light chains, including at least one chimaeric antibody chain, as disclosed above.

The inserted human heavy chain variable regions may be any of those described herein, and may be inserted at the positions described above for insertion 5' of the lambda and kappa constant regions. Likewise the inserted human light chain variable regions may be those described above, and may be inserted at the positions described above for insertion 5' of the heavy chain constant region.

For example, the genome or the cell or non-human mammal of the invention may encode an antibody comprising an antibody chain having a human heavy chain variable region upstream of a mouse light chain constant region, or an antibody chain having a human light chain variable region upstream of a mouse heavy chain constant region, in combination with one of:
  a fully human antibody light chain;
  a fully human antibody heavy chain;
  a non-human vertebrate (e.g., mouse or rat) antibody light chain;
  a non-human vertebrate (e.g., mouse or rat) antibody heavy chain;
  a chimaeric non-human vertebrate (e.g., mouse or rat)—human antibody chain;
  an antibody chain having a human heavy chain variable region upstream of a non-human vertebrate (e.g., mouse or rat) light chain constant region;
  an antibody chain having a human light chain variable region upstream of a non-human vertebrate (e.g., mouse or rat) heavy chain constant region.

The invention also relates to a transgene encoding a plurality of human IgH V regions, one or more human D regions and one or more human J regions upstream of a host non-human mammal light chain constant region, optionally comprised within a vector.

The invention also relates to a transgene encoding a plurality of human Ig light chain V regions, and one or more human light chain J regions upstream of a host non-human mammal heavy chain constant region, optionally comprised within a vector.

In one aspect the invention relates to a cell, or non-human mammal, the genome of which comprises: one or more human Ig light chain kappa V regions and one or more human Ig light chain kappa J regions upstream of all or part of the human kappa constant region.

In another aspect the invention relates to a cell, or non-human mammal, the genome of which comprises: one or more human Ig light chain lambda V regions and one or more human Ig light chain lambda J regions upstream of all or part of the human lambda constant region.

Suitably the light chain VJ and C regions are able to form antibody chains in vivo capable of specifically reacting with an antigen.

In one aspect of the invention there is no non-human coding sequence in the inserted light chain region.

In such aspects a human kappa and/or lambda region is inserted into the genome, in combination with insertion of the heavy chain VDJ region or part thereof, upstream of the host heavy chain constant region as disclosed herein.

The cell or non-human mammal of the invention may comprise:
(a) a plurality of human IgH V regions, one or more human D regions and one or more human J regions upstream of the host non-human mammal constant region; and
(b) one or more human Ig light chain kappa V regions and one or more human Ig light chain kappa J regions upstream of all or part of the non-human kappa constant region, wherein the non-human mammal is able to produce a repertoire of antibodies having an antibody chain comprising non-human mammal constant region and a human variable region.

The cell or non-human mammal of the invention may comprise
(a) a plurality of human IgH V regions, one or more human D regions and one or more human J regions upstream of the host non-human mammal constant region; and
one or more human Ig light chain lambda V regions and one or more human Ig light chain lambda J regions upstream of the host non-human mammal lambda constant region; wherein the non-human mammal is able to produce a repertoire of antibodies having an antibody chain comprising a non-human mammal constant region and a human variable region.

Suitably the insertion of the human VJC light chain DNA, or part thereof as disclosed above, is made at the equivalent mouse locus. In one aspect the human light chain kappa VJC DNA, or part thereof, is inserted immediately upstream or downstream of the mouse kappa VJC region. In one aspect, the human light chain lambda VJC region or part thereof is inserted immediately upstream or downstream of the mouse lambda VJC region. In one aspect only the human kappa VJC locus is inserted and not the human lambda VJC locus. In one aspect only the human lambda VJC locus is inserted and not the human kappa VJC locus. Insertions may be made using the techniques disclosed herein, and suitably do not remove the host sequences from the genome. In one aspect the non-human mammal host VJC sequences may be inactivated in some way, by mutation, or inversion, or by insertion of the human variable region DNA, or by any other means. In one aspect the cell or non-human mammal of the invention may comprise an insertion of the complete VJC human region.

The human kappa variable region DNA might be inserted into the genome in functional arrangement with a lambda constant region, for example inserted upstream of a lambda constant region. Alternatively human lambda region variable DNA might be inserted in functional arrangement with a kappa constant region, for example inserted upstream of a kappa constant region.

In one aspect one or more non-human mammal control sequences such as the enhancer sequence(s) is maintained upstream of the nonhuman mammal Mu constant region, suitably in its native position with respect to the distance from the constant region.

In one aspect one or more non-human mammal control sequences such as an enhancer sequence(s) are maintained downstream of the nonhuman mammal Mu constant region, suitably in its native position with respect to the distance from the constant region.

In one aspect a non-human mammal switch sequence, suitably the endogenous switch sequence, is maintained upstream of the non-human mammal Mu constant region, suitably in its native position with respect to distance from the constant region.

In such location the host enhancer or switch sequences are operative in vivo with the host constant region sequence(s).

In one aspect a switch sequence is neither human, nor native in the non-human mammal, for example in one aspect a non-human mammal switch sequence is not a mouse or human switch sequence. The switch sequence may be, for example, a rodent or primate sequence, or a synthetic sequence. In particular the switch sequence may be a rat sequence where the non-human mammal is a mouse. By way of example, a mouse or human constant mu sequence may be placed under the control of a switch sequence from a rat, or chimp, or other switch sequence, suitably capable of allowing isotype switching to occur in vivo.

In one aspect the switch sequence of the invention is a switch sequence comprising 3, 4, 5, 6 or more (up to 82) contiguous repeats of the repeat sequence GGGCT (SEQ ID no 46-50), such as a rat switch sequence. By "rat switch" herein it is meant that the switch is a wild-type switch corresponding to a switch from a rat genome or derived from such a switch.

In one aspect the switch sequence of the invention is a rat switch sequence comprising the following repeats: GAGCT (296 repeats; SEQ ID No 18), GGGGT (50 repeats; SEQ ID No 19), and GGGCT (83 repeats; SEQ ID No 20).

In one example the rat switch sequence comprises or consists of the sequence of SEQ ID no 1.

In these embodiments, and where the non-human mammal is a mouse or the cell is a mouse cell, the switch is optionally a rat switch as described herein.

Alternatively, the switch sequence present in cells or mammal of the invention is a mouse switch, eg, is from a mouse such as a mouse 129 strain or mouse $C_{5-7}$ strain, or from a strain derived therefrom, optionally comprising or consisting of the sequence of SEQ ID no 4 or 5. By "mouse switch" herein it is meant that the switch is a wild-type switch corresponding to a switch from a mouse genome or derived from such a switch. In this embodiment, and where the non-human mammal is a mouse or the cell is a mouse cell, the mouse switch sequence is optionally the endogenous switch or is a mouse switch from another mouse strain.

The cell or mammal of the invention may therefore comprise a human or non-human mammal switch sequence and a human or non-human mammal enhancer region or regions. They may be upstream of a human or non-human mammal constant region. Preferably the control sequences are able to direct expression or otherwise control the production of antibodies comprising a constant region with which they are associated. One combination envisaged is a rat switch with mouse enhancer sequences and mouse constant regions in a mouse cell.

In one aspect the invention relates to a cell, preferably a non-human cell, or non-human mammal comprising an immunoglobulin heavy chain or light chain locus having DNA from 3 or more species. For example, the cell or animal may comprise host cell constant region DNA, one or more human V, D or J coding sequences and one or more non-human, non-host DNA regions that are able to control a region of the immunoglobulin locus, such as a switch sequence, promoter or enhancer which are able to control expression or isotype switching in vivo of the Ig DNA. In one aspect the cell or animal is a mouse and comprises additionally human DNA from the human Ig locus and additionally a non-mouse DNA sequence, such as a rat DNA sequence, capable of regulation of the mouse or human DNA.

In another aspect the invention relates to a cell, preferably non-human cell, or non-human mammal comprising an immunoglobulin heavy chain or light chain locus having DNA from 2 or more different human genomes. For example, it could comprise heavy chain V(D)J sequences from more than one human genome within a heavy or light chain, or heavy chain VDJ DNA from one genome and light chain VJ sequences from a different genome.

In one aspect the invention relates to a DNA fragment or cell or non-human mammal comprising an immunoglobulin heavy chain or light chain locus, or part thereof, having DNA from 2 or more species, where one species contributes a non-coding region such as a regulatory region, and the other species coding regions such as V, D, J or constant regions.

In one aspect the human promoter and/or other control elements that are associated with the different human V, D or J regions are maintained after insertion of the human VDJ into the mouse genome.

In a further aspect one or more of the promoter elements, or other control elements, of the human regions, such as the human V regions, are optimised to interact with the transcriptional machinery of a non-human mammal.

Suitably a human coding sequence may be placed under the control of an appropriate non-human mammal promoter, which allows the human DNA to be transcribed efficiently in the appropriate non-human animal cell. In one aspect the human region is a human V region coding sequence, and a human V region is placed under the control of a non-human mammal promoter.

The functional replacement of human promoter or other control regions by non-human mammal promoter or control regions may be carried out by use of recombineering, or other recombinant DNA technologies, to insert a part of the human Ig region (such as a human V region) into a vector (such as a BAC) containing a non-human Ig region. The recombineering/recombinant technique suitably replaces a portion of the non-human (e.g. mouse) DNA with the human Ig region, and thus places the human Ig region under control of the non-human mammal promoter or other control region. Suitably the human coding region for a human V region replaces a mouse V region coding sequence. Suitably the human coding region for a human D region replaces a mouse D region coding sequence. Suitably the human coding region for a human J region replaces a mouse J region coding sequence. In this way human V, D or J regions may be placed under the control of a non-human mammal promoter, such as a mouse promoter.

In one aspect the only human DNA inserted into the non-human mammalian cell or animal are V, D or J coding regions, and these are placed under control of the host regulatory sequences or other (non-human, non-host) sequences, In one aspect reference to human coding regions includes both human introns and exons, or in another aspect simply exons and no introns, which may be in the form of cDNA.

It is also possible to use recombineering, or other recombinant DNA technologies, to insert a non-human-mammal (e.g. mouse) promoter or other control region, such as a promoter for a V region, into a BAC containing a human Ig region. A recombineering step then places a portion of human DNA under control of the mouse promoter or other control region.

The approaches described herein may also be used to insert some or all of the V, D and J regions from the human heavy chain upstream of a light chain constant region, rather than upstream of the heavy chain constant region. Likewise some or all of the human light chain V and J regions may be inserted upstream of the heavy chain constant region. Insertion may be at the endogenous constant region locus, for example between the endogenous constant and J region, and may be of some, or all, of the V, D or J genes alone, excluding promoter or enhancer sequences, or may be of some, or all, of the V, D or J genes with one or more or all respective promoter or enhancer sequences. In one aspect the full repertoire of V, D or J fragments in germline orientation may be inserted upstream and in functional arrangement with a host constant region.

Thus the present invention allows V and/or D and/or J regions from a human, or any species, to be inserted into a chromosome of a cell from a different species that comprises a constant region, allowing a chimaeric antibody chain to be expressed.

In one aspect the invention requires only that some human variable region DNA is inserted into the genome of a non-human mammal in operable arrangement with some, or all, of the human heavy chain constant region at the region of the endogenous heavy chain constant region locus such that an antibody chain can be produced. In this aspect of the invention and where human light chain DNA is additionally inserted, the light chain DNA insertion can be in the form of a completely human construct, having both human variable DNA and human constant region DNA, or have human variable region DNA and constant region DNA from a non-human, non-host species. Other variations are also possible, such as insertion of both of the light chain human variable region and host genome constant region. In addition the insertion of said light chain transgenes need not be at the equivalent endogenous locus, but may be anywhere in the genome. In such a scenario the cell or mammal may produce chimaeric heavy chains (comprising human variable region DNA and mouse constant region DNA) and light chains comprising human variable and human constant region DNA. Thus in one aspect of the invention the lambda and or kappa human variable region DNA can be inserted upstream of the endogenous locus, or downstream, or indeed on a different chromosome to the endogenous locus, and inserted with or without constant region DNA.

As well insertion of human light chain DNA upstream of the host non-human mammal constant region, a further aspect of the invention relates to insertion of one or both light chain human variable regions downstream of the equivalent endogenous locus constant region, or elsewhere in the genome.

Generally, insertion of human variable region DNA at or close to the equivalent endogenous locus in the recipient genome is preferred, for example within 1, 2, 3, 4, 5, 6, 7, 8, 9, or 10 kb of the boundary (upstream or downstream) of a host immunoglobulin locus.

Thus in one aspect the invention can relate to a cell or non-human mammal whose genome comprises:
  (a) a plurality of human IgH V regions, one or more human D regions and one or more human J regions upstream of the host non-human mammal constant region; and
  (b) one or more human Ig light chain kappa V regions and one or more human Ig light chain kappa J regions, and/or, one or more human Ig light chain lambda V regions and one or more human Ig light chain lambda J regions;
wherein the non-human mammal is able to produce a repertoire of chimaeric antibodies, or chimaeric light or heavy chains, having a non-human mammal constant region and a human variable region.

In one particular aspect the genome of the cell or non-human mammal comprises:
  a plurality of human IgH V regions, one or more human D regions and one or more human J regions upstream of the host non-human mammal constant region;
  one or more human Ig light chain kappa V regions and one or more human Ig light chain kappa J regions upstream of the host non-human mammal kappa constant region, and
  one or more human Ig light chain lambda V regions and one or more human Ig light chain lambda J regions downstream of the host non-human mammal lambda constant region,
  optionally in which the human lambda variable region may be inserted upstream or downstream of the endogenous host lambda locus in operable linkage with a human lambda constant region, such that the non-human mammal or cell can produce fully human antibody light chains and chimaeric heavy chains.

In a further, different, aspect of the invention, the use of the methods of the invention allows a locus to be built up in a stepwise manner by sequential insertions, and thus allows for the insertion of human variable DNA together with human or non-human constant region DNA at any suitable location in the genome of a non-human host cell. For example, methods of the invention can be used to insert human immunoglobulin variable region DNA together with constant region DNA from the host genome anywhere in the genome of a non-human host cell, allowing a chimaeric antibody chain to be produced from a site other than the endogenous heavy region. Any human heavy chain or light chain DNA construct contemplated above can be inserted into any desired position into the genome of a non-human host cell using the techniques described herein. The present invention thus also relates to cells and mammals having genomes comprising such insertions.

The invention also relates to a vector, such as a BAC, comprising a human V, D or J region in a functional arrangement with a non-human mammal promoter, or other control sequence, such that the expression of the human V, D or J region is under the control of the non-human mammal promoter in a cell of the non-human mammal, such as an ES cell, in particular once inserted into the genome of that cell.

The invention also relates to cells and non-human mammals containing said cells, which cells or mammals have a human V, D or J region in a functional arrangement with a non-human mammal promoter, or other control sequence, such that the expression of the human V, D or J region is under the control of the non-human mammal promoter in the cells or mammal.

Generally, one aspect of the invention thus relates to a non-human mammal host cell capable of expression of a human V, D or J coding sequence under the control of a host promoter or control region, the expression capable of producing a humanised antibody having a human variable domain and non-human mammal constant region.

In one aspect the invention relates to a cell, such as a non mammalian cell, such as an ES cell, the genome of which comprises
  (a) a plurality of human IgH V regions, one or more human D regions and one or more human J regions upstream of the host non-human mammal constant region; and
  (b) optionally one or more human Ig light chain kappa V regions and one or more human Ig light chain kappa J regions upstream of the host non-human mammal kappa constant region and/or one or more human Ig light chain lambda V regions and one or more human Ig light chain lambda J regions upstream of the host non-human mammal lambda constant region;

In another aspect the invention relates to a cell, such as a non-human mammal cells, such as ES cells whose genome comprises
  (a) a plurality of human Ig light chain kappa V regions and one or more human Ig light chain kappa J regions upstream of the host non-human mammal kappa constant region and/or a plurality of human Ig light chain lambda V regions and one or more human Ig light chain lambda J regions upstream of the host non-human mammal lambda constant region; and
  (b) optionally one or more human IgH V regions, one or more human D regions and one or more human J regions upstream of the host non-human mammal constant region In one aspect the cell is an ES cell is capable of developing into a non-human mammal able to produce a repertoire of antibodies which are chimaeric, said chimaeric antibodies having a non-human mammal constant region and a human variable region. Optionally the genome of the cell is modified to prevent expression of fully host-species specific antibodies.

In one aspect the cell is an induced pluripotent stem cell (iPS cell).

In one aspect cells are isolated non-human mammalian cells.

In one aspect a cell as disclosed herein is preferably a non-human mammalian cell.

In one aspect the cell is a cell from a mouse strain selected from C57BL/6, M129 such as 129/SV, BALB/c, and any hybrid of C57BL/6, M129 such as 129/SV, or BALB/c.

The invention also relates to a cell line which is grown from or otherwise derived from cells as described herein, including an immortalised cell line. The cell line may comprise inserted human V, D or J genes as described herein, either in germline configuration or after rearrangement following in vivo maturation. The cell may be immortalised by fusion (eg, electrofusion or using PEG according to standard procedures.) to a tumour cell (eg, P3X63-Ag8.653 (obtainable from LGC Standards; CRL-1580), SP2/0-Ag14 (obtainable from ECACC), NSI or NS0), to provide an antibody producing cell and cell line, or be made by direct cellular immortalisation.

The present invention also relates to vectors for use in the invention. In one aspect such vectors are BACs (bacterial artificial chromosomes). It will be appreciated that other cloning vectors may be used in the invention, and therefore reference to BACs herein may be taken to refer generally to any suitable vector.

In one aspect BACs used for generation of human DNA to be inserted, such as the VDJ or VJ regions are trimmed so that in the final human VDJ or VJ region or part thereof in the non-human mammal, no sequence is duplicated or lost when compared to the original human genomic sequence.

In one aspect the invention relates to a vector comprising an insert, preferably comprising a region of human DNA from some of the human VDJ or VJ locus, flanked by DNA which is not from that locus. The flanking DNA may comprise one or more selectable markers or one or more site specific recombination sites. In one aspect the vector comprises 2 or more, such as 3, heterospecific and incompatible site specific recombination sites. In one aspect the site specific recombination sites may be loxP sites, or variants thereof, or FRT sites or variants thereof. In one aspect the vector comprises one or more transposon ITR (inverted terminal repeat) sequences.

In one aspect the non-human animals of the invention suitably do not produce any fully humanised antibodies. In one aspect this is because there is no DNA inserted from the human constant region. Alternatively there is no human constant region DNA in the genome capable of forming an antibody in conjunction with the inserted human variable region DNA component, for example due to mutation within any human constant region DNA or distance from any constant region human DNA and human variable region DNA.

In one aspect human light chain constant region DNA may be included in the cell genome, such that a fully human lambda or kappa human antibody chain might be generated, but this would only be able to form an antibody with a chimaeric heavy chain, and not produce a fully human antibody having human variable and constant regions.

In one aspect the non-human mammal genome is modified to prevent expression of fully host-species specific antibodies. Fully host species specific antibodies are antibodies that have both variable and constant regions from the host organism. In this context the term 'specific' is not intended to relate to the binding of the antibodies produced by the cells or animals of the invention but rather to the origin of the DNA which encodes those antibodies.

In one aspect the non-human mammal genome is modified to prevent expression of the native (fully host species specific) antibodies in the mammal by inactivation of all or a part of the host non-human mammal Ig loci. In this context, inactivation or prevention of endogenous antibody or gene segment usage (using any inactivation technique described herein) is, for example, substantially complete inactivation or prevention (substantially 100%, ie, essentially none (eg, less than 10, 5, 4, 3, 2, 1 or 0.5%) of the endogenous antibody chain (eg, no endogenous heavy chains) is expressed). This can be determined, for example, at the antibody chain (protein) level by assessing the antibody repertoire produced by the non-human vertebrate, mammal or at the nucleotide level by assessing mRNA transcripts of antibody chain loci, eg, using RACE. In an embodiment, inactivation is more than 50% (ie, 50% or less of the antibodies or transcripts are of an endogenous antibody chain), 60%, 70%, 80%, 85%, 90%, 95%, 96%, 97%, 98% or 99%. For example, in an embodiment, endogenous heavy chain expression is substantially inactivated such that no more than 85%, 90%, 95%, 96%, 97%, 98% or 99% of the heavy chain repertoire of the vertebrate (mammal) is provided by endogenous heavy chains. For example, endogenous heavy chain expression is substantially inactivated such that substantially none of the heavy chain repertoire of the vertebrate (mammal) is provided by endogenous heavy chains. For example, in an embodiment, endogenous heavy chain expression is substantially inactivated such that no more than 85%, 90%, 95%, 96%, 97%, 98% or 99% of the kappa chain repertoire of the vertebrate (mammal) is provided by endogenous kappa chains. For example, endogenous kappa chain expression is substantially inactivated such that substantially none of the kappa chain repertoire of the vertebrate (mammal) is provided by endogenous kappa chains. For example, in an embodiment, endogenous heavy chain expression is substantially inactivated such that no more than 85%, 90%, 95%, 96%, 97%, 98% or 99% of the lambda chain repertoire of the vertebrate (mammal) is provided by endogenous lambda chains. For example, endogenous lambda chain expression is substantially inactivated such that substantially none of the lambda chain repertoire of the vertebrate (mammal) is provided by endogenous lambda chains.

In one aspect this is achieved by inversion of all or part of the non-human mammal VDJ region, or VJ region, optionally by insertion of one or more site specific recombinase sites into the genome and then use of these sites in recombinase-mediated excision or inversion of all or a part of the non-human mammal Ig locus. In one aspect a double inversion, may be employed, the first to move the V(D)Js away from the endogenous locus and then a more local inversion which puts them in the correct orientation. In one aspect a single loxP site is used to invert the non-human mammal VDJ region to a centromeric locus or telomeric locus.

In one example, a mouse or mouse cell of the invention comprises inverted endogenous heavy chain gene segments (eg, VH, D and JH, such as the entire endogenous heavy chain VDJ region) that are immediately 3' of position 119753123, 119659458 or 120918606 on an endogenous mouse chromosome 12. Optionally, the genome of the mouse or cell is homozygous for said chromosome 12.

The invention also provides:—

A cassette for inversion and inactivation of endogenous non-human vertebrate (eg, mouse or rat) antibody chain gene segments, the segments being part of an antibody chain locus sequence on a chromosome of a non-human vertebrate (eg, mouse or rat) cell (eg, ES cell) wherein the sequence is flanked at its 3' end by a site-specific recombination site (eg, lox, rox or frt), the cassette comprising a nucleotide sequence encoding an expressible label or selectable marker and a compatible site-specific recombination site (eg, lox, rox or frt) flanked by a 5' and a 3' homology arm, wherein the homology arms correspond to or are homologous to adjacent stretches of sequence in the cell genome on a different chromosome or on said chromosome at least 10, 15, 20, 25, 30, 35, 40, 45 or 50 mb away from the endogenous gene segments.

The invention also provides:—

A cassette for inversion and inactivation of endogenous mouse antibody heavy chain gene segments, the segments being part of a heavy chain locus sequence on chromosome 12 of a mouse cell (eg, ES cell) wherein the sequence is flanked at its 3' end by a site-specific recombination site (eg, lox, rox or frt), the cassette comprising a nucleotide sequence encoding an expressible label or selectable marker and a compatible site-specific recombination site (eg, lox, rox or frt) flanked by a 5' and a 3' homology arm, wherein the homology arms correspond to or are homologous to adjacent stretches of sequence in the mouse cell genome on a different chromosome or on chromosome 12 at least 10, 15, 20, 25, 30, 35, 40, 45 or 50 mb away from the endogenous gene segments.

The invention provides:—

A cassette for inversion and inactivation of endogenous mouse antibody heavy chain gene segments, the segments being part of a heavy chain locus sequence on chromosome 12 of a mouse cell (eg, ES cell) wherein the sequence is flanked at its 3' end by a site-specific recombination site (eg, lox, rox or frt), the cassette comprising a nucleotide sequence encoding an expressible label or selectable marker and a compatible site-specific recombination site (eg, lox, rox or frt) flanked by a 5' and a 3' homology arm, wherein (i) the 5' homology arm is mouse chromosome 12 DNA from coordinate 119753124 to coordinate 119757104 and the 3' homology arm is mouse chromosome 12 DNA from coordinate 119749288 to 119753123; or (ii) the 5' homology arm is mouse chromosome 12 DNA from coordinate 119659459 to coordinate 119663126 and the 3' homology arm is mouse chromosome 12 DNA from coordinate 119656536 to 119659458; or (iii) the 5' homology arm is mouse chromosome 12 DNA from coordinate 120918607 to coordinate 120921930 and the 3' homology arm is mouse chromosome 12 DNA from coordinate 120915475 to 120918606.

Embodiment (i) results in an inversion of mouse chromosome 12 from coordinate 119753123 to coordinate 114666436.

Embodiment (ii) results in an inversion of mouse chromosome 12 from coordinate 119659458 to coordinate 114666436

Embodiment (iii) results in an inversion of mouse chromosome 12 from coordinate 12091806 to coordinate 114666436.

Thus, the invention provides a mouse or mouse cell whose genome comprises an inversion of a chromosome 12, wherein the inversion comprises inverted endogenous heavy chain gene segments (eg, VH, D and JH, such as the entire endogenous heavy chain VDJ region); wherein the mouse comprises a transgenic heavy chain locus comprising a plurality of human VH gene segments, a plurality of human D segments and a plurality of human JH segments operably connected upstream of an endogenous constant region (eg, C mu) so that the mouse or cell (optionally following differentiation into a B-cell) is capable of expressing an antibody comprising a variable region comprising sequences derived from the human gene segments; and wherein the inversion is (i) an inversion of mouse chromosome 12 from coordinate 119753123 to coordinate 114666436; (ii) an inversion of mouse chromosome 12 from coordinate 119659458 to coordinate 114666436; or (iii) an inversion of mouse chromosome 12 from coordinate 12091806 to coordinate 114666436.

In one embodiment, the endogenous gene segments are from a 129-derived mouse cell (eg, segments from an AB2.1 cell) and the homology arms are isogenic DNA (ie, identical to 129-derived endogenous sequences demarcated by the respective coordinates stated in (i) to (iii) above). Thus, no new sequence is created by homologous recombination using these homology arms. In another embodiment, the arms are from a mouse strain that is different from the endogenous strain. The site-specific recombination sites are mutually compatible and mutually inverted such that, on expression of an associated recombinase enzyme (eg, Cre, Dre or Flp), recombination between the site in the inserted inversion cassette and the site flanking the endogenous gene segments is carried out, thereby inverting and moving the endogenous gene segments far upstream (5') of their original location in the heavy chain locus. This inactivates endogenous heavy chain expression. Similarly, light chain inactivation can be performed by choosing the homology arms of the inversion cassette with reference to a chromosomal region spaced at least 10, 15, 20, 25, 30, 35, 40, 45 or 50 mb away from the endogenous light chain locus, the latter comprising a site-specific recombination site that is compatible with the site in the inversion cassette.

In one embodiment, the expressible label is a fluorescent label, eg, GFP or a variant thereof (eg, YFP, CFP or RFP). Thus, a label is used instead of a selection marker, such as one that confers resistance to allow for selection of transformants.

The invention provides a method of inactivating gene segments of an endogenous antibody locus, the method comprising
  (i) Providing a non-human vertebrate cell (eg, an ES cell, eg, a mouse ES cell) whose genome comprises an antibody chain locus comprising endogenous variable region gene segments;
  (ii) Targeting a site-specific recombination site to flank the 3' of the 3'-most of said endogenous gene segments;
  (iii) Targeting a second site-specific recombination site at least 10 mb away from said endogenous gene segments, the second site being compatible with the first site inverted with respect to the first site;
  (iv) Expressing a recombinase compatible with said sites to effect site-specific recombination between said sites, thereby inverting and moving said gene segments away from said locus, wherein the endogenous gene segments are inactivated; and
  (v) Optionally developing the cell into a progeny cell or vertebrate (eg, mouse or rat) whose genome is homozygous for the inversion.

The genome of the progeny cell or vertebrate can comprise transgenic heavy and/or light chain loci, each capable of expressing antibody chains comprising human variable regions. Optionally, endogenous heavy and kappa light chain expression is inactivated by inverting endogenous heavy and kappa variable region gene segments according to the method of the invention. Optionally, endogenous lambda chain expression is also inactivated in this way.

In an alternative to the method and inversion cassettes of the invention, instead of inverting and moving variable region gene segments only, other parts of the endogenous locus can alternatively or additionally be inverted and moved to effect inactivation. For example, one or more endogenous regulatory elements (eg, Smu and/or Emu) and/or one or more endogenous constant regions (eg, Cmu and/or Cgamma) can be inverted and moved.

Sites that "flank" in the above contexts of the invention can be provided such that a site-specific recombination site immediately flanks the endogenous sequence or is spaced therefrom, eg, by no more than 250, 200, 250, 100, 50 or 20 kb in the 3' direction.

In one aspect the non-human mammal genome into which human DNA is inserted comprises endogenous V, (D) and J regions, and the endogenous sequences have not been deleted.

The invention comprises a method for insertion of multiple DNA fragments into a DNA target, suitably to form a contiguous insertion in which the inserted fragments are joined together directly without intervening sequences. The method is especially applicable to the insertion of a large DNA fragment into a host chromosome which can be carried out in a stepwise fashion.

In one aspect the method comprises insertion of a first DNA sequence into a target, the sequence having a DNA vector portion and a first sequence of interest (X1); insertion of a second DNA sequence into the vector portion of the first sequence, the second DNA sequence having a second sequence of interest (X2) and a second vector portion; and then excising any vector sequence DNA separating X1 and X2 to provide a contiguous X1X2, or X2X1 sequence within the target. There is optionally insertion of a further one or more DNA sequences, each DNA sequence having a further sequence of interest (X3, . . . ) and a further vector portion, into the vector portion of the preceding DNA sequence, to build up a contiguous DNA fragment in the target.

The DNA target for insertion of the first DNA sequence may be a specific site or any point in the genome of a particular cell.

The general method is described herein in relation to the insertion of elements of the human VDJ region, but is applicable to insertion of any DNA region, from any organism, and in particular insertion of large DNA fragments of >100 kB, such as 100-250 kb, or even larger, such as that of the TCR or HLA. Features and approaches described herein in respect of the VDJ insertion may be equally applied to the any of the methods disclosed In one aspect the inserted DNA is human DNA, such as the human VDJ or VJ region, is built up in the genome of a cell, such as an ES cell, in a stepwise manner using 2, 3, 4, 5, 6, 7, 8, 9, 10, 11, 12, 13, 14, 15, 20 or more separate insertions for each heavy chain or light chain region. Fragments are suitably inserted at the same or substantially the same cell locus, e.g. ES cell locus, one after another, to form the complete VDJ or VJ region, or part thereof. The present invention also relates to cells and non-human animals comprising intermediates in the process whose genomes may comprise only a partial VDJ region, such as only human variable region DNA.

In a further aspect the method for producing a transgenic non-human mammal comprises the insertion of human VDJ or VJ regions upstream of the host non-human mammal constant region by step-wise insertion of multiple fragments by homologous recombination, preferably using an iterative process. Suitably fragments of approximately 100 KB from the human VDJ and VJ locus are inserted, suitably to form part of, or a complete, VDJ or VJ region after the final iteration of the insertion process, as disclosed herein.

In one aspect the insertion process commences at a site where an initiation cassette has been inserted into the genome of a cell, such as an ES cell, providing a unique targeting region. In one aspect the initiation cassette is inserted in the non-human mammal heavy chain locus, for use in insertion of human heavy chain DNA. Similarly an initiation cassette may be inserted in the non-human mammal light chain locus, for use in insertion of human light chain VJ DNA The initiation cassette suitably comprises a vector backbone sequence with which a vector having a human DNA fragment in the same backbone sequence can recombine to insert the human DNA into the cell (e.g. ES) cell genome, and suitably a selection marker, such as a negative selection marker. Suitably the vector backbone sequence is that of a BAC library, to allow BACs to be used in the construction of the ES cells and mammals. The vector backbone sequence may however be any sequence which serves as a target site into which a homologous sequence can insert, for example by homologous recombination, for example RMCE, and is preferably not DNA encoding any of the VDJ or constant region.

In one aspect the insertion of the first DNA fragment into an initiation cassette is followed by insertion of a second DNA fragment into a portion of the first DNA fragment, suitably a part of the vector backbone of the second DNA fragment. In one aspect an inserted DNA fragment comprises a part of the human VDJ region flanked by 5' and/or 3' sequences that are not from the human VDJ region. In one aspect the 5' and/or 3' flanking sequences may each contain one or more selectable markers, or be capable of creating a selectable system once inserted into the genome. In one aspect one or both flanking sequences may be removed from the genome in vitro, or in vivo, following insertion. In one aspect the method comprises insertion of a DNA fragment followed by selection of both 5' and 3' ends of the inserted fragment flanking the human VDJ DNA. In one aspect the iterative insertion is made by insertion of DNA fragments at the 5' end of the previous inserted fragment, and in this aspect there may be deletion in vivo of the vector DNA which separates the inserted human DNA sequences, to provide a contiguous human DNA sequence.

In one aspect insertion of human VDJ DNA into a genome may be achieved without leaving any flanking DNA in the genome, for example by transposase mediate DNA excision. One suitable transposase is the Piggybac transposase.

In one aspect the first human variable region fragment is inserted by homologous recombination at the initiation cassette backbone sequence and then the DNA of any negative selection marker and initiation cassette are subsequently removed by recombination between recombinase target sequences, such as FRT using in this example, FLPase expression. Generally repeated targeted insertions at the (e.g. BAC) backbone initiation sequence and subsequent removal by rearrangement between recombinase target sequences are repeated to build up the entire human VDJ region upstream of the host non-mammal constant region.

In one aspect a selectable marker or system may be used in the method. The marker may be generated upon insertion of a DNA fragment into a genome, for example forming a selectable marker in conjunction with a DNA element already present in the genome.

In one aspect the cell (e.g. ES) cell genome does not contain 2 identical selectable markers at the same time during the process. It can be seen that the iterative process of insertion and selection can be carried out using only 2 different selection markers, as disclosed in the examples herein, and for example the third selectable marker may be identical to the first marker, as by the time of insertion of the third vector fragment the first vector fragment and the first marker has been removed.

In one aspect a correct insertion event, is confirmed before moving to the next step of any multistep cloning process, for example by confirmation of BAC structure using high density genomic arrays to screen ES cells to identify those with intact BAC insertions, sequencing and PCR verification.

Initiation cassette (also called a "landing pad")

The invention also relates to a polynucleotide 'landing pad' sequence, the polynucleotide comprising nucleic acid regions homologous to regions of a target chromosome to allow for insertion by homologous recombination into the target chromosome, and comprising a nucleic acid site which permits recombinase-driven insertion of nucleic acid into the landing pad. The invention also relates to vectors, cells and mammals of the invention comprising a landing pad as disclosed herein inserted into the genome of the cell.

The landing pad optionally comprises a non-endogenous S-mu, e.g. a rat S-mu switch The landing pad optionally comprises (in 5' to 3' orientation) a mouse Eμ sequence, a non-human, non-mouse (e.g. rat) Switch μ and at least a portion of a mouse Cμ or the entire mouse Cμ.

The rat switch sequence optionally comprises or consists of SEQ ID NO 1.

The landing pad optionally comprises the 5' homology arm of SEQ ID NO 6.

The landing pad optionally has the sequence of SEQ ID 2 or SEQ ID NO 3.

In one embodiment, the landing pad comprises an expressible label. For example the label is a fluorescent label, eg, GFP or a variant thereof (eg, YFP, CFP or RFP). Thus, a label is used instead of a selection marker (such as one that confers resistance to allow for selection of transformants).

In an embodiment, the landing pad comprises 5' and 3' homology arms for insertion into the cell genome using homologous recombination. The homology arms can be isogenic DNA (eg, identical to 129-derived endogenous sequences of when a 129-derived ES cell is used). Thus, no new sequence is created by homologous recombination using these homology arms. In another embodiment, the arms are from a mouse strain that is different from the endogenous strain (ES cell strain).

The methods of the invention include methods wherein the landing pad sequence comprises any of the configurations or sequences as disclosed herein.

Another method of the invention comprises the step of insertion of the landing pad into a mouse chromosome by homologous recombination between mouse J1-4 and mouse C mu sequences.

Another method of the invention comprises the step of insertion of the landing pad into the mouse chromosome 12 by homologous recombination between mouse J1-4 and E mu.

In one aspect the method uses site specific recombination for insertion of one or more vectors into the genome of a cell, such as an ES cell. Site specific recombinase systems are well known in the art and may include Cre-lox, and FLP/FRT or combinations thereof, in which recombination occurs between 2 sites having sequence homology.

Additionally or alternatively to any particular Cre/Lox or FLP/FRT system described herein, other recombinases and sites that may be used in the present invention include Dre recombinase, rox sites, and PhiC31 recombinase.

Suitable BACs are available from the Sanger centre, see "A genome-wide, end-sequenced 129Sv BAC library resource for targeting vector construction". Adams D J, Quail M A, Cox T, van der Weyden L, Gorick B D, Su Q, Chan W I, Davies R, Bonfield J K, Law F, Humphray S, Plumb B, Liu P, Rogers J, Bradley A. Genomics. 2005 December; 86(6):753-8. Epub 2005 Oct. 27. The Wellcome Trust Sanger Institute, Hinxton, Cambridgeshire CB10 ISA, UK. BACs containing human DNA are also available from, for example, Invitrogen™. A suitable library is described in Osoegawa K et al, Genome Research 2001. 11: 483-496.

In one aspect a method of the invention specifically comprises:

(1) insertion of a first DNA fragment into a non-human ES cell, the fragment containing a first portion of human VDJ or VJ region DNA and a first vector portion containing a first selectable marker;

(2) optionally deletion of the a part of the first vector portion;

(3) insertion of a second DNA fragment into a non-human ES cell containing the first DNA fragment, the insertion occurring within the first vector portion, the second DNA fragment containing a second portion of the human VDJ or VJ region and a second vector portion containing a second selectable marker, (4) deletion of the first selectable marker and first vector portion, preferably by a recombinase enzyme action;

(5) insertion of a third DNA fragment into a non-human ES cell containing the second DNA fragment, the insertion occurring within the second vector portion, the third DNA fragment containing a third portion of the human VDJ or VJ region and a third vector portion containing third selectable marker, (6) deletion of the second selectable marker and second vector portion; and (7) iteration of the steps of insertion and deletion, as necessary, for fourth and further fragments of the human VDJ or VJ human regions, as necessary, to produce an ES cell with a part or all of the human VDJ or VJ region inserted as disclosed herein, and suitably to remove all the vector portions within the ES cell genome.

In another aspect the invention comprises (1) insertion of DNA forming an initiation cassette into the genome of a cell;

(2) insertion of a first DNA fragment into the initiation cassette, the first DNA fragment comprising a first portion of a human DNA and a first vector portion containing a first selectable marker or generating a selectable marker upon insertion;

(3) optionally removal of part of the vector DNA (4) insertion of a second DNA fragment into the vector portion of the first DNA fragment, the second DNA fragment containing a second portion of human DNA and a second vector portion, the second vector portion containing a second selectable marker, or generating a second selectable marker upon insertion;

(5) optionally, removal of any vector DNA to allow the first and second human DNA fragments to form a contiguous sequence; and (6) iteration of the steps of insertion of human VDJ DNA and vector DNA removal, as necessary, to produce a cell with all or part of the human VDJ or VJ region sufficient to be capable of generating a chimaeric antibody in conjunction with a host constant region, wherein the insertion of one, or more, or all of the DNA fragments uses site specific recombination.

In one aspect the non-human mammal is able to generate a diversity of at least $1\times10^6$ different functional chimaeric immunoglobulin sequence combinations.

In one aspect the targeting is carried out in ES cells derived from the mouse C57BL/6N, C57BL/6J, 129S5 or 129Sv strain.

In one aspect non-human animals, such as mice, are generated in a RAG-1-deficient or a RAG-2-deficient background, or other suitable genetic background which prevents the production of mature host B and T lymphocytes.

In one aspect the non-human mammal is a rodent, suitably a mouse, and cells of the invention, are rodent cells or ES cells, suitably mouse ES cells.

The ES cells of the present invention can be used to generate animals using techniques well known in the art, which comprise injection of the ES cell into a blastocyst followed by implantation of chimaeric blastocystys into females to produce offspring which can be bred and selected for homozygous recombinants having the required insertion. In one aspect the invention relates to a chimeric animal comprised of ES cell-derived tissue and host embryo derived tissue. In one aspect the invention relates to genetically-altered subsequent generation animals, which include animals having a homozygous recombinants for the VDJ and/or VJ regions.

In a further aspect the invention relates to a method for producing an antibody specific to a desired antigen the method comprising immunizing a transgenic non-human mammal as above with the desired antigen and recovering the antibody (see e.g. Harlow, E. & Lane, D. 1998, 5$^{th}$ edition, Antibodies: A Laboratory Manual, Cold Spring Harbor Lab. Press, Plainview, N.Y.; and Pasqualini and Arap, Proceedings of the National Academy of Sciences (2004) 101:257-259). Suitably an immunogenic amount of the antigen is delivered. The invention also relates to a method for detecting a target antigen comprising detecting an antibody produced as above with a secondary detection agent which recognises a portion of that antibody.

In a further aspect the invention relates to a method for producing a fully humanised antibody comprising immunizing a transgenic non-human mammal as above with the desired antigen, recovering the antibody or cells expressing the antibody, and then replacing the non-human mammal constant region with a human constant region. This can be done by standard cloning techniques at the DNA level to replace the non-human mammal constant region with an appropriate human constant region DNA sequence—see e.g. Sambrook, J and Russell, D. (2001, 3'd edition) Molecular Cloning: A Laboratory Manual (Cold Spring Harbor Lab. Press, Plainview, N.Y.).

In a further aspect the invention relates to humanised antibodies and antibody chains produced according to the present invention, both in chimaeric and fully humanised form, and use of said antibodies in medicine. The invention also relates to a pharmaceutical composition comprising such an antibodies and a pharmaceutically acceptable carrier or other excipient.

Antibody chains containing human sequences, such as chimaeric human—non-human antibody chains, are considered humanised herein by virtue of the presence of the human protein coding regions region. Fully humanised antibodies may be produced starting from DNA encoding a chimaeric antibody chain of the invention using standard techniques.

Methods for the generation of both monoclonal and polyclonal antibodies are well known in the art, and the present invention relates to both polyclonal and monoclonal antibodies of chimaeric or fully humanised antibodies produced in response to antigen challenge in non-human mammals of the present invention.

In a yet further aspect, chimaeric antibodies or antibody chains generated in the present invention may be manipulated, suitably at the DNA level, to generate molecules with antibody-like properties or structure, such as a human variable region from a heavy or light chain absent a constant region, for example a domain antibody; or a human variable region with any constant region from either heavy or light chain from the same or different species; or a human variable region with a non-naturally occurring constant region; or human variable region together with any other fusion partner. The invention relates to all such chimaeric antibody derivatives derived from chimaeric antibodies identified according to the present invention.

In a further aspect, the invention relates to use of animals of the present invention in the analysis of the likely effects of drugs and vaccines in the context of a quasi-human antibody repertoire.

The invention also relates to a method for identification or validation of a drug or vaccine, the method comprising delivering the vaccine or drug to a mammal of the invention and monitoring one or more of: the immune response, the safety profile; the effect on disease.

The invention also relates to a kit comprising an antibody or antibody derivative as disclosed herein and either instructions for use of such antibody or a suitable laboratory reagent, such as a buffer, antibody detection reagent.

The invention also relates to a method for making an antibody, or part thereof, the method comprising providing:
(i) a nucleic acid encoding an antibody, or a part thereof, obtained according to the present invention; or
(ii) sequence information from which a nucleic acid encoding an antibody obtained according to the present invention, or part thereof, can be expressed to allow an antibody to be produced.

The present invention also relates to a chimaeric antibody comprising a human variable region and a non-human vertebrate or mammal (optionally a rat or mouse) constant region (optionally a C gamma or C mu), wherein the antibody is encoded by a nucleotide sequence corresponding to the nucleotide sequence of a chimaeric heavy chain locus of a cell (optionally a B-cell, ES cell or hybridoma), the locus comprising a non-human vertebrate constant region nucleotide sequence and a rearranged VDJ nucleotide sequence produced by the in vivo rearrangement of a human V region, a human D region and a human J region, the V region being selected from one of a V1-3 region, V2-5 region, V4-4 region, V1-2 region or V6-1 region, and optionally a V1-3 or V6-1 segment. Optionally, the J region is any of JH1, JH2, JH3, JH4, JH5 or JH6, and in one aspect is JH4 or JH6. The D region is, in one aspect, any D3-9, D3-10, D6-13 or D6-19. In one example, rearranged VDJ nucleotide sequence is produced by the in vivo rearrangement of human V1-3 and JH4 (optionally with D3-9, D3-10, D6-13 or D-19); or V1-3 and JH6 (optionally with D3-9, D3-10, D6-13 or D-19); or V6-1 and JH4 (optionally with D3-9, D3-10, D6-13 or D-19); or V6-1 and JH6 (optionally with D3-9, D3-10, D6-13 or D-19). In one example the rearranged VDJ nucleotide sequence is produced by the in vivo rearrangement of human V6-1 DH3-10, V1-3 DH3-10, V1-3 DH6-19, V1-3 Dh3-9 or V6-1 DH6-19. In one aspect the antibody comprises any combination exemplified in the Examples and Figures herein. Optionally, the in vivo rearrangement is in a cell (eg, B cell or ES cell) derived from the same non-human vertebrate species as the constant region sequence (eg, a mouse B cell or ES cell). The invention also relates to a non-human vertebrate or mammal cell (eg, a B-cell or ES cell or hybridoma) whose genome comprises a chimaeric heavy chain locus as described above in this paragraph. The invention also relates to a non-human vertebrate or mammal (eg, a mouse or rat) whose genome comprises a chimaeric heavy chain locus as described above in this paragraph.

The present invention also relates to a non-human vertebrate or mammal having a genome encoding a chimaeric antibody, the chimaeric antibody comprising a human variable region and a non-human vertebrate or mammal (optionally a rat or mouse) constant region (optionally a C gamma or C mu), the mammal:
- expressing more V1-3 antibodies than V2-5, V4-4, V1-2 or V6-1 antibodies; and/or
- expressing more V1-3 JH4 or V1-3 JH6 antibodies than any of, individually, V1-3 JH1, V1-3 JH2, V1-3 JH3 or V1-3 JH5 antibodies, and/or
- expressing more V6-1 JH4 or V6-1 JH6 antibodies than any of, individually, V6-1 JH1, V6-1 JH2, V6-1 JH3 or V6-1 JH5 antibodies and/or
- expressing a greater number of V1-3 DH3-10 antibodies than antibodies V1-3 with any other D region. Expression of antibodies can be assessed by methods readily available to the skilled person and as conventional in the art. For example, expression can be assessed at the mRNA level as shown in the examples below.

The invention also relates to a chimaeric antibody comprising a human variable region and a non-human vertebrate or mammal (optionally a rat or mouse) constant region (optionally a light chain constant region), wherein the antibody is obtainable from a mammal (optionally a rat or mouse) whose genome comprises an antibody chain locus comprising a germline human kappa V1-8 and germline human kappa J1 sequence, and wherein the antibody is obtainable by in vivo recombination in said mammal of the V1-8 and J1 sequences and wherein the antibody has a variable region sequence which is different from that which is encoded by germline human kappa V1-8 and germline human kappa J1 sequences. Thus, in this aspect of the invention the human germline sequences are able to undergo productive rearrangement to form a coding sequence which, in conjunction with the non-human constant region sequence, can be expressed as a chimaeric antibody chain having at least a complete human variable region and a non-human constant region. This is in contrast (as the examples show below) to the combination of the germline human kappa V1-8 and germline human kappa J1 sequences per se, which do not provide for an antibody coding sequence (due to the inclusion of stop codons). In one aspect the rearranged sequence of the chimaeric antibody is a result of somatic hypermutation. In one aspect the antibody is a kappa antibody; in another aspect the antibody comprises a non-human heavy chain constant region (eg, a rat or mouse C gamma or C mu). The antibody sequence optionally comprises a $X_1X_2$ T F G Q, where $X_1X_2$=PR, RT, or PW (SEQ ID No 21); optionally a $X_1X_2$ T F G Q G T K V E I K R A D A (SEQ ID No 22) motif. Such motifs are not found in the equivalent position in the germline sequence as shown in the examples. The invention also relates to a non-human vertebrate or mammal cell (eg, a B-cell or ES cell or hybridoma) whose genome comprises a chimaeric antibody chain locus as described above in this paragraph. The invention also relates to a non-human vertebrate or mammal (eg, a mouse or rat) whose genome comprises a chimaeric antibody chain locus as described above in this paragraph.

The invention also relates to a chimaeric antibody comprising a human variable region and a non-human vertebrate or mammal (optionally a rat or mouse) constant region (optionally a light chain constant region), wherein the antibody is obtainable from a mammal (optionally a rat or mouse) whose genome comprises an antibody chain locus comprising a germline human kappa V1-6 and germline human kappa J1 sequence, and wherein the antibody is obtainable by in vivo recombination in said mammal of the V1-6 and J1 sequences and wherein the antibody has a variable region sequence which is different from that which is encoded by germline human kappa V1-6 and germline human kappa J1 sequences. Thus, in this aspect of the invention the human germline sequences are able to undergo productive rearrangement to form a coding sequence which, in conjunction with the non-human constant region sequence, can be expressed as a chimaeric antibody chain having at least a complete human variable region and a non-human constant region. This is in contrast (as the examples show below) to the combination of the germline human kappa V1-6 and germline human kappa J1 sequences per se, which do not provide for an antibody coding sequence (due to the inclusion of stop codons). In one aspect the rearranged sequence of the chimaeric antibody is a result of somatic hypermutation. In one aspect the antibody is a kappa antibody; in another aspect the antibody comprises a non-human heavy chain constant region (eg, a rat or mouse C gamma or C mu). The antibody sequence optionally comprises a $X_3X_4$ T F G Q, where $X_3X_4$=PR or PW (SEQ ID No 23); optionally a $X_3X_4$ T F G Q G T K V E I K R A D A (SEQ ID No 24) motif. Such motifs are not found in the equivalent position in the germline sequence as shown in the examples. The invention also relates to a non-human vertebrate or mammal cell (eg, a B-cell or ES cell or hybridoma) whose genome comprises a chimaeric antibody chain locus as described above in this paragraph. The invention also relates to a non-human vertebrate or mammal (eg, a mouse or rat) whose genome comprises a chimaeric antibody chain locus as described above in this paragraph.

The invention also relates to a chimaeric antibody comprising a human variable region and a non-human (optionally a rat or mouse) constant region (optionally a C gamma or C mu or a C kappa), wherein the antibody is obtainable from a mammal (optionally a rat or mouse) whose genome comprises an antibody chain locus comprising a germline human kappa V1-5 and germline human kappa J1 sequence, and wherein the antibody is obtainable by in vivo recombination in said mammal of the V1-5 and J1 sequences. The invention also relates to a non-human vertebrate or mammal cell (eg, a B-cell or ES cell or hybridoma) whose genome comprises a chimaeric antibody chain locus as described above in this paragraph. The invention also relates to a non-human vertebrate or mammal (eg, a mouse or rat) whose genome comprises a chimaeric antibody chain locus as described above in this paragraph.

The invention also relates to a chimaeric antibody comprising a human variable region and a non-human (optionally a rat or mouse) constant region (optionally a C gamma or C mu or a C kappa), wherein the antibody is obtainable from a mammal (optionally a rat or mouse) whose genome comprises an antibody chain locus comprising a germline human kappa V1-5 and germline human kappa J4 sequence, and wherein the antibody is obtainable by in vivo recombination in said mammal of the V1-5 and J4 sequences. The invention also relates to a non-human vertebrate or mammal cell (eg, a B-cell or ES cell or hybridoma) whose genome comprises a chimaeric antibody chain locus as described above in this paragraph. The invention also relates to a non-human vertebrate or mammal (eg, a mouse or rat) whose genome comprises a chimaeric antibody chain locus as described above in this paragraph.

Antibodies of the invention may be isolated, in one aspect being isolated from the cell or organism in which they are expressed.

A non-human mammal whose genome comprises:
(a) the human IgH VDJ region upstream of the host non-human mammal constant region; and
(b) the human Ig light chain kappa V and J regions upstream of the host non-human mammal kappa constant region and/or the human Ig light chain lambda V and J regions upstream of the host non-human mammal lambda constant region;

wherein the non-human mammal is able to produce a repertoire of chimaeric antibodies having a non-human mammal constant region and a human variable region, and optionally wherein the non-human mammal genome is modified to prevent expression of fully host-species specific antibodies.

A non-human mammal ES cell whose genome comprises:
(a) the human IgH V, D and J region upstream of a non-human mammal constant region; and
(b) the human Ig locus light chain kappa V and J regions upstream of the host non-human mammal kappa constant region, and/or the human Ig locus light chain lambda V and J regions upstream of the host non-human mammal lambda constant region wherein the ES cell is capable of developing into a non-human mammal, being able to produce a repertoire of antibodies which are chimaeric, having a non-human mammal constant region and a human variable region.

A method for producing a transgenic non-human mammal able to produce a repertoire of chimaeric antibodies, the antibodies having a non-human mammal constant region and a human variable region, the method comprising inserting by homologous recombination into a non-human mammal ES cell genome
(a) the human IgH VDJ region upstream of the host non-human mammal heavy chain constant region, and
(b) the human IgL VJ region for lambda or kappa chains upstream of the host non-human mammal lambda or kappa chain constant region, respectively such that the non-human mammal is able to produce a repertoire of chimaeric antibodies having a non-human mammal constant region and a human variable region, wherein steps (a) and (b) can be carried out in either order and each of steps (a) and (b) can be carried out in a stepwise manner or as a single step.

In one aspect the insertion of human VDJ or VJ regions upstream of the host non-human mammal constant region is accomplished by step-wise insertion of multiple fragments by homologous recombination.

In one aspect the step-wise insertions commence at a site where an initiation cassette has been inserted into the genome of an ES cell providing a unique targeting region consisting of a BAC backbone sequence and a negative selection marker.

In one aspect the first human variable region fragment is inserted by homologous recombination at the initiation cassette BAC backbone sequence and said negative selection marker and initiation cassette are subsequently removed by recombination between recombinase target sequences.

In one aspect repeated targeted insertions at the BAC backbone initiation sequence and subsequent removal of the backbone by rearrangement between recombinase target sequences is repeated to build up the entire human VDJ region upstream of the host non-mammal constant region.
Insertion of Human Variable Region Gene Segments Precisely within the Endogenous Mouse JH4-Cmu Intron There is further provided a cell or non human mammal according to the invention wherein the mammal is a mouse or the cell is a mouse cell and wherein the insertion of the human heavy chain DNA is made in a mouse genome between coordinates 114,667,091 and 114,665,190 of mouse chromosome 12.

There is further provided a cell or non human mammal according to the invention wherein the insertion of the human heavy chain DNA is made at coordinate 114,667,091.

There is further provided a cell or non human mammal according to the invention wherein the human IgH VDJ region comprises nucleotides 105,400,051 to 106,368,585 from human chromosome 14 (coordinates refer to NCBI36 for the human genome).

There is further provided a method, cell or non human mammal according to the invention wherein a human coding region DNA sequence is in a functional arrangement with a non-human mammal control sequence, such that transcription of the human DNA is controlled by the non-human mammal control sequence. In one example, the initiation cassette is inserted between the mouse J4 and C alpha exons. There is further provided an initiation cassette suitable for use in the method comprising a vector backbone sequence and a selection marker.

The invention provides the following aspects (starting at aspect number 103):—

103. A cell or non human mammal according to any one of the above configurations, examples, embodiments or aspects, wherein the mammal is a mouse or the cell is a mouse cell and wherein the insertion of the human heavy chain DNA is made in a mouse genome between coordinates 114,667,091 and 114,665,190 of mouse chromosome 12.

104. A cell or non human mammal according to any one of the above configurations, examples, embodiments or aspects, wherein the insertion of the human heavy chain DNA is made at coordinate 114,667,091.

105. A cell or mammal according to any one of the above configurations, examples, embodiments or aspects, wherein the human IgH VDJ region comprises nucleotides 105,400,051 to 106,368,585 from human chromosome 14 (coordinates refer to NCBI36 for the human genome).

106. A method, cell or mammal according to any one of the above configurations, examples, embodiments or aspects, wherein a human coding region DNA sequence is in a functional arrangement with a non-human mammal control sequence, such that transcription of the human DNA is controlled by the non-human mammal control sequence.

107. A method according to aspect 106 wherein the initiation cassette is inserted between the mouse J4 and C alpha exons.

108. An initiation cassette suitable for use in the method of aspect 107 comprising a vector backbone sequence and a selection marker.

Inactivation of endogenous antibody chain expression by insertion of human antibody variable region gene segments 109. A non-human vertebrate (optionally a mouse or rat) or non-human vertebrate cell (optionally a mouse or rat cell) having a genome that
(i) comprises a transgenic antibody chain locus capable of expressing an antibody chain comprising a human variable region (optionally following antibody gene rearrangement); and (ii) is inactivated for endogenous non-human vertebrate antibody chain expression; wherein the transgenic locus comprises (iii) a DNA sequence comprising a plurality of human antibody variable region gene segments inserted between endogenous antibody variable region gene segments and an endogenous antibody constant region, whereby endogenous antibody chain expression is inactivated.

The transgenic locus is a heavy chain or light chain locus.

Inactivation of endogenous heavy chain expression in non-human vertebrates such as mice and rats has involved the deletion of all or part of the endogenous heavy chain VDJ region (including sequences between gene segments). The ADAM6 genes are present in the endogenous mouse VDJ region. In mouse, there are two copies of ADAM6 (ADAM6a, ADAM6b) located between the VH and D gene segments in the IgH locus of chromosome 12 (in the intervening region between mouse VH5-1 and D1-1 gene segments). These two adjacent intronless ADAM6 genes have 95% nucleotide sequence identity and 90% amino acid identity. In human and rat, there is only one ADAM6 gene. Expression pattern analysis of mouse ADAM6 shows that it is exclusively expressed in testis [1]. Although ADAM6 transcripts can be detected in lymphocytes, it is restricted to the nucleus, suggesting that the transcription of ADAM6 gene in particular was due to transcriptional read-through from the D region rather than active messenger RNA production [2]. In rat, ADAM6 is on chromosome 6.

Mature ADAM6 protein is located on the acrosome and the posterior regions of sperm head. Notably, ADAM6 forms a complex with ADAM2 and ADAM3, which is required for fertilization in mice [3]. Reference [4] implicates ADAM6 in a model where this protein interacts with ADAM3 after ADAM6 is sulphated by TPST2, sulphation of ADAM6 being critical for stability and/or complex formation involving ADAM6 and ADAM3, and thus ADAM6 and ADAM3 are lost from Tpst2-null sperm. The study observes that Tpst2-deficient mice have male infertility, sperm mobility defects and possible abnormalities in sperm-egg membrane interactions.

Thus, the maintenance of ADAM6 expression in sperm is crucial for fertility. Thus, it is thought that transgenic male mice and rats in which ADAM6 genes have been deleted are not viably fertile. This hampers breeding of colonies and hampers the utility of such mice as transgenic antibody-generating platforms. It would be desirable to provide improved non-human transgenic antibody-generating vertebrates that are fertile.

[1]. Choi I, et. al., Characterization and comparative genomic analysis of intronless Adams with testicular gene expression. Genomics. 2004 April; 83(4):636-46.

[2]. Featherstone K, Wood A L, Bowen A J, Corcoran A E. The mouse immunoglobulin heavy chain V-D intergenic sequence contains insulators that may regulate ordered V(D)J recombination. J Biol Chem. 2010 Mar. 26; 285 (13):9327-38. Epub 2010 Jan. 25.

[3]. Han C, et. al., Comprehensive analysis of reproductive ADAMs: relationship of ADAM4 and ADAM6 with an ADAM complex required for fertilization in mice. Biol Reprod. 2009 May; 80(5):1001-8. Epub 2009 Jan. 7.

[4]. Marcello et al, Lack of tyrosylprotein sulfotransferase-2 activity results in altered sperm-egg interactions and loss of ADAM3 and ADAM6 in epididymal sperm, J Biol. Chem. 2011 Apr. 15; 286(15):13060-70. Epub 2011 Feb. 21.

According to aspect 109 of the invention, inactivation does not involve deletion of the VDJ region or part thereof including endogenous ADAM6, but instead inactivation by insertion allows for the preservation of endogenous ADAM6 and thus does not risk infertility problems.

The final mouse resulting from the method (or a mouse derived from a cell produced by the method) is in one embodiment a male, so that the invention improves upon the prior art male transgenic mice that are infertile as a result of genomic manipulation. Fertile mice produce sperm that can fertilise eggs from a female mouse. Fertility is readily determined, for example, by successfully breeding to produce an embryo or child mouse. In another embodiment, the method of the invention makes a final female mouse. Such females are, of course, useful for breeding to create male progeny carrying ADAM6 and which are fertile.

In one embodiment of aspect 109, the genome is homozygous for the transgenic locus. For example, the genome is homozygous for endogenous ADAM6 genes.

In one embodiment of the vertebrate of aspect 109, the genome is inactivated for expression of endogenous heavy and kappa (and optionally also lambda) chains.

In one embodiment, in part (iii) of aspect 109 said DNA comprises human VH, D and JH gene segments or human VL and JL gene segments (eg, Vκ and Jκ gene segments). In an example, the DNA comprises a landing pad having a selectable marker, eg, a HPRT gene, neomycin resistance gene or a puromycin resistance gene; and/or a promoter.

In one embodiment, in part (iii) of aspect 109 the endogenous gene segments are the entire endogenous VDJ region of a heavy chain locus and/or the endogenous constant region is a Cmu or Cgamma.

In one embodiment, in part (iii) of aspect 109 the endogenous gene segments are the entire endogenous VJ region of a kappa chain locus and/or the endogenous constant region is a Ckappa In one embodiment, in part (iii) of aspect 109 the endogenous gene segments are the entire endogenous VJ region of a lambda chain locus and/or the endogenous constant region is a Clambda.

The non-human vertebrate cell can be a hybridoma, B-cell, ES cell or an IPS cell. When the cell is an ES cell or IPS cell, the endogenous antibody chain expression is inactivated following differentiation of the cell into a progeny B-cell (eg, in a B-cell in a non-human vertebrate).

The invention further provides:—

110. The vertebrate or cell according to aspect 109, wherein said plurality of human antibody gene segments comprises at least 11 human V segments and/or at least 6 human J segments, eg at least 11 human VH gene segments and at least 6 human JH segments and optionally also at least 27 human D segments; optionally with the human inter-gene segment intervening sequences. In an embodiment, the human antibody gene segments are provided by a stretch of DNA sequence of human chromosome 14, comprising the gene segments and intervening sequences in germline configuration.

111. The vertebrate or cell according to aspect 109 or 110, wherein said inserted DNA sequence comprises a human nucleotide sequence comprising said antibody gene segments, wherein the nucleotide sequence is at least 110, 130, 150, 170, 190, 210, 230, 250, 270 or 290 kb. In an embodiment, the nucleotide sequence corresponds to a stretch of DNA sequence of human chromosome 14, comprising the gene segments and intervening sequences in germline configuration, eg, at least a sequence corresponding to the nucleotide sequence from coordinate 106328951 to coordinate 106601551 of a human chromosome 14, eg, a sequence in the GRCH37/hg19 sequence database.
112. The vertebrate or cell according to aspect 109, wherein the transgenic locus is a light chain kappa locus and the human antibody gene segments are between the 3'-most endogenous Jλ gene segment and endogenous Ck; optionally wherein the human antibody gene segments comprise five functional human Jλ-Cλ clusters and at least one human Vλ gene segment, eg, at least a sequence corresponding to the nucleotide sequence from coordinate 23217291 to 23327884 of a lambda locus found on a human chromosome 22.
113. The vertebrate or cell according to any one of aspects 109 to 112, wherein the transgenic locus is a heavy chain locus and the human antibody gene segments are between the 3'-most endogenous JH gene segment (eg, JH4 in a mouse genome) and endogenous Cmu.
114. The vertebrate or cell according to any one of aspects 109 to 113, wherein the genome is homozygous for said transgenic locus.
115. A mouse or mouse cell or a rat or rat cell according to any one of aspects 109 to 114.
116. A method of making a non-human vertebrate cell (optionally a mouse or rat cell), the method comprising
    (a) providing a non-human ES cell whose genome comprises an endogenous antibody chain locus comprising endogenous antibody variable region gene segments and an endogenous antibody constant region; and
    (b) making a transgenic antibody chain locus by inserting into said endogenous locus a DNA sequences comprising a plurality of human antibody variable region gene segments between said endogenous antibody variable region gene segments and said endogenous constant region, so that the human antibody variable region gene segments are operably connected upstream of the endogenous constant region,
    whereby a non-human vertebrate ES cell is produced that is capable of giving rise to a progeny cell in which endogenous antibody expression is inactivated and wherein the progeny is capable of expressing antibodies comprising human variable regions; and
    (c) optionally differentiating said ES cell into said progeny cell or a non-human vertebrate (eg, mouse or rat) comprising said progeny cell.
117. The method according to aspect 116, wherein said plurality of human antibody gene segments comprises at least 11 human V segments.
118. The method according to aspect 116 or 117, wherein said plurality of human antibody gene segments comprises at least 6 human J segments.
119. The method according to aspect 116, 117 or 118, wherein a human nucleotide sequence is inserted in step (b), the nucleotide sequence comprising said antibody gene segments, wherein the nucleotide sequence is at least 110 kb.
120. The method according to any one of aspects 110 to 113, wherein the endogenous locus is a heavy chain locus and the human antibody gene segments are between the 3'-most endogenous JH gene segment and endogenous Cmu.
121. The method according to any one of aspects 116 to 120, wherein the progeny cell is homozygous for said transgenic locus.

In one embodiment of the method of aspect 116, the method comprises inactivating the genome for expression of endogenous heavy and kappa (and optionally also lambda) chains.

In one embodiment of the method of aspect 116, in part (b) said DNA sequence comprises human VH, D and JH gene segments or human VL and JL gene segments (eg, Vκ and Jκ gene segments). In an example, the DNA comprises a landing pad having a selectable marker, eg, a HPRT gene, neomycin resistance gene or a puromycin resistance gene; and/or a promoter.

In one embodiment, in part (b) of aspect 116 the endogenous gene segments are the entire endogenous VDJ region of a heavy chain locus and/or the endogenous constant region is a Cmu or Cgamma.

In one embodiment, in part (b) of aspect 116 the endogenous gene segments are the entire endogenous VJ region of a kappa chain locus and/or the endogenous constant region is a Ckappa In one embodiment, in part (b) of aspect 116 the endogenous gene segments are the entire endogenous VJ region of a lambda chain locus and/or the endogenous constant region is a Clambda.

The non-human vertebrate cell can be a hybridoma, B-cell, ES cell or an IPS cell. When the cell is an ES cell or IPS cell, the endogenous antibody chain expression is inactivated following differentiation of the cell into a progeny B-cell (eg, in a B-cell in a non-human vertebrate).

The invention further provides:—

The method according to aspect 116, wherein said inserted DNA sequence comprises a human nucleotide sequence comprising said human antibody gene segments, wherein the nucleotide sequence is at least 110, 130, 150, 170, 190, 210, 230, 250, 270 or 290 kb. In an embodiment, the nucleotide sequence corresponds to a stretch of DNA sequence of human chromosome 14, comprising the gene segments and intervening sequences in germline configuration, eg, at least a sequence corresponding to the nucleotide sequence from coordinate 106328951 to coordinate 106601551 of a human chromosome 14, eg, a sequence in the GRCH37/hg19 sequence database.

The method according to aspect 116, wherein the transgenic locus is a light chain kappa locus and the human antibody gene segments are between the 3'-most endogenous Jk gene segment and endogenous Ck; optionally wherein the human antibody gene segments comprise five functional human Jλ-Cλ clusters and at least one human Vλ gene segment, eg, at least a sequence corresponding to the nucleotide sequence from coordinate 23217291 to 23327884 of a lambda locus found on a human chromosome 22.

The method according to aspect 116, wherein, wherein the transgenic locus is a heavy chain locus and the human antibody gene segments are inserted between the 3'-most endogenous JH gene segment (eg, JH4 in a mouse genome) and endogenous Cmu.

122. The method according to any one of aspects 116 to 121, comprising making the genome of the progeny homozygous for said transgenic locus.

Isolating antibodies from transgenic non-human vertebrates of the invention & useful antigen-specific antibodies of therapeutically-relevant affinities 123. A method of isolating an antibody that binds a predetermined antigen, the method comprising
    (a) providing a vertebrate (optionally a mammal; optionally a mouse or rat according to any one of the above configurations, examples, embodiments or aspects;

(b) immunising said vertebrate with said antigen (optionally wherein the antigen is an antigen of an infectious disease pathogen);
(c) removing B lymphocytes from the vertebrate and selecting one or more B lymphocytes expressing antibodies that bind to the antigen;
(d) optionally immortalising said selected B lymphocytes or progeny thereof, optionally by producing hybridomas therefrom; and
(e) isolating an antibody (eg, and IgG-type antibody) expressed by the B lymphocytes.
124. The method of aspect 123, comprising the step of isolating from said B lymphocytes nucleic acid encoding said antibody that binds said antigen; optionally exchanging the heavy chain constant region nucleotide sequence of the antibody with a nucleotide sequence encoding a human or humanised heavy chain constant region and optionally affinity maturing the variable region of said antibody; and optionally inserting said nucleic acid into an expression vector and optionally a host.
125. The method of aspect 123 or 124, further comprising making a mutant or derivative of the antibody produced by the method of aspect 122 or 123.

As demonstrated by the examples below, the non-human vertebrates of the invention are able to produce antigen-specific antibodies of sub-50 nM affinity with human sequences in their CDR3 regions. Thus, the invention further provides:—

126. An antibody or fragment (eg, a Fab or Fab$_2$) thereof comprising variable regions that specifically bind a predetermined antigen with a sub-50 nM affinity (optionally sub-40, 30, 20, 10, 1, 0.1 or 0.01 nM) as determined by surface plasmon resonance, wherein the antibody is isolated from a non-human vertebrate (optionally a mammal; optionally a mouse or rat) according to any one of the above configurations, examples, embodiments or aspects and comprises heavy chain CDR3s (as defined by Kabat) encoded by a rearranged VDJ of said vertebrate, wherein the VDJ is the product of rearrangement in vivo of a human JH gene segment of a heavy chain locus of said vertebrate with D (optionally a human D gene segment of said locus) and VH gene segments.

In one embodiment, the surface plasmon resonance (SPR) is carried out at 25° C. In another embodiment, the SPR is carried out at 37° C.

In one embodiment, the SPR is carried out at physiological pH, such as about pH7 or at pH7.6 (eg, using Hepes buffered saline at pH7.6 (also referred to as HBS-EP)).

In one embodiment, the SPR is carried out at a physiological salt level, eg, 150 mM NaCl.

In one embodiment, the SPR is carried out at a detergent level of no greater than 0.05% by volume, eg, in the presence of P20 (polysorbate 20; eg, Tween-20™) at 0.05% and EDTA at 3 mM.

In one example, the SPR is carried out at 25° C. or 37° C. in a buffer at pH7.6, 150 mM NaCl, 0.05% detergent (eg, P20) and 3 mM EDTA. The buffer can contain 10 mM Hepes. In one example, the SPR is carried out at 25° C. or 37° C. in HBS-EP. HBS-EP is available from Teknova Inc (California; catalogue number H8022).

In an example, the affinity of the antibody is determined using SPR by
1. Coupling anti-mouse (or other relevant non-human vertebrate) IgG (eg, Biacore BR-1008-38) to a biosensor chip (eg, GLM chip) such as by primary amine coupling;
2. Exposing the anti-mouse IgG (non-human vertebrate antibody) to a test IgG antibody to capture test antibody on the chip;
3. Passing the test antigen over the chip's capture surface at 1024 nM, 256 nM, 64 nM, 16 nM, 4 nM with a 0 nM (i.e. buffer alone); and
4. And determining the affinity of binding of test antibody to test antigen using surface plasmon resonance, eg, under an SPR condition discussed above (eg, at 25° C. in physiological buffer). SPR can be carried out using any standard SPR apparatus, such as by Biacore™ or using the ProteOn XPR36™ (Bio-Rad®).

Regeneration of the capture surface can be carried out with 10 mM glycine at pH1.7. This removes the captured antibody and allows the surface to be used for another interaction. The binding data can be fitted to 1:1 model inherent using standard techniques, eg, using a model inherent to the ProteOn XPR36™ analysis software.

The invention also relates to an scFv, diabody or other antibody fragment comprising a VH and VL domain from an antibody or fragment of aspect 126 (optionally following affinity maturation, eg, by phage display).

In one embodiment, the antigen is a serpin, eg, ovalbumin, antithrombin or antitrypsin. Serpins are a group of proteins with similar structures that were first identified as a set of proteins able to inhibit proteases. The acronym serpin was originally coined because many serpins inhibit chymotrypsin-like serine proteases (serine protease inhibitors). The first members of the serpin superfamily to be extensively studied were the human plasma proteins antithrombin and antitrypsin, which play key roles in controlling blood coagulation and inflammation, respectively. Initially, research focused upon their role in human disease: antithrombin deficiency results in thrombosis and antitrypsin deficiency causes emphysema. In 1980 Hunt and Dayhoff made the surprising discovery that both these molecules share significant amino acid sequence similarity to the major protein in chicken egg white, ovalbumin, and they proposed a new protein superfamily.

127. An antibody or fragment that is identical to an antibody of aspect 126 or a derivative thereof (optionally a derivative whose constant regions are human and/or an affinity matured derivative) that specifically binds said antigen with a sub-50 nM affinity as determined by surface plasmon resonance.
128. A pharmaceutical composition comprising an antibody or fragment of aspect 126 or 127 and a pharmaceutically-acceptable diluent, excipient or carrier.
129. A nucleotide sequence encoding a heavy chain variable region of an antibody or fragment of aspect 126 or 127, optionally as part of a vector (eg, an expression vector).
130. The nucleotide sequence of aspect 129, wherein the sequence is a cDNA derived from a B-cell of the vertebrate from which the antibody of aspect 126 is isolated, or is identical to such a cDNA.
131. An isolated host cell (eg, a hybridoma or a CHO cell or a HEK293 cell) comprising a nucleotide sequence according to aspect 129 or 130.
132. A method of isolating an antibody that binds a predetermined antigen, the method comprising
(a) providing a vertebrate (optionally a mammal; optionally a mouse or rat according to any one of the above configurations, examples, embodiments or aspects;
(b) immunising said vertebrate with said antigen;
(c) removing B lymphocytes from the vertebrate and selecting a B lymphocyte expressing an antibody that binds to the antigen with sub-nM affinity, wherein the antibody is according to aspect 126;
(d) optionally immortalising said selected B lymphocyte or progeny thereof, optionally by producing hybridomas therefrom; and
(e) isolating an antibody (eg, and IgG-type antibody) expressed by the B lymphocyte.
133. The method of aspect 132, comprising the step of isolating from said B lymphocyte nucleic acid encoding said antibody that binds said antigen; optionally exchanging the heavy chain constant region nucleotide sequence of the antibody with a nucleotide sequence encoding a human or humanised heavy chain constant region and optionally affinity maturing the variable region of said antibody; and optionally inserting said nucleic acid into an expression vector and optionally a host.
134. The method of aspect 132 or 133, further comprising making a mutant or derivative of the antibody produced by the method of aspect 132 or 133.

Inactivation by inversion of endogenous VDJ to genome desert regions

135. A mouse or mouse cell comprising inverted endogenous heavy chain gene segments (eg, VH, D and JH, such as the entire endogenous heavy chain VDJ region) that are immediately 3' of position 119753123, 119659458 or 120918606 on an endogenous mouse chromosome 12, wherein the mouse comprises a transgenic heavy chain locus comprising a plurality of human VH gene segments, a plurality of human D segments and a plurality of human JH segments operably connected upstream of an endogenous constant region (eg, C mu) so that the mouse or cell (optionally following differentiation into a B-cell) is capable of expressing an antibody comprising a variable region comprising sequences derived from the human gene segments.
136. The mouse or cell of aspect 135, wherein the genome of the mouse or cell is homozygous for said chromosome 12.
137. A cassette for inversion and inactivation of endogenous non-human vertebrate (eg, mouse or rat) antibody chain gene segments, the segments being part of an antibody chain locus sequence on a chromosome of a non-human vertebrate (eg, mouse or rat) cell (eg, ES cell) wherein the sequence is flanked at its 3' end by a site-specific recombination site (eg, lox, rox or frt), the cassette comprising a nucleotide sequence encoding an expressible label or selectable marker and a compatible site-specific recombination site (eg, lox, rox or frt) flanked by a 5' and a 3' homology arm, wherein the homology arms correspond to or are homologous to adjacent stretches of sequence in the cell genome on a different chromosome or on said chromosome at least 10 mb away from the endogenous gene segments.
138. A cassette for inversion and inactivation of endogenous mouse antibody heavy chain gene segments, the segments being part of a heavy chain locus sequence on chromosome 12 of a mouse cell (eg, ES cell) wherein the sequence is flanked at its 3' end by a site-specific recombination site (eg, lox, rox or frt), the cassette comprising a nucleotide sequence encoding an expressible label or selectable marker and a compatible site-specific recombination site (eg, lox, rox or frt) flanked by a 5' and a 3' homology arm, wherein (i) the 5' homology arm is mouse chromosome 12 DNA from coordinate 119753124 to coordinate 119757104 and the 3' homology arm is mouse chromosome 12 DNA from coordinate 119749288 to 119753123; (ii) the 5' homology arm is mouse chromosome 12 DNA from coordinate 119659459 to coordinate 119663126 and the 3' homology arm is mouse chromosome 12 DNA from coordinate 119656536 to 119659458; or (iii) the 5' homology arm is mouse chromosome 12 DNA from coordinate 120918607 to coordinate 120921930 and the 3' homology arm is mouse chromosome 12 DNA from coordinate 120915475 to 120918606.
139. A method of inactivating gene segments of an endogenous antibody locus, the method comprising
(i) Providing a non-human vertebrate cell (eg, an ES cell, eg, a mouse ES cell) whose genome comprises an antibody chain locus comprising endogenous variable region gene segments;
(ii) Targeting a site-specific recombination site to flank the 3' of the 3'-most of said endogenous gene segments;
(iii) Targeting a second site-specific recombination site at least 10 mb away from said endogenous gene segments, the second site being compatible with the first site inverted with respect to the first site;
(iv) Expressing a recombinase compatible with said sites to effect site-specific recombination between said sites, thereby inverting and moving said gene segments away from said locus, wherein the endogenous gene segments are inactivated; and
(v) Optionally developing the cell into a progeny cell or vertebrate (eg, mouse or rat) whose genome is homozygous for the inversion.
140. A mouse or mouse cell whose genome comprises an inversion of a chromosome 12, wherein the inversion comprises inverted endogenous heavy chain gene segments (eg, VH, D and JH, such as the entire endogenous heavy chain VDJ region); wherein the mouse comprises a transgenic heavy chain locus comprising a plurality of human VH gene segments, a plurality of human D segments and a plurality of human JH segments operably connected upstream of an endogenous constant region (eg, C mu) so that the mouse or cell (optionally following differentiation into a B-cell) is capable of expressing an antibody comprising a variable region comprising sequences derived from the human gene segments; and wherein the inversion is (i) an inversion of mouse chromosome 12 from coordinate 119753123 to coordinate 114666436; (ii) an inversion of mouse chromosome 12 from coordinate 119659458 to coordinate 114666436; or (iii) an inversion of mouse chromosome 12 from coordinate 12091806 to coordinate 114666436.

Other aspects include:

A method for producing an antibody specific to a desired antigen the method comprising immunizing a non-human mammal as disclosed herein with the desired antigen and recovering the antibody or a cell producing the antibody.

A method for producing a fully humanised antibody comprising immunizing a non-human mammal as disclosed herein and then replacing the non-human mammal constant region of an antibody specifically reactive with the antigen with a human constant region, suitably by engineering of the nucleic acid encoding the antibody.

A method, cell or mammal as disclosed herein wherein a human coding region DNA sequence is in a functional arrangement with a non-human mammal control sequence, such that transcription of the DNA is controlled by the non-human mammal control sequence. In one aspect the human coding region V, D or J region is in a functional arrangement with a mouse promoter sequence.

The invention also relates to a humanised antibody produced according to any methods disclosed herein and use of a humanised antibody so produced in medicine.

Endogenous Light Chain Inactivation & High Expression of Human Lambda Variable Regions in Transgenic Non-Human Vertebrates & Cells As explained further in the examples below, the inventors have surprisingly observed very high expression levels of light chains comprising human lambda variable regions (at least 80% human V lambda) from transgenic light chain loci produced by targeted insertion of human lambda gene segments into endogenous non-human vertebrate light chain loci. This is possible even in the presence of endogenous non-human vertebrate V and J gene segments in the vertebrate genome. Also, the surprisingly high levels of expression are achieved when insertion of human lambda gene segments are in the endogenous kappa or lambda locus. Such high levels by targeted insertion has not hitherto been published in the art.

The inventors also surprisingly observed that endogenous kappa chain expression can be completely inactivated by targeted insertion of human lambda gene sequence into the endogenous kappa locus, as explained further in the examples.

The targeted insertion of human gene segments into endogenous Ig loci is advantageous because it enables the operable location of inserted human Ig sequences with respect to endogenous Ig constant regions and endogenous control regions, such as enhancers and other locus control regions for example. Thus, targeted insertion allows one to harness endogenous control important in one or more of Ig gene segment recombination, allelic exclusion, affinity maturation, class switching, levels of Ig expression and desirable development of the B-cell compartment. As such, targeted insertion is superior to early attempts in the art to produce transgenic Ig loci and expression, which attempts relied on the introduction into non-human vertebrate cells of vectors such as YACs bearing human Ig gene segments. YACs are randomly integrated into the vertebrate cell genome, so that it is difficult to achieve the control provided by targeted insertion and the concomitant benefits that are brought in terms of harnessing endogenous control mechanisms. In addition, random insertion often results in the inserted human Ig gene segments coming under the control of heterologous control elements and/or epigenetic chromosomal modifications such as methylation and chromatin confirmations, either of which can be detrimental to proper Ig gene segment recombination, allelic exclusion, affinity maturation, class switching, levels of Ig expression and desirable development of the B-cell compartment. Random insertion typically results in 2 or more copies of the introduced transgene which can cause chromosomal instability and therefore result in poor breeding performance of the animals in addition to detrimental effects on proper Ig gene segment recombination, allelic exclusion, affinity maturation, class switching, levels of Ig expression and desirable development of the B-cell compartment. Thus, prior art attempts using random insertion have tended to lead to poor B-cell development, relatively small B-cell compartments and inferior Ig expression and a concomitant difficulty in isolating an antibody with a desired characteristic.

The invention therefore provides the following aspects:—

≥80% human lambda variable regions

1. A non-human vertebrate (eg, a mouse or rat) whose genome comprises an Ig gene segment repertoire produced by targeted insertion of human Ig gene segments into one or more endogenous Ig loci, the genome comprising human Vλ and Jλ gene segments upstream of a constant region, wherein the human Vλ and Jλ gene segments have been provided by insertion into an endogenous light chain locus of the vertebrate, wherein the vertebrate expresses immunoglobulin light chains comprising lambda variable regions (lambda light chains), and wherein at least 80% of the variable regions of the lambda light chains expressed by the vertebrate are derived from recombination of human Vλ and Jλ gene segments. This is demonstrated in the examples below.

For example, at least 80, 84, 85, 90, 95, 96, 97, 98 or 99%, or 100% of the variable regions of the lambda light chains expressed by the vertebrate are derived from recombination of human Vλ and Jλ gene segments. This is demonstrated in the examples below.

In one embodiment, there is provided a non-human vertebrate ES cell (eg, a mouse ES cell or rat ES cell) whose genome comprises an Ig gene segment repertoire produced by targeted insertion of human Ig gene segments into one or more endogenous Ig loci, the genome comprising human Vλ and Jλ gene segments upstream of a constant region, wherein the human Vλ and Jλ gene segments have been provided by insertion into an endogenous light chain locus of the vertebrate cell, wherein the cell can develop into a vertebrate that expresses immunoglobulin light chains comprising lambda variable regions (lambda light chains), and wherein at least 80% (for example, at least 80, 84, 85, 90, 95, 96, 97, 98 or 99%, or 100%) of the variable regions of the lambda light chains expressed by the vertebrate are derived from recombination of human Vλ and Jλ gene segments.

2. The vertebrate or cell of aspect 1, optionally wherein the human Vλ and Jλ insertion comprises at least the functional human V and J gene segments (optionally also human Cλ) comprised by a human lambda chain Ig locus from Vλ2-18 to Cλ7. In one example, the insertion also comprises lambda inter-gene segment sequences. These are human sequences or they can be sequences of the non-human vertebrate species (eg, where the vertebrate is a mouse, sequences between corresponding mouse lambda gene segments can be used).

3. The vertebrate or cell of aspect 1 or 2, optionally wherein the genome is homozygous for the human Vλ and Jλ gene segment insertion and endogenous kappa chain expression in said vertebrate is substantially or completely inactive. In one example, less than 10, 5, 4, 3, 2, 1 or 0.5% of light chains are provided by endogenous kappa chains (ie, kappa chains whose variable regions are derived from recombination of non-human vertebrate V and J gene segments).

4. The vertebrate or cell of any preceding aspect, optionally wherein the endogenous locus is an endogenous kappa locus.

5. The vertebrate or cell of any preceding aspect, optionally wherein the endogenous locus is an endogenous lambda locus.

≥60% of all light chains have human lambda V regions

6. A non-human vertebrate (eg, a mouse or rat) whose genome comprises an Ig gene segment repertoire produced by targeted insertion of human Ig gene segments into one or more endogenous Ig loci, the genome comprising (i) human Vλ and Jλ gene segments upstream of a constant region, wherein the human Vλ and Jλ gene segments have been provided by insertion into an endogenous light chain locus of the vertebrate and (ii) kappa V gene segments upstream of a constant region, wherein the vertebrate expresses immunoglobulin light chains comprising human lambda variable regions (human lambda light chains), and wherein at least 60% of the light chains expressed by the vertebrate are provided by said human lambda light chains. This is demonstrated in the examples below.

For example, at least 65, 70, 80, 84, 85, 90, 95, 96, 97, 98 or 99%, or 100% of the light chains expressed by the vertebrate are provided by said human lambda light chains. For example, at least 84% of the light chains expressed by the vertebrate are provided by said human lambda light chains. For example, at least 95% of the light chains expressed by the vertebrate are provided by said human lambda light chains. This is demonstrated in the examples below.

In one embodiment, there is provided a non-human vertebrate ES cell (eg, a mouse ES cell or rat ES cell) whose genome comprises an Ig gene segment repertoire produced by targeted insertion of human Ig gene segments into one or more endogenous Ig loci, the genome comprising (i) human Vλ and Jλ gene segments upstream of a constant region, wherein the human Vλ and Jλ gene segments have been provided by insertion into an endogenous light chain locus of the vertebrate and (ii) kappa V gene segments upstream of a constant region, wherein the cell can develop into a vertebrate that expresses immunoglobulin light chains comprising human lambda variable regions (human lambda light chains), and wherein at least 60% of the light chains expressed by the vertebrate are provided by said human lambda light chains.

7. A non-human vertebrate or a non-human vertebrate cell (eg, a mouse, rat, mouse cell or a rat cell) whose genome comprises an Ig gene segment repertoire produced by targeted insertion of human Ig gene segments into one or more endogenous Ig loci, the genome comprising a targeted insertion of human immunoglobulin Vλ and Jλ gene segments into an endogenous non-human vertebrate light kappa or lambda chain locus downstream of endogenous VL and JL gene segments for expression of a light chains comprising human lambda variable regions; wherein the human Vλ and Jλ insertion comprises at least the functional human V and J (and optionally also functional human Cλ) gene segments comprised by a human lambda chain Ig locus from Vλ2-18 to Cλ7.

As demonstrated in the examples, endogenous light chain expression from said locus is inactivated and also human lambda variable region expression dominates over endogenous lambda variable region expression.

By "downstream" is meant 3' of the gene segments on the same chromosome. In one example, the endogenous V and J gene segments are inverted with respect to the human gene segments and optionally moved out of the endogenous light chain locus. In one example, the human gene segments are downstream of all of the endogenous V and J segments of said kappa or lambda locus. The possibility of retaining the endogenous V-J sequences and intergenic sequences is advantageous since embedded control regions and/or genes are retained that may be desirable in the vertebrate.

Optionally the insertion also comprises lambda inter-gene segment sequences. These are human sequences or they can be sequences of the non-human vertebrate species (eg, where the vertebrate is a mouse, sequences between corresponding mouse lambda gene segments can be used).

Expression of VJCλ Lambda Chains

8. A non-human vertebrate or a non-human vertebrate cell (eg, a mouse, rat, mouse cell or a rat cell) whose genome comprises an Ig gene segment repertoire produced by targeted insertion of human Ig gene segments into one or more endogenous Ig loci, the genome comprising a targeted insertion of human immunoglobulin Vλ, Jλ and Cλ genes into an endogenous non-human vertebrate kappa or lambda light chain locus upstream of an endogenous non-human vertebrate kappa or lambda constant region for expression of a human VJC light chain; optionally wherein the human VJC insertion comprises at least the functional human V, J and C gene segments comprised by a human lambda chain Ig locus from Vλ3-1 to Cλ7 (eg, comprised by a human lambda chain Ig locus from 2-18 to Cλ7).

As demonstrated in the examples, human lambda variable region expression dominates over endogenous kappa variable region expression. Endogenous kappa chain expression from the endogenous locus can be inactivated.

Optionally the insertion also comprises lambda inter-gene segment sequences. These are human sequences or they can be sequences of the non-human vertebrate species (eg, where the vertebrate is a mouse, sequences between corresponding mouse lambda gene segments can be used).

9. A non-human vertebrate or a non-human vertebrate cell (eg, a mouse, rat, mouse cell or a rat cell) whose genome comprises an Ig gene segment repertoire produced by targeted insertion of human Ig gene segments into one or more endogenous Ig loci, the genome comprising a targeted insertion of at least the functional human Vλ and Jλ (and optionally human functional Cλ) gene segments comprised by a human lambda chain Ig locus from Vλ3-1 to Cλ7 (optionally from Vλ2-18 to Cλ7) into an endogenous non-human vertebrate kappa light chain locus downstream of the mouse Vκ and Jκ gene segments for expression of a light chain comprising a human lambda variable region, whereby in the presence of said insertion expression of endogenous kappa light chains derived from said mouse Vκ and Jκ gene segments is substantially or completely inactivated.

In one example, less than 10, 5, 4, 3, 2, 1 or 0.5% of light chains are provided by endogenous kappa chains (ie, kappa chains whose variable regions are derived from recombination of non-human vertebrate Vκ and Jκ gene segments).

Optionally the insertion also comprises lambda inter-gene segment sequences. These are human sequences or they can be sequences of the non-human vertebrate species (eg, where the vertebrate is a mouse, sequences between corresponding mouse lambda gene segments can be used).

10. A non-human vertebrate or a non-human vertebrate cell (eg, a mouse, rat, mouse cell or a rat cell), wherein in the genome of which the mouse IgK-VJ has been moved away from the mouse Eκ enhancer, thereby inactivating endogenous IgK-VJ regions. This is demonstrated in the examples.

11. The vertebrate of cell of aspect 10, optionally wherein the IgK-VJ has been moved away from the mouse Eκ enhancer by insertion of human VL and JL gene segments between the mouse IgK-VJ and the Eκ enhancer; optionally wherein the insertion is an insertion as recited in any preceding aspect 1-9 or an insertion of human Vκ and Jκ gene segments.

12. The vertebrate or cell of any preceding aspect, optionally wherein the human Vλ and Jλ gene segments have been inserted within 100, 75, 50, 40, 30, 20, 15, 10 or 5 kb of an endogenous non-human vertebrate light chain enhancer. In one example, the enhancer is a lambda enhancer (eg, mouse Eλ2-4, Eλ4-10 or Eλ3-1) when the insertion is into an endogenous lambda locus. In one example, the enhancer is a kappa enhancer (eg, iEκ or 3'Eκ) when the insertion is into an endogenous kappa locus.

13. The vertebrate or cell of any preceding aspect, optionally wherein the human Vλ and Jλ gene segments are provided in the genome by the targeted insertion of at least 10 human Vλ gene segments with human Jλ gene segments upstream of an endogenous non-human vertebrate light chain constant region of said light chain locus. For example, the human gene segments are provided by insertion of at least a portion of a human Ig lambda chain locus from Vλ2-18 to Vλ3-1; or at least a portion of a human Ig lambda chain locus from Vλ2-18 to Vλ3-1 inserted with Jλ1, Jλ2, Jλ3, Jλ6 and Jλ7; or at least a portion of a human Ig lambda chain locus from Vλ2-18 to Cλ7 (optionally excluding Jλ4Cλ4 and/or Jλ5Cλ5).

Optionally at least 2, 3, 4 or 5 human Jλ are inserted. In one embodiment, the inserted Jλs are different from each other. For example, human Jλ1, Jλ2, Jλ3, Jλ6 and Jλ7 are inserted, optionally as part of respective human JλCλ clusters.

Optionally a human light chain enhancer, eg Eλ, is inserted. For example, insertion of human Eλ between the human Jλ segments and the endogenous constant region; or between human Cλ gene segments (when these are inserted) and the endogenous constant region.

14. The vertebrate or cell of any preceding aspect, optionally wherein the lambda light chains provide a repertoire of human lambda variable regions derived from human Vλ gene segments Vλ3-1 and optionally one or more of Vλ2-18, Vλ3-16, V2-14, Vλ3-12, Vλ2-11, Vλ3-10, Vλ3-9, Vλ2-8 and Vλ4-3 that have been provided in the genome by targeted insertion into said light chain locus.

This is useful because Vλ3-1 is a highly-used lambda gene segment in humans (FIG. 59; Ignatovich et al 1997) and thus it is desirable that cells and vertebrates of the invention provide for the inclusion of lambda variable regions based on this gene segment for selection against antigen, particularly for the development of antibody therapeutics for human use.

15. The vertebrate or cell of any preceding aspect, optionally wherein the lambda light chains provide a repertoire of human lambda variable regions derived from human Vλ gene segments Vλ2-14 and one or more of Vλ2-18, Vλ3-16, Vλ3-12, Vλ2-11, Vλ3-10, Vλ3-9, Vλ2-8, Vλ4-3 and Vλ3-1 that have been provided in the genome by targeted insertion into said light chain locus.

This is useful because Vλ2-14 is a highly-used lambda gene segment in humans and thus it is desirable that cells and vertebrates of the invention provide for the inclusion of lambda variable regions based on this gene segment for selection against antigen, particularly for the development of antibody therapeutics for human use.

The vertebrate or cell of any preceding aspect, optionally wherein the lambda light chains provide a repertoire of human lambda variable regions derived from human Vλ gene segments Vλ2-8 and one or more of Vλ2-18, Vλ3-16, V2-14, Vλ3-12, Vλ2-11, Vλ3-10, Vλ3-9, Vλ2-8, Vλ4-3 and Vλ3-1 that have been provided in the genome by targeted insertion into said light chain locus.

This is useful because Vλ2-8 is a highly-used lambda gene segment in humans and thus it is desirable that cells and vertebrates of the invention provide for the inclusion of lambda variable regions based on this gene segment for selection against antigen, particularly for the development of antibody therapeutics for human use.

The vertebrate or cell of any preceding aspect, optionally wherein the lambda light chains provide a repertoire of human lambda variable regions derived from human Vλ gene segments Vλ3-10 and one or more of Vλ2-18, Vλ3-16, V2-14, Vλ3-12, Vλ2-11, Vλ2-14, Vλ3-9, Vλ2-8, Vλ4-3 and Vλ3-1 that have been provided in the genome by targeted insertion into said light chain locus.

This is useful because Vλ3-10 is a highly-used lambda gene segment in humans and thus it is desirable that cells and vertebrates of the invention provide for the inclusion of lambda variable regions based on this gene segment for selection against antigen, particularly for the development of antibody therapeutics for human use.

16. The vertebrate or cell of any preceding aspect, optionally wherein the human Vλ gene segments comprise the functional Vλ comprised by a human lambda chain Ig locus from Vλ2-18 to Vλ3-1.

For example, the human Vλ gene segments comprise at least human V gene segment Vλ3-1 or at least segments Vλ2-18, Vλ3-16, V2-14, Vλ3-12, Vλ2-11, Vλ3-10, Vλ3-9, Vλ2-8, Vλ4-3 and Vλ3-1.

17. The vertebrate of any preceding aspect, optionally wherein the vertebrate expresses more lambda chains than kappa chains. Lambda chains comprise variable regions derived from recombination of Vλ and Jλ gene segments—for example, expressed with a lambda constant region. Kappa chains comprise variable regions derived from recombination of Vκ and Jκ gene segments—for example, expressed with a kappa constant region.

18. The vertebrate of any preceding aspect, optionally wherein the vertebrate expresses no endogenous kappa chains. For example, endogenous kappa chain expression can be inactivated by any of the means described herein, such as by inversion of all or part of the endogenous kappa VJ region or by insertion of a marker (eg, neo) or other interfering sequence in an endogenous kappa locus (a locus not comprising human lambda gene segments according to the invention).

19. The vertebrate of any preceding aspect, optionally wherein kappa chain expression is substantially or completely inactive in said vertebrate. In one example, less than 10, 5, 4, 3, 2, 1 or 0.5% of light chains are provided by kappa chains.

20. The vertebrate or cell of any preceding aspect, optionally wherein a human Eλ enhancer is inserted in said endogenous non-human vertebrate locus. For example, there is inserted a human 5' MAR and human Eλ (and optionally the human 3' MAR) in germline configuration. For example, there is inserted a sequence corresponding to the human lambda intronic region immediately 3' of human Jλ7-Cλ7 to, and including, at least the human Eλ (and optionally also the human 3' MAR)—optionally including at least 30 kb of intronic region 3' of the human Eλ.

21. The vertebrate or cell of any preceding aspect, wherein optionally at least human JC gene segments Jλ1-Cλ1, Jλ2-Cλ2, Jλ3-Cλ3, Jλ6-Cλ6 and Jλ7-Cλ7 are inserted in addition to the other human gene segments.

22. The vertebrate or cell of any preceding aspect, wherein optionally the inserted human gene segments are in germline configuration; optionally with the human inter-gene segment sequences or the corresponding endogenous non-human vertebrate inter-gene segment sequences.

23. The vertebrate or cell of any preceding aspect, wherein optionally an endogenous non-human vertebrate light chain enhancer is maintained in the endogenous locus; optionally in germline configuration. For example, when the endogenous locus is a kappa locus, an endogenous kappa enhancer is maintained. This can be the iEk and/or the 3'Ek, optionally in germline configuration with respect to an endogenous light chain constant region. This may be useful to help control of light chain expression in the non-human vertebrate or cell.

24. The vertebrate or cell of any preceding aspect, optionally wherein the genome is heterozygous for the human lambda insertion at the endogenous locus. For example, heterozygous for the human VJ or VJC insertion at an endogenous kappa (eg, mouse or rat kappa) locus. This aids and simplifies breeding of the vertebrates since the other endogenous locus (eg, the other kappa locus) can be used to provide a different transgenic Ig locus, such as a transgenic kappa locus comprising human kappa V and J gene segments either upstream of the endogenous mouse kappa constant region or upstream of a human kappa constant region. In this case, the kappa enhancers (iEk and/or the 3'Ek) can be maintained in that kappa locus to aid expression in the vertebrate by using endogenous control mechanisms.

In another embodiment, there is provided a non-human vertebrate or cell according to any preceding aspect, wherein (a) the endogenous locus is an endogenous lambda locus (eg, in a mouse), the genome being heterozygous for the insertion at the lambda locus, thus one allele of the lambda locus comprising the human Vλ and Jλ gene segment insertion (optionally with the human Cλ gene segment insertion; optionally with the human Eλ insertion) as described above; (b) the other endogenous lambda allele comprises a plurality of human Vκ gene segments and one or more human Jκ gene segments upstream of a constant region (eg, a kappa constant region of said non-human vertebrate species; a human kappa constant region; the endogenous lambda constant region; or a human lambda constant region); optionally with one or more kappa enhancers (eg, iEk and/or the 3'Ek, eg, of said non-human vertebrate species); and
(c) endogenous lambda and kappa chain expression has been inactivated.

Thus, there is no expression of light chains comprising variable regions derived from recombination of endogenous V and J regions, but there is expression of human lambda and human kappa light chains from the alleles at the endogenous lambda locus. This is beneficial, since the design greatly aids construction and breeding of vertebrates by avoiding need to provide transgenic loci at both the endogenous lambda and kappa loci. The endogenous kappa locus (and thus endogenous kappa chain expression) can be inactivated by inversion, deletion of kappa gene segments (eg, endogenous V and/or J and/or C kappa) and/or by insertion of an interrupting sequence such as a marker (eg, neo) into the endogenous kappa locus.

The human kappa segment insertion into the endogenous lambda can be carried out, for example, by inserting a sequence corresponding to a portion of a human kappa locus comprising in germline configuration all functional human Vκ and Jκ (ie, optionally excluding pseudogenes and ORFs; see the IMGT database); and optionally also a human iEκ.

25. The vertebrate or cell of aspect 24, optionally wherein the genome comprises said human lambda gene segment insertion at one endogenous non-human vertebrate kappa locus allele, and wherein the other endogenous kappa locus allele comprises an insertion of human kappa immunoglobulin V and J genes upstream of an endogenous non-human vertebrate kappa constant region; optionally wherein an endogenous kappa light chain enhancer is maintained in one or both kappa locus; optionally in germline configuration.

The vertebrate or cell of aspect 24, optionally wherein the genome comprises said human lambda gene segment insertion at one endogenous non-human vertebrate lambda locus allele, and wherein the other endogenous lambda locus allele comprises an insertion of human kappa immunoglobulin V and J genes upstream of an endogenous non-human vertebrate kappa constant region; optionally wherein an endogenous lambda light chain enhancer is maintained in one or both lambda locus; optionally in germline configuration.

26. The vertebrate or cell of claim 24, optionally wherein the genome comprises said human lambda gene segment insertion at one endogenous non-human vertebrate lambda locus allele, and wherein the other endogenous lambda locus allele comprises an insertion of human kappa immunoglobulin V and J genes upstream of an endogenous non-human vertebrate kappa constant region; optionally wherein an endogenous lambda light chain enhancer is maintained in one or both kappa locus; optionally in germline configuration.

27. The vertebrate or cell of any one of aspects 1 to 23, optionally wherein the genome is homozygous for the human lambda insertion at the endogenous non-human vertebrate locus.

28. The vertebrate or cell of any one of aspects 1 to 23, optionally wherein the genome is homozygous for a human lambda gene segment insertion at the endogenous non-human vertebrate kappa and lambda loci.

29. The vertebrate or cell of any one of aspects 1 to 23 and 28, optionally wherein the genome is homozygous for a human lambda gene segment insertion at the endogenous non-human vertebrate lambda loci, one endogenous kappa locus allele comprising a human lambda gene segment insertion and the other endogenous kappa locus allele comprising an insertion of a plurality of human Vκ and Jκ gene segments upstream of a Cκ region for the expression of kappa light chains comprising human kappa variable regions. Human kappa variable regions are those derived from the recombination of human Vκ and Jκ.

30. The vertebrate or cell of aspect 27 or 28, optionally wherein the human lambda gene segment insertions at the kappa and lambda loci are insertions of the same repertoire of human lambda gene segments.

31. The vertebrate or cell of aspect 27 or 28, optionally wherein the human lambda gene segment insertions at the kappa loci are different from the human lambda gene segment insertions at the lambda loci. This is useful for expanding the potential repertoire of variable regions for subsequent selection against antigen.

32. A non-human vertebrate or a non-human vertebrate cell (eg, a mouse, rat, mouse cell or a rat cell) whose genome comprises an Ig gene segment repertoire produced by targeted insertion of human Ig gene segments into one or more endogenous Ig loci, the genome comprising the following light chain loci arrangement
  (a) L at one endogenous kappa chain allele and K at the other endogenous kappa chain allele; or
  (b) L at one endogenous lambda chain allele and K at the other endogenous lambda chain allele; or
  (c) L at both endogenous kappa chain alleles;
  (d) L at both endogenous lambda chain alleles;
  (e) L at one endogenous kappa chain allele and the other endogenous kappa chain allele has been inactivated; or
  (f) L at one endogenous lambda chain allele and the other endogenous lambda chain allele has been inactivated;
  Wherein
  L represents a human lambda gene segment insertion of at least the functional human Vλ and Jλ (optionally also Cλ gene segments) comprised by a human lambda chain Ig locus from Vλ3-1 to Cλ7 (eg, comprised by a human lambda chain Ig locus from 2-18 to Cλ7); and K represents a human Vκ and Jκ insertion;

Wherein in the genome the human gene segments are inserted upstream of a constant region for expression of light chains comprising variable regions derived from the recombination of human V and J gene segments.

33. The vertebrate or cell according to aspect 32, optionally wherein the genome comprises arrangement
   (a) and L at one or both endogenous lambda chain alleles; or
   (a) and K at one or both endogenous lambda chain alleles; or
   (a) and L at one endogenous lambda chain allele and K at the other endogenous lambda chain allele; or
   (b) and L at one or both endogenous kappa chain alleles; or
   (b) and K at one or both endogenous kappa chain alleles; or
   (b) and L at one endogenous kappa chain allele and K at the other endogenous kappa chain allele; or
   (c) and K at one or both endogenous lambda chain alleles; or
   (c) and L at one or both endogenous lambda chain alleles; or
   (c) and L at one endogenous lambda chain allele and K at the other endogenous lambda chain allele; or
   (c) and both endogenous lambda chain alleles have been inactivated; or
   (d) and L at one or both endogenous kappa chain alleles; or
   (d) and K at one or both endogenous kappa chain alleles; or
   (d) and L at one endogenous kappa chain allele and K at the other endogenous kappa chain allele; or
   (d) and both endogenous kappa chain alleles have been inactivated.

34. The vertebrate or cell of aspect 32 or 33, optionally wherein endogenous kappa chain expression is substantially or completely inactivated. Endogenous kappa chains are kappa light chains comprising variable regions derived from the recombination of endogenous (non-human vertebrate) Vκ and Jκ gene segments.

35. The vertebrate or cell of aspect 32, 33 or 34, optionally wherein endogenous lambda chain expression is substantially or completely inactive. Endogenous lambda chains are lambda light chains comprising variable regions derived from the recombination of endogenous (non-human vertebrate) Vλ and Jλ gene segments.

36. The vertebrate or cell of any one of aspects 32 to 35, optionally wherein each L insertion is upstream of an endogenous lambda or kappa constant region.

37. The vertebrate or cell of any one of aspects 32 to 36, optionally wherein each L insertion into a lambda locus is upstream of an endogenous lambda constant region.

38. The vertebrate or cell of any one of aspects 32 to 36, optionally wherein each L insertion into a kappa locus is upstream of an endogenous kappa constant region.

39. The vertebrate or cell of any one of aspects 32 to 35, optionally wherein each L insertion into a lambda locus is upstream of a human lambda constant region.

40. The vertebrate or cell of any one of aspects 32 to 35, optionally wherein each L insertion into a kappa locus is upstream of a human kappa constant region.

41. The vertebrate or cell of any one of aspects 32 to 40, optionally wherein each K insertion is upstream of an endogenous lambda or kappa constant region.

42. The vertebrate or cell of any one of aspects 32 to 41, optionally wherein each K insertion into a lambda locus is upstream of an endogenous lambda constant region.

43. The vertebrate or cell of any one of aspects 32 to 42, optionally wherein each K insertion into a kappa locus is upstream of an endogenous kappa constant region.

44. The vertebrate or cell of any one of aspects 32 to 40, optionally wherein each K insertion into a lambda locus is upstream of a human lambda constant region.

45. The vertebrate or cell of any one of aspects 32 to 40 and 44, optionally wherein each K insertion into a kappa locus is upstream of a human kappa constant region.

46. The vertebrate or cell of any one of aspects 32 to 45, optionally wherein the insertions are according to any one of aspects 1 to 9, 11 to 16 and 20 to 31.

47. The vertebrate or cell of any one of aspects 32 to 46, optionally wherein each human lambda insertion is according to any one of aspects 1 to 9, 11 to 16 and 20 to 31.

48. The vertebrate or cell of any one of aspects 32 to 47, optionally wherein each human kappa insertion is according to any one of aspects 1 to 9, 11 to 16 and 20 to 31.

49. The vertebrate or cell of any one of aspects 32 to 48, optionally wherein each human lambda insertion comprises the repertoire of human Vλ and Jλ (and optionally Cλ) gene segments.

50. The vertebrate or cell of any one of aspects 32 to 48, optionally wherein first and second (and optionally third) human lambda insertions are made and the insertions comprise different repertoires of human Vλ and Jλ (and optionally Cλ) gene segments.

51. The vertebrate or cell of any one of aspects 32 to 50, optionally wherein each human kappa insertion comprises the repertoire of human Vκ and Jκ (and optionally Cκ) gene segments.

52. The vertebrate or cell of any one of aspects 32 to 50, optionally wherein first and second (and optionally third) human kappa insertions are made and the insertions comprise different repertoires of human Vκ and Jκ (and optionally Cκ) gene segments.

53. The vertebrate or cell of any preceding aspect, optionally wherein the genome comprises an immunoglobulin heavy chain locus comprising human VH gene segments, eg, a heavy chain locus as herein described which comprises human V, D and J gene segments.

54. A method for producing an antibody or light chain comprising a lambda variable region specific to a desired antigen, the method comprising immunizing a vertebrate according to any preceding aspect with the desired antigen and recovering the antibody or light chain or recovering a cell producing the antibody or light chain.

55. A method for producing a fully humanised antibody or antibody light chain comprising carrying out the method of aspect 54 to obtain an antibody or light chain comprising a lambda chain non-human vertebrate constant region, and replacing the non-human vertebrate constant region with a human constant region, optionally by engineering of the nucleic acid encoding the antibody or light chain.

56. A humanised antibody or antibody light chain produced according to aspect 54 or a derivative thereof; optionally for use in medicine.

57. Use of a humanised antibody or chain produced according to aspect 54 or a derivative thereof in medicine.

58. A method of inactivating endogenous Ig-VJ regions in the genome of a non-human vertebrate or a non-human vertebrate cell (eg, a mouse, rat, mouse cell or a rat cell), wherein the method comprises inserting human immunoglobulin gene segments (eg, V and J gene segments) in the genome between the endogenous Ig-VJ and an endogenous enhancer or endogenous constant region to move the endogenous Ig-VJ away from the enhancer or constant region, thereby inactivating endogenous Ig-VJ regions.

In one embodiment, the endogenous Ig-VJ are heavy chain gene segments, the enhancer is an endogenous heavy chain enhancer, the constant region is an endogenous heavy chain constant region and the human Ig gene segments comprise human VH, DH and JH gene segments.

In one embodiment, the endogenous Ig-VJ are lambda light chain gene segments, the enhancer is an endogenous lambda chain enhancer, the constant region is an endogenous lambda chain constant region and the human Ig gene segments comprise human Vλ and Jλ gene segments.

In one embodiment, the endogenous Ig-VJ are kappa light chain gene segments, the enhancer is an endogenous kappa chain enhancer, the constant region is an endogenous kappa chain constant region and the human Ig gene segments comprise human Vκ and Jκ gene segments.

A method of inactivating endogenous IgK-VJ regions in the genome of a non-human vertebrate or a non-human vertebrate cell (eg, a mouse, rat, mouse cell or a rat cell), wherein the method comprises inserting human immunoglobulin gene segments in the genome between the endogenous IgK-VJ and Eκ enhancer to move the IgK-VJ away from the Eκ enhancer, thereby inactivating endogenous IgK-VJ regions.

59. The method of aspect 58, wherein optionally the human gene segments comprise human VL and JL gene segments; optionally wherein the insertion is an insertion as recited in any one of aspects 1 to 9, 11 to 16 and 20 to 31 or an insertion of human Vκ and Jκ gene segments.

60. A method of expressing immunoglobulin light chains in a non-human vertebrate (eg, a mouse or rat), the light chains comprising lambda variable regions (lambda light chains), wherein at least 80% (for example, at least 80, 84, 85, 90, 95, 96, 97, 98 or 99%) of the variable regions of the lambda light chains expressed by the vertebrate are derived from recombination of human Vλ and Jλ gene segments, the method comprising providing in the genome of the vertebrate an Ig gene segment repertoire produced by targeted insertion of human Ig gene segments into one or more endogenous Ig loci, the genome comprising human Vλ and Jλ gene segments upstream of a constant region, wherein the method comprises inserting at least the functional human Vλ and Jλ (optionally also human Cλ) gene segments (and optionally inter-gene segment sequences) comprised by a human lambda chain Ig locus from Vλ2-18 to Cλ7 into an endogenous light chain locus of the vertebrate, wherein at least 80% (for example, at least 80, 84, 85, 90, 95, 96, 97, 98 or 99%) of the variable regions of the lambda light chains expressed by the vertebrate are derived from recombination of human Vλ and Jλ gene segments; the method comprising expressing said light chains in the vertebrate and optionally isolating one or more of said light chains (eg, as part of a 4-chain antibody).

In one embodiment, the method further comprises isolating from the vertebrate a lambda light chain comprising a variable region derived from recombination of human Vλ and Jλ gene segments. In an example, the method comprises immunising the mouse with an antigen (eg, a human antigen) prior to isolating the lambda light chain. In an example, the light chain is part of an antibody, eg, an antibody that specifically binds the antigen.

In one embodiment, the use further comprises isolating splenic tissue (eg, the spleen) from the mouse; optionally followed by isolating at least one antigen-specific B-cell from the tissue, wherein the B-cell(s) expresses said lambda light chain. For example, said lambda light chain is provided by an antibody that specifically binds a predetermined antigen (eg, a human antigen). In one example, the use comprises immunising the mouse with the antigen (eg, a human antigen) prior to isolating the splenic tissue or lambda light chain. In an example, the use comprises isolating the lambda light chain produced by the B-cell (or by a hybridoma produced by fusion of the B-cell with a myeloma cell). In an example, the use comprises making a hybridoma from a B-cell isolated from the splenic tissue, wherein the hybridoma expresses said lambda light chain or a derivative thereof. Optionally, the use comprises making a derivative of the isolated antibody or lambda light chain. Examples of derivative antibodies (according to any aspect herein) are antibodies that have one or more mutations compared to the isolated antibody (eg, to improve antigen-binding affinity and/or to enhance or inactivate Fc function) Such mutants specifically bind the antigen. Mutation or adaptation to produce a derivative includes, eg, mutation to produce Fc enhancement or inactivation. A derivative can be an antibody following conjugation to a toxic payload or reporter or label or other active moiety. In another example, a chimaeric antibody chain or antibody isolated from a cell of vertebrate of the invention is modified by replacing one or all human constant regions thereof by a corresponding human constant region. For example, all constant regions of an antibody isolated from such a cell or vertebrate are replaced with human constant regions to produce a fully human antibody (ie, comprising human variable and constant regions). Such an antibody is useful for administration to human patients to reduce anti-antibody reaction by the patient.

61. A method of expressing immunoglobulin light chains in a non-human vertebrate (eg, a mouse or rat), wherein at least 60% (for example, at least 65, 70, 80, 84, 85, 90, 95, 96, 97, 98 or 99%) of the light chains expressed by the vertebrate are provided by human lambda light chains, the method comprising providing in the genome of the vertebrate an Ig gene segment repertoire produced by targeted insertion of human Ig gene segments into one or more endogenous Ig loci, the genome comprising (i) human Vλ and Jλ gene segments upstream of a constant region, wherein the human Vλ and Jλ gene segments are provided by inserting at least the functional human Vλ and Jλ (optionally also human Cλ) gene segments (and optionally inter-gene segment sequences) comprised by a human lambda chain Ig locus from Vλ2-18 to Cλ7 into an endogenous light chain locus of the vertebrate and (ii) kappa V gene segments upstream of a constant region, wherein the vertebrate expresses immunoglobulin light chains comprising human lambda variable regions (human lambda light chains) and at least 60% (for example, greater than 65, 70, 80, 84, 85, 90, 95, 96, 97, 98 or 99%) of the light chains expressed by the vertebrate are provided by said human lambda light chains; the method comprising expressing said light chains in the vertebrate and optionally isolating one or more of said light chains (eg, as part of a 4-chain antibody).

In one embodiment, the method further comprises isolating from the vertebrate a lambda light chain comprising a variable region derived from recombination of human Vλ and Jλ gene segments. In an example, the method comprises immunising the mouse with an antigen (eg, a human antigen) prior to isolating the lambda light chain. In an example, the light chain is part of an antibody, eg, an antibody that specifically binds the antigen.

In one embodiment, the use further comprises isolating splenic tissue (eg, the spleen) from the mouse; optionally followed by isolating at least one antigen-specific B-cell from the tissue, wherein the B-cell(s) expresses said lambda light chain. For example, said lambda light chain is provided by an antibody that specifically binds a predetermined antigen (eg, a human antigen). In one example, the use comprises immunising the mouse with the antigen (eg, a human antigen) prior to isolating the splenic tissue or lambda light chain. In an example, the use comprises isolating the lambda light chain produced by the B-cell (or by a hybridoma produced by fusion of the B-cell with a myeloma cell). In an example, the use comprises making a hybridoma from a B-cell isolated from the splenic tissue, wherein the hybridoma expresses said lambda light chain or a derivative thereof. Optionally, the use comprises making a derivative of the isolated antibody or lambda light chain. Examples of derivative antibodies (according to any aspect herein) are antibodies that have one or more mutations compared to the isolated antibody (eg, to improve antigen-binding affinity and/or to enhance or inactivate Fc function) Such mutants specifically bind the antigen.

62. A method of expressing human immunoglobulin VJC light chains in a non-human vertebrate (eg, a mouse or rat), the method comprising providing in the genome of the vertebrate an Ig gene segment repertoire produced by targeted insertion of human Ig gene segments into one or more endogenous Ig loci, wherein the method comprises inserting at least the functional human Vλ, Jλ and Cλ gene segments (and optionally inter-gene segment sequences) comprised by a human lambda chain Ig locus from Vλ3-1 to Cλ7 (eg, comprised by a human lambda chain Ig locus from 2-18 to Cλ7) into an endogenous non-human vertebrate kappa light chain locus upstream of an endogenous non-human vertebrate kappa constant region for expression of a human VJC light chain; the method comprising expressing said light chains in the vertebrate and optionally isolating one or more of said light chains (eg, as part of a 4-chain antibody).

In one embodiment, the method further comprises isolating from the vertebrate a lambda light chain comprising a variable region derived from recombination of human Vλ and Jλ gene segments. In an example, the method comprises immunising the mouse with an antigen (eg, a human antigen) prior to isolating the lambda light chain. In an example, the light chain is part of an antibody, eg, an antibody that specifically binds the antigen.

In one embodiment, the use further comprises isolating splenic tissue (eg, the spleen) from the mouse; optionally followed by isolating at least one antigen-specific B-cell from the tissue, wherein the B-cell(s) expresses said lambda light chain. For example, said lambda light chain is provided by an antibody that specifically binds a predetermined antigen (eg, a human antigen). In one example, the use comprises immunising the mouse with the antigen (eg, a human antigen) prior to isolating the splenic tissue or lambda light chain. In an example, the use comprises isolating the lambda light chain produced by the B-cell (or by a hybridoma produced by fusion of the B-cell with a myeloma cell). In an example, the use comprises making a hybridoma from a B-cell isolated from the splenic tissue, wherein the hybridoma expresses said lambda light chain or a derivative thereof. Optionally, the use comprises making a derivative of the isolated antibody or lambda light chain. Examples of derivative antibodies (according to any aspect herein) are antibodies that have one or more mutations compared to the isolated antibody (eg, to improve antigen-binding affinity and/or to enhance or inactivate Fc function) Such mutants specifically bind the antigen.

63. The method of any one of aspects 38 to 40, optionally wherein the vertebrate is according to any one of the other aspects.
64. An antibody light chain isolated according to the method of any one of aspects 58 to 63 or a derivative thereof, or an antibody comprising such a light chain or derivative; optionally for use in medicine.
65. Use of an antibody light chain isolated according to the method of any one of aspects 58 to 63 or a derivative thereof (or an antibody comprising such a light chain or derivative) in medicine.
66. A non-human vertebrate (eg, a mouse or rat) according to any one of aspects 1 to 53 for expressing light chains comprising lambda variable regions (lambda light chains), wherein at least 80% (for example, at least 80, 84, 85, 90, 95, 96, 97, 98 or 99% or 100%) of the variable regions of the lambda light chains expressed by the vertebrate are derived from recombination of human Vλ and Jλ gene segments.

A non-human vertebrate (eg, a mouse or rat) according to any one of aspects 1 to 53 expressing light chains comprising lambda variable regions (lambda light chains), wherein at least 80% (for example, at least 80, 84, 85, 90, 95, 96, 97, 98 or 99% or 100%) of the variable regions of the lambda light chains expressed by the vertebrate are derived from recombination of human Vλ and Jλ gene segments.

67. A non-human vertebrate (eg, a mouse or rat) according to any one of aspects 1 to 53 for expressing light chains, wherein at least 60% (for example, greater than 65, 70, 80, 84, 85, 90, 95, 96, 97, 98 or 99% or 100%) of the light chains expressed by the vertebrate are provided by human lambda light chains.

A non-human vertebrate (eg, a mouse or rat) according to any one of aspects 1 to 53 expressing light chains, wherein at least 60% (for example, greater than 65, 70, 80, 84, 85, 90, 95, 96, 97, 98 or 99% or 100%) of the light chains expressed by the vertebrate are provided by human lambda light chains.

68. A non-human vertebrate (eg, a mouse or rat) according to aspect 7 for expressing light chains comprising lambda variable regions (lambda light chains), wherein expression of lambda light chains comprising human lambda variable regions dominates over expression of lambda light chains comprising endogenous non-human vertebrate lambda variable regions: and optionally for inactivating expression of endogenous non-human vertebrate lambda variable regions from the endogenous light chain locus.

A non-human vertebrate (eg, a mouse or rat) according to aspect 7 expressing light chains comprising lambda variable regions (lambda light chains), wherein expression of lambda light chains comprising human lambda variable regions dominates over expression of lambda light chains comprising endogenous non-human vertebrate lambda variable regions: and optionally for inactivating expression of endogenous non-human vertebrate lambda variable regions from the endogenous light chain locus.

69. A non-human vertebrate (eg, a mouse or rat) according to aspect 7, 8, 9 or 10 for inactivating expression of endogenous non-human vertebrate lambda variable regions from the endogenous light chain locus.

The percentage expression or level of expression of antibody chains can be determined at the level of light chain mRNA transcripts in B-cells (eg, peripheral blood lymphocytes). Alternatively or additionally, the percentage expression is determined at the level of antibody light chains in serum or blood of the vertebrates. Additionally or alternatively, the expression can be determined by FACS (fluorescence activated cell sorting) analysis of B cells. For example, by assessing mouse C kappa or human C lambda expression on cell surface when the human lambda variable regions are expressed with mouse C kappa or human C lambda regions respectively.

The term a "lambda light chain" in these aspects refers to a light chain comprising a variable region sequence (at RNA or amino acid level) derived from the recombination of Vλ and Jλ gene segments. Thus a "human lambda variable region", for example, is a variable region derived from the recombination of human Vλ and Jλ gene segments. The constant region can be a kappa or lambda constant region, eg, a human or mouse constant region.

The vertebrate in these aspects is, for example naïve (ie, not immunised with a predetermined antigen, as the term is understood in the art; for example, such a vertebrate that has been kept in a relatively sterile environment as provided by an animal house used for R&D). In another example, the vertebrate has been immunised with a predetermined antigen, eg, an antigen bearing a human epitope.

Reference to "functional" human gene segments acknowledges that in a human Ig lambda locus some V gene segments are non-functional pseudogenes (eg, Vλ3-17, Vλ3-15, Vλ3-13, Vλ3-7, Vλ3-6, Vλ2-5, Vλ3-4, Vλ3-2; see the IMGT database: at World Wide Web (www) imgtorg/IMGTrepertoire/index.php?section=LocusGenes&repertoire=locus&species=human &group=IGL. Also, Jλ4-Cλ4 and Jλ5-Cλ5 are not functional in humans. The term "functional" when referring to gene segments excludes pseudogenes. An example of functional human Vλ gene segments is the group Vλ2-18, Vλ3-16, V2-14, Vλ3-12, Vλ2-11, Vλ3-10, Vλ3-9, Vλ2-8, Vλ4-3 and Vλ3-1. An example of functional human Jλ gene segments is the group Jλ1, Jλ2 and Jλ3; or Jλ1, Jλ2 and Jλ7; or Jλ2, Jλ3 and Jλ7; or Jλ1, Jλ2, Jλ3 and Jλ7. An example of functional human Cλ gene segments is the group Cλ1, Cλ2 and Cλ3; or Cλ1, Cλ2 and Cλ7; or Cλ2, Cλ3 and Cλ7; or Cλ1, Cλ2, Cλ3 and Cλ7.

In one embodiment, the lambda light chains, together with heavy chains expressed in the cells or vertebrates of the invention, form antibodies. The heavy chains can be expressed from a transgenic heavy chain locus as herein described. For example the genome of the cell or vertebrate comprises a heavy chain locus in which is a chimaeric immunoglobulin heavy chain locus comprising one or more human V gene segments, one or more human D gene segments and one or more human J gene segments upstream of a mu constant region of said non-human species; endogenous heavy chain expression has been substantially inactivated; and the heavy chain locus comprises an Eμ enhancer of said non-human vertebrate species.

In one embodiment of the vertebrate or cell, all endogenous enhancers are deleted from the endogenous locus in which the human gene segments are inserted. Thus, when a human enhancer (eg, Eλ) is inserted, this controls the transgenic locus in the absence of the effect of other, endogenous, enhancers (for example, kappa enhancers if the locus is an endogenous kappa enhancer). This may be useful to avoid non-human vertebrate-like kappa:lambda expression ratios (eg, to steer expression to a higher ratio of lambda:kappa in mice).

When endogenous light chain (eg, kappa or lambda) expression is substantially inactive or inactivated as described herein, less than 10, 5, 4, 3, 2, 1 or 0.5% of such endogenous light chains are expressed or expressible. In one example, there is complete inactivation so no such light chains are expressed or expressible.

Optionally the vertebrate of the invention is naïve. Thus, the vertebrate has not been immunised with a predetermined antigen.

Where, for example, a cell of the invention is an ES cell or other IPS stem cell or other pluripotent stem cell, the cell can develop into a vertebrate of the invention. For example, the cell can be implanted into a blastocyst from a foster mother and developed into an embryo and animal according to standard techniques.

In one embodiment, where human kappa gene segments are inserted, each insertion comprises human kappa gene segments
(i) $V_K1-5$, $V_K1-6$, $V_K1-8$ and $V_K1-9$ (and optionally $V_K5-2$ and $V_K4-1$); or
(ii) $V_K1-5$, $V_K1-6$, $V_K1-8$, $V_K1-9$, $V_K3-11$, $V_K1-12$, $V_K3-15$, $V_K1-16$, $V_K1-17$, $V_K3-20$ (and optionally $V_K2-24$ and/or $V_K1-13$); or
(iii) $V_K1-5$, $V_K1-6$, $V_K1-8$, $V_K1-9$, $V_K3-11$, $V_K1-12$, $V_K3-15$, $V_K1-16$, $V_K1-17$, $V_K3-20$, $V_K2-24$, $V_K1-27$, $V_K2-28$, $V_K2-30$ and $V_K1-33$ (and optionally $V_K2-29$ and/or $V_K2-40$ and/or $V_K1-39$);
and optionally
(iv) $J_K1$, $J_K2$, $J_K3$, $J_K4$ and $J_K5$.

In one embodiment, the human kappa insertion also comprises a human $iE_K$ and/or human $3'E_K$ downstream of the human J gene segments in the locus.

Transgenic Mice of the Invention Expressing Essentially Exclusively Human Heavy Chain Variable Regions Develop Normal Splenic and BM Compartments & Normal Ig Expression in which the Ig Comprise Human Heavy Chain Variable Regions The present inventors surprisingly observed normal Ig subtype expression & B-cell development in transgenic mice of the invention expressing antibodies with human heavy chain variable regions substantially in the absence of endogenous heavy and kappa chain expression. See Example 16 below.

The inventors observed that surprisingly the inactivation of endogenous heavy chain variable region expression in the presence of human variable region expression does not change the ratio of B-cells in the splenic compartment (FIG. 66) or bone marrow B progenitor compartment (FIG. 67) and the immunoglobulin levels in serum are normal and the correct Ig subtypes are expressed (FIG. 68). These data demonstrate that inserted human heavy chain gene segments according to the invention (eg, an insertion of at least human $V_H$ gene segments $V_H2-5$, 7-4-1, 4-4, 1-3, 1-2, 6-1, and all the human D and $J_H$ gene segments D1-1, 2-2, 3-3, 4-4, 5-5, 6-6, 1-7, 2-8, 3-9, 5-12, 6-13, 2-15, 3-16, 4-17, 6-19, 1-20, 2-21, 3-22, 6-25, 1-26 and 7-27; and J1, J2, J3, J4, J5 and J6) are fully functional for VDJ gene segment rearrangement from the transgenic heavy chain locus, B-cell receptor (BCR) signalling and proper B-cell maturation The invention therefore provides the following aspects (numbering starting at aspect 70):—
70. A mouse that expresses or for expressing immunoglobulin heavy chains comprising human variable regions, wherein the heavy chains expressed by the mouse are essentially exclusively said heavy chains comprising human variable regions; and said heavy chains comprising human variable regions are expressed as part of serum IgG1, IgG2b and IgM (and optionally IgG2a) antibodies in the mouse;
  the mouse comprising an immunoglobulin heavy chain locus comprising human VH, DH and JH gene segments upstream of a mouse constant region (eg, C-mu and/or C-delta and/or C-gamma; such as (in a 5' to 3' orientation) mouse C-mu and mouse C-delta and mouse C-gamma), wherein
  (a) the mouse is capable of expressing immunoglobulin heavy chains comprising human variable regions and the heavy chains expressed by the mouse are essentially exclusively said heavy chains comprising human variable regions; and
  (b) the mouse expresses serum IgG1, IgG2b and IgM (and optionally IgG2a) antibodies comprising said heavy chains.

Ig isotypes can be determined, for example, using isotype-matched tool antibodies as will be readily familiar to the skilled person (and as illustrated in Example 16).

In an embodiment, the mouse is naïve.

71. The mouse of aspect 70 for expressing a normal relative proportion of serum IgG1, IgG2a, IgG2b and IgM antibodies.

By "normal" is meant comparable to expression in a mouse (eg, a naïve mouse) expressing only mouse antibody chains, eg, a mouse whose genome comprises only wild-type functional Ig heavy and light chain loci, eg, a wild-type mouse.

72. The mouse of aspect 70 or 71, wherein the mouse expresses a normal relative proportion of serum IgG1, IgG2a, IgG2b and IgM antibodies.

By "normal" is meant comparable to expression in a mouse (eg, a naïve mouse) expressing only mouse antibody chains, eg, a mouse whose genome comprises only wild-type functional Ig heavy and light chain loci, eg, a wild-type mouse.

73. The mouse of any one of aspects 70 to 72, for expressing in the mouse
  (i) serum IgG1 at a concentration of about 25-350 µg/ml;
  (ii) serum IgG2a at a concentration of about 0-200 µg/ml;
  (iii) serum IgG2b at a concentration of about 30-800 µg/ml; and
  (iv) serum IgM at a concentration of about 50-300 µg/ml;
  as determined by Ig capture on a plate followed by incubation (eg, for one hour at RT, eg, for one hour at 20° C.) with anti-mouse isotype-specific labelled antibodies and quantification of Ig using the label (eg, using anti-mouse Ig isotype specific antibodies each conjugated to horseradish peroxidase conjugated at a ratio of 1/10000 in PBS with 0.1% Tween™, followed by development of the label with tetramethylbenzidine substrate (TMB) for 4-5 minutes in the dark at room temperature (eg, 20° C.), adding sulfuric acid to stop development of the label and reading of the label at 450 nm).

For example, the mouse of any one of aspects 70 to 72, for expressing in the mouse
  (i) serum IgG1 at a concentration of about 25-150 µg/ml;
  (ii) serum IgG2a at a concentration of about 0-200 µg/ml;
  (iii) serum IgG2b at a concentration of about 30-300 µg/ml; and
  (iv) serum IgM at a concentration of about 50-200 µg/ml;
  as determined by Ig capture on a plate followed by incubation (eg, for one hour at RT, eg, for one hour at 20° C.) with anti-mouse isotype-specific labelled antibodies and quantification of Ig using the label (eg, using anti-mouse Ig isotype specific antibodies each conjugated to horseradish peroxidase conjugated at a ratio of 1/10000 in PBS with 0.1% Tween™, followed by development of the label with tetramethylbenzidine substrate (TMB) for 4-5 minutes in the dark at room temperature (eg, 20° C.), adding sulfuric acid to stop development of the label and reading of the label at 450 nm).

The mouse of any one of aspects 70 to 72, for expressing in the mouse Ig in the relative proportions of
  (i) serum IgG1 at a concentration of about 25-350 µg/ml;
  (ii) serum IgG2a at a concentration of about 0-200 µg/ml;
  (iii) serum IgG2b at a concentration of about 30-800 µg/ml; and
  (iv) serum IgM at a concentration of about 50-300 µg/ml;
  as determined by Ig capture on a plate followed by incubation (eg, for one hour at RT, eg, for one hour at 20° C.) with anti-mouse isotype-specific labelled antibodies and quantification of Ig using the label (eg, using anti-mouse Ig isotype specific antibodies each conjugated to horseradish peroxidase conjugated at a ratio of 1/10000 in PBS with 0.1% Tween™, followed by development of the label with tetramethylbenzidine substrate (TMB) for 4-5 minutes in the dark at room temperature (eg, 20° C.), adding sulfuric acid to stop development of the label and reading of the label at 450 nm).

For example, the mouse of any one of aspects 70 to 72, for expressing in the mouse Ig in the relative proportions of
  (i) serum IgG1 at a concentration of about 25-150 µg/ml;
  (ii) serum IgG2a at a concentration of about 0-200 µg/ml;
  (iii) serum IgG2b at a concentration of about 30-300 µg/ml; and
  (iv) serum IgM at a concentration of about 50-200 µg/ml;
  as determined by Ig capture on a plate followed by incubation (eg, for one hour at RT, eg, for one hour at 20° C.) with anti-mouse isotype-specific labelled antibodies and quantification of Ig using the label (eg, using anti-mouse Ig isotype specific antibodies each conjugated to horseradish peroxidase conjugated at a ratio of 1/10000 in PBS with 0.1% Tween™, followed by development of the label with tetramethylbenzidine substrate (TMB) for 4-5 minutes in the dark at room temperature (eg, 20° C.), adding sulfuric acid to stop development of the label and reading of the label at 450 nm).

74. The mouse of any one of aspects 70 to 73, wherein the mouse expresses
  (i) serum IgG1 at a concentration of about 25-350 µg/ml;
  (ii) serum IgG2a at a concentration of about 0-200 µg/ml;
  (iii) serum IgG2b at a concentration of about 30-800 µg/ml; and
  (iv) serum IgM at a concentration of about 50-300 µg/ml;
  as determined by Ig capture on a plate followed by incubation (eg, for one hour at RT, eg, for one hour at 20° C.) with anti-mouse isotype-specific labelled antibodies and quantification of Ig using the label (eg, using anti-mouse Ig isotype specific antibodies each conjugated to horseradish peroxidase conjugated at a ratio of 1/10000 in PBS with 0.1% Tween™, followed by development of the label with tetramethylbenzidine substrate (TMB) for 4-5 minutes in the dark at room temperature (eg, 20° C.), adding sulfuric acid to stop development of the label and reading of the label at 450 nm).

For example, the mouse of any one of aspects 70 to 72, the mouse expresses
  (i) serum IgG1 at a concentration of about 25-150 µg/ml;
  (ii) serum IgG2a at a concentration of about 0-200 µg/ml;
  (iii) serum IgG2b at a concentration of about 30-300 µg/ml; and
  (iv) serum IgM at a concentration of about 50-200 µg/ml;
  as determined by Ig capture on a plate followed by incubation (eg, for one hour at RT, eg, for one hour at 20° C.) with anti-mouse isotype-specific labelled antibodies and quantification of Ig using the label (eg, using anti-mouse Ig isotype specific antibodies each conjugated to horseradish peroxidase conjugated at a ratio of 1/10000 in PBS with 0.1% Tween™, followed by development of the label with tetramethylbenzidine substrate (TMB) for 4-5 minutes in the dark at room temperature (eg, 20° C.), adding sulfuric acid to stop development of the label and reading of the label at 450 nm).

The mouse of any one of aspects 70 to 73, wherein the mouse expresses Ig in the relative proportions of
  (i) serum IgG1 at a concentration of about 25-350 µg/ml;
  (ii) serum IgG2a at a concentration of about 0-200 µg/ml;
  (iii) serum IgG2b at a concentration of about 30-800 µg/ml; and
  (iv) serum IgM at a concentration of about 50-300 µg/ml;
  as determined by Ig capture on a plate followed by incubation (eg, for one hour at RT, eg, for one hour at 20° C.) with anti-mouse isotype-specific labelled antibodies and quantification of Ig using the label (eg, using anti-mouse Ig isotype specific antibodies each conjugated to horseradish peroxidase conjugated at a ratio of 1/10000 in PBS with 0.1% Tween™, followed by development of the label with tetramethylbenzidine substrate (TMB) for 4-5 minutes in the dark at room temperature (eg, 20° C.), adding sulfuric acid to stop development of the label and reading of the label at 450 nm).

For example, the mouse of any one of aspects 70 to 72, the mouse expresses Ig in the relative proportions of
  (i) serum IgG1 at a concentration of about 25-150 µg/ml;
  (ii) serum IgG2a at a concentration of about 0-200 µg/ml;
  (iii) serum IgG2b at a concentration of about 30-300 µg/ml; and
  (iv) serum IgM at a concentration of about 50-200 µg/ml;
  as determined by Ig capture on a plate followed by incubation (eg, for one hour at RT, eg, for one hour at 20° C.) with anti-mouse isotype-specific labelled antibodies and quantification of Ig using the label (eg, using anti-mouse Ig isotype specific antibodies each conjugated to horseradish peroxidase conjugated at a ratio of 1/10000 in PBS with 0.1% Tween™, followed by development of the label with tetramethylbenzidine substrate (TMB) for 4-5 minutes in the dark at room temperature (eg, 20° C.), adding sulfuric acid to stop development of the label and reading of the label at 450 nm).

75. The mouse of any one of aspects 70 to 74 for expressing said heavy chains from splenic B-cells in a mouse that produces a normal proportion or percentage of mature splenic B-cells, eg as determined by FACS.

By "normal" is meant comparable to mature splenic B-cell production in a mouse (eg, a naïve mouse) expressing only mouse antibody chains, eg, a mouse whose genome comprises only wild-type functional Ig heavy and light chain loci, eg, a wild-type mouse.

For example, at least 40, 50, 60 or 70% of total splenic B-cells produced by the mouse of the invention are mature B-cells. Splenic B-cells are B220$^+$ and express B220 at relatively high levels as the skilled person will know. Mature splenic B-cells express B220 and IgD, both at relatively high levels as will be known by the skilled person. IgM expression is relatively low in mature splenic B-cells, again as is known in the art. For example, see J Exp Med. 1999 Jul. 5; 190(1):75-89; "B cell development in the spleen takes place in discrete steps and is determined by the quality of B cell receptor-derived signals"; Loder F et al.

Optionally the mouse produces a normal ratio of T1, T2 and mature splenic B-cells, eg, as determined by FACS. For example, the mouse of the invention produces about 40-70% mature splenic B-cells, 15-35% splenic T1 cells; and 5-10% splenic T2 cells (percentage with reference to the total splenic B220-positive (high) population). For example, about 40-60% mature splenic B-cells, 15-30% splenic T1 cells; and 5-10% splenic T2 cells. By "normal" is meant comparable to a T1/T2/mature splenic B-cell proportion in a mouse (eg, a naïve mouse) expressing only mouse antibody chains, eg, a mouse whose genome comprises only wild-type functional Ig heavy and light chain loci, eg, a wild-type mouse.

76. The mouse of any one of aspects 70 to 75, wherein the mouse produces a normal proportion or percentage of mature splenic B-cells, eg as determined by FACS.

77. A mouse that expresses or for expressing immunoglobulin heavy chains comprising human variable regions, wherein the heavy chains expressed by the mouse are essentially exclusively said heavy chains comprising human variable regions and are expressed in a mouse that produces a normal proportion or percentage of mature splenic B-cells (eg, as determined by FACS); the mouse comprising an immunoglobulin heavy chain locus comprising human VH, DH and JH gene segments upstream of a mouse constant region (eg, C-mu and/or C-delta and/or C-gamma; such as (in a 5' to 3' orientation) and wherein the mouse produces a normal proportion or percentage of mature splenic B-cells.

By "normal" is meant comparable to mature splenic B-cell production in a mouse (eg, a naïve mouse) expressing only mouse antibody chains, eg, a mouse whose genome comprises only wild-type functional Ig heavy and light chain loci, eg, a wild-type mouse.

For example, at least 40, 50, 60 or 70% of total splenic B-cells produced by the mouse of the invention are mature B-cells. Splenic B-cells are B220$^+$ and express B220 at relatively high levels as the skilled person will know. Mature splenic B-cells express B220 and IgD, both at relatively high levels as will be known by the skilled person. IgM expression is relatively low in mature splenic B-cells, again as is known in the art. For example, see J Exp Med. 1999 Jul. 5; 190(1):75-89; "B cell development in the spleen takes place in discrete steps and is determined by the quality of B cell receptor-derived signals"; Loder F et al.

Optionally the mouse produces a normal ratio of T1, T2 and mature splenic B-cells, eg, as determined by FACS. For example, the mouse of the invention produces about 40-70% mature splenic B-cells, 15-35% splenic T1 cells; and 5-10% splenic T2 cells (percentage with reference to the total splenic B220-positive (high) population). For example, about 40-60% mature splenic B-cells, 15-30% splenic T1 cells; and 5-10% splenic T2 cells. By "normal" is meant comparable to a T1/T2/mature splenic B-cell proportion in a mouse (eg, a naïve mouse) expressing only mouse antibody chains, eg, a mouse whose genome comprises only wild-type functional Ig heavy and light chain loci, eg, a wild-type mouse.

78. The mouse of any one of aspects 70 to 77 for expressing said heavy chains in a mouse that produces a normal proportion or percentage of bone marrow B-cell progenitor cells (eg as determined by FACS).

In one embodiment, the mouse is for expressing said heavy chains in a mouse that produces a normal proportion or percentage of bone marrow pre-, pro and prepro-B-cells (eg as determined by FACS). See J Exp Med. 1991 May 1; 173(5):1213-25; "Resolution and characterization of pro-B and pre-pro-B cell stages in normal mouse bone marrow"; Hardy R R et al for more discussion on progenitor cells.

By "normal" is meant comparable to bone marrow B-cell production in a mouse (eg, a naïve mouse) expressing only mouse antibody chains, eg, a mouse whose genome comprises only wild-type functional Ig heavy and light chain loci, eg, a wild-type mouse.

79. The mouse of any one of aspects 70 to 78, wherein the mouse produces a normal proportion or percentage of bone marrow B-cell progenitor cells (eg, as determined by FACS).

In one embodiment, the mouse produces a normal proportion or percentage of bone marrow pre-, pro and prepro-B-cells (eg as determined by FACS).

By "normal" is meant comparable to bone marrow B-cell production in a mouse (eg, a naïve mouse) expressing only mouse antibody chains, eg, a mouse whose genome comprises only wild-type functional Ig heavy and light chain loci, eg, a wild-type mouse.

80. A mouse that expresses or for expressing immunoglobulin heavy chains comprising human variable regions, wherein the heavy chains expressed by the mouse are essentially exclusively said heavy chains comprising human variable regions and are expressed in a mouse that produces a normal proportion or percentage of bone marrow B-cell progenitor cells (eg, as determined by FACS), the mouse comprising an immunoglobulin heavy chain locus comprising human VH, DH and JH gene segments upstream of a mouse constant region (eg, C-mu and/or C-delta and/or C-gamma; such as (in a 5' to 3' orientation) and wherein the mouse produces a normal proportion or percentage of bone marrow B-cell progenitor cells.

In one embodiment, the mouse is for expressing said heavy chains in a mouse that produces a normal proportion or percentage of bone marrow pre-, pro and prepro-B-cells (eg as determined by FACS).

By "normal" is meant comparable to bone marrow B-cell production in a mouse (eg, a naïve mouse) expressing only mouse antibody chains, eg, a mouse whose genome comprises only wild-type functional Ig heavy and light chain loci, eg, a wild-type mouse.

81. The mouse of any one of aspects 70 to 80, wherein at least 90% of the heavy chains are heavy chains comprising human variable regions.

For example, at least 90, 95, 96, 97, 98, 99 or 99.5% or 100% of the heavy chains comprise human variable regions, ie, variable regions derived from the recombination of human VH with human D and JH gene segments.

82. The mouse of any one of aspects 70 to 81, wherein the mouse constant region comprises a mouse C-mu region, a C-delta region and a C-gamma region.

In one embodiment, each of the C regions is an endogenous, mouse C-region. In one embodiment at least the C-mu and the C-delta regions are mouse C regions. This is useful for harnessing the endogenous control mechanisms involved in the development of the various B-cell types and progenitors in the spleen and bone marrow.

In one embodiment, the C-gamma region is a human C-gamma region. This is beneficial for producing class-switched gamma-type heavy chains in the mouse in which essentially all of the expressed heavy chains have human variable regions and human constant regions.

83. The mouse of any one of aspects 70 to 82, wherein there is a mouse heavy chain enhancer between the human gene segments and the mouse constant region. This is useful for harnessing the endogenous mouse antibody- and B-cell development control mechanisms.

84. The mouse of any one of aspects 70 to 83, wherein there is a mouse S-mu switch between the human gene segments and the mouse constant region.

85. The mouse of any one of aspects 70 to 84, wherein the genome of the mouse comprises endogenous mouse heavy chain locus V, D and J gene segments upstream of the human gene segments.

86. The mouse of aspect 85, wherein the mouse V, D and J gene segments are present together with the endogenous inter-gene segment sequences.

87. The mouse of aspect 85 or 86, wherein the mouse gene segments are in inverted orientation. Thus, they are inverted with respect to the wild-type orientation in a mouse genome. They are thus inverted relative to the orientation of the mouse constant region.

88. The mouse of any one of aspects 70 to 87, wherein the mouse expresses light chains comprising human variable regions (eg, kappa light chains comprising human kappa variable regions). Thus, the human variable regions are derived from the recombination of human VL and JL gene segments, eg, human Vκ and human Jκ.

89. The mouse of aspect 88, comprising human Vκ and Jκ gene segments upstream of a mouse CL (eg, endogenous Cκ); optionally wherein the human Vκ and Jκ gene segments comprise Vκ2-24, Vκ3-20, Vκ1-17, Vκ1-16, Vκ3-15, Vκ1-13, Vκ1-12, Vκ3-11, Vκ1-9, Vκ1-8, Vκ1-6, Vκ1-5, Vκ5-2, Vκ4-1, Jκ1, Jκ2, Jκ3, Jκ4 and Jκ5.

90. The mouse of any one of aspects 70 to 89, wherein the human VH, DH and JH gene segments comprise human $V_H$ gene segments $V_H$2-5, 7-4-1, 4-4, 1-3, 1-2, 6-1, and all the human D and $J_H$ gene segments D1-1, 2-2, 3-3, 4-4, 5-5, 6-6, 1-7, 2-8, 3-9, 5-12, 6-13, 2-15, 3-16, 4-17, 6-19, 1-20, 2-21, 3-22, 6-25, 1-26 and 7-27; and J1, J2, J3, J4, J5 and J6. For example, the human VH, DH and JH gene segments comprise human $V_H$ gene segments $V_H$2-5, 7-4-1, 4-4, 1-3, 1-2, 6-1, and all the human D and $J_H$ gene segments D1-1, 2-2, 3-3, 4-4, 5-5, 6-6, 1-7, 2-8, 3-9, 3-10, 4-11, 5-12, 6-13, 1-14, 2-15, 3-16, 4-17, 5-18, 6-19, 1-20, 2-21, 3-22, 4-23, 5-24, 6-25, 1-26 and 7-27; and J1, J2, J3, J4, J5 and J6.

91. Use of the mouse of any one of aspects 70 to 90 for expressing immunoglobulin heavy chains comprising human variable regions, wherein the heavy chains expressed by the mouse are essentially exclusively said heavy chains comprising human variable regions; and said heavy chains comprising human variable regions are expressed as part of serum IgG1, IgG2b and IgM (and optionally IgG2a) antibodies in the mouse. The use is non-therapeutic, non-diagnostic and non-surgical use.

In one embodiment, the use comprises immunising the mouse with an antigen (eg, a human antigen) and isolating an IgG1 antibody that specifically binds the antigen.

In one embodiment, the use comprises immunising the mouse with an antigen (eg, a human antigen) and isolating an IgG2a antibody that specifically binds the antigen.

In one embodiment, the use comprises immunising the mouse with an antigen (eg, a human antigen) and isolating an IgG2b antibody that specifically binds the antigen.

Optionally, the use comprises making a derivative of the isolated antibody. Examples of derivative antibodies (according to any aspect herein) are antibodies that have one or more mutations compared to the isolated antibody (eg, to improve antigen-binding affinity and/or to enhance or inactivate Fc function) Such mutants specifically bind the antigen.

92. Use of the mouse of any one of aspects 70 to 90 for expressing immunoglobulin heavy chains comprising human variable regions, wherein the heavy chains expressed by the mouse are essentially exclusively said heavy chains comprising human variable regions and are expressed in a mouse that produces a normal proportion or percentage of mature splenic B-cells. The use is non-therapeutic, non-diagnostic and non-surgical use.

In one embodiment, the use further comprises isolating splenic tissue (eg, the spleen) from the mouse; optionally followed by isolating at least one antigen-specific B-cell from the tissue, wherein the B-cell(s) expresses an antibody that specifically binds a predetermined antigen. In one example, the use comprises immunising the mouse with the antigen prior to isolating the splenic tissue. In an example, the use comprises isolating an antibody produced by the B-cell (or by a hybridoma produced by fusion of the B-cell with a myeloma cell). Optionally, the use comprises making a derivative of the isolated antibody. Examples of derivative antibodies (according to any aspect herein) are antibodies that have one or more mutations compared to the isolated antibody (eg, to improve antigen-binding affinity and/or to enhance or inactivate Fc function) Such mutants specifically bind the antigen.

93. Use of the mouse of any one of aspects 70 to 90 for expressing immunoglobulin heavy chains comprising human variable regions, wherein the heavy chains expressed by the mouse are essentially exclusively said heavy chains comprising human variable regions and are expressed in a mouse that produces a normal proportion or percentage of bone marrow B-cell progenitor cells. The use is non-therapeutic, non-diagnostic and non-surgical use.

94. Use of the mouse of any one of aspects 70 to 90 for the purpose stated in one or more of aspects 70, 71, 73, 75 and 78.

The expression (eg, percentage expression or expression proportion or level) of Ig can be determined at the level of antibody chain mRNA transcripts in B-cells (eg, peripheral blood lymphocytes). Alternatively or additionally, the percentage expression is determined at the level of antibody in serum or blood of the vertebrates. Additionally or alternatively, the expression can be determined by FACS analysis of B cells.

In these aspects, "heavy chains comprising human variable regions" means variable regions derived from the recombination of human VH, D and JH gene segments.

"Essentially exclusively" the expressed heavy chains comprise human variable regions, ie, there is only a relatively very low or even no endogenous mouse heavy chain variable region expression. For example, at least 90, 95, 96, 97, 98, 99 or 99.5% or 100% of the heavy chains are heavy chains comprising human variable regions. In one embodiment, at least 90% of the heavy chains are heavy chains comprising human variable regions. The percentage expression can be determined at the level of heavy chain mRNA transcripts in B-cells (eg, peripheral blood lymphocytes). Alternatively or additionally, the percentage expression is determined at the level of heavy chains or antibodies in serum or blood of the mice. Additionally or alternatively, the expression can be determined by FACS analysis of B-cells.

The mouse can comprise any endogenous heavy chain locus in which human V, D and J gene segments are present, as described herein. In one example, the mouse genome comprises a mouse heavy chain locus in which at least human $V_H$ gene segments $V_H$2-5, 7-4-1, 4-4, 1-3, 1-2, 6-1, and all the human D and $J_H$ gene segments D1-1, 2-2, 3-3, 4-4, 5-5, 6-6, 1-7, 2-8, 3-9, 5-12, 6-13, 2-15, 3-16, 4-17, 6-19, 1-20, 2-21, 3-22, 6-25, 1-26 and 7-27; and J1, J2, J3, J4, J5 and J6 are upstream of the mouse constant region.

The vertebrate in these aspects is, for example naïve (ie, not immunised with a predetermined antigen, as the term is understood in the art; for example, such a vertebrate that has been kept in a relatively sterile environment as provided by an animal house used for R&D). In another example, the vertebrate has been immunised with a predetermined antigen, eg, an antigen bearing a human epitope.

In one embodiment, the heavy chains, together with light chains expressed in the mice of the invention, form antibodies (Ig). The light chains can be expressed from any transgenic light chain locus as herein described. For example the genome of the mouse comprises a heavy chain locus in which is a chimaeric immunoglobulin heavy chain locus comprising one or more human V gene segments, one or more human D gene segments and one or more human J gene segments upstream of a mu constant region of said non-human species; endogenous heavy chain expression has been substantially inactivated; and the heavy chain locus comprises an Eµ enhancer of said non-human vertebrate species.

In one embodiment of any aspect, endogenous light chain (eg, kappa and/or lambda) expression is substantially inactive or inactivated, for example using method as described herein. In this case, less than 10, 5, 4, 3, 2, 1 or 0.5% of such endogenous lambda light chains are expressed or expressible. Additionally or alternatively, less than 10, 5, 4, 3, 2, 1 or 0.5% of such endogenous kappa light chains are expressed or expressible. In one example, there is complete inactivation of endogenous kappa and/or lambda expression so no such light chains are expressed or expressible.

In one embodiment, the genome of the mouse comprises human kappa gene segments
  (i) Vκ1-5, Vκ1-6, Vκ1-8 and Vκ1-9 (and optionally Vκ5-2 and Vκ4-1); or
  (ii) Vκ1-5, Vκ1-6, Vκ1-8, Vκ1-9, Vκ3-11, Vκ1-12, Vκ3-15, Vκ1-16, Vκ1-17, Vκ3-20 (and optionally Vκ2-24 and/or Vκ1-13); or
  (iii) Vκ1-5, Vκ1-6, Vκ1-8, Vκ1-9, Vκ3-11, Vκ1-12, Vκ3-15, Vκ1-16, Vκ1-17, Vκ3-20, Vκ2-24, Vκ1-27, Vκ2-28, Vκ2-30 and Vκ1-33 (and optionally Vκ2-29 and/or Vκ2-40 and/or Vκ1-39);
  and optionally
  (iv) Jκ1, Jκ2, Jκ3, Jκ4 and Jκ5.

In one embodiment, the genome also comprises (i) at least human $V_H$ gene segments $V_H$2-5, 7-4-1, 4-4, 1-3, 1-2, 6-1, and all the human D and $J_H$ gene segments D1-1, 2-2, 3-3, 4-4, 5-5, 6-6, 1-7, 2-8, 3-9, 5-12, 6-13, 2-15, 3-16, 4-17, 6-19, 1-20, 2-21, 3-22, 6-25, 1-26 and 7-27; and J1, J2, J3, J4, J5 and J6 and (ii) at least human gene segments Vκ2-24, Vκ3-20, Vκ1-17, Vκ1-16, Vκ3-15, Vκ1-13, Vκ1-12, Vκ3-11, Vκ1-9, Vκ1-8, Vκ1-6, Vκ1-5, Vκ5-2, Vκ4-1, Jκ1, Jκ2, JK3, JK4 and JK5. As demonstrated in Example 16, such mice are fully functional in the aspect of rearrangement, BCR signalling and B cell maturation. Greater than 90% of the antibodies expressed by the mice comprised human heavy chain variable regions and human kappa light chain variable regions. These mice are, therefore, very useful for the selection of antibodies having human variable regions that specifically bind human antigen following immunisation of the mice with such antigen. Following isolation of such an antibody, the skilled person can replace the mouse constant regions with human constant regions using conventional techniques to arrive at totally human antibodies which are useful as drug candidates for administration to humans (optionally following mutation or adaptation to produce a further derivative, eg, with Fc enhancement or inactivation or following conjugation to a toxic payload or reporter or label or other active moiety).

In one embodiment, the genome also comprises a human iEκ and/or human 3'EK downstream of the human J gene segments in the locus.

The invention also includes the following clauses:

Clause 1. A mouse that expresses immunoglobulin heavy chains containing human variable regions,
  wherein the mouse comprises a genome that includes an immunoglobulin heavy chain locus comprising human VH, DH, and JH gene segments positioned upstream to a mouse constant region;
  wherein the mouse expresses immunoglobulin heavy chains, characterized in that at least 90% of the immunoglobulin heavy chains expressed by the mouse comprise a human variable region; and
  wherein the mouse expresses serum IgG1, IgG2b, and IgM antibodies comprising said heavy chains containing a human variable region.

Clause 2. A mouse that expresses immunoglobulin heavy chains containing human variable regions,
  wherein the mouse comprises a genome that includes an immunoglobulin heavy chain locus comprising human VH, DH, and JH gene segments which are positioned upstream to a mouse constant region;
  wherein the mouse expresses immunoglobulin heavy chains, characterized in that at least 90% of the immunoglobulin heavy chains expressed by the mouse comprise a human variable region; and
  wherein the mouse produces a normal proportion of mature splenic B-cells;
  wherein said normal proportion is a proportion of mature splenic B-cells produced by a mouse that expresses immunoglobulin heavy chains containing mouse variable regions and does not express immunoglobulin heavy chains containing human variable regions.

Clause 3. A mouse that expresses immunoglobulin heavy chains containing human variable regions,
  wherein the mouse comprises a genome that includes an immunoglobulin heavy chain locus comprising human VH, DH, and JH gene segments which are positioned upstream to a mouse constant region;
  wherein the mouse expresses immunoglobulin heavy chains, characterized in that it at least 90% of the immunoglobulin heavy chains expressed by the mouse comprise a human variable region; and
  wherein the mouse produces a normal proportion of bone marrow B-cell progenitor cells;
  wherein the normal proportion is a proportion of bone marrow B-cell progenitor cells produced by a mouse that expresses immunoglobulin heavy chains containing mouse variable regions and does not expresses immunoglobulin heavy chains containing human variable regions.

Clause 4. The mouse of any of the preceding clauses, wherein the mouse expresses a normal proportion of IgG1, IgG2b, and IgM in a sample of serum obtained from the mouse;
  wherein the normal proportion is as produced by a mouse that expresses immunoglobulin heavy chains containing mouse variable regions and does not expresses immunoglobulin heavy chains containing human variable regions.

Clause 5. The mouse of any of the preceding clauses, wherein the mouse constant region is C-mu, C-delta, and/or C-gamma.

Clause 6. The mouse of clause 5, wherein the mouse constant region is at least C-mu, C-delta and C-gamma.

Clause 7. The mouse of any of the preceding clauses, wherein the mouse constant region is an endogenous mouse C-region.

Clause 8. The mouse of any of the preceding clauses, wherein the mouse expresses a human C-gamma region.

Clause 9. The mouse of any of the preceding clauses, wherein the mouse is a naïve mouse.

Clause 10. The mouse of clause 1, wherein the mouse expresses serum IgG2a comprising said heavy chains containing a human variable region.

Clause 11. The mouse of any of the preceding clauses, wherein the mouse expresses Ig subtypes in a relative proportion of
  (i) serum IgG1 at a concentration of about 25-350 μg/ml;
  (ii) serum IgG2a at a concentration of about 0-200 μg/ml;
  (iii) serum IgG2b at a concentration of about 30-800 μg/ml; and
  (iv) serum IgM at a concentration of about 50-300 μg/ml;
  as determined by immunoglobulin capture on a plate followed by incubation with an anti-mouse isotype-specific antibodies each comprising a label and quantification of each immunoglobulin based on the level of each label.

Clause 12. The mouse of any of the preceding clauses, wherein the mouse expresses Ig subtypes in a relative proportion of
  (i) total serum IgG and IgM at a concentration of about 200-2500 μg/ml; and
  (ii) serum IgM at a concentration of about 100-800 μg/ml;
  as determined by immunoglobulin capture on a plate followed by incubation with an anti-mouse isotype-specific antibodies each comprising a label and quantification of each immunoglobulin based on the level of each label.

Clause 13. The mouse of any of the preceding clauses, wherein the mouse expresses said immunoglobulin heavy chains from splenic B-cells and wherein the mouse produces a normal proportion of mature splenic B-cells in total spleen cells comprising mature B-cells, and splenic T1 and T2 cells.

Clause 14. The mouse of any one of clauses 1-3, wherein, at least 95, 96, 97, 98, 99, or 99.5% of the immunoglobulin heavy chains expressed by the mouse are immunoglobulin heavy chains comprising human variable regions.

Clause 15. The mouse of any of the preceding clauses, wherein a mouse immunoglobulin heavy chain enhancer is positioned in said mouse heavy chain immunoglobulin locus between the human VH, DH, and JH gene segments and the mouse constant region.

Clause 16. The mouse of any of the preceding clauses, wherein a mouse S-mu switch is positioned in said mouse heavy chain immunoglobulin locus between the human VH, DH, and JH gene segments and the mouse constant region.

Clause 17. The mouse of any of the preceding clauses, wherein endogenous mouse immunoglobulin heavy chain V, D and J gene segments are positioned in said mouse heavy chain immunoglobulin locus upstream to the human VH, DH, and JH gene segments.

Clause 18. The mouse of clause 17, wherein the mouse immunoglobulin heavy chain V, D and J gene segments are present in said mouse heavy chain immunoglobulin locus with endogenous inter-gene segment sequences.

Clause 19. The mouse of clause 17 or 18, wherein the mouse immunoglobulin heavy chain V, D and J gene segments are positioned in said mouse heavy chain immunoglobulin locus in an orientation that is inverted relative to its natural endogenous orientation.

Clause 20. The mouse of any of the preceding clauses, wherein the mouse expresses light chains containing human kappa variable regions.

Clause 21. The mouse of clause 20, wherein the mouse expresses immunoglobulin light chains derived from recombination of $V\kappa$ with human $J\kappa$.

Clause 22. The mouse of any of the preceding clauses, wherein the mouse expresses light chains containing human lambda variable regions.

Clause 23. The mouse of clause 22, wherein the mouse expresses immunoglobulin light chains derived from recombination of $V\lambda$ with human $J\lambda$.

Clause 24. The mouse of clause 21, comprising a genome that includes human $V_K$ and $J_K$ gene segments positioned in said mouse heavy chain immunoglobulin locus upstream to a mouse CL.

Clause 25. The mouse of clause 24, wherein the mouse CL is an endogenous $C_K$.

Clause 26. The mouse of clauses 24 or 25, wherein the human $V_K$ and $J_K$ gene segments comprise $V_K2$-24, $V_K3$-20, $V_K1$-17, $V_K1$-16, $V_K3$-15, $V_K1$-13, $V_K1$-12, $V_K3$-11, $V_K1$-9, $V_K1$-8, $V_K1$-6, $V_K1$-5, $V_K5$-2, $V_K4$-1, $J_K1$, $J_K2$, $J_K3$, $J_K4$ and $J_K5$.

Clause 27. The mouse of any the preceding clauses, wherein the human VH, DH and JH gene segments contain
human VH gene segments: VH2-5, 7-4-1, 4-4, 1-3, 1-2, 6-1; human DH gene segments: D1-1, 2-2, 3-3, 4-4, 5-5, 6-6, 1-7, 2-8, 3-9, 5-12, 6-13, 2-15, 3-16, 4-17, 6-19, 1-20, 2-21, 3-22, 6-25, 1-26 and 7-27; and human JH gene segments: J1, J2, J3, J4, J5 and J6.

Clause 28. A method for obtaining one or more immunoglobulin heavy chains containing human variable regions, comprising providing the mouse of any of the preceding clauses and
isolating one or more immunoglobulin heavy chains.

Clause 29. The method of clause 28, wherein each immunoglobulin heavy chain is included in an antibody.

Clause 30. The method of clause 29, wherein said heavy chain and/or said antibody containing said heavy chain is modified after said isolating.

Clause 31. The method of clause 28, wherein a step of immunizing the mouse with an antigen is performed before the step of isolating the immunoglobulin heavy chains.

Clause 31. The method of clause 30, wherein the antigen is a human antigen.

Clause 32. The method of clause 30 or 31, wherein the immunoglobulin heavy chains are included in an IgG1 antibody, antibody fragment, or antibody derivative that specifically binds the antigen.

Clause 33. The method of clause 30 or 31, wherein the immunoglobulin heavy chains are included in an IgG2a antibody, antibody fragment, or antibody derivative that specifically binds the antigen.

Clause 34. The method of clause 32 or 33, wherein the immunoglobulin heavy chains are included in an IgG2b antibody, antibody fragment, or antibody derivative that specifically binds the antigen.

Clause 35. The method of clause 32 or 33, wherein the immunoglobulin heavy chains are included in an IgM antibody, antibody fragment, or antibody derivative that specifically binds the antigen.

Clause 36. An antibody or immunoglobulin heavy chain isolated in the method of any one of clauses 28 to 35, or a antigen-binding fragment or derivative of the antibody or heavy chain.

Clause 37. A pharmaceutical composition comprising the antibody, antibody fragment, or antibody derivative of clause 36 and a pharmaceutically acceptable carrier, excipient, or diluent.

Clause 38. A method for isolating splenic tissue comprising providing the mouse of 1 to 27,
collecting a spleen or portion thereof from the mouse, and obtaining tissue from the spleen or portion.

Clause 39. The method of clause 38, further comprising isolating at least one antigen-specific B-cell from the splenic tissue, wherein the B-cell expresses a heavy chain containing a human variable region.

Clause 40. The method of clause 38 or 39, wherein a step of immunizing the mouse with an antigen is performed before the step of collecting a spleen from the mouse.

Clause 41. The method of clause 40, wherein the antigen is a human antigen.

Clause 42. The method of clause 40 or 41 wherein the at least one antigen-specific B-cell produces an IgG1, IgG2a, IgG2b or IgM antibody comprising said heavy chain, wherein the antibody specifically binds the antigen.

Clause 43. The method of clauses 38 to 42, wherein the at least one antigen-specific B-cell that produces said heavy chain is fused with an immortal myeloma cell to produce a hybridoma cell.

Clause 44. The method of clauses 38 to 43, further comprising a step of isolating an immunoglobulin heavy chain from the B-cell or the hybridoma cell.

Clause 45. An antibody or immunoglobulin heavy chain isolated in the method of clause 44, or a antigen-binding fragment or derivative of the antibody or heavy chain.

Clause 46. A pharmaceutical composition comprising the antibody, antibody fragment, or antibody derivative of clause 45 and a pharmaceutically acceptable carrier, excipient, or diluent.

Clause 47. A method for obtaining a humanised antibody, comprising
selecting a mouse that expresses immunoglobulin heavy chains containing human variable regions,
wherein the mouse comprises a genome that includes an immunoglobulin heavy chain locus comprising human VH, DH, and JH gene segments positioned upstream to a mouse constant region,
wherein the mouse expresses immunoglobulin heavy chains, characterized in that at least 90% of the immunoglobulin heavy chains expressed by the mouse are immunoglobulin heavy chains containing a human variable region,
wherein the mouse expresses serum IgG1, IgG2b, and IgM antibodies comprising said heavy chains containing a human variable region,
wherein the mouse produces a normal proportion of mature splenic B-cells, wherein the mouse produces a normal proportion of bone marrow B-cell progenitor cells, and wherein the mouse expresses a normal proportion of IgG1, IgG2a, IgG2b, and IgM in a sample of serum obtained from the mouse, and wherein each said normal proportion is a proportion produced by a mouse that expresses immunoglobulin heavy chains containing mouse variable regions and does not expresses immunoglobulin heavy chains containing human variable regions;

collecting serum from said mouse; and obtaining a pool of humanised antibodies comprising IgG1, IgG2b, and IgM antibodies from the serum.

Clause 48. The method of clause 47, comprising a step of immunizing the mouse with an antigen before the step of collecting serum from said mouse.

Clause 49. The method of clause 48, further comprising steps of contacting said pool of humanised antibodies with said antigen;

binding said antigen with a humanised antibody in said pool of humanised antibodies; and isolating the humanised antibody that binds to said antigen.

Clause 50. The method of clause 49, further comprising steps of contacting the humanised antibody that binds to said antigen with an isotype-specific antibody, wherein the isotype-specific antibody recognizes IgG1, IgG2a, IgG2b, or IgM; and isolating the humanised antibody that binds to said isotype-specific antibody.

Clause 51. The method of clause 48, further comprising the steps of collecting the spleen or tissue thereof from said mouse, isolating B-cells from splenic tissue, fusing said B-cells with immortal myeloma cells to produce hybridoma cells expressing a pool of humanised antibodies comprising IgG antibodies from the serum, wherein the pool of antibodies is used in the method of clause 48.

Clause 52. The method of any of clauses 47-51, wherein said selected mouse comprises mouse immunoglobulin heavy chain V, D and J gene segments which are positioned in said mouse heavy chain immunoglobulin locus in an orientation that is inverted relative to its natural endogenous orientation.

Clause 53. The method of any of clauses 47-52 wherein the mouse expresses Ig subtypes in a relative proportion of (i) serum IgG1 at a concentration of about 25-350 µg/ml;
(ii) serum IgG2a at a concentration of about 0-200 µg/ml;
(iii) serum IgG2b at a concentration of about 30-800 µg/ml; and
(iv) serum IgM at a concentration of about 50-300 µg/ml;

as determined by immunoglobulin capture on a plate followed by incubation with an anti-mouse isotype-specific antibodies each comprising a label and quantification of each immunoglobulin based on the level of each label.

Clause 54. The method of any one of clauses 47 to 53, wherein, at least 95, 96, 97, 98, 99, or 99.5% of the immunoglobulin heavy chains expressed by the mouse are immunoglobulin heavy chains comprising human variable regions.

Clause 55. The method of any clauses 47-54, wherein a mouse immunoglobulin heavy chain enhancer is positioned in said mouse heavy chain immunoglobulin locus between the human VH, DH, and JH gene segments and the mouse constant region.

Clause 56. The method of any of clauses 47-55, wherein a mouse S-mu switch is positioned in said mouse heavy chain immunoglobulin locus between the human VH, DH, and JH gene segments and the mouse constant region.

Clause 57. The method of any of clauses 47-56, wherein endogenous mouse immunoglobulin heavy chain V, D and J gene segments are positioned in said mouse heavy chain immunoglobulin locus upstream to the human VH, DH, and JH gene segments.

Clause 58. The method of clause 57, wherein the mouse immunoglobulin heavy chain V, D and J gene segments are present in said mouse heavy chain immunoglobulin locus with endogenous inter-gene segment sequences.

Clause 59. The method of clause 57 or 58, wherein the mouse immunoglobulin heavy chain V, D and J gene segments are positioned in said mouse heavy chain immunoglobulin locus in an orientation that is inverted relative to its natural endogenous orientation.

Clause 60. The method of any of clauses 47-59, wherein the mouse expresses light chains containing human kappa variable regions.

Clause 61. The method of clause 60, wherein the mouse expresses immunoglobulin light chains containing human $J\kappa$.

Clause 62. The method of any of clauses 47-51, wherein the mouse expresses light chains containing human lambda variable regions.

Clause 63. The method of clause 62, wherein the mouse expresses immunoglobulin light chains containing human $J\lambda$.

Clause 64. The method of clause 61, comprising a genome that includes human $V\kappa$ and $J\kappa$ gene segments positioned in said mouse heavy chain immunoglobulin locus upstream to a mouse CL.

Clause 65. The mouse of clause 64, wherein the mouse CL is an endogenous $C\kappa$.

Clause 66. The mouse of clauses 64 or 65, wherein the human $V\kappa$ and $J\kappa$ gene segments comprise $V\kappa$2-24, $V\kappa$3-20, $V\kappa$1-17, $V\kappa$1-16, $V\kappa$3-15, $V\kappa$1-13, $V\kappa$1-12, $V\kappa$3-11, $V\kappa$1-9, $V\kappa$1-8, $V\kappa$1-6, $V\kappa$1-5, $V\kappa$5-2, $V\kappa$4-1, $J\kappa$1, $J\kappa$2, $J\kappa$3, $J\kappa$4 and $J\kappa$5.

Clause 69. The method of any of clauses 47-51, wherein the human VH, DH and JH gene segments contain human VH gene segments: VH2-5, 7-4-1, 4-4, 1-3, 1-2, 6-1;

human DH gene segments: D1-1, 2-2, 3-3, 4-4, 5-5, 6-6, 1-7, 2-8, 3-9, 5-12, 6-13, 2-15, 3-16, 4-17, 6-19, 1-20, 2-21, 3-22, 6-25, 1-26 and 7-27; and human JH gene segments: J1, J2, J3, J4, J5 and J6.

The invention also includes the following Attributes:

Attribute 1. An isolated non-human vertebrate, optionally a mammal, cell whose genome comprises an Ig H chain locus, the locus comprising, in 5' to 3' transcriptional orientation, a V region, a J region, a D region, a rat switch sequence, and a C region, wherein the C region is not a rat C region.

Attribute 1a. An isolated non-human vertebrate, optionally a mammal, cell whose genome comprises an Ig H chain locus, the locus comprising, in 5' to 3' transcriptional orientation, a V region, a J region, a D region, a rat switch sequence, wherein the locus comprises a human-rat and/or a mouse-rat sequence junction, and wherein the rat sequence is provided by the rat switch sequence.

Attribute 2. An isolated non-human vertebrate, optionally a mammal, cell whose genome comprises an Ig H chain locus, the locus comprising, in 5' to 3' transcriptional orientation, a V region, a J region, a D region, a rat switch sequence, and a C region, wherein the rat switch sequence is a rat S-mu sequence that comprises at least 3 contiguous repeats of the repeat sequence GGGCT (SEQ ID No. 46-50).

Attribute 3. An isolated non-human vertebrate, optionally a mammal, cell whose genome comprises an Ig H chain locus, the locus comprising, in 5' to 3' transcriptional orientation, a V region, a J region, a D region, a rat switch sequence and a C region, wherein the rat switch is a rat S-mu sequence that comprises GAGCT (296 repeats), GGGGT (50 repeats), and/or GGGCT (83 repeats).

Attribute 4. A non-human vertebrate organism, optionally a mammal, whose genome comprises an Ig H chain locus, the locus comprising, in 5' to 3' transcriptional orientation, a V region, a J region, a D region, a rat switch sequence, and a C region, wherein the C region is not a rat C region.

Attribute 4a. An non-human vertebrate organism, optionally a mammal, whose genome comprises an Ig H chain locus, the locus comprising, in 5' to 3' transcriptional orientation, a V region, a J region, a D region, a rat switch sequence,
  wherein the locus comprises a human-rat and/or a mouse-rat sequence junction, and
  wherein the rat sequence is provided by the rat switch sequence.

Attribute 5. A non-human vertebrate organism, optionally a mammal, whose genome comprises an Ig H chain locus, the locus comprising, in 5' to 3' transcriptional orientation, a V region, a J region, a D region, a rat switch sequence and a C region, wherein the rat switch sequence is a rat S-mu sequence that comprises at least 3 contiguous repeats of the repeat sequence GGGCT (SEQ ID NO. 46-50).

Attribute 6. A non-human vertebrate organism, optionally a mammal, whose genome comprises an Ig H chain locus, the locus comprising, in 5' to 3' transcriptional orientation, a V region, a J region, a D region, a rat switch sequence and a C region, wherein the rat switch sequence is a rat S-mu sequence that comprises GAGCT (296 repeats), GGGGT (50 repeats), and/or GGGCT (83 repeats).

Attribute 7. An isolated non-human vertebrate cell or organism, optionally a mammal, whose genome comprises an Ig H chain locus comprising DNA sequences from three or more vertebrate species, the Ig H chain locus comprising in 5' to 3' transcriptional orientation at least a V region, a D region, a J region, an enhancer, a rat switch sequence, and a C region.

Attribute 8. The non-human vertebrate cell or organism of any of attributes 1 to 7, wherein the genome of the cell or organism further comprises an Ig L chain locus comprising DNA sequences from three or more vertebrate species and wherein the Ig L chain locus comprises in 5' to 3' transcriptional orientation at least a human V region, a human J region, and a C region.

Attribute 9. The non-human vertebrate cell or organism of attribute 7 or 8, wherein said three or more vertebrate species are mouse, human and rat.

Attribute 10. The non-human vertebrate cell or organism of any of attributes 1 to 9, wherein said C region is endogenous to the cell or organism, and said V, D and/or J regions are human.

Attribute 11. The non-human vertebrate cell or organism of any of attributes 1-10, wherein the Ig H chain locus comprises a plurality of V regions, one or more D regions, and one or more J regions and/or wherein the Ig L chain locus comprises a plurality of V regions and one or more J regions.

Attribute 12. The non-human vertebrate cell or organism of any of attributes 1-11, wherein said V region is or said plurality of V regions are human.

Attribute 13. The non-human vertebrate cell or organism of any of attributes 1-11, wherein said D region is or said one or more D regions are human.

Attribute 14. The non-human vertebrate cell or organism of any of attributes 1-11, wherein said J region is or said one or more J regions are human.

Attribute 15. The non-human vertebrate cell or organism of any of attributes 11-14, wherein said V region is or said plurality of V regions are human, said D region is or said one or more D regions are human, and said J region is or said one or more J regions are human.

Attribute 16. The non-human vertebrate cell or organism of any of attributes 1, 1a, 4a, 4, 7-11 and 15, wherein said rat switch sequence is rat S-mu.

Attribute 17. The non-human vertebrate cell or organism of any of attributes 1, 4, 7-11, and 15 further comprising a mouse enhancer sequence positioned upstream of and operatively associated with said rat switch sequence.

Attribute 18. The non-human vertebrate cell or organism of attribute 16, further comprising a mouse enhancer sequence positioned upstream of and operatively associated with said rat S-mu sequence.

Attribute 19. The non-human vertebrate cell or organism of any of attributes 1-4, 7-15, wherein the C region is one of a mouse C region or a human C region.

Attribute 20. The non-human vertebrate cell or organism of attribute 19, wherein the C region is CH1.

Attribute 21. The non-human vertebrate cell or organism of attribute 19, wherein the mouse C region is one or more of a C-mu or a C-gamma.

Attribute 22. The non-human vertebrate cell or organism of attribute 21, wherein the mouse C region is a C-mu and a C-gamma.

Attribute 23. The non-human vertebrate cell or organism of attribute 7, wherein the cell is a mouse cell or the vertebrate is a mouse and wherein the mouse C region is the endogenous mouse C region.

Attribute 24. The non-human vertebrate cell or organism of any of attributes 1, 1a, 4, 4a, and 7, wherein the rat S-mu sequence comprises at least 3 and up to 83 contiguous repeats of the repeat sequence GGGCT (SEQ ID NO. 46-50).

Attribute 25. The non-human vertebrate cell or organism of any of attributes 1, 1a, 2, 4, 4a, 5 and 7, comprising a rat S-mu sequence which comprises 296 repeats of the motif GAGCT.

Attribute 26. The non-human vertebrate cell or organism of any of attributes 1, 1a, 2, 4, 4a, 5 and 7, comprising a rat S-mu sequence which comprises 50 repeats of the motif GGGGT.

Attribute 27. The non-human vertebrate cell or organism of any of attributes 1, 1a, 2, 4, 4a, 5 and 7, comprising a rat S-mu sequence which comprises 83 repeats of the motif GGGCT.

Attribute 28. The non-human vertebrate cell or organism of any preceding attributes wherein the rat S-mu sequence comprises SEQ ID NO 1.

Attribute 29. The non-human vertebrate cell of any preceding attribute, wherein the cell is an ES cell, hematopoietic stem cell or hybridoma.

Attribute 30. The non-human vertebrate cell or organism of any preceding attribute, wherein the cell or organism is a mouse ES cell or a mouse, respectively.

Attribute 31. The non-human vertebrate cell or organism of any of attributes 1-10, wherein said Ig H chain locus comprises a human JH, a human DH, and human VH2-5 operatively associated with a rat S-mu sequence Attribute 32. The non-human vertebrate cell or organism of any of attributes 1-10, wherein said Ig H chain locus comprises human JH1-5, a human DH, and a human operatively associated with a rat S-mu sequence.

Attribute 33. The non-human vertebrate cell or organism of any of attributes 1-10, wherein said cell is a mouse cell or said organism is a mouse;
wherein said Ig H chain locus comprises a mouse enhancer positioned upstream of and operatively associated with a rat switch sequence which is rat S-mu and wherein said C region is a mouse constant region.

Attribute 34. The non-human vertebrate cell or organism of attribute 33, wherein said Ig H chain V, D and J regions are human and/or said Ig L chain V and J regions are human.

Attribute 35. The non-human vertebrate cell or organism of attributes 1-10, wherein said Ig H chain locus comprises a rearranged VDJ region.

Attribute 36. The non-human vertebrate cell or organism of attribute 35, wherein said rearranged VDJ region is human.

Attribute 37. The non-human vertebrate cell or organism of any of attributes 1-10, wherein the cell or organism comprises a genome comprises human DNA comprising a plurality of human IgH V regions, one or more human D regions and one or more human J regions upstream of the host non-human mammal constant region and wherein the human IgH VDJ region comprises nucleotides 105,400,051 to 106,368,585 from human chromosome 14 (co-ordinates refer to NCBI36 for the human genome, ENSEMBL Release 54), or an equivalent human region from another human.

Attribute 38. The non-human vertebrate cell or organism of attribute 37, wherein human DNA is positioned between a non-human mammalian constant region and a non-human mammal J region positioned 3' distal to any other non-human J region.

Attribute 39. The non-human vertebrate cell or organism according to attribute 37, when the cell is a mouse cell or the organism is a mouse said V, D and J regions are human and positioned between coordinates 114,667,091 and 114,665,190 of mouse chromosome 12 (coordinates refer to NCBI m37, for the mouse C57BL/6J strain), or at an equivalent position in another non-human mammal genome.

Attribute 40. The non-human vertebrate cell or organism of attribute 39, when the cell is a mouse cell or the organism is a mouse said V, D and J regions are human and positioned between coordinates 114,667,089 and 114,667,090 (co-ordinates refer to NCBI m37, for the mouse C57BL/6J strain), or at an equivalent position in another non-human mammal genome.

Attribute 41. The non-human vertebrate cell or organism of attribute 37, wherein the cell is a mouse cell or the organism is a mouse, and wherein said V, D and J regions are human and positioned between coordinates 114,666,183 and 114,666,725, such as between coordinates 114,666,283 and 114,666,625, optionally between coordinates 114,666,335 and 114,666,536, optionally between coordinates 114,666,385 and 114,666,486, optionally between coordinates 114,666,425 and 114,666,446, such as between coordinates 114,666,435 and 114,666,436 of mouse chromosome 12, with reference to NCBI m37 for the mouse genome relating to mouse strain C57BL/6J or an equivalent position of mouse chromosome 12 from a different mouse strain or an equivalent position in the genome of another non-human vertebrate.

Attribute 42. The non-human vertebrate cell or organism according to any of attributes 1-10, wherein the cell is a mouse cell or the organism is a mouse and wherein said Ig H chain V, D and J regions or said Ig L chain V and J regions are human.

Attribute 43. The non-human vertebrate cell or organism according to any of attributes 1-10, wherein said V, D and J regions are human and comprise or consist of nucleotides 106,328,851-107,268,544, such as nucleotides 106,328,901-107,268,494, such as nucleotides 106,328,941-107,268,454, such as nucleotides 106,328,951-107,268,444 of human Chromosome 14, with reference to the GRCH37/hg19 sequence database, or equivalent nucleotides relating to chromosome 14 from a different human sequence or database.

Attribute 44. The non-human vertebrate cell or organism according to any of attributes 1-10, comprising a human kappa VJ region DNA comprising, in germline configuration, all of the V and J regions and intervening sequences from a human.

Attribute 45. The non-human vertebrate cell or organism according to attribute 44, wherein the human kappa VJ region DNA is positioned between coordinates 70,673,918-70,675,517, such as between coordinates 70,674,418-70675,017, such as between coordinates 70,674,655 70,674,856, such as between coordinates 70,674,705-70,674,906, such as between coordinates 70,674,745-70,674,766, such as between coordinates 70,674,755 and 70,674,756 of mouse chromosome 6 (with reference to NCBI m37 for the mouse genome, relating to mouse strain C57BL/6J), or at an equivalent position in another genome.

Attribute 46. The non-human vertebrate cell or organism according to attribute 45, wherein the human kappa VJ region DNA comprises or consists of a fragment from human chromosome 2, numbered with reference to the GRCH37/hg19 sequence database, or equivalent nucleotides relating to chromosome 2 from a different human sequence or database, the fragment selected from 1 or more of: (i) nucleotides 89,158,979-89,630,537, such as 89,159,029-89,630,487, such as 89,159,069-89,630,447, such as 89,159,079-89,630,437, optionally in addition to fragment (ii); (ii) nucleotides 89,941,614-90,267,076, such as 89,941,664-90,267,026, such as 89, 941,704-90,266,986, such as 89,941,714-90,266,976; optionally in addition to fragment (i); and (iii) nucleotides 89,158,979-90,267, 076, such as nucleotides 89,159,079-90,266,976.

Attribute 47. The non-human vertebrate cell or organism according to any of attributes 1-10, comprising human lambda region DNA which comprises at least one human Jλ region and at least one human Cλ region, optionally Cλ6 and/or Cλ7.

Attribute 48. The non-human vertebrate cell or organism according to attribute 47, comprising a plurality of human Jλ regions, optionally two or more of Jλ1, Jλ2, Jλ6 and Jλ7, optionally all of Jλ1, Jλ2, Jλ6 and Jλ7.

Attribute 49. The non-human vertebrate cell or organism according to attribute 47, comprising at least one human Jλ-Cλ cluster, optionally at least Jλ7-Cλ7.

Attribute 50. The non-human vertebrate cell or organism according to any of attributes 1-10, comprising a human Eλ enhancer.

Attribute 51. The non-human vertebrate cell or organism according to any of attributes 1-10, comprising human lambda VJ region DNA which comprises, in germline configuration, all of the V and J regions and intervening sequences from a human.

Attribute 52. The non-human vertebrate cell or organism according to attribute 51, wherein the human lambda VJ region DNA comprises or consists of nucleotides 22,375, 509-23,327,984, such as nucleotides 22,375,559-23,327, 934, such as nucleotides 22,375,599-23,327,894, such as nucleotides 22,375,609-23,327,884 from human chromosome 22, with reference to the GRCH37/hg19 sequence database, or equivalent nucleotides relating to human chromosome 22 from a different human sequence or database.

Attribute 53. The non-human vertebrate cell or organism according to any of attributes 1-10, wherein non-mouse DNA is positioned in the mouse genome between co-ordinates 19,027,763 and 19,061,845, such as between co-ordinates 19,037,763 and 19,051,845, such as between co-ordinates 19,047,451 and 19,047,652, such as between co-ordinates 19,047,491 and 19,047,602, such as between co-ordinates 19,047,541 and 19,047,562, such as between co-ordinates 19,047,551 and 19,047,552 of mouse chromosome 16, with reference to NCBI m37 for the mouse genome, or at an equivalent position in other genome.

Attribute 54. The non-human vertebrate cell or organism according to any of attributes 1-10, wherein non-human DNA is positioned in the mouse genome between co-ordinates 70,673,918 and 70,675,517 such as between co-ordinates 70,674,418 and 70,675,017, such as between co-ordinates 70,674,655 and 70,674,856, such as between co-ordinates 70,674,705 and 70,674,806, such as between co-ordinates 70,674,745 and 70,674,766, such as between co-ordinates 70,674,755 and 70,674,756 of mouse chromosome 6, with reference to NCBI m37 for the mouse genome, relating to mouse strain C57BL/6J) or at an equivalent position in another genome.

Attribute 55. The non-human vertebrate cell or organism according to any of attributes 1-10, wherein said V, D and J regions are human and human light chain kappa VJC DNA, or part thereof, is inserted immediately upstream of the mouse kappa VJC region.

Attribute 56. The non-human vertebrate cell or organism according to any of attributes 1-10, wherein the genome of the cell or organism is modified to prevent or reduce expression of fully host-species specific antibodies.

Attribute 57. The non-human vertebrate cell or organism according to attribute 56, wherein the genome of the cell or organism is modified by inversion of all or part of the non-human mammal VDJ region, or VJ region.

Attribute 58. The non-human vertebrate cell or organism according to attribute 56, wherein the genome of the cell or organism comprises human DNA and non-human DNA, and said non-human DNA comprises endogenous V and J regions or V, D, and J regions which have not been deleted.

Attribute 59. The non-human vertebrate organism according to any of attributes 1-10 generated in a genetic background which prevents the production of mature host B and T lymphocytes.

Attribute 60. The non-human vertebrate organism according to attribute 59 generated in a Rag-1 or Rag-2 deficient background.

Attribute 61. The non-human vertebrate cell according to attribute 29 which is an ES cell or hematopoietic stem cell capable of developing into a non-human mammal able to produce a repertoire of antibodies or antibody chains which are chimaeric, said chimaeric antibodies or chains having a non-human mammal constant region and a human variable region.

Attribute 62. The non-human vertebrate cell according to attribute 29 which is an ES cell or hematopoietic stem cell capable of contributing to tissues and organs of a non-human mammal which is able to produce a repertoire of antibodies or antibody chains which are chimaeric, said chimaeric antibodies or chains having a non-human mammal constant region and a human variable region.

Attribute 63. The non-human vertebrate cell or organism according to any of attributes 1-10, comprising human variable region DNA from at least a human heavy and human light chain.

Attribute 64. The non-human vertebrate cell or organism according to any of attributes 1-10, wherein the cell or organism is homozygous at one, two or all three immunoglobulin loci for DNA encoding a chimaeric antibody chain.

Attribute 65. The non-human vertebrate cell or organism according to any of attributes 1-10, wherein the cell or organism is heterozygous at one, two or all three immunoglobulin loci for DNA encoding a chimaeric heavy or light chain.

Attribute 66. The non-human vertebrate cell or organism according to attributes 1-10, wherein the genome of the cell or organism does not comprise constant region DNA from another cell or organism.

Attribute 67. The non-human vertebrate cell according to attribute 29 which is immortalised.

Attribute 68. The non-human vertebrate cell according to attribute 67 which is an ES cell line AB2.1, or a cell from a mouse strain selected from C57BL/6, M129, 129/SV, BALB/c, and any hybrid of C57BL/6, M129, 129/SV or BALB/c.

Attribute 69. A method for obtaining immunoglobulin heavy chain comprising human immunoglobulin variable region,
  comprising providing the mouse of any of attributes attribute 1a, 4, 4a, 5-28, 30-60, and 63-66 and
  isolating polypeptide comprising immunoglobulin heavy chain comprising said human variable region.

Attribute 69a. The method of attribute 69, wherein said immunoglobulin heavy chain is a heavy chain of two chain or four chain antibody.

Attribute 69b. An antibody isolated according to the method of attribute 69.

Attribute 69c. A pharmaceutical composition comprising the antibody of attribute 69b and a pharmaceutically acceptable carrier, excipient, or diluent.

Attribute 69d. The method of attribute 69 or 69a, wherein a step of immunizing the mouse with an antigen is performed before the step of isolating the immunoglobulin heavy chains.

Attribute 69e. The method of attribute 69d, wherein the antigen is a human antigen.

Attribute 69f. The method of attribute 69 or 69a, wherein said immunoglobulin heavy chain is one of isotype IgG1, IgG2, IgG3, and IgM said human variable region specifically binds said antigen.

Attribute 69g. The method of attribute 69f, wherein said immunoglobulin heavy chain is a heavy chain of a two chain or four chain antibody and said antibody specifically binds said antigen.

Attribute 70. A polynucleotide landing pad sequence, the polynucleotide comprising nucleic acid regions homologous to regions of a target chromosome to allow for insertion by homologous recombination into the target chromosome, and comprising a nucleic acid site which permits recombinase-driven insertion of a nucleic acid into the landing pad, wherein the polynucleotide sequence comprises one or more of: (i) a rat switch sequence, optionally a rat S-mu switch, which is optionally the sequence of SEQ ID NO 1; (ii) in a 5' to 3' direction, a mouse Eμ sequence, a rat switch sequence, and mouse Cμ; and/or (iii) a 3' homology arm having the sequence of SEQ ID NO 6.

Attribute 71. The non-human vertebrate organism, optionally a mammal, comprising a landing pad sequence according to attribute 70 which has been inserted into the genome of the cell.

Attribute 72. The non-human vertebrate cell or organism, optionally a mammal, or landing pad according to attribute 70 or 71, wherein the rat switch sequence comprises 3, 4, 5, 6 or more contiguous repeats of the sequence GGGCT, optionally being SEQ ID NO 1.

Attribute 73. The non-human vertebrate cell or organism, optionally a mammal, or landing pad according to any of attributes 70 to 72, wherein the landing pad sequence comprises the sequence of SEQ ID NO 2.

Attribute 74. The non-human vertebrate cell or organism, optionally a mammal, or landing pad according to any of attributes 70 to 73, wherein the landing pad sequence comprises the sequence of SEQ ID NO 3.

Attribute 75. A method for producing an isolated non-human vertebrate, optionally a mammal, cell comprising:
  inserting one or more non-native DNA constructs into a non-human mammal cell genome,
  thereby producing a cell whose genome includes an Ig H chain locus having a V region, a J region, a D region, a rat switch sequence, and a C region in a 5' to 3' transcriptional orientation, wherein the C region is not a rat C region.

Attribute 76. A method for producing an isolated non-human vertebrate, optionally a mammal, cell comprising:
  inserting one or more non-native DNA constructs into a non-human mammal cell genome,
  thereby producing a cell whose genome includes an Ig H chain locus having a V region, a J region, a D region, a rat switch sequence, and a C region in a 5' to 3'transcriptional orientation, wherein the rat switch sequence is a rat S-mu sequence that comprises at least 3 contiguous repeats of the repeat sequence GGGCT (SEQ ID NO. 46-50).

Attribute 77. A method for producing a non-human vertebrate, optionally a mammal, cell comprising:
  inserting one or more non-native DNA constructs into a non-human mammal cell genome,
  thereby producing a cell whose genome includes an Ig H chain locus having a V region, a J region, a D region, a rat switch sequence, and a C region in a 5' to 3' transcriptional orientation, wherein the rat switch is a rat S-mu sequence that comprises GAGCT (296 repeats), GGGGT (50 repeats), and/or GGGCT (83 repeats).

Attribute 78. A method for producing a non-human vertebrate organism, optionally a mammal, comprising:
  inserting one or more non-native DNA constructs into a non-human mammal cell genome,
  thereby producing a genome including an Ig H chain locus having a V region, a J region, a D region, a rat switch sequence, and a C region in a 5' to 3' transcriptional orientation, wherein the C region is not a rat C region.

Attribute 79. A method for producing a non-human vertebrate organism, optionally a mammal, comprising:
  inserting one or more non-native DNA constructs into a non-human mammal cell genome,
  thereby producing a genome including an Ig H chain locus having a V region, a J region, a D region, a rat switch sequence, and a C region in a 5' to 3' transcriptional orientation, wherein the rat switch is a rat S-mu sequence that comprises at least 3 contiguous repeats of the repeat sequence GGGCT (SEQ ID NO. 46-50).

Attribute 80. A method for producing a non-human vertebrate organism, optionally a mammal, comprising:
  inserting one or more non-native DNA constructs into a non-human mammal cell genome,
  thereby producing a genome including an Ig H chain locus having a V region, a J region, a D region, a rat switch sequence, and a C region in a 5' to 3' transcriptional orientation wherein the rat switch is a rat S-mu sequence that comprises GAGCT (296 repeats), GGGGT (50 repeats), and/or GGGCT (83 repeats).

Attribute 81. A method for producing an isolated non-human vertebrate cell or organism, optionally a mammal, comprising:
  inserting one or more non-native DNA constructs into a non-human mammal cell genome,
  thereby producing a genome including an Ig H chain locus having DNA from three or more mammalian species, wherein the Ig H chain locus includes, in a 5' to 3' transcriptional orientation, at least a V region, a D region, a J region, an enhancer, a rat switch sequence, and a C region.

Attribute 82. The method of any of attributes 75 to 81, further comprising:
  inserting one or more non-native DNA constructs into the non-human mammal cell genome,
  thereby producing a genome including an Ig L chain locus comprising in 5' to 3' transcriptional orientation at least a human VL region, a human JL region, and a CL region.

Attribute 83. The method attribute 81 or 82, wherein said constant region (CL) is a mouse or human constant region.

Attribute 84. The method of attribute 81 or 82, wherein the enhancer is a mouse enhancer sequence.

Attribute 85. The method of any of attributes 75, 78, or 81-84, wherein said rat switch sequence is rat S-mu.

Attribute 86. The method of any of attributes 75 to 85, wherein said V, D and/or J region is human or V and/or J region is human.

Attribute 87. The method of any of attributes 75 to 86, wherein the IgH locus C region is one of a mouse C region or a human C region.

Attribute 88. The method according to any of attributes 75 to 87, wherein the non-human mammal cell genome is then modified to prevent expression of native (fully host species specific) antibodies in the cell or vertebrate organism, optionally by inversion of all or part of host non-human mammal Ig locus, optionally by insertion of one or more site specific recombinase sites into the genome and then use of these sites in recombinase-mediated excision or inversion of all or a part of the host non-human mammal Ig locus.

Attribute 89. The method according to any of attributes 75 to 88, wherein the cell is an ES cell.

Attribute 90. The method according to any of attributes 75 to 89, wherein the step of inserting DNA is accomplished by step-wise insertion of multiple constructs by homologous recombination and wherein said DNA is inserted upstream of the host non-human mammal constant region.

Attribute 91. The method according to any of attributes 75 to 90, wherein the step of inserting DNA occurs at a site where an initiation cassette has been inserted into the genome of an ES cell, thereby providing a unique targeting region.

Attribute 92. The method according to any of attributes 75 to 91, wherein one or more insertion events utilises site specific recombination.

Attribute 93. The method according to attribute 92, wherein said one or more insertion events is mediated by, or involves, one or more of Frt sites, Flp recombinase, Dre recombinase, Rox sites, or PhiC31 recombinase.

Attribute 94. The method according to any of attributes 75 to 93, wherein inserting one or more non-native DNA constructs into a non-human mammal cell genome comprises the steps of:
1 insertion of DNA forming an initiation cassette (also called a landing pad herein) into the genome of a cell;
2 insertion of a first DNA fragment into the insertion site, the first DNA fragment comprising a first portion of a human DNA and a first vector portion containing a first selectable marker or generating a selectable marker upon insertion;
3 optionally removal of part of the vector DNA;
4 insertion of a second DNA fragment into the vector portion of the first DNA fragment, the second DNA fragment containing a second portion of human DNA and a second vector portion, the second vector portion containing a second selectable marker, or generating a second selectable marker upon insertion;
5 removal of any vector DNA to allow the first and second human DNA fragments to form a contiguous sequence; and
6 iteration of the steps of insertion of a part of the human V(D)J DNA and vector DNA removal, as necessary, to produce a cell with all or part of the human VDJ or VJ region sufficient to be capable of generating a chimaeric antibody in conjunction with a host constant region,
wherein the insertion of at least one DNA fragment uses site specific recombination.

Attribute 95. The method according to any of attributes 75 to 94, wherein the landing pad sequence comprises SEQ ID NO 6, SEQ ID NO. 2, or SEQ ID NO. 3.

Attribute 96. The method according to any of attributes 75 to 95, wherein the landing pad is inserted into the mouse cell genome by homologous recombination between mouse J1-4 and mouse C mu sequences.

Attribute 97. The method according to any of attributes 75 to 96, wherein the landing pad is recombined into the mouse cell genome by homologous recombination between mouse J1-4 and E mu sequences.

Attribute 98. The method according to any of attributes 75 to 97, wherein the landing pad comprises a non-host S-mu, such as a rat S-mu switch.

Attribute 99. The method, cell or mammal as attributed in any of attributes 1 to 98, wherein a human coding region DNA sequence is in a functional arrangement with a non-human mammal control sequence, such that transcription of the human DNA is controlled by the non-human mammal control sequence.

Attribute 100. A method for producing an antibody or antibody heavy or light chain specific to a desired antigen, the method comprising immunizing the non-human vertebrate as attributed in attribute 4-28, 30-60, 63-66, or 71-74 with the desired antigen and recovering the antibody or antibody chain or recovering a cell producing the antibody or heavy or light chain.

Attribute 101. The method for producing a fully humanised antibody or antibody chain comprising carrying out the method according to attribute 100 and then replacing the non-human mammal constant region of the recovered antibody or antibody chain with a human constant region, suitably by engineering of the nucleic acid encoding the antibody or antibody chain.

Attribute 102. A humanised antibody or antibody chain produced according to attribute 100 or 101 or a derivative thereof that binds the desired antigen.

Attribute 103. Use of the humanised antibody or chain produced according to attribute 100 or 101 or a derivative thereof that binds the desired antigen in medicine.

Attribute 104. The humanised antibody or antibody chain produced according to attribute 100 or 101 or a derivative thereof that binds the desired antigen for use in medicine.

Attribute 105. A pharmaceutical composition comprising an antibody or antibody chain according to attribute 100 or 101 or a derivative thereof that binds the desired antigen and a pharmaceutically acceptable carrier or other excipient.

Attribute 106. A chimaeric antibody derivative of a chimaeric antibody produced according to attribute 100, wherein the derivative binds the desired antigen.

Attribute 107. A mouse whose genome comprises an insertion of human IgH VDJ DNA between co-ordinates 114,667,090 and 114,665,190 of mouse chromosome 12, such as between co-ordinates 114,667,089 and 114,667,090, the insert comprising nucleotides 105,400,051 to 106,368,585 from human chromosome 14 (co-ordinates refer to NCBI36 for the human genome and NCBI m37, for the mouse C57BL/6J strain, or equivalent coordinates in another human chromosome 14 sequence or in another mouse genome respectively), the insertion being upstream of the host non-human mammal constant region such that the mouse is able to produce a repertoire of chimaeric heavy chains having a non-human mammal constant region and a human variable region, wherein the mammal also comprises an insertion of the complete VJC human light chain region such that a fully human lambda or kappa human antibody chain may be generated which is able to form an antibody with a chimaeric heavy chain.

Attribute 108. A mouse whose genome comprises an insertion of human IgH VDJ DNA between co-ordinates 114,667,090 and 114,667,091 of mouse chromosome 12, the insert comprising or consisting of nucleotides 105,400,051 to 106,368,585 from human chromosome 14 (co-ordinates refer to NCBI36 for the human genome and NCBI m37 for the mouse C57BL/6J strain, or equivalent coordinates in another human chromosome 14 sequence or in another mouse genome respectively), the insertion being upstream of the mouse constant region such that the mouse is able to produce a repertoire of chimaeric heavy chains having a mouse constant region and a human variable region, wherein the mouse also comprises an insertion of the complete VJC human light chain region such that a fully human lambda or kappa human antibody chain may be generated which is able to form an antibody with a chimaeric heavy chain.

Attribute 109. A mouse whose genome comprises an insertion of human IgH VDJ DNA between co-ordinates 114,667,090 and 114,665,190 of mouse chromosome 12, where co-ordinates refer to NCBI m37, for the mouse C57BL/6J strain, or an insertion at an equivalent position in another mouse strain, the insert comprising or consisting of nucleotides 106,328,951-107,268,444 from human chromosome 14, where co-ordinates refer to the GRCH37/hg19 sequence database for humans, or the same nucleotides from an equivalent position in another human chromosome 14 sequence, the insertion being upstream of the host mouse constant region such that the mouse is able to produce a repertoire of chimaeric heavy chains having a mouse constant region and a human variable region, wherein the mouse also comprises an insertion of the complete VJC human light chain region which is functional to generate a fully human lambda or kappa human antibody chain which forms an antibody with a chimaeric heavy chain.

Attribute 110. A mouse according to attribute 109, wherein the insertion is between co-ordinates 114,666,435 and 114,666,436 of mouse chromosome 12.

Attribute 116. A method of making a non-human vertebrate cell, optionally a mouse or rat, the method comprising:
  (a) providing the non-human ES cell of attribute 29, 61, 62, or 68 and whereby the non-human ES cell is capable of giving rise to a progeny cell in which endogenous antibody expression is inactivated and wherein the progeny cell is capable of expressing antibodies comprising human variable regions; and
  (b) optionally differentiating said non-human ES cell into said progeny cell or a non-human vertebrate organism comprising said progeny cell.

Attribute 117. The method according to attribute 116, wherein said plurality of human antibody gene segments comprises at least eleven human V segments.

Attribute 118. The method according to attribute 116 or 117, wherein said plurality of human antibody gene segments comprises at least six human J segments.

Attribute 119. The method according to any one of attributes 116 to 118, wherein a human nucleotide sequence is inserted in step (b), the nucleotide sequence comprising said antibody gene segments, wherein the nucleotide sequence is at least 110 kb.

Attribute 120. The method according to any one of attributes 116 to 119, wherein the endogenous locus is a heavy chain locus and the human antibody gene segments are between the 3'-most endogenous JH gene segment and endogenous C-mu.

Attribute 121. The method according to any one of attributes 116 to 120, wherein the progeny cell is homozygous for said transgenic locus.

Attribute 122. A method of isolating an antibody that binds a predetermined antigen, the method comprising
  (a) providing a vertebrate organism, mouse, or mammal, optionally a rat, according to any one of attributes 1a, 4, 4a, 5-28, 30-60, 63-66, or 71-74, and 107-110;
  (b) immunising said vertebrate organism, mouse, or mammal with said antigen (optionally wherein the antigen is an antigen of an infectious disease pathogen);
  (c) removing B lymphocytes from the vertebrate organism, mouse, or mammal and selecting one or more B lymphocytes expressing antibodies that bind to the antigen;
  (d) optionally immortalising said selected B lymphocytes or progeny thereof, optionally by producing hybridomas therefrom; and
  (e) isolating an antibody (e.g., and IgG-type antibody) expressed by the B lymphocytes.

Attribute 123. The method of attribute 122, comprising the step of isolating from said B lymphocytes nucleic acid encoding said antibody that binds said antigen; optionally exchanging the heavy chain constant region nucleotide sequence of the antibody with a nucleotide sequence encoding a human or humanised heavy chain constant region and optionally affinity maturing the variable region of said antibody; and optionally inserting said nucleic acid into an expression vector and optionally a host.

Attribute 124. The method of attribute 122 or 123, further comprising making a mutant or derivative of the antibody produced by the method of attribute 122 or 123.

Attribute 125. An antibody or fragment thereof comprising variable regions that specifically bind a predetermined antigen with a sub-50 nM affinity as determined by surface plasmon resonance, wherein the antibody is isolated from a non-human vertebrate organism, mouse, or mammal, optionally a rat, according to any one of attributes 1a, 4, 4a, 5-28, 30-60, 63-66, or 71-74, and 107-110 and comprises heavy chain CDR3s (as defined by Kabat) encoded by a rearranged VDJ of said vertebrate organism, mouse, or mammal, wherein the VDJ is the product of rearrangement in vivo of a human JH gene segment of a heavy chain locus of said vertebrate with D (optionally a human D gene segment of said locus) and VH gene segments.

Attribute 126. An antibody or fragment that is identical to an antibody of attribute 125 or a derivative thereof, optionally a derivative whose constant regions are human and/or an affinity matured derivative, that specifically binds said antigen with a sub-50 nM affinity as determined by surface plasmon resonance.

Attribute 127. A pharmaceutical composition comprising an antibody or fragment of attribute 125 or 126 and a pharmaceutically-acceptable diluent, excipient or carrier.

Attribute 128. A nucleotide sequence encoding a heavy chain variable region of an antibody or fragment of attribute 125 or 126, optionally as part of a vector (e.g., an expression vector).

Attribute 129. The nucleotide sequence of attribute 128, wherein the sequence is a cDNA derived from a B-cell of the vertebrate from which the antibody of attribute 125 is isolated, or is identical to such a cDNA.

Attribute 130. An isolated host cell (e.g., a hybridoma or a CHO cell or a HEK293 cell) comprising a nucleotide sequence according to attribute 128 or 129.

Attribute 131. A method of isolating an antibody that binds a predetermined antigen, the method comprising
  (a) providing a vertebrate organism, mouse, or mammal, optionally a rat, according to any one of attributes 1a, 4, 4a, 5-28, 30-60, 63-66, or 71-74, and 107-110;
  (b) immunising said vertebrate organism, mouse, or mammal with said antigen;
  (c) removing B lymphocytes from the vertebrate organism, mouse, or mammal and selecting a B lymphocyte expressing an antibody that binds to the antigen with sub-nM affinity, wherein the antibody is according to attribute 125;
  (d) optionally immortalising said selected B lymphocyte or progeny thereof, optionally by producing hybridomas therefrom; and
  (e) isolating an antibody (e.g., and IgG-type antibody) expressed by the B lymphocyte.

Attribute 132. The method of attribute 131, comprising the step of isolating from said B lymphocyte nucleic acid encoding said antibody that binds said antigen; optionally exchanging the heavy chain constant region nucleotide sequence of the antibody with a nucleotide sequence encoding a human or humanised heavy chain constant region and optionally affinity maturing the variable region of said antibody; and optionally inserting said nucleic acid into an expression vector and optionally a host.

Attribute 133. The method of attribute 131 or 132, further comprising making a mutant or derivative of the antibody produced by the method of attribute 131 or 132.

Attribute 137. A cassette for inversion and inactivation of endogenous mouse antibody heavy chain gene segments, the segments being part of a heavy chain locus sequence on chromosome 12 of a mouse cell (e.g., ES cell) wherein the sequence is flanked at its 3' end by a site-specific recombination site (e.g., lox, rox or frt), the cassette comprising a nucleotide sequence encoding an expressible label or selectable marker and a compatible site-specific recombination site (e.g., lox, rox or frt) flanked by a 5' and a 3' homology arm, wherein (i) the 5' homology arm is mouse chromosome 12 DNA from coordinate 119,753,124 to coordinate 119,757,104 and the 3' homology arm is mouse chromosome 12 DNA from coordinate 119,749,288 to 119,753,123; (ii) the 5' homology arm is mouse chromosome 12 DNA from coordinate 119,659,459 to coordinate 119,663,126 and the 3' homology arm is mouse chromosome 12 DNA from coordinate 119,656,536 to 119,659,458; or (iii) the 5' homology arm is mouse chromosome 12 DNA from coordinate 120,918,607 to coordinate 120,921,930 and the 3' homology arm is mouse chromosome 12 DNA from coordinate 120,915,475 to 120,918,606.

Attribute 138. A mouse or mouse cell whose genome comprises an inversion of a chromosome 12, wherein the inversion comprises inverted endogenous heavy chain gene segments (e.g., VH, D and JH, such as the entire endogenous heavy chain VDJ region); wherein the genome of the mouse or mouse cell comprises a transgenic heavy chain locus comprising a plurality of human VH gene segments, a plurality of human D segments and a plurality of human JH segments upstream of and operatively associated with an endogenous constant region (e.g., C mu) so that the mouse or mouse cell (optionally following differentiation into a B-cell) is capable of expressing an antibody comprising a variable region comprising sequences derived from the human gene segments; and wherein the inversion is (i) an inversion of mouse chromosome 12 from coordinate 119,753,123 to coordinate 114,666,436; (ii) an inversion of mouse chromosome 12 from coordinate 119,659,458 to coordinate 114,666,436; or (iii) an inversion of mouse chromosome 12 from coordinate 120,918,606 to coordinate 114,666,436.

The invention also includes the following provisions:

≥80% of all LIGHT chain are human Vλ

Provision 1. A non-human vertebrate having a genome comprising a recombinant immunoglobulin light chain locus, said locus comprising a targeted insert positioned in an endogenous light chain locus,
wherein the targeted insert comprises human lambda light chain locus DNA and is positioned upstream to a lambda light chain constant region,
wherein said targeted insert includes a repertoire of human Vλ and Jλ gene segments,
wherein the vertebrate expresses immunoglobulin light chains comprising human lambda variable regions, and
wherein at least 80% of the immunoglobulin light chains expressed in said vertebrate comprises human lambda variable regions.

Provision 2. The vertebrate of provision 1, wherein the repertoire of human Vλ and Jλ insertion comprises at least the functional human V and J gene segments comprised by a human lambda chain immunoglobulin locus from Vλ2-18 to Cλ7.

Provision 3. The vertebrate of provision 1, wherein the endogenous light chain locus is the endogenous kappa locus.

Provision 4. The vertebrate of provision 3, wherein the genome is homozygous for the repertoire of human Vλ and Jλ gene segments and wherein the endogenous kappa chain expression is substantially inactive.

Provision 5. The vertebrate of provision 4, wherein the endogenous kappa chain expression is completely inactive.

Provision 6. The vertebrate of provision 1, wherein the endogenous light chain locus is the endogenous lambda locus.

Provision 7. The vertebrate of provision 6, wherein the genome is homozygous for the repertoire of human Vλ and Jλ gene segments and wherein expression of the endogenous lambda chain is substantially inactive.

Provision 8. The vertebrate of provision 7, wherein expression of the endogenous lambda chain is completely inactive.

Provision 9. The vertebrate of provision 1, wherein the targeted insert is positioned downstream of endogenous V and J light chain gene segments.

Provision 10. The vertebrate of provision 1, wherein the targeted insert includes a constant region of a human lambda light chain locus.

Provision 11. The vertebrate of provision 10, wherein said light chains expressed by said vertebrate comprise V-C regions derived from recombination of human Vλ, Jλ, and Cλ gene segments.

Provision 12. The vertebrate of provision 1, wherein the vertebrate is derived from a mouse ES cell or a rat ES cell.

Provision 13. The vertebrate of provision 1, wherein the vertebrate is a mouse or a rat.

Provision 14. The vertebrate of provision 1, wherein the targeted insert comprises inter-gene segment intervening sequences being human lambda light chain locus DNA which is between functional human V and J light chain gene segments in a human locus or comprises inter-gene segment intervening sequences being lambda light chain locus DNA which is between corresponding lambda light chain gene segments in an endogenous non-human vertebrate genome.

Provision 15. The vertebrate of provision 14, wherein the targeted insert includes a human lambda immunoglobulin gene segment pseudogene.

Provision 16. The vertebrate of provision 14, wherein the targeted insert lacks a human lambda immunoglobulin gene segment pseudogene.

Provision 17. The vertebrate of provision 1, wherein at least 80, 84, 85, 90, 95, 96, 97, 98, or 99%, or 100% of immunoglobulin light chains expressed by said vertebrate comprise human V regions derived from recombination of human Vλ and Jλ gene segments.

Provision 18. The vertebrate of provision 17, wherein at least 90% of immunoglobulin light chains expressed by said vertebrate comprise human V regions derived from recombination of human Vλ and Jλ gene segments.

≥60% of all LIGHT chains have human Vλ regions

Provision 19. A non-human vertebrate having a genome comprising a recombinant immunoglobulin light chain locus, said locus comprising a targeted insert positioned in an endogenous light chain locus,
wherein the targeted insert comprises human lambda light chain locus DNA which is positioned upstream to a lambda light chain constant region and includes a repertoire of human Vλ and Jλ gene segments,
wherein said genome comprises kappa V gene segments positioned upstream to a light chain constant region,
wherein the vertebrate expresses immunoglobulin light chains comprising lambda variable regions, and
wherein at least 60% of immunoglobulin light chains expressed by said vertebrate comprises human lambda variable regions.

Provision 20. The vertebrate provision 19, wherein at least 65, 70, 80, 84, 85, 90, 95, 96, 97, 98, or 99%, or 100% of immunoglobulin light chains expressed by said vertebrate comprises human variable regions derived from recombination of human Vλ and Jλ gene segments.

Provision 21. The vertebrate of provision 20, wherein at least 84% of immunoglobulin light chains expressed by said vertebrate comprises human variable regions derived from recombination of human Vλ and Jλ gene segments.

Provision 22. The vertebrate of provision 21, wherein at least 95% of immunoglobulin light chains expressed by said vertebrate comprises human variable regions derived from recombination of human Vλ and Jλ gene segments.

Provision 23. The vertebrate of provision 19, wherein the vertebrate is derived from a mouse ES cell or a rat ES cell.

Provision 24. The vertebrate of provision 19, wherein the vertebrate is a mouse or a rat.

Provision 25. The vertebrate or cell of provision 19, wherein the targeted insert is positioned downstream of endogenous V and J light chain gene segments.

Provision 25a. The vertebrate of provisions 19, wherein the kappa V gene segments positioned upstream to a light chain constant region are endogenous kappa V gene segments.

Vλ Jλ into kappa or lambda locus

Provision 26. A non-human vertebrate or cell having a genome comprising a recombinant immunoglobulin light chain locus, said locus comprising a targeted insert positioned downstream to endogenous V and J light chain gene segments,
  wherein the targeted insert comprises human immunoglobulin Vλ and Jλ gene segments,
  wherein said human Vλ and Jλ gene segments are positioned upstream to a light chain constant region,
  wherein said human Vλ and Jλ gene segments comprise at least the functional V and J gene segments from Vλ2-18 to Cλ7 of a human lambda light chain locus, and
  wherein said vertebrate or cell expresses immunoglobulin light chains comprising human lambda variable regions.

Provision 27. The vertebrate or cell of provision 26, wherein the targeted insert includes a constant region of a human lambda light chain locus.

Provision 28. The vertebrate or cell of provision 27, wherein said light chains expressed by said vertebrate or cell comprise human V-C regions derived from recombination of human Vλ, Jλ, and Cλ gene segments.

Provision 29. The vertebrate or cell of provision 26, wherein the endogenous V and J light chain gene segments are V kappa and J kappa gene segments.

Provision 30. The vertebrate or cell of provision 26, wherein endogenous kappa chain expression is substantially inactive.

Provision 31. The vertebrate or cell of provision 30, wherein the endogenous kappa chain expression is completely inactive.

Provision 32. The vertebrate or cell of provision 26, wherein the endogenous V and J light chain gene segments are V lambda and J lambda gene segments.

Provision 33. The vertebrate or cell of provision 26, wherein endogenous lambda chain expression is substantially inactive.

Provision 34. The vertebrate or cell of provision 30, wherein the endogenous lambda chain expression is completely inactive.

Provision 35. The vertebrate or cell of provision 25, wherein the targeted insert comprises inter-gene segment intervening sequences being human lambda light chain locus DNA which is between functional human V and J light chain gene segments in a human locus or comprises inter-gene segment intervening sequences being lambda light chain locus DNA which is between corresponding lambda light chain gene segments in an endogenous genome.

Provision 36. The vertebrate or cell of provision 35, wherein the targeted insert includes a pseudogene.

Provision 37. The vertebrate of provision 25, wherein the vertebrate is derived from a mouse ES cell or a rat ES cell.

Provision 38. The vertebrate of provision 25, wherein the vertebrate is a mouse or a rat.

Provision 38a. The vertebrate of provisions 25, wherein said human Vλ and Jλ gene segments are positioned upstream to an endogenous light chain constant region.

VJCλ into kappa locus

Provision 39. A non-human vertebrate or cell having a genome comprising a recombinant immunoglobulin kappa light chain locus, said locus comprising a targeted insert of human Vλ, Jλ and Cλ gene segments positioned upstream to an endogenous kappa constant region,
  wherein said vertebrate or cell expresses immunoglobulin light chains comprising human V-C regions derived from recombination of human Vλ, Jλ, and Cλ gene segments, and
  wherein said targeted insert comprises at least the functional V, J and C gene segments from Vλ3-1 to Cλ7 of a human lambda chain immunoglobulin locus.

Provision 40. The vertebrate or cell of provision 39, wherein said targeted insert comprises at least the functional V, J and C gene segments from Vλ2-18 to Cλ7 of a human lambda light chain immunoglobulin locus.

Provision 41. The vertebrate or cell of provision 39, wherein the targeted insert comprises inter-gene segment intervening sequences being human lambda light chain locus DNA which is between functional human V and J or J and C light chain gene segments in a human locus or comprises inter-gene segment intervening sequences being lambda light chain locus DNA which is between corresponding lambda light chain gene segments in an endogenous non-human vertebrate genome.

Provision 42. The vertebrate or cell of provision 41, wherein the targeted insert includes a pseudogene.

Provision 43. The vertebrate of provision 39, wherein the vertebrate is derived from a mouse ES cell or a rat ES cell.

Provision 44. The vertebrate of provision 39, wherein the vertebrate is a mouse or a rat.

Provision 45. The vertebrate or cell of provision 39, wherein the endogenous kappa chain expression is substantially inactive.

Provision 46. The vertebrate or cell of provision 45, wherein the endogenous kappa chain expression is completely inactive.

Provision 47. The vertebrate or cell of provision 39, wherein the targeted insert is positioned downstream of endogenous V and J light chain gene segments.

VJλ into kappa locus

Provision 48. A non-human vertebrate or cell having a genome comprising a recombinant immunoglobulin kappa light chain locus, said locus comprising endogenous Vκ and Jκ gene segments upstream to a targeted insert,
  wherein the targeted insert comprises at least the functional Vλ and Jλ gene segments from Vλ3-1 to Cλ7 of a human lambda light chain immunoglobulin locus,
  wherein said vertebrate or cell expresses an immunoglobulin light chain comprising a human lambda variable region, and
  wherein expression of light chains comprising endogenous kappa variable regions derived from recombination of endogenous Vκ and Jκ gene segments is substantially inactive.

Provision 49. The vertebrate of provision 48, wherein the vertebrate is derived from a mouse ES cell or a rat ES cell.

Provision 50. The vertebrate of provision 48, wherein the vertebrate is a mouse or a rat.

Provision 51. The vertebrate or cell of provision 48, wherein said targeted insert comprises at least the functional Vλ and Jλ gene segments from Vλ2-18 to Cλ7 of a human lambda light chain immunoglobulin locus.

Provision 52. The vertebrate or cell of provision 48, wherein endogenous Vκ and Jκ light chain expression is completely inactive.

Provision 53. The vertebrate or cell of provision 48, wherein less than 10, 5, 4, 3, 2, 1, or 0.5% of immunoglobulin light chains expressed by said vertebrate or cell comprise endogenous kappa variable regions.

Provision 54. The vertebrate or cell of provision 48, wherein the targeted insert comprises inter-gene segment intervening sequences being human lambda light chain locus DNA which is between functional human V and J gene segments in a human locus or comprises inter-gene segment intervening sequences being lambda light chain locus DNA which is between corresponding lambda light chain gene segments in an endogenous genome.

Provision 55. A non-human vertebrate or cell, having a recombinant genome comprising endogenous immunoglobulin kappa light chain locus sequences comprising at least one endogenous kappa enhancer (Eκ) sequence, at least one endogenous V kappa gene segment, at least one endogenous J kappa gene segment, and at least one endogenous C kappa constant region,
  wherein endogenous V kappa and J kappa gene segments are separated from a respective endogenous Eκ sequence on the same chromosome by a distance that substantially prevents production of an endogenous immunoglobulin kappa light chain polypeptide.

Provision 56. The vertebrate or cell of provision 55, wherein the endogenous V kappa and J kappa gene segments are separated from the respective endogenous Eκ sequence by a distance that is greater than the distance between endogenous V kappa and J kappa gene segments and a respective endogenous Eκ sequence in an endogenous, non recombinant kappa light chain locus.

Provision 57. The cell of provision 55, wherein the cell is a mouse cell or a rat cell.

Provision 57a. The vertebrate of provision 55, wherein the vertebrate is derived from a mouse ES cell or a rat ES cell.

Provision 58. The vertebrate of provision 55, wherein the vertebrate is a mouse or a rat.

Provision 59. The vertebrate or cell of provision 55, wherein said recombinant genome comprises a targeted insert comprising one or more human V light chain gene segments and one or more human J light chain gene segments,
  wherein the targeted insert is positioned between said endogenous V kappa and J kappa gene segments and said respective endogenous Eκ sequence.

Provision 59a. The vertebrate or cell of provision 59, wherein said recombinant genome is homozygous for the targeted insert.

Provision 60. The vertebrate or cell of provision 59, wherein the targeted insert comprises light chain gene segments comprising one or more human Vκ and one or more Jκ gene segments.

Provision 60a. The vertebrate or cell of provision 60, wherein said recombinant genome is homozygous for the targeted insert.

Provision 61. The vertebrate or cell of any preceding provision, wherein the targeted insert comprises a repertoire of human Vλ and Jλ gene segments and wherein the targeted insert has been inserted within 100 kb of an endogenous light chain locus enhancer sequence.

Provision 62. The vertebrate or cell of any preceding provision, wherein the targeted insert comprises a repertoire of at least 10 human Vλ gene or human Jλ gene segments and wherein the targeted insert is positioned upstream to an endogenous light chain constant region.

Provision 63. The vertebrate or cell of provision 62, wherein the targeted insert comprises at least a portion of a human immunoglobulin lambda chain locus from Vλ2-18 to Vλ3-1.

Provision 64. The vertebrate or cell of provision 62, wherein the targeted insert comprises at least 2, 3, 4, or 5 human Jλ gene segments.

Provision 65. The vertebrate or cell of provision 64, wherein the human Jλ gene segments are different from each other.

Provision 66. The vertebrate or cell of provision 65, wherein the human Jλ gene segments are Jλ1, Jλ2, Jλ3, Jλ6, and Jλ7.

Provision 67. The vertebrate or cell of provision 62, wherein the targeted insert includes at least a portion of a human immunoglobulin lambda chain locus from Vλ2-18 to Cλ7.

Provision 68. The vertebrate or cell of provision 62, wherein the targeted insert excludes human Jλ4Cλ4 and/or human Jλ5Cλ5.

Provision 69. The vertebrate or cell of provision 62, wherein the targeted insert includes a human light chain enhancer.

Provision 70. The vertebrate or cell of provision 69, wherein the human light chain enhancer is an Eλ sequence and wherein the Eλ sequence is positioned between the human Jλ gene segments and an endogenous light chain constant region.

Provision 71. The vertebrate or cell of provision 70, wherein the human Jλ gene segments are part of a human JλCλ cluster.

Provision 72. The vertebrate or cell of any preceding provision, wherein the vertebrate or cell expresses lambda immunoglobulin light chains comprising a repertoire of human lambda variable regions encoded by human Vλ and Jλ gene segments, wherein the human Vλ includes Vλ3-1 and, optionally, one or more of Vλ2-18, Vλ3-16, V2-14, Vλ3-12, Vλ2-11, Vλ3-10, Vλ3-9, Vλ2-8, and Vλ4-3, wherein the human Vλ and Jλ gene segments are included in the targeted insert.

Provision 73. The vertebrate or cell of any preceding provision, wherein the vertebrate or cell expresses lambda immunoglobulin light chains comprising a repertoire of human lambda variable regions encoded by human Vλ and Jλ gene segments, wherein the human Vλ includes Vλ2-14 and, optionally, one or more of Vλ2-18, Vλ3-16, V2-14, Vλ3-12, Vλ2-11, Vλ3-10, Vλ3-9, Vλ2-8, Vλ4-3, and Vλ3-1, wherein the human Vλ and Jλ gene segments are included in the targeted insert.

Provision 74. The vertebrate or cell of any preceding provision, wherein the vertebrate or cell expresses lambda immunoglobulin light chains comprising a repertoire of human lambda variable regions encoded by human Vλ and Jλ gene segments, wherein the human Vλ includes including Vλ2-8 and, optionally, one or more of Vλ2-18, Vλ3-16, V2-14, Vλ3-12, Vλ2-11, Vλ3-10, Vλ3-9, Vλ4-3, and Vλ3-1, wherein the human Vλ and Jλ gene segments are included in the targeted insert.

Provision 75. The vertebrate or cell of any preceding provision, wherein the vertebrate or cell expresses lambda immunoglobulin light chains comprising a repertoire of human lambda variable regions encoded by human Vλ and Jλ gene segments, wherein the human Vλ includes Vλ3-10 and, optionally, one or more of Vλ2-18, Vλ3-16, V2-14, Vλ3-12, Vλ2-11, Vλ3-10, Vλ3-9, Vλ2-8, Vλ4-3, and Vλ3-1, wherein the human Vλ and Jλ gene segments are included in the targeted insert.

Provision 76. The vertebrate or cell of any preceding provision, wherein the targeted insert comprises each functional Vλ gene segment from Vλ2-18 to Vλ3-1 of a human lambda light chain locus.
Provision 77. The vertebrate or cell of any preceding provision, wherein at least a human Vλ3-1 is included in the targeted insert.
Provision 78. The vertebrate or cell of provision 77, wherein at least Vλ2-18, Vλ3-16, V2-14, Vλ3-12, Vλ2-11, Vλ3-10, Vλ3-9, Vλ2-8, Vλ4-3, and Vλ3-1 are included in the targeted insert.
Provision 79. The vertebrate of any preceding provision, wherein the vertebrate expresses more lambda chains than kappa chains.
Provision 80. The vertebrate of any preceding provision, wherein the vertebrate expresses no endogenous kappa chains.
Provision 81. The vertebrate of any preceding provision, wherein endogenous kappa chain expression is substantially inactive.
Provision 82. The vertebrate of provision 81, wherein the endogenous kappa chain expression is completely inactive.
Provision 83. The vertebrate of any preceding provision, wherein the vertebrate expresses immunoglobulin heavy chains.
Provision 84. The vertebrate or cell of any preceding provision, wherein the targeted insert includes a human lambda enhancer (EA) sequence and wherein the Eλ sequence is positioned in said endogenous light chain locus.
Provision 85. The vertebrate or cell of provision 84, wherein the Eλ sequence is positioned downstream to a 3'-most downstream Cλ region that is included in the targeted insert.
Provision 86. The vertebrate or cell of any preceding provision, wherein at least human JC gene segments Jλ1-Cλ1, Jλ2-Cλ2, Jλ3-Cλ3, Jλ6-Cλ6, and Jλ7-Cλ7 are included in the targeted insert.
Provision 87. The vertebrate or cell of any preceding provision, wherein the human gene segments included in the targeted insert are in germline configuration.
Provision 88. The vertebrate or cell of provision 87, wherein the targeted insertion comprises inter-gene segment sequences of a human light chain locus or inter-gene segment sequences of an endogenous light chain locus.
Provision 89. The vertebrate or cell of any preceding provision, wherein an endogenous light chain enhancer remains in the endogenous locus.
Provision 90. The vertebrate or cell of provision 89, wherein the endogenous enhancer is in germline configuration.
Provision 91. The vertebrate or cell of provision 90, wherein the endogenous locus is a kappa locus.
Provision 92. The vertebrate or cell of provision 90, wherein the endogenous kappa enhancer is present.
Provision 93. The vertebrate or cell of provision 92, wherein the endogenous enhancer is an iEκ and/or 3'Eκ sequence.
Provision 94. The vertebrate or cell of provision 90, wherein the germline configuration is with respect to an endogenous light chain constant region.
Provision 95. The vertebrate or cell of any preceding provision, wherein the genome is heterozygous for the targeted insert.
Provision 96. The vertebrate or cell of provision 95, wherein the targeted insert comprises human V and J or human V, J, and C light chain gene segments.
Provision 97. The vertebrate or cell of provision 96, wherein the targeted insert is positioned in an endogenous light chain lambda locus.
Provision 98. The vertebrate or cell of provision 96, wherein the targeted insert is positioned in an endogenous light chain kappa locus.
Provision 99. The vertebrate or cell of provision 98, wherein the endogenous kappa enhancer is present and is an iEκ and/or 3'Eκ sequence.
Provision 100. The vertebrate of provision 95, wherein the vertebrate is derived from a mouse ES cell or a rat ES cell.
Provision 101. The vertebrate of provision 95, wherein the vertebrate is a mouse or a rat.
Provision 102. The vertebrate or cell of provision 95, wherein the genome comprises a first targeted insert comprising a human lambda gene segment and a second targeted insert comprising human kappa immunoglobulin V and J gene segments,
  wherein the first targeted insert is positioned in a first endogenous kappa locus and wherein the second targeted insert is positioned in a second endogenous kappa locus and upstream to an endogenous kappa constant region.
Provision 103. The vertebrate or cell of provision 102, wherein an endogenous kappa light chain enhancer is present in the first and/or second endogenous kappa locus.
Provision 104. The vertebrate or cell of provision 103, wherein the endogenous kappa loci are optionally in germline configuration.
Provision 105. The vertebrate or cell of provision 95, wherein the genome comprises a first targeted insert comprising a human lambda gene segment and a second targeted insert comprising human kappa immunoglobulin V and J gene segments,
  wherein the first targeted insert is positioned in a first endogenous lambda locus and wherein the second targeted insert is positioned in a second endogenous lambda locus and upstream to an endogenous lambda constant region.
Provision 106. The vertebrate or cell of provision 105, wherein an endogenous lambda light chain enhancer is present in the first and/or second endogenous lambda locus.
Provision 106. The vertebrate or cell of provision 105, wherein the endogenous kappa loci are optionally in germline configuration.
Provision 107. The vertebrate or cell of any preceding provision, wherein the genome is homozygous for a targeted insert comprising a human lambda gene segment and positioned in the endogenous immunoglobulin light chain locus.
Provision 108. The vertebrate or cell of any preceding provision, wherein the genome comprises two or more targeted inserts comprising human lambda gene segments and positioned in the endogenous kappa and/or lambda locus.
Provision 109. The vertebrate or cell of provision 108, wherein the genome is homozygous for a first targeted insert comprising a human lambda gene segment and positioned in each endogenous lambda locus, wherein the vertebrate or cell expresses lambda light chains comprising human lambda variable regions;
  wherein a second targeted insert comprising a human lambda gene segment is positioned in a first endogenous kappa locus,
  wherein a third targeted insert comprising a plurality of human Vκ and Jκ gene segments is positioned upstream to an endogenous Cκ gene segment in a second endogenous kappa locus, and
  wherein the vertebrate or cell expresses kappa light chains comprising human kappa variable regions.

Provision 110. The vertebrate or cell of provision 108, wherein the targeted inserts comprising a lambda gene segment is positioned in the endogenous kappa and lambda loci comprise the same repertoire of human lambda gene segments.

Provision 111. The vertebrate or cell of provision 109, wherein the first and second targeted inserts comprise the same repertoire of human lambda gene segments.

Provision 112. The vertebrate or cell of provision 108, wherein the targeted inserts comprising a lambda gene segment is positioned in the kappa loci and the targeted inserts positioned in the lambda loci comprise a different repertoire of human lambda gene segments.

Provision 113. The vertebrate or cell of provision 109, wherein the first and second targeted inserts comprise a different repertoire of human lambda gene segments.

Provision 114. A non-human vertebrate or cell having a genome comprising one or more first and/or second targeted inserts positioned in at least one endogenous immunoglobulin locus, wherein the one or more first and/or second targeted inserts each comprise a repertoire of human immunoglobulin gene segments, the genome comprising one of the following light chain loci arrangements:
(a) an L positioned in a first endogenous kappa chain locus and a K positioned in a second endogenous kappa chain locus;
(b) an L positioned in a first endogenous lambda chain locus and a K positioned in a second endogenous lambda chain allele;
(c) an L positioned in each endogenous kappa chain loci;
(d) an L positioned in each endogenous lambda chain loci;
(e) an L positioned in a first endogenous kappa chain locus and with a second endogenous kappa chain locus is inactive; or
(f) an L positioned in a first endogenous lambda chain locus and with a second endogenous lambda chain locus is inactive; wherein
an L represents a first targeted insert comprising at least functional human Vλ and Jλ gene segments from Vλ3-1 to Cλ7 comprised by a human lambda chain immunoglobulin locus;
wherein
a K represents a second targeted insert comprising human Vκ and Jκ gene segments; and
wherein each L or K is positioned upstream to a constant region, thereby allowing expression of light chains comprising human V regions derived from recombination of human V and J gene segments.

Provision 115. The vertebrate of provision 114, wherein the vertebrate is derived from a mouse ES cell or a rat ES cell.

Provision 116. The vertebrate of provision 114, wherein the vertebrate is a mouse or a rat.

Provision 117. The vertebrate or cell of provision 114, wherein L further comprises a human Cλ region Provision 118. The vertebrate or cell of provision 114, wherein the L comprises functional human lambda chain immunoglobulin gene segments from Vλ2-18 to Cλ7.

Provision 119. The vertebrate or cell of provision 114, wherein the genome comprises one of the following light chain loci arrangements:
(a) and an L positioned in the first or in the first and second endogenous lambda chain loci;
(a) and a K positioned in the first or in the first and second endogenous lambda chain loci;
(a) and an L positioned in the first endogenous lambda chain locus and a K positioned in the second endogenous lambda chain locus;
(b) and an L positioned in the first or in the first and second endogenous kappa chain loci;
(b) and a K positioned in the first or in the first and second endogenous kappa chain loci;
(b) and an L positioned in the first endogenous kappa chain locus and a K positioned in the second endogenous kappa chain locus;
(c) and a K positioned in the first or in the first and second endogenous lambda chain loci;
(c) and an L positioned in the first or in the first and second endogenous lambda chain loci;
(c) and an L positioned in the first endogenous lambda chain locus and a K positioned in the second endogenous lambda chain locus;
(c) and with the first and second endogenous lambda chain loci is inactive;
(d) and an L positioned in the first or in the first and second endogenous kappa chain loci;
(d) and a K positioned in the first or in the first and second endogenous kappa chain loci;
(d) and an L positioned in the first endogenous kappa chain locus and a K positioned in the second endogenous kappa chain locus; or
(d) and with the first and second endogenous kappa chain loci is inactive.

Provision 120. The vertebrate or cell of provision 114, wherein endogenous kappa chain expression is substantially inactive.

Provision 121. The vertebrate or cell of provision 120, wherein the endogenous kappa chain expression is completely inactive.

Provision 122. The vertebrate or cell of provision 114, wherein endogenous lambda chain expression is substantially inactive.

Provision 123. The vertebrate or cell of provision 122, wherein the endogenous lambda chain expression is completely inactive.

Provision 124. The vertebrate or cell of provision 114, wherein one or more L's are positioned upstream to an endogenous lambda or kappa constant region.

Provision 125. The vertebrate or cell of provision 114, wherein one or more L's positioned in a lambda locus is positioned upstream to an endogenous lambda constant region.

Provision 126. The vertebrate or cell of provision 114, wherein one or more L's positioned in a kappa locus is positioned upstream to an endogenous kappa constant region.

Provision 127. The vertebrate or cell of provision 114, wherein each L positioned in a lambda locus is positioned upstream to a human lambda constant region.

Provision 128. The vertebrate or cell of provision 114, wherein each L positioned in a kappa locus is positioned upstream to a human kappa constant region.

Provision 129. The vertebrate or cell of provision 114, wherein one or more K's are positioned upstream to an endogenous lambda or kappa constant region.

Provision 130. The vertebrate or cell of provision 114, wherein one or more K's positioned in a lambda locus is positioned upstream to an endogenous lambda constant region.

Provision 131. The vertebrate or cell of provision 114, wherein each K positioned in a kappa locus is positioned upstream to an endogenous kappa constant region.

Provision 132. The vertebrate or cell of provision 114, wherein each K positioned in a lambda locus is positioned upstream to a human lambda constant region.

Provision 133. The vertebrate or cell of provision 114, wherein each K positioned in a kappa locus is positioned upstream to a human kappa constant region.

Provision 134. The vertebrate or cell of provision 114, wherein the genome comprises more than one L and each L comprises a different repertoire of human Vλ and Jλ gene segments.

Provision 135. The vertebrate or cell of provision 134, wherein the genome comprises two L's.

Provision 136. The vertebrate or cell of provision 134, wherein the genome comprises three L's.

Provision 137. The vertebrate or cell of provision 114, wherein the genome comprises more than one L and each L comprises a different repertoire of human Vλ, Jλ, and Cλ gene segments.

Provision 138. The vertebrate or cell of provision 114, wherein the genome comprises more than one K and each K comprises a different repertoire of human Vκ and Jκ gene segments.

Provision 139. The vertebrate or cell of provision 138, wherein the genome comprises two L's.

Provision 140. The vertebrate or cell of provision 138, wherein the genome comprises three K's.

Provision 141. The vertebrate or cell of provision 114, wherein the genome comprises more than one L and each L comprises a different repertoire of human Vκ, Jκ, and Cκ gene segments.

Provision 141a. The vertebrate of provision 114, wherein the vertebrate is derived from a mouse ES cell or a rat ES cell.

Provision 142. The vertebrate or cell of any preceding provision, wherein the genome comprises an immunoglobulin heavy chain locus comprising human VH gene segments.

Provision 143. A method for producing an antibody or light chain comprising a lambda variable region specific to a desired antigen, the method comprising immunizing a vertebrate according to any preceding provision with the desired antigen and recovering the antibody or light chain or recovering a cell producing the antibody or light chain.

Provision 144. The method of provision 143, further comprising a step of replacing the non-human vertebrate constant region with a human constant region thereby producing a humanised antibody or antibody light chain.

Provision 145. The method of provision 144, wherein the humanised antibody or antibody light chain is produced by engineering a nucleic acid encoding the fully humanised antibody or light chain.

Provision 146. A humanised antibody or antibody light chain produced by the method of provision 143.

Provision 147. A derivative of the humanised antibody or antibody light chain of provision 146.

Provision 148. A pharmaceutically composition comprising the humanised antibody or antibody light chain produced by the method of provision 143 a pharmaceutically acceptable carrier, excipient, or diluent.

Provision 149. A method for inactivating endogenous IgK-VJ gene segments in a genome of a non-human vertebrate or cell, the method comprises positioning in the genome a targeted insert comprising human immunoglobulin gene segments, wherein the targeted insert is positioned between an endogenous IgK-VJ gene segment and Eκ enhancer sequence which increases the physical distance between the endogenous IgK-VJ and the EK enhancer, thereby inactivating the endogenous IgK-VJ gene segments.

Provision 150. The method of provision 149, wherein the non-human vertebrate is a mouse or rat.

Provision 150a. The method of provision 148, wherein the vertebrate developed from a mouse ES cell or a rat ES cell.

Provision 151. The method of provision 149, wherein the cell is a mouse cell or a rat cell.

Provision 152. The method of provision 149, wherein the human immunoglobulin gene segments comprise human VL and JL gene segments.

Provision 153. The method of provision 152, wherein human VL and JL gene segments comprise human Vλ and Jλ gene segments and/or human Vκ and Jκ gene segments.

Provision 154. A method for obtaining a pool of immunoglobulin light chains wherein at least 80% of the immunoglobulin light chains comprise human Vλ and Jλ regions, the method comprising
  providing the vertebrate or cell of provision 1 and
  isolating a sample comprising the immunoglobulin light chains.

Provision 154a. The method of provision 154, further comprising a step of isolating the immunoglobulin light chains from the sample.

Provision 154b. The method of provision 154a, wherein the sample is serum, spleen, thymus, lymph node, or appendix.

Provision 154c. The method of provision 154b wherein the spleen comprises splenic tissue containing B-cells.

Provision 154d. The method of provision 154c, further comprising a step of isolating B-cells from splenic tissue.

Provision 155. The method of provision 154, wherein the immunoglobulin light chains are included in antibodies or antibody fragments.

Provision 156. An antibody or antibody fragment isolated in the method of provision 155.

Provision 156a. A derivative of the antibody or antibody fragment of provision 156.

Provision 157. A pharmaceutical composition comprising the antibody or antibody fragment of provision 156 and a pharmaceutically acceptable carrier, excipient, or diluent.

Provision 158. The method of provision 154, comprising a step of immunizing the vertebrate with an antigen before the step of isolating a sample comprising the immunoglobulin light chains.

Provision 159. A method for obtaining a pool of immunoglobulin light chains wherein at least 60% of the immunoglobulin light chains comprise human lambda light chains, the method comprising
  providing the vertebrate or cell of provision 19 and
  isolating a sample comprising the immunoglobulin light chains.

Provision 159a. The method of provision 159, further comprising a step of isolating the immunoglobulin light chains from the sample.

Provision 159b. The method of provision 159a, wherein the sample is serum, spleen, thymus, lymph node, or appendix.

Provision 159c. The method of provision 159b wherein the spleen comprises splenic tissue containing B-cells.

Provision 159d. The method of provision 159c, further comprising a step of isolating B-cells from splenic tissue.

Provision 160. The method of provision 159, wherein the immunoglobulin light chains are included in antibodies or antibody fragments.

Provision 161. An antibody or antibody fragment isolated in the method of provision 160.

Provision 161a. A derivative of the antibody or antibody fragment of provision 161.

Provision 162. A pharmaceutical composition comprising the antibody or antibody fragment of provision 161 and a pharmaceutically acceptable carrier, excipient, or diluent.

Provision 163. The method of provision 159, comprising a step of immunizing the vertebrate with an antigen before the step of isolating a sample comprising the immunoglobulin light chains.

Provision 164. A method for expressing human immunoglobulin VJC light chains in a non-human vertebrate, the method comprising providing the vertebrate or cell of provision 40 and isolating a sample comprising the immunoglobulin VJC light chains.

Provision 164a. The method of provision 164, wherein the non-human vertebrate develops from an ES cell.

Provision 164a. The method of provision 164, further comprising a step of isolating the immunoglobulin light chains from the sample.

Provision 164b. The method of provision 164a, wherein the sample is serum, spleen, thymus, lymph node, or appendix.

Provision 164c. The method of provision 164b wherein the spleen comprises splenic tissue containing B-cells.

Provision 164d. The method of provision 164c, further comprising a step of isolating B-cells from splenic tissue.

Provision 165. The method of provision 164, wherein the immunoglobulin VJC light chains are included in antibodies or antibody fragments.

Provision 166. An antibody or antibody fragment isolated in the method of provision 165.

Provision 166a. A derivative of the antibody or antibody fragment of provision 166.

Provision 167. A pharmaceutical composition comprising the antibody or antibody fragment of provision 166 and a pharmaceutically acceptable carrier, excipient, or diluent.

Provision 168. The method of provision 164, comprising a step of immunizing the vertebrate with an antigen before the step of isolating a sample comprising the immunoglobulin VJC light chains.

Provision 169. The method of provision 164, wherein the vertebrate developed from a mouse ES cell or a rat ES cell.

The following definitions apply to any configuration, aspect, provision, clause, attribute, example or embodiment of the invention.

"Derived from" is used in the ordinary sense of the term. Exemplary synonyms include "produced as", "resulting from", "received from", "obtained from", "a product of", "consequence of", and "modified from" For example, a human variable region of a heavy chain can be derived from recombination of human VH, D and JH gene segments and this reflects the in vivo recombination of these gene segments in, for example, a transgenic heavy chain locus according to the invention with any accompanying mutation (eg, junctional mutation).

Samples from which B-cells can be obtained include but are not limited to blood, serum, spleen, splenic tissue, bone marrow, lymph, lymph node, thymus, and appendix. Antibodies and immunoglobulin chains can be obtained form each of the previous-mentioned samples and also from the following non-limiting list of B-cells, ascites fluid, hybridomas, and cell cultures.

"Plurality" is used in the ordinary sense of the term and means "at least one" or "more than one".

The term "germline configuration" refers to a germline genomic configuration. For example, human immunoglobulin gene segments of a transgenic immunoglobulin locus are in a germline configuration when the relative order of the gene segments is the same as the order of corresponding gene segments in a human germline genome. For example, when the transgenic locus is a heavy chain locus of the invention comprising hypothetical human immunoglobulin gene segments A, B and C, these would be provided in this order (5' to 3' in the locus) when the corresponding gene segments of a human germline genome comprises the arrangement 5'-A-B-C-3'. In an example, when elements of a human immunoglobulin locus (eg, gene segments, enhancers or other regulatory elements) are provided in a transgenic immunoglobulin locus according to the invention, the human Ig locus elements are in germline configuration when the relative order of the gene segments is the same as the order of corresponding gene segments in a human germline genome and human sequences between the elements are included, these corresponding to such sequences between corresponding elements in the human germline genome. Thus, in a hypothetical example the transgenic locus comprises human elements in the arrangement 5'-A-S1-B-S2-C—S3-3', wherein A, B and C are human immunoglobulin gene segments and S1-S3 are human inter-gene segment sequences, wherein the corresponding arrangement 5'-A-S1-B-S2-C—S3-3' is present in a human germline genome. For example, this can be achieved by providing in a transgenic immunoglobulin locus of the invention a DNA insert corresponding to the DNA sequence from A to C in a human germline genome (or the insert comprising the DNA sequence from A to C). The arrangements in human germline genomes and immunoglobulin loci are known in the art (eg, see the IMGT at the World Wide Web (see above), Kabat and other antibody resources referenced herein).

The term "antibody" includes monoclonal antibodies (including full length antibodies which have an immunoglobulin Fc region), antibody compositions with polyepitopic specificity, multispecific antibodies (e.g., bispecific antibodies, diabodies, and single-chain molecules, as well as antibody fragments (e.g., dAb, Fab, F(ab')2, and Fv). The term "antibody" also includes H2 antibodies that comprise a dimer of a heavy chain (5'-VH-(optional Hinge)-CH2-CH3-3') and are devoid of a light chain (akin to naturally-occurring H2 antibodies; see, eg, Nature. 1993 Jun. 3; 363(6428):446-8; Naturally occurring antibodies devoid of light chains; Hamers-Casterman C, Atarhouch T, Muyldermans S, Robinson G, Hamers C, Songa E B, Bendahman N, Hamers R). Thus, in an embodiment of the present invention, RNA produced from the transgenic heavy chain locus encodes for heavy chains that re devoid of a CH1 gene segment and comprise no functional antibody light chain. In an example, RNA produced from the transgenic heavy chain locus encodes for VH single variable domains (dAbs; domain antibodies). These can optionally comprise a constant region.

The term "immunoglobulin" (Ig) is used interchangeably with "antibody" herein.

An "isolated" antibody is one that has been identified, separated and/or recovered from a component of its production environment (e.g., naturally or recombinantly). Preferably, the isolated polypeptide is free of association with all other components from its production environment, eg, so that the antibody has been isolated to an FDA-approvable or approved standard. Contaminant components of its production environment, such as that resulting from recombinant transfected cells, are materials that would typically interfere with research, diagnostic or therapeutic uses for the antibody, and may include enzymes, hormones, and other proteinaceous or non-proteinaceous solutes. In preferred embodiments, the polypeptide will be purified: (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or, preferably, silver stain. Isolated antibody includes the antibody in situ within recombinant cells since at least one component of the antibody's natural environment will not be present. Ordinarily, however, an isolated polypeptide or antibody will be prepared by at least one purification step.

An "antibody fragment" comprises a portion of an intact antibody, preferably the antigen binding and/or the variable region of the intact antibody. Examples of antibody fragments include dAb, Fab, Fab', F(ab')2 and Fv fragments; diabodies; linear antibodies; single-chain antibody molecules and multispecific antibodies formed from antibody fragments.

An antibody that "specifically binds to" or is "specific for" a particular polypeptide, antigen, or epitope is one that binds to that particular polypeptide, antigen, or epitope without substantially binding to other polypeptides, antigens or epitopes. For example, binding to the antigen or epitope is specific when the antibody binds with a $K_D$ of 100 μM or less, 10 μM or less, 1 μM or less, 100 nM or less, eg, 10 nM or less, 1 nM or less, 500 pM or less, 100 pM or less, or 10 pM or less. The binding affinity ($K_D$) can be determined using standard procedures as will be known by the skilled person, eg, binding in ELISA and/or affinity determination using surface plasmon resonance (eg, Biacore™ or KinExA™ solution phase affinity measurement which can detect down to fM affinities (Sapidyne Instruments, Idaho)). "Pharmaceutically acceptable" refers to approved or approvable by a regulatory agency of the USA Federal or a state government or listed in the U.S. Pharmacopeia or other generally recognized pharmacopeia for use in animals, including humans. A "pharmaceutically acceptable carrier, excipient, or adjuvant" refers to an carrier, excipient, or adjuvant that can be administered to a subject, together with an agent, e.g., any antibody or antibody chain described herein, and which does not destroy the pharmacological activity thereof and is nontoxic when administered in doses sufficient to deliver a therapeutic amount of the agent.

BRIEF DESCRIPTION OF THE FIGURES

FIG. 35 illustrates JH and JK usage FIG. 39 illustrates Distribution of JH Usage Within Each VHs FIG. 40 illustrates Distribution of DH Usage Within Each VHs FIG. 41 illustrates Nucleotide Gain or Loss at VJ Joints Generates IGK Variants (SEQ ID NOs 69-92, respectively).

FIG. 42 illustrates Hypermutation in J Regions Generates IGK Variants (SEQ ID NOs 93-114, respectively).

FIG. 43 illustrates Joint Diversity Produces Functional CDS (SEQ ID NOs 115-120, respectively).

FIGS. 54 & 55 illustrate normal IgH isotypes and serum levels are obtained in transgenic animals of the invention following immunisation with antigens FIG. 56, part 1 illustrates the first and second BACs used for insertion into mouse endogenous light chain loci. The human DNA in each BAC is shown. Part 2 of FIG. 56 shows the insertion point of human lambda Ig locus DNA into the mouse endogenous kappa chain locus. Part 3 of FIG. 56 shows the insertion point of human lambda Ig locus DNA into the mouse endogenous lambda chain locus.

FIG. 62 shows the distribution of mouse Vκ and human Vλ gene segment usage from the chimaeric kappa locus in P2 homozygous mice (P2/P2).

FIG. 66A: Splenic B-Cell Compartment Analysis. This figure shows the results of FACS analysis on splenic B-cells from transgenic S1F/HA, KA/+ mice of the invention expressing heavy chain variable regions which are all human (where endogenous heavy chain expression has been inactivated by inversion), compared with splenic B-cells from mice expressing only mouse antibodies. The results show that the splenic B-cell compartments in the mice of the invention are normal (ie, equivalent to the compartments of mice expressing only mouse antibody chains).

S1F/HA, +/KA=(i) S1F—first endogenous heavy chain allele has one human heavy chain locus DNA insertion, endogenous mouse VDJ region has been inactivated by inversion and movement upstream on the chromosome; (ii) HA—second endogenous heavy chain allele has been inactivated (by insertion of an endogenous interrupting sequence); (iii)+—first endogenous kappa allele is a wild-type kappa allele; and (iv) KA—the second endogenous kappa allele has been inactivated (by insertion of an endogenous interrupting sequence). This arrangement encodes exclusively for heavy chains from the first endogenous heavy chain allele.

FIG. 66B: Splenic B-Cell Compartment Analysis. This figure shows the results of FACS analysis on splenic B-cells from transgenic S1F/HA, K2/KA mice of the invention expressing heavy chain variable regions which are all human (where endogenous heavy chain expression has been inactivated by inversion) and human kappa chain variable regions, compared with splenic B-cells from +/HA, K2/KA mice. The results show that the splenic B-cell compartments in the mice of the invention are normal.

S1F/HA, K2/KA=(i) K2—the first endogenous kappa allele has two kappa chain locus DNA insertions between the most 3' endogenous Jκ and the mouse Cκ, providing an insertion of 14 human Vκ and Jκ1-Jκ5; and (ii) KA—the second endogenous kappa allele has been inactivated (by insertion of an endogenous interrupting sequence). This arrangement encodes exclusively for heavy chains comprising human variable regions and substantially kappa light chains from the first endogenous kappa allele.

+/HA, K2/KA—this arrangement encodes for mouse heavy chains and human kappa chains.

FIG. 67A: Bone marrow B progenitor compartment analysis. This figure shows the results of FACS analysis on bone marrow (BM) B-cells from transgenic S1F/HA, KA/+ mice of the invention expressing heavy chain variable regions which are all human (where endogenous heavy chain expression has been inactivated by inversion), compared with BM B-cells from mice expressing only mouse antibodies. The results show that the BM B-cell compartments in the mice of the invention are normal (ie, equivalent to the compartments of mice expressing only mouse antibody chains).

FIG. 67B: Bone marrow B progenitor compartment analysis. This figure shows the results of FACS analysis on bone marrow (BM) B-cells from transgenic S1F/HA, K2/KA mice of the invention expressing heavy chain variable regions which are all human (where endogenous heavy chain expression has been inactivated by inversion) and human kappa chain variable regions, compared with BM B-cells from +/HA, K2/KA mice. The results show that the BM B-cell compartments in the mice of the invention are normal.

Figure 68:
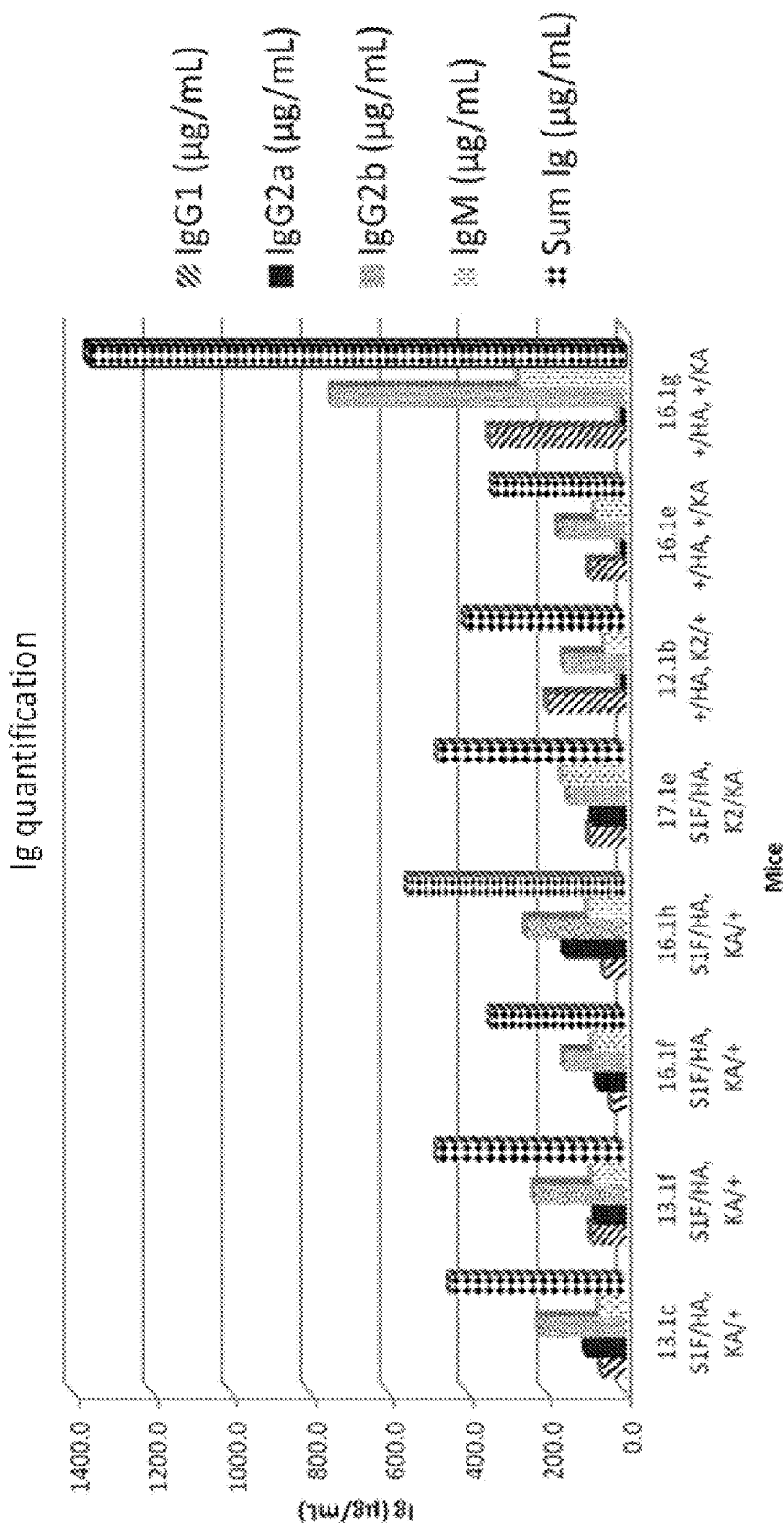

FIG. 68: shows Ig quantification for subtype and total Ig in various mice:

S1F/HA, KN+=(i) S1F—first endogenous heavy chain allele has one human heavy chain locus DNA insertion, endogenous mouse VDJ region has been inactivated by inversion and movement upstream on the chromosome; (ii) HA—second endogenous heavy chain allele has been inactivated (by insertion of an endogenous interrupting sequence); (iii) KA—the first endogenous kappa allele has been inactivated (by insertion of an endogenous interrupting sequence); and (iv) +—second endogenous kappa allele is a wild-type kappa allele. This arrangement encodes exclusively for heavy chains from the first endogenous heavy chain allele.

S1F/HA, K2/KA=(i) K2—the first endogenous kappa allele has two kappa chain locus DNA insertions between the most 3' endogenous Jκ and the mouse Cκ, providing an insertion of 14 human Vκ and Jκ1-Jκ5; and (ii) KA—the second endogenous kappa allele has been inactivated (by insertion of an endogenous interrupting sequence). This arrangement encodes exclusively for heavy chains comprising human variable regions and substantially kappa light chains from the first endogenous kappa allele.

+/HA, K2/+—this arrangement encodes for mouse heavy chains and both mouse and human kappa chains.

+/HA, +/KA—this arrangement encodes for mouse heavy and kappa chains.

In this figure, "Sum Ig" is the sum of IgG and IgM isotypes.

SEQUENCES

SEQ ID No 1 is a Rat switch sequence
SEQ ID No 2 is a landing pad targeting vector (long version)
SEQ ID No 3 is a landing pad targeting vector (shorter version)
SEQ ID No 4 is the mouse strain 129 switch
SEQ ID No 5 is the mouse strain C57 switch
SEQ ID No 6 is the 5' homology arm of a landing pad
SEQ ID No 7 is oligo HV2-5
SEQ ID No 8 is oligo HV4-4
SEQ ID No 9 is oligo HV1-3
SEQ ID No 10 is oligo HV1-2
SEQ ID No 11 is oligo HV6-1
SEQ ID No 12 is oligo Cμ
SEQ ID No 13 is oligo KV1-9
SEQ ID No 14 is oligo KV1-8
SEQ ID No 15 is oligo KV1-6
SEQ ID No 16 is oligo KV1-5
SEQ ID No 17 is oligo Cκ
SEQ ID Nos 18-20 are rat switch sequences
SEQ ID No 21 is $X_1X_2$ T F G Q, where $X_1X_2$=PR, RT, or PW
SEQ ID No 22 is $X_1X_2$ T F G Q G T K V E I K R A D A, where $X_1X_2$=PR, RT, or PW;
SEQ ID No 23 is $X_3X_4$ T F G Q, where $X_3X_4$=PR or PW
SEQ ID No 24 is $X_3X_4$ T F G Q G T K V E I K R A D A, where $X_3X_4$=PR or PW
SEQ ID No 25 is Primer E1554
SEQ ID No 26 is Primer E1555
SEQ ID No 27 is Primer ELP1352_Cγ1
SEQ ID No 28 is Primer ELP1353_Cγ2b
SEQ ID No 29 is Primer ELP1354_Cγ2a
SEQ ID No 30 is Primer ELP1356_VH4-4
SEQ ID No 31 is Primer ELP1357_VH1-2,3
SEQ ID No 32 is Primer ELP1358_VH6-1
SEQ ID No 33 is Primer mIgG1_2 rev
SEQ ID No 34 is Primer mIgG2b rev
SEQ ID No 35 is Primer mIgG2a_2 rev
SEQ ID No 36 is Primer mCH1 unirev
SEQ ID No 37 is Primer mCH1 unirev_2
SEQ ID Nos 38-45 are CDRH3 sequences
SEQ ID Nos 46-50 is 3, 4, 5, 6 or more (up to 82) repeats of GGGCT
SEQ ID NOs 51-55 are heavy chain CDR1 sequences against CTB (cloned and reference)
SEQ ID NOs 56-60 are heavy chain CDR2 sequences against CTB (cloned and reference)
SEQ ID NOs 61-63 are heavy chain CDR3 sequences against CTB (cloned and reference)
SEQ ID NOs 64-68 are J Region sequences against CTB (cloned and reference)

DETAILED DESCRIPTION OF THE INVENTION

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine study, numerous equivalents to the specific procedures described herein. Such equivalents are considered to be within the scope of this invention and are covered by the claims.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps The term "or combinations thereof" as used herein refers to all permutations and combinations of the listed items preceding the term. For example, "A, B, C, or combinations thereof is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

As a source of antibody gene segment sequences, the skilled person will also be aware of the following available databases and resources (including updates thereof) the contents of which are incorporated herein by reference:

The Kabat Database (G. Johnson and T. T. Wu, 2002; World Wide Web (www) kabatdatabase.com). Created by E. A. Kabat and T. T. Wu in 1966, the Kabat database publishes aligned sequences of antibodies, T-cell receptors, major histocompatibility complex (MHC) class I and II molecules, and other proteins of immunological interest. A searchable interface is provided by the SeqhuntII tool, and a range of utilities is available for sequence alignment, sequence subgroup classification, and the generation of variability plots. See also Kabat, E. A., Wu, T. T., Perry, H., Gottesman, K., and Foeller, C. (1991) *Sequences of Proteins of Immunological Interest*, 5th ed., NIH Publication No. 91-3242, Bethesda, Md., which is incorporated herein by reference, in particular with reference to human gene segments for use in the present invention.

KabatMan (A. C. R. Martin, 2002; World Wide Web (www) bioinf.org.uk/abs/simkab.html). This is a web interface to make simple queries to the Kabat sequence database.

IMGT (the International ImMunoGeneTics Information System®; M.-P. Lefranc, 2002; World Wide Web (www) imgt.cines.fr). IMGT is an integrated information system that specializes in antibodies, T cell receptors, and MHC molecules of all vertebrate species. It provides a common portal to standardized data that include nucleotide and protein sequences, oligonucleotide primers, gene maps, genetic polymorphisms, specificities, and two-dimensional (2D) and three-dimensional (3D) structures. IMGT includes three sequence databases (IMGT/LIGM-DB, IMGT/MHC-DB, IMGT/PRIMERDB), one genome database (IMGT/GENE-DB), one 3D structure database (IMGT/3Dstructure-DB), and a range of web resources ("IMGT Marie-Paule page") and interactive tools.

V-BASE (I. M. Tomlinson, 2002; World Wide Web (www) mrc-cpe.cam.ac.uk/vbase). V-BASE is a comprehensive directory of all human antibody germline variable region sequences compiled from more than one thousand published sequences. It includes a version of the alignment software DNAPLOT (developed by Hans-Helmar Althaus and Werner Müller) that allows the assignment of rearranged antibody V genes to their closest germline gene segments.

Antibodies—Structure and Sequence (A. C. R. Martin, 2002; World Wide Web (www) bioinf.org.uk/abs). This page summarizes useful information on antibody structure and sequence. It provides a query interface to the Kabat antibody sequence data, general information on antibodies, crystal structures, and links to other antibody-related information. It also distributes an automated summary of all antibody structures deposited in the Protein Databank (PDB). Of particular interest is a thorough description and comparison of the various numbering schemes for antibody variable regions.

AAAAA (A Ho's Amazing Atlas of Antibody Anatomy; A. Honegger, 2001; World Wide Web (www) unizh.ch/~antibody). This resource includes tools for structural analysis, modeling, and engineering. It adopts a unifying scheme for comprehensive structural alignment of antibody and T-cell-receptor sequences, and includes Excel macros for antibody analysis and graphical representation.

WAM (Web Antibody Modeling; N. Whitelegg and A. R. Rees, 2001; World Wide Web (www) antibody.bath.ac.uk). Hosted by the Centre for Protein Analysis and Design at the University of Bath, United Kingdom. Based on the AbM package (formerly marketed by Oxford Molecular) to construct 3D models of antibody Fv sequences using a combination of established theoretical methods, this site also includes the latest antibody structural information.

Mike's Immunoglobulin Structure/Function Page (M. R. Clark, 2001; World Wide Web (www) path.cam.ac.uk/~mrc7/mikeimages.html) These pages provide educational materials on immunoglobulin structure and function, and are illustrated by many colour images, models, and animations. Additional information is available on antibody humanization and Mike Clark's Therapeutic Antibody Human Homology Project, which aims to correlate clinical efficacy and anti-immunoglobulin responses with variable region sequences of therapeutic antibodies.

The Antibody Resource Page (The Antibody Resource Page, 2000; World Wide Web (www) antibodyresource.com). This site describes itself as the "complete guide to antibody research and suppliers." Links to amino acid sequencing tools, nucleotide antibody sequencing tools, and hybridoma/cell-culture databases are provided.

Humanization by Design (J. Saldanha, 2000; World Wide Web (www) people.cryst.bbk.ac.uk/~ubcg07s). This resource provides an overview on antibody humanization technology. The most useful feature is a searchable database (by sequence and text) of more than 40 published humanized antibodies including information on design issues, framework choice, framework back-mutations, and binding affinity of the humanized constructs.

See also Antibody Engineering Methods and Protocols, Ed. Benny K C Lo, Methods in Molecular Biology™, Human Press. Also at World Wide Web (www) blogsua.com/pdf/antibody-engineering-methods-and-protocolsantibody-engineering-methods-and-protocols.pdf Any part of this disclosure may be read in combination with any other part of the disclosure, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

The following examples are put forth so as to provide those of ordinary skill in the art with a complete disclosure and description of how to make and use the invention, and are not intended to limit the scope of what the inventors regard as their invention.

EXAMPLES

Example 1

BAC Recombineering

Overall Strategy:

A mouse model of the invention can be achieved by inserting ~960 kb of the human heavy chain locus containing all the V, D and J-regions upstream of the mouse constant region and 473 kb of the human kappa region upstream of the mouse constant region. Alternatively, or in tandem, the human lambda region is inserted upstream of the mouse constant region. This insertion is achieved by gene targeting in ES cells using techniques well known in the art.

High fidelity insertion of intact V-D-J regions into each locus in their native (wild-type) configuration is suitably achieved by insertion of human bacterial artificial chromosomes (BACs) into the locus. Suitably the BACs are trimmed so that in the final locus no sequence is duplicated or lost compared to the original. Such trimming can be carried out by recombineering.

The relevant human BACs, suitably trimmed covering these loci are on average 90 kb in size.

In one approach the full complement of human D and J-elements as well as seven or eight human V-regions are covered by the first BACs to be inserted in the experimental insertion scheme described below. The first BACs to be inserted in the IgH and IgK loci may contain the following V-regions. IgH: V6-1, VII-1-1, V1-2, VIII-2-1, V1-3, V4-4, V2-5 and IgK: V4-1, V5-2, V7-3, V2-4, V1-5, V1-6, V3-7, V1-8.

Suitably the performance of each locus is assessed after the first BAC insertion using chimaeric mice and also after each subsequent BAC addition. See below for detailed description of this performance test.

Nine additional BAC insertions will be required for the IgH locus and five for IgK to provide the full complement of human V-regions covering all 0.96 Mb and 0.473 Mb of the IgH and IgK loci, respectively.

Not all BACs retain their wild-type configuration when inserted into the ES cell genome. Thus, high density genomic arrays were deployed to screen ES cells to identify those with intact BAC insertions (Barrett, M. T., Scheffer, A., Ben-Dor, A., Sampas, N., Lipson, D., Kincaid, R., Tsang, P., Curry, B., Baird, K., Meltzer, P. S., et al. (2004). Comparative genomic hybridization using oligonucleotide microarrays and total genomic DNA. Proceedings of the National Academy of Sciences of the United States of America 101, 17765-17770.). This screen also enables one to identify and select against ES clones in which the ES cell genome is compromised and thus not able to populate the germ line of chimeric animals. Other suitable genomic tools to facilitate this assessment include sequencing and PCR verification.

Thus in one aspect the correct BAC structure is confirmed before moving to the next step.

It is implicit from the description above that in order to completely engineer the loci with 90 kb BACs, it is necessary to perform a minimum of 10 targeting steps for IgH and 5 steps for the IgK. Mice with an IgL locus can be generated in a similar manner to the IgK locus. Additional steps are required to remove the selection markers required to support gene targeting. Since these manipulations are being performed in ES cells in a step-wise manner, in one aspect germ line transmission capacity is retained throughout this process.

Maintaining the performance of the ES cell clones through multiple rounds of manipulation without the need to test the germ line potential of the ES cell line at every step may be important in the present invention. The cell lines currently in use for the KOMP and EUCOMM global knockout projects have been modified twice prior to their use for this project and their germ line transmission rates are unchanged from the parental cells (these lines are publicly available, see World Wide Web (www) komp.org and World Wide Web (www) eucomm.org). This cell line, called JM8, can generate 100% ES cell-derived mice under published culture conditions (Pettitt, S. J., Liang, Q., Rairdan, X. Y., Moran, J. L., Prosser, H. M., Beier, D. R., Lloyd, K. C., Bradley, A., and Skarnes, W. C. (2009). Agouti C57BL/6N embryonic stem cells for mouse genetic resources. Nature Methods.). These cells have demonstrated ability to reproducibly contribute to somatic and germ line tissue of chimaeric animals using standard mouse ES cell culture conditions. This capability can be found with cells cultured on a standard feeder cell line (SNL) and even feeder-free, grown only on gelatine-coated tissue culture plates. One particular sub-line, JM8A3, maintained the ability to populate the germ line of chimeras after several serial rounds of sub-cloning. Extensive genetic manipulation via, for example, homologous recombination—as would be the case in the present invention—cannot compromise the pluripotency of the cells. The ability to generate chimeras with such high percentage of ES cell-derived tissue has other advantages. First, high levels of chimerism correlates with germ line transmission potential and provide a surrogate assay for germ line transmission while only taking 5 to 6 weeks. Second, since these mice are 100% ES cell derived the engineered loci can be directly tested, removing the delay caused by breeding. Testing the integrity of the new Ig loci is possible in the chimera since the host embryo will be derived from animals that are mutant for the RAG-1 gene as described in the next section.

Another cell line that may be used is an HPRT-ve cell line, such as AB2.1, as disclosed in Ramirez-Solis R, Liu P and Bradley A, "Chromosome engineering in mice," Nature, 1995; 378; 6558; 720-4.

RAG-1 Complementation:

While many clones will generate 100% ES derived mice some will not. Thus, at every step mice are generated in a RAG-1-deficient background. This provides mice with 100% ES-derived B- and T-cells which can be used directly for immunization and antibody production. Cells having a RAG-2 deficient background, or a combined RAG-1/RAG-2 deficient background may be used, or equivalent mutations in which mice produce only ES cell-derived B cells and/or T cells.

In order that only the human-mouse IgH or IgK loci are active in these mice, the human-mouse IgH and IgK loci can be engineered in a cell line in which one allele of the IgH or IgK locus has already been inactivated. Alternatively the inactivation of the host Ig locus, such as the IgH or IgK locus, can be carried out after insertion.

Figure 19:
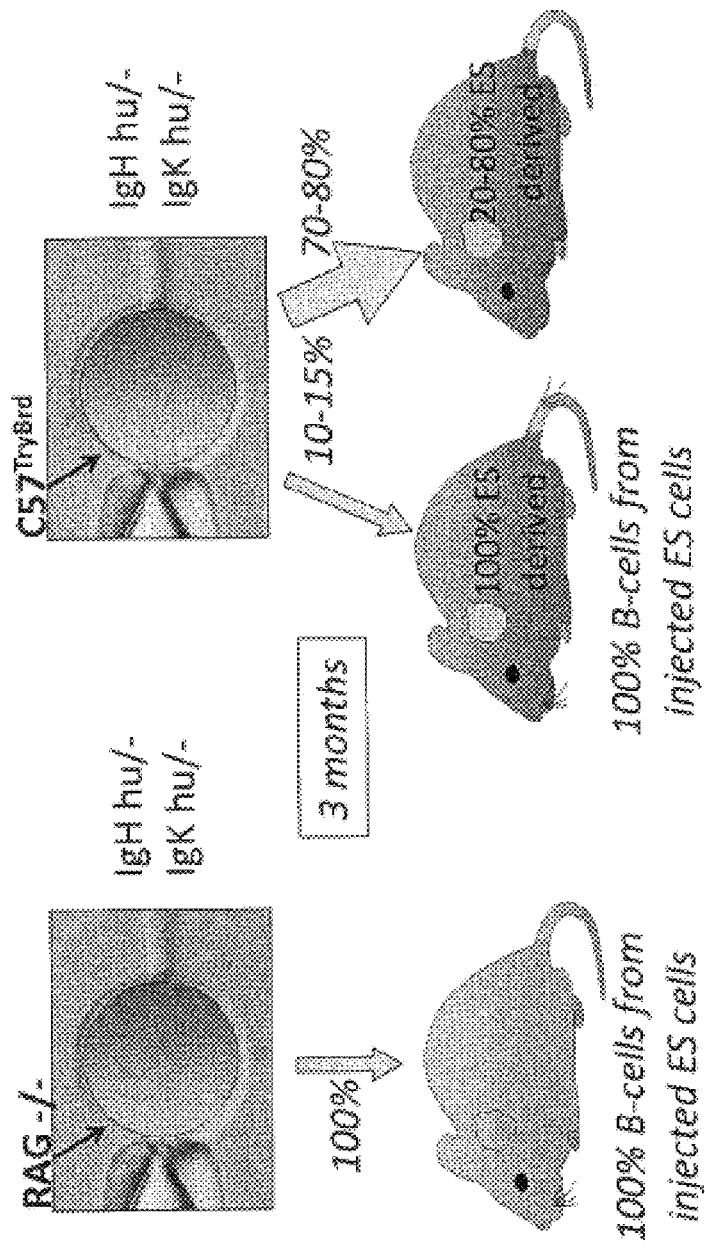
FIGS. 19 and 20 show the principles behind antibody generation in chimaeric mice
Figure 20:
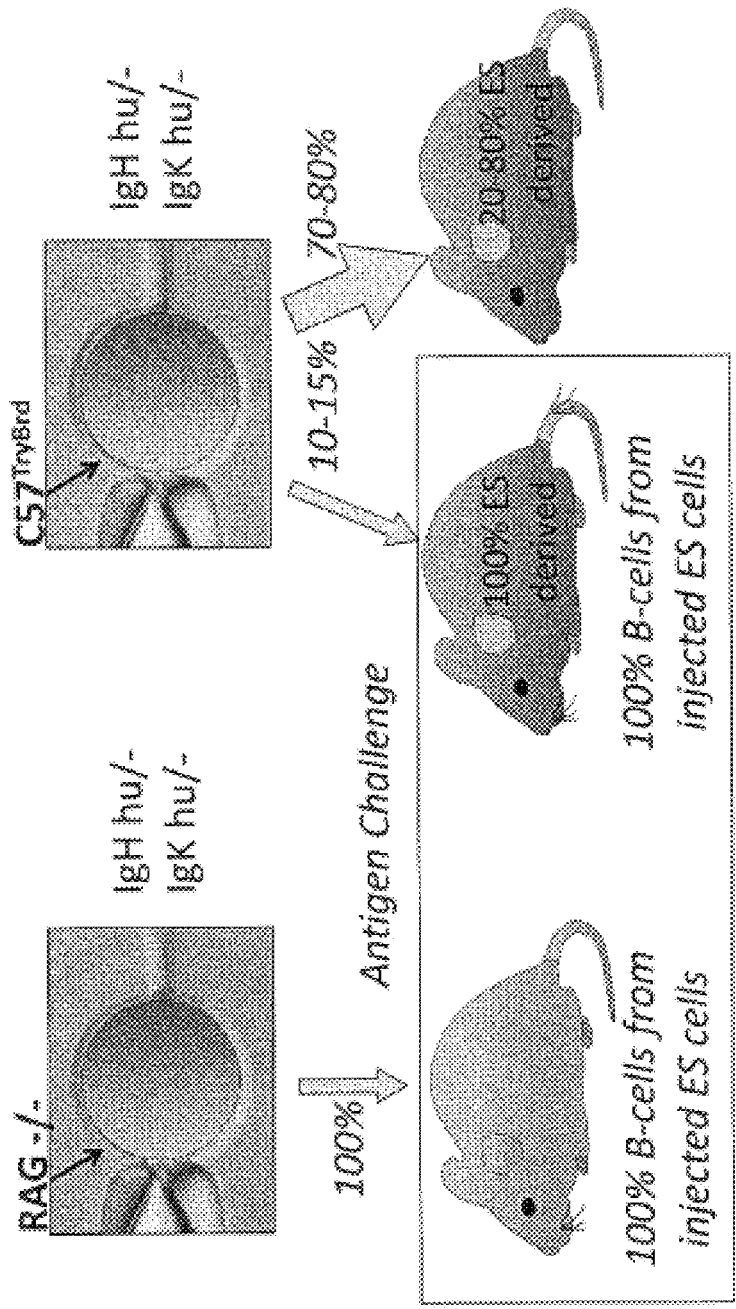
Figure 21:
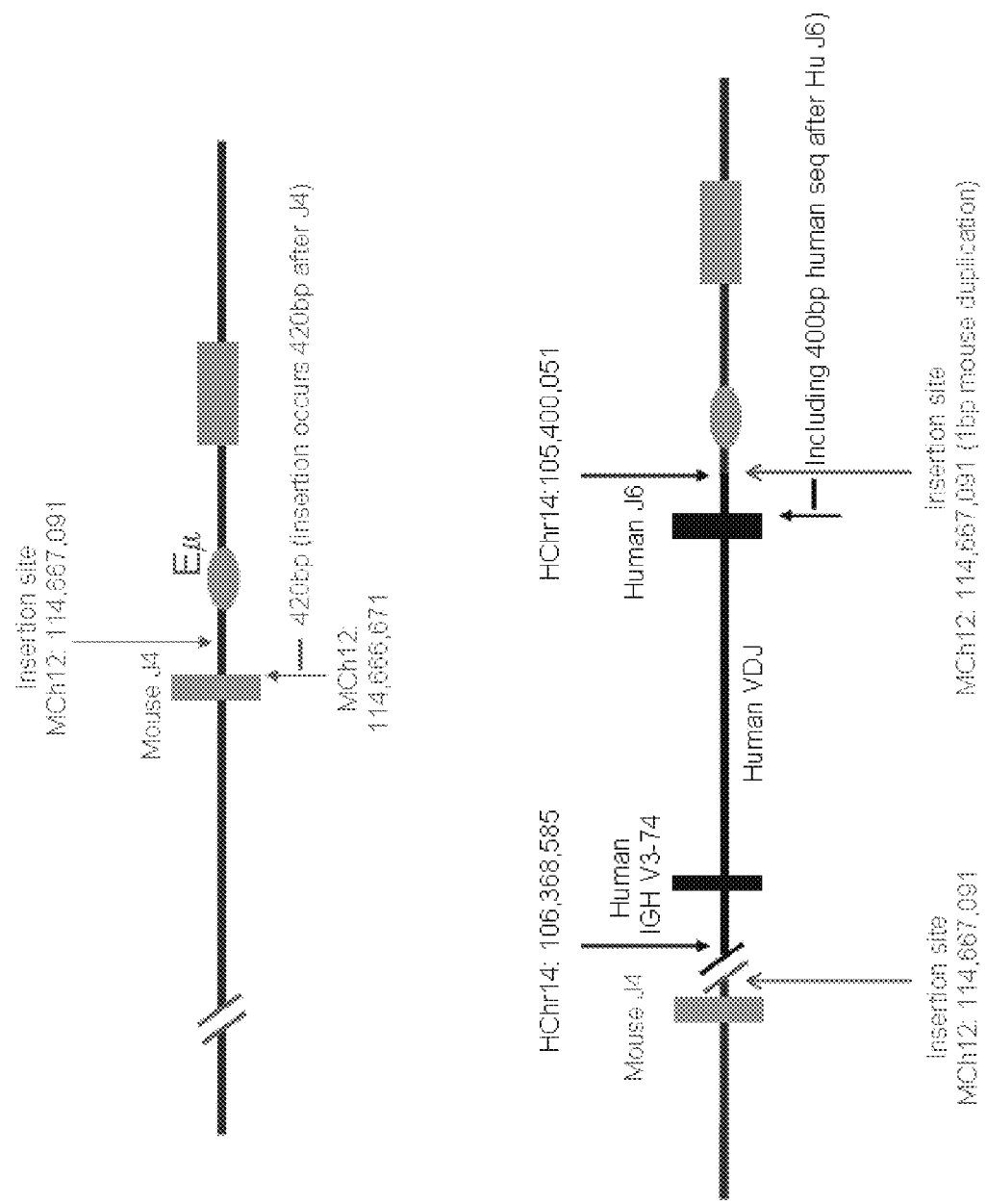
FIG. 21 shows a possible insertion site for the human DNA in a mouse chromosome FIGS. 22-26 disclose an alternative iterative process for insertion of a series of human BACs into a mouse Ig locus

Mouse strains that have the RAG-1 gene mutated are immunodeficient as they have no mature B- or T-lymphocytes (U.S. Pat. No. 5,859,307). T- and B-lymphocytes only differentiate if proper V(D)J recombination occurs. Since RAG-1 is an enzyme that is crucial for this recombination, mice lacking RAG-1 are immunodeficient. If host embryos are genetically RAG-1 homozygous mutant, a chimera produced by injecting such an embryo will not be able to produce antibodies if the animal's lymphoid tissues are derived from the host embryo. However, JM8 cells and AB2.1 cells, for example, generally contribute in excess of 80% of the somatic tissues of the chimeric animal and would therefore usually populate the lymphoid tissue. JM8 cells have wild-type RAG-1 activity and therefore antibodies produced in the chimeric animal would be encoded by the engineered JM8 ES cell genome only. Therefore, the chimeric animal can be challenged with an antigen by immunization and subsequently produce antibodies to that antigen. This allows one skilled in the art to test the performance of the engineered human/mouse IgH and IgK loci as described in the present invention. See FIGS. 19 and 20.

One skilled in the art would use the chimeric animal as described to determine the extent of antibody diversity (see e.g. Harlow, E. & Lane, D. 1998, $5^{th}$ edition, *Antibodies: A Laboratory Manual*, Cold Spring Harbor Lab. Press, Plainview, N.Y.). For example, the existence in the chimeric animal's serum of certain antibody epitopes could be ascertained by binding to specific anti-idiotype antiserum, for example, in an ELISA assay. One skilled in the art could also sequence the genomes of B-cell clones derived from the chimeric animal and compare said sequence to wild-type sequence to ascertain the level of hypermutation, such hypermutation indicative of normal antibody maturation.

One skilled in the art would also use said chimeric animal to examine antibody function wherein said antibodies are encoded from the engineered Ig loci (see e.g. Harlow, E. & Lane, D. 1998, $5^{th}$ edition, Antibodies: A Laboratory Manual, Cold Spring Harbor Lab. Press, Plainview, N.Y.). For example, antisera could be tested for binding an antigen, said antigen used to immunize the chimeric animal. Such a measurement could be made by an ELISA assay. Alternatively, one skilled in the art could test for neutralization of the antigen by addition of the antisera collected from the appropriately immunized chimeric animal.

It is well known to those skilled in the art that positive outcomes for any of these tests demonstrate the ability of the engineered Ig loci, the subject of the instant invention, to encode antibodies with human variable regions and mouse constant regions, said antibodies capable of functioning in the manner of wild-type antibodies.

Experimental Techniques:

Recombineering for the production of vectors for use in homologous recombination in ES cells is disclosed in, for example, WO9929837 and WO0104288, and the techniques are well known in the art. In one aspect the recombineering of the human DNA takes place using BACs as a source of said human DNA. Human BAC DNA will be isolated using QIAGEN®, BAC purification kit. The backbone of each human BAC will be modified using recombineering to the exact same or similar configuration as the BAC already inserted into the mouse IgH region. The genomic insert of each human BAC will be trimmed using recombineering so that once the BACs are inserted, a seamless contiguous part of the human V(D)J genomic region will form at the mouse IgH or IgK locus. BAC DNA transfection by electroporation and genotyping will be performed accordingly to standard protocols (Prosser, H. M., Rzadzinska, A. K., Steel, K. P., and Bradley, A. (2008). "Mosaic complementation demonstrates a regulatory role for myosin VIIa in actin dynamics of stereocilia." Molecular and Cellular Biology 28, 1702-1712; Ramirez-Solis, R., Davis, A. C., and Bradley, A. (1993). "Gene targeting in embryonic stem cells." Methods in Enzymology 225, 855-878.). Recombineering will be performed using the procedures and reagents developed by Pentao Liu and Don Court's laboratories (Chan, W., Costantino, N., Li, R., Lee, S. C., Su, Q., Melvin, D., Court, D. L., and Liu, P. (2007). "A recombineering based approach for high-throughput conditional knockout targeting vector construction." Nucleic Acids Research 35, e64).

These and other techniques for gene targeting and recombination of BAC-derived chromosomal fragments into a non-human mammal genome, such as a mouse are well-known in the art and are disclosed in, for example, in World Wide Web (www) eucomm.org/information/targeting and World Wide Web (www) eucomm.org/information/publications.

Cell culture of C57BL/6N-derived cell lines, such as the JM8 male ES cells will follow standard techniques. The JM8 ES cells have been shown to be competent in extensively contributing to somatic tissues and to the germline, and are being used for large mouse mutagenesis programs at the Sanger Institute such as EUCOMM and KOMP (Pettitt, S. J., Liang, Q., Rairdan, X. Y., Moran, J. L., Prosser, H. M., Beier, D. R., Lloyd, K. C., Bradley, A., and Skarnes, W. C. (2009). "Agouti C57BL/6N embryonic stem cells for mouse genetic resources." Nature Methods.). JM8 ES cells ($1.0 \times 10^7$) will be electroporated (500 µF, 230V; Bio-Rad®) with 10 µg I-SceI linearized human BAC DNA. The transfectants will be selected with either Puromycin (3 µg/ml) or G418 (150 µg/ml). The selection will begin either 24 hours (with G418) or 48 hours (with Puromycin) post electroporation and proceed for 5 days. 10 µg linearized human BAC DNA can yield up to 500 Puromycin or G418 resistant ES cell colonies. The antibiotic resistant ES cell colonies will be picked into 96-well cell culture plates for genotyping to identify the targeted clones.

Once targeted mouse ES cell clones are identified, they will be analyzed by array Comparative Genomic Hybridization (CGH) for total genome integrity (Chung, Y. J., Jonkers, J., Kitson, H., Fiegler, H., Humphray, S., Scott, C., Hunt, S., Yu, Y., Nishijima, I., Velds, A., et al. (2004). "A whole-genome mouse BAC microarray with 1-Mb resolution for analysis of DNA copy number changes by array comparative genomic hybridization." Genome research 14, 188-196. and Liang, Q., Conte, N., Skarnes, W. C., and Bradley, A. (2008). "Extensive genomic copy number variation in embryonic stem cells." Proceedings of the National Academy of Sciences of the United States of America 105, 17453-17456.). ES cells that have abnormal genomes do not contribute to the germline of the chimeric mice efficiently. BAC integrity will be examined by PCR-amplifying each known functional V gene in the BAC. For example, in one approach the first human BAC chosen for the IgH locus has 6 functional V genes. To confirm the integrity of this BAC for the presence of these 6 IGH V genes, at least 14 pairs of PCR primers will be designed and used to PCR-amplify genomic DNA from the targeted ES cells. The human wild-type size and sequence of these fragments will ensure that the inserted BAC has not been rearranged.

More detailed CGH will also confirm the integrity of the inserted BACs. For example, one skilled in the art could use an oligo aCGH platform, which is developed by Agilent Technologies, Inc. This platform not only enables one to study genome-wide DNA copy number variation at high resolution (Barrett, M. T., Scheffer, A., Ben-Dor, A., Sampas, N., Lipson, D., Kincaid, R., Tsang, P., Curry, B., Baird, K., Meltzer, P. S., et al. (2004). "Comparative genomic hybridization using oligonucleotide microarrays and total genomic DNA." Proceedings of the National Academy of Sciences of the United States of America 101, 17765-17770.), but permit examination of a specific genome region using custom designed arrays. Comparing the traditional aCGH techniques which rely on cDNA probes or whole BAC probes, the 60-mer oligonucleotides probes can ensure specific hybridization and high sensitivity and precision that is needed in order to detect the engineered chromosome alterations that were made. For example, oligos designed to hybridize at regular intervals along the entire length of the inserted BAC would detect even quite short deletions, insertions or other rearrangements. Also, this platform provides the greatest flexibility for customized microarray designs. The targeted ES cell genomic DNA and normal human individual genomic DNA will be labelled separately with dyes and hybridized to the array. Arrays slides will be scanned using an Agilent Technologies DNA microarray scanner. Reciprocal fluorescence intensities of dye Cy5 and dye Cy3 on each array image and the log 2 ratio values will be extracted by using Bluefuse software (Bluegnome). Spots with inconsistent fluorescence patterns ("confidence"<0.29 or "quality"=0) will be excluded before normalizing all log 2 ratio values. Within an experiment, Log 2 ratio between −0.29 and +0.29 for the signal from any oligo probe are regarded as no copy number change. The log 2 ratio threshold for "Duplication" is usually >0.29999, and for deletion is <0.29999.

Once the first human BAC is inserted into the mouse IgH locus and confirmed to be in its intact, native configuration, the FRT-flanked BAC backbone will be excised by using Flp site-specific recombinase. If regular Flp-catalyzed FRT recombination is not high enough, one can use Flo, an improved version of Flpo recombinase which in certain tests is 3-4 times more efficient than the original Flp in ES cells. After the BAC backbone is excised, ES cells will become sensitive to Puromycin (or G418) and resistant to FIAU (for loss of the TK cassette). The excision events will be further characterized by PCR amplification of the junction fragment using human genomic DNA primers. These FRT-flanked BAC backbone-free ES cells will be used for the next round of human BAC insertion and for blastocyst injection.

Targeting of the genome of an ES cell to produce a transgenic mouse may be carried out using a protocol as explained by reference to the attached FIGS. 1-18.

Figure 1:
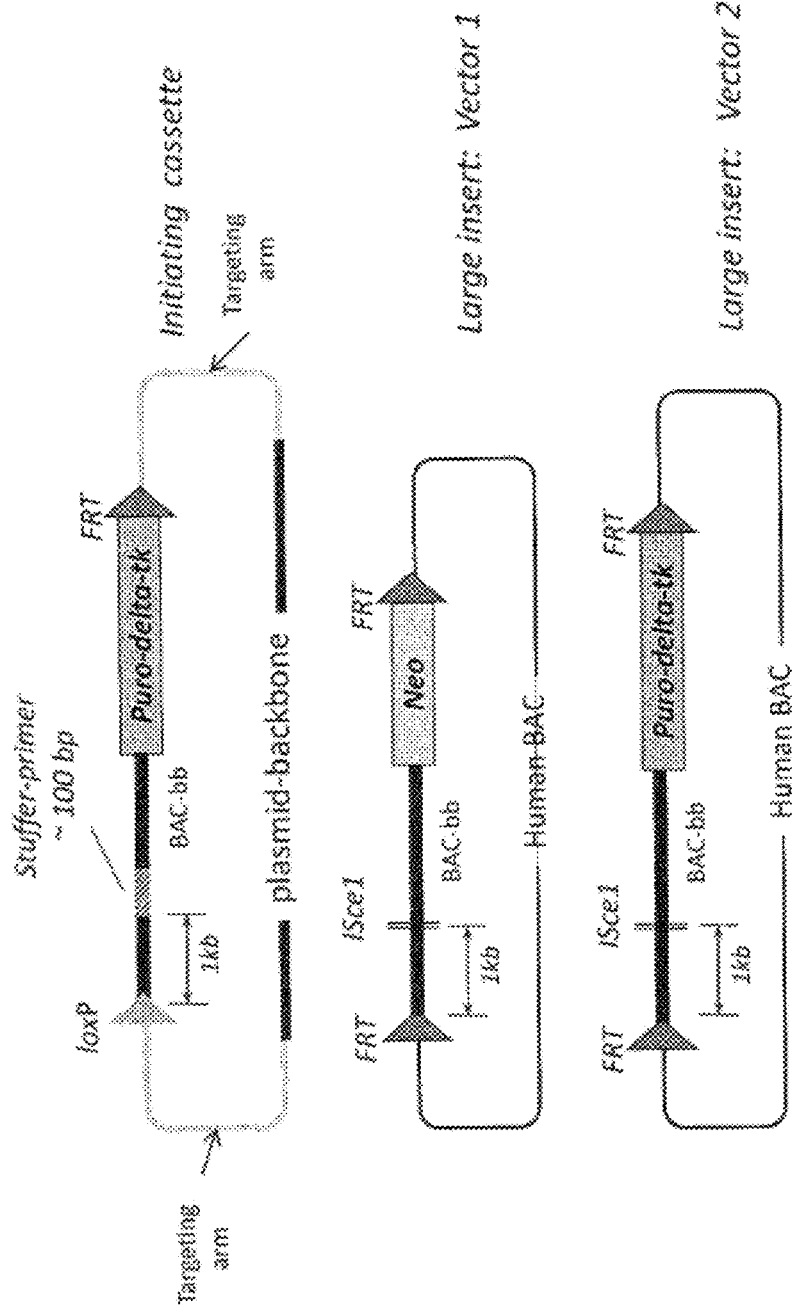
FIGS. 1-8 show an iterative process for insertion of a series of human BACs into a mouse Ig locus

FIG. 1 illustrates three basic backbone vectors; an initiating cassette and 2 large insert vectors 1 and 2 respectively. The initiating cassette comprises sequences homologous to the desired site of insertion into the mouse genome, those sites flanking a selectable marker and stuffer primer sequence for PCR based genotyping to confirm correct insertion of BACs. The Stuffer-primer sequence provides the basis for genotyping each BAC addition step. This sequence is considered to provide a robust well validated sequence template for PCR primer and may be located at the IScel site, ideally ~1 kb from the BAC insert.

The large insert vectors comprise human DNA on plasmids with selectable markers and a unique restriction site for linearisation of the plasmid to aid in homologous recombination into the genome of the ES cell.

Figure 2:
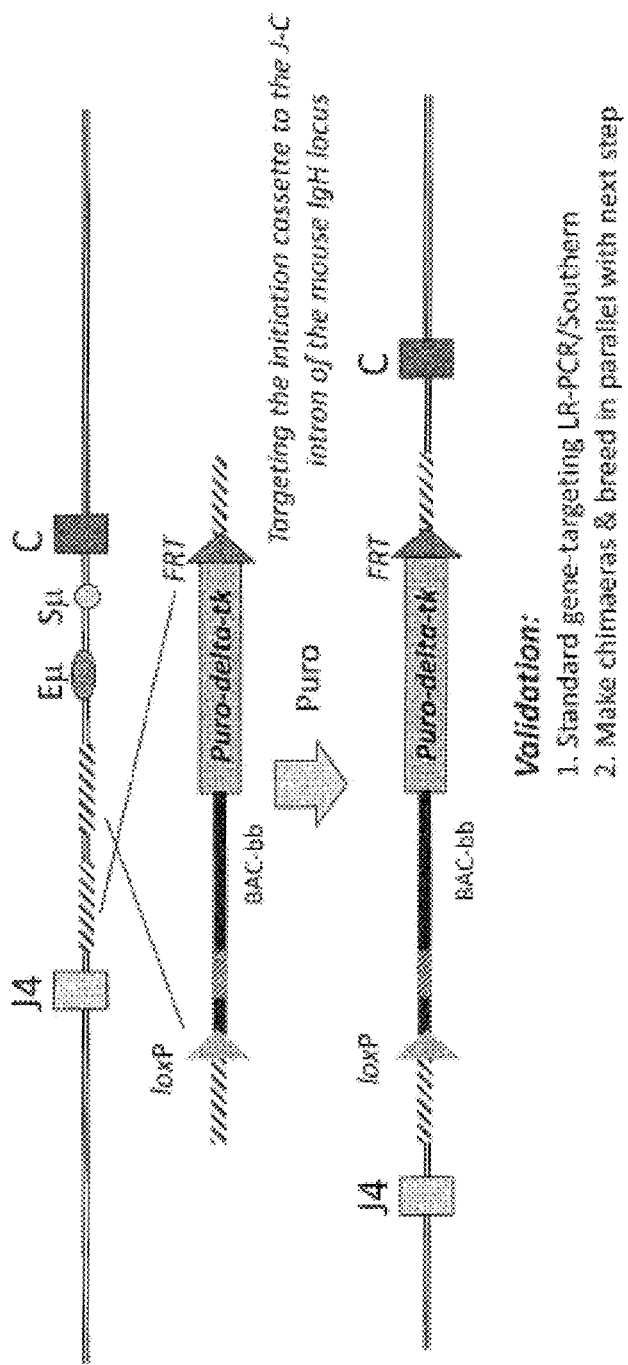

FIG. 2 illustrates insertion of an initiating cassette into the mouse genome by Homologous recombination between the mouse J4 and C alpha exons. Puromycin selection allows identification of ES cells with insertion of the cassette. pu(Delta)tk is a bifunctional fusion protein between puromycin N-acetyltransferase (Puro) and a truncated version of herpes simplex virus type 1 thymidine kinase (DeltaTk). Murine embryonic stem (ES) cells transfected with pu(Delta)tk become resistant to puromycin and sensitive to 1-(-2-deoxy-2-fluoro-1-beta-D-arabino-furanosyl)-5-iodouracil (FIAU). Unlike other HSV1 tk transgenes, puDeltatk is readily transmitted through the male germ line. Thus pu(Delta)tk is a convenient positive/negative selectable marker that can be widely used in many ES cell applications.

Figure 3:
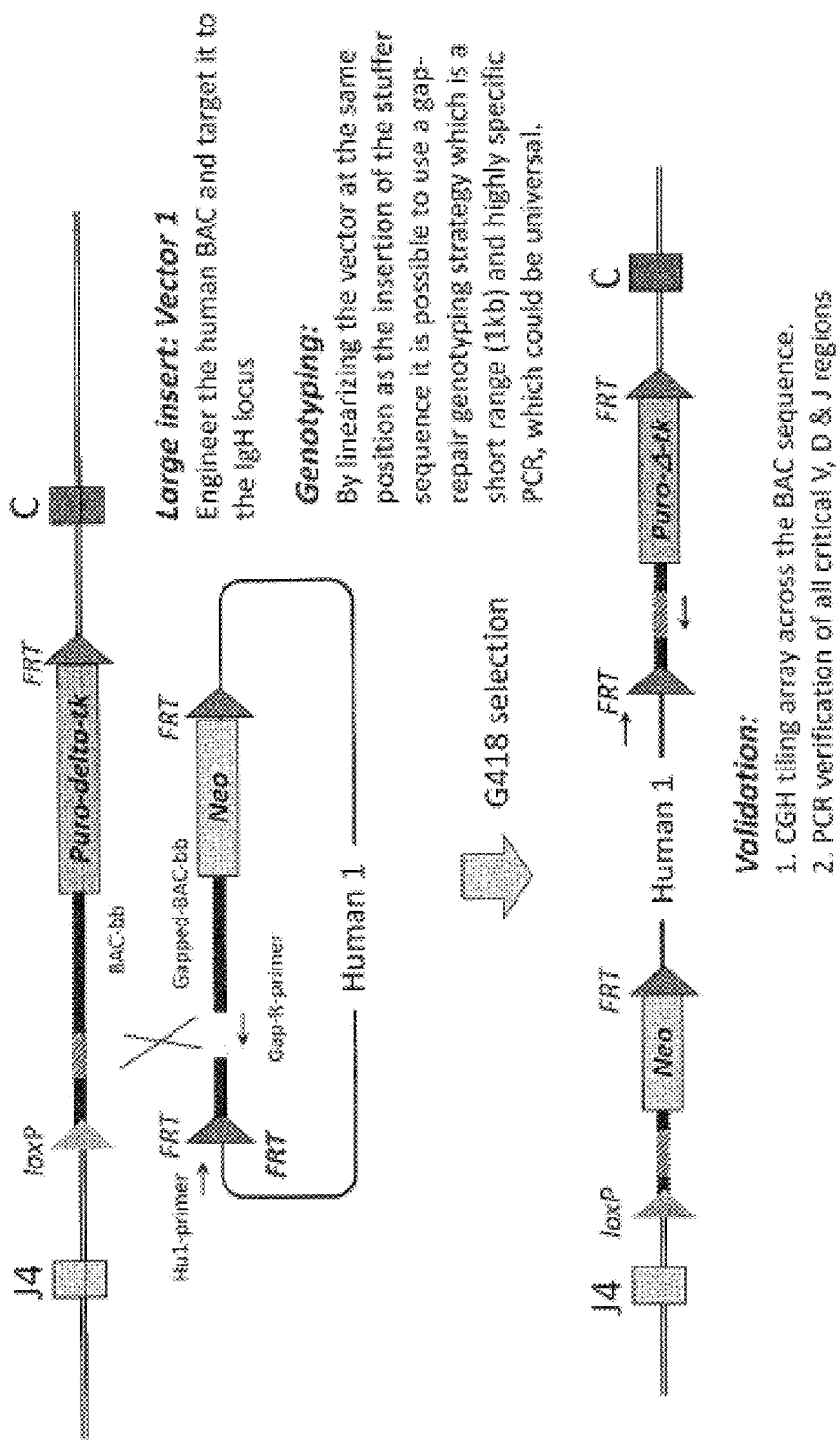

FIG. 3 illustrates targeting of the large insert vector 1 to the mouse ES cell genome. Linearisation of the vector is made at the same position as the stuffer primer sequence which allows for a gap repair genotyping strategy, well known in the art—see Zheng et al NAR 1999, Vol 27, 11, 2354-2360. In essence, random insertion of the targeting vector into the genome will not 'repair' the gap whereas a homologous recombination event will repair the gap. Juxtaposition of appropriate PCR primer sequences allows colonies to be screened individually for a positive PCR fragment indicating proper insertion. Positive selection using G418 allows for identification of mouse ES cells containing the neo selection marker. PCR verification can be made of all critical V, D and J regions. Array comparative genomic hybridization can be used to validate the BAC structure.

Figure 4:
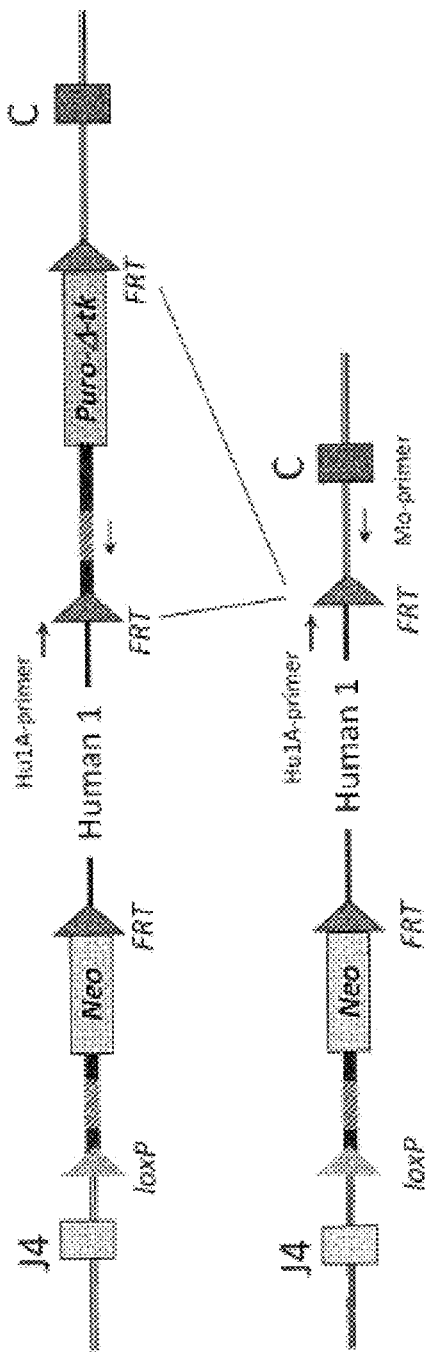

FIG. 4 illustrates the puro-delta-tk cassette and the BAC plasmid backbone is deleted using Flpe and select in FIAU. Since Flpe works inefficiently in mouse ES cells (5% deletion with transient Flpe expression), it is expected that in most cases, the recombination occurs between the two FRT sites flanking the BAC backbone. Flpo can also be tested to find out the recombination efficiency between two FRT sites that are 10 kb away.

Given that the FRT deletion step is selectable it is possible to pool FIAU resistant clones and proceed immediately to the next step in parallel with clonal analysis. Alternatively it may be desirable to show by short range PCR that the human sequences are now adjacent to those of the mouse as shown (Hu-primer 1 and Mo-primer)

At this stage a 200 kb human locus will have been inserted.

Figure 5:
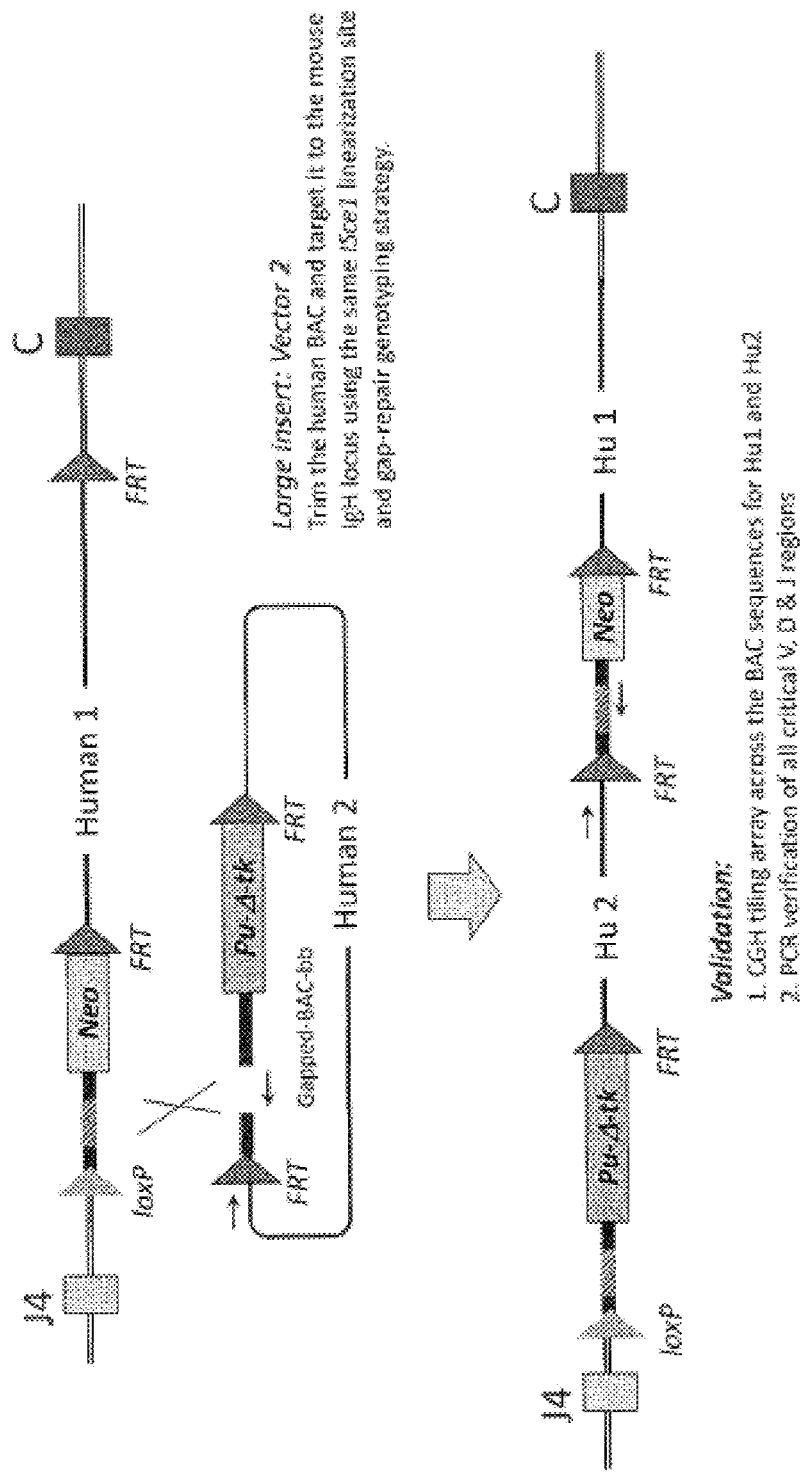

FIG. 5 illustrates a second large insert vector is targeted into the ES cell chromosome. The human BAC is targeted to the mouse IgH locus using the same initiation cassette insertion followed by IScel BAC linearization, BAC targeting to the initiation cassette and gap-repair genotyping strategy. Verification of the BAC insertion is carried out as before.

Figure 6:
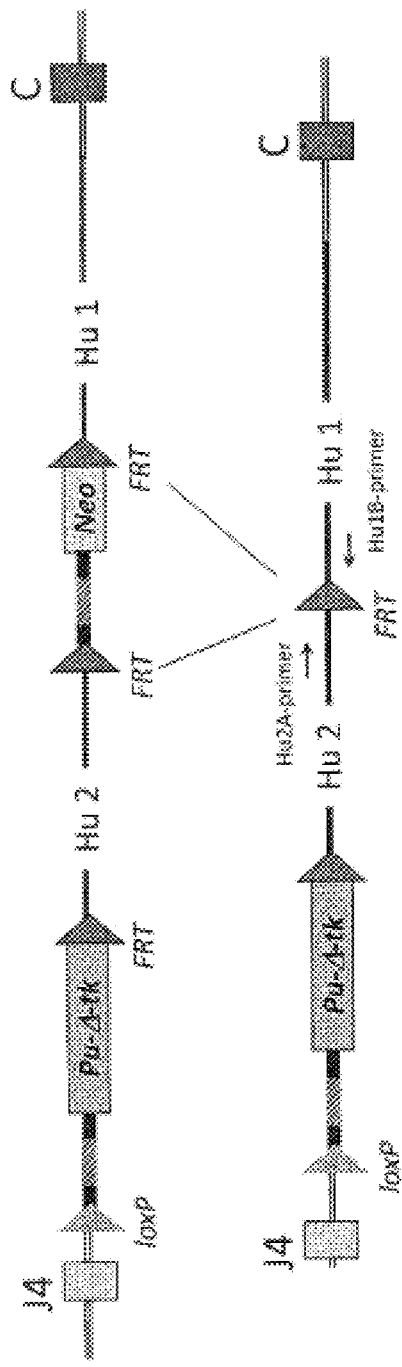

FIG. 6 illustrates the FRTY flanked BAC backbone of large insert vector 2 and the neo marker are deleted via Flpo. Note that this is not selectable, thus it will be necessary for clonal analysis at this point. This will enable confirmation of the juxtaposition of the human 2 insert with human 1 and other validation efforts.

At this stage a ~200 kb human locus will have been inserted.

Figure 7:
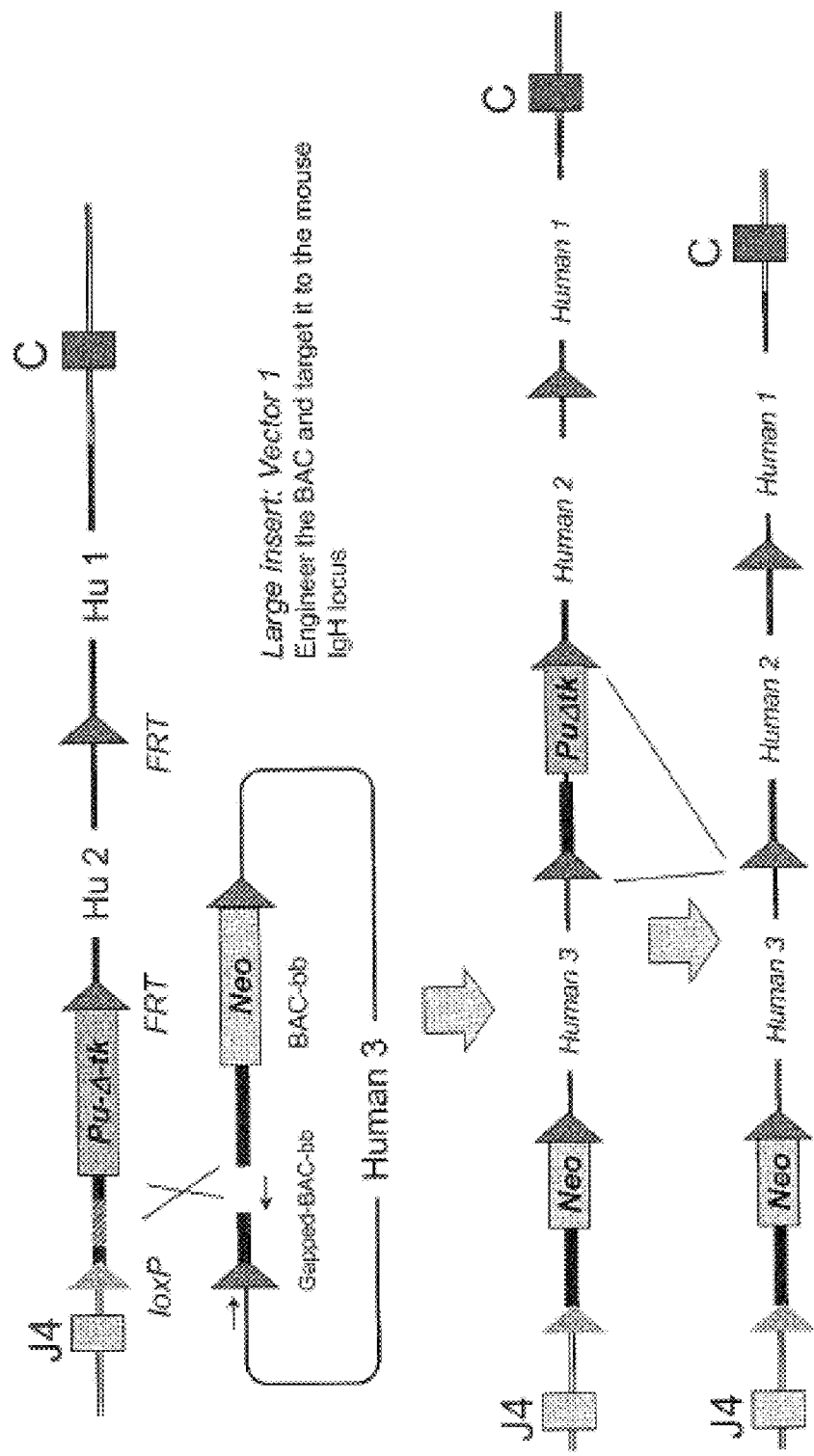

FIG. 7 illustrates the next large insert vector targeted to the mouse IgH locus. The pu-delta TK cassette is then removed, as for FIG. 4. The process can be repeated to incorporate other BACs.

Figure 8:
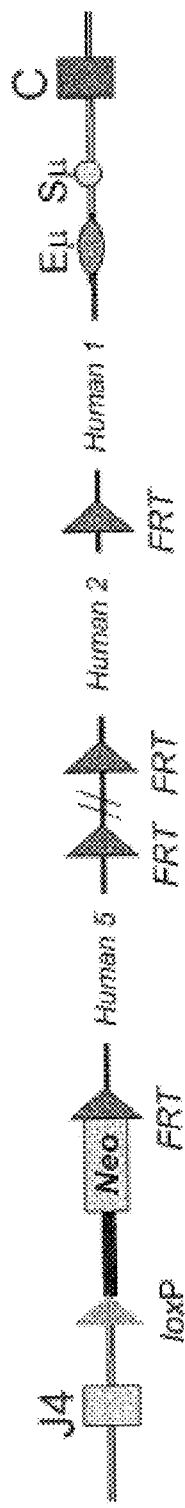
Figure 9:
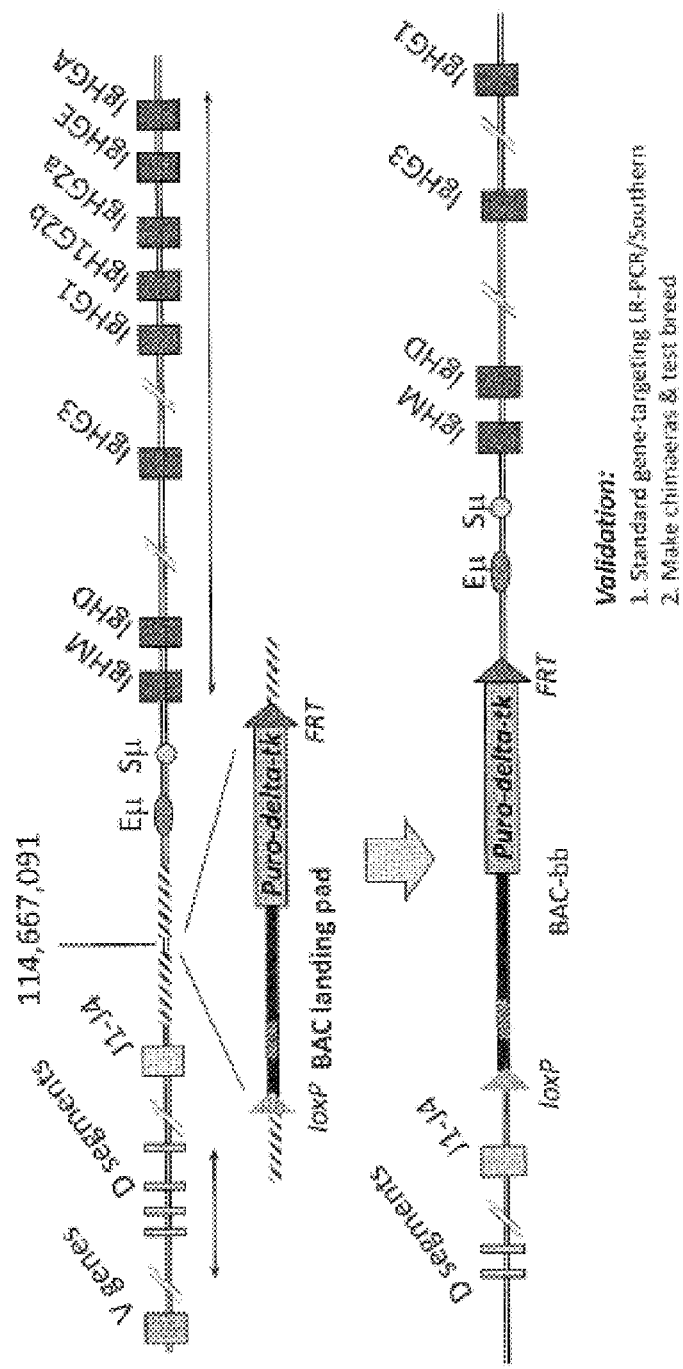
FIGS. 9-18 show in more detail the process of FIGS. 1-8 for the IgH and kappa locus
Figure 10:
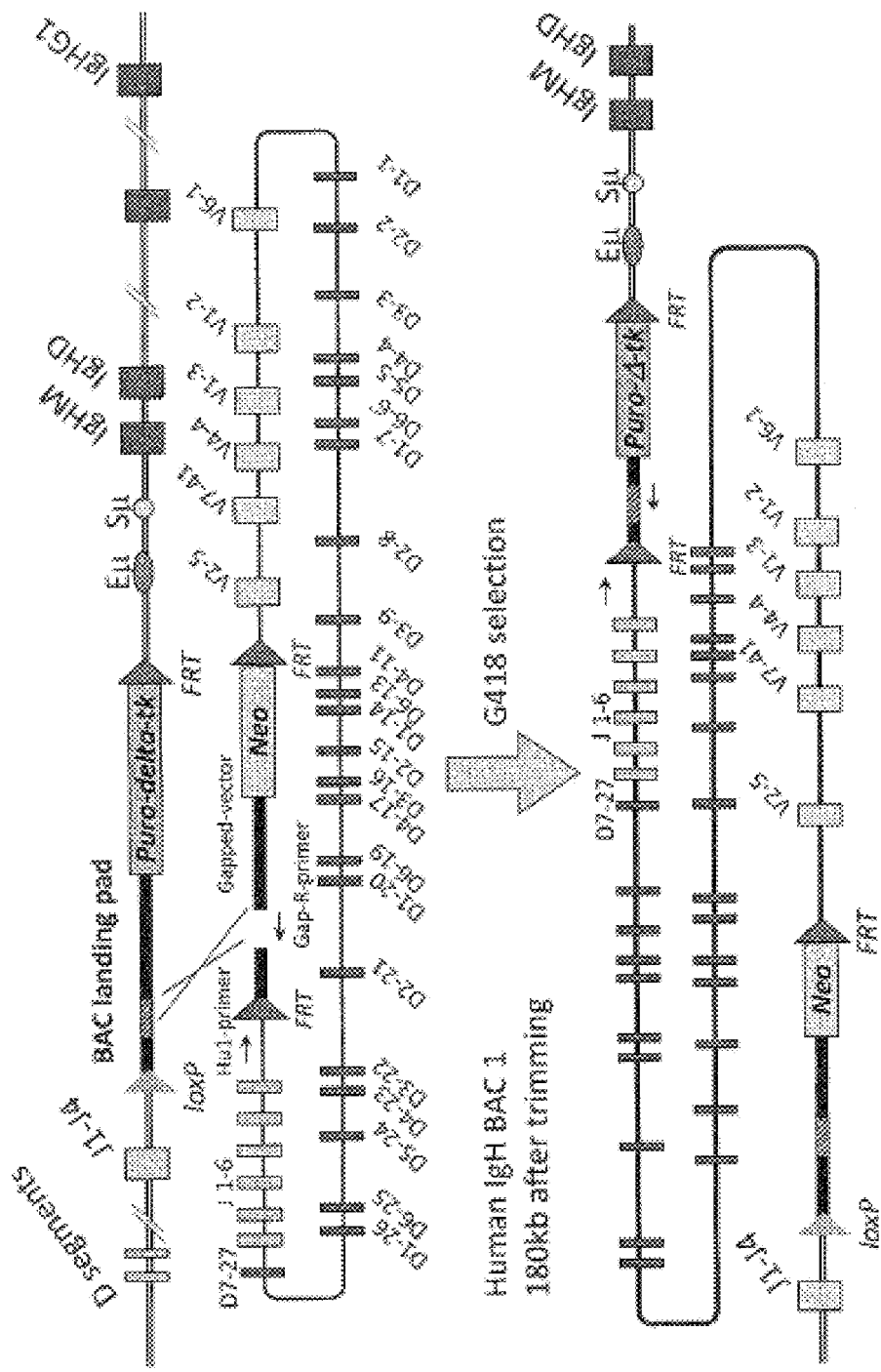
Figure 11:
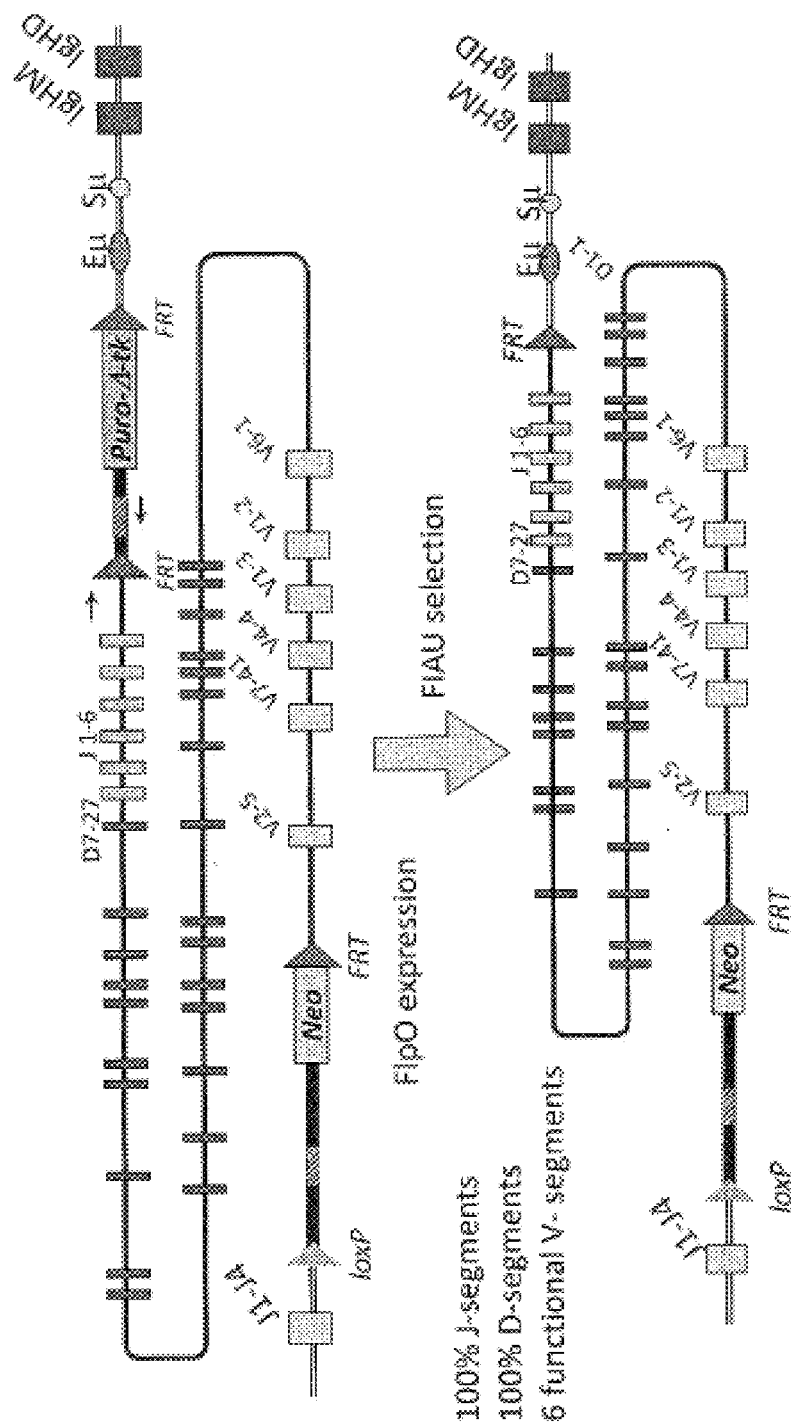
Figure 12:
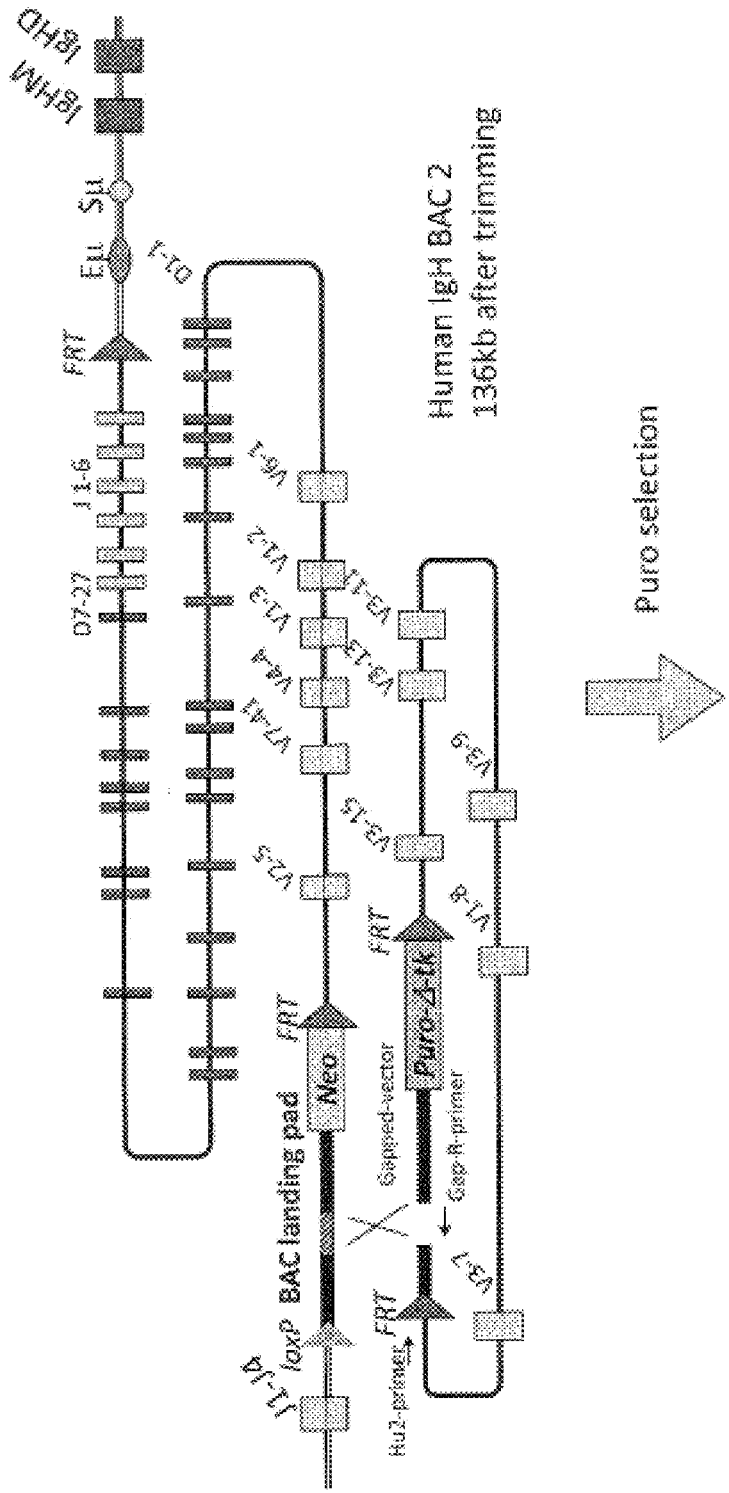
Figure 13:
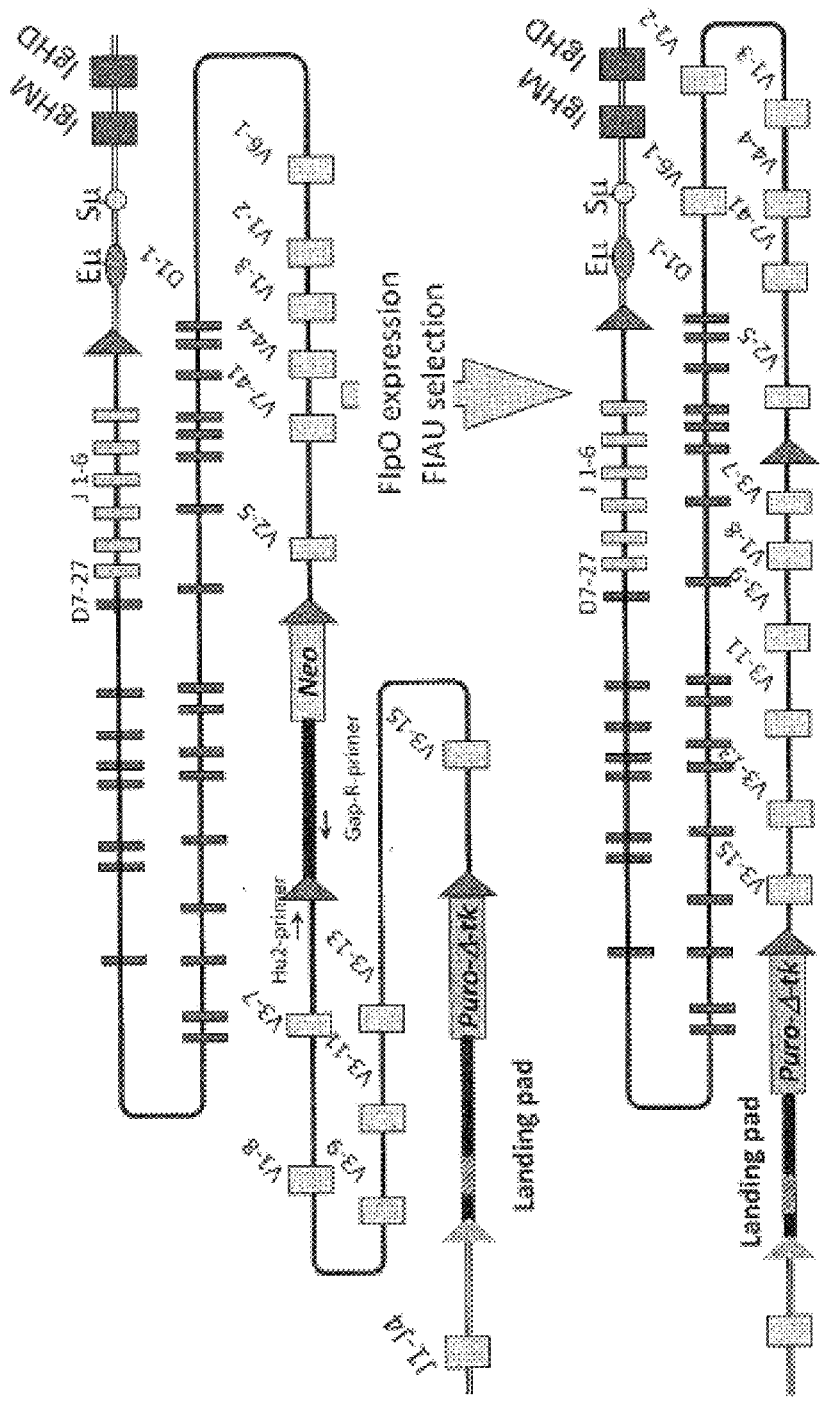
Figure 14:
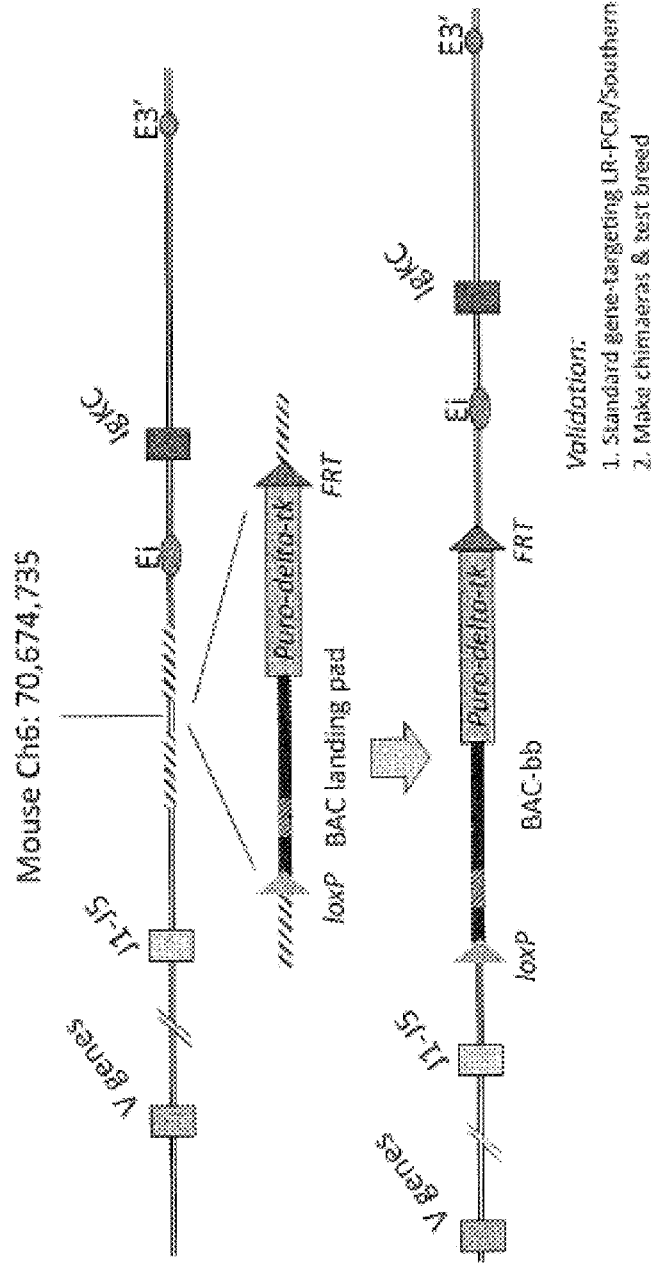
Figure 15:
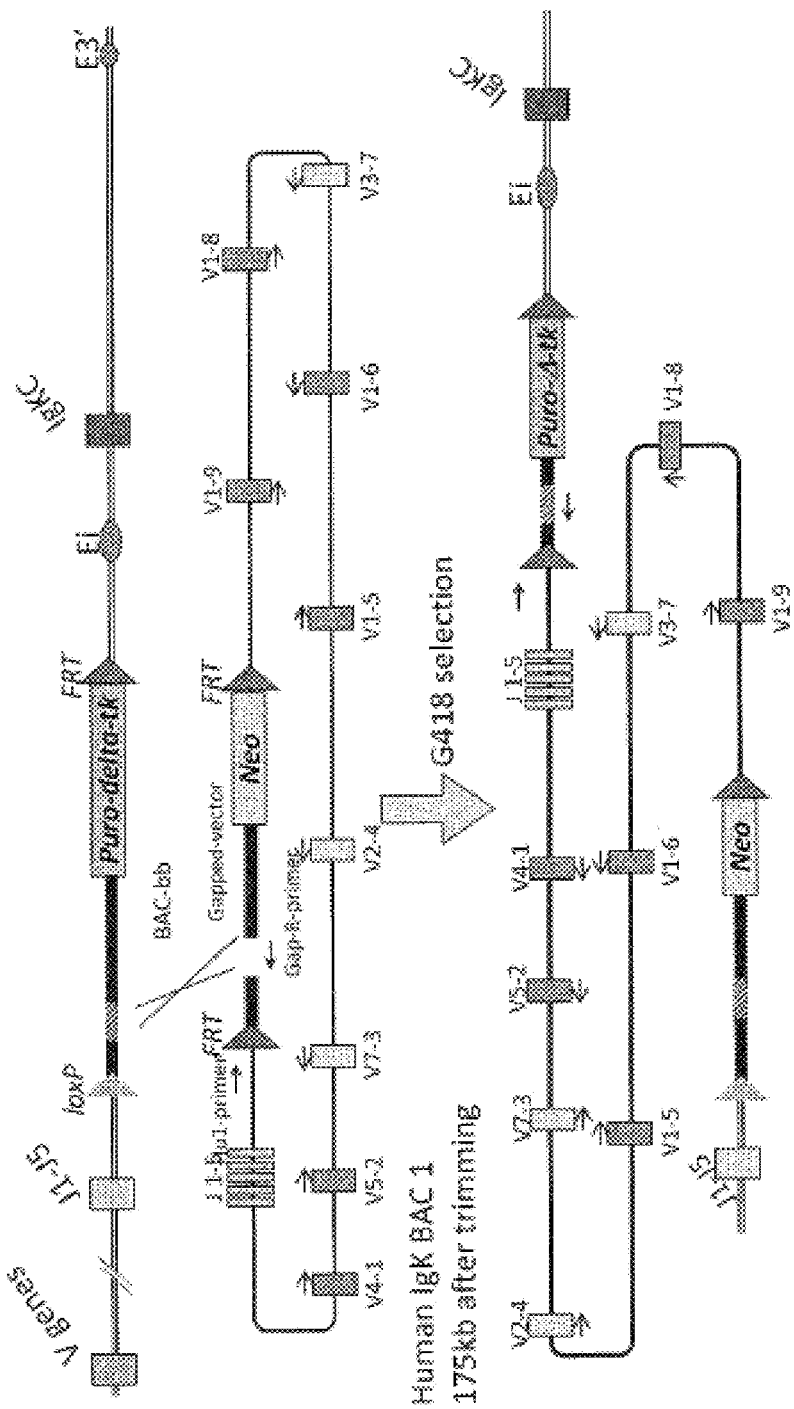
Figure 16:
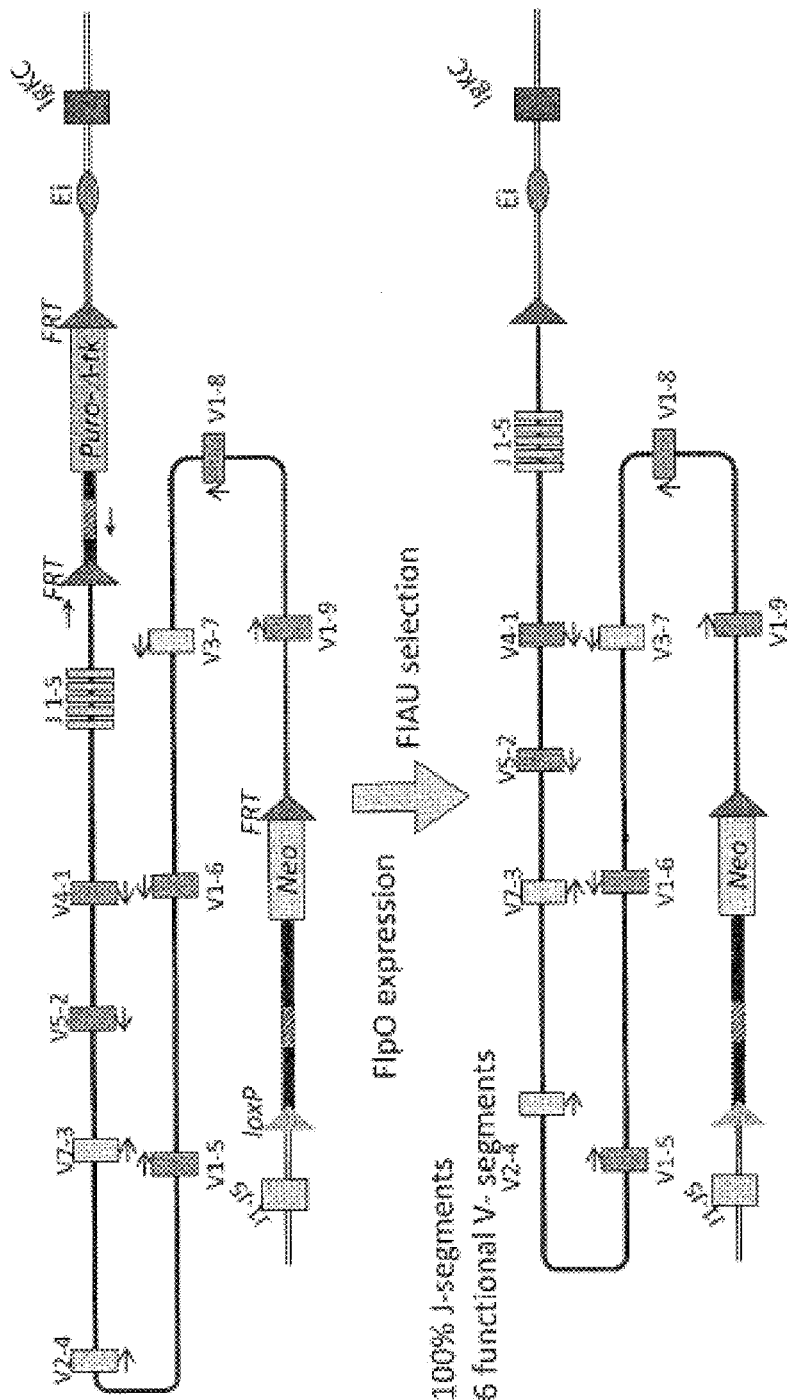
Figure 17:
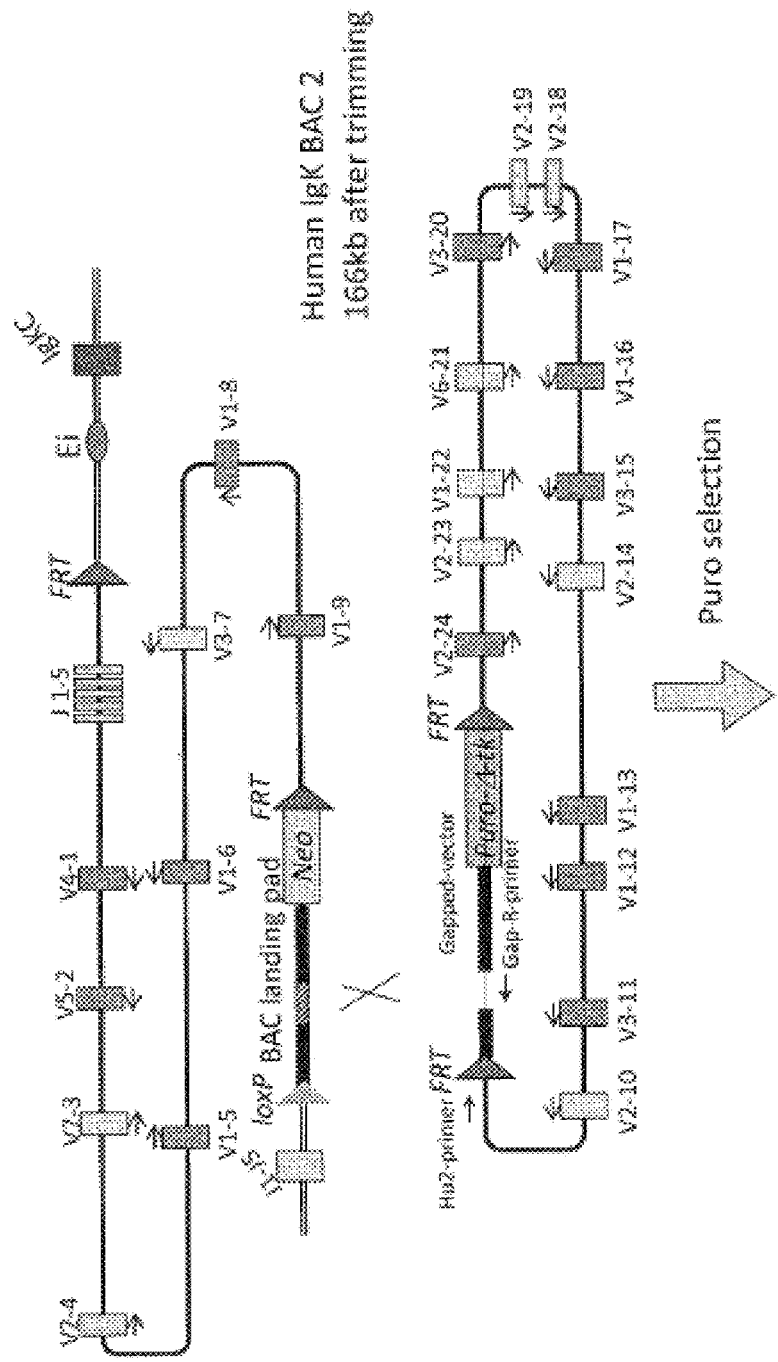
Figure 18:
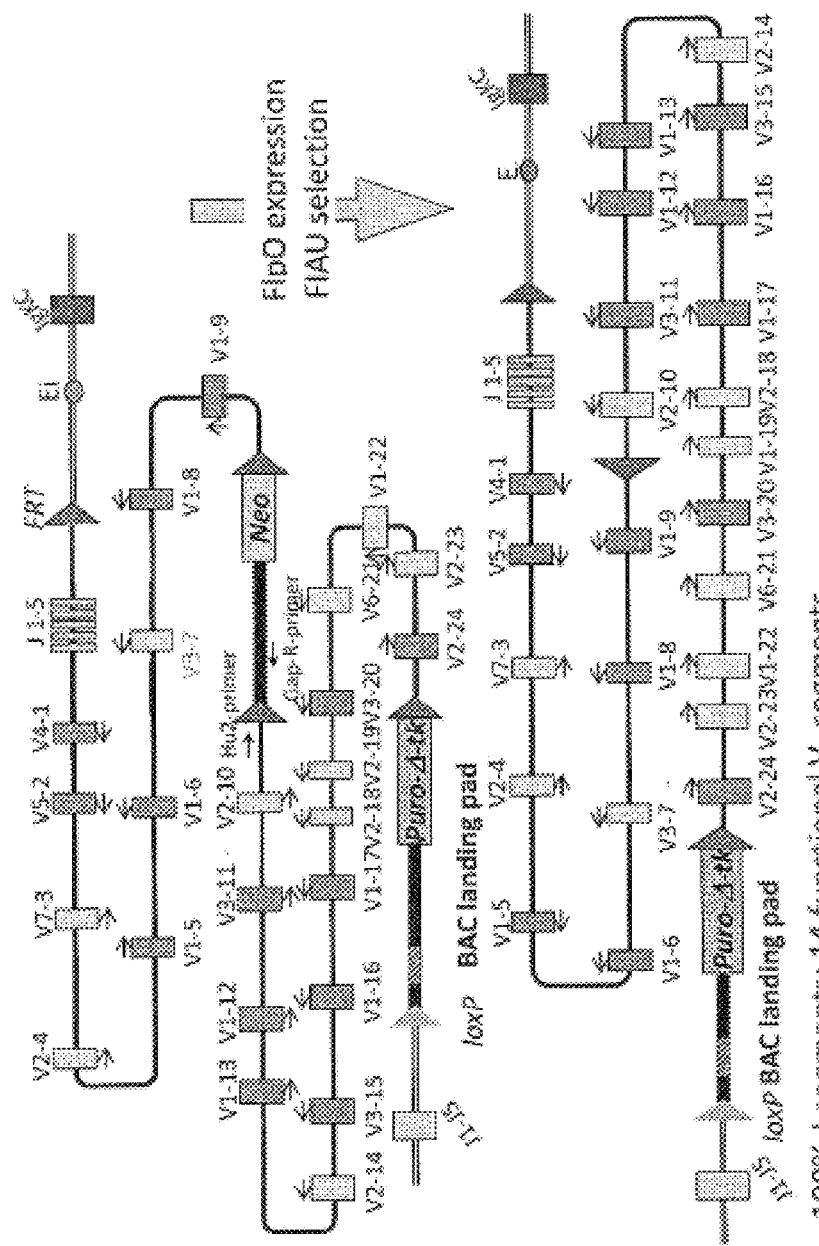

FIG. 8 illustrates the final predicted ES cell construct.

FIGS. 9-18 provide a further level of detail of this process.

Example 2

Site-Specific Recombination

In a further method of the invention site specific recombination can also be employed. Site-specific recombination (SSR) has been widely used in the last 20-years for the integration of transgenes into defined chromosomal loci. SSR involves recombination between homologous DNA sequences.

The first generation of SSR-based chromosomal targeting involved recombination between (i) a single recombination target site (RT) such as loxP or FRT in a transfected plasmid with (ii) a chromosomal RT site provided by a previous integration. A major problem with this approach is that insertion events are rare since excision is always more efficient than insertion. A second generation of SSR called RMCE (recombinase-mediated cassette exchange) was introduced by Schlake and Bode in 1994 (Schlake, T.; J. Bode (1994). "Use of mutated FLP-recognition-target-(FRT-)sites for the exchange of expression cassettes at defined chromosomal loci". *Biochemistry* 33: 12746-12751). Their method is based on using two heterospecific and incompatible RTs in the transfected plasmid which can recombine with compatible RT sites on the chromosome resulting in the swap of one piece of DNA for another—or a cassette exchange. This approach has been successfully exploited in a variety of efficient chromosomal targeting, including integration of BAC inserts of greater than 50 kb (Wallace, H. A. C. et al. (2007). "Manipulating the mouse genome to engineering precise functional syntenic replacements with human sequence". Cell 128: 197-209; Prosser, H. M. et al. (2008). "Mosaic complementation demonstrates a regulatory role for myosin VIIa in actin dynamics of Stereocilia". Mol. Cell. Biol. 28: 1702-12).

The largest insert size of a BAC is about 300-kb and therefore this places an upper limit on cassette size for RMCE.

In the present invention a new SSR-based technique called sequential RMCE (SRMCE) was used, which allows continuous insertion of BAC inserts into the same locus.

The method comprises the steps of
1 insertion of DNA forming an initiation cassette (also called a landing pad herein) into the genome of a cell;

2 insertion of a first DNA fragment into the insertion site, the first DNA fragment comprising a first portion of a human DNA and a first vector portion containing a first selectable marker or generating a selectable marker upon insertion;

3 removal of part of the vector DNA;

4 insertion of a second DNA fragment into the vector portion of the first DNA fragment, the second DNA fragment containing a second portion of human DNA and a second vector portion, the second vector portion containing a second selectable marker, or generating a second selectable marker upon insertion;

5 removal of any vector DNA to allow the first and second human DNA fragments to form a contiguous sequence; and 6 iteration of the steps of insertion of a part of the human V(D)J DNA and vector DNA removal, as necessary, to produce a cell with all or part of the human VDJ or VJ region sufficient to be capable of generating a chimaeric antibody in conjunction with a host constant region, wherein the insertion of at least one DNA fragment uses site specific recombination.

Figure 22:
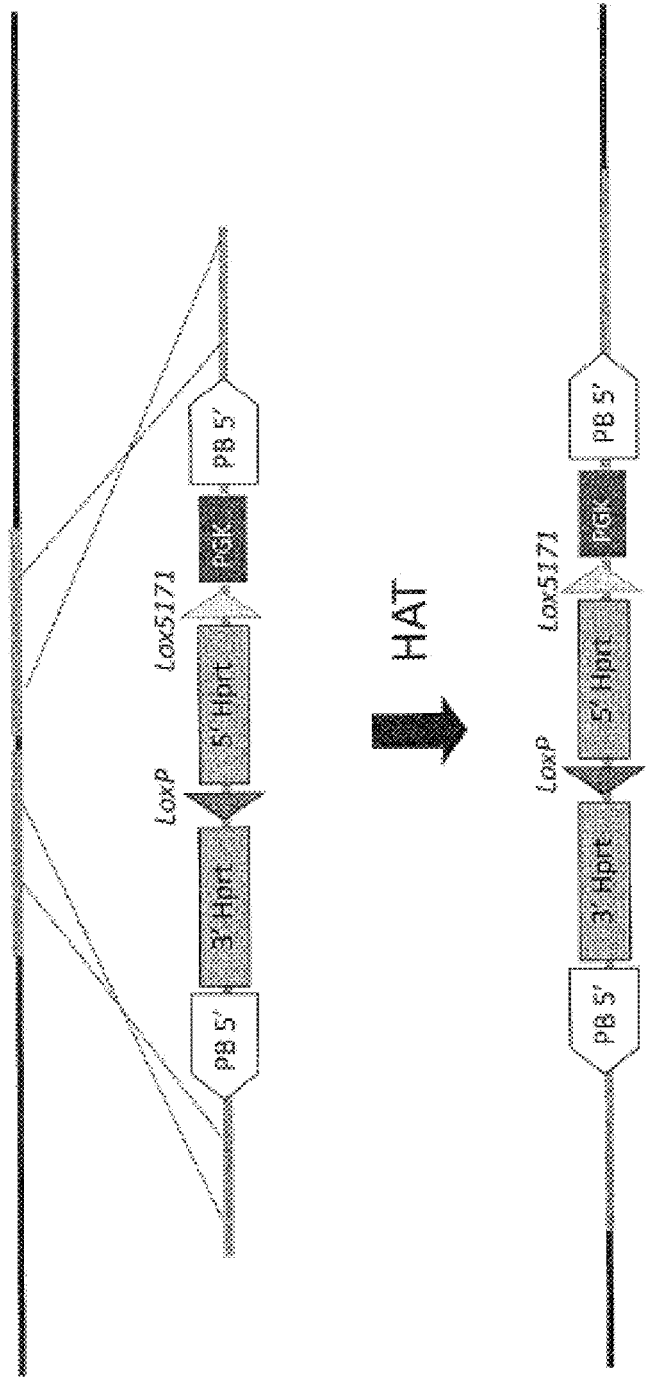

In one specific aspect the approach utilizes three heterospecific and incompatible loxP sites. The method is comprised of the steps as follows, and illustrated in FIGS. 22-26:

1. Targeting a landing pad into the defined locus. An entry vector containing an HPRT mini-gene flanked by inverted piggyBac (PB) ITRs is targeted into defined region (for example: a region between IGHJ and Eμ or IGKJ and Eκ or IGLC1 and Eλ3-1) to serve as a landing pad for BAC targeting. The HPRT mini-gene is comprised of two synthetic exons and associated intron. The 5' HPRT exon is flanked by two heterospecific and incompatible loxP sites (one wild-type and the other a mutated site, lox5171) in inverted orientation to each other (FIG. 22). These two loxP sites provide recombination sites for the BAC insertion through RMCE.

Figure 23:
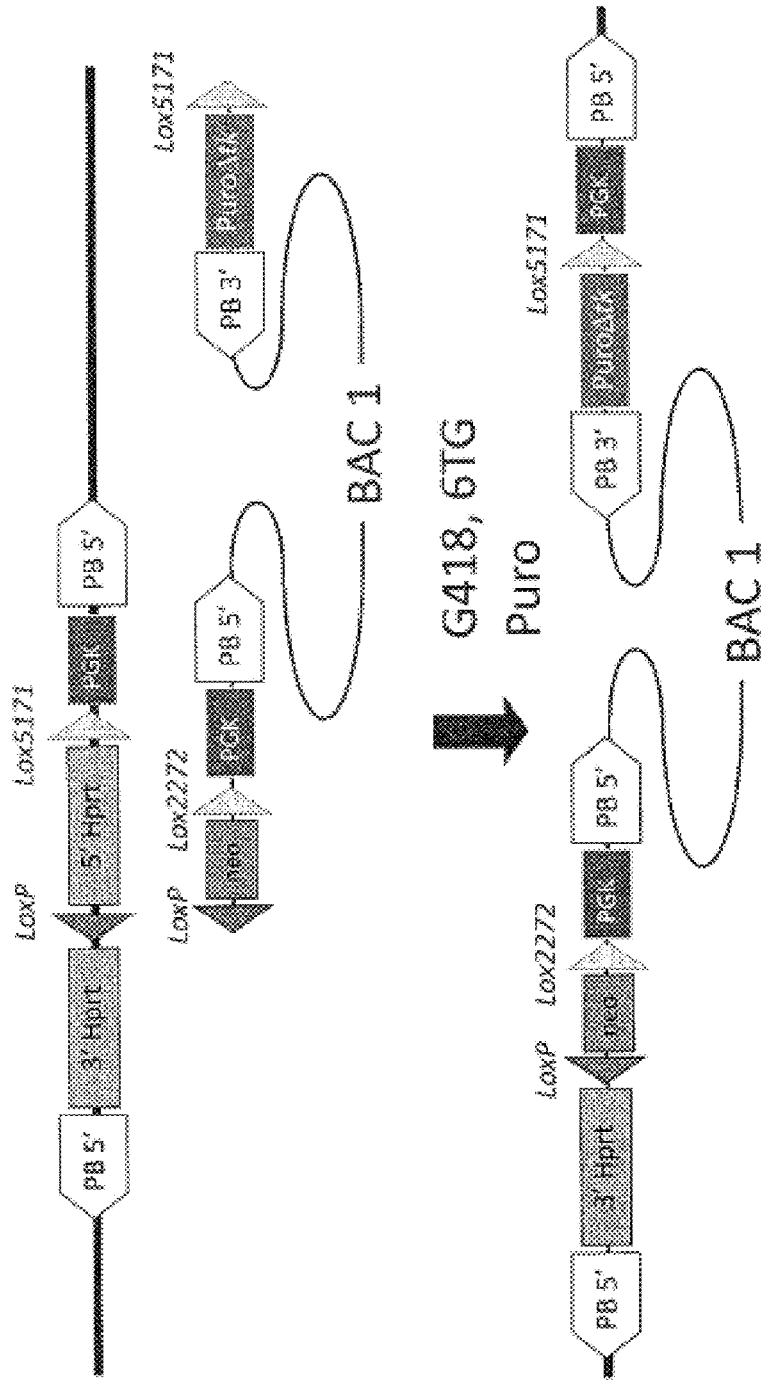

2. Insertion of the $1^{st}$ modified BAC into the targeted landing pad. The $1^{st}$ BAC has a length of DNA to be inserted into the genome flanked by engineered modifications. The 5' modification (loxP—neo gene—lox2272—PGK promoter—PB 5'LTR) and 3' modification (PB3'LTR—puroΔTK gene—lox5171) is depicted in FIG. 23 along with the relative orientations of the lox sites and PB LTRs. With transient CRE expression from a co-electroporated vector, the DNA sequence would be inserted into the defined locus through RMCE. The cells in which a correct insertion has occurred can be selected as follows: (i) Puromycin-resistance (the puroΔTK gene has acquired a promoter—"PGK"—from the landing pad), (ii) 6TG-resistance (the HPRT mini-gene has been disrupted), and (iii) G418-resistance (selects for any insertion via the 5' region PGK-neo arrangement). Any combination of these selection regimes can be used. G418- and 6TG-resistance select for correct events on the 5' end while puro-resistance selects for correct events on the 3' end.

3. Curing (removing) the 3' modification of the $1^{st}$ insertion. A properly inserted $1^{st}$ BAC results the 3' end having a puroΔTK gene flanked by inverted PB LTRs (FIG. 24)—essentially a proper transposon structure. This transposon can then be removed by the transient expression of the piggyBac transposase (from an electroporated vector). Cells with the correct excision event can be selected by FIAU resistance—ie, no thymidine kinase activity from the puroΔTK gene. This completely removes the 3' modification leaving no trace nucleotides.

Figure 25:
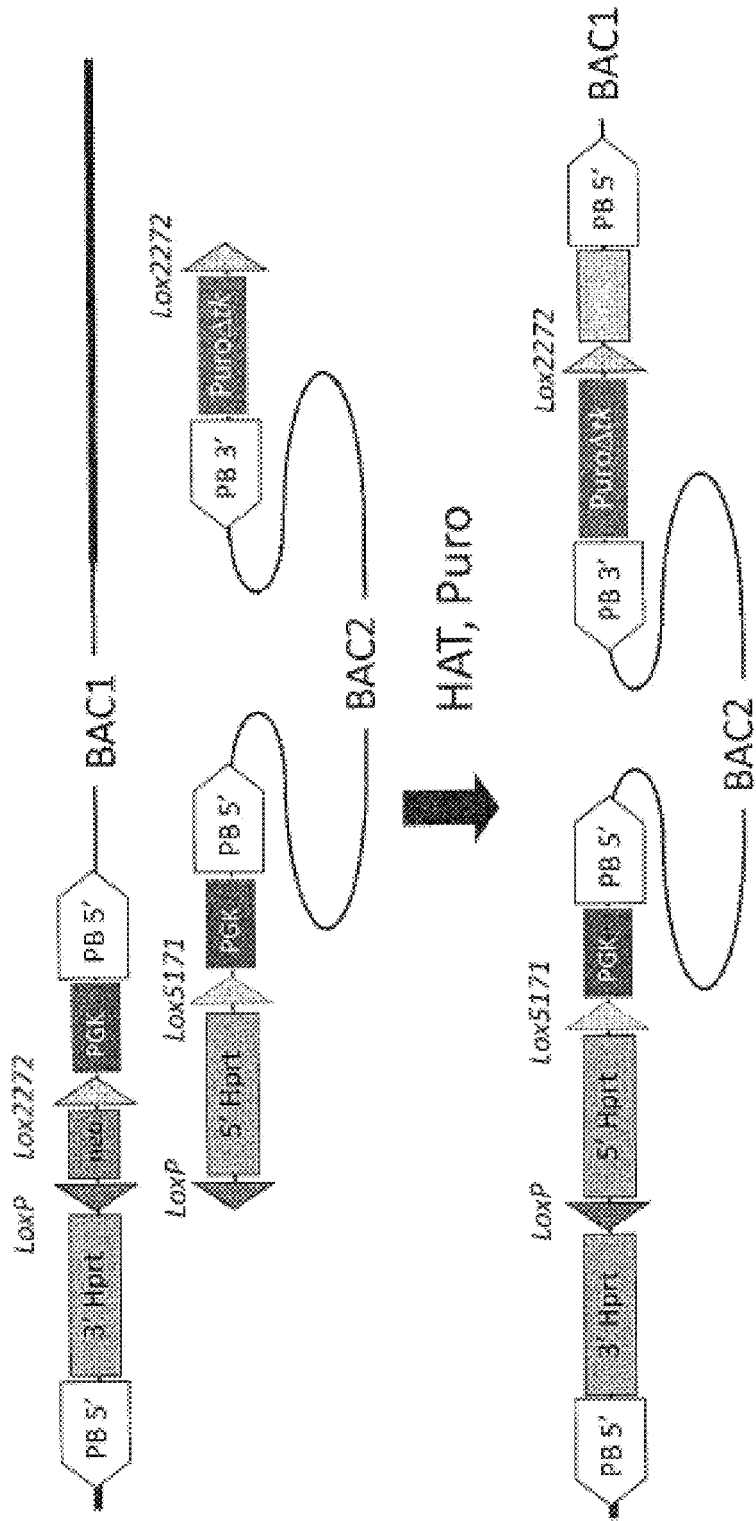
Figure 26:
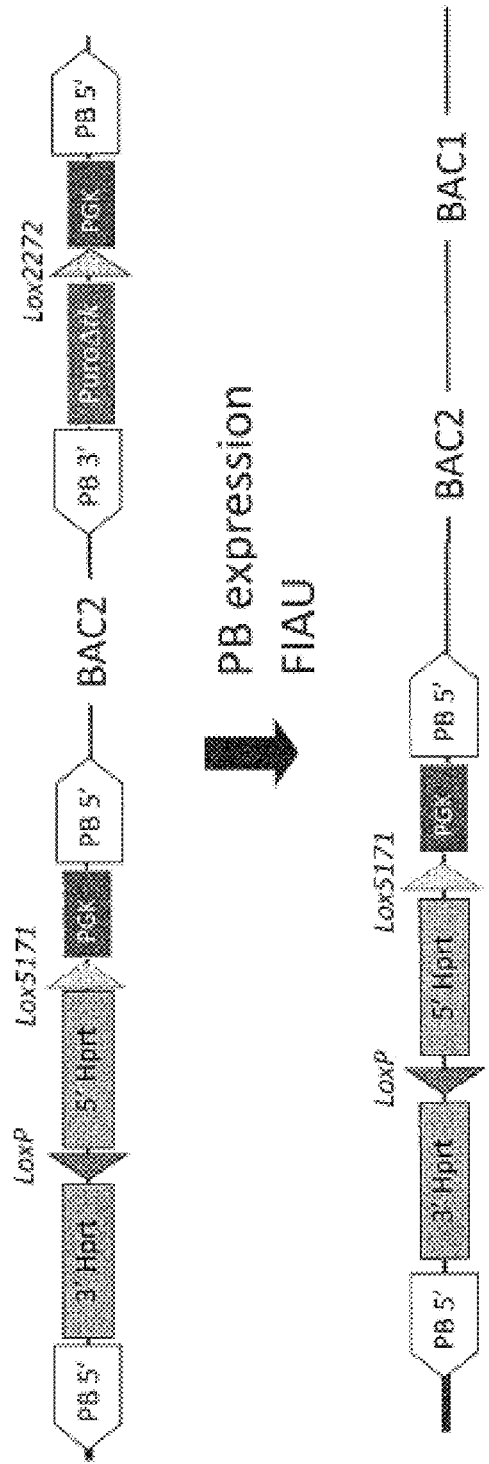

4. Insertion of a $2^{nd}$ modified BAC into the 5' end of $1^{st}$ insertion. The $2^{nd}$ BAC has a length of DNA to be inserted into the genome (usually intended to be contiguous with the DNA inserted with the $1^{st}$ BAC) flanked by engineered modifications. The 5' modification (loxP—HPRT mini gene 5' portion—lox5171—PGK promoter—PB5'LTR) and 3' modification (PB3'LTR—puroΔTK—lox2272) is depicted in FIG. 25 along with the relative orientations of the lox sites and PB LTRs. With transient CRE expression from a co-electroporated vector, the DNA sequence would be inserted into the defined locus through RMCE. The cells in which a correct insertion has occurred can be selected as follows: (i) HAT-resistance (the HPRT mini-gene is reconstituted by a correct insertion event, ie: the 5' and 3' exon structures are brought together), and (ii) puromycin-resistance (puroΔTK gene has acquired a promoter—"PGK"—from the landing pad).

5. Curing (removing) the 3' modification of the $2^{nd}$ insertion. A properly inserted $2^{nd}$ BAC results the 3' end having a puroΔTK gene flanked by inverted PB LTRs (FIG. 26)—essentially a proper transposon structure, exactly analogous to the consequence of a successful $1^{st}$ BAC insertion. And therefore this transposon can likewise be removed by the transient expression of the piggyBac transposase (from an electroporated vector). Cells with the correct excision event can be selected by FIAU resistance—ie, no thymidine kinase activity from the puroΔTK gene. This completely removes the 3' modification leaving no trace nucleotides.

6. After curing of the 3' modification of the $2^{nd}$ BAC insertion, the landing pad becomes identical to the original. This entire process, steps 2 through 5, can be repeated multiple times to build up a large insertion into the genome. When complete, there are no residual nucleotides remaining other than the desired insertion.

Figure 27:
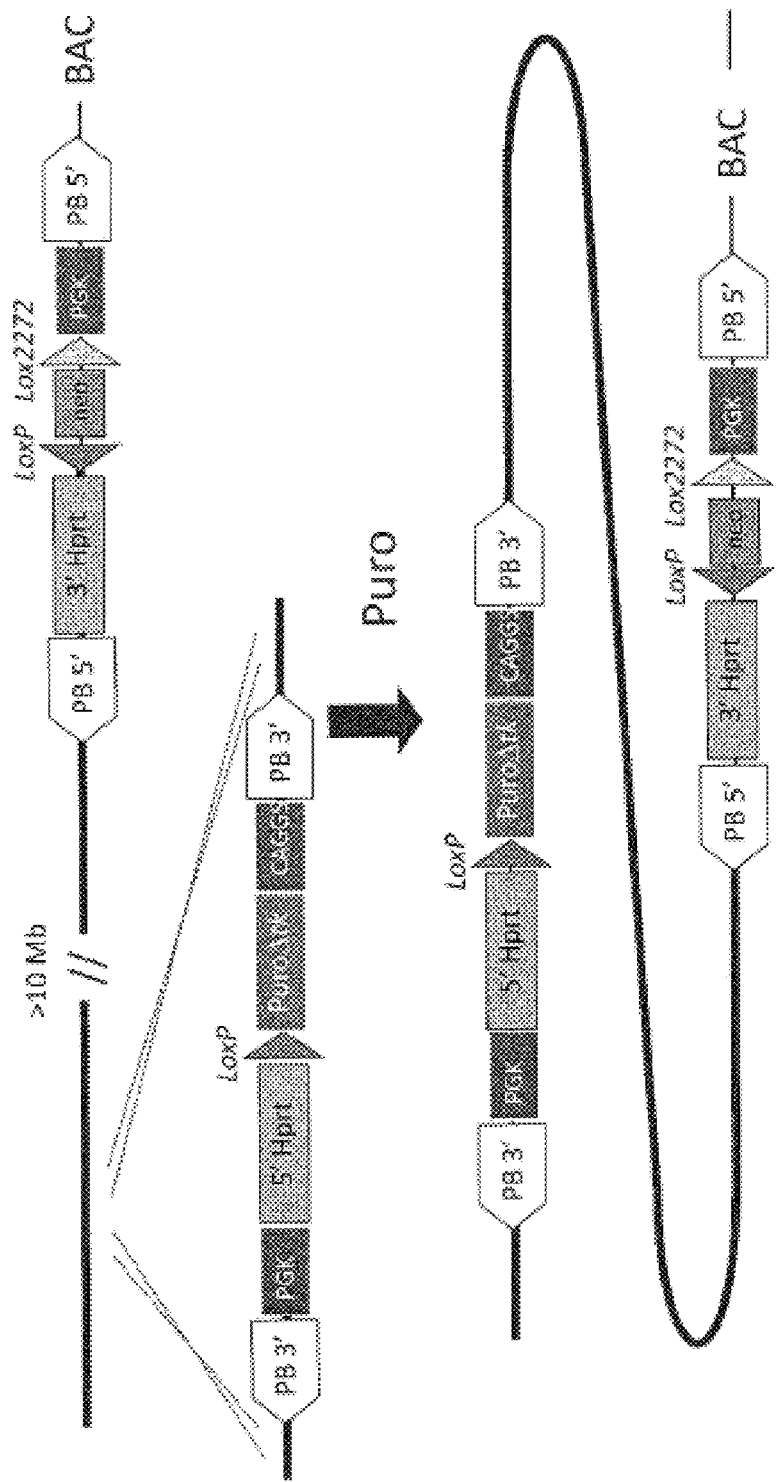
FIGS. 27-29 illustrate a mechanism for inversion of the host VDJ region

With the insertion of an odd number of BACs into the Ig loci, the endogenous VDJ or VJ sequences can be inactivated through an inversion via chromosomal engineering as follows (see FIGS. 27-29):

1. Targeting a "flip-over" cassette into a 5' region 10 to 40 megabases away from the endogenous VDJ or VJ. The flip-over vector (PB3'LTR—PGK promoter—HPRT mini gene 5' portion—loxP—puroΔTK—CAGGS promoter—PB3'LTR) is depicted in FIG. 27 along with the relative orientations of the lox sites and PB LTRs.

Figure 28:
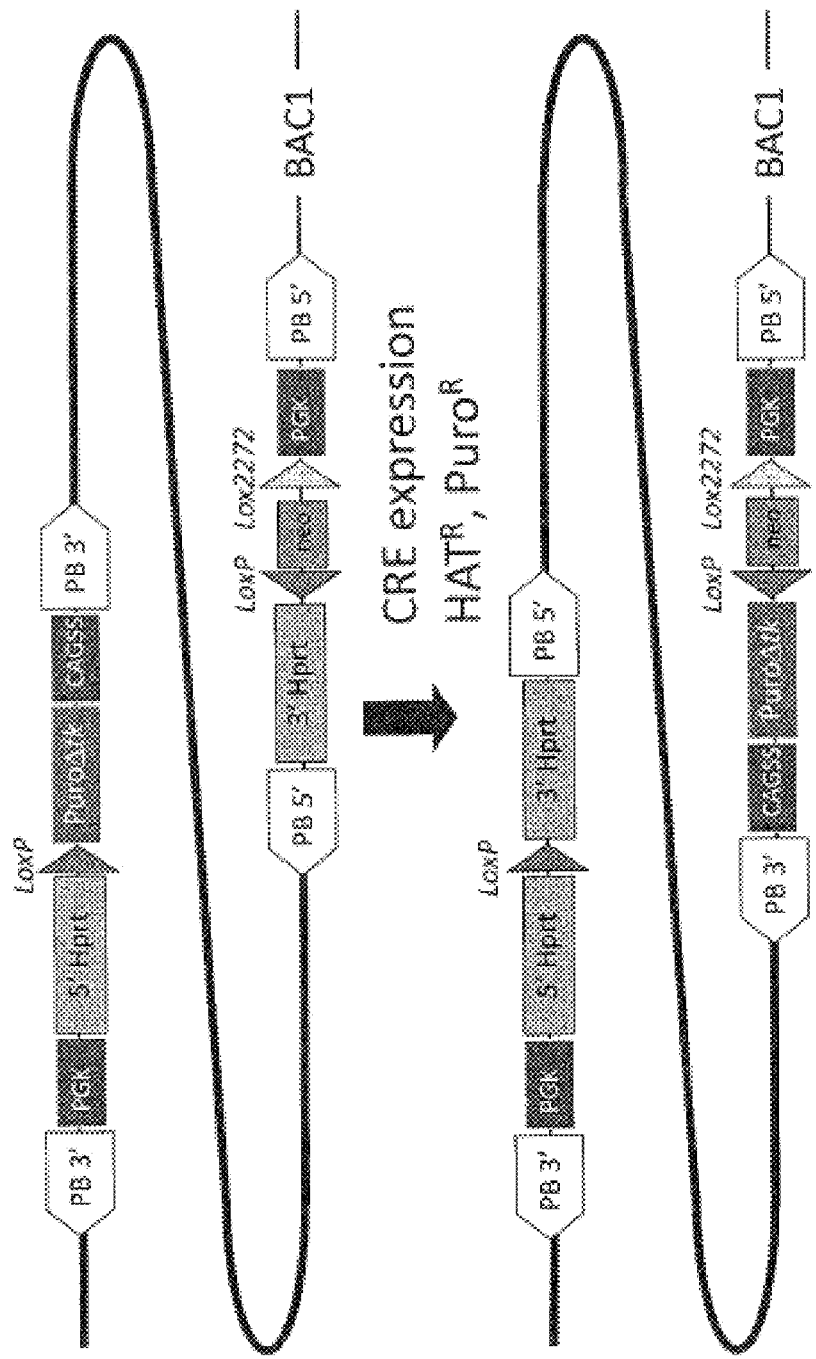

2. Transient CRE expression will result in recombination between the loxP site in the "flip-over" cassette and the loxP site in the 5' modification. This 5' modification is as described in Steps 2 and 3 above—essentially the modification resulting from insertion of an odd number of BACs, after the 3' modification has been cured. The loxP sites are inverted relative to one another and therefore the described recombination event results in an inversion as depicted in FIG. 28. Cells with the correct inversion will be HAT-resistance since the HPRT mini-gene is reconstituted by a correct inversion.

Figure 29:
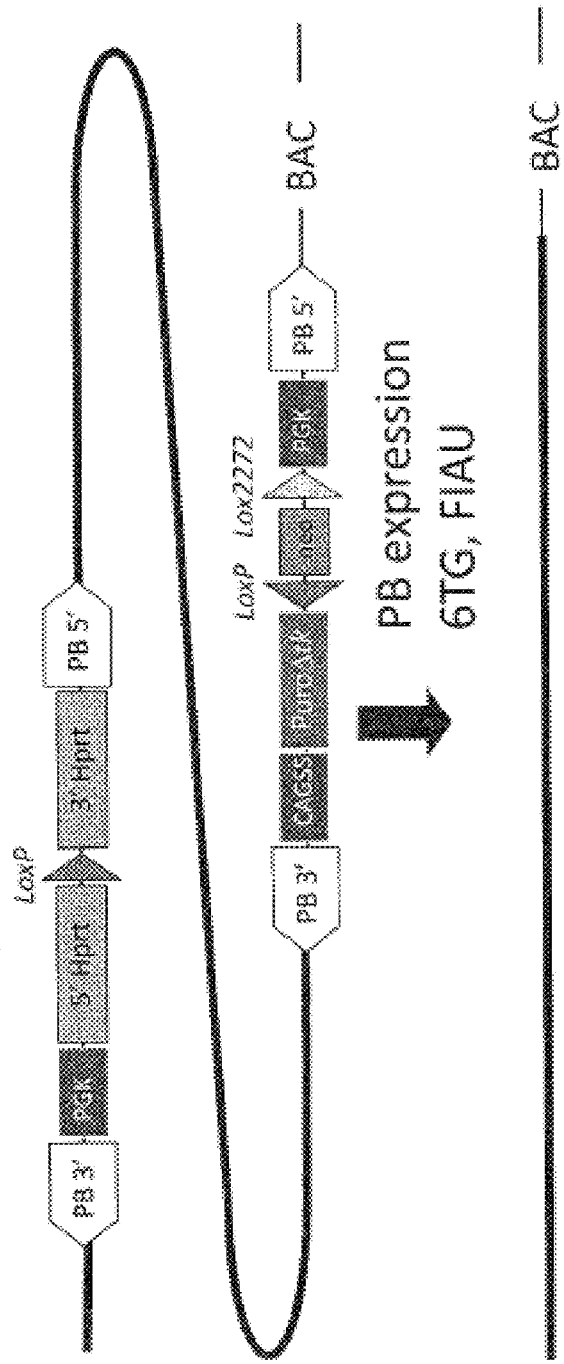

3. A correct inversion also leaves two transposon structures flanking the "flip-over" cassette and the 5' modification. Both can be excised with transient piggyBAC transposase expression, leaving no remnant of either modification (FIG. 29). Cells with the correct excisions can be selected as follows: (i) 6TG-resistance (the HPRT mini-gene is deleted) and (ii) FIAU-resistance (the puroΔTK gene is deleted). An inversion as described in the Ig loci would move the endogenous IGH-VDJ or IGK-VJ region away from the Eμ or Eκ enhancer region, respectively, and lead to inactivation of the endogenous IGH-VDJ or IGK-VJ regions.

The methods of insertion of the invention suitably provide one or more of:

Selection at both 5' and 3' ends of the inserted DNA fragment;

Efficient curing of the 3' modification, preferably by transposase mediated DNA excision;

Inactivation of endogenous IGH or IGK activity through an inversion; and

Excision of modifications, leaving no nucleotide traces remaining in the chromosome.

Example 3

Insertion of a Test Vector into the Genome at a Defined Location

Figure 30:
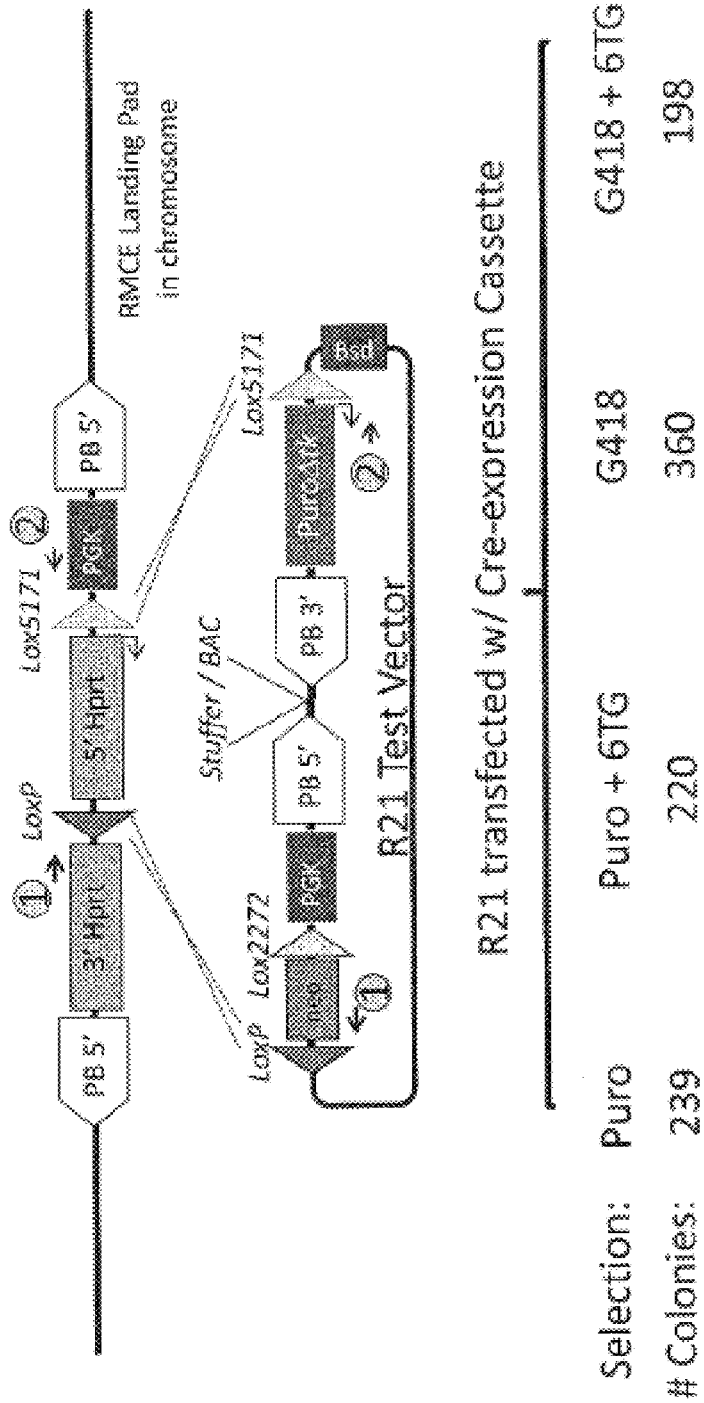
FIG. 30 illustrates proof of principle for insertion of a plasmid using an RMCE approach

Proof of concept of the approach is disclosed in FIG. 30. In FIG. 30 a landing pad as shown in FIG. 22 was inserted into the genome of a mouse by homologous recombination, followed by insertion of the R21 plasmid into that landing pad via cre-mediated site specific recombination. The insertion event generated a number of general insertion events, 360 G418 resistant colonies, of which ~220 were inserted into the desired locus, as demonstrated by disruption of the HRPT minilocus.

Figure 31:
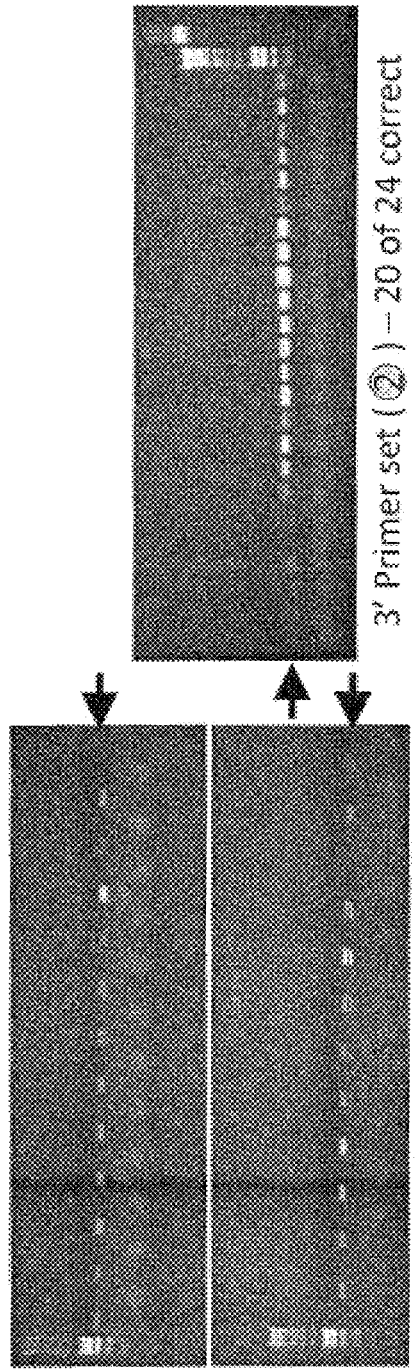
FIG. 31 illustrates sequential RMCE—Integration into Landing Pad

The R21 vector mimics the $1^{st}$ BAC insertion vector at the 5' and 3' ends, including all selection elements and recombinase target sites. In place of BAC sequences, there is a small 'stuffer' sequence. This vector will both test all the principals designed in the invention and allow easy testing of the results in that PCR across the stuffer is feasible and therefore allows both ends of the insertion to be easily tested. R21 was co-electroporated with a cre-expressing vector into the ES cells harbouring the landing pad in the IGH locus. Four sets of transformed cells were transfected in parallel and then placed under different selection regimes as indicated in FIG. 30. G418 selection (neo gene expression) resulted in the largest number of colonies due to there being no requirement for specific landing-pad integration. Any integration of R21 into the genome will provide neo expression leading to G418-resistance. Puro selection resulted in a similar colony number to Puro+6TG or G418+6TG, suggesting that the stringency of Puro selection is due to the PuroΔTK lacking a promoter in the vector. Puro expression is only acquired when an integration occurs near a promoter element—in this design most likely specifically in the landing pad. These conclusions are supported by the results from junction PCR which is shown in FIG. 31.

Figure 32:
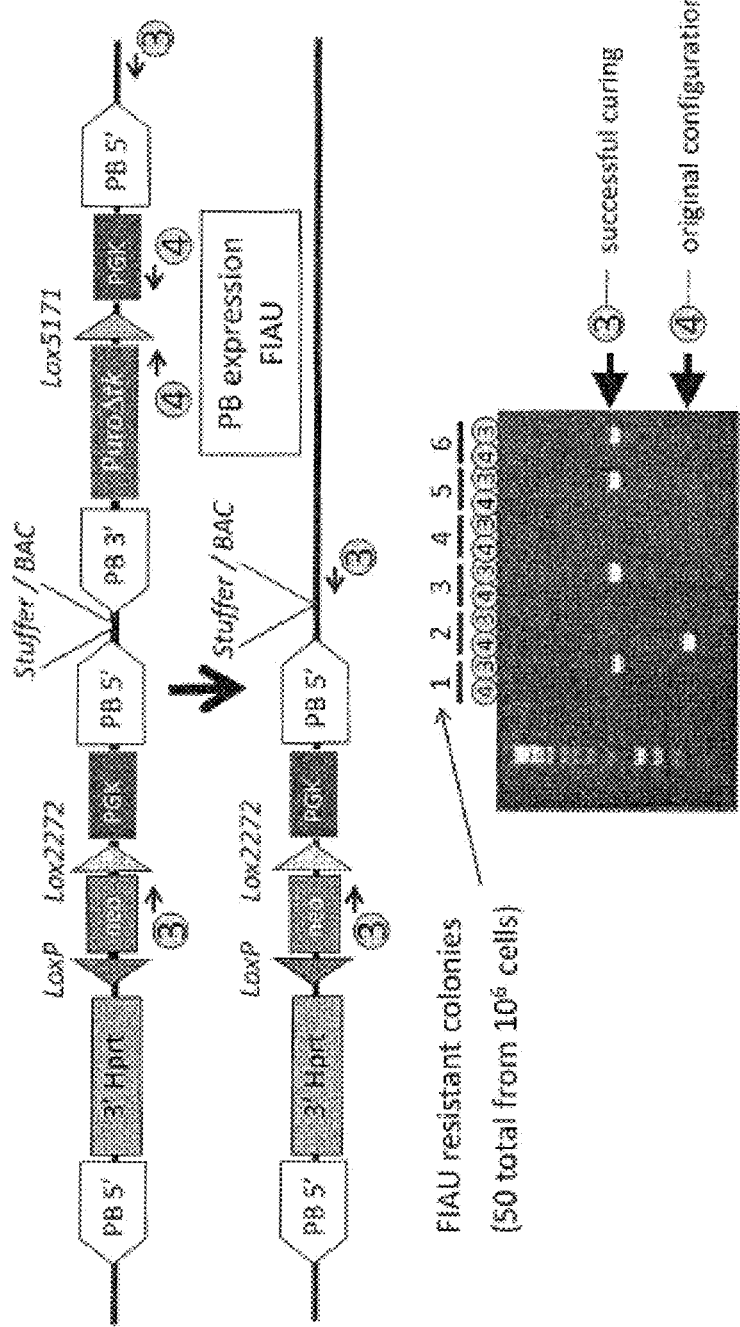
FIG. 32 illustrates confirmation of Successful Insertion into Landing Pad

The next step in the invention is to 'cure' the 3' end of the integrated BAC vector, leaving a seamless transition between the insertion and the flanking genome. This curing was demonstrated by expanding an individual clone from above (R21 inserted into the landing pad) and expressing piggyBac recombinase in this clone via transfection of an expressing plasmid. FIAU was used to select colonies in which the 3' modification was excised—ie, through loss of the 'PGK-puroΔTK' element between the piggyBac terminal repeats. Fifty such clones resulted from a transfection of $10^6$ cells; of these six were tested for the expected genomic structure. Successful curing resulted in positive PCR between the primer set labelled "3" in FIG. 32. Of the 6 clones, 4 had correct excisions, 1 clone remained in the original configuration and 1 other had a deletion.

These data demonstrate iterative insertion of DNA into a landing pad at a defined genomic locus using the approaches outlined above.

Example 4

Insertion of Large Parts of the Human IG Loci into Defined Positions in the Mouse Genome Example 3 demonstrated that the design of the claimed invention was capable of providing for the insertion of a test vector into the genome at a defined location, in this case the R21 vector into the mouse IGH locus. The use of the appropriate selection media and the expression of cre-recombinase resulted in a genomic alteration with the predicted structure.

The same design elements described in this invention were built into the 5' and 3' ends of a BAC insert. Said insert comprised human sequences from the IGH locus and was approximately 166-kb. This engineered BAC was electroporated along with a cre-expressing plasmid DNA into mouse ES cells harbouring the landing pad at the mouse IGH locus. The transfected cell population was grown in puro-containing media to select for appropriate insertion events.

Figure 33:
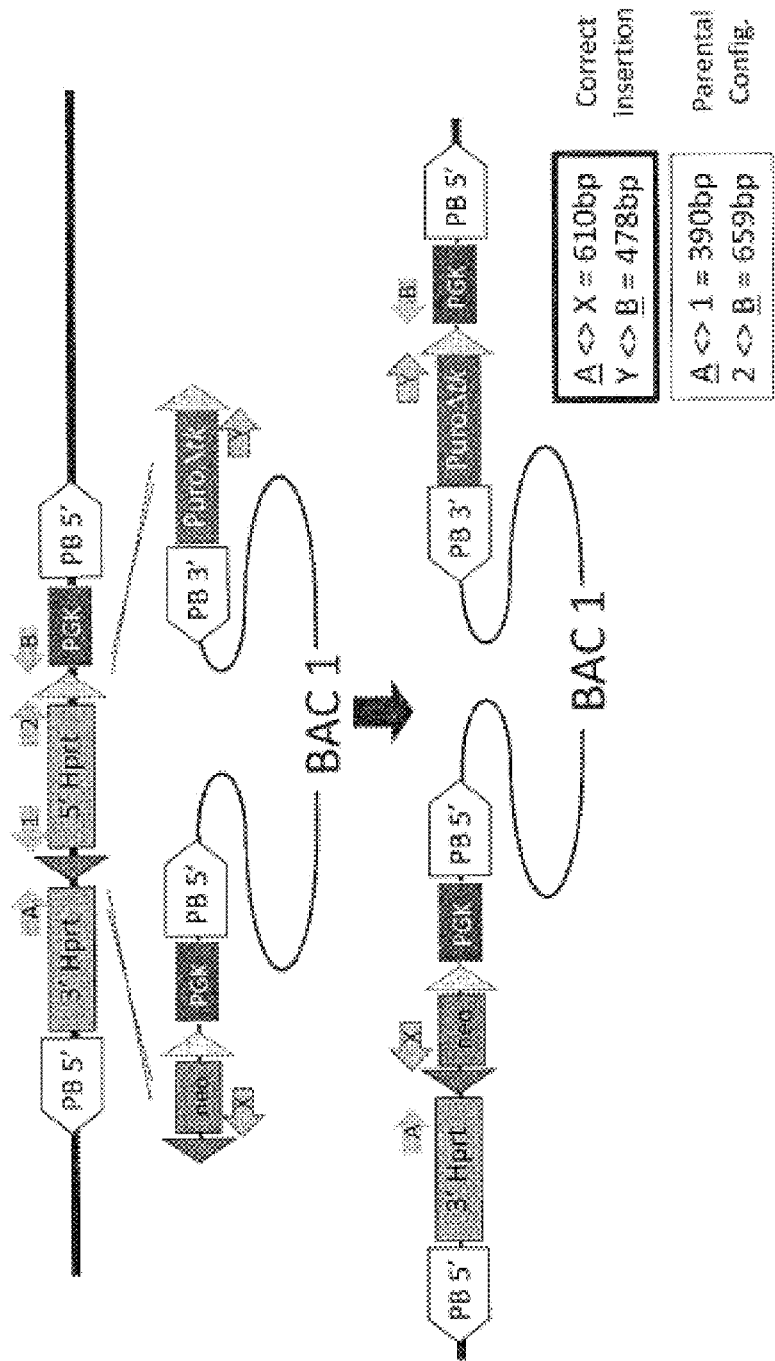
FIG. 33 illustrates PCR Confirmation of 3' End Curing
Figure 34:
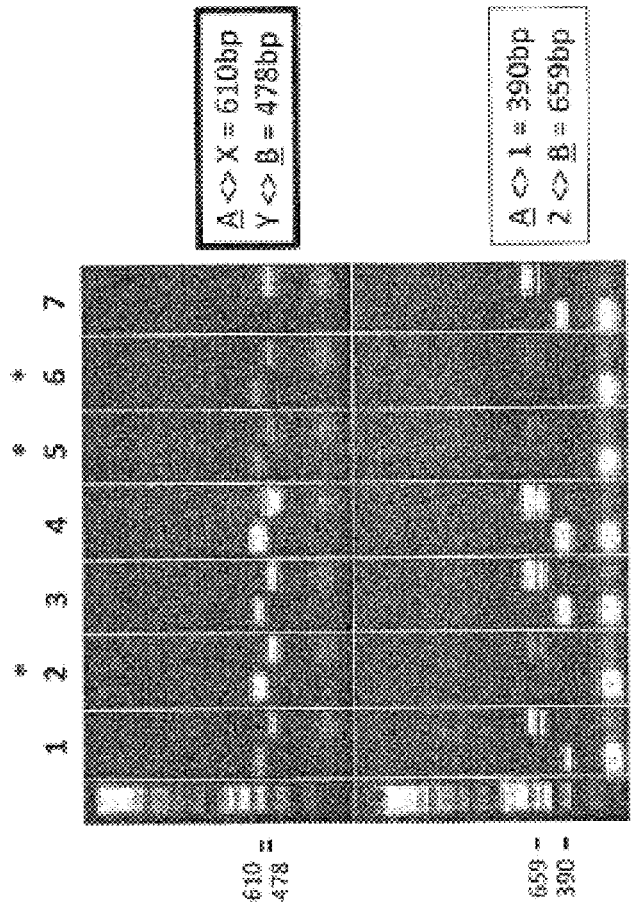
FIG. 34 illustrates insertion of BAC#1 and PCR Diagnostics

Seven resulting clones were isolated and further analysed. The expected recombination event and resulting structure are depicted in FIG. 33. Based upon data from the R21 experiment outlined in Example 3, a stringent selection for correct clones was expected when the transfected population was selected in puro-containing media. This is because the puro-coding region requires a promoter element and this is preferentially supplied by the landing pad after recombination. Accordingly, the majority of the 7 isolated clones had inserted correctly into the genome at the landing pad as determined by the diagnostic PCR. The primers for diagnosing a correct insertion are depicted in FIG. 33. Correct junctions are present in the genome if a 610-bp fragment is amplified between primers 'A' and 'X' and a 478-bp fragment is amplified between primers 'Y' and 'B' (FIGS. 33 and 34). Note that there are amplified fragments between 'A' and '1' primers and '2' and 'B' primers indicating the presence of parental genome (that is, the landing pad alone). These result from parental cells present internally in the cell colonies under puro-selection that escape the selection due to the geometry of a colony. After passaging the colony through puro-containing media, these parental junction fragments disappear indicating that the parental cells are removed from the population. In addition, all the clones were shown to be resistant to 6-TG as expected if the HPRT gene is inactivated by the correct insertion event.

These data indicate that the disclosed strategy for inserting large parts of the human IG loci into defined positions in the mouse genome will enable the construction of a mouse with a plurality of the variable regions of human IG regions upstream of the mouse constant regions as described.

Example 5

Inserted Loci are Functional in Terms of Gene Rearrangement, Junctional Diversity as Well as Expression Bacterial artificial chromosomes (BACs) were created, wherein the BACs had inserts of human Ig gene segments (human V, D and/or J gene segments). Using methods described herein, landing pads were used in a method to construct chimaeric Ig loci in mouse embryonic stem cells (ES cells), such that chimaeric IgH and IgK loci were provided in which human gene segments are functionally inserted upstream of endogenous constant regions. To test if the human IgH-VDJ or IgK-VJ gene segments in the chimaera mice derived from human BAC-inserted ES cell clones appropriately rearrange and express, RT-PCR was performed for the RNA samples of white blood cells from those mice with the primer pairs of human variable (V) region and mouse constant (C) region. The sequences of oligos are shown as follows (Table 1). Each V oligo is paired with C oligo (HV with Cμ; KV with CK) for PCR reaction.

TABLE 1

| Oligo | Sequence |
|---|---|
| HV2-5 | AGATCACCTTGAAGGAGTCTGGTCC (SEQ ID NO 7) |
| HV4-4 | TGGTGAAGCCTTCGGAGACCCTGTC (SEQ ID NO 8) |
| HV1-3 | CACTAGCTATGCTATGCATTGGGTG (SEQ ID NO 9) |
| HV1-2 | ATGGATCAACCCTAACAGTGGTGGC (SEQ ID NO 10) |
| HV6-1 | GGAAGGACATACTACAGGTCCAAGT (SEQ ID NO 11) |
| Cμ | TAGGTACTTGCCCCCTGTCCTCAGT (SEQ ID NO 12) |
| KV1-9 | AGCCCAGTGTGTTCCGTACAGCCTG (SEQ ID NO 13) |
| KV1-8 | ATCCTCATTCTCTGCATCTACAGGA (SEQ ID NO 14) |
| KV1-6 | GGTAAGGATGGAGAACACTGGCAGT (SEQ ID NO 15) |
| KV1-5 | TTAGTAGCTGGTTGGCCTGGTATCA (SEQ ID NO 16) |
| CK | CTTTGCTGTCCTGATCAGTCCAACT (SEQ ID NO 17) |

Using the one-step formulation of SuperScript™ III One-Step RT-PCR System with Platinum® Taq High Fidelity (Invitrogen™; World Wide Web (www) invitrogen.com/site/us/en/home/References/protocols/nucleic-acid-amplification-and-expression-profiling/pcr-protocol/superscript-3-one-step-rt-per-system-with-platinum-taq-high-fidelity.html#prot3), both cDNA synthesis and PCR amplification were achieved in a single tube using gene-specific primers and target RNAs.

The RT-PCR results showed most of the human IGH-VDJ or IGK-VJ gene segments appropriately rearrange and express in the chimaera mice. To investigate the details about the diversity generated from VDJ/VJ rearrangement, those specific RT-PCR fragments were cloned into a common vector for sequencing.

Figure 36:
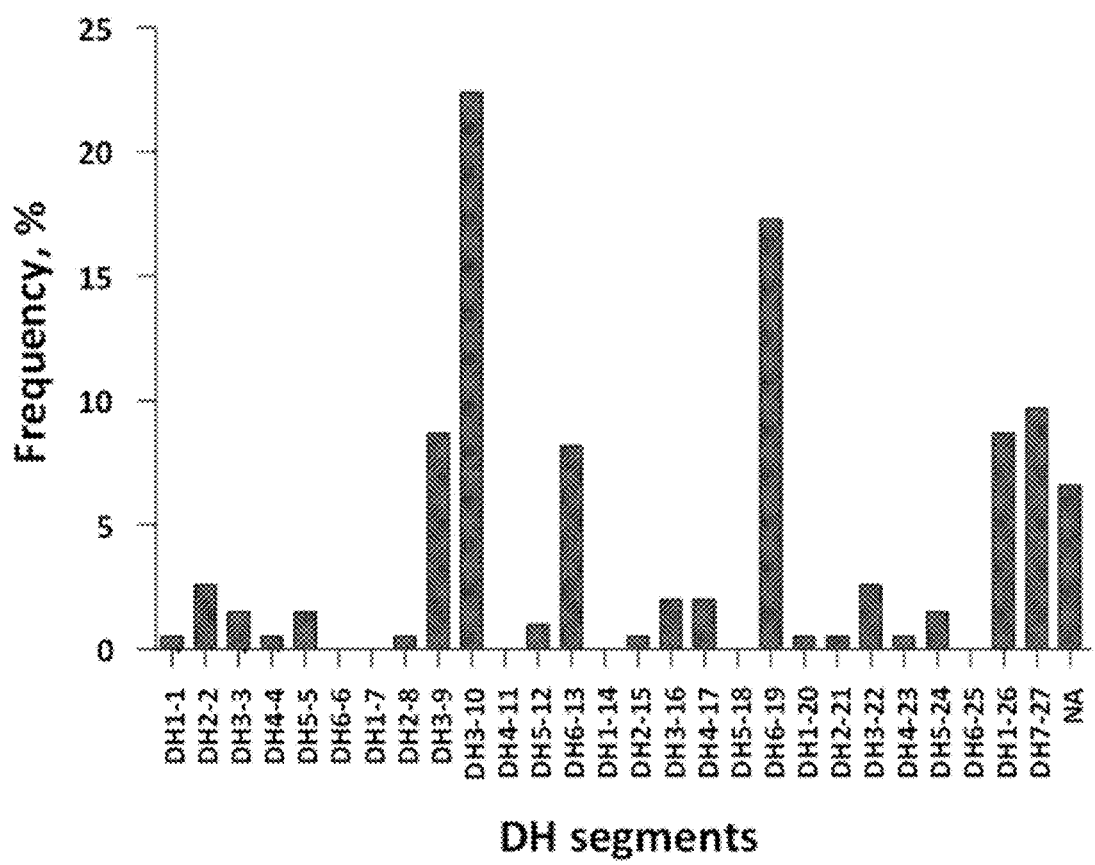
FIG. 36 illustrates DH usage
Figure 37:
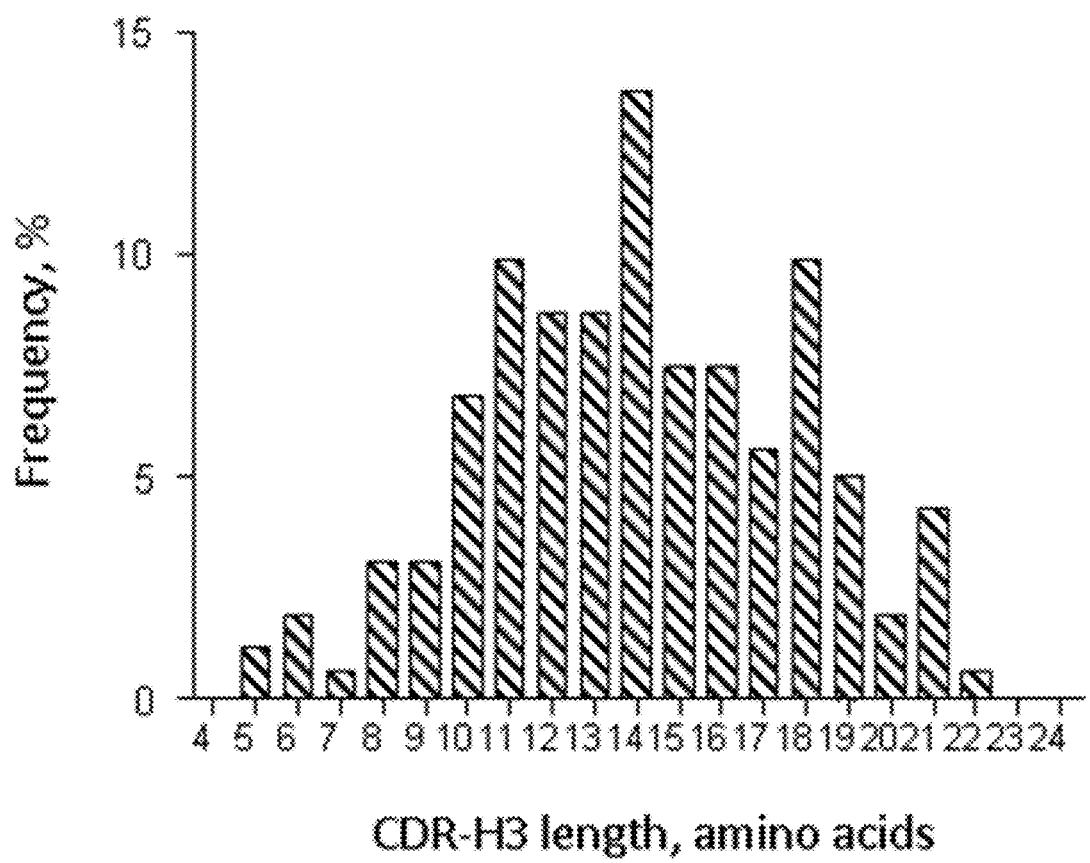
FIG. 37 illustrates the distribution of CDR-H3 length in human VDJCμ transcripts from chimera mice
Figure 38:
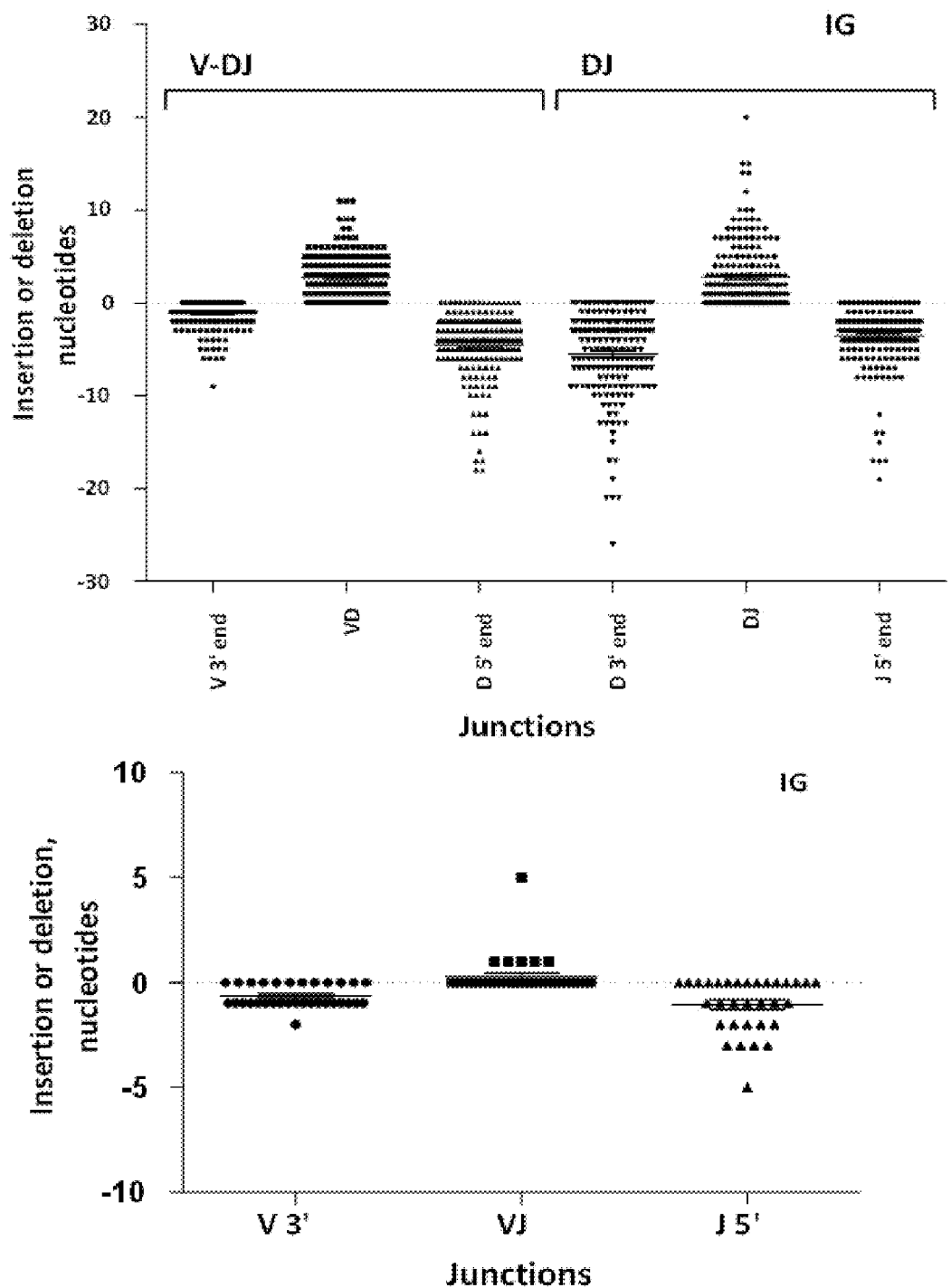
FIG. 38 illustrates the distribution of nucleotide numbers of deletion and insertion in IGH-VDI or IGK-VJ junctions

Sequencing results indicate that JH, DH, and JK usages (FIG. 35 and FIG. 36) are similar to human results. In addition, the results from the IGH-VDJCμ transcripts show that the range and mean of CDR-H3 length (FIG. 37) are similar to that observed in human. The junctional diversity generated from exonuclease and nucleotide addition activities (FIG. 38) was also observed. The IGH rearrangement possessed a higher frequency of these activities compared to the IGK one. These data suggest that the inserted loci are functional in terms of gene rearrangement, junctional diversity as well as expression.

Example 6

Productive VJ Rearrangement and Somatic Hypermutation can be Obtained

Figure 43:
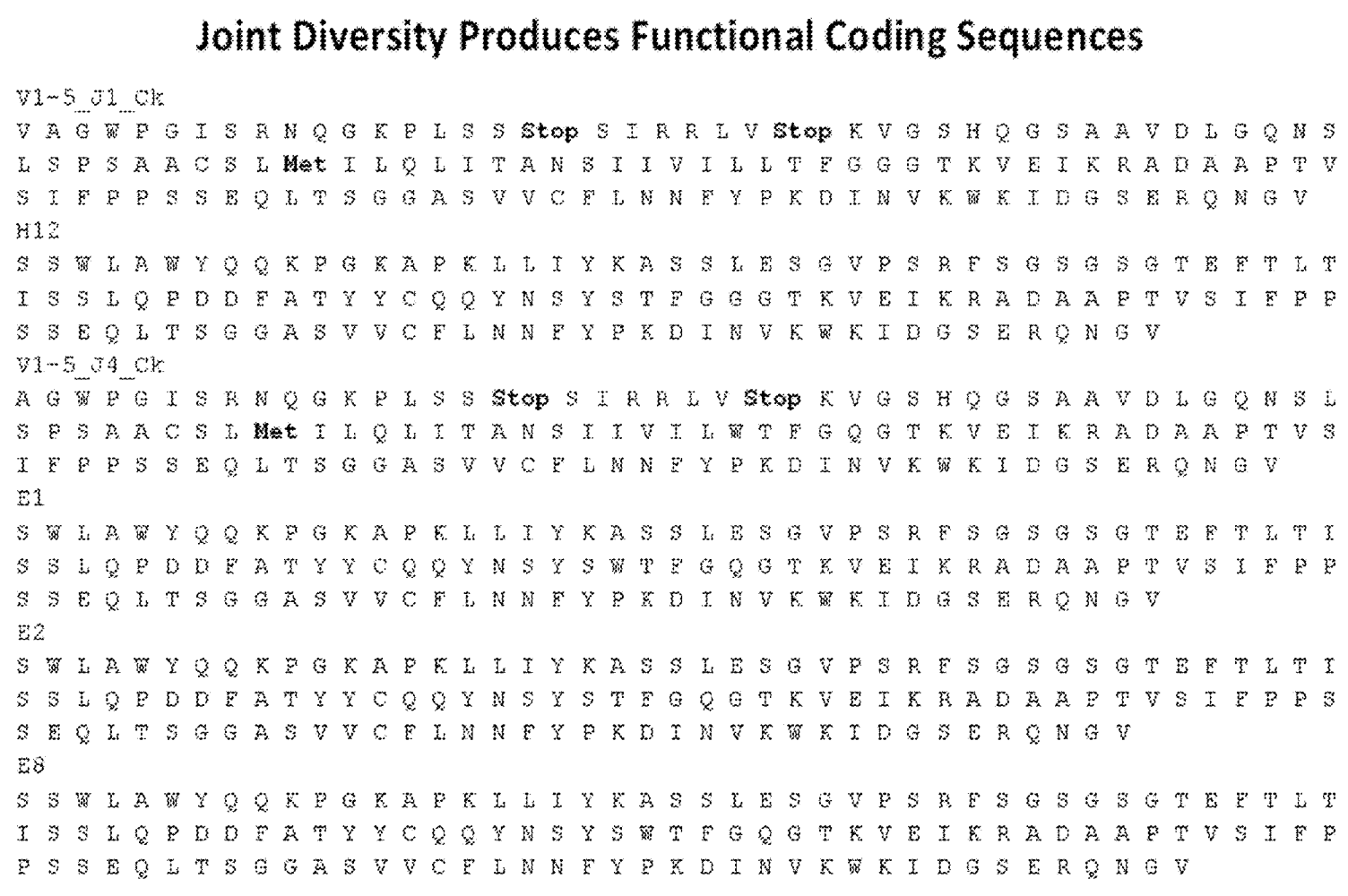

FIG. 41 shows an analysis of kappa mRNA from mice B-cells bearing rearranged VJ, the VJ having been rearranged from human germline kappa V1-8 and J1, and demonstrates that both that productive VJ rearrangement and somatic hypermutation can be obtained, the latter as seen from the changes in antibodies encoded by mRNA with respect to the germline sequences. The same is displayed for V1-6 and J1 in FIG. 42. Importantly, the recombination eliminates stop codons that are encoded by the combination of (unmutated) human germline gene segments, thereby allowing for antibody-encoding mRNA sequences. FIG. 43 demonstrates that inserted human kappa V1-5 J1 and V1-5 J4 can produce functional coding sequences in vivo and junctional diversity.

Example 7

Figure 44:
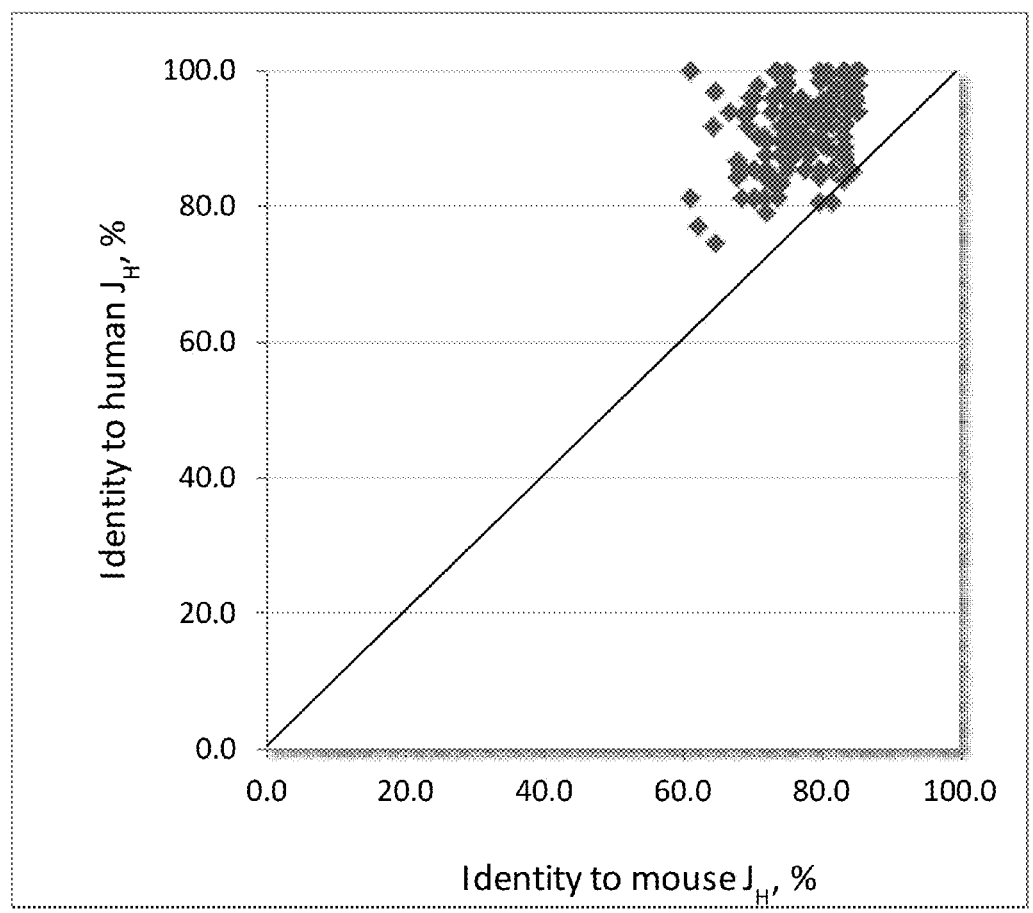
FIG. 44 illustrates a plot of identity of $J_H$ gene segment use a 5'-RACE Cμ-specific library generated from the splenic B lymphocytes of transgenic mice according to the invention in which endogenous gene segment use has been inactivated by inversion

Inactivation of Use of Endogenous IGHV Gene Segments for Expressed Rearranged Heavy Chain by Inversion Introduction A 5'-RACE Cμ-specific library was generated from the splenic B lymphocytes of transgenic mice, denoted S1 mice. These mice comprise transgenic heavy chain loci, each locus containing the six most 3' functional human $V_H$ gene segments ($V_H$2-5, 7-4-1, 4-4, 1-3, 1-2, 6-1), and all the human D and $J_H$ gene segments (comprising functional human D gene segments D1-1, 2-2, 3-3, 4-4, 5-5, 6-6, 1-7, 2-8, 3-9, 5-12, 6-13, 2-15, 3-16, 4-17, 6-19, 1-20, 2-21, 3-22, 6-25, 1-26 and 7-27; and functional human J gene segments J1, J2, J3, J4, J5 and J6) inserted into the endogenous heavy chain locus between endogenous IGHJ4 and Eμ (mouse chromosome 12: between coordinates 114666435 and 114666436). The human DNA was obtained from a bacterial artificial chromosome (BAC) containing the sequence of human chromosome 14 from coordinate 106328951 to coordinate 106494908. Further details on the construction of transgenic antibody loci using sRMCE is given elsewhere herein and in WO2011004192 (which is incorporated herein by reference). 4×96-well plates of clones were randomly picked for sequencing to determine the usage of the gene segments. All detected immunoglobulin heavy chains were rearranged from mouse $V_H$ or human $V_H$ with human D-$J_H$. No mouse D and $J_H$ segments were detected in rearranged products (FIG. 44).

This result indicates that insertion of human $V_H$-D-$J_H$ gene segments into an endogenous locus between the last endogenous J region (in this case, $J_H$4) and the Eμ enhancer effectively inactivates the use of endogenous D and $J_H$ gene segments for expressed rearranged immunoglobulin heavy chains.

Figure 45:
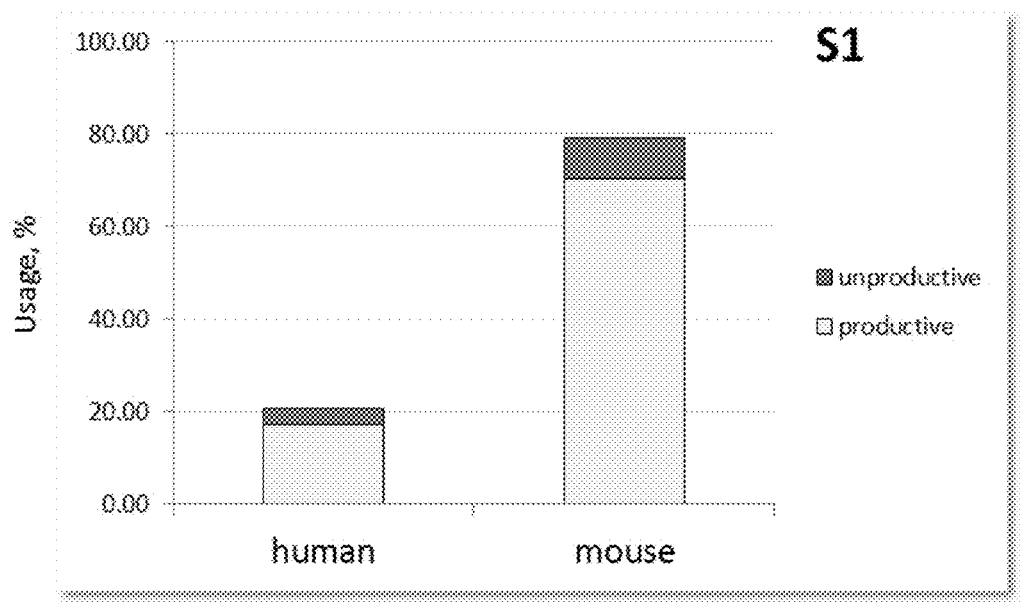
FIG. 45 illustrates the ratio of mouse $V_H$ to human $V_H$ usage as determined from antibody sequences from splenic B lymphocytes of transgenic mice according to the invention in which endogenous gene segment use has been inactivated by inversion

The ratio of mouse $V_H$ to human $V_H$ usage was around 3 to 1 (FIG. 45). To completely eliminate mouse $V_H$ use for antibody generation, the endogenous mouse $V_H$-D-$J_H$ was inverted and moved to a distant region of the same chromosome. The rearrangement of mouse $V_H$s to human D-$J_H$ segments was totally blocked by effects of inversion and distance from the heavy chain locus.

The inversion strategy included three steps: (a) targeting of an inversion cassette, (b) inversion of endogenous VDJ and (c) excision of markers (FIG. 46).

(a) Targeting of the Inversion Cassette:

The inversion cassette consists of four components: a CAGGS promoter-driven puromycin-resistant-delta-thymidine kinase (puroΔtk) gene, a 5' HPRT gene segment under the PGK promoter control, a loxP site between them and inversely oriented to another loxP site already in the heavy chain locus, and two flanking piggyback LTRs (PB3'LTRs).

Figure 46:
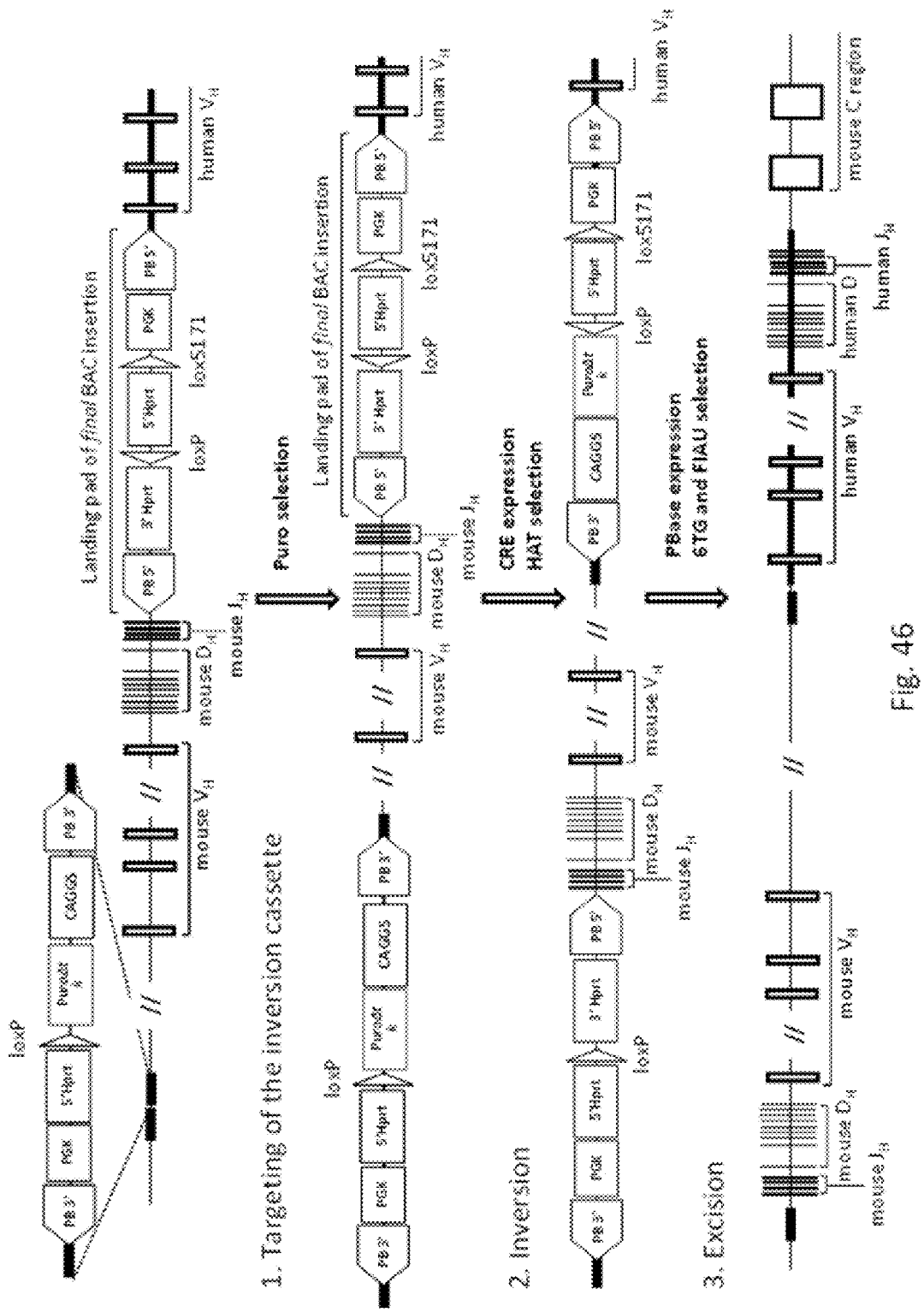
FIG. 46 illustrates inversion strategy schematic

The inversion targeting cassette was inserted to a region that is 5' and distant to the endogenous IGH locus at chromosome 12 as shown in FIG. 46. The targeted ES clones were identified and confirmed by PCR.

(b) Inversion:

Following the insertion, transient expression of cre from a transfected plasmid resulted in inversion of a section of chromosome 12 fragment including the endogenous $V_H$-D-$J_H$ locus and intervening sequences through recombination of two inverted loxP sites, ie, those in the inversion cassette and the landing pad for the BAC insertion respectively. The invertants were selected by HAT and confirmed by junction PCRs cross the two recombed loxP sites.

(c) Excision of Markers:

The inversion rearranged the relative orientation of the PB3'LTRs from the inversion cassette and PB5'LTR from the landing pad to generate two piggyBac transposon structures flanking the inverted region. With transient expression of piggyBac transposase (PBase), these two transposons were excised from the chromosome (and thus the mouse cell genome). The cured ES clones were selected by 1-(-2-deoxy-2-fluoro-1-b-D-arabinofuranosyl)-5-iodouracil (FIAU) and 6TG, and confirmed by junction PCRs cross the excised regions.

Methods

Tissue Culture:

The procedures for ES cell culture, electroporation and drug selection have been described previously (Ramirez-Solis, R., A. C. Davis, and A. Bradley. 1993. Gene targeting in mouse embryonic stem cells. Methods Enzymol. 225: 855-878).

Figure 47:
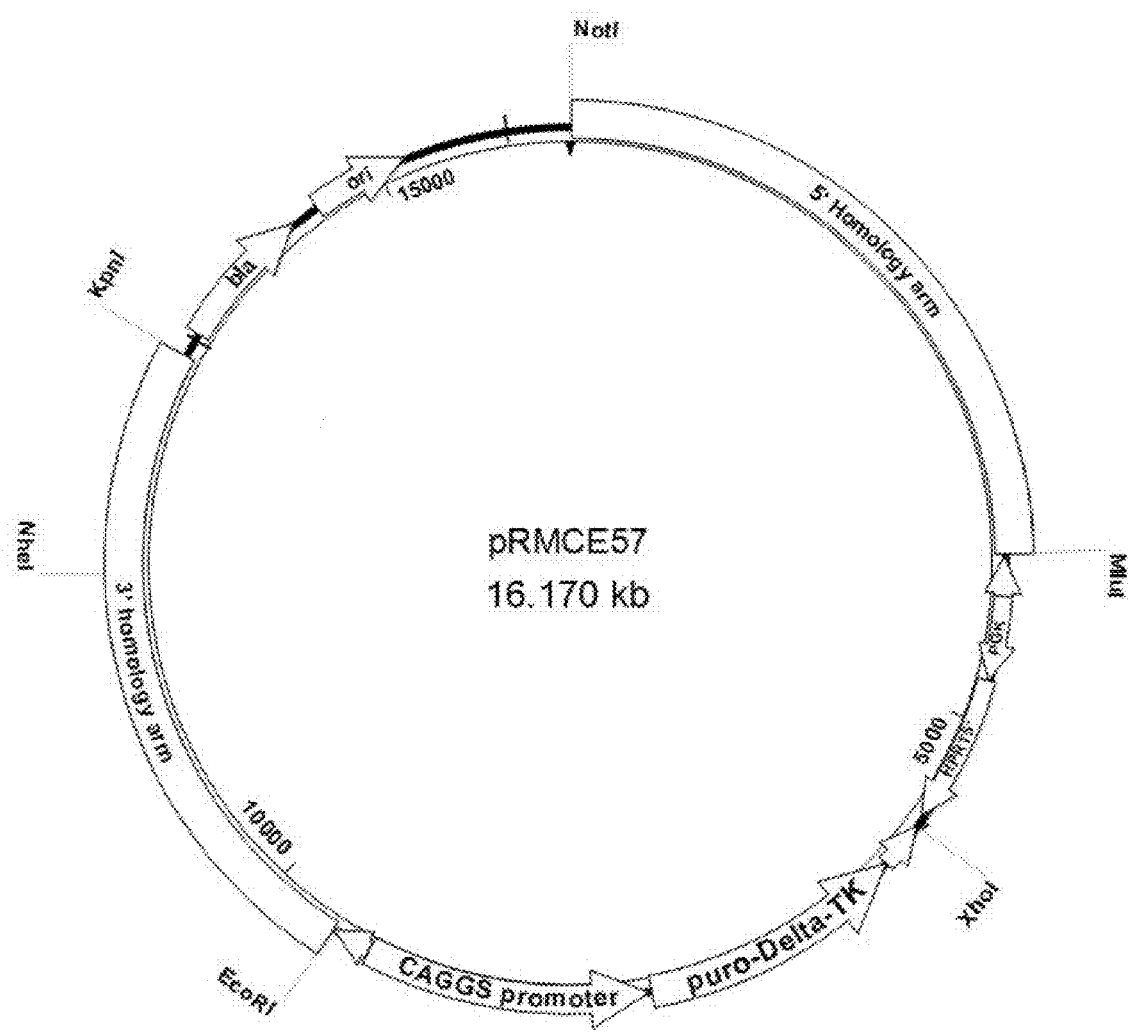
FIG. 47 illustrates targeting construct R57 for inversion

Targeting of the Locus for Inversion:

Briefly, S1 cell line (S1.11.1) was cultured in M15 medium (Knockout™ DMEM supplemented with 15% fetal bovine serum, 2 mM glutamine, antibiotics, and 0.1 mM 2-mercaptoethonal). Targeting construct R57 (FIG. 47) was linearized outside the region of homology by NotI. A total of 20 μg of the linearized construct was electroporated into S1 cell lines (AB2.1-derived) with a Bio-Rad® Gene Pulser™, and 107 cells were plated onto three 90-mm-diameter SNL76/7 feeder plates containing M15 medium. At 24 h after electroporation, M15 containing puromycin (3 μg of the active ingredient per ml) was added to each 90-mm-diameter plate, and the cells were maintained under selection for 9 days. 96 puromycin-resistant clones were then picked and expanded in 96-well plates. The targeting events were identified by long-range PCR.

Cre-loxP Mediated Inversion:

12 positive clones were pooled together and cultured in a E-well tissue culture plate with M15 medium. The cells were transfected with 10 μg of pCAGGS-Cre plasmid for the inversion of mouse endogenous locus and then plated onto three 90-mm-diameter SNL76/7 feeder plates containing M15 medium. At 24 h after electroporation, M15 containing 1×HAT (hypoxanthine-aminopterin-thymidine) was added to each 90-mm-diameter plate, and the cells were maintained under selection for 7 days and then treated with 1×HT (hypoxanthine-thymidine) for 2 days. 48 HAT resistant colonies were picked and genotyped by PCR amplification of the junctions after Cre-loxP mediated inversion.

HyPBase-Mediated Marker Excision:

12 positive clones were pooled together and cultured in 6-well tissue culture plate using M15 medium. The cells were transfected with 5 pg of HyPBase plasmid to activate the PB transposon LTRs flanking two selection markers (Hprt-mini gene and PGK-puroΔtk gene) and plated onto one 90-mm-diameter SNL76/7 feeder plates containing M15 medium. At 72 h after electroporation, a serial dilution of the cells was then plated onto three 90-mm-diameter SNL76/7 feeder plates containing M15 supplemented with 1-(-2-deoxy-2-fluoro-1-b-D-arabinofuranosyl)-5-iodouracil (FIAU). Cells were maintained under selection for 10 days, and FIAU-resistant colonies were counted, picked, and expanded in 96-well plates. Positive clones were identified by PCR amplification of the junctions after excision of the selection markers. Positive clones were then expanded for blastocyst microinjection.

Generation of Chimera and Breeding:

Mouse chimaeras were generated by microinjection of ES cells into C57/BL6 blastocysts and transferred into pseudo-pregnant recipients. Male chimaeras were test-crossed with C57/BL6 mice. Agouti F1 offspring were genotyped by S1 3' junction PCR. Test-cross positive heterozygotes were further intercrossed to generate homozygotes.

Determination of VH-D-JH Usage by Rapid Amplification of 5'-cDNA Ends (5' RACE) PCR:

Total RNA was extracted from the spleen of S1inv1 mouse (KMSF30.1d) with TRIzol® Reagent (Invitrogen™, Life Technologies Ltd™) and treated with DNase I. Rapid amplification of 5'-cDNA ends (5' RACE) PCR was performed using 573' RACE kit (2nd Generation, Roche) following the protocol supplied by the manufacturer. The first-strand cDNA was synthesised using primer E1554 (5'-ATGACTTCAGTGTTGTTCTGGTAG-3'; SEQ ID No 25) which is located at the mouse endogenous Cμ region. The synthesised first cDNA strand was purified using High Pure PCR Product Purification Kit (Roche). Poly(A) tail was added following the protocol supplied with the 5'13' RACE kit (2nd Generation, Roche). The 5' end of the $V_H$-D-$J_H$ rearranged transcript was amplified by nested PCR with forward primers Oligo dT, which is included in the kit, and nested Cμ-specific reverse primers E1555 (5'-CACCAGAT-TCTTATCAGAC-3'; SEQ ID No 26). Following reaction, the 5' RACE PCR product was checked on a 1% agarose gel and purified using QIAquick® Gel Extraction Kit (QIA-GEN) as the protocol supplied with the kit, then cloned into pDrive vector using QIAGEN PCR Cloning Kit (QIAGEN) for sequencing analysis.

Results

Figure 48:
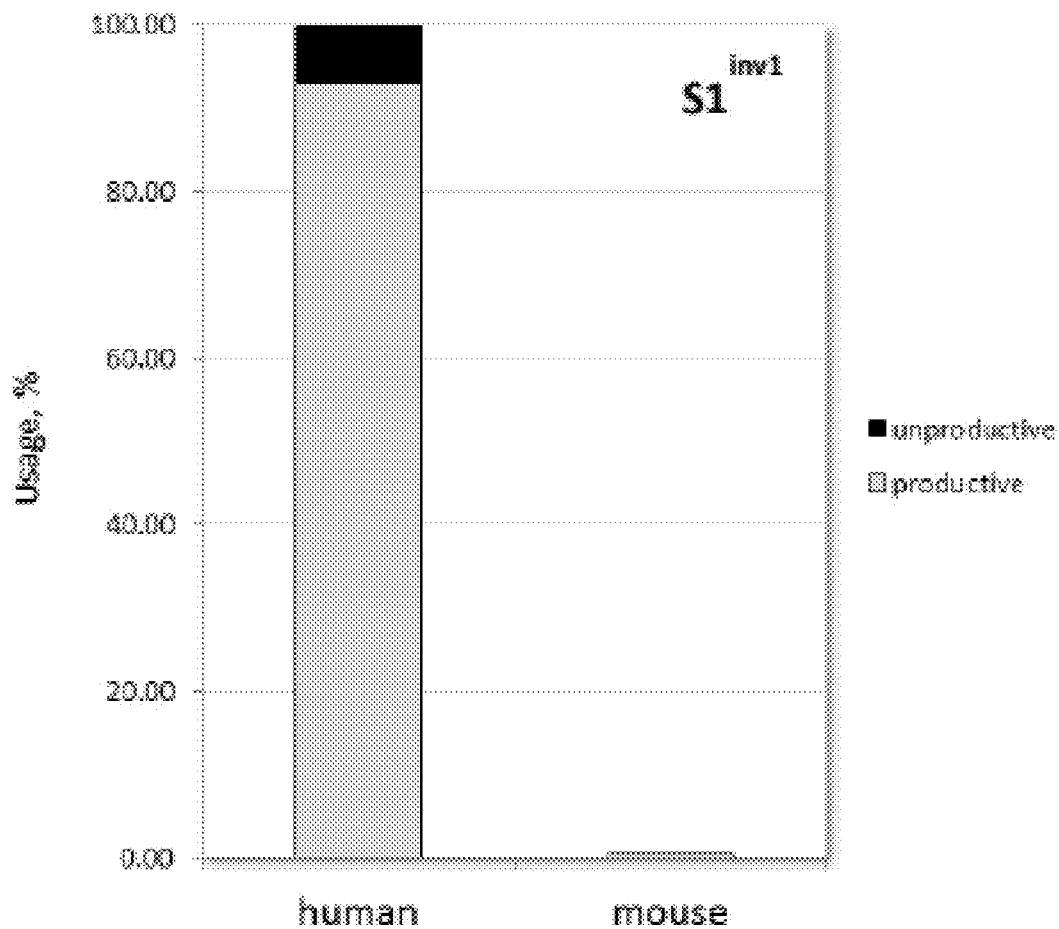
FIG. 48 illustrates sequence analysis from a Cμ-specific 5'-RACE library of splenic B lymphocytes of S1$^{inv1}$ (one human IGH BAC (ie, multiple human VH, all functional human D and JH) with an inverted endogenous IGH locus) mouse shows that practically all the transcripts came from rearranged human $V_H$-D-$J_H$ gene segments

The sequence analysis from a Cμ-specific 5'-RACE library of splenic B lymphocytes of S1$^{inv1}$ (one human IGH BAC (ie, multiple human VH, all functional human D and JH) with an inverted endogenous IGH locus version 1) mouse shows that practically all the transcripts came from rearranged human $V_H$-D-$J_H$ gene segments (FIG. 48). Mouse $V_H$ usage was rarely detected (0.4%), and no mouse D and $J_H$ usage was detected. Human $V_H$ usage was 99.6% and only human D and $J_H$ were used; it was hypothesized that the rare mouse $V_H$ usage was due to trans-switching with another chromosome and not due to use of moue $V_H$ from the inverted sequences. The inversion resulted in complete inactivation of the endogenous $V_H$ use.

This Result Indicates that Inversion is an Effective Way to Inactivate the Rearrangement of Endogenous $V_H$ Gene Segments.

Figure 49:
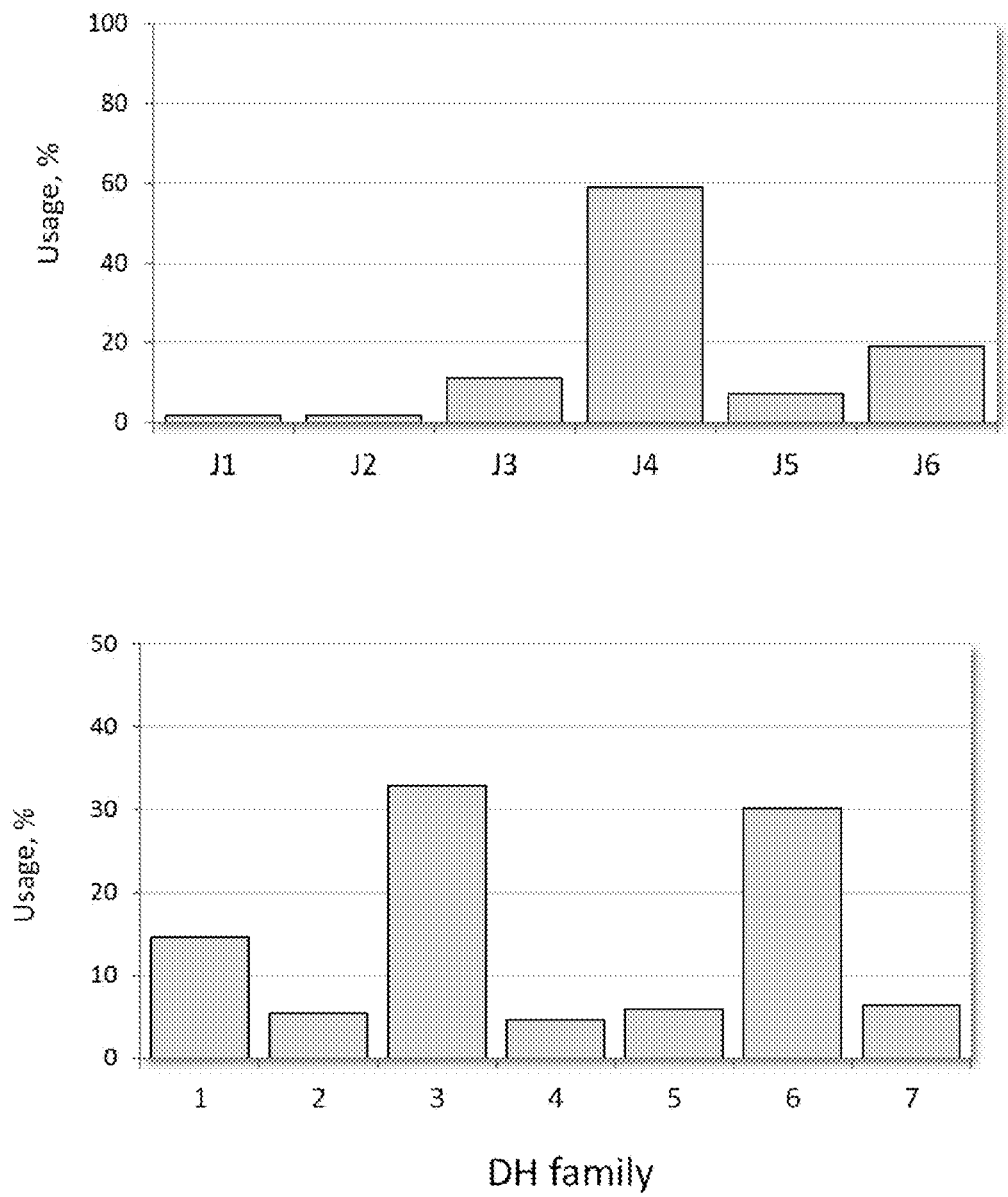
FIG. 49 illustrates that the S1$^{inv1}$ mouse shows a similar usage of both D and $J_H$ gene segments to human

The S1$^{inv1}$ mouse also shows a similar usage of both D and $J_H$ gene segments to human (FIG. 49) (Link, J M et al. Mol. Immunol. 2005. 42, 943-955). Thus, a mouse was produced that comprises a transgenic heavy chain locus that expresses heavy chains comprising human variable regions, but no mouse variable regions, and furthermore the human variable regions demonstrated a normal, human sequence distribution corresponding to human D and J usage observed in humans.

Example 8

Inactivation of Use of Endogenous IGHV Gene Segments for Expressed Rearranged Heavy Chain by Insertion of Human IgH Genomic DNA Introduction Insertion of human BACs with $V_H$-D-$J_H$ gene segments into an endogenous mouse heavy chain locus between $J_H4$ and Eµ in chromosome 12 allows human $V_H$-D-$J_H$ gene segments to effectively use mouse Eµ and 3' enhancers and rearrange to generate chimeric antibody with human variable region and mouse constant region. Meanwhile, the endogenous $V_H$-D-$J_H$ gene segments are pushed away from endogenous enhancers and constant regions. This distance effect results in inactivation of mouse D and $J_H$ use for expressed rearranged antibody products. As the distance increases by stepwise BAC insertion, it is expected that the mouse VH usage would be significantly reduced.

Results

Insertion of human DNA from a $1^{st}$ human BAC (BAC comprising a the sequence of mouse Chromosome 14 from coordinate 106328951 to coordinate 106494908; containing six most 3' functional $V_H$ gene segments ($V_H$2-5, 7-4-1, 4-4, 1-3, 1-2, 6-1), and all the human D and $J_H$ gene segments) into the heavy chain endogenous locus of a AB2.1 ES cell genome between endogenous IGHJ4 and Eµ (at mouse chromosome 12: between coordinates 114666435 and 114666436) effectively inactivates the use of endogenous D and $J_H$ gene segments for expressed rearranged immunoglobulin heavy chain (FIG. 44). The rearranged transcripts with mouse $V_H$ gene segments are reduced in the resulting S1 mouse. The proportion of transcripts using mouse $V_H$ is around 75% of all observed sequences (FIG. 45).

Figure 24:
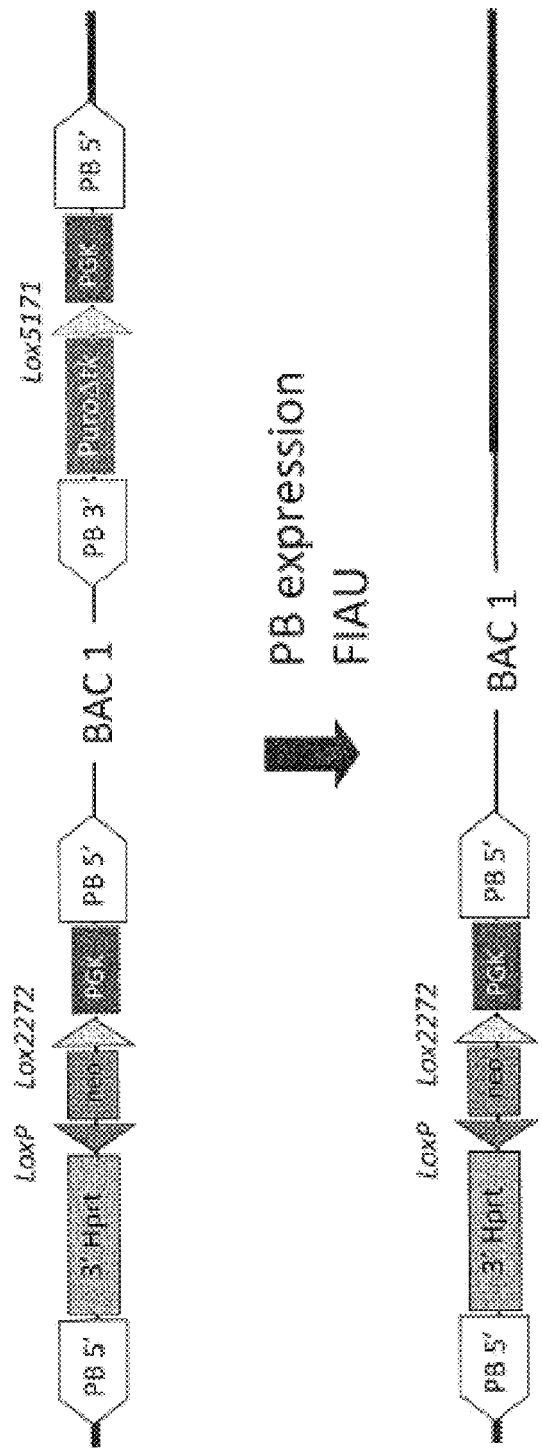
Figure 50:
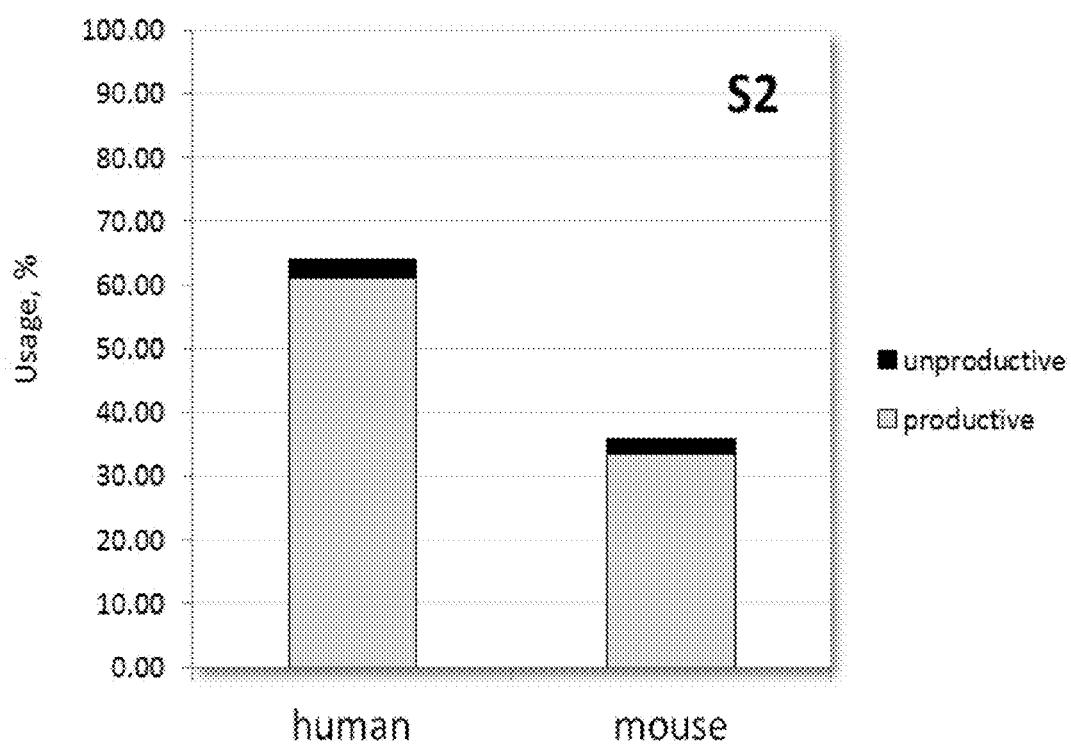
FIG. 50 illustrates that mouse $V_H$ usage is further significantly reduced following insertion of the $2^{nd}$ human BAC into the endogenous heavy chain locus

Following the $1^{st}$ BAC DNA insertion, human DNA from a $2^{nd}$ human BAC (Chr14: 106494909-106601551) (BAC comprising a the sequence of mouse Chromosome 14 from coordinate 106494909 to coordinate 106601551; containing 5 more functional VH gene segments ($V_H$3-13, 3-11, 3-9, 1-8, 3-7)) was inserted into the landing pad left behind after curing following the $1^{st}$ BAC insertion (see, eg, FIG. 24). The mouse $V_H$ usage is further significantly reduced following this insertion of the $2^{nd}$ BAC into the locus. The proportion of transcripts using mouse VH was further reduced to 35% of all observed sequences (FIG. 50).

This result indicate that the endogenous $V_H$-D-$J_H$ gene segments could be inactivated (ie, not used for expressed rearranged heavy chains) through insertion of human VDJ sequences from one or more BACs. As the distance increases by stepwise BAC insertion, it is expected that the mouse VH usage would be significantly reduced.

Example 9

Normal Class Switch and Hypermutation in Transgenic Mice of the Invention

Introduction

The B cell arm of the immune system has evolved to produce high affinity, antigen-specific antibodies in response to antigenic challenge. Antibodies are generated in B lymphocytes by a process of gene rearrangement in which variable (V), diversity (D; for the IGH locus) and joining (J) gene segments are recombined, transcribed and spliced to a Cµ (for IGH) or a CK or Cλ (for IGL) constant region gene segment to form an IgM antibody. Depending on the stage of B cell development, IgM is either located on the cell surface or secreted. The recombination process generates a primary antibody repertoire with sufficient germ line diversity to bind a wide range of antigens. However, it is usually not large enough to provide the high affinity antibodies that are required for an effective immune response to an antigen such as an infectious agent. Therefore, the immune system adopts a two-stage diversification process to increase diversity further. When challenged with antigens, B cells undergo selection and maturation by a process called somatic mutation. B cells expressing antibodies which bind to antigen undergo multiple rounds of diversification, clonal expansion and antigen selection in the germinal centres (GCs) of the secondary lymphoid organs. During this process, the rearranged variable regions of the immunoglobulin genes acquire somatic hypermutation through nucleotide substitution, addition or deletion. This stepwise process creates a secondary repertoire from the weak binders selected originally from the primary repertoire and combines rapid proliferation of antigen-reactive B cells with intense selection for quality of binding, eventually giving rise to high affinity antibodies with broad epitope coverage. During this process, antibodies undergo class switching in which the Cµ constant region is replaced by Cγ, Cα or Cε to produce respectively IgG, A or E classes of antibody with different effector functions.

Insertion of $1^{st}$ human BAC (Chr14: 106328951-106494908) containing six most 3' functional $V_H$ gene segments ($V_H$2-5, 7-4-1, 4-4, 1-3, 1-2, 6-1), and all the D and $J_H$ gene segments into the locus between endogenous IGHJ4 and Eµ (Chr12: 114666435 and 114666436) produces transgenic mice that generate chimeric immunoglobulin heavy chains containing human variable and mouse constant regions. This result demonstrates that human immunoglobulin gene segments are able to be rearranged and expressed in mice. Here, RT-PCR experiments and sequence analysis were performed to further demonstrate that immunized transgenic mice have proper class switch and hypermutation for generated antibodies.

Methods

RT-PCR and Sequence Analysis:

Wild type or S1 chimera mice at 6-8 weeks of age were primed by intraperitoneal injection of $10^6$ sheep RBCs suspended in phosphate buffer saline (PBS). The immunized mice were boosted twice with the same amount of sheep RBCs two and four weeks after priming. Four days after the last boost, peripheral blood cells were collected from the immunized mice. Total RNA was isolated from peripheral blood cells with TRIzol® reagent (Invitrogen™) and treated with DNase I. Reverse transcription polymerase chain reaction (RT-PCR) was performed using SuperScript® III First-Strand Synthesis System (Invitrogen™) following the protocol supplied by the manufacturer. The 1st strand cDNA was synthesized with the specific Cγ primers (Cγ1, Cγ2a, Cγ2b), following by PCR with specific human V primers (VH1-2,3, VH4-4, VH6-1) and Cγ primers (Table 2). Following reaction, the RT-PCR product was checked on a 1% agarose gel and purified using QIAquick® Gel Extraction Kit (QIAGEN) as the protocol supplied with the kit, then cloned into pDrive vector using QIAGEN PCR Cloning Kit (QIAGEN) for sequencing analysis.

TABLE 2

| | | |
|---|---|---|
| ELP1352_Cγ1 | 5'-AGAGCGGCCGCTGGGCAACGTTGCAGGTGACGGTC-3' | SEQ ID No 27 |
| ELP1353_Cγ2b | 5'-AGAGCGGCCGCTTTGTCCACCGTGGTGCTGCTGG-3' | SEQ ID No 28 |
| ELP1354_Cγ2a | 5'-AGAGCGGCCGCACATTGCAGGTGATGGACTGGC-3' | SEQ ID No 29 |
| ELP1356_VH4-4 | 5'-AGGACGCGTGAAACACCTGTGGTTCTTCCTCCTGC-3' | SEQ ID No 30 |
| ELP1357_VH1-2,3 | 5'-AGGACGCGTCACCATGGACTGGACCTGGAGGAT-3' | SEQ ID No 31 |
| ELP1358_VH6-1 | 5'-AGGACGCGTATGTCTGTCTCCTTCCTCATCTTCC-3' | SEQ ID No 32 |

Results

Figure 51:
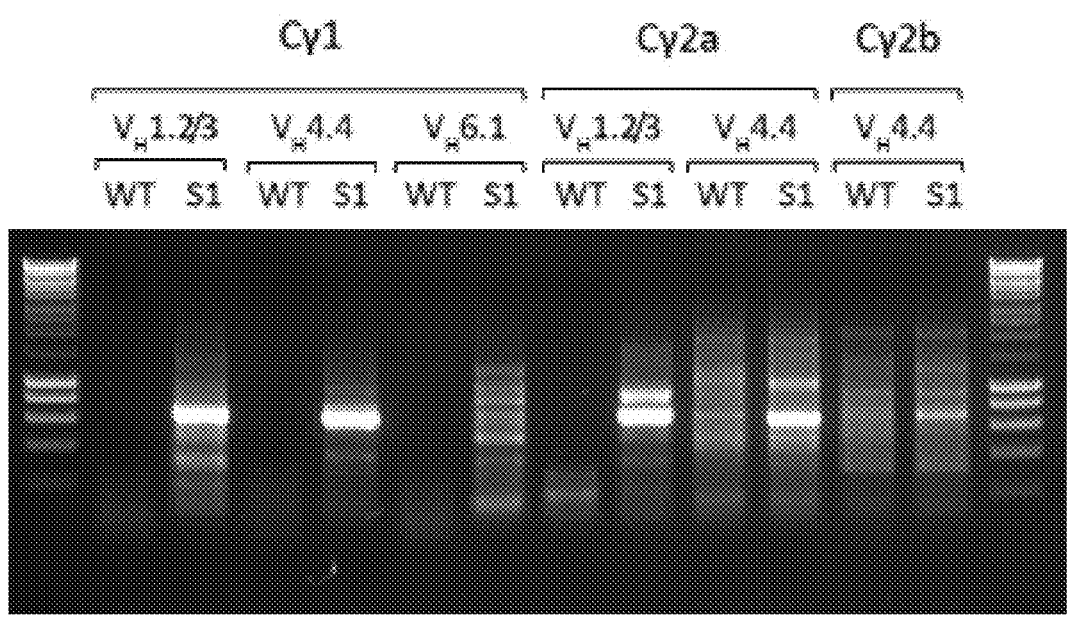
FIG. 51 illustrates a gel showing that normal class-switching (to IgG-type) was observed in transcripts from mice of the invention. The rearranged transcripts were detected using RT-PCR with human VH-specific and mouse Cγ-specific primers for amplification from peripheral blood cells of immunized transgenic mice
Figure 52:
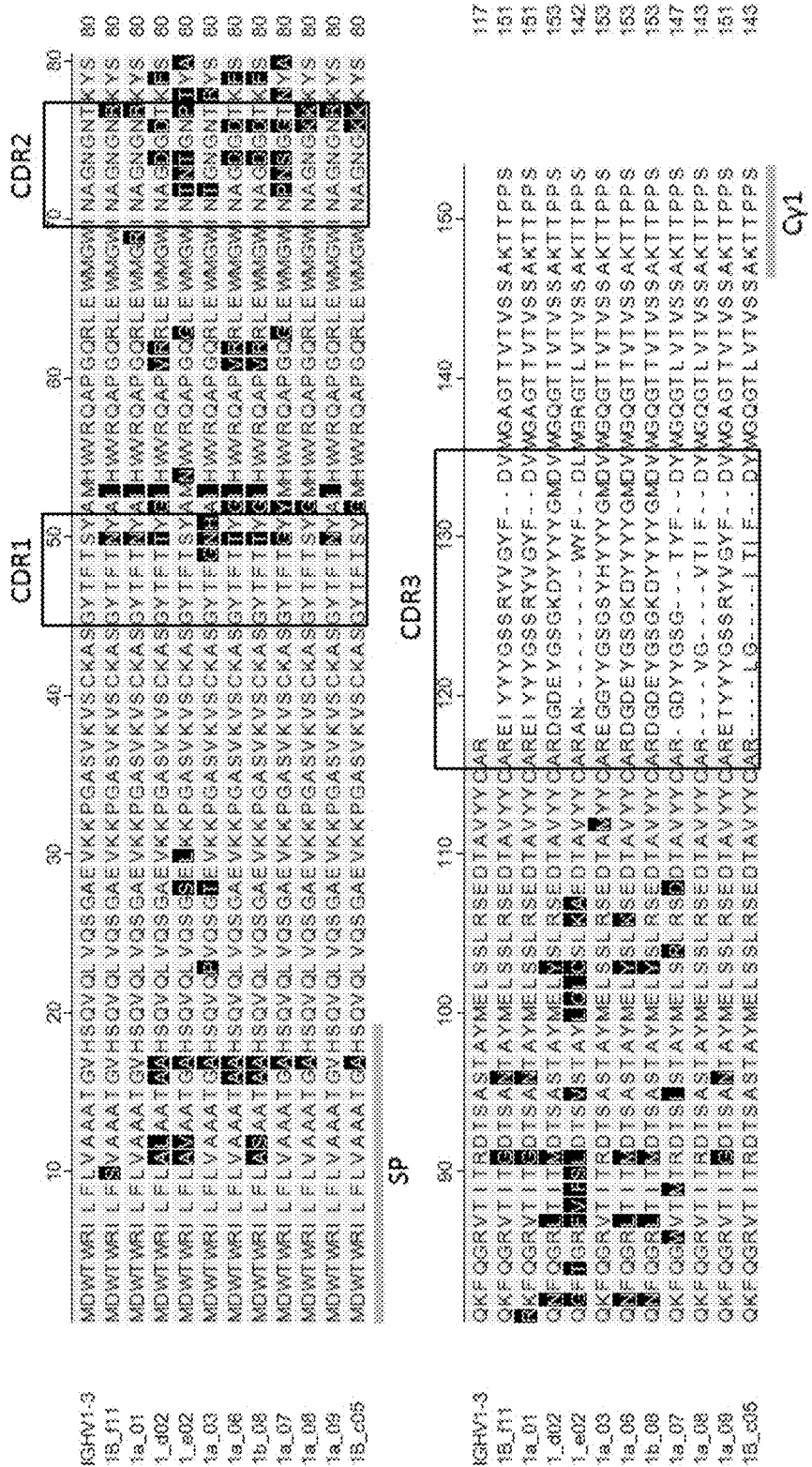
FIG. 52 illustrates sequence analysis amplified fragments demonstrate Hypermutation occurred within the human variable regions of these IGγ chains from mice of the invention (SEQ ID NOs: 121-132, respectively).

The rearranged transcripts were detected using RT-PCR with human VH-specific and mouse Cγ-specific primers for amplification from peripheral blood cells of immunized transgenic mice (FIG. 51). Further sequence analysis of these amplified fragments demonstrated hypermutation happened within the human variable regions of these IGγ chains (FIG. 52). These results indicate that loci of the invention comprising insertion of human IGH BAC containing $V_H$, D and $J_H$ gene segments into the locus between endogenous IGHJ4 and Eμ regions has normal class switching and hypermutation functionality (IgM to IgG) following antigen challenge.

Example 10

Normal B Cell Compartments in Transgenic Mice of the Invention

Introduction

In mice, about $2 \times 10^7$ bone marrow immature B cells are produced daily. Among them, only 10-20% of these cells survive to exit the bone marrow and enter the spleen. The immature splenic B cell population is divided into two distinct subsets: transitional 1 (T1) and transitional 2 (T2) B cells. In vivo experiments indicate that T1 cells give rise to T2 cells, whereas T2 cells can further differentiate into mature (M) B cells. In contrast to immature B cells (3-4 days old), mature B cells are long-lived (15-20 weeks old) and are ready to respond to antigens (Pillai S et al; Immunol. Reviews. 2004. 197: 206-218). Thus, the component of mature B cell population is directly linked to the efficiency of humoral immune response.

The T1, T2 and M cell populations can be categorized by their cell surface IgM and IgD levels. A normal phenotype of splenic B cell compartment is required to mount a robust immune response.

Methods

Flow Cytometric Analysis of Mature B Lymphocytes:

To obtain a single cell suspension from spleen, the spleens of mice listed below were gently passaged through a 30 μm cell strainer. Single cells were resuspended in PBS supplemented with 3% heat inactivated foetal calf serum (FCS; Gibco®). The following antibodies were used for staining:

Antibody against B220/CD45R conjugated with allophycocyanin (APC) (eBioscience, clone RA3-6B2), antibody against IgD receptor conjugated with phycoerythrin (PE) (eBioscience, clone 11-26) and IgM receptor conjugated with fluorescein isothiocyanate (FITC) (eBioscience, clone 11/41).

$5 \times 10^6$ cells were used for each staining. To each vial containing splenocytes a cocktail of antibodies was added consisting of: IgD (PE) (eBioscience, clone 11-26), IgM (FITC) and B220/CD45R (APC). Cells were incubated at 6° C. for 15 minutes, washed to remove excess of unbound antibodies and analysed using a fluorescence-activated cell sorting (FACS) analyser from Miltenyi Biotech. B-cells were gated as $B220^+IgM^+IgD^-$ for T1 population, $B220^+IgM^+IgD^+$ for T2 population and $B220^+IgM^-IgD^+$ for M population. Percentage of cells was calculated using gating system.

Results

Four different genotypes of mice were generated:—
Wild type (WT);
A transgenic mouse homozygous for a heavy chain transgene comprising insertion of the $1^{st}$ BAC human DNA noted above in which there are 6 human VH, all functional human D and JH gene segments (S1/S1);
A transgenic mouse homozygous for a heavy chain transgene comprising insertion of a human VH, all functional human D and JH gene segments (H1/H1); and
A transgenic mouse homozygous for a kappa chain transgene comprising insertion of 6 functional human Vκ and 5 functional Jκ gene segments (K1/K1).

Figure 53:
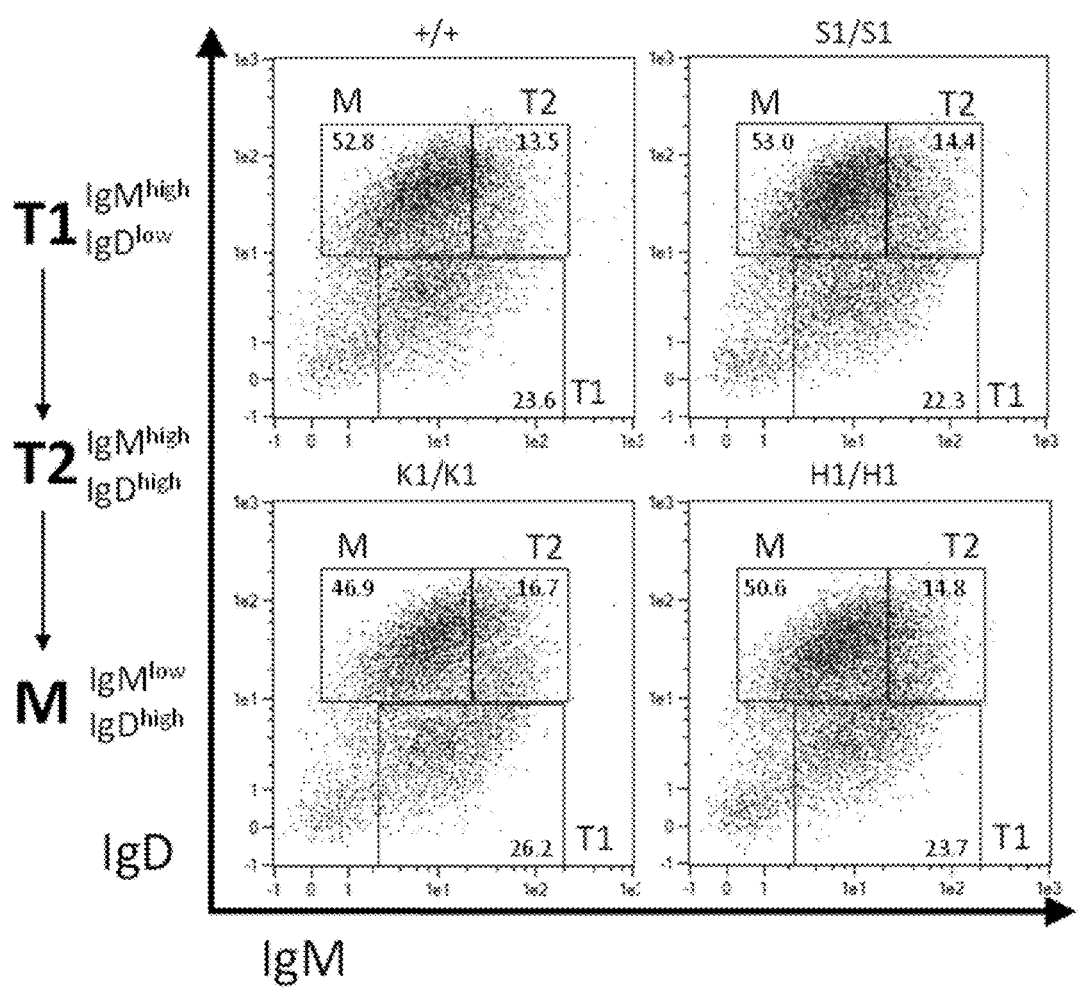
FIG. 53 illustrates Flow cytometric analysis showing normal B-cell compartments in transgenic mice of the invention

Spleens from these naïve mice were collected and analysed for their B cell compartments. The number and percentages of T1, T2 and M cells among those mice are similar (FIG. 53), indicating that genetic manipulation of endogenous IG loci in transgenic mice according to the invention do not compromise their B cell development. These data help to establish that animals according to the invention provide a robust platform for antibody discovery.

As explained in Example 16 below, further analysis was performed on S1 mice in which endogenous heavy chain expression has been inactivated (S1F mice in which there is inactivation by inversion as herein described). As explained, normal splenic and bone marrow compartments are seen in such mice of the invention (ie, equivalent to the compartments of mice expressing only mouse antibody chains).

Example 11

Normal IgH Isotypes & Serum Levels in Transgenic Animals of the Invention

Figure 55A:
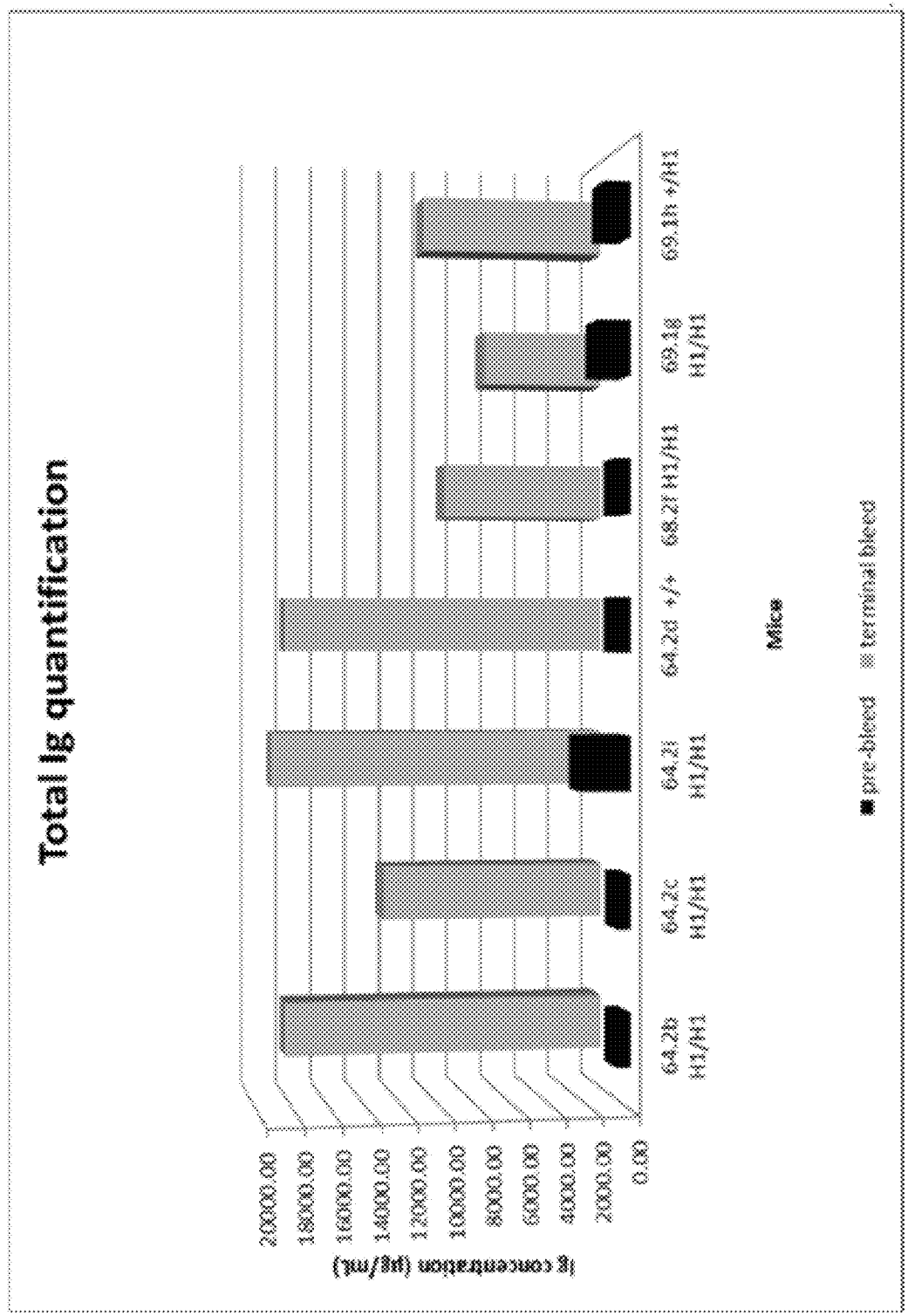
Figure 55B:
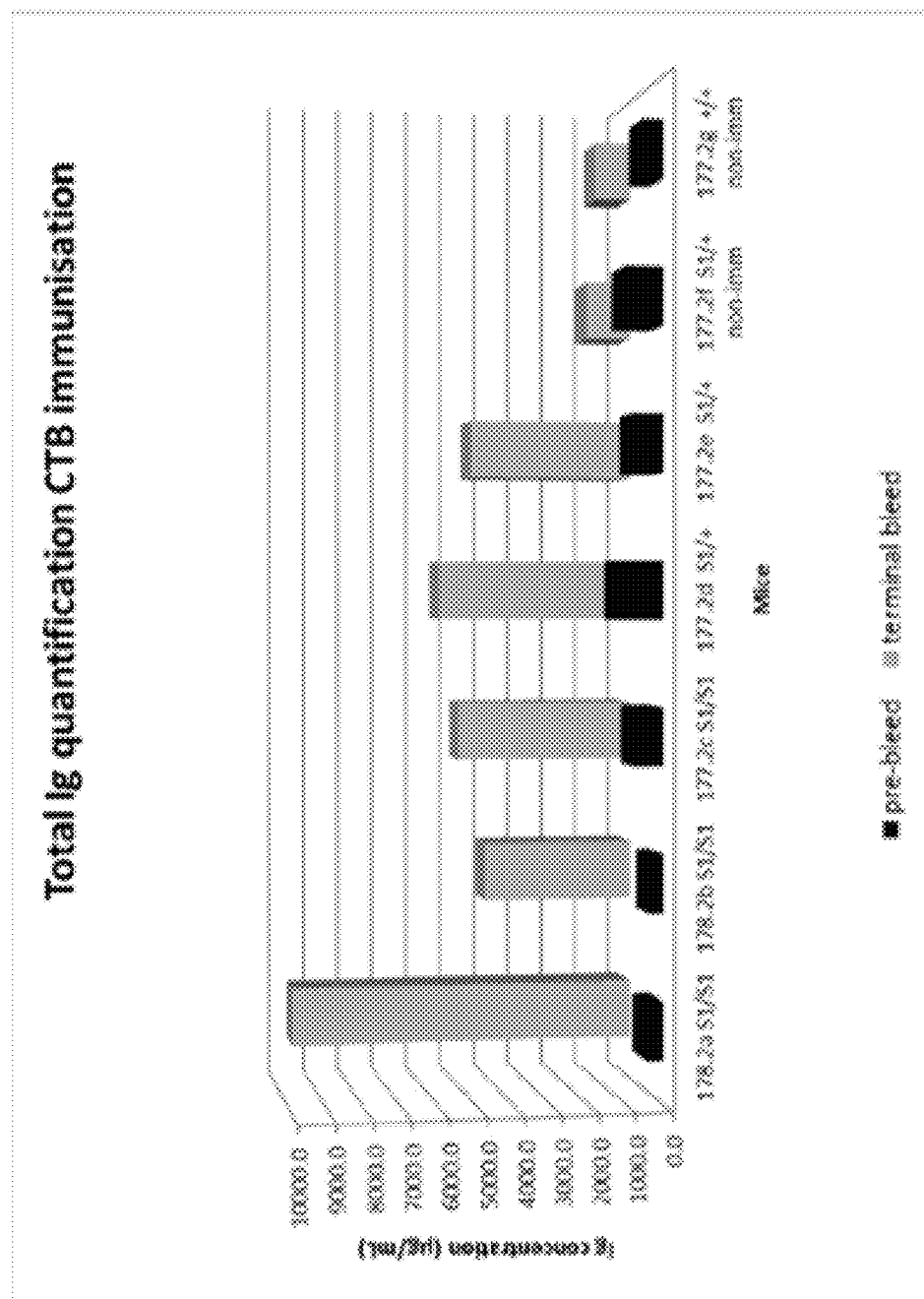

Transgenic mice (H1) carrying all human JH, all human DH and human Vh2-5 under control of a rat switch region or mice (S1) carrying all human JH, all human DH and human Vh2-5, Vh7-41, Vh4-4, Vh1-3, Vh1-2 and Vh6-1 under control of a mouse switch region were immunised with 100 μg Cholera Toxin B subunit (CTB; Sigma-Aldrich® C9903) emulsified in Complete Freund's Adjuvant CFA; Sigma-Aldrich® F 5881). At least three animals were injected sc or ip and then boosted with 25 μg antigen in Incomplete Freund's Adjuvant (IFA; Sigma-Aldrich® F 5506) at (i) 14 days and 21 days or (ii) 28 days after priming. Blood was taken before priming at day "−1" (pre-bleeds) and on the day the spleens were taken (usually 4d after last boost). Serum was analysed by ELISA using an antigen independent assessment of Ig isotypes. This assay detects total serum antibodies of all species. Specific detection for mouse IgG1, IgG2a, IgG2b and IgM was used ((Anti-mouse IgG1 HRP AbD Serotec STAR132P, Anti-mouse IgG2a HRP AbD Serotec STAR133P, Anti-mouse IgG2b HRP AbD Serotec STAR134P, Anti-mouse IgM HRP Abcam® ab97230) and concentrations were read off a standard curve produced for each isotype using polyclonal isotype controls (IgG1, Kappa murine myeloma Sigma-Aldrich® M9269, IgG2a, Kappa murine myeloma Sigma-Aldrich® M9144, IgG2b, Kappa from murine myeloma Sigma-Aldrich® M8894, IgM, Kappa from murine myeloma Sigma-Aldrich® M3795). Results (FIGS. 54 & 55 for H1 homozygous and S1 homozygous and heterozygous mice) showed that even with these relatively short immunisation regimes mice showed an increase in overall IgG levels after immunisation over pre-bleeds. In cases where control mice (+/+) not carrying any human immunoglobulin genes were included and immunised, these mice showed comparable changes in total observed Ig levels (FIG. 54). Individual isotype levels were more variable between animals possibly showing various stages of class switching. IgM levels never exceeded 800 µg/ml whereas IgG levels reached more than 6 mg/ml in some animals. Non-immunised controls showed no such increases in switched isotype Ig levels.

These results demonstrate that mice comprising multiple human VDJ gene segments under the control of a rat Sµ rat or mouse switch are able to undergo productive recombination and class switching in response to antigen challenge and that the mice produce antibody levels that are broadly comparable to unmodified mice The transgenic mice are able to produce antibodies of each of the IgG1, IgG2a, IgG2b and IgM isotypes after immunisation. Titers for CTB-specific Ig in pre-bleeds and terminal bleeds were determined and all immunised animals showed at CTB-specific titres of at least 1/100 000.

Example 12

Generation of Anti-Ovalbumin Antibodies with Sub-50 nm Affinities from Animals of the Invention Transgenic mice carrying all human JH, all human DH and human Vh2-5 under control of a rat Sµ switch region were immunised with 25 µg ovalbumin (OVA; Sigma-Aldrich® A7641) in Sigma-Aldrich® adjuvant (Sigma Adjuvant System® S6322) ip and then boosted with the same amount of OVA in adjuvant at day 14 and day 21. Spleenocytes were taken 4 days later and fused using 1 ml polyethyleneglycol (PEG Average MW1450; Sigma-Aldrich® P7306) with a myeloma line. Fused hybridoma cells were plated on 5 96-well plates and after selection with hypoxanthine-aminopterin-thymidine (HAT) wells tested for expression of OVA-specific antibodies by ELISA. Clones positive by ELISA were re-tested by surface plasmon resonance (SPR) and binding kinetics determined using the ProteOn™ XPR36 (Bio-Rad®). Briefly, anti-mouse IgG (GE Biacore™ BR-1008-38) was coupled to a GLM biosensor chip by primary amine coupling, this was used to capture the antibodies to be tested directly from tissue culture supernatants. Ovalbumin was used as the analyte and passed over the captured antibody surface at 1024 nM, 256 nM, 64 nM, 16 nM, 4 nM with a 0 nM (i.e. buffer alone) used to double reference the binding data. Regeneration of the anti-mouse IgG capture surface was by 10 mM glycine pH1.7, this removed the captured antibody and allowed the surface to be used for another interaction. The binding data was fitted to 1:1 model inherent to the ProteOn™ XPR36 analysis software. The run was carried out 1×HBS-EP (10 mM Hepes, 150 mM NaCl, 3 mM EDTA, 0.05% polysorbate, pH7.6 (Teknova H8022)) used as running buffer and carried out at 25° C.

For 8 positive clones, heavy chain V-regions were recovered by RT-PCR (Access RT-PCR System, A1250, Promega) using forward primers specific for Ig signal sequences (Wardemann et al Science 301, 1374 (2003)) and the following reverse primers for the constant regions of mouse IgG (Table 3):

TABLE 3

| Primer Name | Sequence | bp | |
|---|---|---|---|
| mIgG1_2 rev | GGGGCCAGTGGATAGACAGAT | 21 | SEQ ID No 33 |
| mIgG2b rev | CAGTGGATAGACTGATGG | 18 | SEQ ID No 34 |
| mIgG2a_2 rev | CAGTGGATAGACCGATGG | 21 | SEQ ID No 35 |
| mCH1 unirev | KCAGGGGCCAGTGGATAGAC | 20 | SEQ ID No 36 |
| mCH1 unirev_2 | TARCCYTTGACMAGGCATCC | 20 | SEQ ID No 37 |

RT-PCR products were either directly sequenced using the same primer pairs or cloned in to TA plasmids (TOPO® TA Cloning® Kit for Sequencing, K4595-40, Invitrogen™) and submitted for plasmid sequencing. Results (Table 4, below) show that CDRH3 sequences had variable CDRs except for two identical clones (16C9 and 20B5) that also had near identical KD kinetic values. The determined equilibrium binding constant KD ranged from 0.38 nM to 40.60 nM, as determined by SPR at 25° C.

These results demonstrate that mice comprising multiple human VDJ gene segments under the control of a rat Cµ switch are able to undergo productive recombination and produce high affinity antigen-specific antibodies whose CDR3 regions have sequences encoded by human gene segments (human JH was separately identified by V-Quest, IMGT).

TABLE 4

| KD [nM] | clone code | CDR3 and FR4 (underlined) according to Kabat definition | |
|---|---|---|---|
| 0.38 | 16C9 | QEVINYYYYGMDVWGQGTTVTVSS | SEQ ID No 38 |
| 0.52 | 20B5 | QEVINYYYYGMDVWGQGTTVTVSS | SEQ ID No 39 |
| 5.89 | 19F4 | LEMATINYYYYGMDVWGQGTTMVTVSS | SEQ ID No 40 |
| 39.70 | 19E1 | QEFGNYYYYGMDVWGQGTTVTVSS | SEQ ID No 41 |
| 3.10 | 19G8 | QEDGNPYYFGMDFWGQGTTVTVSS | SEQ ID No 42 |
| 8.95 | 20H10 | GSSYYYDGMDVWGQGTTVTVSS | SEQ ID No 43 |

TABLE 4 -continued

| KD [nM] | clone code | CDR3 and FR4 (underlined) according to Kabat definition | |
|---|---|---|---|
| 4.46 | 18D10 | LENDYGYYYYGMDVWGQGTTVTVSS | SEQ ID No 44 |
| 40.60 | 16F2 | RGGLSPLYGMDVWGQGTTVTVSS | SEQ ID No 45 |

Example 13

Generation of Anti-Cholera Toxin B Antibodies with Human Vh Regions from Animals of the Invention Transgenic mice carrying all human JH, all human DH and human Vh2-5, Vh7-41, Vh4-4, Vh1-3, Vh1-2 and Vh6-1 under control of a mouse Sμ switch region were immunised and fused as described in Example 11. Fused hybridoma cells were plated on 5 96-well plates and after selection with hypoxanthine-aminopterin-thymidine (HAT) or G418 (Gibco® Cat No 10131-027, Lot 503317) and wells tested for expression of CTB-specific antibodies by ELISA. Clones positive by ELISA were re-tested by surface plasmon resonance SPR and binding kinetics determined using the ProteOn XPR36™ (Bio-Rad®).

Briefly, anti-mouse IgG (GE Biacore™ BR-1008-38) was coupled to a GLM biosensor chip by primary amine coupling, this was used to capture the antibodies to be tested directly from tissue culture supernatants. Cholera toxin B was used as analyte and passed over the captured antibody surface at 256 nM, 64 nM, 16 nM, 4 nM and 1 nM, with a 0 nM (i.e. buffer alone) used to double reference the binding data. Regeneration of the anti-mouse IgG capture surface was by 10 mM glycine pH1.7, this removed the captured antibody and allowed the surface to be used for another interaction. The binding data was fitted to 1:1 model inherent to the ProteOn XPR36™ analysis software. The run was carried out 1×HBS-EP (10 mM Hepes, 150 mM NaCl, 3 mM EDTA, 0.05% polysorbate, pH7.6 (Teknova H8022)) used as running buffer and carried out at 37° C.

From the clones initially identified by ELISA, binding to CTB was confirmed by SPR. However, due to the pentameric nature of the cholera toxin B, the majority of fits to the 1:1 model were poor and the equilibrium binding constant KDs could not be accurately determined. Where fits were acceptable, equilibrium binding constant KDs determined ranged from 0.21 nM to 309 nM but due to the pentameric nature of cholera toxin B these are likely to be the result of multimeric interactions and therefore apparent affinities with possible avidity components.

Clones identified by SPR for binding to CTB were subjected to RT-PCR as described in Example 12 to recover the Vh regions. RT-PCR products were directly sequenced using the same primer pairs. Results were obtained for only 14 clones presumably because the human primers described in Wardemann et al were not designed to amplify mouse Vh regions and therefore may have failed to amplify certain mouse Vh classes. Results showed that 3 of the 14 CTB-specific recovered heavy chain V-region sequences were human V, D and J regions as identified by V-Quest, IMGT (Table 5).

TABLE 5

Alignment of heavy chain CDRs and J-region of 3 clones identified as binding to CTB and preferentially matching with human reference sequences from IMGT database; note that the KD values given here are apparent values due to the avidity of the CTB-antibody interaction

| Vh region | Clone Name | Sequence (Kabat definitions) | | | | KD [nM] |
|---|---|---|---|---|---|---|
| | | CDR1 | CDR2 | CDR3 | J-regions | |
| IGHV4-4*02 | — | SSNWWSS (SEQ ID NO 51) | EIYHSGSTNYNPSLKS (SEQ ID NO 56) | n/a | IGHJ2*01 YWYFDLWGRGTLVTVSS (SEQ ID NO 64) | — |
| | 12D10 | SGNWWS (SEQ ID NO 52) | EIYHSGNTNYNPSLKS (SEQ ID NO 57) | GPLTGEKYYFDL (SEQ ID NO 61) | -YYFDLWGRGTLVTVSS (SEQ ID NO 65) | 0..27 |
| | 1283 | RSNWWS (SEQ ID NO 53) | EIYHSGSTNYNPSLKS (SEQ ID NO 58) | IGDWYFDL (SEQ ID NO 62) | -WYFDLWGRGTLVTVSS (SEQ ID NO 66) | 0.85 |
| IGHV6-1*01 | — | SNSAAWN (SEQ ID NO 54) | RTYYRSKWYNDYAVSVKS (SEQ ID NO 59) | n/a | IGHJ3*01 DAFDVWGQGTMVTVSS (SEQ ID NO 67) | — |
| | 4A12 | SNSAAWN (SEQ ID NO 55) | RTYYRSKWNDYKVSVKS (SEQ ID NO 60) | EGSHSGSWYLDAFDI (SEQ ID NO 63) | DAFDIWGQGTKVTVSS (SEQ ID NO 68) | 1.61 |

Example 14

Figure 56:
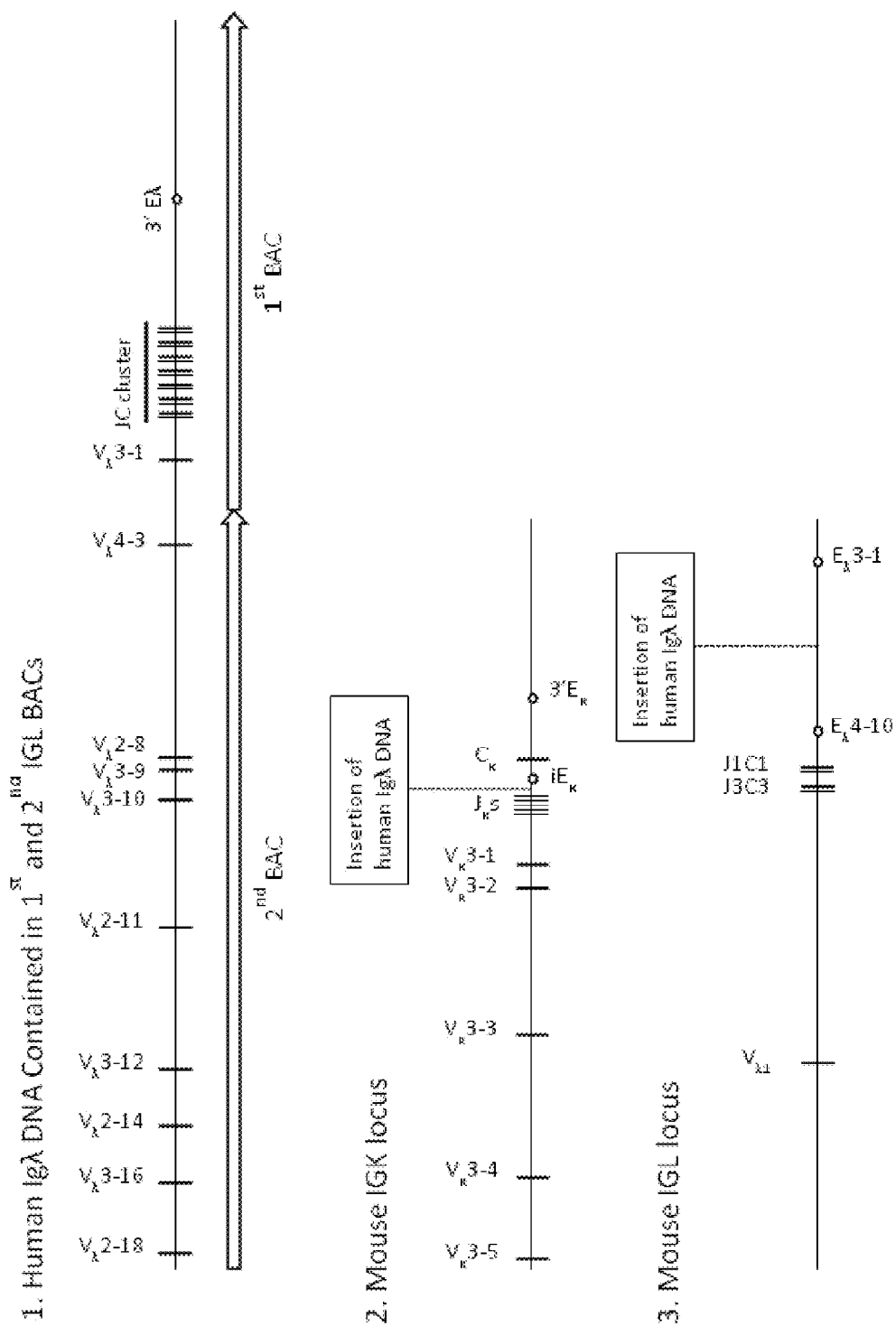

High Human Lambda Variable Region Expression in Transgenic Mice Comprising Human Lambda Gene Segments Inserted into Endogenous Kappa Locus Insertion of human lambda gene segments from a 1$^{st}$ IGL BAC to the IGK locus of mouse AB2.1 ES cells (Baylor College of Medicine) was performed to create a chimaeric light chain allele denoted the P1 allele (FIG. 56). The inserted human sequence corresponds to the sequence of human chromosome 22 from position 23217291 to position 23327884 and comprises functional lambda gene segments Vλ3-1, Jλ1-Cλ1, Jλ2-Cλ2, Jλ3-Cλ3, Jλ6-Cλ6 and Jλ7-Cλ7. The insertion was made between positions 70674755 and 706747756 on mouse chromosome 6, which is upstream of the mouse Cκ region and 3'Eκ (ie, within 100 kb of the endogenous light chain enhancer) as shown in FIG. 56. The mouse Vκ and Jκ gene segments were retained in the chimaeric locus, immediately upstream of the inserted human lambda DNA. The mouse lambda loci were left intact. Mice homozygous for the chimaeric P1 locus were generated from the ES cells using standard procedures.

A second type of mice were produced (P2 mice) in which more human functional Vλ gene segments were inserted upstream (5') of human Vλ3-1 by the sequential insertion of the BAC1 human DNA and then BAC2 DNA to create the P2 allele. The inserted human sequence from BAC2 corresponds to the sequence of human chromosome 22 from position 23064876 to position 23217287 and comprises functional lambda gene segments Vλ2-18, Vλ3-16, V2-14, Vλ3-12, Vλ2-11, Vλ3-10, Vλ3-9, Vλ2-8 and Vλ4-3. Mice homozygous for the chimaeric P2 locus were generated from the ES cells using standard procedures.

FACS analysis of splenic B cells from the P1 and P2 homozygotes was performed to assess lambda versus kappa expression and human lambda versus mouse lambda expression in the transgenic mice.

Standard 5'-RACE was carried out to analyse RNA transcripts from the light chain loci in P2 homozygotes.

Light Chain Expression & FACS Analysis

To obtain a single cell suspension from spleen, the spleen was gently passage through a 30 μm cell strainer. Single cells were resuspended in Phosphate-Buffered Saline (PBS) supplemented with 3% heat inactivated foetal calf serum (FCS).

The following antibodies were used for staining:

Rat anti-mouse lambda (mCλ) phycoerythrin (PE) antibody (Southern Biotech), rat anti-mouse kappa (mCκ) (BD Pharmingen, clone 187.1) fluorescein isothiocyanate (FITC), anti-human lambda (hCλ) (eBioscience, clone 1-155-2) phycoerythrin (PE), anti-B220/CD45R (eBioscience, clone RA3-6B2) allophycocyanin (APC). NB: light chains bearing human Cλ was expected to have variable regions derived from the rearrangement of inserted human Vλ and human Jλ. Light chains bearing mouse Cλ was expected to have variable regions derived from the rearrangement of mouse Vλ and Jλ from the endogenous lambda loci.

$5\times10^6$ cells were added to individual tubes, spun down to remove excess of fluid, and resuspended in fresh 100 μl of PBS+3% FCS. To each individual tube the following antibodies were added:

For staining of mλ versus mκ 1 μl of each antibody was added in addition to 1 μl of B220/CD45R antibody. For detection of B cells expressing human lambda light chain, the mλ antibody was substituted with hλ antibody. Cells were incubated in the dark at 6° C. for 15 minutes followed by several washes with fresh PBS+3% FCS to remove unbound antibody. Cells were analysed using fluorescence-activated cell sorting (FACS) analyser from Miltenyi Biotech.

Alive spleenocytes were gated using side scatter (SSC) and forward scatter (FSC). Within the SSC and FSC gated population, a subpopulation of B220/CD45R (mouse B-cells) was detected using the APC fluorochrome. Single positive B220/CD45R population was further subdivided into a cell bearing either mλ or hλ PE fluorochrome in conjunction with mκ FITC fluorochrome. The percentage of each population was calculated using a gating system.

Figure 57:
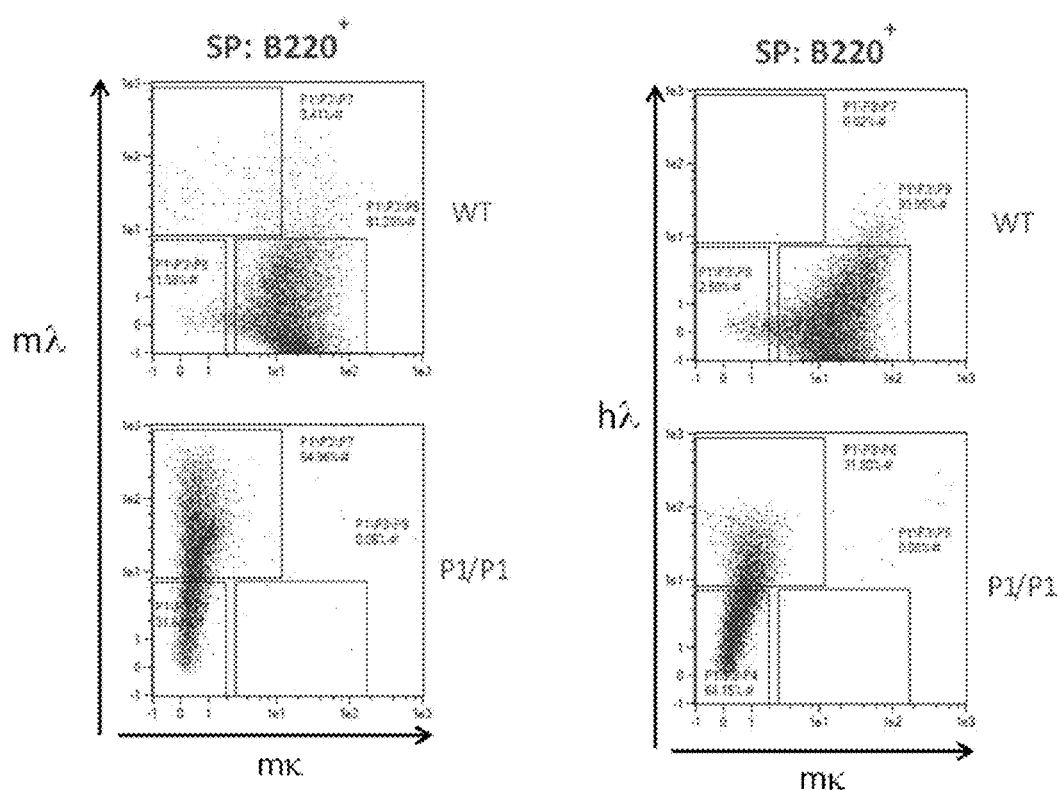
FIG. 57 shows the results of FACS analysis to determine mouse and human Cλ expression (and thus correspondingly mouse and human variable region expression) in B220$^+$ splenic B cells from P1 homozygous mice (P1/P1) compared to wild-type mice (WT).

Surprisingly, FACS analysis of splenic B cells from the P1 homozygotes showed no detectable mouse Cκ expression (FIG. 57), indicating that insertion of the human lambda locus DNA from BAC1 interrupts expression of the endogenous IGK chain.

The strong expression of endogenous Cλ and weak expression of human Cλ in the splenic B cells grouped by FACS analysis (mouse Cλ:human Cλ=65:32) in these mice suggest that inserted human IGL sequence, although interrupts the IGK activity, cannot totally compete with the endogenous IGL genes.

Figure 58A:
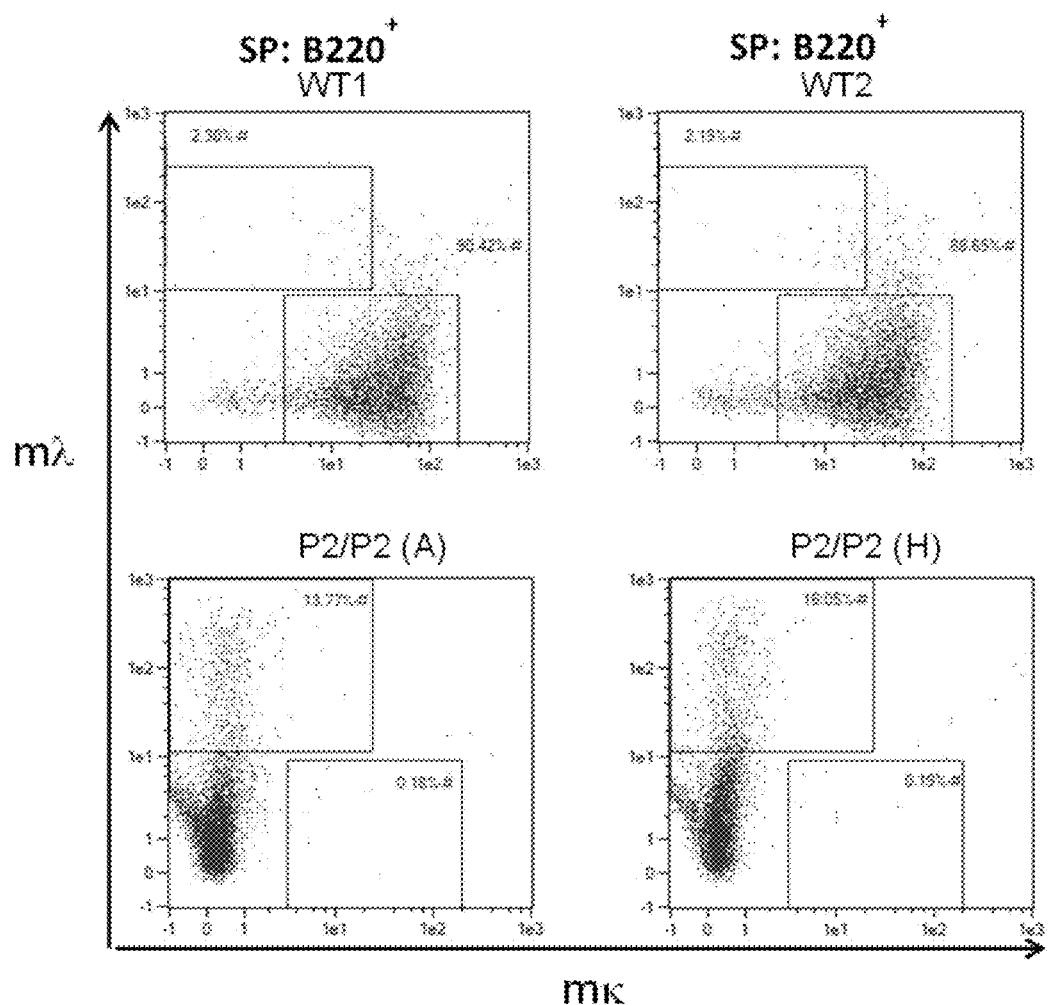
FIG. 58A shows the results of FACS analysis to determine mouse Cκ and Cλ expression in B220+ splenic B cells from P2 homozygous mice (P2/P2) compared to wild-type mice (WT). No detectable mouse Cκ expression was seen.
Figure 58B:
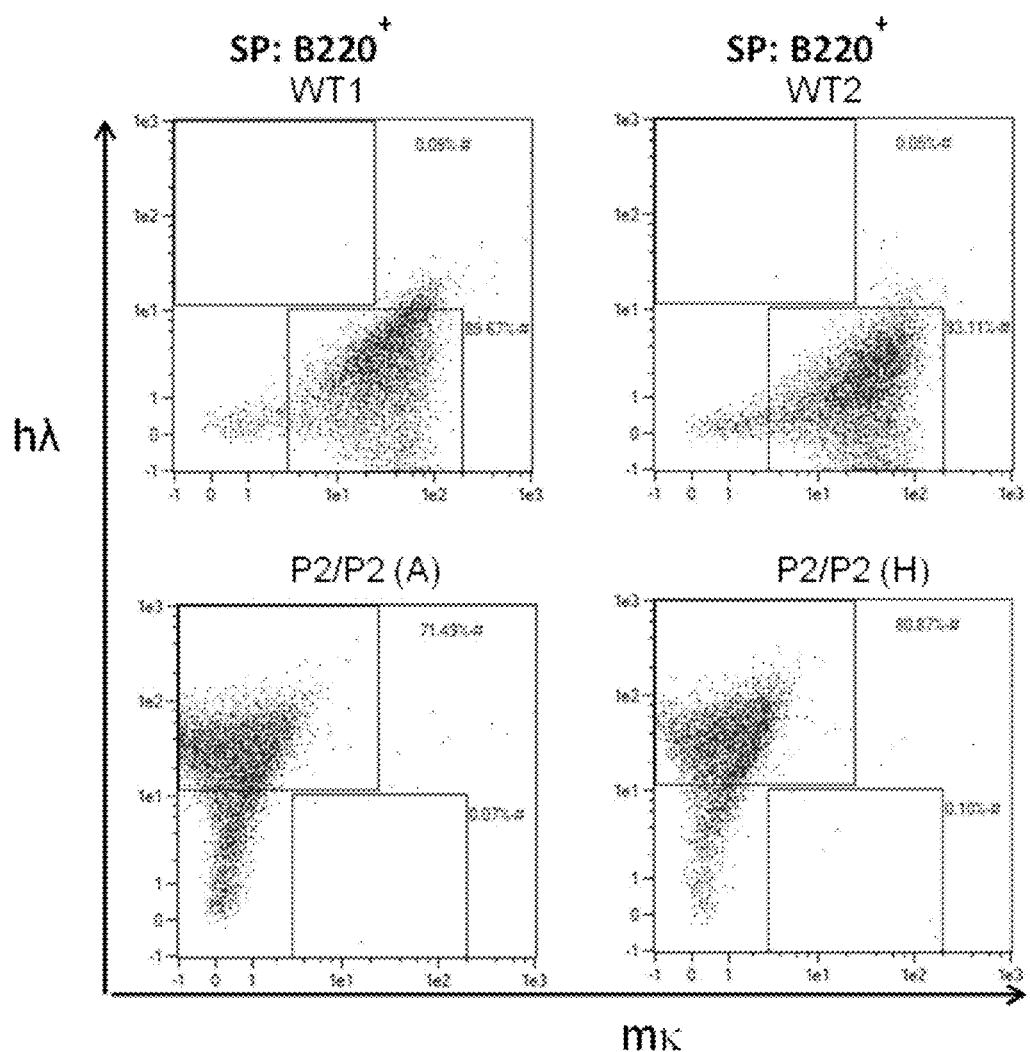
FIG. 58B shows the results of FACS analysis to determine human Cλ expression (and thus correspondingly human variable region expression) in B220+ splenic B cells from P2 homozygous mice (P2/P2) compared to wild-type mice (WT).

The FACS analysis again surprisingly showed no detectable mouse Cκ expression in the P2 homozygotes (FIGS. 58A & B). However, the human Cλ greatly predominates in expressed B cells grouped as mouse or human Cλ following FACS analysis (mouse Cλ:human Cλ=15:80 corresponding to a ratio of 15 mouse lambda variable regions:80 human lambda variable regions, ie, 84% human lambda variable regions with reference to the grouped B-cells—which corresponds to 80% of total B-cells) from the P2 homozygotes. While not wishing to be bound by any theory, we suggest that the inserted human lambda locus sequence from the $2^{nd}$ BAC provides some advantages to compete with endogenous lambda gene segment rearrangement or expression.

Figure 59:
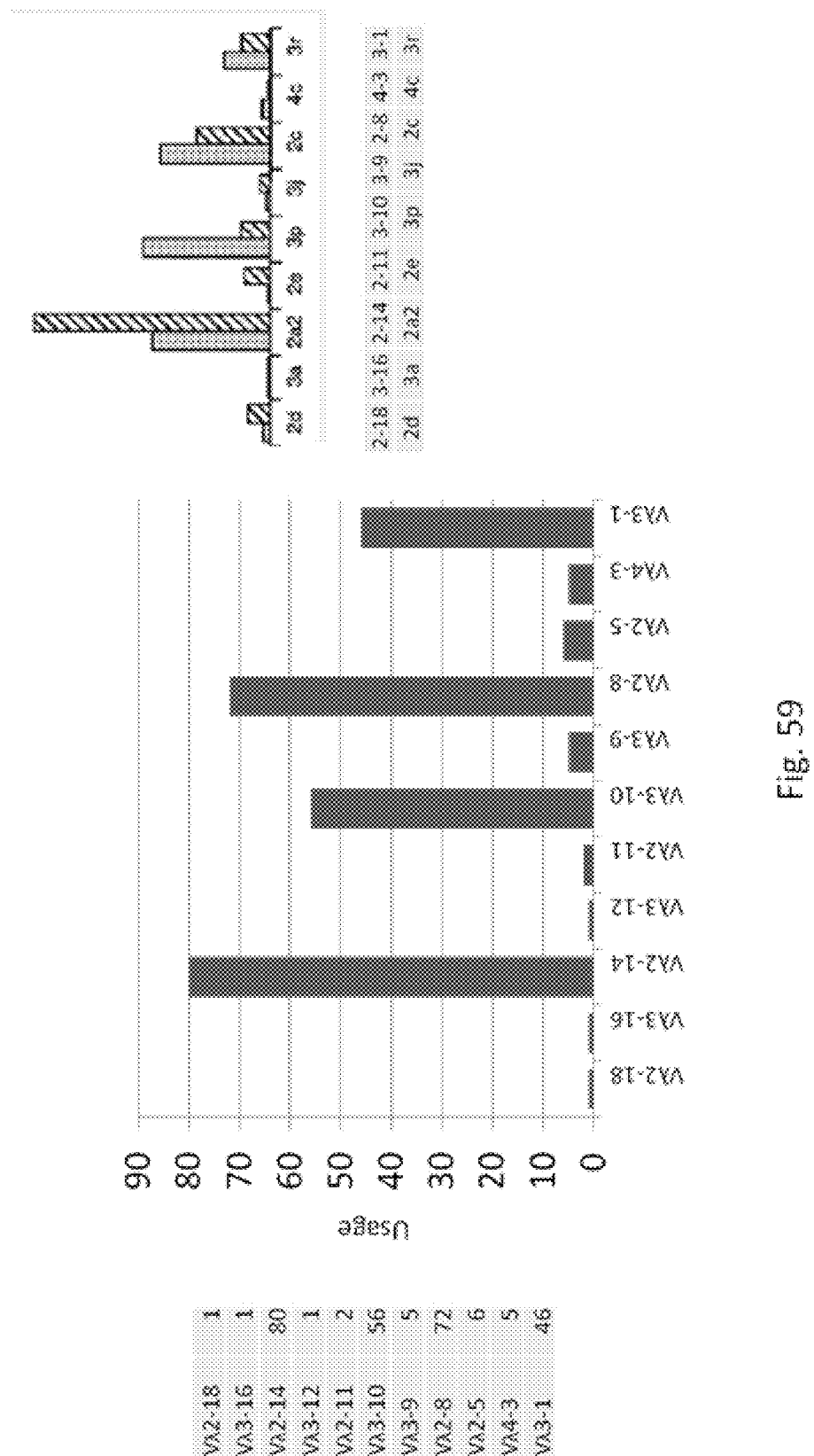
FIG. 59 shows human Vλ usage in P2 homozygous mice (P2/P2) and typical Vλ usage in humans (inset)
Figure 60:
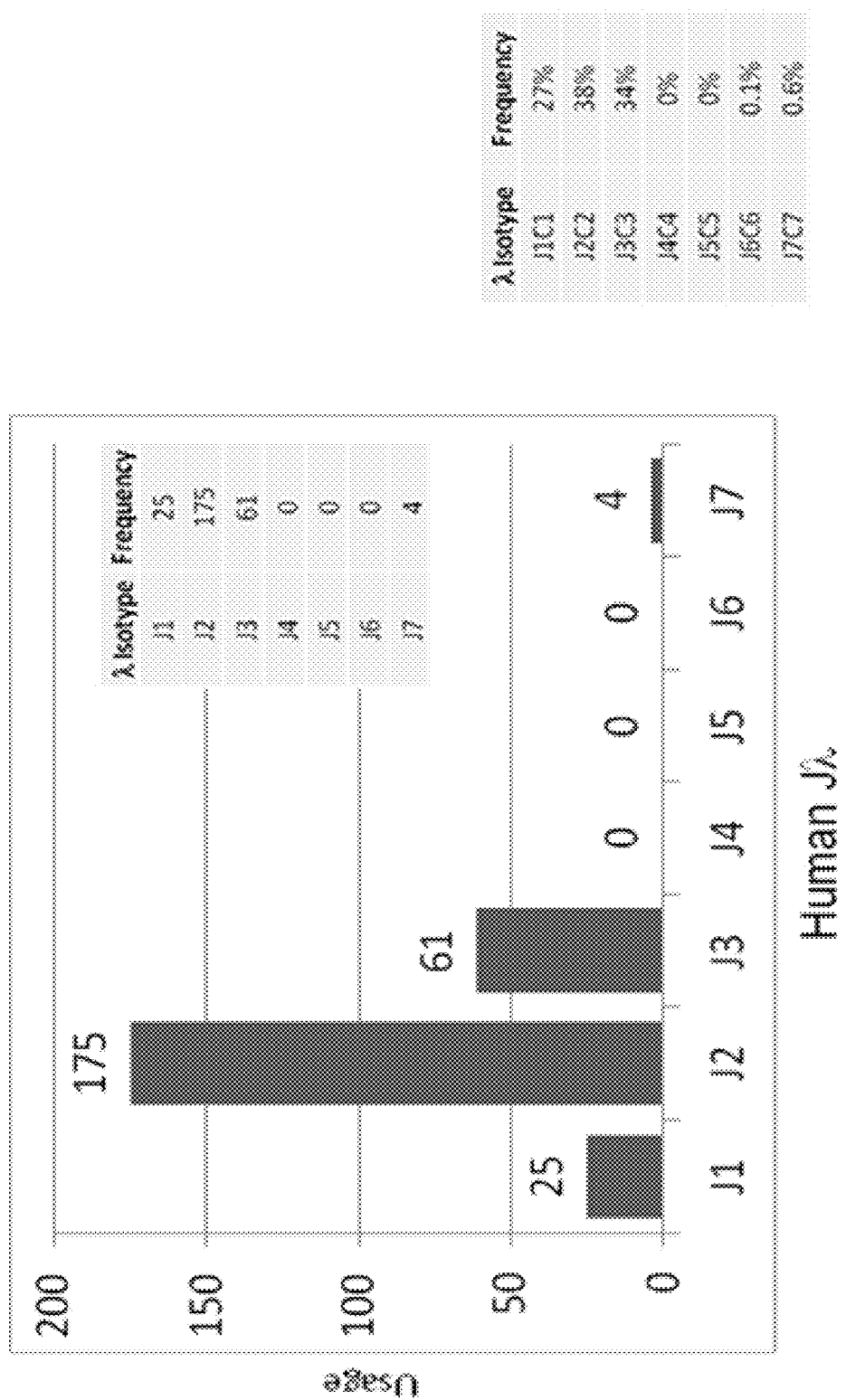
FIG. 60 shows human Jλ usage in P2 homozygous mice (P2/P2) and typical Jλ usage in humans (inset)
Figure 61:
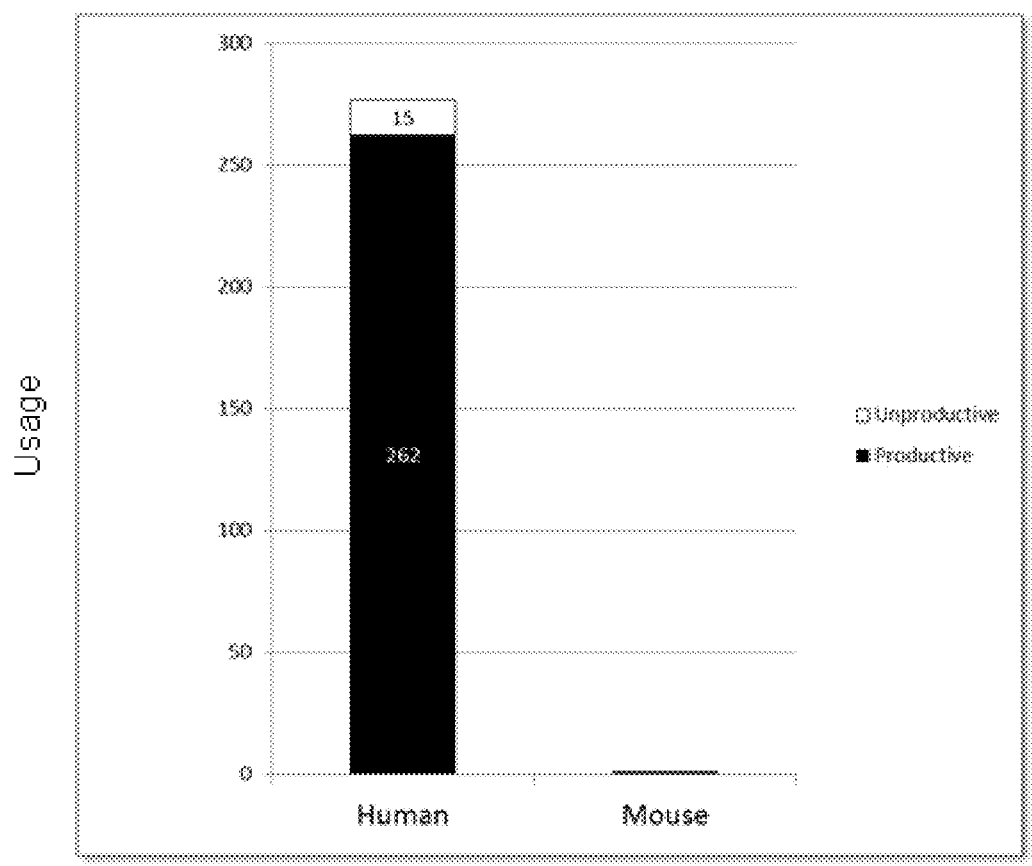
FIG. 61 shows Vλ usage is very high in P2 homozygous mice (P2/P2).
Figure 63:
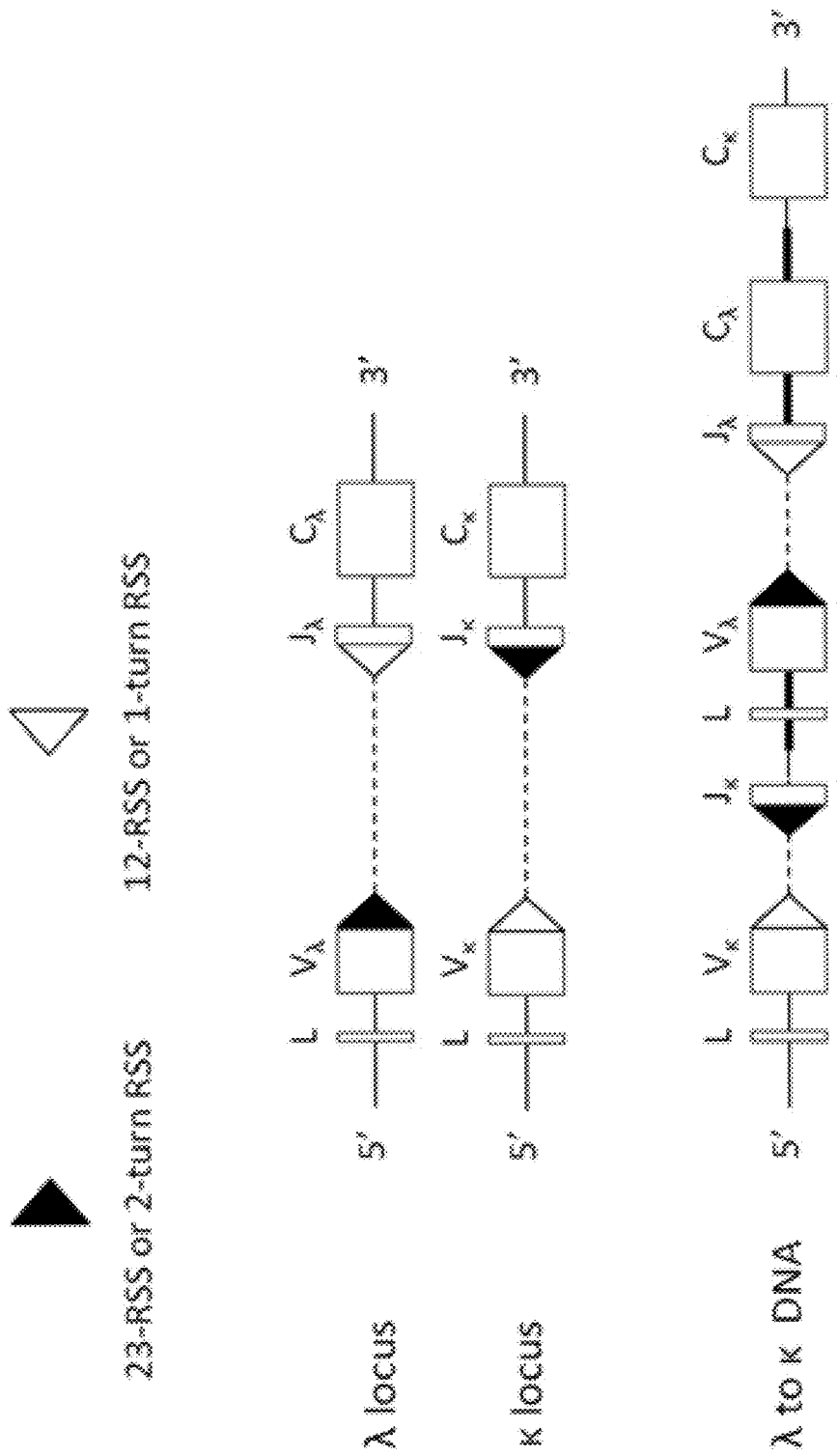
FIG. 63 illustrates RSS arrangement in the lambda and kappa loci.

We analysed human Vλ and Jλ usage in the P2 homozygotes. See FIG. 59 which shows the human Vλ usage in P2 homozygotes. The observed usage was similar to that seen in humans (as per J Mol Biol. 1997 Apr. 25; 268(1):69-77; "The creation of diversity in the human immunoglobulin V(lambda) repertoire"; Ignatovich O et al). Further, the human Jλ usage was similar to that seen in humans (FIG. 60). The Vλ versus Vκ usage analysis of human Cλ transcripts by sequencing of non-bias 5'-RACE (rapid amplification of cDNA ends) PCR clones showed that among 278 clone sequences, only one used Vκ for rearrangement to Jλ (human Jλ), and all others (277 clones) used human Vλ (FIGS. 61 & 62; Vλ2-5 was detected at the RNA transcript level, but this is a pseudogene which is usually not picked up by usage a the protein level). While not wishing to be bound by any theory, we suggest that the retained mouse Vκ gene segments essentially cannot efficiently rearrange with the inserted human Jλ gene segments because they have the same type of RSSs (recombination signal sequences; see explanation below) and are incompatible for rearrangement (FIG. 63). This result also indicates that the inactivation of the endogenous IGK activity and predominate expression of the inserted human lambda sequence can be achieved without further modification of the IGK locus, for example, deletion or inversion of endogenous kappa loci gene segments is not necessary, which greatly simplifies the generation of useful transgenic mice expressing light chains bearing human lambda variable regions (ie, variable regions produced by recombination of human Vλ and Jλ gene segments).

The arrangement of recombination signal sequences (RSSs) that mediate V(D)J recombination in vivo is discussed, eg, in Cell. 2002 April; 109 Suppl:S45-55; "The mechanism and regulation of chromosomal V(D)J recombination"; Bassing C H, Swat W, Alt FW (the disclosure of which is incorporated herein by reference). Two types of RSS element have been identified: a one-turn RSS (12-RSS) and a two-turn RSS (23-RSS). In natural VJ recombination in the lambda light chain locus, recombination is effected between a two-turn RSS that lies 3' of a V lambda and a one-turn RSS that lies 5' of a J lambda, the RSSs being in opposite orientation. In natural VJ recombination in the kappa light chain locus, recombination if effected between a one-turn RSS that lies 3' of a V kappa and a two-turn RSS that lies 5' of a J kappa, the RSSs being in opposite orientation. Thus, generally a two-turn RSS is compatible with a one-turn RSS in the opposite orientation.

Thus, the inventors have demonstrated how to (i) inactivate endogenous kappa chain expression by insertion of human lambda gene segments into the kappa locus; and (ii) how to achieve very high human lambda variable region expression (thus providing useful light chain repertoires for selection against target antigen)—even in the presence of endogenous lambda and kappa V gene segments. Thus, the inventors have shown how to significantly remove (lambda) or totally remove (kappa) V gene segment competition and thus endogenous light chain expression by the insertion of at least the functional human lambda gene segments comprised by BACs 1 and 2. In this example a very high level of human lambda variable region expression was surprisingly achieved (84% of total lambda chains and total light chains as explained above).

Example 15

High Human Lambda Variable Region Expression in Transgenic Mice Comprising Human Lambda Gene Segments Inserted into Endogenous Lambda Locus Insertion of human lambda gene segments from the $1^{st}$ and $2^{nd}$ IGL BACs to the lambda locus of mouse AB2.1 ES cells (Baylor College of Medicine) was performed to create a lambda light chain allele denoted the L2 allele (FIG. 56). The inserted human sequence corresponds to the sequence of human chromosome 22 from position 23064876 to position 23327884 and comprises functional lambda gene segments Vλ2-18, Vλ3-16, V2-14, Vλ3-12, Vλ2-11, Vλ3-10, Vλ3-9, Vλ2-8, Vλ4-3, Vλ3-1, Jλ1-Cλ1, Jλ2-Cλ2, Jλ3-Cλ3, Jλ6-Cλ6 and Jλ7-Cλ7. The insertion was made between positions 19047551 and 19047556 on mouse chromosome 16, which is upstream of the mouse Cλ region and between Eλ4-10 and Eλ3-1 (ie, within 100 kb of the endogenous light chain enhancers) as shown in FIG. 56. The mouse Vλ and Jλ gene segments were retained in the locus, immediately upstream of the inserted human lambda DNA. The mouse kappa loci were inactivated to prevent kappa chain expression. Mice homozygous for the L2 locus were generated from the ES cells using standard procedures.

Using a similar method to that of Example 14, FACS analysis of splenic B cells from the L2 homozygotes was performed to assess lambda versus kappa expression and human lambda versus mouse lambda expression in the transgenic mice.

Light Chain Expression & FACS Analysis

Figure 64A:
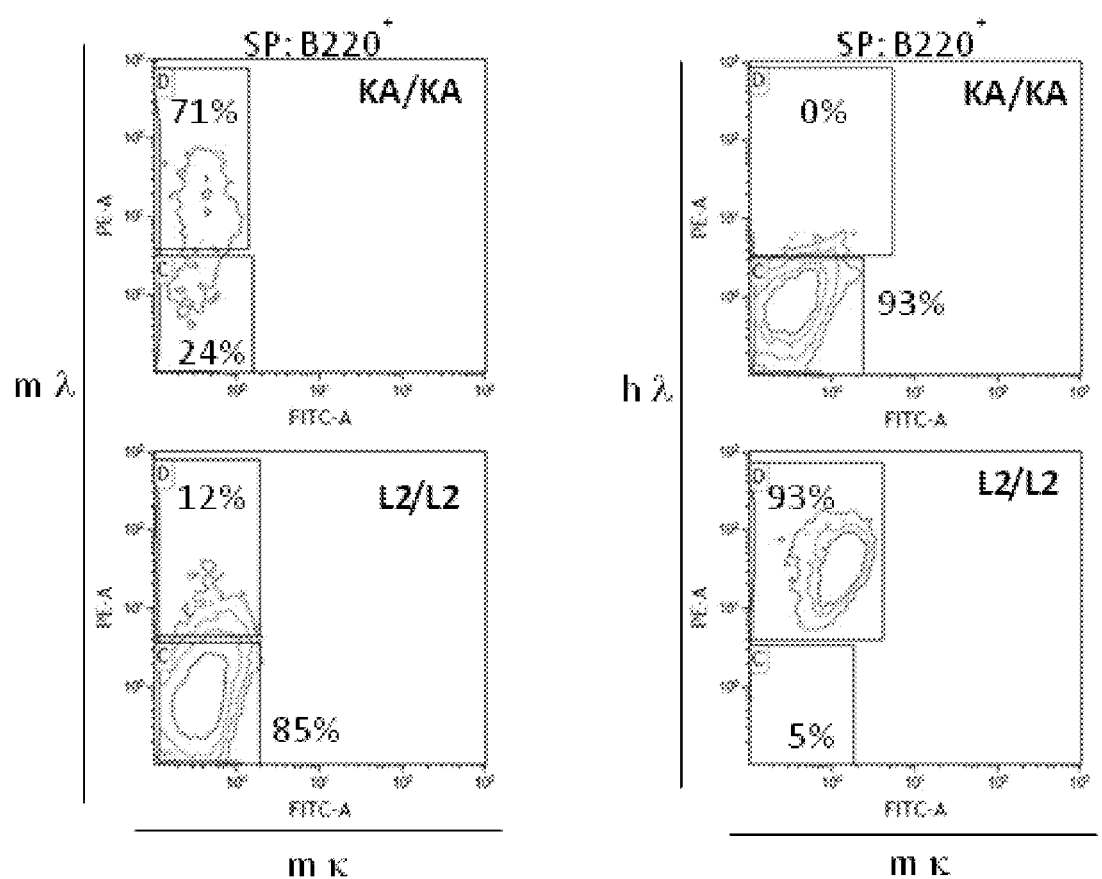
FIG. 64A shows the results of FACS analysis to determine mouse and human Cλ expression (and thus correspondingly mouse and human variable region expression) in B220+ splenic B cells from L2 homozygous mice in which endogenous kappa chain expression has been inactivated (L2/L2; KA/KA) compared to mice having no human lambda DNA inserted and in which endogenous kappa chain expression has been inactivated (KA/KA). Very high human Vλ usage was seen in the L2/L2; KA/KA) mice, almost to the exclusion of mouse Vλ use.

The FACS analysis of splenic B-cells in L2 homozygotes under the IGK knockout background (in which Vκ and Jκ gene segments have been retained) surprisingly showed that expression of human Cλ greatly predominates in B-cells grouped as mouse or human Cλ following FACS analysis (mouse Cλ:human Cλ=5:93 corresponding to a ratio of 5 mouse lambda variable regions:93 human lambda variable regions, ie, 95% human lambda variable regions with reference to the grouped B-cells—which corresponds to 93% of total B-cells) (FIG. 64A), demonstrating that inserted human IGA gene segments within the endogenous IGA locus can outcompete the endogenous IGA gene segment rearrangement or expression.

Thus, the inventors have demonstrated how to achieve very high human lambda variable region expression (thus providing useful light chain repertoires for selection against target antigen)—even in the presence of endogenous lambda and kappa V gene segments. Thus, the inventors have shown how to significantly remove endogenous lambda V gene segment competition and thus endogenous lambda light chain expression by the insertion of at least the functional human lambda gene segments comprised by BACs 1 and 2. In this example a very high level of human lambda variable region expression was surprisingly achieved (95% of total lambda chains and total light chains as explained above).

These data indicate that mice carrying either P (Example 14) or L (Example 15) alleles produced by targeted insertion of the functional gene segments provided by BAC1 and BAC2 can function in rearrangement and expression in mature B cells. These two types of alleles are very useful for providing transgenic mice that produce human Ig lambda chains for therapeutic antibody discovery and as research tools.

Figure 65:
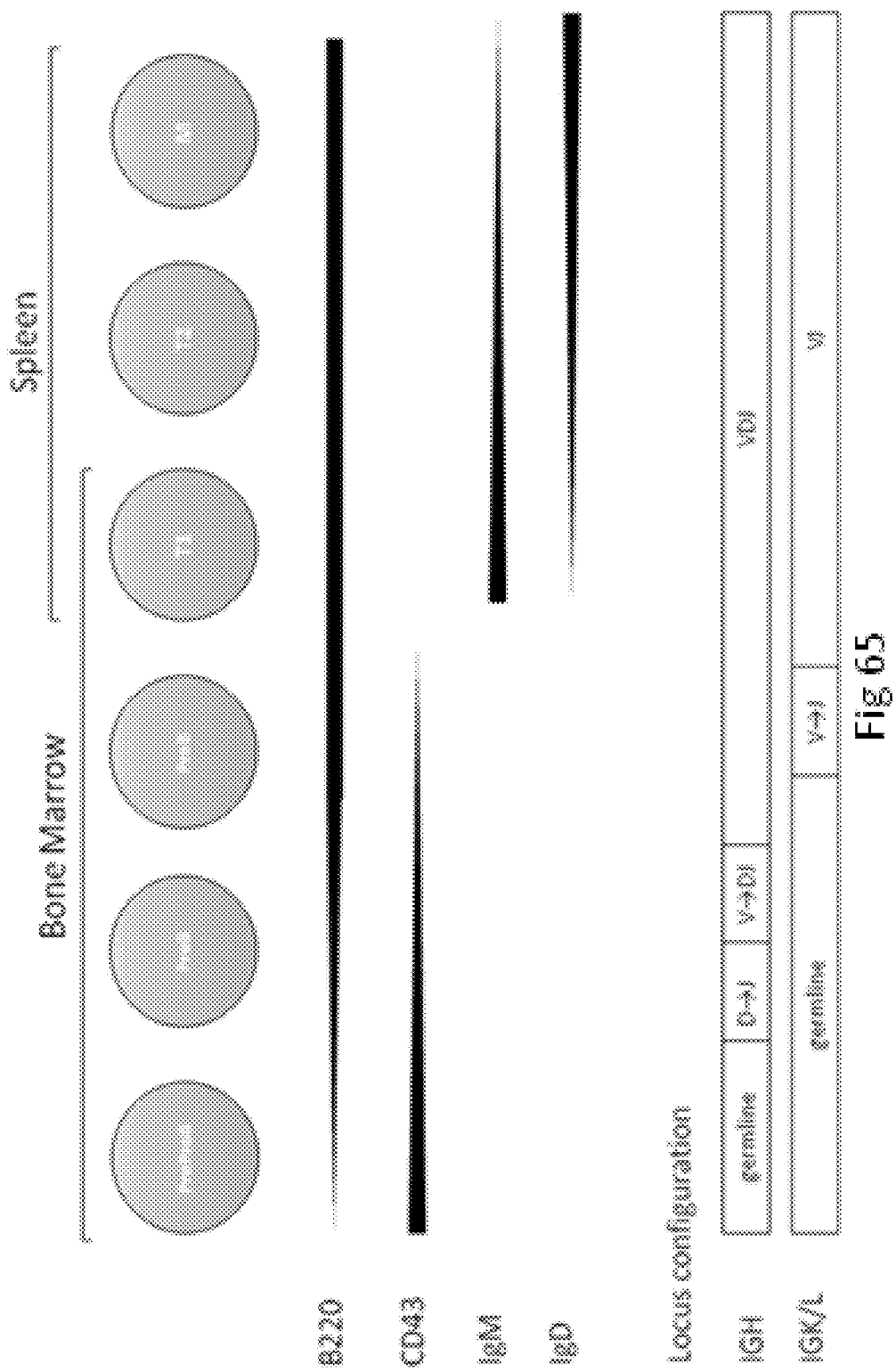
FIG. 65: B-cell development and markers in the bone marrow and splenic compartments.

Transgenic Mice of the Invention Expressing Human Lambda Variable Regions Develop Normal Splenic Compartments In spleen, B cells are characterized as immature (T1 and T2) and mature (M) based on the levels of cell surface markers, IgM and IgD. T1 cells have high IgM and low IgD. T2 cells have medium levels of both them. M cells have low IgM but high IgD (FIG. 65). See also J Exp Med. 1999 Jul. 5; 190(1):75-89; "B cell development in the spleen takes place in discrete steps and is determined by the quality of B cell receptor-derived signals"; Loder F et al.

Figure 64B:
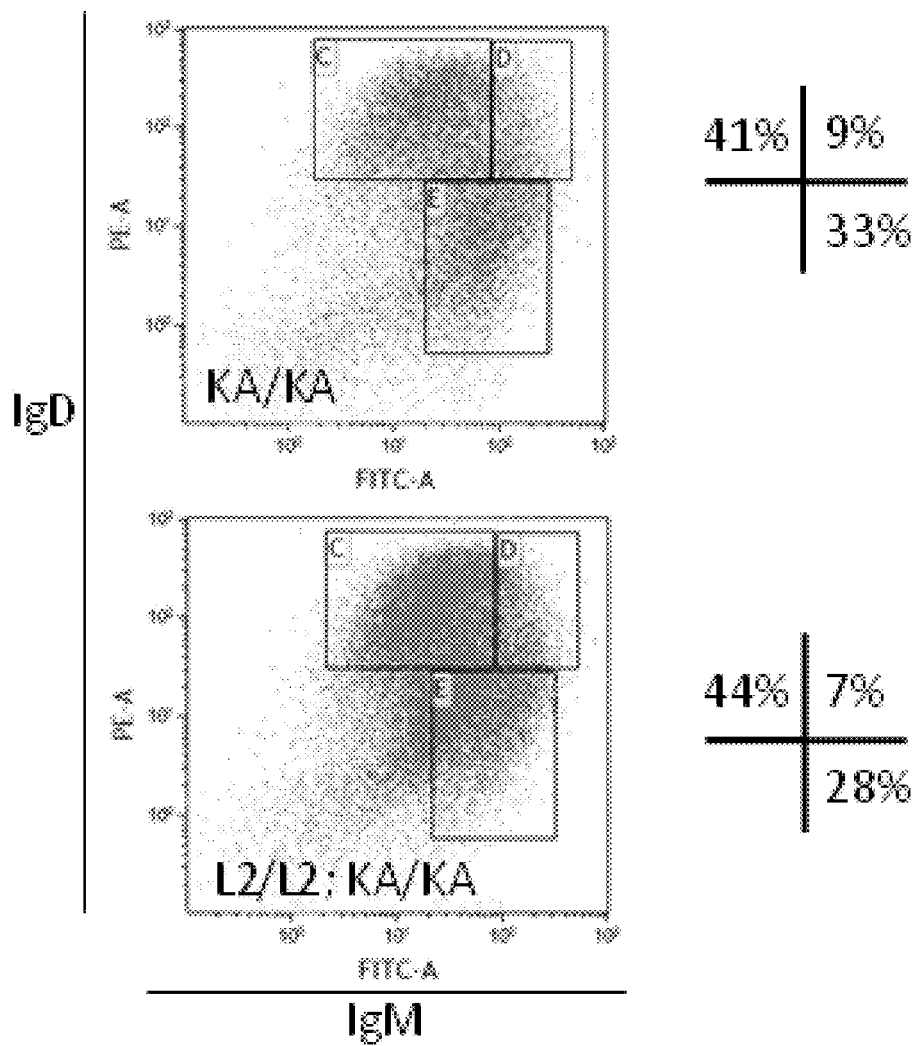
FIG. 64B: Splenic B-Cell Compartment Analysis. This figure shows the results of FACS analysis on splenic B-cells from transgenic L2/L2; KA/KA mice (L2 homozygotes; homozygous for human lambda gene segment insertion into endogenous lambda loci; endogenous kappa chain expression having been inactivated) compared with splenic B-cells from mice expressing only mouse antibodies (KA/KA mice). The results show that the splenic B-cell compartments in the mice of the invention are normal (ie, equivalent to the compartments of mice expressing only mouse antibody chains).

Using methods similar to those described in Example 16 below, splenic B-cells from the animals were scored for IgD and IgM expression using FACS. We compared control mice KA/KA (in which endogenous kappa chain expression has been inactivated, but not endogenous lambda chain expression) with L2/L2; KA/KA mice (L2 homozyotes). The L2 homozygotes surprisingly showed comparable splenic B-cell compartments to the control mice (FIG. 64B).

Example 16

Assessment of B-Cell and Ig Development in Transgenic Mice of the Invention

We observed normal Ig subtype expression & B-cell development in transgenic mice of the invention expressing antibodies with human heavy chain variable regions substantially in the absence of endogenous heavy and kappa chain expression.

Using ES cells and the RMCE genomic manipulation methods described above, mice were constructed with combinations of the following Ig locus alleles:—

S1F/HA, +/KA=(i) S1F—first endogenous heavy chain allele has one human heavy chain locus DNA insertion, endogenous mouse VDJ region has been inactivated by inversion and movement upstream on the chromosome (see the description above, where this allele is referred to as S1$^{inv1}$); (ii) HA—second endogenous heavy chain allele has been inactivated (by insertion of an endogenous interrupting sequence); (iii) +—first endogenous kappa allele is a wild-type kappa allele and (iv) KA—the second endogenous kappa allele has been inactivated (by insertion of an endogenous interrupting sequence). This arrangement encodes exclusively for heavy chains from the first endogenous heavy chain allele.

S1F/HA, K2/KA=(i) K2—the first endogenous kappa allele has two kappa chain locus DNA insertions between the most 3' endogenous Jκ and the mouse Cκ, providing an insertion of 14 human Vκ and Jκ1-Jκ5; and (ii) KA—the second endogenous kappa allele has been inactivated (by insertion of an endogenous interrupting sequence). This arrangement encodes exclusively for heavy chains comprising human variable regions and substantially kappa light chains from the first endogenous kappa allele.

+/HA, K2/KA—this arrangement encodes for mouse heavy chains and human kappa chains.

+/HA, +/KA—this arrangement encodes for mouse heavy and kappa chains—the mice only produce mouse heavy and light chains.

In bone marrow, B progenitor populations are characterized based their surface markers, B220 and CD43. PreProB cells carry germline IGH and IGK/L configuration and have low B220 and high CD43 on their cell surface. ProB cells start to initiate VDJ recombination in the IGH locus and carry medium levels of both B220 and CD43. PreB cells carry rearranged IGH VDJ locus and start to initiate light chain VJ rearrangement, and have high B220 but low CD43. In spleen, B cells are characterized as immature (T1 and T2) and mature (M) based on the levels of cell surface markers, IgM and IgD. T1 cells have high IgM and low IgD. T2 cells have medium levels of both them. M cells have low IgM but high IgD (FIG. 65). See also J Exp Med. 1991 May 1; 173(5):1213-25; "Resolution and characterization of pro-B and pre-pro-B cell stages in normal mouse bone marrow"; Hardy R R et al and J Exp Med. 1999 Jul. 5; 190(1):75-89; "B cell development in the spleen takes place in discrete steps and is determined by the quality of B cell receptor-derived signals"; Loder F et al.

Transgenic Mice of the Invention Develop Normal Splenic and BM Compartments (a) Analysis of the Splenic Compartment For each mouse, to obtain a single cell suspension from spleen, the spleen was gently passaged through a 30 μm cell strainer. Single cells were resuspended in Phosphate-Buffered Saline (PBS) supplemented with 3% heat inactivated foetal calf serum (FCS). $5 \times 10^6$ cells were added to individual tubes, spun down to remove excess of fluid and resuspended in fresh 100 μl of PBS+3% FCS. To each individual tube the following antibodies were added: anti-B220/CD45R (eBioscience, clone RA3-6B2) allophycocyanin (APC), antibody against IgD receptor conjugated with phycoerythrin (PE) (eBioscience, clone 11-26) and antibody against IgM receptor conjugated with fluorescein isothiocyanate (FITC) (eBioscience, clone 11/41).

For staining of IgM vs IgD, $5 \times 10^6$ cells were used for each staining. To each vial containing splenocytes a cocktail of antibodies was added consisting of: anti-IgD (PE), anti-IgM (FITC) and anti-B220/CD45R (APC). Cells were incubated at 6° C. for 15 minutes, washed to remove excess unbound antibodies and analysed using a fluorescence-activated cell sorting (FACS) analyser from Miltenyi Biotech. B-cells were gated as $B220^{HIGH}$ $IgM^{HIGH}$ $IgD^{LOW}$ (ie, B220+ IgM+ IgD−) for T1 population, $B220^{HIGH}$ $IgM^{HIGH}$ $IgD^{HIGH}$ (B220+ IgM+ IgD+) for T2 population and $B220^{HIGH}$ $IgM^{LOW}$ $IgD^{HIGH}$ (B220+ IgM− IgD+) for M population. Percentage of cells was calculated using gating system. We used gates to identify and define subsets of cell populations on plots with logarithmic scale. Before gates are applied a single stain antibody for each fluorochrome is used to discriminate between a positive (high intensity fluorochrome) and negative (no detectable intensity fluorchrome) population. Gates are applied based on fluorochrome intensities in the same manner to all samples. The single stains were:

IgD-PE
IgM-FITC
B220-APC

Alive spleenocytes were gated using side scatter (SSC) and forward scatter (FSC). Within the SSC and FSC gated population, a subpopulation of B220/CD45R positive cells (mouse B-cells) was detected using the APC fluorochrome. The single positive B220/CD45R population was further subdivided into a cell bearing either IgM fluorescein isothiocyanate (FITC) or IgD fluorochrome in conjunction with mκ FITC fluorochrome. The percentage of each population was calculated using gating system. The splenic B-Cell compartments in the mice of the invention are normal (ie, equivalent to the compartments of mice expressing only mouse antibody chains).

(b) Bone Marrow B Progenitor Analysis

To obtain a single cell suspension from bone marrow for each mouse, the femur and tibia were flushed with Phosphate-Buffered Saline (PBS) supplemented with 3% heat inactivated foetal calf serum (FCS). Cells were further passage through a 30 μm cell strainer to remove bone pieces or cell clumps. Cells were resuspended in cold PBS supplemented with 3% serum. $2 \times 10^6$ cells were added to individual tubes, spun down to remove excess of buffer, and resuspended in fresh 100 μl of PBS+3% FCS. To each individual tube the following antibodies were added: anti-Leukosialin (CD43) fluorescein isothiocyanate (FITC) (eBioscience, clone eBioR2/60) and anti-B220/CD45R (eBioscience, clone RA3-6B2) allophycocyanin (APC). Cells were incubated in the dark at 6° C. for 15 minutes followed by several washes with fresh PBS+3% FCS to remove unbound antibody. Cells were analysed using a fluorescence-activated cell sorting (FACS) analyser from Miltenyi Biotech. Alive bone marrow cells were gated using side scatter (SSC) and forward scatter (FSC). We used gates to identify and define subsets of cell populations on plots with logarithmic scale. Before gates are applied a single stain antibody for each fluorochrome is used to discriminate between a positive (high intensity fluorochrome) and negative (no detectable intensity fluorchrome) population. Gates are applied based on fluorochrome intensities in the same manner to all samples. The single stains were:

B220-APC
CD43-FITC

Within the alive population a double population of B220/CD45R and CD43 positive cells was identified as a pre-B, pro-B and pre-pro B cells. The splenic B-Cell compartments in the mice of the invention are normal (ie, equivalent to the compartments of mice expressing only mouse antibody chains).

Transgenic Mice of the Invention Develop Normal Ig Expression

Quantification of Serum IgM and IgG 96-well NUNC plates were coated initially with a capture antibody (goat anti-mouse Fab antibody at 1 μg/ml) overnight at 4° C.). The IgG plates used anti-Fab, (M4155 Sigma) and the IgM plates used anti-Fab (OBT1527 AbD Serotec). Following three washes with phosphate buffer saline (PBS) containing 0.1% v/v Tween20, plates were blocked with 200 μl of PBS containing 1% w/v bovine serum albumin (BSA) for 1 hour at room temperature (RT). The plates were washed three times as above and then 50 μl of standards (control mouse isotype antibodies, IgG1 (M9269 Sigma), IgG2a (M9144 Sigma), IgG2b (M8894 sigma), IgM (M3795 Sigma) or serum samples diluted in PBS with 0.1% BSA were added to each well, and incubated for 1 hour at RT. After washing three times as above 100 μl of detection antibody (goat anti-mouse isotype specific antibody-horseradish peroxidase conjugated, 1/10000 in PBS with 0.1% Tween) (anti-mouse IgG1 (STAR132P AbD Serotec), anti-mouse IgG2a (STAR133P AdD Serotec), anti-mouse IgG2b (STAR134P AbD Serotec) and anti-mouse IgM (ab97230 Abcam) were added into each well and incubated for 1 hour at RT. The plates were washed three times as above and developed using tetramethylbenzidine substrate (TMB, Sigma) for 4-5 minutes in the dark at RT.

Development was stopped by adding 50 µl/well of 1 M sulfuric acid. The plates were read with a Biotek Synergy HT plate reader at 450 nm.

CONCLUSION

Inversion of endogenous $V_H$-D-$J_H$ following the human IGH BAC insertion results in inactivation of rearrangement of endogenous $V_H$ to inserted human D-$J_H$. The inventors observed, however, that surprisingly the inactivation of endogenous heavy chain expression does not change the ratio of B-cells in the splenic compartment (FIG. 66) or bone marrow B progenitor compartment (FIG. 67) and the immunoglobulin levels in serum are normal and the correct Ig subtypes are expressed (FIG. 68). This was shown in mice expressing human heavy chain variable regions with mouse light chains (FIGS. 66A and 67A) as well as in mice expressing both human heavy chain variable regions and human light chain variable regions (FIGS. 66B and 67B). These data demonstrate that inserted human IGH gene segments (an insertion of at least human $V_H$ gene segments $V_H$2-5, 7-4-1, 4-4, 1-3, 1-2, 6-1, and all the human D and $J_H$ gene segments D1-1, 2-2, 3-3, 4-4, 5-5, 6-6, 1-7, 2-8, 3-9, 5-12, 6-13, 2-15, 3-16, 4-17, 6-19, 1-20, 2-21, 3-22, 6-25, 1-26 and 7-27; and J1, J2, J3, J4, J5 and J6) are fully functional in the aspect of rearrangement, BCR signalling and B cell maturation. Functionality is retained also when human light chain VJ gene segments are inserted to provide transgenic light chains, as per the insertion used to create the K2 allele. This insertion is an insertion comprising human gene segments Vκ2-24, Vκ3-20, Vκ1-17, Vκ1-16, Vκ3-15, Vκ1-13, Vκ1-12, Vκ3-11, Vκ1-9, Vκ1-8, Vκ1-6, Vκ1-5, Vκ5-2, Vκ4-1, Jκ1, Jκ2, Jκ3, Jκ4 and Jκ5. Greater than 90% of the antibodies expressed by the S1F/HA; K2/KA mice comprised human heavy chain variable regions and human kappa light chain variable regions. These mice are, therefore, very useful for the selection of antibodies having human variable regions that specifically bind human antigen following immunisation of the mice with such antigen. Following isolation of such an antibody, the skilled person can replace the mouse constant regions with human constant regions using conventional techniques to arrive at totally human antibodies which are useful as drug candidates for administration to humans (optionally following mutation or adaptation to produce a further derivative, eg, with Fc enhancement or inactivation or following conjugation to a toxic payload or reporter or label or other active moiety).

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference

We claim:
1. A mouse whose genome comprising a homozygous recombinant immunoglobulin light chain locus,
said homozygous recombinant immunoglobulin light chain locus comprising unrearranged human V light chain gene segments positioned (i) at an endogenous mouse immunoglobulin light chain locus comprising an endogenous light chain enhancer and (ii) upstream of a constant region,
said homozygous recombinant light chain locus being functional to rearrange to express an Ig light chain comprising a human V region,
wherein said homozygous recombinant immunoglobulin light chain locus comprises human Vλ gene segments and Jλ gene segments operatively linked to an endogenous kappa light chain enhancer at an endogenous kappa locus,
wherein at least 80% of the immunoglobulin light chains that comprise λ variable regions expressed in said mouse comprise human λ variable regions,
and wherein said mouse comprises IgG comprising human Vλ,
wherein said human Vλ and Jλ gene segments comprise at least the functional V and J gene segments from Vλ2-18 to Cλ7 of a human λ light chain locus,
wherein said mouse expresses endogenous λ light chain;
wherein said mouse comprises B cells expressing an immunoglobulin chain comprising a human Vλ and B cells comprising an immunoglobulin chain comprising an endogenous Vλ, and among said human and endogenous Vλ said human Vλ predominates,
wherein the recombinant immunoglobulin light chain locus comprising human Vλ gene segments and Jλ gene segments is positioned upstream of an endogenous constant kappa region, wherein B cells of said mouse comprise immunoglobulin comprising human λ variable region relative to immunoglobulin comprising mouse λ variable region at a ratio of 80:15.

2. A mouse whose genome comprising a homozygous recombinant immunoglobulin light chain locus,
said homozygous recombinant immunoglobulin light chain locus comprising unrearranged human V light chain gene segments positioned (i) at an endogenous mouse immunoglobulin light chain locus comprising an endogenous light chain enhancer and (ii) upstream of a constant region,
said homozygous recombinant light chain locus being functional to rearrange to express an Ig light chain comprising a human V region,
wherein said homozygous recombinant immunoglobulin light chain locus comprises human Vλ gene segments and Jλ gene segments operatively linked to an endogenous kappa light chain enhancer at an endogenous kappa locus,
wherein at least 80% of the immunoglobulin light chains that comprise λ variable regions expressed in said mouse comprise human λ variable regions,
and wherein said mouse comprises IgG comprising human Vλ,
wherein said human Vλ and Jλ gene segments comprise at least the functional V and J gene segments from Vλ2-18 to Cλ7 of a human λ light chain locus,
wherein said mouse expresses endogenous λ light chain;
wherein said mouse comprises B cells expressing an immunoglobulin chain comprising a human Vλ and B cells comprising an immunoglobulin chain comprising an endogenous Vλ, and among said human and endogenous Vλ said human Vλ predominates, wherein the recombinant immunoglobulin light chain locus comprising human Vλ gene segments and Jλ gene segments is positioned upstream of an endogenous constant kappa region, and wherein 80% of total splenic B cells of said mouse comprise human λ variable regions.

3. A mouse whose genome comprising a homozygous recombinant immunoglobulin light chain locus,
said homozygous recombinant immunoglobulin light chain locus comprising unrearranged human V light chain gene segments positioned (i) at an endogenous mouse immunoglobulin light chain locus comprising an endogenous light chain enhancer and (ii) upstream of a constant region,
said homozygous recombinant light chain locus being functional to rearrange to express an Ig light chain comprising a human V region,
wherein said homozygous recombinant immunoglobulin light chain locus comprises human Vλ gene segments and Jλ gene segments operatively linked to an endogenous kappa light chain enhancer at an endogenous kappa locus,
wherein at least 80% of the immunoglobulin light chains that comprise λ variable regions expressed in said mouse comprise human λ variable regions,
and wherein said mouse comprises IgG comprising human Vλ,
wherein said human Vλ and Jλ gene segments comprise at least the functional V and J gene segments from Vλ2-18 to Cλ7 of a human λ light chain locus,
wherein said mouse expresses endogenous λ light chain;
wherein said mouse comprises B cells expressing an immunoglobulin chain comprising a human Vλ and B cells comprising an immunoglobulin chain comprising an endogenous Vλ, and among said human and endogenous Vλ said human Vλ predominates, wherein the recombinant immunoglobulin light chain locus comprising human Vλ gene segments and Jλ gene segments is positioned upstream of an endogenous constant kappa region, and wherein 84% of light chains of total splenic B cells of said mouse comprise human λ variable regions.

4. A mouse whose genome comprising a homozygous recombinant immunoglobulin light chain locus, said homozygous recombinant immunoglobulin light chain locus comprising unrearranged human V light chain gene segments positioned (i) at an endogenous mouse immunoglobulin light chain locus comprising an endogenous light chain enhancer and (ii) upstream of a constant region, said homozygous recombinant light chain locus being functional to rearrange to express an Ig light chain comprising a human V region,
wherein said homozygous recombinant immunoglobulin light chain locus comprises human Vλ gene segments and Jλ gene segments operatively linked to an endogenous kappa light chain enhancer at an endogenous kappa locus, wherein at least 80% of the immunoglobulin light chains that comprise λ variable regions expressed in said mouse comprise human λ variable regions,
and wherein said mouse comprises IgG comprising human Vλ,
wherein said human Vλ and Jλ gene segments comprise at least the functional V and J gene segments from Vλ2-18 to Cλ7 of a human v light chain locus, wherein said mouse exhibits relative usage of Vλ gene segments in splenic B cells typical of the relative usage of Vλ gene segments in splenic B cells of humans.

5. The mouse of claim 4, wherein said unrearranged human V light chain gene segments comprise a 3' human V segment which is positioned within 100 kb of said endogenous light chain enhancer.

6. The mouse of claim 4, wherein said endogenous light chain enhancer is in germline order relative to an endogenous constant region.

7. The mouse of claim 4, wherein said endogenous kappa enhancer comprises an iEκ or 3'Eκ enhancer or both.

8. The mouse of claim 4, wherein the recombinant immunoglobulin light chain locus comprising human Vλ gene segments and Jλ gene segments is positioned upstream of an endogenous constant kappa region, wherein the endogenous lambda loci are intact, wherein said mouse does not comprise endogenous kappa chain.

9. The mouse of claim 8, wherein B cells of said mouse comprise immunoglobulin comprising human λ constant region relative to immunoglobulin comprising mouse λ constant region at a ratio of 80:15.

10. The mouse of claim 8, wherein 80% of total splenic B cells of said mouse comprise human λ variable regions.

11. The mouse of claim 8, wherein 84% of light chains of total splenic B cells of said mouse comprise human λ variable regions.

12. The mouse of claim 4, wherein said IgG comprising human Vλ regions comprises antigen specific human Vλ.

13. The mouse of claim 4, wherein said IgG comprising human Vλ regions comprises a repertoire of human λ variable regions.

14. The mouse of claim 4, wherein said mouse produces subsequent generation mice comprising unrearranged human Vλ and Jλ light chain gene segments positioned (i) at an endogenous mouse immunoglobulin light chain locus comprising an endogenous light chain enhancer and (ii) upstream of a constant region, said recombinant light chain locus being functional to rearrange to express an Ig light chain comprising a human V region.

15. The mouse of claim 4, wherein endogenous Vκ expression is inactive,
wherein said mouse expresses λ immunoglobulin light chains comprising a plurality of human λ variable regions encoded by human Vλ and Jλ gene segments,
wherein said human Vλ comprises VA3 1, Vλ2-18, Vλ3-16, V2-14, Vλ3-12, Vλ2-11, Vλ3-10, Vλ3-9, Vλ2-8, and Vλ4-3, and wherein said human Vλ and Jλ gene segments are included in said human λ locus DNA.

16. A mouse whose genome comprising a homozygous recombinant immunoglobulin light chain locus,
said homozygous recombinant immunoglobulin light chain locus comprising unrearranged human V light chain gene segments positioned (i) at an endogenous mouse immunoglobulin light chain locus comprising endogenous light chain enhancer and (ii) upstream of a constant region,
said homozygous recombinant light chain locus being functional to rearrange to express an Ig light chain comprising a human V region,
wherein said homozygous recombinant immunoglobulin light chain locus comprises human Vλ gene segments and Jλ gene segments operatively linked to an endogenous kappa light chain enhancer at an endogenous kappa locus, wherein at least 80% of the immunoglobulin light chains that comprise λ variable regions expressed in said mouse comprise human λ variable regions,
and wherein said mouse comprises IgG comprising human Vλ,
wherein said human Vλ and Jλ gene segments comprise at least the functional V and J gene segments from Vλ2-18 to Cλ7 of a human λ light chain locus,
and wherein said mouse expresses light chains comprising an endogenous Vλ,
wherein said mouse comprises B cells expressing an immunoglobulin chain comprising a human Vλ and B cells comprising an immunoglobulin chain comprising an endogenous Vλ, and among said human and endogenous Vλ said human Vλ predominates,
wherein said mouse exhibits relative usage of Jλ gene segments in splenic B cells typical of the relative usage of Jλ gene segments in splenic B cells of humans.

17. The mouse of claim 16, wherein said unrearranged human V light chain gene segments comprise a 3' human V segment which is positioned within 100 kb of said endogenous light chain enhancer.

18. The mouse of claim 16, wherein said endogenous light chain enhancer is in germline order relative to an endogenous constant region.

19. The mouse of claim 16, wherein said endogenous kappa enhancer comprises an iEκ or 3'Eκ enhancer or both.

20. The mouse of claim 16, wherein the recombinant immunoglobulin light chain locus comprising human Vλ gene segments and Jλ gene segments is positioned upstream of an endogenous constant kappa region, wherein the endogenous lambda loci are intact, wherein said mouse does not comprise endogenous kappa chain.

21. The mouse of claim 20 wherein B cells of said mouse comprise immunoglobulin comprising human λ constant region relative to immunoglobulin comprising mouse λ constant region at a ratio of 80:15.

22. The mouse of claim 20, wherein 80% of total splenic B cells of said mouse comprise human λ variable regions.

23. The mouse of claim 20, wherein 84% of light chains of total splenic B cells of said mouse comprise human λ variable regions.

24. The mouse of claim 16, wherein said IgG comprising human Vλ regions comprises antigen specific human Vλ.

25. The mouse of claim 16, wherein said IgG comprising human Vλ regions comprises a repertoire of human λ variable regions.

26. The mouse of claim 16, wherein said mouse produces subsequent generation mice comprising unrearranged human Vλ and Jλ light chain gene segments positioned (i) at an endogenous mouse immunoglobulin light chain locus comprising an endogenous light chain enhancer and (ii) upstream of a constant region, said recombinant light chain locus being functional to rearrange to express an Ig light chain comprising a human V region.

27. The mouse of claim 16, wherein endogenous Vκ expression is inactive, wherein said mouse expresses λ immunoglobulin light chains comprising a plurality of human λ variable regions encoded by human Vλ and Jλ gene segments, wherein said human Vλ comprises Vλ3 1, Vλ2-18, Vλ3-16, V2-14, Vλ3-12, Vλ2-11, Vλ3-10, Vλ3-9, Vv2-8, and Vλ4-3, and wherein said human Vλ and Jλ gene segments are included in said human λ locus DNA.

* * * * *

SEQUENCE LISTING

```
<160> NUMBER OF SEQ ID NOS: 132

<210> SEQ ID NO 1
<211> LENGTH: 4272
<212> TYPE: DNA
<213> ORGANISM: Rattus norvegicus

<400> SEQUENCE: 1
agatctgccc atctcaggct agttaaatta gttcatccca gtttggccca acttacccca      60
tctagagtag cgaaactaat ctgagcctag ctaagtccag tttagtttaa tgtagcccag     120
cttggcacag gctaatacat actgctacag tttggtctag cctaccctaa ttaagctgat     180
ccaggcctgg gtagacctag ctcatctcag cccagttaag gttatccagt acatctcttt     240
ccagttcagc tcaggttacc ataccttatc tcaattcagc tcagctagtg taattcatct     300
tagttcatcc cctacccctc tagactccct gttgatctta actcagttta gacatggcca     360
acaaagcctg gcccaactca ggccaggtta gtgtagctca gcataagcag tctagccttg     420
ctcagtctag ctcacccttc ctcatctaaa ttcaactcag ctatgccggc cctgcagcag     480
gtcccctcag ctcacccaag tccaaccagt tcagtctggc tcatttaagt cttgacaatc     540
cccaattcat cccagctcag cttagcataa ctcaggcagt ccattcttag cccaacccag     600
tttagcccag tttatcccag ttcatcctgg ctgtactcag tgcaactcga ttcatgttct     660
cccaggccac ctcagcccag ttcatggtag ctcatctgag cccaacttat cccagctcat     720
cccaaaccac ctcacctaag ccctgctcag cctagctcat ctgagcctag ttcaacctct     780
```

```
ctcatcctgc cagctagccc agtttagtcc acatcatctt gcaaagctca accagcccaa    840
gtcagccggg tccagctcat tcatgtccaa accagctcag tcatgctcat cctaactcag    900
cctcaccatc atccacatca gctagcccag ttcagctgag ctcatcccag cccacttcaa    960
tcacagctca tttaagtaca gctcaccca gctctattta gctcaagcta gcttatttag   1020
cctacttcat cccagctcag cccagccaac tcaactcatc ctagctcagc taaaccctgc   1080
tcagctcacc caagcaaagc tgactccaac ccagatcctt tcagctcagc tcacccagct   1140
caggccagct cacccatccc agctcaccca gcttagctca cccagcccag ctcagcccag   1200
ctcacccagc ccagctcagc ccagctcacc cagcccagct cagcccagct cagctcagct   1260
cagctcagct cagctcagct cacccagctc agctcagcca gctcagctca ccccagctca   1320
gtccagctca gttcagctca ccccagctca gctcacccaa ctcagctcac tcaactcagc   1380
tcacccaact cagctcagct cagttcaccc agctcagctc acccagccca gcacagctca   1440
tctcacccag ctcagctcac ccagcccagc tcccccagc tcaccccagc tcagctcagc   1500
tcaccccagc tcagcccagc tcagctcacc cagctcagct cacccaactc agctcagctc   1560
agttcacccca gctcagctca cccagcccag cacagctcat ctcacccagc ccagctcacc   1620
ccagctcacc ccagctcagc tcagctcagc ccagctcacc cagctcagct cagctcaccc   1680
cagctcagct cacccagctc agctcaccca gcccagctca gctcagctca cccagctca   1740
gcccagctca gctcacccag ctcagctcac ccagcccagc tcaccccagc tcaccccagc   1800
tcagtccagc tcagttcagc tcacccagct cagctcaccc aactcaactc agctcagttc   1860
acccagctca gctcagctca ccccagctca cccagctca cccagctcag ttcagctcac   1920
cccagctcag ttcacccagc tcagctcacc cagcccagct cagcccagct caccccagct   1980
cagctcaacc agatcagctc agcccagctc accctagttt agttcaccca gcccagctca   2040
ccccagctca gctcacccca actcagctca cccagctcat cccagctcag ccagctaatc   2100
ccagctcagc tcaccccagc tcagctcacc cagctcagct cacccaactc agctcacccc   2160
agctcacccc agctcatccc agctcatccc agttcagacc tgttcagctc atctcacccc   2220
agctcagctc accccagttc agctcaccta gcccaactca cccagctca gtccagctca   2280
gttcagctca ccccaactca tctcacccag ctcagctcac cccagctcat cccagctcag   2340
ctcaccccag ttcagccctg ttcagctcat ctcaccagc tcagctcatc cagcccagct   2400
caccccagct caccccagct cagtccagct cagttcagct cacccagctc agctcaccca   2460
actcaactca gctcagttca cccagctcag ctcagctcac cccagctcac cagctcagt   2520
tcagctcacc ccagctcagt tcacccagct cagctcaccc agcccagctc aaccagatca   2580
gctcagccca gctcaccca gtttagttca cccagcccag ctcacccag ctcagctcac   2640
cccaactcag ctcacctagc tcatcccagc tcagctcacc ccagctcagc tcaccccagc   2700
tcatctcacc ccagctcagc tcacccagct catcccagct cagctcagcc agctcatcc   2760
cagccctgct catcccagct cagctcagct cagcccagct cagcccagct cagcccagct   2820
cagcccagct cagcccagct cagctcaacc cagctcagct cacccagccc agctcagccc   2880
agctcaccca gctcagctca cccagctca gctcacccca gctcatctca cccagctcag   2940
ctcacccagc tcagcccagc tcagctcagc tcacccagct catctcaccc agctcagctc   3000
acccagctc atcccagctc agctcacccc agttcagccc tgttcagctc atctcacccc   3060
agctcagctc acccagttca gctcatccca gcccatccca gctcagctca gcccagctca   3120
gcccagctca gcccagccca gcccagccca gctcagctca gcccagctca gcccagctca   3180
```

```
gtccagctca gcttagccca gcccagctca gctcagccca gctcagccca gctcagccca    3240
gctcagctca cccagctcac cccagctcag cccagctcag cccagctcag ctcacccagc    3300 tcacccacc ccagctcacc ccagttcagc ccagctcagc ccagctcagc ccagcccagc    3360
ccagcccagc ccagcccagc tcagcccagc tcagctcagc ccagcccagc tcagctcagc    3420
ccagctcagc ccagctcatc ccagctcagc tcacccagc tcagcccagc tcagcccagc    3480
tcagctcacc cagctcaccc caccccagct caccccagtt cagcccagct catccagctc    3540
agctcacccc cagctctgct cacccagctc agctcagctt acccagctca gctcaactca    3600
cccagctcag ctcacccagc tcagctcagc tcaccccagc ccagctcagc tcagctcacc    3660
ccagctctgc tcacccagct cagctcagct cacctcagct ctgctcaccc agctcagctc    3720
aaccacctca ggtcagccca gctcaccca gcttacccca gctcacccag ctcagctcag    3780
ctcacccagc tcagctcacc cagctcagct caccccagct taccccagct caccccagct    3840
cagctaaccc agctcagctc acccagctca gctcacccag ctcagctcat cccagctcac    3900
cccagctacc acagagtagc tcatgctagc tcagctcacc ccagcacaac acagcccaac    3960
acagctcagt tcagagcagt ccagtagagt ttagctccaa tcagcccaga tcaagacaat    4020
tcattccaat ttggctatct tggttaagtc agcctagttt agcttagccg gcctagctca    4080
attcagctca ttgcagtcta cctcgttcct gctcaagtcc agctttggct acctcagagt    4140
aatcatctca gcttagcaca tttttgaagg gctcagggaa gcctacacat ctcagtccaa    4200
ctgtgcttaa ctagagccta gcttcctagc caggctgtca accttgttca ctaaattttg    4260
ctcagcaagc tt                                                        4272
```

<210> SEQ ID NO 2
<211> LENGTH: 22190
<212> TYPE: DNA
<213> ORGANISM: Artificial Sequence
<220> FEATURE:
<223> OTHER INFORMATION: Tragetting Vector (long version)

<400> SEQUENCE: 2

```
gcggccgcaa cctgggcaaa tgggagctta gcaacaatgt aggggctgg acctagactt      60 cctacacatt tgtagcagat gtgcagcttg gtcttcatgt gtgtattacc ctaacatttg     120
gagcaggagc tgtctctgac tctgttgcct gccattggat cccttcccc tgcttgggct     180 gccttgtttg gccttagtag gaaaggatgt gcttagtcct gctgtgactt gatgtcccta    240
ggcagaatga taccccaggg gggctcccca tctctgagga gatgggcaaa gggtaatggt    300
tggagggact tgtgaggctg ggactgggag gagagaaagg agacagctgt aactggaatg    360
atgttaagtg aacaaatgaa tggatagatt agatagacag atagacagac agacagacag    420
acagacagac agacagacag acagatagaa agatagatag ataaggggaa aaagaaacgt    480
agctgagcaa gccagagaga gcaagccaaa taagcagcat cctccatga cttttccttc    540 agctcctgcc tatgagtctg ccttgacttc cctcagtgat tggttgtaag ttaaaaggtg    600
aaataaaccc tttctttgac aagttgcttt tggttctgat ttttatcaca gcaagagaaa    660
atcaaactag aacaaacatg tattttcct ggcacatgtc catagtaagg cagaaatgat    720
cttcagacct agaccataga tactacagag agcagaagtg tagataggtg gacttactgt    780
atgattgtaa tccaagtaaa tctacatagc tagagagcta gaggaaaggc caaagcttcc    840
tctgggaggt cagatcctgt cgcactgtag ccaataaggc atattgcatc acaggaaagg    900
```

```
actaagaccc aggctggcaa tagtgtctgt atcttaacta gacctctcta gtgagtgagg    960
aaggaagttt gtgagagccc agactgtggg ctcggaaggt acctgccatg ccctgttag   1020
taactgagta ctacagcagg agcaggtgtt ctctagaaag cctgagacaa ctctacttct   1080
tctctcaaga gaccacctaa tacaggcctg agagaacaga ctctggaaat agatgggact   1140
taaggagcta agatctagag ctcatctaca gagcagaatc ccagccaaga gaacaaagaa   1200
tactggctct ctctcctgtt ccctactcct agagttctaa aacacactat agggaaggga   1260
gcctctagac ctccgtccat tccccatctt gctcattcca tcttcccatg tccccaggtc   1320
tccaagccac agacactacc tttcctattc acccacctTT ctgtgtccct aggtccccag   1380
gccatagtca cctccccca cacacacccc actcaccctg ccccatctat gccctagat   1440
gcttacttac cagagtcttt tgtctgacgt ggggctacaa gcatctatgc tccctaagca   1500
cctactgctg acctgtagga cccagctctg aaccaactca tataagtaaa tacagactct   1560
cccctgtctt aggatggcct cctggatcag gaggagacca ctgccaaaga accttctctc   1620
agagcactga actcctcccc tgtaccactt aggacagacc tgagacctat tattactgat   1680
taccagagct ctggcagtga ccacggagga gataggtcca ccctggacac aggaaacaca   1740
gcagcagaga tactgctcca tcacaacagt agagtgacac tttagacttt aatttgggtc   1800
actttcctgc tgcagaggtg ggatcagaaa gcaaagagca gtatgagtgc ctgataggca   1860
cccaagtaca ctatagagta ctcatggtga ataaggtacc tccatggctt cccagggagg   1920
ggcactgccc cacccccacc atcacagacc tttctccata gttgataact cagacacaag   1980
tgaatgacag atggacctcc atctactctt attttaaaaa gaagacaaac cccacaggct   2040
cgagaacttt agcgactgtt ttgagagaaa tcattggtcc ctgactcaag agatgactgg   2100
cagattgggg atcagaatac ccatactctg tggctagtgt gaggtttaag cctcagagtc   2160
cctgtggtct ctgactggtg caaggttttg actaagcgga gcaccacagt gctaactggg   2220
accacggtga cacgtggctc aacaaaaacc ttctgtttgg agctctccag ggcagcctg    2280
agctatgagg aagtagagag gcttgagaaa tctgaggaag aaaagagtag atctgagagg   2340
aaaggtagct ttctggaggt caggagacag tgcagagaag aacgagttac tgtgacagg    2400
tcttagatgg ggaaagaatg agcaaatgca agcatcagaa gggtggatgc aatgtcctgc   2460
caaggactta ccaagaggat ccccggacag agcaggcagg tggagttgac tgagaggaca   2520
gggtaggtgc aggtccctct ctcgtttcct ttctccttct cctgtttcct tcctctcttg   2580
tcacaggtct cactatgcta gccaaggcta gcctgaaaga ttaccatcct acagatgggc   2640
ccatccagtt gagttaaggt ggagatctct ccaaacatct gagtttctga ggcttggatg   2700
ccactgggga cgccaaggga ctttgggctg gtttggttg gccccagatg aagggctact   2760
tcactgggtc tataattact ctgatgtcta ggaccagggg gctcaggtca ctcaggtcag   2820
gtgagtcctg catctgggga ctgtgggtt caggtgtcct aaggcaggat gtggagagag   2880
ttttagtata ggaacagagg cagaacagag actgtgctac tggtacttcg atgtctgggg   2940
cgcagggacc acggtcaccg tctcctcagg taagctggct ttttctttc tgcacattcc   3000
attctgaaat gggaaaagat attctcagat ctccccatgt caggccatct gccacactct   3060
gcatgctgca gaagcttttc tgtaaggata gggtcttcac tcccaggaaa agaggcagtc   3120
agaggctagc tgcctgtgga acagtgacaa tcatggaaaa taggcattta cattgttagg   3180
ctacatgggt agatgggttt ttgtacaccc actaaagggg tctatgatag tgtgactact   3240
ttgactactg gggccaaggc accactctca cagtctcctc aggtgagtcc ttacaacctc   3300
```

```
tctcttctat tcagcttaaa tagattttac tgcatttgtt ggggggggaaa tgtgtgtatc    3360
tgaatttcag gtcatgaagg actagggaca ccttgggagt cagaaagggt cattgggagc    3420
cctggctgat gcagacagac atcctcagct cccagacttc atggccagag atttataggg    3480
atcctggcca gcattgccgc taggtccctc tcttctatgc tttctttgtc cctcactggc    3540
ctccatctga gatcatcctg gagccctagc caaggatcat ttattgtcag gggtctaatc    3600
attgttgtca caatgtgcct ggtttgctta ctggggccaa gggactctgg tcactgtctc    3660
tgcaggtgag tcctaacttc tcccattcta aatgcatgtt gggggggattc tgagccttca    3720
ggaccaagat tctctgcaaa cgggaatcaa gattcaaccc ctttgtccca aagttgagac    3780
atgggtctgg gtcagggact ctctgcctgc tggtctgtgg tgacattaga actgaagtat    3840
gatgaaggat ctgccagaac tgaagcttga agtctgaggc agaatcttgt ccagggtcta    3900
tcggactctt gtgagaatta ggggctgaca gttgatggtg acaatttcag ggtcagtgac    3960
tgtctggttt ctctgaggtg aggctggaat ataggtcacc ttgaagacta agaggggtc     4020
caggggcttc tgcacaggca gggaacagaa tgtggaacaa tgacttgaat ggttgattct    4080
tgtgtgacac caggaattgg cataatgtct gagttgccca ggggtgattc tagtcagact    4140
ctggggtttt tgtcgggtat agaggaaaaa tccactattg tgattactat gctatggact    4200
actgggtca aggaacctca gtcaccgtct cctcaggtaa gaatggcctc tccaggtctt     4260
tattttaac ctttgttatg gagttttctg agcattgcag actaatcttg gatatttgtc     4320
cctgagggag ccggctgaga gaagttggga aataaactgt ctagggatct cagagccttt    4380
aggacagatt atctccacat cttttgaaaaa ctaagaatct gtgtgatggt gttggtggag   4440
tccctggatg atgggatagg gactttggag gctcatttga gggagatgct aaaacaatcc    4500
tatggctgga gggatagttg gggctacgcg ttttttaaccc tagaaagata gtctgcgtaa   4560
aattgacgca tgcattcttg aaatattgct ctctctttct aaatagcgcg aatccgtcgc    4620
tgtgcattta ggacatctca gtcgccgctt ggagctcccg tgaggcgtgc ttgtcaatgc    4680
ggtaagtgtc actgattttg aactataacg accgcgtgag tcaaaatgac gcatgattat    4740
cttttacgtg acttttaaga tttaactcat acgataatta tattgttatt tcatgttcta    4800
cttacgtgat aacttattat atatatattt tcttgttata gatatcgcta gtggatccgg    4860
ctggttcttt ccgcctcaga aggtactttt tttttttttt tttttttttt tttttttttt    4920
tttttttttt tttttttttt tttttttaaat ttttgggaat ttattgattt gcatttaaaa   4980
gggaactgct gacaaagatt cactggtaat aatttgaaca agttggaaaa tacagtcaac    5040
attactgaaa cactactaaa ataattccag gacagaacaa aacttcttag atgctgtctt    5100
tgatgtgaaa attgactgct tcttactttt ctaacacacg gtggtataat taacaatatt    5160
caatcacttc tattctttcc tgcatatata aaaattaaaa taccaattaa aaaactaata    5220
tatcttctct ttatttctta cagatatgag ttcaatgttt cactcaatag tgctgtggtt    5280
taagagaatt ttttcattta caagttaaac aacaatccgc ccaaagggaa ctgatagtct    5340
ataggctcat agtgcaaata aacagtttag gaatgcagca actgacattt ctaaagtaca    5400
aaacagataa aattccttaga agatacatgc aaaaagctct actaagcaga tggccacaga   5460
actagaacat tgataatttt actggcgatg tcaataggac tccagatgtt tccaaactca    5520
acttgaactc tcatccttagg cttttgtattt tgcttttcca gtttcactaa tgacacaaac   5580
atgattcaaa tccctgaagt attcattata gtcaagggca tatcctacaa caaacttgtc    5640
```

```
tggaatttca aatccaacaa agtctggctt atatccaaca cttcgtgggg tccttttcac    5700
cagcaagctt gcgaccttga ccatctttgg attatactgc ctgaccaagg aaagcaaagt    5760
ctgcattgtt ttgccagtgt caattatatc ttccacaatc aagacattct ttccagttaa    5820
agttgagaga tcatctccac caattacttt tatgtcccct gttgactggt cattacaata    5880
gctcttcagt ctgataaaat ctacagtcat aggaatggat ctatcactat ttctattcag    5940
tgctttgatg taatccagca ggtcagcaaa gaatttatag ccccccttga gcacacagag    6000
ggctacaatg tgatggcctc ccatctcctt catcacatct cgagcaagac gttcagtcct    6060
acagaaataa aatcaggaat ttaatagaaa gtttcataca ttaaacttta taacaaacac    6120
ctcttagtca ttaaacttcc acaccaacct gggcaatata gtgagacccc atgcctgcaa    6180
aaaaaaaaaa attagccagg catggtagca tgtacctgta gtcccagcta cttgagaggt    6240
gaggtgggaa aatcacttta gtgcaggatg ttgaggctgg agtgaactgt gattgtgcca    6300
ctgcactcca gcctggacaa tagagcaaga ccttgtctca aaaaaatgca ttaaaaattt    6360
tttttaaatc ttccacgtaa cacatccttt gccctcatgt ttcataaggt aaaaaatttg    6420
ataccttcaa aaaaaccaag cataccacta tcataatttt ttttaaatgc aaataaaaac    6480
aagataccat tttcacctat cagactggca ggttctgatt aaatgaaatt tcttggataa    6540
tatacaatat taagagagac tgtagaaact gggccagtgg ctcatgcctg taatcccagc    6600
actttgggag gctgggtaac atggcgaacc ctgtttctac aaaataaaaa tattagctgg    6660
gagtggtggc gcacacctat agtcccagct actcaggagg ctgaggtgga aggatcgctt    6720
gaacccagga ggttgagact gcagtgaact gtgatcattc tgctgcactg caccccagcc    6780
tgggcaacag agaccttgtc tcaaaaaaaa aaaaaaaga gacaaattgt gaagagaaag    6840
gtactctcat ataacatcag gagtatataaa tgattcaact tcttagagga aaatttggca    6900
ataccaaaat attcaataaa ctcttcccc ttgacccaga aattccactt gaataaagct    6960
gaacaagtac caaacatgta aaagaatgtt tcttctagta cagtcggtaa gaacaaaata    7020
gtgtctatca atagtggact ggttaaatca gttatggtat ctccataaga cagaatgcta    7080
tgcaaccttt aaaatatatt agatagctct agacagtgga tccctcgag ggacctaata    7140 acttcgtata gcatacatta tacgaagtta tattaagggt tattgaatat gtcgactaga    7200
cacactaata ttaaaagtgt ccaataacat ttaaaactat actcatacgt taaaatataa    7260
atgtatatat gtacttttgc atatagtata catgcatagc cagtgcttga aagaaatgt    7320 gtacagaagg ctgaaaggag agaacttag tcttcttgtt tatggcctcc atagttagaa    7380
tattttataa cacaaatatt ttgatattat aattttaaaa taaaaacaca gaatagccag    7440
acatacaatg caagcattca ataccaggta aggttttca ctgtaattga cttaacagaa    7500
aattttcaag ctagatgtgc ataataataa aaatctgacc ttgccttcat gtgattcagc    7560
cccagtccat taccctgttt aggactgaga atgcaagac tctggctaga gttccttctt    7620
ccatctccct tcaatgttta ctttgttctg gtccctacag agtcccacta taccacaact    7680
gatactaagt aattagtaag gccctcctct tttatttta ataagaaga ttttagaaag    7740 catcagttat ttaataagtt ggcctagttt atgttcaaat agcaagtact cagaacagct    7800
gctgatgttt gaaattaaca caagaaaag taaaaaaacct cattttaaga tcttacttac    7860
ctgtccataa ttagtccatg gggaataaac acccctttcca aatcctcagc ataatgatta    7920
ggtatgcaaa ataaatcaag gtcataacct ggttcatcat cactaatcac gacgccaggg    7980
ctgcgggtcg ccataacgga gccggccggc gcgcgggctg aataacttcg tataatgtgt    8040
```

```
actatacgaa gttatttgtt caggaggagg aagccggtgg cggagcagag gaggaggcgg    8100
aggcgcagca agaccccccc cccctgcag gtcgaaaggc ccggagatga ggaagaggag    8160
aacagcgcgg cagacgtgcg cttttgaagc gtgcagaatg ccgggcctcc ggaggacctt    8220
cgggcgcccg ccccgcccct gagcccgccc ctgagcccgc ccccggaccc acccttccc     8280 agcctctgag cccagaaagc gaaggagcaa agctgctatt ggccgctgcc ccaaaggcct    8340
acccgcttcc attgctcagc ggtgctgtcc atctgcacga gactagtgag acgtgctact    8400
tccatttgtc acgtcctgca cgacgcgagc tgcggggcgg gggggaactt cctgactagg    8460
ggaggagtag aaggtggcgc gaaggggcca ccaaagaacg gagccggttg gcgcctaccg    8520
gtggatgtgg aatgtgtgcg aggccagagg ccacttgtgt agcgccaagt gcccagcggg    8580
gctgctaaag cgcatgctcc agactgccctt gggaaaagcg cctcccctac ccggtagata   8640
tctataacaa gaaatatat atataataag ttatcacgta agtagaacat gaaataacaa     8700
tataattatc gtatgagtta aatcttaaaa gtcacgtaaa agataatcat gcgtcatttt    8760
gactcacgcg gtcgttatag ttcaaaatca gtgacactta ccgcattgac aagcacgcct    8820
cacgggagct ccaagcggcg actgagatgt cctaaatgca cagcgacgga ttcgcgctat    8880
ttagaaagag agagcaatat ttcaagaatg catgcgtcaa ttttacgcag actatctttc    8940
tagggttaaa agaattcgat atcaagctta tcgatgtagt tggagatttt cagttttttag   9000 aataaaagta ttagttgtgg aatatacttc aggaccacct ctgtgacagc atttatacag    9060
tatccgatgc atagggacaa agagtggagt ggggcacttt cttttagattt gtgaggaatg   9120 ttccgcacta gattgtttaa aacttcattt gttggaagga gagctgtctt agtgattgag    9180
tcaagggaga aaggcatcta gcctcggtct caaagggta gttgctgtct agagaggtct     9240
ggtggagcct gcaaaagtcc agctttcaaa ggaacacaga agtatgtgta tggaatatta    9300
gaagatgttg cttttactct taagttggtt cctaggaaaa atagttaaat actgtgactt    9360
taaaatgtga gagggttttc aagtactcat ttttttaaat gtccaaaatt tttgtcaatc    9420
aatttgaggt cttgtttgtg tagaactgac attacttaaa gtttaaccga ggaatgggag    9480
tgaggctctc tcataccta ttcagaactg acttttaaca ataataaatt aagtttaaaa     9540 tattttaaa tgaattgagc aatgttgagt tggagtcaag atggccgatc agaaccagaa     9600
cacctgcagc agctggcagg aagcaggtca tgtggcaagg ctatttgggg aagggaaaat    9660
aaaaccacta ggtaaacttg tagctgtggt ttgaagaagt ggttttgaaa cactctgtcc    9720
agccccacca aaccgaaagt ccaggctgag caaaacacca cctgggtaat ttgcatttct    9780
aaaataagtt gaggattcag ccgaaactgg agaggtcctc ttttaactta ttgagttcaa    9840
ccttttaatt ttagcttgag tagttctagt ttccccaaac ttaagtttat cgacttctaa    9900
aatgtattta gaattcattt tcaaaattag gttatgtaag aaattgaagg actttagtgt    9960
ctttaatttc taatatattt agaaaacttc ttaaaattac tctattattc ttccctctga   10020
ttattggtct ccattcaatt cttttccaat acccgaagca tttacagtga ctttgttcat   10080 gatcttttt agttgtttgt tttgccttac tattaagact ttgacattct ggtcaaaacg    10140
gcttcacaaa tctttttcaa gaccactttc tgagtattca ttttaggaga aatacttttt   10200
ttttaaatga atgcaattat ctagacttat ttcagttgaa catgctggtt ggtggttgag   10260
aggacactca gtcagtcagt gacgtgaagg gcttctaagc cagtccacat gctctgtgtg   10320
aactccctct ggccctgctt attgttgaat gggccaaagg tctgagacca ggctgctgct   10380
```

```
gggtaggcct ggactttggg tctcccaccc agacctggga atgtatggtt gtggcttctg    10440
ccacccatcc acctggctgc tcatggacca gccagcctcg gtggctttga aggaacaatt    10500
ccacacaaag actctggacc tctccgaaac caggcaccgc aaatggtaag ccagaggcag    10560
ccacagctgt ggctgctgct cttaaagctt gtaaactgtt tctgcttaag agggactgag    10620
tcttcagtca ttgctttagg gggagaaaga gacatttgtg tgtcttttga gtaccgttgt    10680
ctgggtcact cacatttaac tttccttgaa aaactagtaa aagaaaaatg ttgcctgtta    10740
accaataatc atagagctca tggtattttg aggaaatctt agaaacgtg tatacaattg     10800 tctggaatta tttcagttaa gtgtattagt tgaggtactg atgctgtctc tacttcagtt    10860
atacatgtgg gtttgaattt tgaatctatt ctggctcttc ttaagcagaa aatttagata    10920
aaatggatac ctcagtggtt tttaatggtg ggtttaatat agaaggaatt taaattggaa    10980
gctaatttag aatcagtaag gagggaccca ggctaagaag gcaatcctgg gattctggaa    11040
gaaaagatgt ttttagtttt tatagaaaac actactacat tcttgatcta caactcaatg    11100
tggtttaatg aatttgaagt tgccagtaaa tgtacttcct ggttgttaaa gaatggtatc    11160
aaaggacagt gcttagatcc aaggtgagtg tgagaggaca ggggctgggg tatggatacg    11220
cagaaggaag gccacagctg tacagaattg agaaagaata gagacctgca gttgaggcca    11280
gcaggtcggc tggactaact ctccagccac agtaatgacc cagacagaga aagccagact    11340
cataaagctt gctgagcaaa atttagtgaa caaggttgac agcctggcta ggaagctagg    11400
ctctagttaa gcacagttgg actgagatgt gtaggcttcc ctgagcccctt caaaaatgtg    11460 ctaagctgag atgattactc tgaggtagcc aaagctggac ttgagcagga acgaggtaga    11520
ctgcaatgag ctgaattgag ctaggccggc taagctaaac taggctgact taaccaagat    11580
agccaaattg gaatgaattg tcttgatctg ggctgattgg agctaaactc tactggactg    11640
ctctgaactg agctgtgttg ggctgtgttg tgctggggtg agctgagcta gcatgagcta    11700
ctctgtggta gctggggtga gctgggatga gctgagctgg gtgagctgag ctgggtgagc    11760
tgagctgggt tagctgagct ggggtgagct ggggtaagct ggggtgagct gagctgggtg    11820
agctgagctg ggtgagctga gctgagctgg gtgagctggg gtaagctggg gtgagctggg    11880
ctgacctgag gtggttgagc tgagctgggt gagcagagct gaggtgagct gagctgagct    11940
gggtgagcag agctggggtg agctgagctg agctgggctg gggtgagctg agctgagctg    12000
ggtgagctga gctgggtgag ttgagctgag ctgggtaagc tgagctgagc tgggtgagca    12060
gagctggggg tgagctgagc tggatgagct gggctgaact ggggtgagct ggggtggggt    12120
gagctgggtg agctgagctg gctgagctg gctgagctg gggtgagctg agctgggatg      12180
agctgggctg agctgggctg agctgagctg gctgggctg agctgagctg ggctgagctg     12240
ggctgggctg ggctgggctg ggctgggctg agctgggctg agctgggctg aactgggtg     12300 agctggggtg gggtgagctg ggtgagctga gctgggctga gctgggctga gctgggtga     12360 gctgggtgag ctgagctggg ctgagctggg ctgagctggg ctgagctgag ctgggctggg    12420
ctaagctgag ctggactgag ctgggctgag ctgggctgag ctgagctggg ctgggctggg    12480
ctgggctgag ctgggctgag ctgggctgag ctgagctggg atgggctggg atgagctgaa    12540
ctgggtgagc tgagctgggg tgagatgagc tgaacagggc tgaactgggg tgagctgagc    12600
tgggatgagc tggggtgagc tgagctgggt gagatgagct gggtgagctg agctgagctg    12660
ggctgagctg ggtgagctga gctgggtgag atgagctggg gtgagctgag ctggggtgag    12720
ctgagctggg tgagctgggc tgagctgggc tgggtgagct gagctgggtt gagctgagct    12780
```

```
gggctgagct gggctgagct gggctgagct gggctgagct gggctgagct gagctgagct    12840
gggatgagca gggctgggat gagctgggct gagctgagct gggatgagct gggtgagctg    12900
agctggggtg agatgagctg gggtgagctg agctggggtg agctgagctg ggatgagcta    12960
ggtgagctga gttggggtga gctgagctgg ggtgagctgg gctgggtgaa ctaaactagg    13020
gtgagctggg ctgagctgat ctggttgagc tgggctgggt gagctgagct gggtgaactg    13080
agctggggtg agctgaactg agctgggtga gctggggtga gctgagctga gctgggtgaa    13140
ctgagctgag ttgagttggg tgagctgagc tgggtgagct gaactgagct ggactgagct    13200
ggggtgagct ggggtgagct gggctggatg agctgagctg ggtgagatga gctgaacagg    13260
gctgaactgg ggtgagctga gctgggatga gctggggtga gctgagctgg gtgagatgag    13320
ttggggtgag ctgaactgag ctggactgag ctggggtgag ttgggctagg tgagctgaac    13380
tggggtgagc tgagctgggg tgagatgagc tgaacaggtc tgaactggga tgagctggga    13440
tgagctgggg tgagctgggg tgagctgagt tgggtgagct gagctgggtg agctgagctg    13500
gggtgagctg agctgggatt agctggctga gctgggatga gctgggtgag ctgagttggg    13560
gtgagctgag ctggggtgag ctgggctggg tgaactaaac tagggtgagc tgggctgagc    13620
tgatctggtt gagctgagct ggggtgagct gggctgagct gggctgggtg agctgagctg    13680
ggtgaactga gctggggtga gctgaactga gctgggtgag ctggggtgag ctggggtgag    13740
ctgagctgag ctgggtgaac tgagctgagt tgagttgggt gagctgagct gggtgagctg    13800
aactgagctg gactgagctg gggtgagctg gggtgagctg gctgggtga gctgagctgg     13860
gtgagctgag ctgggctgag ctggggtgag ctgagctgag ctgggctggg tgagctgagc    13920
tgggtgagct gagctggggt gagctgagct gagctgggtg agctgggctg agctgagctg    13980
agctggggtg agctggggtg agctgggctg ggtgagatga gctgtgctgg gctgggtgag    14040
ctgagctggg tgaactgagc tgagctgagt tgggtgagct gagctgggtg agctgagctg    14100
ggctgagctg gggtgagctg agctgagctg gggtgagctg gggtgagctg ggctgggtga    14160
gctgagctgg gtgagatgag ctgtgctggg ctgggtgagc tgagctgggt gaactgagct    14220
gagctgagtt gggtgagctg agttgagtga gctgagttgg gtgagctgag ctgggggtgag   14280
ctgaactgag ctggactgag ctggggtgag ctgagctggc tgagctgagc tgggtgagct    14340
gagctgagct gagctgagct gagctgagct gggctgagct gggctgggtg agctgggctg    14400
agctgggctg ggtgagctgg gctgagctgg gctgggtgag ctaagctggg tgagctggga    14460
tgggtgagct ggcctgagct gggtgagctg agctgaaagg atctggggttg gagtcagctt    14520
tgcttgggtg agctgagcag ggtttagctg agctaggatg agttgagttg gctgggctga    14580
gctgggatga agtaggctaa ataagctagc ttgagctaaa tagagctggg gtgagctgta    14640
cttaaatgag ctgtgattga agtgggctgg gatgagctca gctgaactgg gctagctgat    14700
gtggatgatg gtgaggctga gttaggatga gcatgactga gctggtttgg acatgaatga    14760
gctggacccg gctgacttgg gctggttgag ctttgcaaga tgatgtggac taaactgggc    14820
tagctggcag gatgagagag gttgaactag gctcagatga gctaggctga gcagggctta    14880
ggtgaggtgg tttgggatga gctgggataa gttgggctca gatgagctac catgaactgg    14940
gctgaggtgg cctgggagaa catgaatcga gttgcactga gtacagccag gatgaactgg    15000
gataaactgg gctaaactgg gttgggctaa gaatggactg cctgagttat gctaagctga    15060
gctgggatga attggggatt gtcaagactt aaatgagcca gactgaactg gttggacttg    15120
```

```
ggtgagctga ggggacctgc tgcagggccg gcatagctga gttgaattta gatgaggaag    15180
ggtgagctag actgagcaag gctagactgc ttatgctgag ctacactaac ctggcctgag    15240
ttgggccagg cttttgttggc catgtctaaa ctgagttaag atcaacaggg agtctagagg   15300
ggtaggggat gaactaagat gaattacact agctgagctg aattgagata aggtatggta    15360
acctgagctg aactggaaag agatgtactg gataacctta actgggctga gatgagctag    15420
gtctacccag gcctggatca gcttaattag ggtaggctag accaaactgt agcagtatgt    15480
attagcctgt gccaagctgg gctacattaa actaaactgg acttagctag gctcagatta    15540
gtttcgctac tctagatggg gtaagttggg ccaaactggg atgaactaat ttaactagcc    15600
tgagatgggc agatctgaat gagcagagct gggatgaact gaatgagttt caccaggcct    15660
ggaccagtta ggctaggacc tcgttctata gaggcagact gtgtgctaca gtggagtttc    15720
aagatgattc catgagtcct ccccgccccc aacataaccc accttcctcc taccctacaa    15780
gcctgtctgg tgtgtaaatc ccagctttgt gtgctgatac agaagcctga gcccctcccc    15840
cacctccacc tacctattac tttgggatga gaatagttct cccagccagt gtctcagagg    15900
gaagccaagc aggacaggcc caaggctact tgagaagcca ggatctaggc ctctccctga    15960
gaacgggtgt tcatgcccct agagttggct gaagggccag atccacctac tctagaggca    16020
tctctccctg tctgtgaagg cttccaaagt cacgttcctg tggctagaag gcagctccat    16080
agccctgctg cagtttcgtc ctgtatacca ggttcaccta ctaccatatc tagccctgcc    16140
tgccttaaga gtagcaacaa ggaaatagca gggtgtagag ggatctcctg tctgacagga    16200
ggcaagaaga cagattctta ccccctccatt tctcttttat ccctctctgg tcctcagaga   16260
gtcagtcctt cccaaatgtc ttcccctcg tcctgcga gagcccctg tctgataaga        16320 atctggtggc catgggctgc ctggccaggg acttcctgcc cagcaccatt tccttcacct    16380
ggaactacca gaacaacact gaagtcatcc agggtatcag aaccttccca acactgagga    16440 caggggggcaa gtacctagcc acctcgcagg tgttgctgtc tcccaagagc atccttgaag   16500
gttcagatga ataccctggta tgcaaaatcc actacggagg caaaaacaaa gatctgcatg   16560
tgcccattcc aggtaagaac caaaccctcc cagcaggggt gccaggccc aggcatggcc     16620 cagagggagc agcggggtgg ggcttaggcc aagctgagct cacaccttga cctttcattc    16680
cagctgtcgc agagatgaac cccaatgtaa atgtgttcgt cccaccacgg gatgccttct    16740
ctggccctgc accacgcaag tctaaactca tctgcgaggc cacgaacttc actccaaaac    16800
cgatcacagt atcctggcta aaggatggga agctcgtgga atctggcttc accacagatc    16860
cggtgaccat cgagaacaaa ggatccacac cccaaaccta caaggtcata agcacactta    16920
ccatctctga aatcgactgg ctgaacctga atgtgtacac ctgccgtgtg atcacaggg    16980 gtctcacctt cttgaagaac gtgtcctcca catgtgctgc cagtgagtgg cctgggataa    17040
gcccaatgcc tagccctccc agattaggga agtcctccta caattatggc caatgccacc    17100
cagacatggt catttgctcc ttgaactttg gctccccaga gtggccaagg acaagaatga    17160
gcaataggca gtagaggggt gagaatcagc tggaaggacc agcatcttcc cttaagtagg    17220
tttgggggat ggagactaag cttttttcca acttcacaac tagatatgtc ataacctgac    17280
acagtgttct cttgactgca ggtccctcca cagacatcct aaccttcacc atccccccct    17340
cctttgccga catcttcctc agcaagtccg ctaacctgac ctgtctggtc tcaaacctgg    17400 caacctgatga aaccctgaat atctcctggg cttctcaaag tggtgaacca ctggaaacca    17460
aaattaaaat catggaaagc catcccaatg gcaccttcag tgctaagggt gtggctagtg    17520
```

```
tttgtgtgga agactggaat aacaggaagg aatttgtgtg tactgtgact cacagggatc   17580
tgccttcacc acagaagaaa ttcatctcaa aacccaatgg taggtatccc cccttcccctt  17640 cccctccaat tgcaggaccc ttcctgtacc tcatagggag ggcaggtcct cttccaccct   17700
atcctcacta ctgtcttcat ttacagaggt gcacaaacat ccacctgctg tgtacctgct   17760
gccaccagct cgtgagcaac tgaacctgag ggagtcagcc acagtcacct gcctggtgaa   17820
gggcttctct cctgcagaca tcagtgtgca gtggcttcag agagggcaac tcttgcccca   17880
agagaagtat gtgaccagtg ccccgatgcc agagcctggg gccccaggct tctactttac   17940
ccacagcatc ctgactgtga cagaggagga atggaactcc ggagagacct atacctgtgt   18000
tgtaggccac gaggccctgc cacacctggt gaccgagagg accgtggaca agtccactgg   18060
taaacccaca ctgtacaatg tctccctgat catgtctgac acaggcggca cctgctattg   18120
accatgctag cgctcaacca ggcaggccct gggtgtccag ttgctctgtg tatgcaaact   18180
aaccatgtca gagtgagatg ttgcattttta taaaaattag aaataaaaaa aatccattca   18240
aacgtcactg gttttgatta tacaatgctc atgcctgctg agacagttgt gttttgcttg   18300
ctctgcacac accctgcata cttgcctcca ccctggccct tcctctacct tgccagtttc   18360
ctccttgtgt gtgaactcag tcaggcttac aacagacaga gtatgaacat gcgattcctc   18420
cagctacttc tagatatatg gctgaaagct tgcctaacct ggtgcaggca gcattcaggc   18480
acatatatag acacacatgc atttatacat agatatatag gtacacatgt gtagacacat   18540
acatgaatgt gtattcatgg acacacagac aaaggtacac atatatacac atgagttcat   18600
gcgcacacac atgcatggac acttacaaac gccttcagag acaaataggc atagacacac   18660
aaccactcac agaaacagat accaatatgc atggtcctgt gtacacagaa acagactata   18720
ggcaaatata cacaaataaa ctatatagat acaaagatat gcatatacac acatgtacag   18780
aaacatcttc acatgtgtac actaacatgt ggacaggtat agcacacaga tacacctgga   18840
ctctgaccag ggctgtaatc tccaaggctc acggctcaga gagcctacac taggctgggt   18900
cactgatact cctcaggagc ccactctatg attgggagag ataacccag gtacaaagta    18960 tgcctatctg tctcaacacc atggggcaga agatactcca ctaaccaccc atgacagaaa   19020
gttagccttg gctgtgtctc cattaataga acacctcaga agaccaatgt gaaattgcct   19080
aacccactca cacccaccct gatctccagt tcaaaatgca gaaaacataa tgcagttgtc   19140
caaaagatgc cccaaccaca cacacacaca cacacacaca cacacacaca cacacacaca   19200
cacacataca cacacacaca ccatcaagga gcctctgtaa ggagtcacca cccaataaca   19260 ctgcctctttt gggctcatat cctggacatt cttcatattc atatccattt ggggcctagg   19320
ctttagatat ccccaagggc tcatctttac agggatcaga gatcccaata aatgccctgg   19380
tcccacagcc tccctcaggt atctgtctgt ttatctcttg gtacctttct tagacgttag   19440
gtggcacttt tcggggaaat gtgcgcggaa cccctatttg tttattttttc taaatacatt   19500 caaatatgta tccgctcatg agacaataac cctgataaat gcttcaataa tattgaaaaa   19560
ggaagagtat gagtattcaa catttccgtg tcgcccttat tccctttttt gcggcatttt   19620
gccttcctgt ttttgctcac ccagaaacgc tggtgaaagt aaaagatgct gaagatcagt   19680
tgggtgcacg agtgggttac atcgaactgg atctcaacag cggtaagatc cttgagagtt   19740
ttcgccccga agaacgtttt ccaatgatga gcacttttaa agttctgcta tgtggcgcgg   19800
tattatcccg tgttgacgcc gggcaagagc aactcggtcg ccgcatacac tattctcaga   19860
```

-continued

```
atgacttggt tgagtactca ccagtcacag aaaagcatct tacggatggc atgacagtaa   19920
gagaattatg cagtgctgcc ataaccatga gtgataacac tgcggccaac ttacttctga   19980
caacgatcgg aggaccgaag gagctaaccg cttttttgca caacatgggg gatcatgtaa   20040
ctcgccttga tcgttgggaa ccggagctga atgaagccat accaaacgac gagcgtgaca   20100
ccacgatgcc tgcagcaatg gcaacaacgt tgcgcaaact attaactggc gaactactta   20160
ctctagcttc ccggcaacaa ttaatagact ggatggaggc ggataaagtt gcaggaccac   20220
ttctgcgctc ggcccttccg gctggctggt ttattgctga taaatctgga gccggtgagc   20280
gtgggtctcg cggtatcatt gcagcactgg ggccagatgg taagccctcc cgtatcgtag   20340
ttatctacac gacggggagt caggcaacta tggatgaacg aaatagacag atcgctgaga   20400
taggtgcctc actgattaag cattggtaac tgtcagacca agtttactca tatatacttt   20460
agattgattt aaaacttcat ttttaattta aaaggatcta ggtgaagatc cttttttgata   20520
atctcatgac caaaatccct taacgtgagt tttcgttcca ctgagcgtca gacccgtag    20580
aaaagatcaa aggatcttct tgagatcctt ttttttctgcg cgtaatctgc tgcttgcaaa   20640
caaaaaaacc accgctacca gcggtggttt gtttgccgga tcaagagcta ccaactcttt   20700
ttccgaaggt aactggcttc agcagagcgc agataccaaa tactgtcctt ctagtgtagc   20760
cgtagttagg ccaccacttc aagaactctg tagcaccgcc tacataccttc gctctgctaa   20820
tcctgttacc agtggctgct gccagtggcg ataagtcgtg tcttaccggg ttggactcaa   20880
gacgatagtt accggataag gcgcagcggt cgggctgaac ggggggttcg tgcacacagc   20940
ccagcttgga gcgaacgacc tacaccgaac tgagatacct acagcgtgag ctatgagaaa   21000
gcgccacgct tcccgaaggg agaaaggcgg acaggtatcc ggtaagcggc agggtcggaa   21060
caggagagcg cacgagggag cttccagggg gaaacgcctg gtatctttat agtcctgtcg   21120
ggtttcgcca cctctgactt gagcgtcgat ttttgtgatg ctcgtcaggg ggcggagcc    21180
tatggaaaaa cgccagcaac gcggcctttt tacggttcct ggccttttgc tggccttttg   21240
ctcacatgtt ctttcctgcg ttatcccctg attctgtgga taaccgtatt accgcctttg   21300
agtgagctga taccgctcgc cgcagccgaa cgaccgagcg cagcgagtca gtgagcgagg   21360
aagcggaaga gcgcctgatg cggtattttc tccttacgca tctgtgcggt atttcacacc   21420
gcatatggtg cactctcagt acaatctgct ctgatgccgc atagttaagc cagtatacac   21480
tccgctatcg ctacgtgact gggtcatggc tgcgccccga cacccgccaa cacccgctga   21540
cgcgccctga cgggcttgtc tgctcccggc atccgcttac agacaagctg tgaccgtctc   21600
cgggagctgc atgtgtcaga ggttttcacc gtcatcaccg aaacgcgcga ggcagctgcg   21660
gtaaagctca tcagcgtggt cgtgaagcga ttcacagatg tctgcctgtt catccgcgtc   21720
cagctcgttg agtttctcca gaagcgttaa tgtctggctt ctgataaagc gggccatgtt   21780
aagggcggtt ttttcctgtt tggtcactga tgcctccgtg taaggggat ttctgttcat    21840
gggggtaatg ataccgatga aacgagagag gatgctcacg atacgggtta ctgatgatga   21900
acatgcccgg ttactggaac gttgtgaggg taaacaactg gcggtatgga tgcggcggga   21960
ccagagaaaa atcactcagg gtcaatgcca gcgcttcgtt aatacagatg taggtgttcc   22020
acagggtagc cagcagcatc ctgcgatgca gatccggaac ataatggtgc agggcgctga   22080
cttccgcgtt tccagacttt acgaaacacg gaaaccgaag accattcatg ttgttgctca   22140
ggtcgcagac gttttgcagc agcagtcgct tcacgttcgc tcgcgtatcg                22190
```

```
<210> SEQ ID NO 3
<211> LENGTH: 14130
<212> TYPE: DNA
<213> ORGANISM: Artificial Sequence
<220> FEATURE:
<223> OTHER INFORMATION: Targetting vector (short version)

<400> SEQUENCE: 3
gcggccgcaa cctgggcaaa tgggagctta gcaacaatgt aggggctgg acctagactt      60 cctacacatg tgtaacagat gtgcagcttg gtcttcatgt gtgtattacc ctaacatttg    120
gagcaggagc tgtctctgac tctgttgcct gccattggat ccccttcccc tgcttgggct    180
gccttgtttg gccttagtag gaaaggatgt gcttagtcct gctgtgactt gatgtcccta    240
ggcagaatga taccccaggg gggctcccca tctctgagga gatgggcaaa gggtaatggt    300
tggagggact tgtgaggctg ggactgggag gagagaaagg agacagctgt aactggaatg    360
atgttaagtg aacaaatgaa tggatagatt agatagacag atagacagac agacagacag    420
acagacagac agacagacag acagacagat agaaagatag atagataagg ggaaaaagaa    480
acgtagctga gcaagccaga gagagcaagc caaataagca gcattcctcc atgacttttc    540
cttcagctcc tgcctatgag tctgccttga cttccctcag tgattggttg taagttaaaa    600
ggtgaaataa acccttttctt tgacaagttg cttttggttc tgatttttat cacagcaaga   660
gaaaatcaaa ctagaacaaa catgtatttt tcctggcaca tgtccatagt aaggcagaaa    720
tgatcttcag acctagacca tagatactac agagagcaga agtgtagata ggtggactta    780
ctgtatgatt gtaatccaag taaatctaca tagctagaga gctagaggaa aggccaaagc    840
ttcctctggg aggtcagatc ctgtcgcact gtagccaata aggcatattg catcacagga    900
aaggactaag acccaggctg gcaatagtgt ctgtatctta actagatctc tctagtgagt    960
gaggaagtaa atttgtgaga gcccagactg tgggctcgga aggtacctgc catgcccctg    1020
ttagtaactg agtactacag caggagcagg tgttctctag aaagcctgag acaactctac   1080
ttcttctctc aagagaccac ctaatacagg cctgagagaa cagactctgg aaatagatgg   1140
gacttacgga gctaagatct agagctcatc tacagagcag aatcccagcc aagagaacaa   1200
agaatactga ctctctcctg ttccctactc ctagagttct aaaacacact atagggaagg   1260
gagcctctag acctccgtcc attccccatc ttgctcattc catcttccca tgtccccagg   1320
tctccaagcc acagacacca cctttcctat tcacccacct ttctgtgtcc ctaggtcccc   1380
aggccatagt cacctccccc cacaccccgc tcaccctgcc ccatctatgc ccctagatgc   1440
ttacttacca gagtctttg tctgacgtgg ggctacaagc atctatgctc cctaagcacc    1500
tactgctgac ctgtaggacc cagctctgaa ccaactcata taagtaaata cagactctcc   1560
cctgtcttag gatggcccccc tgggtcagga ggagaccact gccaaggaac cttctcttag  1620
agcactgaac tcctcccctg taccacttag gacagacctg agacctatta ttactgatta   1680
ccagagctct ggcagtgacc acggaggaga tagatccacc ctggacacag gaaacacagc   1740
accagagata ctgcttcatc acaacagtag agtgacactt tagactttaa tttgggtcac   1800
tttcctgctg tagaggtggg atcagaaagc aaagagcagt atgagtgcct gataggcacc   1860
caagtacact atagagtact catggtgaat aaggtacctc catggcttcc cagggagggg   1920
cactgcccca cccccaccat cacagacctt tctccatagt tgataactca gacacaagtg   1980
aatgacagat ggacctccat ctgctcttat tttaaaaaga agacaaaccc cacaggctcg   2040
agaactttag cgactgtttt gagagaaatc attggtccct gactcaagag atgactggca   2100
```

```
gattgggat  cagaatacccc  atactctgtg  gctagtgtga  ggtttaagcc  tcagagtccc   2160
tgtggtctct  gactggtgca  aggttttgac  taagcggagc  accacagtgc  taactgggac   2220
cacggtgaca  cgtggctcaa  caaaaacctt  ctgtttggag  ctctccaggg  gcagcctgag   2280
ctatgaggaa  gtagagaggc  ttgagaaatc  tgaggaagaa  aagagtagat  ctgagaggaa   2340
aggtagcttt  ctggaggtca  ggagacagtg  cagagaagaa  cgagttactg  tggacaggtc   2400
ttagatgggg  aaagaatgag  caaatgcaag  catcagaagg  gtggatgcaa  tgtcctgcca   2460
aggacttacc  aagaggatcc  ccggacagag  caggcaggtg  gagttgactg  agaggacagg   2520
ataggtgcag  gtccctctct  tgtttccttt  ctccttctcc  tgtttccttc  ttctcttgtc   2580
acaggtctca  ctatgctagc  caaggctagc  ctgaaagatt  accatcctac  agatgggccc   2640
atccagttga  attaaggtgg  agatctctcc  aaacatctga  gtttctgagg  cttggatgcc   2700 actgggacg   ccaagggact  ttgggatggg  tttggttggc  cccagatgaa  gggctacttc   2760
actgggtcta  taattactct  gatgtctagg  accagggggc  tcaggtcact  caggtcaggt   2820
gagtcctgca  tctggggact  gtggggttca  ggtggcctaa  gcaggatgt   ggagagagtt   2880 ttagtatagg  aacagaggca  gaacagagac  tgtgctactg  gtacttcgat  gtctggggca   2940
cagggaccac  ggtcaccgtc  tcctcaggta  agctggcttt  tttctttctg  cacattccat   3000
tctgaaacgg  gaaagatat   tctcagatct  ccccatgtca  ggccatctgc  cacactctgc   3060
atgctgcaga  agcttttctg  taaggatagg  gtcttcactc  ccaggaaaag  aggcagtcag   3120
aggctagctg  cctgtggaac  agtgacaatc  atggaaaata  ggcatttaca  ttgttaggct   3180
acatgggtag  atgggttttt  gtacacccac  taaaggggtc  tatgatagtg  tgactacttt   3240
gactactggg  gccaaggcac  cactctcaca  gtctcctcag  gtgagtcctt  acaacctctc   3300
tcttctattc  agcttaaata  gattttactg  catttgttgg  gggggaaatg  tgtgtatctg   3360
aatttcaggt  catgaaggac  tagggacacc  ttgggagtca  gaaagggtca  ttgggagccc   3420
tggctgacgg  agacagacat  cctcagctcc  catacttcat  ggccagagat  ttatagggat   3480
cctggccagc  attgccgcta  ggtccctctc  ttctatgctt  tctttgtccc  tcactggcct   3540
ccatctgaga  tcatcctgga  gccctagcca  aggatcattt  attgtcaggg  gtctaatcat   3600
tgttgtcaca  atgtgcctgg  tttgcttact  ggggccaagg  gactctggtc  actgtctctg   3660
caggtgagtc  ctaacttctc  ccattctaaa  tgcatgttgg  ggggattctg  ggccttcagg   3720
accaagattc  tctgcaaacg  ggaatcaaga  ttcaacccct  ttgtcccaaa  gttgagacat   3780
gggtctgggt  cagggactct  ctgcctgctg  gtctgtggtg  acattagaac  tgaagtatga   3840
tgaaggatct  gccagaactg  aagcttgaag  tctgaggcag  aatcttgtcc  agggtctatc   3900
ggactcttgt  gagaattagg  ggctgacagt  tgatggtgac  aatttcaggg  tcagtgactg   3960
tctggtttct  ctgaggtgag  gctggaatat  aggtcacctt  gaagactaaa  gagggtcca   4020 ggggcttctg  cacaggcagg  gaacagaatg  tggaacaatg  acttgaatgg  ttgattcttg   4080
tgtgacacca  ggaattggca  taatgtctga  gttgcccagg  ggtgattcta  gtcagactct   4140 ggggttttg   tcgggtatag  aggaaaaatc  cactattgtg  attactatgc  tatggactac   4200
tggggtcaag  gaacctcagt  caccgtctcc  tcaggtaaga  atggcctctc  caggtctta   4260 ttttaacct   ttgttatgga  gttttctgag  cattgcagac  taatcttgga  tatttgtccc   4320
tgagggagcc  ggctgagaga  agttgggaaa  taaactgtct  agggatctca  gagcctttag   4380
gacagattat  ctccacatct  ttgaaaaact  aagaatctgt  gtgatggtgt  tggtggagtc   4440
cctggatgat  gggataggga  ctttggaggc  tcatttgaag  aagatgctaa  aacaatccta   4500
```

```
tggctggagg datagttggg gctacgcgtt tttaacccta gaaagatagt ctgcgtaaaa    4560
ttgacgcatg cattcttgaa atattgctct ctctttctaa atagcgcgaa tccgtcgctg    4620
tgcatttagg acatctcagt cgccgcttgg agctcccgtg aggcgtgctt gtcaatgcgg    4680
taagtgtcac tgattttgaa ctataacgac cgcgtgagtc aaaatgacgc atgattatct    4740
tttacgtgac ttttaagatt taactcatac gataattata ttgttatttc atgttctact    4800
tacgtgataa cttattatat atatattttc ttgttataga tatcgctagt ggatcctggt    4860
tctttccgcc tcagaaggta cttttttttt tttttttttt tttttttttt tttttttttt    4920
tttttttttt tttttttttt taaattttg ggaatttatt gatttgcatt taaaagggaa     4980
ctgctgacaa agattcactg gtaataattt gaacaagttg gaaaatacag tcaacattac    5040
tgaaacacta ctaaaataat tccaggacag aacaaaactt cttagatgct gtctttgatg    5100
tgaaaattga ctgcttctta cttttctaac acacggtggt ataattaaca atattcaatc    5160
acttctattc tttcctgcat atataaaaat taaaatacca attaaaaaac taatatatct    5220
tctctttatt tcttacagat atgagttcaa tgtttcactc aatagtgctg tggtttaaga    5280 gaatttttc atttacaagt taaacaacaa tccgcccaaa gggaactgat agtctatagg     5340
ctcatagtgc aaataaacag tttaggaatg cagcaactga catttctaaa gtacaaaaca    5400
gataaaattc ttagaagata catgcaaaaa gctctactaa gcagatggcc acagaactag    5460
aacattgata attttactgg cgatgtcaat aggactccag atgtttccaa actcaacttg    5520
aactctcatc ttaggctttg tattttgctt ttccagtttc actaatgaca caaacatgat    5580
tcaaatccct gaagtattca ttatagtcaa gggcatatcc tacaacaaac ttgtctggaa    5640
tttcaaatcc aacaaagtct ggcttatatc caacacttcg tggggtcctt ttcaccagca    5700
agcttgcgac cttgaccatc tttggattat actgcctgac caaggaaagc aaagtctgca    5760
ttgttttgcc agtgtcaatt atatcttcca caatcaagac attctttcca gttaaagttg    5820
agagatcatc tccaccaatt actttatgt cccctgttga ctggtcatta caatagctct     5880
tcagtctgat aaaatctaca gtcataggaa tggatctatc actatttcta ttcagtgctt    5940
tgatgtaatc cagcaggtca gcaaagaatt tatagccccc cttgagcaca cagagggcta    6000
caatgtgatg gcctcccatc tccttcatca catctcgagc aagacgttca gtcctacaga    6060
aataaaatca ggaatttaat agaaagtttc atacattaaa ctttataaca aacacctctt    6120
agtcattaaa cttccacacc aacctgggca atatagtgag accccatgcc tgcaaaaaaa    6180
aaaaaattag ccaggcatgg tagcatgtac ctgtagtccc agctacttga gaggtgaggt    6240
gggaaaatca ctttagtgca ggatgttgag gctggagtga actgtgattg tgccactgca    6300
ctccagcctg gacaatagag caagaccttg tctcaaaaaa atgcattaaa aattttttt     6360 aaatcttcca cgtaacacat cctttgccct catgtttcat aaggtaaaaa atttgatacc    6420
ttcaaaaaaa ccaagcatac cactatcata attttttta aatgcaaata aaacaagat     6480 accattttca cctatcagac tggcaggttc tgattaaatg aaatttcttg gataatatac    6540
aatattaaga gagactgtag aaactgggcc agtggctcat gcctgtaatc ccagcacttt    6600
gggaggctgg gtaacatggc gaaccctgtt tctacaaaat aaaatatta gctgggagtg     6660 gtggcgcaca cctatagtcc cagctactca ggaggctgag gtggaaggat cgcttgaacc    6720
caggaggttg agactgcagt gaactgtgat cattctgctg cactgcaccc cagcctgggc    6780
aacagagacc ttgtctcaaa aaaaaaaaaa aagagacaa attgtgaaga gaaaggtact      6840
```

```
ctcatataac atcaggagta taaaatgatt caacttctta gaggaaaatt tggcaatacc    6900
aaaatattca ataaactctt tccccttgac ccagaaattc cacttgaata aagctgaaca    6960
agtaccaaac atgtaaaaga atgtttcttc tagtacagtc ggtaagaaca aaatagtgtc    7020
tatcaatagt ggactggtta aatcagttat ggtatctcca taagacagaa tgctatgcaa    7080
cctttaaaat atattagata gctctagaca gtggatcccc tcgagggacc taataacttc    7140
gtatagcata cattatacga agttatatta agggttattg aatatgtcga ctagacacac    7200
taatattaaa agtgtccaat aacatttaaa actatactca tacgttaaaa tataaatgta    7260
tatatgtact tttgcatata gtatacatgc atagccagtg cttgagaaga aatgtgtaca    7320
gaaggctgaa aggagagaac tttagtcttc ttgtttatgg cctccatagt tagaatattt    7380
tataacacaa atattttgat attataattt taaaataaaa acacagaata gccagacata    7440
caatgcaagc attcaatacc aggtaaggtt tttcactgta attgacttaa cagaaaattt    7500
tcaagctaga tgtgcataat aataaaaatc tgaccttgcc ttcatgtgat tcagccccag    7560
tccattaccc tgtttaggac tgagaaatgc aagactctgg ctagagttcc ttcttccatc    7620
tcccttcaat gtttactttg ttctggtccc tacagagtcc cactatacca caactgatac    7680
taagtaatta gtaaggccct cctctttat ttttaataaa gaagatttta gaaagcatca    7740
gttatttaat aagttggcct agtttatgtt caaatagcaa gtactcagaa cagctgctga    7800
tgtttgaaat taacacaaga aaaagtaaaa aacctcattt taagatctta cttacctgtc    7860
cataattagt ccatggggaa taaacaccct ttccaaatcc tcagcataat gattaggtat    7920
gcaaaataaa tcaaggtcat aacctggttc atcatcacta atcacgacgc cagggctgcg    7980
ggtcgccata acggagccgg ccggcgcgcg ggctgaataa cttcgtataa tgtgtactat    8040
acgaagttat ttgttcagga ggaggaagcc ggtggcggag cagaggagga ggcggaggcg    8100
cagcaagacc ccccccccc tgcaggtcga aaggcccgga gatgaggaag aggagaacag    8160
cgcggcagac gtgcgctttt gaagcgtgca gaatgccggg cctccggagg accttcgggc    8220
gcccgccccg cccctgagcc cgcccctgag cccgcccccg gacccacccc ttcccagcct    8280
ctgagcccag aaagcgaagg agccaaagct gctattggcc gctgccccaa aggcctaccc    8340
gcttccattg ctcagcggtg ctgtccatct gcacgagact agtgagacgt gctacttcca    8400
tttgtcacgt cctgcacgac gcgagctgcg gggcggggg gaacttcctg actaggggag    8460
gagtagaagg tggcgcgaag gggccaccaa agaacggagc cggttggcgc ctaccggtgg    8520
atgtggaatg tgtgcgaggc cagaggccac ttgtgtagcg ccaagtgccc agcggggctg    8580
ctaaagcgca tgctccagac tgccttggga aaagcgcctc ccctacccgg tagatatcta    8640
taacaagaaa atatatatat aataagttat cacgtaagta gaacatgaaa taacaatata    8700
attatcgtat gagttaaatc ttaaaagtca cgtaaaagat aatcatgcgt cattttgact    8760
cacgcggtcg ttatagttca aaatcagtga cacttaccgc attgacaagc acgcctcacg    8820
ggagctccaa gcggcgactg agatgtccta aatgcacagc gacggattcg cgctatttag    8880
aaagagagag caatatttca agaatgcatg cgtcaatttt acgcagacta tctttctagg    8940
gttaaaagaa ttcgtagttg gagattttca gtttttagaa taaagtatt agctgcggaa    9000 tatacttcag gaccacctct gtgacagcat ttatacagta tccgatgcat agggacaaag    9060
agtggagtgg ggcactttct ttagatttgt gaggaatgtt ccacactaga ttgtttaaaa    9120
cttcatttgt tggaaggaga gctgtcttag tgattgagtc aagggagaaa ggcatctagc    9180
ctcggtctca aagggtagt tgctgtctag agaggtctgg tggagcctgc aaaagtccag    9240
```

```
ctttcaaagg aacacagaag tatgtgtatg gaatattaga agatgttgct tttactctta   9300
agttggttcc taggaaaaat agttaaatac tgtgacttta aaatgtgaga gggttttcaa   9360
gtactcattt ttttaaatgt ccaaaatttt tgtcaatcaa tttgaggtct tgtttgtgta   9420
gaactgacat tacttaaagt ttaaccgagg aatgggagtg aggctctctc atacccatt    9480 cagaactgac ttttaacaat aataaattaa gtttaaaata tttttaaatg aattgagcaa   9540
tgttgagttg gagtcaagat ggccgatcag aaccagaaca cctgcagcag ctggcaggaa   9600
gcaggtcatg tggcaaggct atttggggaa gggaaaataa aaccactagg taaacttgta   9660
gctgtggttt gaagaagtgg ttttgaaaca ctctgtccag ccccaccaaa ccgaaagtcc   9720
aggctgagca aaacaccacc tgggtaattt gcatttctaa aataagttga ggattcagcc   9780
gaaactggag aggtcctctt ttaacttatt gagttcaacc ttttaatttt agcttgagta   9840
gttctagttt ccccaaactt aagtttatcg acttctaaaa tgtatttaga attcattttc   9900
aaaattaggt tatgtaagaa attgaaggac tttagtgtct ttaatttcta atatatttag   9960
aaaacttctt aaaattactc tattattctt ccctctgatt attggtctcc attcaattct  10020
tttccaatac ccgaagcatt tacagtgact ttgttcatga tcttttttag ttgtttgttt  10080
tgccttacta ttaagacttt gacattctgg tcaaaacggc ttcacaaatc ttttttcaaga  10140 ccactttctg agtattcatt ttaggagaaa tacttttttt ttaaatgaat gcaattatct  10200
agacttattt cggttgaaca tgctggttgg tggttgagag gacactcagt cagtcagtgg  10260
cgtgaagggc ttctaagcca gtccacatgc tctgtgtgaa ctccctctgg ccctgcttat  10320
tgttgaatgg gccaaaggtc tgagaccagg ctgctgctgg gtaggcctgg actttgggtc  10380
tcccacccag acctgggaat gtatggttgt ggcttctgcc acccatccac ctggctgctc  10440
atggaccagc cagcctcggt ggcttttgaag gaacaattcc acacaaagac tctggacctc  10500
tccgaaacca ggcaccgcaa atggtaagcc agaggcagcc acagctgtgg ctgctgctct  10560
taaagcttgt aaactgtttc tgcttaagag ggactgagtc ttcagtcatt gctttagggg  10620
gagaaagaga catttgtgtg tcttttgagt accgttgtct gggtcactca catttaactt  10680
tccttgaaaa actagtaaaa gaaaaatgtt gcctgttaac caataatcat agagctcatg  10740
gtattttgag gaaatcttag aaaacgtgta tacaattgtc tggaattatt tcagttaagt  10800
gtattagttg aggtactgat gctgtctcta cttcagttat acatgtgggt ttgaattttg  10860
aatctattct ggctcttctt aagcagaaaa tttagataaa atggatacct cagtggtttt  10920
taatggtggg tttaatatag aaggaattta aattggaagc taatttagaa tcagtaagga  10980
gggacccagg ctaagaaggc aatcctggga ttctggaaga aaagatgttt ttagttttta  11040
tagaaaacac tactacattc ttgatctaca actcaatgtg gtttaatgaa tttgaagttg  11100
ccagtaaatg tacttcctgg ttgttaaaga atggtatcaa aggacagtgc ttagatccaa  11160
ggtgagtgtg agaggacagg ggctggggta tggatacgca gaaggaaggc cacagctgta  11220
cagaattgag aaagaataga gacctgcagt tgaggccagc aggtcggctg gactaactct  11280
ccagccacag taatgaccca gacagagaag gccagactca taaagcttta tcgataccgt  11340
cgacctcgag gggggcccg gtaccttcct tagacgtcag gtggcacttt tcggggaaat  11400
gtgcgcggaa cccctatttg tttatttttc taaatacatt caaatatgta tccgctcatg  11460
agacaataac cctgataaat gcttcaataa tattgaaaaa ggaagagtat gagtattcaa  11520
catttccgtg tcgcccttat tcccttttttt gcggcatttt gccttcctgt ttttgctcac  11580
```

```
ccagaaacgc tggtgaaagt aaaagatgct gaagatcagt tgggtgcacg agtgggttac    11640
atcgaactgg atctcaacag cggtaagatc cttgagagtt ttcgccccga agaacgtttt    11700
ccaatgatga gcacttttaa agttctgcta tgtggcgcgg tattatcccg tgttgacgcc    11760
gggcaagagc aactcggtcg ccgcatacac tattctcaga atgacttggt tgagtactca    11820
ccagtcacag aaaagcatct tacggatggc atgacagtaa gagaattatg cagtgctgcc    11880
ataaccatga gtgataacac tgcggccaac ttacttctga caacgatcgg aggaccgaag    11940
gagctaaccg cttttttgca caacatgggg gatcatgtaa ctcgccttga tcgttgggaa    12000
ccggagctga atgaagccat accaaacgac gagcgtgaca ccacgatgcc tgcagcaatg    12060
gcaacaacgt tgcgcaaact attaactggc gaactactta ctctagcttc ccggcaacaa    12120
ttaatagact ggatggaggc ggataaagtt gcaggaccac ttctgcgctc ggcccttccg    12180
gctggctggt ttattgctga taaatctgga gccggtgagc gtgggtctcg cggtatcatt    12240
gcagcactgg ggccagatgg taagccctcc cgtatcgtag ttatctacac gacggggagt    12300
caggcaacta tggatgaacg aaatagacag atcgctgaga taggtgcctc actgattaag    12360
cattggtaac tgtcagacca agtttactca tatatacttt agattgattt aaaacttcat    12420
ttttaattta aaaggatcta ggtgaagatc ctttttgata atctcatgac caaatccctt    12480 aacgtgagt tttcgttcca ctgagcgtca gaccccgtag aaaagatcaa aggatcttct    12540
tgagatcctt ttttttctgcg cgtaatctgc tgcttgcaaa caaaaaaacc accgctacca    12600
gcggtggttt gtttgccgga tcaagagcta ccaactcttt ttccgaaggt aactggcttc    12660
agcagagcgc agataccaaa tactgtcctt ctagtgtagc cgtagttagg ccaccacttc    12720
aagaactctg tagcaccgcc tacatacctc gctctgctaa tcctgttacc agtggctgct    12780
gccagtggcg ataagtcgtg tcttaccggg ttggactcaa gacgatagtt accggataag    12840
gcgcagcggt cgggctgaac ggggggttcg tgcacacagc ccagcttgga gcgaacgacc    12900
tacaccgaac tgagatacct acagcgtgag ctatgagaaa gcgccacgct tcccgaaggg    12960
agaaaggcgg acaggtatcc ggtaagcggc agggtcggaa caggagagcg cacgagggag    13020
cttccagggg gaaacgcctg gtatctttat agtcctgtcg ggtttcgcca cctctgactt    13080
gagcgtcgat ttttgtgatg ctcgtcaggg gggcggagcc tatggaaaaa cgccagcaac    13140
gcggcctttt tacggttcct ggccttttgc tggccttttg ctcacatgtt ctttcctgcg    13200
ttatcccctg attctgtgga taaccgtatt accgcctttg agtgagctga taccgctcgc    13260
cgcagccgaa cgaccgagcg cagcgagtca gtgagcgagg aagcggaaga gcgcctgatg    13320
cggtattttc tccttacgca tctgtgcggt atttcacacc gcatatggtg cactctcagt    13380
acaatctgct ctgatgccgc atagttaagc cagtatacac tccgctatcg ctacgtgact    13440
gggtcatggc tgcgccccga cacccgccaa cacccgctga cgcgccctga cgggcttgtc    13500
tgctcccggc atccgcttac agacaagctg tgaccgtctc cgggagctgc atgtgtcaga    13560
ggttttcacc gtcatcaccg aaacgcgcga ggcagctgcg gtaaagctca tcagcgtggt    13620
cgtgaagcga ttcacagatg tctgcctgtt catccgcgtc cagctcgttg agtttctcca    13680
gaagcgttaa tgtctggctt ctgataaagc gggccatgtt aagggcggtt ttttcctgtt    13740
tggtcactga tgcctccgtg taagggggat ttctgttcat gggggtaatg ataccgatga    13800
aacgagagag gatgctcacg atacgggtta ctgatgatga acatgcccgg ttactggaac    13860
gttgtgaggg taaacaactg gcggtatgga tgcggcggga ccagagaaaa atcactcagg    13920
gtcaatgcca gcgcttcgtt aatacagatg taggtgttcc acagggtagc cagcagcatc    13980
```

```
ctgcgatgca gatccggaac ataatggtgc agggcgctga cttccgcgtt tccagacttt    14040
acgaaacacg gaaaccgaag accattcatg ttgttgctca ggtcgcagac gttttgcagc    14100
agcagtcgct tcacgttcgc tcgcgtatcg                                      14130
```

<210> SEQ ID NO 4
<211> LENGTH: 3551
<212> TYPE: DNA
<213> ORGANISM: Mus musculus
<220> FEATURE:
<221> NAME/KEY: misc_feature
<222> LOCATION: (1399)..(1498)
<223> OTHER INFORMATION: n is a, c, g, or t

<400> SEQUENCE: 4

```
aagcttgctg agcaaaatta agggaacaag gttgagagcc ctagtaagcg aggctctaaa      60
aagcatggct gagctgagat gggtgggctt ctctgagcgc ttctaaaatg cgctaaactg     120
aggtgattac tctgaggtaa gcaaagctgg gcttgagcca aaatgaagta gactgtaatg     180
aactggaatg agctgggccg ctaagctaaa ctaggctggc ttaaccgaga tgagccaaac     240
tggaatgaac ttcattaatc taggttgaat agagctaaac tctactgcct acactggact     300
gttctgagct gagatgagct ggggtgagct cagctatgct acgctgtgtt ggggtgagct     360
gatctgaaat gagctactct ggagtagctg agatggggtg agatgggtg agctgagctg      420 ggctgagctg gactgagctg agctagggtg agctgagctg ggtgagctga gctaagctgg     480
ggtgagctga gctgagcttg actgagctag ggtgagctgg actgagctgg ggtgagctga     540
gctgagctgg ggtaagctgg gatgagctgg ggtgagctga gctgagctgg agtgagctga     600
gctgggctga gctggggtga gctgggctgg gctgagctgg ggtgagctgg gctgagctgg     660
ggtgagctga gctggggtga gctgagctga gctggggtga gctgagctga gctggggtga     720
gctgagctgg ggtgagctga gctgagctgg gctgagctga ggtgagctga gctggggtga     780
gctgagctgg ggtgagctga gctgagctgg ggtaagctgg gatgagctgg ggtgagctga     840
gctgagctgg agtgagctga gctgggctga gctgggctga gctggggtga gctgagctgg     900
ggtgagctga gctgagctgg gctgagctga ggtgagctga gctggggtga gctgagctga     960
gctggggtga gctgagctga gctggggtga gctgagctgg ggtgagctga gctggggtga    1020
gctgagctga gctggggtga gctgagctgg ggtgagctga gctgagctgg ggtgagctga    1080
gctgagctgg ggtgagctga gctgagctga gctggggtga gctgagctga gctggggtga    1140
gctgagctga gctggggtga gctgagctgg ggtgagctgg gctgagctga gctgggctga    1200
gctgagctga gctgagctga gctggggtga gctgagctgg gctgagctgg ggtgagctgg    1260
gctgagctgg ggtgagctga gctggggtga gctgagctga gctggggtga gctgagctga    1320
gctggggtga gctgagctgg ggtgagctga gctgagctgg gctgagctga gctgagctgg    1380
ggtgagctga gctgagctnn nnnnnnnnnn nnnnnnnnnn nnnnnnnnnn nnnnnnnnnn    1440
nnnnnnnnnn nnnnnnnnnn nnnnnnnnnn nnnnnnnnnn nnnnnnnnnn nnnnnnnnag    1500
ctgagctgag ctgagctgag ctgagctggg gtgagctggg gtgagctgag ctggggtgag    1560
ctgagctgag ctggggtgag ctgagctgag ctgagctgag ctgagctgag ctgggtgagc    1620
tgagctgagc tgagctgggg tgagctgagc tggggtgagc tgagctgagc tggggtgagc    1680
tgagctgggg tgagctgagc tgagctgggg tgagctgggg tgagctgggg tgagctgggg    1740
tgagctgagc tgaactgggg tgagctgggc tgagctgggg tgagctgagc tgagctgggc    1800
```

```
tgagctgggg tgagctgggg tgagctgggg tgagctgagc tgagctaggg tgagctgagc    1860
tgagctaggg tgagctgagc tgagctgggg tgagctgagc tgagctgggg tgagctgagc    1920
tgagctgggg tgagctgagc tgagctgggg tgagctgagc tgagctgggg tgagcttggc    1980
tgagctgggg tgagctgggg tgagctgagc tggggtgagc tggggtaagc tgagctgagc    2040
tggggtgagc tgagctgagc tggggtgagc tggggtgagc tgagctgagc tgagctgggt    2100
gatctgagct gagctgagct gggtgagctg agctgagctg agctgggtga gctgagctga    2160
gctgagctga gctgggtgag ctgagctgag ctgagctgag ctgagctgag ctggggtgag    2220
ctgggctgag ctgagctgag ctgggtgag ctgagctgag ctgagctgag ctggggtgag    2280
ctgggctgag ctggggtgag ctgggctgag ctgagctggg tgagctgagc tgaactgagc    2340
tgagctgggt gagctgagct gagctgagct gggtgagctg agctgggctg agctgagctg    2400
ggtgagctga gctgaactga gctgagctgg gtgagctgag ctgagctgag ctgggtgagc    2460
tgagctgggg tgagctgagc tgagctgggg tgagctgagc tgagctgagc tgggtgagct    2520
gagctggggt gagctgagct gagctggggt gagctgagct gagctggggt gagctgagct    2580
gagctggggt gagctgagct gagctggggt gagctgagct agggtgaact gggctgggtg    2640
agctggagtg agctgagctg aggtgaactg gggtgagccg ggatgttttg agttgagctg    2700
gggtaagatg agctgaactg gggtaagatg ggatgagctg tggtgagggg agctggattg    2760
aactgagctg tgtgagctga gctggggtca gctgagcaag agtgagtaga gctggctggc    2820
cagaaccaga atcaattagg ctaagtgagc cagattgcgc tgggatcagc tgtactcaga    2880
tgagctggga tgaggtaggc tgggatgagc tgggctagct gacatggatt atgtgaggct    2940
gagctagcat gggctggcct agctgatgag ctaagcttga atgaacgggg ctgagctgga    3000
ctcagatgtg ctagactgag ctgtactgga tgatctggtg tagggtgatc tggactcaac    3060
tgggctggct gatgggatgc cccaggttga actaggctca gataagttag gctgagtagg    3120
gcctggttga gatggttcgg gatgagctgg gaaaagatgg actgggacca tgaactgggc    3180
tgagctgggt tgggagacca tgaattgagc tgaactgagt gcagctggga taaactgggt    3240
tgagctaaga atagactacc tgaattgtgc caaactgggc tgggatcaat tggaaattat    3300
caggatttag atgagccgga ctaaactatg ctgagctgga ctggttggat gtgttgaact    3360
ggcctgctgc tgggctggca tagctgagtt gaacttaaat gaggaaggat gagcaaggct    3420
agcctgcttg catagagctg aactttagcc tagcctgagc tggaccagcc tgagctgagt    3480
aggtctaaac tgagttaaaa atcaacaggg ataatttaac agctaattta acaagcctga    3540
ggtctgagat t                                                         3551
```

<210> SEQ ID NO 5
<211> LENGTH: 2484
<212> TYPE: DNA
<213> ORGANISM: Mus musculus

<400> SEQUENCE: 5

```
aagcttgctg agcaaaatta agggaacaag gttgagagcc ctagtaagcg aggctctaaa      60
aagcacagct gagctgagat gggtgggctt ctctgagtgc ttctaaaatg cgctaaactg     120
aggtgattac tctgaggtaa gcaaagctgg gcttgagcca aaatgaagta gactgtaatg     180
aactggaatg agctgggccg ctaagctaaa ctaggctggc ttaaccgaga tgagccaaac     240
tggaatgaac ttcattaatc taggttgaat agagctaaac tctactgcct acactggact     300
gttctgagct gagatgagct ggggtgagct cagctatgct acgctgtgtt ggggtgagct     360
```

```
gatctgaaat gagatactct ggagtagctg agatggggtg agatggggtg agctgagctg      420
ggctgagcta gactgagctg agctagggtg agctgagctg ggtgagctga gctaagctgg      480
ggtgagctga gctgagcttg gctgagctag ggtgagctgg gctgagctgg ggtgagctga      540
gctgagctgg ggtaagctgg gatgagctgg ggtgagctga gctgagctgg agtgagctga      600
gctgggctga gctggggtga gctgggctga gctgggctga gctgggctga gctggggtga      660
gctgagctgg ggtgagctga gctgagctgg ggtgagctga gctgagctgg ggtgagctgg      720
ggtgagctga gctggggtga gctggggtga gctggggtga gctgagctgg ggtgagctga      780
gctgagctgg ggtgagctga gctgagctga gctgagctga gctggggtga gctgagctga      840
gctgagctgg ggtgagctgg ggtgagctga gctgagctgg agtgagctga gctgggctga      900
gctggggtga gctgggctga gctggggtga gctgagctga gctgagctga gctggggtga      960
gctgagctga gctggggtga gctgagctgg ggtgagctgg gctgagctga gctgagctga     1020
gctgagctga gctgagctga gctgagctga gctgagctga gctgagctga gctgagctga     1080
gctgagctgg ggtgagctga gctgagctgg gctgagctgg ggtgagctgg gctgagctgg     1140
gctgagctgg gctgagctgg ggtgagctga gctggggtga gctgagctga gctgggctga     1200
gctgagctga gctggggtga gctgagctga gctggggtga gctgagctga gctgagctgg     1260
ggtgagctga gctgggctga gcagggctga gctggggtga gctgagctga gctggggtga     1320
gctgggctga gctgggctga gctgagctga gctgggctga gctgggctga gctgggctga     1380
gctgggctga gctgggctga gctggggtga gctgagctga gctggggtga gctggggtga     1440
gctgagctgg ggtgagctga gctggggtga gctgagctga gctggggtga gctgagctgg     1500
ggtgagctga gctgagctgg ggtgagctga gctgagctgg ggtgagctga gctagggtga     1560
actgggctgg gtgagctgga gtgagctgag ctgaggtgaa ctgggggtgag ccgggatgtt     1620 ttgagttgag ctggggtaag atgagctgaa ctggggtaaa ctgggatgag ctgtggtgag     1680
cggagctgga ttgaactgag ctgtgtgagc tgagctgggg tcagctgagc aagagtgagt     1740
agagctggct ggccagaacc agaatcaatt aggctaagtg agccagattg tgctgggatc     1800
agctgtactc agatgagctg ggatgaggta ggctgggatc agctgggcta gctgacatgg     1860
attatgtgag gctgagctag catgggctgg cctagctgat gagctaagct tgaatgagcg     1920
gggctgagct ggactcagat gtgctagact gagctgtact ggatgatctg gtgtagggtg     1980
atctggactc aactgggctg gctgatggga tgcgccaggt tgaactaggc tcagataagt     2040
taggctgagt agggcctggt tgagatggtt cgggatgagc tgggaaaaga tggactcgga     2100
ccatgaactg ggctgagctg ggttgggaga ccatgaattg agctgaactg agtgcagctg     2160
ggataaactg ggttgagcta agaatagact acctgaattg tgccaaactc ggctgggatc     2220
aattggaaat tatcaggatt tagatgagcc ggactaaact atgctgagct ggactggttg     2280
gatgtgttga actggcctgc tgctgggctg gcatagctga gttgaactta aatgaggaag     2340
gctgagcaag gctagcctgc ttgcatagag ctgaacttta gcctagcctg agctggacca     2400
gcctgagctg agtaggtcta aactgagtta aaaatcaaca gggataattt aacagctaat     2460
ttaacaagcc tgaggtctga gatt                                            2484
```

<210> SEQ ID NO 6
<211> LENGTH: 4515
<212> TYPE: DNA
<213> ORGANISM: Artificial Sequence
<220> FEATURE:

<223> OTHER INFORMATION: 5' homology arm of targetting vector

<400> SEQUENCE: 6

```
aacctgggca aatgggagct tagcaacaat gtagggggct ggacctagac ttcctacaca    60
tgtgtaacag atgtgcagct tggtcttcat gtgtgtatta ccctaacatt tggagcagga   120
gctgtctctg actctgttgc ctgccattgg atcccttcc cctgcttggg ctgccttgtt    180
tggccttagt aggaaaggat gtgcttagtc ctgctgtgac ttgatgtccc taggcagaat   240
gatacccag gggggctccc catctctgag gagatgggca aagggtaatg gttggaggga    300
cttgtgaggc tgggactggg aggagagaaa ggagacagct gtaactggaa tgatgttaag   360
tgaacaaatg aatggataga ttagatagac agatagacag acagacagac agacagacag   420
acagacagac agacagacag atagaaagat agatagataa gggaaaaag aaacgtagct    480
gagcaagcca gagagagcaa gccaaataag cagcattcct ccatgacttt tccttcagct   540
cctgcctatg agtctgcctt gacttccctc agtgattggt tgtaagttaa aaggtgaaat   600
aaacccttc tttgacaagt tgcttttggt tctgatttt atcacagcaa gagaaaatca    660
aactagaaca acatgtatt tttcctggca catgtccata gtaaggcaga aatgatcttc    720
agacctagac catagatact acagagagca gaagtgtaga taggtggact tactgtatga   780
ttgtaatcca agtaaatcta catagctaga gagctagagg aaaggccaaa gcttcctctg   840
ggaggtcaga tcctgtcgca ctgtagccaa taaggcatat tgcatcacag gaaaggacta   900
agacccaggc tggcaatagt gtctgtatct taactagatc tctctagtga gtgaggaagt   960
aaatttgtga gagcccagac tgtgggctcg gaaggtacct gccatgcccc tgttagtaac  1020
tgagtactac agcaggagca ggtgttctct agaaagcctg agacaactct acttcttctc  1080
tcaagagacc acctaataca ggcctgagag aacagactct ggaaatagat gggacttacg  1140
gagctaagat ctagagctca tctacagagc agaatcccag ccaagagaac aaagaatact  1200
gactctctcc tgttccctac tcctagagtt ctaaaacaca ctatagggaa gggagcctct  1260
agacctccgt ccattcccca tcttgctcat tccatcttcc catgtcccca ggtctccaag  1320
ccacagacac cacctttcct attcacccac ctttctgtgt ccctaggtcc caggccata   1380
gtcacctccc cccacacccc gctcaccctg ccccatctat gccctagat gcttacttac   1440
cagagtcttt tgtctgacgt ggggctacaa gcatctatgc tccctaagca cctactgctg  1500
acctgtagga cccagctctg aaccaactca tataagtaaa tacagactct cccctgtctt  1560
aggatggccc cctgggtcag gaggagacca ctgccaagga accttctctt agagcactga  1620
actcctcccc tgtaccactt aggacagacc tgagacctat tattactgat taccagagct  1680
ctggcagtga ccacggagga gatagatcca ccctggacac aggaaacaca gcaccagaga  1740
tactgcttca tcacaacagt agagtgacac tttagacttt aatttgggtc actttcctgc  1800
tgtagaggtg ggatcagaaa gcaaagagca gtatgagtgc ctgataggca cccaagtaca  1860
ctatagagta ctcatggtga ataaggtacc tccatggctt cccagggagg ggcactgccc  1920
cacccccacc atcacagacc tttctccata gttgataact cagacacaag tgaatgacag  1980
atggacctcc atctgctctt attttaaaaa gaagacaaac cccacaggct cgagaacttt  2040
agcgactgtt ttgagagaaa tcattggtcc ctgactcaag agatgactgg cagattgggg  2100
atcagaatac ccatactctg tggctagtgt gaggtttaag cctcagagtc cctgtggtct  2160
ctgactggtg caaggttttg actaagcgga gcaccacagt gctaactggg accacggtga  2220
cacgtggctc aacaaaaacc ttctgtttgg agctctccag gggcagcctg agctatgagg  2280
```

```
aagtagagag gcttgagaaa tctgaggaag aaaagagtag atctgagagg aaaggtagct    2340
ttctggaggt caggagacag tgcagagaag aacgagttac tgtggacagg tcttagatgg    2400
ggaaagaatg agcaaatgca agcatcagaa gggtggatgc aatgtcctgc caaggactta    2460
ccaagaggat ccccggacag agcaggcagg tggagttgac tgagaggaca ggataggtgc    2520
aggtccctct cttgtttcct ttctccttct cctgtttcct tcttctcttg tcacaggtct    2580
cactatgcta gccaaggcta gcctgaaaga ttaccatcct acagatgggc ccatccagtt    2640
gaattaaggt ggagatctct ccaaacatct gagtttctga ggcttggatg ccactgggga    2700
cgccaaggga ctttgggatg ggtttggttg gccccagatg aagggctact tcactgggtc    2760
tataattact ctgatgtcta ggaccagggg gctcaggtca ctcaggtcag gtgagtcctg    2820
catctgggga ctgtggggtt caggtggcct aaggcaggat gtggagagag ttttagtata    2880
ggaacagagg cagaacagag actgtgctac tggtacttcg atgtctgggg cacagggacc    2940
acggtcaccg tctcctcagg taagctggct tttttctttc tgcacattcc attctgaaac    3000
gggaaaagat attctcagat ctccccatgt caggccatct gccacactct gcatgctgca    3060
gaagcttttc tgtaaggata gggtcttcac tcccaggaaa agaggcagtc agaggctagc    3120
tgcctgtgga acagtgacaa tcatggaaaa taggcattta cattgttagg ctacatgggt    3180
agatgggttt ttgtacaccc actaaagggg tctatgatag tgtgactact ttgactactg    3240
gggccaaggc accactctca cagtctcctc aggtgagtcc ttacaacctc tctcttctat    3300
tcagcttaaa tagattttac tgcatttgtt ggggggaaa tgtgtgtatc tgaatttcag    3360
gtcatgaagg actagggaca ccttgggagt cagaaagggt cattgggagc cctggctgac    3420
gcagacagac atcctcagct cccatacttc atggccagag atttataggg atcctggcca    3480
gcattgccgc taggtccctc tcttctatgc tttctttgtc cctcactggc ctccatctga    3540
gatcatcctg gagccctagc caaggatcat ttattgtcag gggtctaatc attgttgtca    3600
caatgtgcct ggtttgctta ctggggccaa gggactctgg tcactgtctc tgcaggtgag    3660
tcctaacttc tcccattcta aatgcatgtt gggggattc tgggccttca ggaccaagat    3720
tctctgcaaa cgggaatcaa gattcaaccc ctttgtccca aagttgagac atgggtctgg    3780
gtcagggact ctctgcctgc tggtctgtgg tgacattaga actgaagtat gatgaaggat    3840
ctgccagaac tgaagcttga agtctgaggc agaatcttgt ccagggtcta tcggactctt    3900
gtgagaatta ggggctgaca gttgatggtg acaatttcag ggtcagtgac tgtctggttt    3960
ctctgaggtg aggctggaat ataggtcacc ttgaagacta agagggggtc caggggcttc    4020
tgcacaggca gggaacagaa tgtggaacaa tgacttgaat ggttgattct tgtgtgacac    4080
caggaattgg cataatgtct gagttgccca ggggtgattc tagtcagact ctggggtttt    4140
tgtcgggtat agaggaaaaa tccactattg tgattactat gctatggact actggggtca    4200 aggaaccctca gtcaccgtct cctcaggtaa gaatggcctc tccaggtctt tattttaac    4260 cttgttatg gagttttctg agcattgcag actaatcttg gatatttgtc cctgagggag    4320
ccggctgaga gaagttggga aataaactgt ctagggatct cagagccttt aggacagatt    4380
atctccacat ctttgaaaaa ctaagaatct gtgtgatggt gttggtggag tccctggatg    4440
atgggatagg gactttggag gctcatttga agaagatgct aaaacaatcc tatggctgga    4500
gggatagttg gggct                                                     4515
```

<210> SEQ ID NO 7

```
<211> LENGTH: 25
<212> TYPE: DNA
<213> ORGANISM: Artificial Sequence
<220> FEATURE:
<223> OTHER INFORMATION: Oligonucleotide HV2-5

<400> SEQUENCE: 7
agatcaccct tgaaggagtct ggtcc                                          25

<210> SEQ ID NO 8
<211> LENGTH: 25
<212> TYPE: DNA
<213> ORGANISM: Artificial Sequence
<220> FEATURE:
<223> OTHER INFORMATION: Oligonucleotide HV4-4

<400> SEQUENCE: 8
tggtgaagcc ttcggagacc ctgtc                                           25

<210> SEQ ID NO 9
<211> LENGTH: 25
<212> TYPE: DNA
<213> ORGANISM: Artificial Sequence
<220> FEATURE:
<223> OTHER INFORMATION: Oligonucleotide HV1-3

<400> SEQUENCE: 9
cactagctat gctatgcatt gggtg                                           25

<210> SEQ ID NO 10
<211> LENGTH: 25
<212> TYPE: DNA
<213> ORGANISM: Artificial Sequence
<220> FEATURE:
<223> OTHER INFORMATION: Oligonucleotide HV1-2

<400> SEQUENCE: 10
atggatcaac cctaacagtg gtggc                                           25

<210> SEQ ID NO 11
<211> LENGTH: 25
<212> TYPE: DNA
<213> ORGANISM: Artificial Sequence
<220> FEATURE:
<223> OTHER INFORMATION: Oligonucleotide HV6-1

<400> SEQUENCE: 11
ggaaggacat actacaggtc caagt                                           25

<210> SEQ ID NO 12
<211> LENGTH: 25
<212> TYPE: DNA
<213> ORGANISM: Artificial Sequence
<220> FEATURE:
<223> OTHER INFORMATION: Oligonucleotide C

<400> SEQUENCE: 12
taggtacttg cccctgtcc tcagt                                            25

<210> SEQ ID NO 13
<211> LENGTH: 25
<212> TYPE: DNA
<213> ORGANISM: Artificial Sequence
<220> FEATURE:
<223> OTHER INFORMATION: Oligonucleotide KV1-9

<400> SEQUENCE: 13
```
agcccagtgt gttccgtaca gcctg                                          25

<210> SEQ ID NO 14
<211> LENGTH: 25
<212> TYPE: DNA
<213> ORGANISM: Artificial Sequence
<220> FEATURE:
<223> OTHER INFORMATION: Oligonucleotide KV1-8

<400> SEQUENCE: 14
atcctcattc tctgcatcta cagga                                          25

<210> SEQ ID NO 15
<211> LENGTH: 25
<212> TYPE: DNA
<213> ORGANISM: Artificial Sequence
<220> FEATURE:
<223> OTHER INFORMATION: Oligonucleotide KV1-6

<400> SEQUENCE: 15
ggtaaggatg gagaacactg gcagt                                          25

<210> SEQ ID NO 16
<211> LENGTH: 25
<212> TYPE: DNA
<213> ORGANISM: Artificial Sequence
<220> FEATURE:
<223> OTHER INFORMATION: Oligonucleotide KV1-5

<400> SEQUENCE: 16
ttagtagctg gttggcctgg tatca                                          25

<210> SEQ ID NO 17
<211> LENGTH: 25
<212> TYPE: DNA
<213> ORGANISM: Artificial Sequence
<220> FEATURE:
<223> OTHER INFORMATION: Oligonucleotide Ck

<400> SEQUENCE: 17
ctttgctgtc ctgatcagtc caact                                          25

<210> SEQ ID NO 18
<211> LENGTH: 10
<212> TYPE: DNA
<213> ORGANISM: Artificial Sequence
<220> FEATURE:
<223> OTHER INFORMATION: Rat Switch
<220> FEATURE:
<221> NAME/KEY: repeat_region
<222> LOCATION: (1)..(10)
<223> OTHER INFORMATION: Repeated 148 times

<400> SEQUENCE: 18
gagctgagct                                                           10

<210> SEQ ID NO 19
<211> LENGTH: 10
<212> TYPE: DNA
<213> ORGANISM: Artificial Sequence
<220> FEATURE:
<223> OTHER INFORMATION: Rat Switch
<220> FEATURE:
<221> NAME/KEY: repeat_region
<222> LOCATION: (1)..(10)
<223> OTHER INFORMATION: Repeat 25 times

```
<400> SEQUENCE: 19
ggggtggggt                                                            10

<210> SEQ ID NO 20
<211> LENGTH: 10
<212> TYPE: DNA
<213> ORGANISM: Artificial Sequence
<220> FEATURE:
<223> OTHER INFORMATION: Rat Switch
<220> FEATURE:
<221> NAME/KEY: repeat_region
<222> LOCATION: (1)..(5)
<223> OTHER INFORMATION: Repeat 82 times

<400> SEQUENCE: 20
gggctgggct                                                            10

<210> SEQ ID NO 21
<211> LENGTH: 6
<212> TYPE: PRT
<213> ORGANISM: Artificial Sequence
<220> FEATURE:
<223> OTHER INFORMATION: Antibody Sequence
<220> FEATURE:
<221> NAME/KEY: MISC_FEATURE
<222> LOCATION: (1)..(2)
<223> OTHER INFORMATION: Xaa Xaa = PR, RT, or PW

<400> SEQUENCE: 21

Xaa Xaa Thr Phe Gly Gln
1               5

<210> SEQ ID NO 22
<211> LENGTH: 17
<212> TYPE: PRT
<213> ORGANISM: Artificial Sequence
<220> FEATURE:
<223> OTHER INFORMATION: Antibody Sequence
<220> FEATURE:
<221> NAME/KEY: MISC_FEATURE
<222> LOCATION: (1)..(2)
<223> OTHER INFORMATION: Xaa Xaa= PR, RT, or PW

<400> SEQUENCE: 22

Xaa Xaa Thr Phe Gly Gln Gly Thr Lys Val Glu Ile Lys Arg Ala Asp
1               5                   10                  15

Ala

<210> SEQ ID NO 23
<211> LENGTH: 6
<212> TYPE: PRT
<213> ORGANISM: Artificial Sequence
<220> FEATURE:
<223> OTHER INFORMATION: Antibody Sequence
<220> FEATURE:
<221> NAME/KEY: MISC_FEATURE
<222> LOCATION: (1)..(2)
<223> OTHER INFORMATION: Xaa Xaa = PR or PW

<400> SEQUENCE: 23

Xaa Xaa Thr Phe Gly Gln
1               5

<210> SEQ ID NO 24
<211> LENGTH: 17
<212> TYPE: PRT
<213> ORGANISM: Artificial Sequence
<220> FEATURE:
```

<223> OTHER INFORMATION: Antibody Sequence
<220> FEATURE:
<221> NAME/KEY: MISC_FEATURE
<222> LOCATION: (1)..(2)
<223> OTHER INFORMATION: Xaa Xaa = PR or PW

<400> SEQUENCE: 24

Xaa Xaa Thr Phe Gly Gln Gly Thr Lys Val Glu Ile Lys Arg Ala Asp
1               5                   10                  15

Ala

<210> SEQ ID NO 25
<211> LENGTH: 24
<212> TYPE: DNA
<213> ORGANISM: Artificial Sequence
<220> FEATURE:
<223> OTHER INFORMATION: Primer E1554

<400> SEQUENCE: 25
atgacttcag tgttgttctg gtag                                          24

<210> SEQ ID NO 26
<211> LENGTH: 19
<212> TYPE: DNA
<213> ORGANISM: Artificial Sequence
<220> FEATURE:
<223> OTHER INFORMATION: Primer E1555

<400> SEQUENCE: 26
caccagattc ttatcagac                                                19

<210> SEQ ID NO 27
<211> LENGTH: 35
<212> TYPE: DNA
<213> ORGANISM: Artificial Sequence
<220> FEATURE:
<223> OTHER INFORMATION: ELP1352_Cy1

<400> SEQUENCE: 27
agagcggccg ctgggcaacg ttgcaggtga cggtc                              35

<210> SEQ ID NO 28
<211> LENGTH: 34
<212> TYPE: DNA
<213> ORGANISM: Artificial Sequence
<220> FEATURE:
<223> OTHER INFORMATION: ELP1353_Cy2b

<400> SEQUENCE: 28
agagcggccg ctttgtccac cgtggtgctg ctgg                               34

<210> SEQ ID NO 29
<211> LENGTH: 33
<212> TYPE: DNA
<213> ORGANISM: Artificial Sequence
<220> FEATURE:
<223> OTHER INFORMATION: ELP1354_Cy2a

<400> SEQUENCE: 29
agagcggccg cacattgcag gtgatggact ggc                                33

<210> SEQ ID NO 30
<211> LENGTH: 35
<212> TYPE: DNA
<213> ORGANISM: Artificial Sequence
<220> FEATURE:

```
<223> OTHER INFORMATION: ELP1356_VH4-4

<400> SEQUENCE: 30
aggacgcgtg aaacacctgt ggttcttcct cctgc                                    35

<210> SEQ ID NO 31
<211> LENGTH: 33
<212> TYPE: DNA
<213> ORGANISM: Artificial Sequence
<220> FEATURE:
<223> OTHER INFORMATION: ELP1357_VH1-2,3

<400> SEQUENCE: 31
aggacgcgtc accatggact ggacctggag gat                                      33

<210> SEQ ID NO 32
<211> LENGTH: 34
<212> TYPE: DNA
<213> ORGANISM: Artificial Sequence
<220> FEATURE:
<223> OTHER INFORMATION: ELP1358_VH6-1

<400> SEQUENCE: 32
aggacgcgta tgtctgtctc cttcctcatc ttcc                                     34

<210> SEQ ID NO 33
<211> LENGTH: 21
<212> TYPE: DNA
<213> ORGANISM: Artificial Sequence
<220> FEATURE:
<223> OTHER INFORMATION: mIgG1_2 rev

<400> SEQUENCE: 33
ggggccagtg gatagacaga t                                                   21

<210> SEQ ID NO 34
<211> LENGTH: 18
<212> TYPE: DNA
<213> ORGANISM: Artificial Sequence
<220> FEATURE:
<223> OTHER INFORMATION: mIgG2b rev

<400> SEQUENCE: 34
cagtggatag actgatgg                                                       18

<210> SEQ ID NO 35
<211> LENGTH: 18
<212> TYPE: DNA
<213> ORGANISM: Artificial Sequence
<220> FEATURE:
<223> OTHER INFORMATION: mIgG2a_2 rev

<400> SEQUENCE: 35
cagtggatag accgatgg                                                       18

<210> SEQ ID NO 36
<211> LENGTH: 20
<212> TYPE: DNA
<213> ORGANISM: Artificial Sequence
<220> FEATURE:
<223> OTHER INFORMATION: mCH1 unirev
<220> FEATURE:
<221> NAME/KEY: misc_feature
<222> LOCATION: (1)..(1)
<223> OTHER INFORMATION: K = G or T

<400> SEQUENCE: 36
```

```
kcaggggcca gtggatagac                                                     20
```

```
<210> SEQ ID NO 37
<211> LENGTH: 20
<212> TYPE: DNA
<213> ORGANISM: Artificial Sequence
<220> FEATURE:
<223> OTHER INFORMATION: mCH1 unirev_2
<220> FEATURE:
<221> NAME/KEY: misc_feature
<222> LOCATION: (3)..(3)
<223> OTHER INFORMATION: R = A or G
<220> FEATURE:
<221> NAME/KEY: misc_feature
<222> LOCATION: (6)..(6)
<223> OTHER INFORMATION: Y = C or T
<220> FEATURE:
<221> NAME/KEY: misc_feature
<222> LOCATION: (12)..(12)
<223> OTHER INFORMATION: M = A or C

<400> SEQUENCE: 37
tarccyttga cmaggcatcc                                                     20

<210> SEQ ID NO 38
<211> LENGTH: 24
<212> TYPE: PRT
<213> ORGANISM: Artificial Sequence
<220> FEATURE:
<223> OTHER INFORMATION: 16C9

<400> SEQUENCE: 38

Gln Glu Val Ile Asn Tyr Tyr Tyr Tyr Gly Met Asp Val Trp Gly Gln
1               5                   10                  15

Gly Thr Thr Val Thr Val Ser Ser
            20

<210> SEQ ID NO 39
<211> LENGTH: 24
<212> TYPE: PRT
<213> ORGANISM: Artificial Sequence
<220> FEATURE:
<223> OTHER INFORMATION: 20B5

<400> SEQUENCE: 39

Gln Glu Val Ile Asn Tyr Tyr Tyr Tyr Gly Met Asp Val Trp Gly Gln
1               5                   10                  15

Gly Thr Thr Val Thr Val Ser Ser
            20

<210> SEQ ID NO 40
<211> LENGTH: 26
<212> TYPE: PRT
<213> ORGANISM: Artificial Sequence
<220> FEATURE:
<223> OTHER INFORMATION: 19F4

<400> SEQUENCE: 40

Leu Glu Met Ala Thr Ile Asn Tyr Tyr Tyr Tyr Gly Met Asp Val Trp
1               5                   10                  15

Gly Gln Gly Thr Met Val Thr Val Ser Ser
            20                  25

<210> SEQ ID NO 41
<211> LENGTH: 24
<212> TYPE: PRT
```

```
<213> ORGANISM: Artificial Sequence
<220> FEATURE:
<223> OTHER INFORMATION: 19E1

<400> SEQUENCE: 41

Gln Glu Phe Gly Asn Tyr Tyr Tyr Gly Met Asp Val Trp Gly Gln
1               5                   10                  15

Gly Thr Thr Val Thr Val Ser Ser
            20

<210> SEQ ID NO 42
<211> LENGTH: 24
<212> TYPE: PRT
<213> ORGANISM: Artificial Sequence
<220> FEATURE:
<223> OTHER INFORMATION: 19G8

<400> SEQUENCE: 42

Gln Glu Asp Gly Asn Pro Tyr Tyr Phe Gly Met Asp Phe Trp Gly Gln
1               5                   10                  15

Gly Thr Thr Val Thr Val Ser Ser
            20

<210> SEQ ID NO 43
<211> LENGTH: 22
<212> TYPE: PRT
<213> ORGANISM: Artificial Sequence
<220> FEATURE:
<223> OTHER INFORMATION: 20H10

<400> SEQUENCE: 43

Gly Ser Ser Tyr Tyr Tyr Asp Gly Met Asp Val Trp Gly Gln Gly Thr
1               5                   10                  15

Thr Val Thr Val Ser Ser
            20

<210> SEQ ID NO 44
<211> LENGTH: 25
<212> TYPE: PRT
<213> ORGANISM: Artificial Sequence
<220> FEATURE:
<223> OTHER INFORMATION: 18D10

<400> SEQUENCE: 44

Leu Glu Asn Asp Tyr Gly Tyr Tyr Tyr Gly Met Asp Val Trp Gly
1               5                   10                  15

Gln Gly Thr Thr Val Thr Val Ser Ser
            20                  25

<210> SEQ ID NO 45
<211> LENGTH: 23
<212> TYPE: PRT
<213> ORGANISM: Artificial Sequence
<220> FEATURE:
<223> OTHER INFORMATION: 16F2

<400> SEQUENCE: 45

Arg Gly Gly Leu Ser Pro Leu Tyr Gly Met Asp Val Trp Gln Gly
1               5                   10                  15

Thr Thr Val Thr Val Ser Ser
            20

<210> SEQ ID NO 46
<211> LENGTH: 15
```

```
<212> TYPE: DNA
<213> ORGANISM: Artificial Sequence
<220> FEATURE:
<223> OTHER INFORMATION: Rat Switch

<400> SEQUENCE: 46
gggctgggct gggct                                                          15

<210> SEQ ID NO 47
<211> LENGTH: 20
<212> TYPE: DNA
<213> ORGANISM: Artificial Sequence
<220> FEATURE:
<223> OTHER INFORMATION: Rat Switch

<400> SEQUENCE: 47
gggctgggct gggctgggct                                                     20

<210> SEQ ID NO 48
<211> LENGTH: 25
<212> TYPE: DNA
<213> ORGANISM: Artificial Sequence
<220> FEATURE:
<223> OTHER INFORMATION: Rat Switch

<400> SEQUENCE: 48
gggctgggct gggctgggct gggct                                               25

<210> SEQ ID NO 49
<211> LENGTH: 30
<212> TYPE: DNA
<213> ORGANISM: Artificial Sequence
<220> FEATURE:
<223> OTHER INFORMATION: Rat Switch

<400> SEQUENCE: 49
gggctgggct gggctgggct gggctgggct                                          30

<210> SEQ ID NO 50
<211> LENGTH: 10
<212> TYPE: DNA
<213> ORGANISM: Artificial Sequence
<220> FEATURE:
<223> OTHER INFORMATION: Rat Switch
<220> FEATURE:
<221> NAME/KEY: repeat_region
<222> LOCATION: (1)..(5)
<223> OTHER INFORMATION: Repeat 6 to 81 times

<400> SEQUENCE: 50
gggctgggct                                                                10

<210> SEQ ID NO 51
<211> LENGTH: 6
<212> TYPE: PRT
<213> ORGANISM: Artificial Sequence
<220> FEATURE:
<223> OTHER INFORMATION: IGHV4-4*02  CDR1

<400> SEQUENCE: 51

Ser Ser Asn Trp Trp Ser
1               5

<210> SEQ ID NO 52
<211> LENGTH: 6
<212> TYPE: PRT
<213> ORGANISM: Artificial Sequence
```

```
<220> FEATURE:
<223> OTHER INFORMATION: 12D10 CDR1

<400> SEQUENCE: 52

Ser Gly Asn Trp Trp Ser
1               5

<210> SEQ ID NO 53
<211> LENGTH: 6
<212> TYPE: PRT
<213> ORGANISM: Artificial Sequence
<220> FEATURE:
<223> OTHER INFORMATION: 1283 CDR1

<400> SEQUENCE: 53

Arg Ser Asn Trp Trp Ser
1               5

<210> SEQ ID NO 54
<211> LENGTH: 7
<212> TYPE: PRT
<213> ORGANISM: Artificial Sequence
<220> FEATURE:
<223> OTHER INFORMATION: IGHV6-1*01 CDR1

<400> SEQUENCE: 54

Ser Asn Ser Ala Ala Trp Asn
1               5

<210> SEQ ID NO 55
<211> LENGTH: 7
<212> TYPE: PRT
<213> ORGANISM: Artificial Sequence
<220> FEATURE:
<223> OTHER INFORMATION: 4A12 CDR1

<400> SEQUENCE: 55

Ser Asn Ser Ala Ala Trp Asn
1               5

<210> SEQ ID NO 56
<211> LENGTH: 16
<212> TYPE: PRT
<213> ORGANISM: Artificial Sequence
<220> FEATURE:
<223> OTHER INFORMATION: IGHV4-4*02 CDR2

<400> SEQUENCE: 56

Glu Ile Tyr His Ser Gly Ser Thr Asn Tyr Asn Pro Ser Leu Lys Ser
1               5                   10                  15

<210> SEQ ID NO 57
<211> LENGTH: 16
<212> TYPE: PRT
<213> ORGANISM: Artificial Sequence
<220> FEATURE:
<223> OTHER INFORMATION: 12D10 CDR2

<400> SEQUENCE: 57

Glu Ile Tyr His Ser Gly Asn Thr Asn Tyr Asn Pro Ser Leu Lys Ser
1               5                   10                  15

<210> SEQ ID NO 58
<211> LENGTH: 16
<212> TYPE: PRT
<213> ORGANISM: Artificial Sequence
<220> FEATURE:
```

<223> OTHER INFORMATION: 1283 CDR2

<400> SEQUENCE: 58

Glu Ile Tyr His Ser Gly Ser Thr Asn Tyr Asn Pro Ser Leu Lys Ser
1               5                   10                  15

<210> SEQ ID NO 59
<211> LENGTH: 18
<212> TYPE: PRT
<213> ORGANISM: Artificial Sequence
<220> FEATURE:
<223> OTHER INFORMATION: IGHV6-1*01 CDR2

<400> SEQUENCE: 59

Arg Thr Tyr Tyr Arg Ser Lys Trp Tyr Asn Asp Tyr Ala Val Ser Val
1               5                   10                  15

Lys Ser

<210> SEQ ID NO 60
<211> LENGTH: 18
<212> TYPE: PRT
<213> ORGANISM: Artificial Sequence
<220> FEATURE:
<223> OTHER INFORMATION: 4A12 CDR2

<400> SEQUENCE: 60

Arg Thr Tyr Tyr Arg Ser Lys Trp Tyr Asn Asp Tyr Lys Val Ser Val
1               5                   10                  15

Lys Ser

<210> SEQ ID NO 61
<211> LENGTH: 12
<212> TYPE: PRT
<213> ORGANISM: Artificial Sequence
<220> FEATURE:
<223> OTHER INFORMATION: 12D10 CDR3

<400> SEQUENCE: 61

Gly Pro Leu Thr Gly Glu Lys Tyr Tyr Phe Asp Leu
1               5                   10

<210> SEQ ID NO 62
<211> LENGTH: 8
<212> TYPE: PRT
<213> ORGANISM: Artificial Sequence
<220> FEATURE:
<223> OTHER INFORMATION: 1283 CDR3

<400> SEQUENCE: 62

Ile Gly Asp Trp Tyr Phe Asp Leu
1               5

<210> SEQ ID NO 63
<211> LENGTH: 16
<212> TYPE: PRT
<213> ORGANISM: Artificial Sequence
<220> FEATURE:
<223> OTHER INFORMATION: 4A12 CDR3

<400> SEQUENCE: 63

Glu Gly Ser His Ser Gly Ser Gly Trp Tyr Leu Asp Ala Phe Asp Ile
1               5                   10                  15

<210> SEQ ID NO 64
<211> LENGTH: 17

```
<212> TYPE: PRT
<213> ORGANISM: Artificial Sequence
<220> FEATURE:
<223> OTHER INFORMATION: IGHJ2*01 J-region

<400> SEQUENCE: 64

Tyr Trp Tyr Phe Asp Leu Trp Gly Arg Gly Thr Leu Val Thr Val Ser
1               5                   10                  15

Ser

<210> SEQ ID NO 65
<211> LENGTH: 16
<212> TYPE: PRT
<213> ORGANISM: Artificial Sequence
<220> FEATURE:
<223> OTHER INFORMATION: 12D10 J-region

<400> SEQUENCE: 65

Tyr Tyr Phe Asp Leu Trp Gly Arg Gly Thr Leu Val Thr Val Ser Ser
1               5                   10                  15

<210> SEQ ID NO 66
<211> LENGTH: 16
<212> TYPE: PRT
<213> ORGANISM: Artificial Sequence
<220> FEATURE:
<223> OTHER INFORMATION: 1283 J-Region

<400> SEQUENCE: 66

Trp Tyr Phe Asp Leu Trp Gly Arg Gly Thr Leu Val Thr Val Ser Ser
1               5                   10                  15

<210> SEQ ID NO 67
<211> LENGTH: 16
<212> TYPE: PRT
<213> ORGANISM: Artificial Sequence
<220> FEATURE:
<223> OTHER INFORMATION: IGHJ3*01 J-Region

<400> SEQUENCE: 67

Asp Ala Phe Asp Val Trp Gly Gln Gly Thr Met Val Thr Val Ser Ser
1               5                   10                  15

<210> SEQ ID NO 68
<211> LENGTH: 16
<212> TYPE: PRT
<213> ORGANISM: Artificial Sequence
<220> FEATURE:
<223> OTHER INFORMATION: 4A12 J-region

<400> SEQUENCE: 68

Asp Ala Phe Asp Ile Trp Gly Gln Gly Thr Lys Val Thr Val Ser Ser
1               5                   10                  15

<210> SEQ ID NO 69
<211> LENGTH: 50
<212> TYPE: DNA
<213> ORGANISM: Artificial Sequence
<220> FEATURE:
<223> OTHER INFORMATION: Vk1-8Jk1

<400> SEQUENCE: 69
accctgtgga cgttcggcca agggaccaag gtggaaatca aacgggctga            50

<210> SEQ ID NO 70
<211> LENGTH: 51
```

<212> TYPE: DNA
<213> ORGANISM: Artificial Sequence
<220> FEATURE:
<223> OTHER INFORMATION: Vk1-8Jk1 variant

<400> SEQUENCE: 70
acccacgtgg acgttcggcc aagggaccaa ggtggaaatc aaacgggctg a         51

<210> SEQ ID NO 71
<211> LENGTH: 51
<212> TYPE: DNA
<213> ORGANISM: Artificial Sequence
<220> FEATURE:
<223> OTHER INFORMATION: Vk1-8Jk1 variant

<400> SEQUENCE: 71
acccacgtgg acgttcggcc aagggaccaa ggtggaaatc aaacgggctg a         51

<210> SEQ ID NO 72
<211> LENGTH: 49
<212> TYPE: DNA
<213> ORGANISM: Artificial Sequence
<220> FEATURE:
<223> OTHER INFORMATION: Vk1-8Jk1 variant

<400> SEQUENCE: 72
acccgtggac gttcggccaa gggaccaagg tggaaatcaa acgggctga            49

<210> SEQ ID NO 73
<211> LENGTH: 49
<212> TYPE: DNA
<213> ORGANISM: Artificial Sequence
<220> FEATURE:
<223> OTHER INFORMATION: Vk1-8Jk1 variant

<400> SEQUENCE: 73
acccgtggac gttcggccaa gggaccaagg tggaaatcaa acgggctga            49

<210> SEQ ID NO 74
<211> LENGTH: 49
<212> TYPE: DNA
<213> ORGANISM: Artificial Sequence
<220> FEATURE:
<223> OTHER INFORMATION: Vk1-8Jk1 variant

<400> SEQUENCE: 74
acccgtggac gttcggccaa gggaccaagg tggaaatcaa acgggctga            49

<210> SEQ ID NO 75
<211> LENGTH: 49
<212> TYPE: DNA
<213> ORGANISM: Artificial Sequence
<220> FEATURE:
<223> OTHER INFORMATION: Vk1-8Jk1 variant

<400> SEQUENCE: 75
acccgtggac gttcggccaa gggaccaagg tggaaatcaa acgggctga            49

<210> SEQ ID NO 76
<211> LENGTH: 46
<212> TYPE: DNA
<213> ORGANISM: Artificial Sequence
<220> FEATURE:
<223> OTHER INFORMATION: Vk1-8Jk1 variant

<400> SEQUENCE: 76
accggacgtt cggccaaggg accaaggtgg aaatcaaacg ggctga                46

<210> SEQ ID NO 77
<211> LENGTH: 46
<212> TYPE: DNA
<213> ORGANISM: Artificial Sequence
<220> FEATURE:
<223> OTHER INFORMATION: Vk1-8Jk1 variant

<400> SEQUENCE: 77
accggacgtt cggccaaggg accaaggtgg aaatcaaacg ggctga                46

<210> SEQ ID NO 78
<211> LENGTH: 46
<212> TYPE: DNA
<213> ORGANISM: Artificial Sequence
<220> FEATURE:
<223> OTHER INFORMATION: Vk1-8Jk1 variant

<400> SEQUENCE: 78
accggacgtt cggccaaggg accaaggtgg aaatcaaacg ggctga                46

<210> SEQ ID NO 79
<211> LENGTH: 46
<212> TYPE: DNA
<213> ORGANISM: Artificial Sequence
<220> FEATURE:
<223> OTHER INFORMATION: Vk1-8Jk1 variant

<400> SEQUENCE: 79
accggacgtt cggccaaggg accaaggtgg aaatcaaacg ggctga                46

<210> SEQ ID NO 80
<211> LENGTH: 49
<212> TYPE: DNA
<213> ORGANISM: Artificial Sequence
<220> FEATURE:
<223> OTHER INFORMATION: Vk1-8Jk1 variant

<400> SEQUENCE: 80
accctcggac gttcggccaa gggaccaagg tggaaatcaa acgggctga             49

<210> SEQ ID NO 81
<211> LENGTH: 49
<212> TYPE: DNA
<213> ORGANISM: Artificial Sequence
<220> FEATURE:
<223> OTHER INFORMATION: Vk1-8Jk1 variant

<400> SEQUENCE: 81
accctcggac gttcggccaa gggaccaagg tggaaatcaa acgggctga             49

<210> SEQ ID NO 82
<211> LENGTH: 49
<212> TYPE: DNA
<213> ORGANISM: Artificial Sequence
<220> FEATURE:
<223> OTHER INFORMATION: Vk1-8Jk1 variant

<400> SEQUENCE: 82
accctcggac gttcggccaa gggaccaagg tggaaatcaa acgggctga             49

<210> SEQ ID NO 83
<211> LENGTH: 49
<212> TYPE: DNA
<213> ORGANISM: Artificial Sequence

```
<220> FEATURE:
<223> OTHER INFORMATION: Vk1-8Jk1 variant

<400> SEQUENCE: 83
accctcggac gttcggccaa gggaccaagg tggaaatcaa acgggctga          49

<210> SEQ ID NO 84
<211> LENGTH: 49
<212> TYPE: DNA
<213> ORGANISM: Artificial Sequence
<220> FEATURE:
<223> OTHER INFORMATION: Vk1-8Jk1 variant

<400> SEQUENCE: 84
accctcggac gttcggccaa gggaccaagg tggaaatcaa acgggctga          49

<210> SEQ ID NO 85
<211> LENGTH: 49
<212> TYPE: DNA
<213> ORGANISM: Artificial Sequence
<220> FEATURE:
<223> OTHER INFORMATION: Vk1-8Jk1 variant

<400> SEQUENCE: 85
accctcggac gttcggccaa gggaccaagg tggaaatcaa acgggctga          49

<210> SEQ ID NO 86
<211> LENGTH: 49
<212> TYPE: DNA
<213> ORGANISM: Artificial Sequence
<220> FEATURE:
<223> OTHER INFORMATION: Vk1-8Jk1 variant

<400> SEQUENCE: 86
acccccggac gttcggccaa gggaccaagg tggaaatcaa acgggctga          49

<210> SEQ ID NO 87
<211> LENGTH: 49
<212> TYPE: DNA
<213> ORGANISM: Artificial Sequence
<220> FEATURE:
<223> OTHER INFORMATION: Vk1-8Jk1 variant

<400> SEQUENCE: 87
acccccggac gttcggccaa gggaccaagg tggaaatcaa acgggctga          49

<210> SEQ ID NO 88
<211> LENGTH: 151
<212> TYPE: PRT
<213> ORGANISM: Artificial Sequence
<220> FEATURE:
<223> OTHER INFORMATION: IgK variant

<400> SEQUENCE: 88
```

Ser Ser Phe Ser Ala Ser Thr Gly Asp Arg Val Thr Ile Thr Cys Arg
1               5                   10                  15

Ala Ser Gln Gly Ile Ser Ser Tyr Leu Ala Trp Tyr Gln Gln Lys Pro
            20                  25                  30

Gly Lys Ala Pro Lys Leu Leu Ile Tyr Ala Ala Ser Thr Leu Gln Ser
        35                  40                  45

Gly Val Pro Ser Arg Phe Ser Gly Ser Gly Ser Gly Thr Asp Phe Thr
    50                  55                  60

Leu Thr Ile Ser Cys Leu Gln Ser Glu Asp Phe Ala Thr Tyr Tyr Cys
65                  70                  75                  80

-continued

```
Gln Gln Tyr Tyr Ser Tyr Pro Arg Thr Phe Gly Gln Gly Thr Lys Val
                85                  90                  95
Glu Ile Lys Arg Ala Asp Ala Ala Pro Thr Val Ser Ile Phe Pro Pro
            100                 105                 110
Ser Ser Glu Gln Leu Thr Ser Gly Gly Ala Ser Val Val Cys Phe Leu
        115                 120                 125
Asn Asn Phe Tyr Pro Lys Asp Ile Asn Val Lys Trp Lys Ile Asp Gly
    130                 135                 140
Ser Glu Arg Gln Asn Gly Val
145                 150

<210> SEQ ID NO 89
<211> LENGTH: 148
<212> TYPE: PRT
<213> ORGANISM: Artificial Sequence
<220> FEATURE:
<223> OTHER INFORMATION: IgK variant

<400> SEQUENCE: 89

Ile Leu Ile Leu Cys Ile Tyr Arg Arg Gln Ser His His Leu Ser
1               5                   10                  15
Gly Glu Ser Gly Tyr Gln Leu Phe Ser Leu Val Ser Ala Lys Thr Arg
            20                  25                  30
Glu Ser Pro Ala Pro Asp Leu Cys Cys Ile His Phe Ala Lys Trp Gly
        35                  40                  45
Pro Ile Lys Val Gln Arg Gln Trp Ile Trp Asp Arg Phe His Ser His
    50                  55                  60
His Gln Leu Pro Ala Val Arg Phe Cys Asn Leu Leu Ser Thr Val
65                  70                  75                  80
Leu Leu Pro Thr Trp Thr Phe Gly Gln Gly Thr Lys Val Glu Ile Lys
                85                  90                  95
Arg Ala Asp Ala Ala Pro Thr Val Ser Ile Phe Pro Pro Ser Ser Glu
            100                 105                 110
Gln Leu Thr Ser Gly Gly Ala Ser Val Val Cys Phe Leu Asn Asn Phe
        115                 120                 125
Tyr Pro Lys Asp Ile Asn Val Lys Trp Lys Ile Asp Gly Ser Glu Arg
    130                 135                 140
Gln Asn Gly Val
145

<210> SEQ ID NO 90
<211> LENGTH: 150
<212> TYPE: PRT
<213> ORGANISM: Artificial Sequence
<220> FEATURE:
<223> OTHER INFORMATION: IgK variant

<400> SEQUENCE: 90

Ser Ser Phe Ser Ala Ser Thr Gly Asp Arg Val Thr Ile Thr Cys Arg
1               5                   10                  15
Ala Ser Gln Gly Ile Ser Ser Tyr Leu Ala Trp Tyr Gln Gln Lys Pro
            20                  25                  30
Gly Lys Ala Pro Lys Leu Leu Ile Tyr Ala Ala Ser Thr Leu Gln Ser
        35                  40                  45
Gly Val Pro Ser Arg Phe Ser Gly Ser Gly Ser Gly Thr Asp Phe Thr
    50                  55                  60
Leu Thr Ile Ser Cys Leu Gln Ser Glu Asp Phe Ala Thr Tyr Tyr Cys
```

```
                65                  70                  75                  80
Gln Gln Tyr Tyr Ser Tyr Arg Thr Phe Gly Gln Gly Thr Lys Val Glu
                    85                  90                  95

Ile Lys Arg Ala Asp Ala Ala Pro Thr Val Ser Ile Phe Pro Pro Ser
                100                 105                 110

Ser Glu Gln Leu Thr Ser Gly Gly Ala Ser Val Val Cys Phe Leu Asn
            115                 120                 125

Asn Phe Tyr Pro Lys Asp Ile Asn Val Lys Trp Lys Ile Asp Gly Ser
        130                 135                 140

Glu Arg Gln Asn Gly Val
145                 150

<210> SEQ ID NO 91
<211> LENGTH: 151
<212> TYPE: PRT
<213> ORGANISM: Artificial Sequence
<220> FEATURE:
<223> OTHER INFORMATION: IgK variant

<400> SEQUENCE: 91

Ser Ser Phe Ser Ala Ser Thr Gly Asp Arg Val Thr Ile Thr Cys Arg
1               5                   10                  15

Ala Ser Gln Gly Ile Ser Ser Tyr Leu Ala Trp Tyr Gln Gln Lys Pro
            20                  25                  30

Gly Lys Ala Pro Lys Leu Leu Ile Tyr Ala Ala Ser Thr Leu Gln Ser
        35                  40                  45

Gly Val Pro Ser Arg Phe Ser Gly Ser Gly Ser Gly Thr Asp Phe Thr
    50                  55                  60

Leu Thr Ile Ser Cys Leu Gln Ser Glu Asp Phe Ala Thr Tyr Tyr Cys
65                  70                  75                  80

Gln Gln Tyr Tyr Ser Tyr Pro Trp Thr Phe Gly Gln Gly Thr Lys Val
                85                  90                  95

Glu Ile Lys Arg Ala Asp Ala Ala Pro Thr Val Ser Ile Phe Pro Pro
            100                 105                 110

Ser Ser Glu Gln Leu Thr Ser Gly Gly Ala Ser Val Val Cys Phe Leu
        115                 120                 125

Asn Asn Phe Tyr Pro Lys Asp Ile Asn Val Lys Trp Lys Ile Asp Gly
    130                 135                 140

Ser Glu Arg Gln Asn Gly Val
145                 150

<210> SEQ ID NO 92
<211> LENGTH: 151
<212> TYPE: PRT
<213> ORGANISM: Artificial Sequence
<220> FEATURE:
<223> OTHER INFORMATION: IgK variant

<400> SEQUENCE: 92

Ser Ser Phe Ser Arg Ser Thr Gly Asp Arg Val Thr Ile Thr Cys Arg
1               5                   10                  15

Ala Ser Gln Gly Ile Ser Ser Tyr Leu Ala Trp Tyr Gln Gln Lys Pro
            20                  25                  30

Gly Lys Ala Pro Lys Leu Leu Ile Tyr Ala Ala Ser Thr Leu Gln Ser
        35                  40                  45

Gly Val Pro Ser Arg Phe Ser Gly Ser Gly Ser Gly Thr Asp Phe Thr
    50                  55                  60
```

```
Leu Thr Ile Ser Cys Leu Gln Ser Glu Asp Phe Ala Thr Tyr Tyr Cys
 65                  70                  75                  80

Gln Gln Tyr Tyr Ser Tyr Pro Arg Thr Phe Gly Gln Gly Thr Lys Val
                 85                  90                  95

Glu Ile Lys Arg Ala Asp Ala Ala Pro Thr Val Ser Ile Phe Pro Pro
            100                 105                 110

Ser Ser Glu Gln Leu Thr Ser Gly Gly Ala Ser Val Val Cys Phe Leu
        115                 120                 125

Asn Asn Phe Tyr Pro Lys Asp Ile Asn Val Lys Trp Lys Ile Asp Gly
    130                 135                 140

Ser Glu Arg Gln Asn Gly Val
145                 150

<210> SEQ ID NO 93
<211> LENGTH: 50
<212> TYPE: DNA
<213> ORGANISM: Artificial Sequence
<220> FEATURE:
<223> OTHER INFORMATION: Vk1-6Jk1

<400> SEQUENCE: 93
taccctgtgg acgttcggcc aagggaccaa ggtggaaatc aaacgggctg             50

<210> SEQ ID NO 94
<211> LENGTH: 49
<212> TYPE: DNA
<213> ORGANISM: Artificial Sequence
<220> FEATURE:
<223> OTHER INFORMATION: Vk1-6Jk1 variant

<400> SEQUENCE: 94
tacccgtgga cgttcggcca agggaccaag gtggaaatca acgggctg               49

<210> SEQ ID NO 95
<211> LENGTH: 49
<212> TYPE: DNA
<213> ORGANISM: Artificial Sequence
<220> FEATURE:
<223> OTHER INFORMATION: Vk1-6Jk1 variant

<400> SEQUENCE: 95
tacccgtgga cgttcggcca agggaccaag gtggaaatca acgggctg               49

<210> SEQ ID NO 96
<211> LENGTH: 49
<212> TYPE: DNA
<213> ORGANISM: Artificial Sequence
<220> FEATURE:
<223> OTHER INFORMATION: Vk1-6Jk1 variant

<400> SEQUENCE: 96
tacccgtgga cgttcggcca agggaccaag gtggaaatca acgggctg               49

<210> SEQ ID NO 97
<211> LENGTH: 49
<212> TYPE: DNA
<213> ORGANISM: Artificial Sequence
<220> FEATURE:
<223> OTHER INFORMATION: Vk1-6Jk1 variant

<400> SEQUENCE: 97
tacccgtgga cgttcggcca agggaccaag gtggaaatca acgggctg               49
```

<210> SEQ ID NO 98
<211> LENGTH: 49
<212> TYPE: DNA
<213> ORGANISM: Artificial Sequence
<220> FEATURE:
<223> OTHER INFORMATION: Vk1-6Jk1 variant

<400> SEQUENCE: 98
tacccgtgga cgttcggcca agggaccaag gtggaaatca aacgggctg                49

<210> SEQ ID NO 99
<211> LENGTH: 49
<212> TYPE: DNA
<213> ORGANISM: Artificial Sequence
<220> FEATURE:
<223> OTHER INFORMATION: Vk1-6Jk1 variant

<400> SEQUENCE: 99
tacccgtgga cgttcggcca agggaccaag gtggaaatca aacgggctg                49

<210> SEQ ID NO 100
<211> LENGTH: 49
<212> TYPE: DNA
<213> ORGANISM: Artificial Sequence
<220> FEATURE:
<223> OTHER INFORMATION: Vk1-6Jk1 variant

<400> SEQUENCE: 100
tacccgtgga cgttcggcca agggaccaag gtggaaatca aacgggctg                49

<210> SEQ ID NO 101
<211> LENGTH: 49
<212> TYPE: DNA
<213> ORGANISM: Artificial Sequence
<220> FEATURE:
<223> OTHER INFORMATION: Vk1-6Jk1 variant

<400> SEQUENCE: 101
tacccgtgga cgttcggcca agggaccaag gtggaaatca aacgggctg                49

<210> SEQ ID NO 102
<211> LENGTH: 49
<212> TYPE: DNA
<213> ORGANISM: Artificial Sequence
<220> FEATURE:
<223> OTHER INFORMATION: Vk1-6Jk1 variant

<400> SEQUENCE: 102
tacccgtgga cgttcggcca agggaccaag gtggaaatca aacgggctg                49

<210> SEQ ID NO 103
<211> LENGTH: 49
<212> TYPE: DNA
<213> ORGANISM: Artificial Sequence
<220> FEATURE:
<223> OTHER INFORMATION: Vk1-6Jk1 variant

<400> SEQUENCE: 103
tacccgtgga cgttcggcca agggaccaag gtggaaatca aacgggctg                49

<210> SEQ ID NO 104
<211> LENGTH: 49
<212> TYPE: DNA
<213> ORGANISM: Artificial Sequence
<220> FEATURE:
<223> OTHER INFORMATION: Vk1-6Jk1 variant

```
<400> SEQUENCE: 104
taccctcgga cgttcggcca agggaccaag gtggaaatca aacgggctg        49

<210> SEQ ID NO 105
<211> LENGTH: 49
<212> TYPE: DNA
<213> ORGANISM: Artificial Sequence
<220> FEATURE:
<223> OTHER INFORMATION: Vk1-6Jk1 variant

<400> SEQUENCE: 105
taccctcgga cgttcggcca agggaccaag gtggaaatca aacgggctg        49

<210> SEQ ID NO 106
<211> LENGTH: 49
<212> TYPE: DNA
<213> ORGANISM: Artificial Sequence
<220> FEATURE:
<223> OTHER INFORMATION: Vk1-6Jk1 variant

<400> SEQUENCE: 106
taccctcgga cgttcggcca agggaccaag gtggaaatca aacgggctg        49

<210> SEQ ID NO 107
<211> LENGTH: 49
<212> TYPE: DNA
<213> ORGANISM: Artificial Sequence
<220> FEATURE:
<223> OTHER INFORMATION: Vk1-6Jk1 variant

<400> SEQUENCE: 107
taccctcgga cgttcggcca agggaccaag gtggaaatca aacgggctg        49

<210> SEQ ID NO 108
<211> LENGTH: 49
<212> TYPE: DNA
<213> ORGANISM: Artificial Sequence
<220> FEATURE:
<223> OTHER INFORMATION: Vk1-6Jk1 variant

<400> SEQUENCE: 108
taccctcgga cgttcggtgg aggcaccaag ctggaaatca aacgggctg        49

<210> SEQ ID NO 109
<211> LENGTH: 49
<212> TYPE: DNA
<213> ORGANISM: Artificial Sequence
<220> FEATURE:
<223> OTHER INFORMATION: Vk1-6Jk1 variant

<400> SEQUENCE: 109
taccctcgga cgttcggtgg aggcaccaag ctggaaatca aacgggctg        49

<210> SEQ ID NO 110
<211> LENGTH: 49
<212> TYPE: DNA
<213> ORGANISM: Artificial Sequence
<220> FEATURE:
<223> OTHER INFORMATION: Vk1-6Jk1 variant

<400> SEQUENCE: 110
taccctcgga cgttcggtgg aggcaccaag ctggaaatca aacgggctg        49

<210> SEQ ID NO 111
<211> LENGTH: 49
```

```
<212> TYPE: DNA
<213> ORGANISM: Artificial Sequence
<220> FEATURE:
<223> OTHER INFORMATION: Vk1-6Jk1 variant

<400> SEQUENCE: 111
taccctcgga cgttcggtgg aggcaccaag ctggaaatca aacgggctg            49

<210> SEQ ID NO 112
<211> LENGTH: 115
<212> TYPE: PRT
<213> ORGANISM: Artificial Sequence
<220> FEATURE:
<223> OTHER INFORMATION: IgK variant

<400> SEQUENCE: 112

Lys Leu Leu Ile Tyr Ala Ala Ser Ser Leu Gln Ser Gly Val Pro Ser
1               5                   10                  15

Arg Phe Ser Gly Ser Gly Ser Gly Thr Asp Phe Thr Leu Thr Ile Ser
            20                  25                  30

Ser Leu Gln Pro Glu Asp Phe Ala Thr Tyr Tyr Cys Leu Gln Asp Tyr
        35                  40                  45

Asn Tyr Pro Trp Thr Phe Gly Gln Gly Thr Lys Val Glu Ile Lys Arg
    50                  55                  60

Ala Asp Ala Ala Pro Thr Val Ser Ile Phe Pro Pro Ser Ser Glu Gln
65                  70                  75                  80

Leu Thr Ser Gly Gly Ala Ser Val Val Cys Phe Leu Asn Asn Phe Tyr
                85                  90                  95

Pro Lys Asp Ile Asn Val Lys Trp Lys Ile Asp Gly Ser Glu Arg Gln
            100                 105                 110

Asn Gly Val
        115

<210> SEQ ID NO 113
<211> LENGTH: 115
<212> TYPE: PRT
<213> ORGANISM: Artificial Sequence
<220> FEATURE:
<223> OTHER INFORMATION: IgK variant

<400> SEQUENCE: 113

Lys Leu Leu Ile Tyr Ala Ala Ser Ser Leu Gln Ser Gly Val Pro Ser
1               5                   10                  15

Arg Phe Ser Gly Ser Gly Ser Gly Thr Asp Phe Thr Leu Thr Ile Ser
            20                  25                  30

Ser Leu Gln Pro Glu Asp Phe Ala Thr Tyr Tyr Cys Leu Gln Asp Tyr
        35                  40                  45

Asn Tyr Pro Arg Thr Phe Gly Gln Gly Thr Lys Val Glu Ile Lys Arg
    50                  55                  60

Ala Asp Ala Ala Pro Thr Val Ser Ile Phe Pro Pro Ser Ser Glu Gln
65                  70                  75                  80

Leu Thr Ser Gly Gly Ala Ser Val Val Cys Phe Leu Asn Asn Phe Tyr
                85                  90                  95

Pro Lys Asp Ile Asn Val Lys Trp Lys Ile Asp Gly Ser Glu Arg Gln
            100                 105                 110

Asn Gly Val
        115

<210> SEQ ID NO 114
```

```
<211> LENGTH: 115
<212> TYPE: PRT
<213> ORGANISM: Artificial Sequence
<220> FEATURE:
<223> OTHER INFORMATION: IgK variant

<400> SEQUENCE: 114

Lys Leu Leu Ile Tyr Ala Ala Ser Ser Leu Gln Ser Gly Val Pro Ser
1               5                   10                  15

Arg Phe Ser Gly Ser Gly Ser Gly Thr Asp Phe Thr Leu Thr Ile Ser
            20                  25                  30

Ser Leu Gln Pro Glu Asp Phe Ala Thr Tyr Tyr Cys Leu Gln Asp Tyr
        35                  40                  45

Asn Tyr Pro Arg Thr Phe Gly Gly Gly Thr Lys Leu Glu Ile Lys Arg
    50                  55                  60

Ala Asp Ala Ala Pro Thr Val Ser Ile Phe Pro Pro Ser Ser Glu Gln
65                  70                  75                  80

Leu Thr Ser Gly Gly Ala Ser Val Val Cys Phe Leu Asn Asn Phe Tyr
                85                  90                  95

Pro Lys Asp Ile Asn Val Lys Trp Lys Ile Asp Gly Ser Glu Arg Gln
            100                 105                 110

Asn Gly Val
        115

<210> SEQ ID NO 115
<211> LENGTH: 128
<212> TYPE: PRT
<213> ORGANISM: Artificial Sequence
<220> FEATURE:
<223> OTHER INFORMATION: V1-5J1Ck

<400> SEQUENCE: 115

Val Ala Gly Trp Pro Gly Ile Ser Arg Asn Gln Gly Lys Pro Leu Ser
1               5                   10                  15

Ser Ser Ile Arg Arg Leu Val Lys Val Gly Ser His Gln Gly Ser Ala
            20                  25                  30

Ala Val Asp Leu Gly Gln Asn Ser Leu Ser Pro Ser Ala Ala Cys Ser
        35                  40                  45

Leu Met Ile Leu Gln Leu Ile Thr Ala Asn Ser Ile Ile Val Ile Leu
    50                  55                  60

Leu Thr Phe Gly Gly Gly Thr Lys Val Glu Ile Lys Arg Ala Asp Ala
65                  70                  75                  80

Ala Pro Thr Val Ser Ile Phe Pro Pro Ser Ser Glu Gln Leu Thr Ser
                85                  90                  95

Gly Gly Ala Ser Val Val Cys Phe Leu Asn Asn Phe Tyr Pro Lys Asp
            100                 105                 110

Ile Asn Val Lys Trp Lys Ile Asp Gly Ser Glu Arg Gln Asn Gly Val
        115                 120                 125

<210> SEQ ID NO 116
<211> LENGTH: 129
<212> TYPE: PRT
<213> ORGANISM: Artificial Sequence
<220> FEATURE:
<223> OTHER INFORMATION: VJC variant

<400> SEQUENCE: 116

Ser Ser Trp Leu Ala Trp Tyr Gln Gln Lys Pro Gly Lys Ala Pro Lys
1               5                   10                  15
```

```
Leu Leu Ile Tyr Lys Ala Ser Ser Leu Glu Ser Gly Val Pro Ser Arg
             20                  25                  30

Phe Ser Gly Ser Gly Ser Gly Thr Glu Phe Thr Leu Thr Ile Ser Ser
         35                  40                  45

Leu Gln Pro Asp Asp Phe Ala Thr Tyr Tyr Cys Gln Gln Tyr Asn Ser
 50                  55                  60

Tyr Ser Thr Phe Gly Gly Gly Thr Lys Val Glu Ile Lys Arg Ala Asp
 65                  70                  75                  80

Ala Ala Pro Thr Val Ser Ile Phe Pro Pro Ser Ser Glu Gln Leu Thr
                 85                  90                  95

Ser Gly Gly Ala Ser Val Val Cys Phe Leu Asn Asn Phe Tyr Pro Lys
             100                 105                 110

Asp Ile Asn Val Lys Trp Lys Ile Asp Gly Ser Glu Arg Gln Asn Gly
         115                 120                 125

Val
```

```
<210> SEQ ID NO 117
<211> LENGTH: 127
<212> TYPE: PRT
<213> ORGANISM: Artificial Sequence
<220> FEATURE:
<223> OTHER INFORMATION: V1-5J4Ck

<400> SEQUENCE: 117

Ala Gly Trp Pro Gly Ile Ser Arg Asn Gln Gly Lys Pro Leu Ser Ser
 1               5                  10                  15

Ser Ile Arg Arg Leu Val Lys Val Gly Ser His Gln Gly Ser Ala Ala
             20                  25                  30

Val Asp Leu Gly Gln Asn Ser Leu Ser Pro Ser Ala Ala Cys Ser Leu
         35                  40                  45

Met Ile Leu Gln Leu Ile Thr Ala Asn Ser Ile Ile Val Ile Leu Trp
 50                  55                  60

Thr Phe Gly Gln Gly Thr Lys Val Glu Ile Lys Arg Ala Asp Ala Ala
 65                  70                  75                  80

Pro Thr Val Ser Ile Phe Pro Pro Ser Ser Glu Gln Leu Thr Ser Gly
                 85                  90                  95

Gly Ala Ser Val Val Cys Phe Leu Asn Asn Phe Tyr Pro Lys Asp Ile
             100                 105                 110

Asn Val Lys Trp Lys Ile Asp Gly Ser Glu Arg Gln Asn Gly Val
         115                 120                 125
```

```
<210> SEQ ID NO 118
<211> LENGTH: 129
<212> TYPE: PRT
<213> ORGANISM: Artificial Sequence
<220> FEATURE:
<223> OTHER INFORMATION: VJCk variant

<400> SEQUENCE: 118

Ser Trp Leu Ala Trp Tyr Gln Gln Lys Pro Gly Lys Ala Pro Lys Leu
 1               5                  10                  15

Leu Ile Tyr Lys Ala Ser Ser Leu Glu Ser Gly Val Pro Ser Arg Phe
             20                  25                  30

Ser Gly Ser Gly Ser Gly Thr Glu Phe Thr Leu Thr Ile Ser Ser Leu
         35                  40                  45

Gln Pro Asp Asp Phe Ala Thr Tyr Tyr Cys Gln Gln Tyr Asn Ser Tyr
 50                  55                  60
```

```
Ser Trp Thr Phe Gly Gln Gly Thr Lys Val Glu Ile Lys Arg Ala Asp
 65                  70                  75                  80

Ala Ala Pro Thr Val Ser Ile Phe Pro Pro Ser Ser Glu Gln Leu Thr
                 85                  90                  95

Ser Gly Gly Ala Ser Val Val Cys Phe Leu Asn Asn Phe Tyr Pro Lys
            100                 105                 110

Asp Ile Asn Val Lys Trp Lys Ile Asp Gly Ser Glu Arg Gln Asn Gly
        115                 120                 125

Val

<210> SEQ ID NO 119
<211> LENGTH: 128
<212> TYPE: PRT
<213> ORGANISM: Artificial Sequence
<220> FEATURE:
<223> OTHER INFORMATION: VJCk variant

<400> SEQUENCE: 119

Ser Trp Leu Ala Trp Tyr Gln Gln Lys Pro Gly Lys Ala Pro Lys Leu
 1               5                  10                  15

Leu Ile Tyr Lys Ala Ser Ser Leu Glu Ser Gly Val Pro Ser Arg Phe
             20                  25                  30

Ser Gly Ser Gly Ser Gly Thr Glu Phe Thr Leu Thr Ile Ser Ser Leu
         35                  40                  45

Gln Pro Asp Asp Phe Ala Thr Tyr Tyr Cys Gln Gln Tyr Asn Ser Tyr
     50                  55                  60

Ser Thr Phe Gly Gln Gly Thr Lys Val Glu Ile Lys Arg Ala Asp Ala
 65                  70                  75                  80

Ala Pro Thr Val Ser Ile Phe Pro Pro Ser Ser Glu Gln Leu Thr Ser
                 85                  90                  95

Gly Gly Ala Ser Val Val Cys Phe Leu Asn Asn Phe Tyr Pro Lys Asp
            100                 105                 110

Ile Asn Val Lys Trp Lys Ile Asp Gly Ser Glu Arg Gln Asn Gly Val
        115                 120                 125

<210> SEQ ID NO 120
<211> LENGTH: 130
<212> TYPE: PRT
<213> ORGANISM: Artificial Sequence
<220> FEATURE:
<223> OTHER INFORMATION: VJCk variant

<400> SEQUENCE: 120

Ser Ser Trp Leu Ala Trp Tyr Gln Gln Lys Pro Gly Lys Ala Pro Lys
 1               5                  10                  15

Leu Leu Ile Tyr Lys Ala Ser Ser Leu Glu Ser Gly Val Pro Ser Arg
             20                  25                  30

Phe Ser Gly Ser Gly Ser Gly Thr Glu Phe Thr Leu Thr Ile Ser Ser
         35                  40                  45

Leu Gln Pro Asp Asp Phe Ala Thr Tyr Tyr Cys Gln Gln Tyr Asn Ser
     50                  55                  60

Tyr Ser Trp Thr Phe Gly Gln Gly Thr Lys Val Glu Ile Lys Arg Ala
 65                  70                  75                  80

Asp Ala Ala Pro Thr Val Ser Ile Phe Pro Pro Ser Ser Glu Gln Leu
                 85                  90                  95

Thr Ser Gly Gly Ala Ser Val Val Cys Phe Leu Asn Asn Phe Tyr Pro
            100                 105                 110
```

```
Lys Asp Ile Asn Val Lys Trp Lys Ile Asp Gly Ser Glu Arg Gln Asn
            115                 120                 125
Gly Val
    130

<210> SEQ ID NO 121
<211> LENGTH: 117
<212> TYPE: PRT
<213> ORGANISM: Artificial Sequence
<220> FEATURE:
<223> OTHER INFORMATION: IgHgamma1-3

<400> SEQUENCE: 121

Met Asp Trp Thr Trp Arg Ile Leu Phe Leu Val Ala Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
            35                  40                  45

Thr Ser Tyr Ala Met His Trp Val Arg Gln Ala Pro Gly Gln Arg Leu
        50                  55                  60

Glu Trp Met Gly Trp Ile Asn Ala Gly Asn Gly Asn Thr Lys Tyr Ser
65                  70                  75                  80

Gln Lys Phe Gln Gly Arg Val Thr Ile Thr Arg Asp Thr Ser Ala Ser
                85                  90                  95

Thr Ala Tyr Met Glu Leu Ser Ser Leu Arg Ser Glu Asp Thr Ala Val
                100                 105                 110

Tyr Tyr Cys Ala Arg
            115

<210> SEQ ID NO 122
<211> LENGTH: 151
<212> TYPE: PRT
<213> ORGANISM: Artificial Sequence
<220> FEATURE:
<223> OTHER INFORMATION: IGgamma variant

<400> SEQUENCE: 122

Met Asp Trp Thr Trp Arg Ile Leu Phe Ser Val Ala Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
            35                  40                  45

Thr Asn Tyr Ala Ile His Trp Val Arg Gln Ala Pro Gly Gln Arg Leu
        50                  55                  60

Glu Trp Met Gly Trp Ile Asn Ala Gly Asn Gly Asn Arg Lys Tyr Ser
65                  70                  75                  80

Gln Lys Phe Gln Gly Arg Val Thr Ile Thr Gly Asp Thr Ser Ala Asn
                85                  90                  95

Thr Ala Tyr Met Glu Leu Ser Ser Leu Arg Ser Glu Asp Thr Ala Val
                100                 105                 110

Tyr Tyr Cys Ala Arg Glu Ile Tyr Tyr Gly Ser Ser Arg Tyr Val
            115                 120                 125

Gly Tyr Phe Asp Val Trp Gly Ala Gly Thr Thr Val Thr Val Ser Ser
        130                 135                 140

Ala Lys Thr Thr Pro Pro Ser
145                 150
```

<210> SEQ ID NO 123
<211> LENGTH: 151
<212> TYPE: PRT
<213> ORGANISM: Artificial Sequence
<220> FEATURE:
<223> OTHER INFORMATION: IGgamma variant

<400> SEQUENCE: 123

Met Asp Trp Thr Trp Arg Ile Leu Phe Leu Val Ala Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asn Tyr Ala Ile His Trp Val Arg Gln Ala Pro Gly Gln Arg Leu
    50                  55                  60

Glu Trp Met Gly Arg Ile Asn Ala Gly Asn Gly Asn Arg Lys Tyr Ser
65                  70                  75                  80

Arg Lys Phe Gln Gly Arg Val Thr Ile Thr Gly Asp Thr Ser Ala Asn
                85                  90                  95

Thr Ala Tyr Met Glu Leu Ser Ser Leu Arg Ser Glu Asp Thr Ala Val
            100                 105                 110

Tyr Tyr Cys Ala Arg Glu Ile Tyr Tyr Gly Ser Ser Arg Tyr Val
        115                 120                 125

Gly Tyr Phe Asp Val Trp Gly Ala Gly Thr Thr Val Thr Val Ser Ser
    130                 135                 140

Ala Lys Thr Thr Pro Pro Ser
145                 150

<210> SEQ ID NO 124
<211> LENGTH: 153
<212> TYPE: PRT
<213> ORGANISM: Artificial Sequence
<220> FEATURE:
<223> OTHER INFORMATION: IGgamma variant

<400> SEQUENCE: 124

Met Asp Trp Thr Trp Arg Ile Leu Phe Leu Ala Leu Ala Ala Thr Ala
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Thr Tyr Gly Ile His Trp Val Arg Gln Ala Pro Val Arg Arg Leu
    50                  55                  60

Glu Trp Met Gly Trp Ile Asn Ala Gly Asp Gly Asp Thr Lys Phe Ser
65                  70                  75                  80

Gln Asn Phe Gln Gly Arg Leu Thr Ile Thr Met Asp Thr Ser Ala Ser
                85                  90                  95

Thr Ala Tyr Met Glu Leu Tyr Ser Leu Arg Ser Glu Asp Thr Ala Val
            100                 105                 110

Tyr Tyr Cys Ala Arg Asp Gly Asp Glu Tyr Gly Ser Gly Lys Asp Tyr
        115                 120                 125

Tyr Tyr Tyr Gly Met Asp Val Trp Gly Gln Gly Thr Thr Val Thr Val
    130                 135                 140

Ser Ser Ala Lys Thr Thr Pro Pro Ser

<210> SEQ ID NO 125
<211> LENGTH: 142
<212> TYPE: PRT
<213> ORGANISM: Artificial Sequence
<220> FEATURE:
<223> OTHER INFORMATION: IGgamma variant

<400> SEQUENCE: 125

```
Met Asp Trp Thr Trp Arg Ile Leu Phe Leu Val Ala Ala Thr Gly
1               5                   10                  15

Ala His Ser Gln Val Gln Leu Val Gln Ser Gly Ser Glu Leu Lys Lys
            20                  25                  30

Pro Gly Ala Ser Val Lys Val Ser Cys Lys Ala Ser Gly Tyr Thr Phe
            35                  40                  45

Thr Ser Tyr Ala Met Asn Trp Val Arg Gln Ala Pro Gly Gln Gly Leu
        50                  55                  60

Glu Trp Met Gly Trp Ile Asn Thr Asn Thr Gly Asn Pro Thr Tyr Ala
65                  70                  75                  80

Gln Gly Phe Thr Gly Arg Phe Val Phe Ser Leu Asp Thr Ser Val Ser
                85                  90                  95

Thr Ala Tyr Leu Gln Ile Gln Ser Leu Lys Ala Glu Asp Thr Ala Val
            100                 105                 110

Tyr Tyr Cys Ala Arg Ala Asn Trp Tyr Phe Asp Leu Trp Gly Arg Gly
        115                 120                 125

Thr Leu Val Thr Val Ser Ser Ala Lys Thr Thr Pro Pro Ser
    130                 135                 140
```

<210> SEQ ID NO 126
<211> LENGTH: 153
<212> TYPE: PRT
<213> ORGANISM: Artificial Sequence
<220> FEATURE:
<223> OTHER INFORMATION: IGgamma variant

<400> SEQUENCE: 126

```
Met Asp Trp Thr Trp Arg Ile Leu Phe Leu Val Ala Ala Thr Gly
1               5                   10                  15

Ala His Ser Gln Val Gln Pro Val Gln Ser Gly Thr Glu Val Lys Lys
            20                  25                  30

Pro Gly Ala Ser Val Lys Val Ser Cys Lys Ala Ser Gly Tyr Thr Phe
            35                  40                  45

Gly Asn His Ala Ile His Trp Val Arg Gln Ala Pro Gly Gln Arg Leu
        50                  55                  60

Glu Trp Met Gly Trp Ile Asn Thr Gly Asn Gly Asn Thr Arg Tyr Ser
65                  70                  75                  80

Gln Lys Phe Gln Gly Arg Val Thr Ile Thr Arg Asp Thr Ser Ala Ser
                85                  90                  95

Thr Ala Tyr Met Glu Leu Ser Ser Leu Arg Ser Glu Asp Thr Ala Met
            100                 105                 110

Tyr Tyr Cys Ala Arg Glu Gly Gly Tyr Tyr Gly Ser Gly Ser Tyr His
        115                 120                 125

Tyr Tyr Tyr Gly Met Asp Val Trp Gly Gln Gly Thr Thr Val Thr Val
    130                 135                 140

Ser Ser Ala Lys Thr Thr Pro Pro Ser
145                 150
```

```
<210> SEQ ID NO 127
<211> LENGTH: 153
<212> TYPE: PRT
<213> ORGANISM: Artificial Sequence
<220> FEATURE:
<223> OTHER INFORMATION: IGgamma variant

<400> SEQUENCE: 127

Met Asp Trp Thr Trp Arg Ile Leu Phe Leu Val Ala Ala Thr Ala
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Thr Tyr Gly Ile His Trp Val Arg Gln Ala Pro Val Arg Arg Leu
    50                  55                  60

Glu Trp Met Gly Trp Ile Asn Ala Gly Asp Gly Asp Thr Lys Phe Ser
65                  70                  75                  80

Gln Asn Phe Gln Gly Arg Leu Thr Ile Thr Met Asp Thr Ser Ala Ser
                85                  90                  95

Thr Ala Tyr Met Glu Leu Tyr Ser Leu Lys Ser Glu Asp Thr Ala Val
            100                 105                 110

Tyr Tyr Cys Ala Arg Asp Gly Asp Glu Tyr Gly Ser Gly Lys Asp Tyr
        115                 120                 125

Tyr Tyr Tyr Gly Met Asp Val Trp Gly Gln Gly Thr Thr Val Thr Val
    130                 135                 140

Ser Ser Ala Lys Thr Thr Pro Pro Ser
145                 150

<210> SEQ ID NO 128
<211> LENGTH: 153
<212> TYPE: PRT
<213> ORGANISM: Artificial Sequence
<220> FEATURE:
<223> OTHER INFORMATION: IGgamma variant

<400> SEQUENCE: 128

Met Asp Trp Thr Trp Arg Ile Leu Phe Leu Ala Ser Ala Thr Ala
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Thr Tyr Gly Ile His Trp Val Arg Gln Ala Pro Val Arg Arg Leu
    50                  55                  60

Glu Trp Met Gly Trp Ile Asn Ala Gly Asp Gly Asp Thr Lys Phe Ser
65                  70                  75                  80

Gln Asn Phe Gln Gly Arg Leu Thr Ile Thr Met Asp Thr Ser Ala Ser
                85                  90                  95

Thr Ala Tyr Met Glu Leu Tyr Ser Leu Arg Ser Glu Asp Thr Ala Val
            100                 105                 110

Tyr Tyr Cys Ala Arg Asp Gly Asp Glu Tyr Gly Ser Gly Lys Asp Tyr
        115                 120                 125

Tyr Tyr Tyr Gly Met Asp Val Trp Gly Gln Gly Thr Thr Val Thr Val
    130                 135                 140

Ser Ser Ala Lys Thr Thr Pro Pro Ser
145                 150
```

```
<210> SEQ ID NO 129
<211> LENGTH: 147
<212> TYPE: PRT
<213> ORGANISM: Artificial Sequence
<220> FEATURE:
<223> OTHER INFORMATION: IGgamma variant

<400> SEQUENCE: 129

Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Gly Tyr Tyr Met His Trp Val Arg Gln Ala Pro Gly Gln Gly Leu
    50                  55                  60

Glu Trp Met Gly Trp Ile Asn Pro Asn Ser Gly Gly Thr Asn Tyr Ala
65                  70                  75                  80

Gln Lys Phe Gln Gly Trp Val Thr Met Thr Arg Asp Thr Ser Ile Ser
                85                  90                  95

Thr Ala Tyr Met Glu Leu Ser Arg Leu Arg Ser Asp Asp Thr Ala Val
            100                 105                 110

Tyr Tyr Cys Ala Arg Gly Asp Tyr Tyr Gly Ser Gly Thr Tyr Phe Asp
        115                 120                 125

Tyr Trp Gly Gln Gly Thr Leu Val Thr Val Ser Ser Ala Lys Thr Thr
    130                 135                 140

Pro Pro Ser
145

<210> SEQ ID NO 130
<211> LENGTH: 143
<212> TYPE: PRT
<213> ORGANISM: Artificial Sequence
<220> FEATURE:
<223> OTHER INFORMATION: IGgamma variant

<400> SEQUENCE: 130

Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Gly Met His Trp Val Arg Gln Ala Pro Gly Gln Arg Leu
    50                  55                  60

Glu Trp Met Gly Trp Ile Asn Ala Gly Asn Gly Lys Lys Lys Tyr Ser
65                  70                  75                  80

Gln Lys Phe Gln Gly Arg Val Thr Ile Thr Arg Asp Thr Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg Val Gly Val Thr Ile Phe Asp Tyr Trp Gly Gln
        115                 120                 125

Gly Thr Leu Val Thr Val Ser Ser Ala Lys Thr Thr Pro Pro Ser
    130                 135                 140
```

```
<210> SEQ ID NO 131
<211> LENGTH: 151
<212> TYPE: PRT
<213> ORGANISM: Artificial Sequence
<220> FEATURE:
<223> OTHER INFORMATION: IGgamma variant

<400> SEQUENCE: 131
```

Met Asp Trp Thr Trp Arg Ile Leu Phe Leu Val Ala Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asn Tyr Ala Ile His Trp Val Arg Gln Ala Pro Gly Gln Arg Leu
    50                  55                  60

Glu Trp Met Gly Trp Ile Asn Ala Gly Asn Gly Asn Arg Lys Tyr Ser
65                  70                  75                  80

Gln Lys Phe Gln Gly Arg Val Thr Ile Thr Gly Asp Thr Ser Ala Asn
                85                  90                  95

Thr Ala Tyr Met Glu Leu Ser Ser Leu Arg Ser Glu Asp Thr Ala Val
            100                 105                 110

Tyr Tyr Cys Ala Arg Glu Thr Tyr Tyr Gly Ser Ser Arg Tyr Val
        115                 120                 125

Gly Tyr Phe Asp Val Trp Gly Ala Gly Thr Thr Val Thr Val Ser Ser
    130                 135                 140

Ala Lys Thr Thr Pro Pro Ser
145                 150

```
<210> SEQ ID NO 132
<211> LENGTH: 143
<212> TYPE: PRT
<213> ORGANISM: Artificial Sequence
<220> FEATURE:
<223> OTHER INFORMATION: IGgamma

<400> SEQUENCE: 132
```

Met Asp Trp Thr Trp Arg Ile Leu Phe Leu Val Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Gly Met His Trp Val Arg Gln Ala Pro Gly Gln Arg Leu
    50                  55                  60

Glu Trp Met Gly Trp Ile Asn Ala Gly Asn Gly Lys Lys Lys Tyr Ser
65                  70                  75                  80

Gln Lys Phe Gln Gly Arg Val Thr Ile Thr Arg Asp Thr Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg Leu Gly Ile Thr Ile Phe Asp Tyr Trp Gly Gln
        115                 120                 125

Gly Thr Leu Val Thr Val Ser Ser Ala Lys Thr Thr Pro Pro Ser
    130                 135                 140